US012447149B2

(12) United States Patent
Hamed

(10) Patent No.: US 12,447,149 B2
(45) Date of Patent: Oct. 21, 2025

(54) FORMULATIONS OF VIMSELTINIB

(71) Applicant: Deciphera Pharmaceuticals, LLC, Waltham, MA (US)

(72) Inventor: Ehab Hamed, Waltham, MA (US)

(73) Assignee: Deciphera Pharmaceuticals, LLC, Waltham, MA (US)

( * ) Notice: Subject to any disclaimer, the term of this patent is extended or adjusted under 35 U.S.C. 154(b) by 0 days.

(21) Appl. No.: 19/079,070

(22) Filed: Mar. 13, 2025

(65) Prior Publication Data

US 2025/0205236 A1 Jun. 26, 2025

Related U.S. Application Data

(63) Continuation of application No. 18/971,846, filed on Dec. 6, 2024.

(Continued)

(51) Int. Cl.

*A61K 31/513* (2006.01)
*A61K 9/48* (2006.01)

(Continued)

(52) U.S. Cl.

CPC .......... *A61K 31/513* (2013.01); *A61K 9/4825* (2013.01); *A61K 9/485* (2013.01);

(Continued)

(58) Field of Classification Search

CPC .............. A61K 2300/00; A61K 31/337; A61K 31/357; A61K 31/4184; A61K 31/437;

(Continued)

(56) References Cited

U.S. PATENT DOCUMENTS 7,144,911 B2 12/2006 Flynn et al.
7,202,257 B2 4/2007 Flynn et al.

(Continued)

FOREIGN PATENT DOCUMENTS

CN 105120864 A 12/2015
CN 105473617 A 4/2016

(Continued)

OTHER PUBLICATIONS

Cao et al. (CN 116283919A) abstract Jun. 23, 2023 (Year: 2023).*

(Continued)

*Primary Examiner* — Savitha M Rao
(74) *Attorney, Agent, or Firm* — Goodwin Procter LLP

(57) ABSTRACT

Described herein, in part, are pharmaceutically acceptable formulations comprising a compound represented by Formula (I) and methods of preparing and using the formulations:

Formula (I)

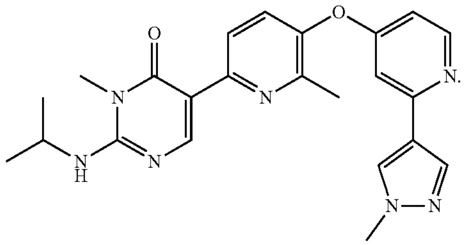

22 Claims, 14 Drawing Sheets

Related U.S. Application Data

(60) Provisional application No. 63/607,697, filed on Dec. 8, 2023.

(51) Int. Cl.
*C07D 401/14* (2006.01)
*A61K 9/00* (2006.01)

(52) U.S. Cl.
CPC .......... *A61K 9/4858* (2013.01); *A61K 9/4866* (2013.01); *C07D 401/14* (2013.01); *A61K 9/0053* (2013.01)

(58) Field of Classification Search
CPC .............. A61K 31/4523; A61K 31/506; A61K 31/513; A61K 31/519; A61K 31/7068; A61K 45/06; A61K 9/0053; A61P 35/00; A61P 35/02; A61P 35/04
See application file for complete search history.

(56) References Cited

U.S. PATENT DOCUMENTS

| | | | |
|---|---|---|---|
| 7,279,576 | B2 | 10/2007 | Flynn et al. |
| 7,342,037 | B2 | 3/2008 | Flynn et al. |
| 7,531,566 | B2 | 5/2009 | Flynn et al. |
| 7,666,895 | B2 | 2/2010 | Flynn et al. |
| 7,737,283 | B2 | 6/2010 | Flynn et al. |
| 7,790,756 | B2 | 9/2010 | Flynn et al. |
| 7,897,762 | B2 | 3/2011 | Flynn et al. |
| 8,143,293 | B2 | 3/2012 | Flynn et al. |
| 8,163,756 | B2 | 4/2012 | Flynn et al. |
| 8,188,113 | B2 | 5/2012 | Flynn et al. |
| 8,278,331 | B2 | 10/2012 | Flynn et al. |
| 8,461,179 | B1 | 6/2013 | Flynn et al. |
| 8,486,951 | B2 | 7/2013 | Flynn et al. |
| 8,569,319 | B2 | 10/2013 | Flynn et al. |
| 8,586,565 | B2 | 11/2013 | Flynn et al. |
| 8,637,672 | B2 | 1/2014 | Flynn et al. |
| 8,741,911 | B2 | 6/2014 | Allgeier et al. |
| 8,921,565 | B2 | 12/2014 | Flynn et al. |
| 8,940,756 | B2 | 1/2015 | Flynn et al. |
| 9,012,635 | B2 | 4/2015 | Flynn et al. |
| 9,133,183 | B2 | 9/2015 | Flynn et al. |
| 9,181,223 | B2 | 11/2015 | Kaufman et al. |
| 9,187,474 | B2 | 11/2015 | Flynn et al. |
| 9,193,719 | B2 | 11/2015 | Flynn et al. |
| 9,309,224 | B2 | 4/2016 | Flynn et al. |
| 9,334,267 | B2 | 5/2016 | Flynn et al. |
| 9,382,228 | B2 | 7/2016 | Flynn et al. |
| 9,387,202 | B2 | 7/2016 | Flynn et al. |
| 9,457,019 | B2 | 10/2016 | Flynn et al. |
| 11,103,507 | B2 | 8/2021 | Flynn et al. |
| 11,679,110 | B2 | 6/2023 | Flynn et al. |
| 2008/0214544 | A1 | 9/2008 | Bellon et al. |
| 2008/0255155 | A1 | 10/2008 | Raeppel et al. |
| 2010/0120806 | A1 | 5/2010 | Flynn et al. |
| 2010/0166699 | A1 | 7/2010 | Thompson et al. |
| 2011/0053906 | A1 | 3/2011 | Huck et al. |
| 2014/0145025 | A1 | 5/2014 | Fang et al. |
| 2015/0073129 | A1 | 3/2015 | Herting et al. |
| 2019/0091217 | A1 | 3/2019 | Flynn et al. |
| 2020/0129489 | A1 | 4/2020 | Flynn et al. |
| 2020/0352920 | A1 | 11/2020 | Flynn et al. |
| 2020/0354346 | A1 | 11/2020 | Flynn et al. |
| 2020/0354352 | A1 | 11/2020 | Flynn et al. |
| 2021/0015801 | A1 | 1/2021 | Flynn et al. |
| 2023/0414614 | A1 | 12/2023 | Flynn et al. |

FOREIGN PATENT DOCUMENTS

| | | | |
|---|---|---|---|
| CN | 113880812 | A | 1/2022 |
| CN | 116283919 | A | 6/2023 |
| EP | 3632907 | A1 | 4/2020 |
| EP | 3682881 | A1 | 7/2020 |
| JP | 6364472 | B2 | 7/2018 |
| RU | 2330024 | C2 | 7/2008 |
| WO | WO-2003/000660 | A1 | 1/2003 |
| WO | WO-2008/079291 | A2 | 7/2008 |
| WO | WO-2010/051373 | A1 | 5/2010 |
| WO | 2014145015 | A2 | 9/2014 |
| WO | 2014145028 | A2 | 9/2014 |
| WO | WO-2014/145025 | A2 | 9/2014 |
| WO | WO-2020/139828 | A1 | 7/2020 |
| WO | WO-2022247786 | A1 | 12/2022 |

OTHER PUBLICATIONS

Caira M. R. et al. "Crystalline Polymorphism of Organic Compounds", Design of Organic Solids. Topics in Current Chemistry, vol. 198, p. 163-208 (1998).

Fang Z. et al. Conformational restriction: an effective tactic in 'follow-on'-based drug discovery, Fugure Med Chem. 2014, 6(8): 885-901.

Kumari A. et al. 3D-QSAR analysis of anilinoquinoline inhibitors of colony stimulating factor-1 kinase(cFMS): implementation of field-based molecular alignment, Med Chem Res 22, 5167-5183 (2013).

PCT/US2019/068311 International Search Report and Written Opinion mailed Jul. 2, 2020.

PCT/US2024/058988 International Search Report and Written Opinion dated Mar. 24, 2025.

Silverman R.B. et al. Lead Discovery, The Organic Chemistry of Drug Design and Drug Action, 3rd Ed, Chapter 2, pp. 19-122, Elsevier (2014).

"Deciphera Pharmaceuticals Announces Positive, Preliminary, Top-Line Clinical Data for the Ongoing Phase 1 Clincial Study with DCC-3014 and an Update on Future Development Plans," 2019, 1-3.

"History of Changes for Study: NCT03069469 Study of DCC-3014 in Patients with Advanced Malignancies," ClinicalTrials.gov Archive, 2018, 1-5.

Al-Muhsen et al., "The Expression of Stem Cell Factor and c-Kit Receptor in Human Asthmatic Airways," Clinical and Experimental Allergy, 2004, 34: 911-917.

Attoub et al., "The C-Kit Tyrosine Kinase Inhibitor STI571 for Colorectal Cancer Therapy," Cancer Research, 2002, 62: 4879-4883.

Blay, JY et al., "P63: Patient-Reported Outcomes Following Treatment with Vimseltinib for Tenosynovial Giant Cell Tumour in a Phase 2 Expansion Study", Value in Health, Elsevier, Amsterdam, NL, vol. 25, No. 12 (Dec. 1, 2022), XP087229982.

Boisson et al., "c-Kit and c-kit mutations in mastocytosis and other hematological diseases," Journal of Leukocyte Biology, 2000, 67(2):135-148.

Brinkmann et al., "Fingolimod (FTY720): Discovery and Development of an Oral Drug to Treat Multiple Sclerosis," Nature Reviews | Drug Discovery, 2010, 9: 883-897.

Brunton et al., "Chemotherapy of Neoplastic Diseases," in, Goodman and Gilman's: The Pharmacological Basis of Therapeutics, 2008, 11th ed.: 853-908.

Burns et al., "C-FMS Inhibitors: A Patent Review," Expert Opinion on Therapeutic Patents, 2011, 147-165.

Caldwell, T. M. et al., "Discovery of vimseltinib (DCC-3014), a highly selective CSF1R switch-control kinase inhibitor, in clinical development for the treatment of Tenosynovial Giant Cell Tumor (TGCT)," Biorg. Med. Chem. Lett. 74, (2022) 128928, 7 pages.

Carvajal et al., "KIT as a Therapeutic Target in Metastatic Melanoma," Journal of the American Medical Association, 2011, 305(22): 2327-2334.

Dewar et al., "Inhibition of c-fms by Imatinib: expanding the spectrum of treatment," Cell Cycle, 2005, 4(7):851-853.

Dewar et al., "Macrophage Colony-Stimulating Factor Receptor C-Fms is a Novel Target of Imatinib," Blood, 2005, 105(8): 3127-3132.

Di Lorenzo et al., "Expression of Proto-Oncogene C-Kit in High Risk Prostate Cancer," European Journal of Surgical Oncology, 2004, 30: 987-992.

(56) References Cited

OTHER PUBLICATIONS

Dorwald, "Side Reactions in Organic Synthesis," Wiley: VCH Weinhem Preface, 2005, 1-15 & 8: 279-308.
El Agamy et al., "Targeting c-Kit in the Therapy of Mast Cell Disorders: Current Update," European Journal of Pharmacology, 2012, 690: 1-3.
Fine et al., "Neoplasms of the Central Nervous System," Cancer Principles & Practice of Oncology, 2005, 1834-1887.
Fogarty et al., "Development of Protein Kinase Activators: AMPK as a Target in Metabolic Disorders and Cancer," Biochimica et Biophysica Acta, 2010, 1804: 581-591.
Gelderblom, H. et al., "475P: Safety and Efficacy of Vimseltinib in Tenosynovial Giant Cell Tumour (TGCT)): Long-term Phase I Update", Annals of Oncology, vol. 33, (Sep. 1, 2022), p. S757, XP093241096.
Gelderblom, H. et al., "Vimseltinib versus placebo for tenosynovial giant cell tumour (MOTION): a multicentre, randomised, double-blind, placebo-controlled, phase 3 trial", The Lancet, vol. 403, No. 10445, (Jun. 3, 2024), pp. 2709-2719, XP093241015.
Girouard et al., "Neurovascular Coupling in the Normal Brain and in Hypertension, Stroke, and Alzheimer Disease," J. Appl Physiol., 2006, 100: 328-335.
Gupta et al., "IL-3 Inhibits Human Osteoclastogenesis and Bone Resorption through Downregulation of c-Fms and Diverts the Cells to Dendritic Cell Lineage," The Journal of Immunology, 2010, 2261-2272.
Heinrich et al., "Inhibition of c-kit receptor tyrosine kinase activity by STI 571, a selective tyrosine kinase inhibitor," Blood, 2000, 96(3):925-932.
Henriksen et al., "Assessment of Osteoclast Number and Function: Application in the Development of New and Improved Treatment Modalities for Bone Diseases," Osteoporosis International, 2006, 18: 681-685.
International Search Report and Written Opinion for International Patent Application No. PCT/US2014/029661 mailed Jun. 11, 2014.
International Search Report and Written Opinion for International Patent Application No. PCT/US2014/029664 mailed Jun. 11, 2014.
International Search Report and Written Opinion for International Patent Application No. PCT/US2019/068311 mailed Feb. 7, 2020.
International Search Report and Written Opinion for International Patent Application No. PCT/US2024/053261 mailed Feb. 6, 2025.
Judge et al., "Potassium Channel Blockers in Multiple Sclerosis: Neuronal Kv Channels and Effects of Symptomatic Treatment," Pharmacology & Therapeutics, 2006, 224-259.
Kung et al., "Structure Activity Relationships of Quinoline-Containing c-Met Inhibitors," European Journal of Medicinal Chemistry 43, 2008, 1321-1329.
Kuster et al., "Kinase Inhibitors Methods and Protocols," Methods in Molecular Biology, 2012, 1-46.
Lewitt, "Levodopa for the Treatment of Parkinson's Disease," New England Journal of Medicine, 2008, 359: 2468-2476.
Luo et al., "Principles of Cancer Therapy: Oncogene and Non-oncogene Addiction," Cell, 2009, 36: 823-837.
Minkin, "Bone Acid Phosphatase: Tartrate-Resistant Acid Phosphatase as a Marker of Osteoclast Function," Calcified Tissue International, 1982, 34: 285-290.
Mitchell et al., "Amyotrophic Lateral Sclerosis," The Lancet, 2007, 369: 2031-2041.
National Cancer Institute (http://www.cancer.gov) 2014.
O'Brien et al., "Vascular Cognitive Impairment," The Lancet Neurology, 2003, 2: 89-98.
Ohno et al., "A c-fms tyrosine kinase inhibitor, Ki20227, suppresses osteoclast differentiation and osteolytic bone destruction in a bone metastasis model," Mol Cancer Ther., 2006, 5(11):2634-2643.
Pyonteck et al., "CSF-1R inhibition alters macrophage polarization and blocks glioma progression," Nature Medicine, 2013, 19(10):1264-1274.
Reber et al., "Stem Cell Factor and its Receptor c-Kit as Targets for Inflammatory Diseases," European Journal of Pharmacology, 2006, 533: 327-340.
Roberts et al., "Antiangiogenic and Antitumor Activity of a Selective PDGFR Tyrosine Kinase Inhibitor, CP-673, 451," Cancer Research, 2005, 957-966.
Rubin et al., "KIT activation is a ubiquitous feature of gastrointestinal stromal tumors," Cancer Research, 2001, 61(22):8118-8121.
Shah et al., "Current Approaches in the Treatment of Alzheimer's Disease," Biomedicine & Pharmacotherapy, 2008, 62: 199-207.
Smith, B. D. et al., "Vimseltinib: A Precision CSF1R Therapy for Tenosynovial Giant Cell Tumors and Diseases Promoted by Macrophages", Molecular Cancer Therapeutics, vol. 20, No. 11, (Aug. 25, 2021), pp. 2098-2109, XP093171464.
Tap et al., "Pexidartinib Versus Placebo for Advanced Tenosynovial Giant Cell Tumour (ENLIVEN): a Randomised Phase 3 Trial," Lancet, 2019, 394: 478-487.
Tap et al., "Structure-Guided Blockade of CSF1R Kinase in Tenosynovial Giant-Cell Tumor," New England Journal of Medicine, 2015, 373(5):428-437.
Tap, W. D. et al., "Efficacy, safety, and patient-reported outcomes of vimseltinib in patients with tenosynovial giant cell tumor: Results from the phase 3 MOTION trial", Journal of Clinical Oncology, vol. 42, No. 16_suppl, (Jun. 1, 2024), pp. 11500-11500, XP093241007.
Tap, W. D. et al., "MOTION: A randomized, phase 3, placebo-controlled, double-blind study of vimseltinib (DCC-3014) for the treatment of tenosynovial giant cell tumour", Journal of Clinical Oncology, vol. 40, No. 16_suppl., (Jun. 2, 2022), pp. TPS11590-TPS11590, XP093241022.
Wen et al., "Osteosarcoma Cell-Intrinsic Colony Stimulating Factor-1 Receptor Functions to Promote Tumor Cell Metastasis Through JAG1 Signaling," American Journal of Cancer Research, 2017, 7(4): 801-815.
Yasuda et al., "The Stem Cell Factor/C-Kit Receptor Pathway Enhance Proliferation and Invasion of Pancreatic Cancer Cells," Molecular Cancer, 2006, 5(46): 1-10.
U.S. Appl. No. 11/963,740, filed Dec. 21, 2007, Patented, U.S. Pat. No. 8,163,756.
U.S. Appl. No. 11/870,388, filed Oct. 10, 2007, Patented, U.S. Pat. No. 7,790,756.
U.S. Appl. No. 12/829,561, filed Jul. 2, 2010, Patented, U.S. Pat. No. 8,586,565.
U.S. Appl. No. 11/854,354, filed Sep. 12, 2007, Patented, U.S. Pat. No. 8,188,113.
U.S. Appl. No. 10/746,460, filed Dec. 24, 2003, Patented, U.S. Pat. No. 7,144,911.
U.S. Appl. No. 10/886,329, filed Jul. 6, 2004, Patented, U.S. Pat. No. 7,202,257.
U.S. Appl. No. 11/450,840, filed Jun. 9, 2006, Patented, U.S. Pat. No. 7,342,037.
U.S. Appl. No. 11/336,708, filed Jan. 20, 2006, Patented, U.S. Pat. No. 7,531,566.
U.S. Appl. No. 11/450,850, filed Jun. 9, 2006, Patented, U.S. Pat. No. 7,666,895.
U.S. Appl. No. 10/746,607, filed Dec. 24, 2003, Patented, U.S. Pat. No. 7,279,576.
U.S. Appl. No. 11/854,293, filed Sep. 12, 2007, Patented, U.S. Pat. No. 7,897,762.
U.S. Appl. No. 12/105,408, filed Apr. 18, 2008, Patented, U.S. Pat. No. 8,143,293.
U.S. Appl. No. 13/590,955, filed Aug. 21, 2012, Patented, U.S. Pat. No. 8,486,951.
U.S. Appl. No. 11/450,849, filed Jun. 9, 2006, Patented, U.S. Pat. No. 7,737,283.
U.S. Appl. No. 13/785,575, filed Mar. 5, 2013, Patented, U.S. Pat. No. 8,741,911.
U.S. Appl. No. 12/608,578, filed Oct. 29, 2009, Patented, U.S. Pat. No. 8,278,331.
U.S. Appl. No. 13/098,247, filed Apr. 29, 2011, Patented, U.S. Pat. No. 8,569,319.
U.S. Appl. No. 13/559,170, filed Jul. 26, 2012, Patented, U.S. Pat. No. 8,637,672.
U.S. Appl. No. 14/214,134, filed Mar. 14, 2014, Patented, U.S. Pat. No. 9,133,183.
U.S. Appl. No. 14/383,803, filed Mar. 5, 2013, Patented, U.S. Pat. No. 9,187,474.

(56) References Cited

OTHER PUBLICATIONS

U.S. Appl. No. 13/491,394, filed Jun. 7, 2012, Patented, U.S. Pat. No. 8,461,179.
U.S. Appl. No. 13/801,753, filed Mar. 13, 2013, Patented, U.S. Pat. No. 8,940,756.
U.S. Appl. No. 16/387,315, filed Apr. 17, 2019, Pending.
U.S. Appl. No. 14/214,127, filed Mar. 14, 2014, Patented, U.S. Pat. No. 9,012,635.
U.S. Appl. No. 13/683,277, filed Nov. 21, 2012, Patented, U.S. Pat. No. 8,921,565.
U.S. Appl. No. 14/549,125, filed Nov. 20, 2014, Patented, U.S. Pat. No. 9,387,202.
U.S. Appl. No. 14/214,160, filed Mar. 14, 2014, Patented, U.S. Pat. No. 9,193,719.
U.S. Appl. No. 14/214,171, filed Mar. 14, 2014, Patented, U.S. Pat. No. 9,181,223.
U.S. Appl. No. 14/214,185, filed Mar. 14, 2014, Patented, U.S. Pat. No. 9,382,228.
U.S. Appl. No. 14/214,179, filed Mar. 14, 2014, Patented, U.S. Pat. No. 9,309,224.
U.S. Appl. No. 14/383,799, filed Mar. 5, 2013, Patented, U.S. Pat. No. 9,334,267.
U.S. Appl. No. 14/535,900, filed Nov. 7, 2014, Patented, U.S. Pat. No. 9,457,019.
U.S. Appl. No. 16/943,821, filed Jul. 30, 2020, Pending, US 2021-0145805 A1.
U.S. Appl. No. 16/943,871, filed Jul. 30, 2020, Pending, US 2020-0352920 A1.
U.S. Appl. No. 16/725,282, filed Dec. 23, 2019, Patented, U.S. Pat. No. 11,103,507.
U.S. Appl. No. 16/870,384, filed May 8, 2020, Patented, U.S. Pat. No. 11,530,206.
U.S. Appl. No. 16/870,418, filed May 8, 2020, Patented, U.S. Pat. No. 11,518,758.
U.S. Appl. No. 16/902,989, filed Jun. 16, 2020, Patented, U.S. Pat. No. 11,590,134.
U.S. Appl. No. 16/991,644, filed Aug. 12, 2020, Pending, US 2022-0047573 A1.
U.S. Appl. No. 17/028,640, filed Sep. 22, 2020, Pending, U.S. Pat. No. 10,966,966.
U.S. Appl. No. 17/180,234, filed Feb. 19, 2021, Patented, U.S. Pat. No. 11,585,535.
U.S. Appl. No. 17/180,241, filed Feb. 19, 2021, Patented, U.S. Pat. No. 11,395,818.
U.S. Appl. No. 17/504,133, filed Oct. 18, 2021, Patented, U.S. Pat. No. 11,576,103.
U.S. Appl. No. 18/314,348, filed May 9, 2023, Patented, U.S. Pat. No. 11,801,237.
U.S. Appl. No. 17/358,137, filed Jun. 25, 2021, Patented, U.S. Pat. No. 11,679,110.
U.S. Appl. No. 17/583,977, filed Jan. 25, 2022, Patented, U.S. Pat. No. 11,436,390.
U.S. Appl. No. 17/583,985, filed Jan. 22, 2022, Patented, U.S. Pat. No. 11,344,536.
U.S. Appl. No. 17/727,307, filed Apr. 22, 2022, Patented, U.S. Pat. No. 11,534,432.
U.S. Appl. No. 17/735,820, filed May 3, 2022, Patented, U.S. Pat. No. 11,612,591.
U.S. Appl. No. 18/148,766, filed Dec. 30, 2022, Patented, U.S. Pat. No. 11,896,585.
U.S. Appl. No. 17/845,275, filed Jun. 21, 2022, Pending, US 2022-0370423 A1.
U.S. Appl. No. 17/845,278, filed Jun. 21, 2022, Pending, US 2022-0370424 A1.
U.S. Appl. No. 17/180,218, filed Feb. 19, 2021, Patented, U.S. Pat. No. 11,266,635.
U.S. Appl. No. 17/583,977, filed Jan. 25, 2022, Patented, U.S. Pat. No. 11,426,390.
U.S. Appl. No. 17/869,108, filed Jul. 20, 2022, Patented, U.S. Pat. No. 11,969,414.
U.S. Appl. No. 17/583,985, filed Jan. 25, 2022, Patented, U.S. Pat. No. 11,344,546.
U.S. Appl. No. 17/735,678, filed May 3, 2022, Patented, U.S. Pat. No. 11,529,336.
U.S. Appl. No. 17/735,682, filed May 3, 2022, Patented, U.S. Pat. No. 11,576,904.
U.S. Appl. No. 17/938,353, filed Oct. 6, 2022, Patented, U.S. Pat. No. 11,779,572.
U.S. Appl. No. 17/735,862, filed May 3, 2022, Patented, U.S. Pat. No. 11,433,056.
U.S. Appl. No. 18/091,743, filed Dec. 30, 2022, Patented, U.S. Pat. No. 11,813,251.
U.S. Appl. No. 18/140,942, filed Apr. 28, 2023, Pending, US 2023-0414614 A1.
U.S. Appl. No. 17/833,272, filed Jun. 6, 2022, Patented, U.S. Pat. No. 12,071,032.
U.S. Appl. No. 17/832,224, filed Jun. 3, 2022, Pending, US 2023-0047915 A1.
U.S. Appl. No. 18/078,269, filed Dec. 9, 2022, Pending, US 2023-0357179 A1.
U.S. Appl. No. 18/078,271, filed Dec. 9, 2022, Pending, US 2023-0257352 A1.
U.S. Appl. No. 18/073,721, filed Dec. 9, 2022, Pending, US 2024-0116877 A1.
U.S. Appl. No. 18/152,993, filed Jan. 11, 2023, Pending, US 2023-0338376 A1.
U.S. Appl. No. 18/464,519, filed Sep. 11, 2023, Pending, US 2024-0261270 A1.
U.S. Appl. No. 18/463,498, filed Sep. 8, 2023, Pending, US 2024-0197696 A1.
U.S. Appl. No. 18/490,188, filed Oct. 19, 2023, Patented, U.S. Pat. No. 11,911,370.
U.S. Appl. No. 18/490,197, filed Oct. 19, 2023, Patented, U.S. Pat. No. 11,918,564.
U.S. Appl. No. 18/512,447, filed Nov. 17, 2023, Pending.
U.S. Appl. No. 18/518,100, filed Nov. 22, 2023, Patented, U.S. Pat. No. 11,969,415.
U.S. Appl. No. 18/518,110, filed Nov. 22, 2023, Patented, U.S. Pat. No. 12,023,328.
U.S. Appl. No. 18/750,014, filed Jun. 21, 2024, Pending, US 2024-0342144 A1.
U.S. Appl. No. 18/758,007, filed Jun. 28, 2024, Pending, US 2024-0350466 A1.
U.S. Appl. No. 18/795,683, filed Aug. 6, 2024, Pending, U.S. Pat. No. 12,213,967.
U.S. Appl. No. 18/795,711, filed Aug. 6, 2024, Pending, U.S. Pat. No. 12,226,406.
U.S. Appl. No. 18/795,731, filed Aug. 6, 2024, Pending, U.S. Pat. No. 12,213,968.
U.S. Appl. No. 18/815,054, filed Aug. 26, 2024, Pending.
U.S. Appl. No. 18/985,885, filed Dec. 18, 2024, Pending.
U.S. Appl. No. 18/980,378, filed Dec. 13, 2024, Pending.
U.S. Appl. No. 18/971,800, filed Dec. 6, 2024, Pending.
U.S. Appl. No. 18/971,846, filed Dec. 6, 2024, Pending.
U.S. Appl. No. 18/980,426, filed Dec. 13, 2024, Pending.
U.S. Appl. No. 19/001,282, filed Dec. 9, 2024, Pending.
U.S. Appl. No. 19/079,010, filed Mar. 13, 2025, Pending.
U.S. Appl. No. 19/079,727, filed Mar. 14, 2025, Pending.
U.S. Appl. No. 19/079,965, filed Mar. 14, 2025, Pending.
U.S. Appl. No. 19/085,149, filed Mar. 20, 2025, Pending.
PCT/US2024/060067 International Search Report and Written Opinion mailed Apr. 10, 2025, 48 pages.
Khadka, P. et al., Pharmaceutical particle technologies: An approach to improve drug solubility, dissolution and bioavailability, Asian Journal of Pharmaceutical Sciences, 9(6): 304-316 (2014).
PCT/US2024/058998 International Search Report and Written Opinion mailed Jun. 2, 2025, 11 pages.
PCT/US2025/027042 International Search Report and Written Opinion mailed Jul. 23, 2025, 12 pages.

* cited by examiner

* = spinning sidebands

FORMULATIONS OF VIMSELTINIB

CROSS-REFERENCE

This application is a continuation of U.S. application Ser. No. 18/971,846 filed on Dec. 6, 2024, which claims priority to U.S. Provisional Application No. 63/607,697 filed Dec. 8, 2023, the contents of which are incorporated herein by reference in their entireties.

The present disclosure relates to pharmaceutically acceptable formulations comprising the compound represented by Formula (I), oral dosage forms comprising the compound represented by Formula (I), such as pharmaceutically acceptable capsules comprising the compound represented by Formula (I), and methods for their preparation and their use.

BACKGROUND

Colony-stimulating factor 1 receptor (CSF-1R) and its ligand, colony stimulating factor 1 (CSF-1) together form a lineage dependency for normal macrophage development and differentiation from monocytes. As such, tumor-associated macrophages (TAMs) are dependent on CSF-1R (also known as FMS) kinase activity for proliferation, and maintenance of their differentiated state and immunosuppressive phenotype. The role of TAMs in promoting an invasive and immunosuppressive tumor microenvironment is well established. TAMs mediate tumor growth, angiogenesis, invasiveness, metastasis, and immunosuppression through the secretion of and response to a variety of cytokines or other soluble factors. TAMs are educated by tumors to enable escape from immune surveillance by dampening a cytotoxic T cell immune response, thereby shielding the tumor from T cell eradication. For example, TAMs express PD-L1, a known immunosuppressive checkpoint that induces T cell anergy.

Several inhibitors targeting CSF-1R have advanced into the clinic as direct antitumor therapies and potential immunotherapies. Many of these drugs also inhibit the closely related Type III receptor tyrosine kinases KIT, PDGFRα/β and FLT3, which may limit their utility due to off-target toxicity. Antibodies targeting CSF-1R are much more specific yet result in >10,000-fold increases in plasma levels of CSF-1, the ligand for CSF-1R, due to blockade of CSF-1 clearance, among other drawbacks.

Tenosynovial giant cell tumor (TGCT) is a proliferative and inflammatory disease that includes entities formerly known as pigmented villonodular synovitis (PVNS), and giant cell tumor of the tendon sheath (GCTTS), intraarticular or extraarticular. It is a rare neoplasm of the joint or tendon sheath, with destructive proliferation of synovial like mononuclear cells, admixed with multinucleate giant cells, foam cells, siderophages and inflammatory cells. There are two types of TGCT: the local or nodular form (where the tumor involves the tendons that support the joint, or in one area of the joint) and the diffuse form (where the entire lining of the joint is involved). Treatment is surgical excision of the tumor. However, it is often difficult to perform a marginal excision for the diffuse form of TGCT resulting in a high recurrence rate. It can be characterized by overexpression of CSF-1.

Thus, there is a need for selective small-molecule CSF-1R inhibitors and formulations thereof, for example oral dosage formulations, that are useful in the treatment of disorders associated with the proliferation of TAMs including solid tumors of various cancers and treatment of mesenchymal tumors including TGCT and diffuse-type tenosynovial giant cell tumor (DTGCT).

Content uniformity is essential to maintain consistency within a production batch or between production batches. It is an important factor regarding the safety and efficacy of a drug. Content uniformity ensures that a patient receives a reliable dose of and exposure to the active substance, thereby enabling the patient to have a safe and efficacious use of the medicine. In view of these considerations, there is a need for formulations providing content uniformity.

SUMMARY

Described herein, in part, are pharmaceutically acceptable formulations comprising a compound represented by Formula (I):

Formula (I)

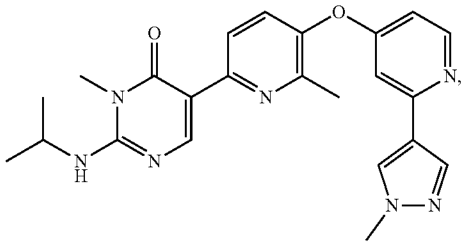

and one or more pharmaceutically acceptable excipients, wherein the compound is present in the pharmaceutically acceptable formulations as a free base, or a pharmaceutically acceptable salt of the compound, and wherein the free base or pharmaceutically acceptable salt is in anhydrous or hydrate form.

In some embodiments, provided herein are pharmaceutically acceptable unit formulations comprising a compound represented by Formula (I):

Formula (I)

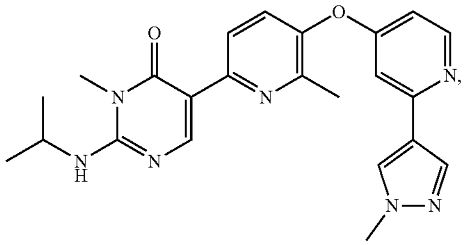

and one or more pharmaceutically acceptable excipients, wherein the compound is present in the pharmaceutically acceptable unit formulations as a free base, or a pharmaceutically acceptable salt of the compound, and wherein the free base or pharmaceutically acceptable salt is in anhydrous or hydrate form.

For example, in some embodiments, provided herein is a pharmaceutically acceptable unit formulation comprising: (a) about 1% by weight to about 70% by weight, based on the weight of the pharmaceutically acceptable unit formulation, of a compound of Formula (I), wherein the compound is present in the pharmaceutically acceptable unit formulation as a free base, or a pharmaceutically acceptable salt of the compound, and wherein the free base or pharmaceutically acceptable salt is in anhydrous or hydrate form, and one or more pharmaceutically acceptable excipients, wherein the one or more pharmaceutically acceptable excipients comprise: (b) about 20% by weight to about 97% by weight of one or more fillers based on the weight of the pharmaceutically acceptable unit formulation; (c) about 1% by weight to about 20% by weight of one or more disintegrants based on the weight of the pharmaceutically acceptable unit formulation; and (d) about 0.1% by weight to about 10% by weight of one or more lubricants based on the weight of the pharmaceutically acceptable unit formulation.

Also provided herein, in some embodiments, are oral dosage forms comprising a compound represented by Formula (I), and one or more pharmaceutically acceptable excipients, wherein the compound is present in the oral dosage forms as a free base, or a pharmaceutically acceptable salt of the compound, and wherein the free base or pharmaceutically acceptable salt is in anhydrous or hydrate form.

For example, in some embodiments, provided herein is an oral dosage form comprising: (a) about 1% by weight to about 70% by weight, based on the total weight of the oral dosage form, of a compound of Formula (I), wherein the compound is present in the oral dosage form as a free base, or a pharmaceutically acceptable salt of the compound, and wherein the free base or pharmaceutically acceptable salt is in anhydrous or hydrate form, and one or more pharmaceutically acceptable excipients, wherein the one or more pharmaceutically acceptable excipients comprise: (b) about 20% by weight to about 97% by weight of one or more fillers based on the total weight of the oral dosage form; (c) about 1% by weight to about 20% by weight of one or more disintegrants based on the total weight of the oral dosage form; and (d) about 0.1% by weight to about 10% by weight of one or more lubricants based on the total weight of the oral dosage form.

In some embodiments, provided herein are pharmaceutically acceptable capsules comprising a compound of Formula (I), and one or more pharmaceutically acceptable excipients, wherein the compound is present in the pharmaceutically acceptable capsules as a free base, or a pharmaceutically acceptable salt of the compound, and wherein the free base or pharmaceutically acceptable salt is in anhydrous or hydrate form.

For example, in some embodiments, provided herein is a pharmaceutically acceptable capsule comprising: (a) about 1% by weight to about 70% by weight, based on the total weight of the pharmaceutically acceptable capsule, of a compound of Formula (I), wherein the compound is present in the pharmaceutically acceptable capsule as a free base, a pharmaceutically acceptable salt of the compound, and wherein the free base or pharmaceutically acceptable salt is in anhydrous or hydrate form, and one or more pharmaceutically acceptable excipients, wherein the pharmaceutically acceptable excipients comprise: (b) about 20% by weight to about 97% by weight of one or more fillers based on the total weight of the pharmaceutically acceptable capsule; (c) about 1% by weight to about 20% by weight of one or more disintegrants based on the total weight of the pharmaceutically acceptable capsule; and (d) about 0.1% by weight to about 10% by weight of one or more lubricants based on the total weight of the pharmaceutically acceptable capsule.

Provided herein, in part, are methods of treating diseases and conditions including, but not limited to, a tenosynovial giant cell tumor (TGCT) including diffuse-type tenosynovial giant cell tumor (DTGCT) and localized tenosynovial giant cell tumor. Provided herein, in part, are methods of treating diseases and conditions including, but not limited to, graft versus host disease (GVHD) including chronic graft versus host disease (cGVHD) and acute graft versus host disease (aGVHD). Provided herein, in part, are methods of treating diseases and conditions including, but not limited to, a neurodegenerative diseases or conditions including Parkinson's disease (PD), Alzheimer's Disease (AD), frontotemporal dementia (FTD), amyotrophic lateral sclerosis (ALS), mild cognitive impairment, and Huntington's Disease (HD). Provided herein, in part, are methods of treating diseases and conditions including, but not limited to, solid tumors, acute myeloid leukemia (AML), relapsed/refractory acute myeloid leukemia (AML), relapsed acute myeloid leukemia (AML), refractory acute myeloid leukemia (AML), myelodysplastic syndrome, acute lymphocytic leukemia (ALL), chronic lymphocytic leukemia (CLL), pancreatic ductal adenocarcinoma (PDAC), ovarian cancer, non-small cell lung cancer (NSCLC), prostate cancer, osteosarcoma, breast cancer, colon cancer, and glioblastoma, wherein solid tumors include, but are not limited to, ovarian cancer, pancreatic cancer, prostate cancer, lung cancer, breast cancer, kidney cancer, liver cancer, cervical cancer, bone metastatic cancer, papillary thyroid cancer, non-small cell lung cancer, colon cancer, and gastrointestinal stromal tumors. Provided herein, in part, are methods of treating diseases and conditions including, but not limited to, tumors known to have expression of colony-stimulating factor 1 receptor (CSF-1R) or its ligands, colony stimulating factor-1 (CSF-1), or interleukin (IL)-34 (IL-34). Provided herein, in part, are methods of treating diseases and conditions including, but not limited to, metabolic diseases, rheumatoid arthritis, osteoarthritis, multiple sclerosis, autoimmune nephritis, lupus, Crohn's disease, asthma, chronic obstructive pulmonary diseases, osteoporosis, hypereosinophilic syndromes, mastocytosis, and histiocytosis.

DETAILED DESCRIPTION

Figure 1:
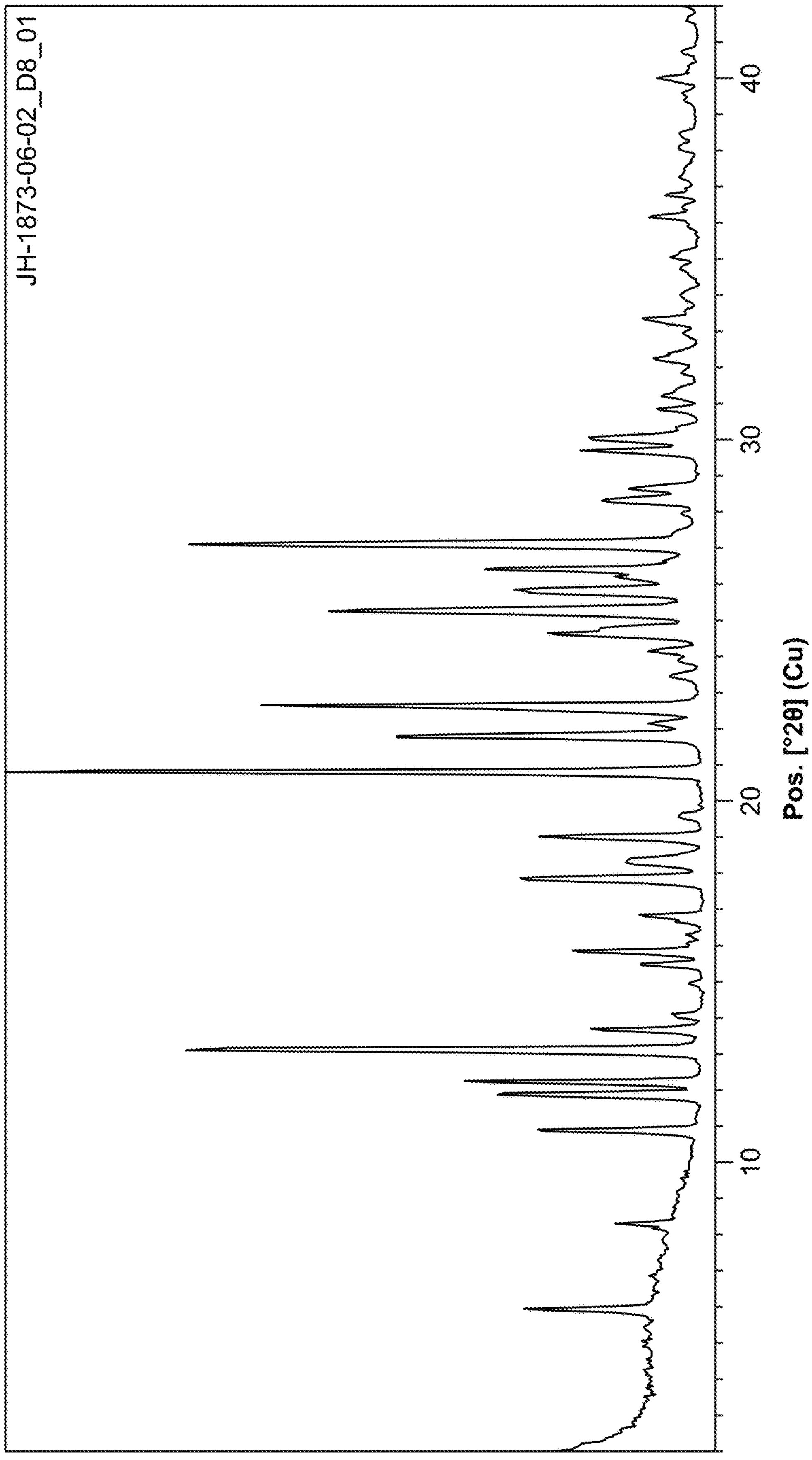
FIG. 1 shows an X-ray powder diffraction ("XRPD") pattern of the crystalline dihydrate form of the compound represented by Formula (I).

The features and other details of the disclosure will now be more particularly described. Certain terms employed in the specification, examples and appended claims are collected here. These definitions should be read in light of the remainder of the disclosure and as understood by a person of skill in the art. Unless defined otherwise, all technical and scientific terms used herein have the same meaning as commonly understood by a person of ordinary skill in the art.

Definitions

Terms used in the singular will also include the plural. For example, "a" means one or more unless indicated otherwise.

All ranges recited herein include the endpoints, including those that recite a range "between" two values. The terms "substantially" and "about" are to be construed as modifying a term or value such that it is not an absolute. This includes, at the very least, the degree of expected experimental variance, experimental error, technique variance, technique error and instrument variance, instrumental error for a given technique used to measure a value.

As used herein, "about" includes and describes the value or parameter per se. For example, "about x" includes and describes "x" per se. In some embodiments, the term "about" when used in association with a measurement, or used to modify a value, a unit, a constant, or a range of values, refers to variations of 10%. "About" in context of XRPD means ±0.2° at 2-theta for XRPD peaks.

As used herein, the term "adding" does not limit the order, method or how the materials being added are combined, unless indicated otherwise. For instance, "adding X to Y" may also describe "adding Y to X." Furthermore, "adding X and Y to Z" may also describe the various other combinations such as "adding X to Y and Z," "adding X and Z to Y," "adding Y to X and Z," "adding Y and Z to X," and "adding Z to X and Y."

As used herein, the term "excipient" refers to a substance that may be beneficial to include in a formulation with an active agent. The term "excipient" includes inert substances as well as functional excipients that may result in beneficial properties of the formulation. Exemplary excipients include but are not limited to polymers, glidants, sugars, lubricants, salts, buffers, fats, fillers, disintegrating agents, binders, surfactants, high surface area substrates, flavorants, carriers, matrix materials, diluents, and so forth.

As used herein, the terms "individual," "patient," or "subject" are used interchangeably and include any animal, including mammals, preferably mice, rats, other rodents, rabbits, dogs, cats, swine, cattle, sheep, horses, or primates, and most preferably humans. The compounds described herein can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like).

As used herein, the terms "pharmaceutically acceptable" or "pharmacologically acceptable" includes molecular entities and formulations that do not produce an adverse, allergic or other untoward reaction when administered to an animal, or a human, as appropriate. For human administration, preparations should meet sterility, pyrogenicity, and general safety and purity standards as required by FDA standards.

As used herein, the term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The formulations may also contain other active compounds providing supplemental, additional, or enhanced therapeutic functions.

As used herein, the term "formulation" as used herein refers to a composition comprising at least one compound as disclosed herein formulated together with one or more pharmaceutically acceptable carriers, excipients or diluents.

As used herein, the term "pharmaceutically acceptable salt(s)" refers to salts of acidic or basic groups that may be present in compounds used in the formulations. Compounds included in the present formulations that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including, but not limited to, malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts.

As used herein, the term "therapeutically effective amount" means the amount of the subject compound that will elicit the biological or medical response of a tissue, system or animal, (e.g., mammal or human) that is being sought by the researcher, veterinarian, medical doctor or other clinician. A compound described herein, e.g., the compound represented by Formula (I), is administered in therapeutically effective amounts to treat a condition, e.g., TGCT, GVHD, or neurodegenerative diseases. Alternatively, a therapeutically effective amount of a compound is the quantity required to achieve a desired therapeutic and/or prophylactic effect, such as an amount which results in the prevention of or a decrease in the symptoms associated with the condition.

As used herein and unless otherwise indicated, the terms "treat," "treating" and "treatment" refer to the alleviation of a disease or disorder and/or at least one of its attendant symptoms, and includes any effect, e.g., lessening, reducing, modulating, or eliminating, that results in the improvement of the condition, disease, disorder and the like.

As used herein and unless otherwise indicated, the terms "prevent," "preventing" and "prevention" refer to the inhibition of a symptom of a disease or disorder or the disease itself.

As used herein, the term "active agent" means a drug, medicament, pharmaceutical, therapeutic agent, for example, the compound represented by Formula (I), as described herein.

As used herein, "TAM" refers to tumor-associated macrophage.

As used herein, "TGCT" refers to tenosynovial giant cell tumor.

As used herein, "DTGCT" refers to diffuse or diffuse-type tenosynovial giant cell tumor.

As used herein, "GCTTS" refers to giant cell tumor of the tendon sheath.

As used herein, "PVNS" refers to pigmented villonodular synovitis.

As used herein, "GVHD" refers to graft versus host disease.

As used herein, "AD" refers to Alzheimer's Disease.

As used herein, "PD" refers to Parkinson's Disease.

As used herein, "HD" refers to Huntington's Disease.

As used herein, "FTD" refers to frontotemporal dementia.

As used herein, "ALS" refers to amyotrophic lateral sclerosis.

As used herein and unless otherwise indicated, the terms "polymorph" and "polymorphic form" refer to solid crystalline forms of a compound or complex. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability).

As used herein, a polymorphic form may be described by reference to patterns, spectra, or other graphical data as "substantially" shown or depicted in a figure, or by one or more data points. It will be appreciated that patterns, spectra, and other graphical data can be shifted in their positions, relative intensities, or other values due to a number of factors known to those of skill in the art. For example, in the crystallographic and powder X-ray diffraction arts, shifts in peak positions or the relative intensities of one or more peaks of a pattern can occur because of, without limitation, the equipment used, the sample preparation protocol, preferred packing and orientations, the radiation source, operator error, method and length of data collection, or the like. However, those of ordinary skill in the art will be able to compare the figures herein with patterns, etc. generated for an unknown form of, in this case, the compound represented by Formula (I), and confirm its identity with the forms disclosed herein. The same holds true for other techniques which may be reported herein.

The occurrence of different polymorphs is possible for some compounds. A single compound may give rise to a variety of solids having distinct physical properties, such as X-ray diffraction patterns, infrared absorption spectra, and NMR spectra. This variation in solid forms may be significant and may result in differences with respect to bioavailability, stability, and other differences for formulated pharmaceutical products. Because polymorphic forms can vary in their physical properties, regulatory authorities require that efforts shall be made to identify all polymorphic forms, e.g., crystalline, amorphous, solvate, hydrate, etc., of new drug substances.

While the existence and possible numbers of polymorphic forms for a given pharmaceutical compound cannot be predicted, different polymorphs can possess different properties such as stability, solubility, melting point, or compressibility. As a result, new forms of a pharmaceutically useful compound may provide an opportunity to improve its characteristics, and ultimately its performance. Further, discovery of additional polymorphic forms, including solvate polymorphs, may help in the identification of the polymorphic content of a batch of an active pharmaceutical ingredient. For example, in some cases, different polymorphs of the same drug can exhibit very different solubility and different dissolution rates.

Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

Polymorphs of a molecule can be obtained by a number of methods known in the art.

Such methods include, but are not limited to, melt recrystallization, melt cooling, solvent recrystallization, desolvation, rapid evaporation, rapid cooling, slow cooling, vapor diffusion and sublimation. Polymorphs can be detected, identified, classified and characterized using well-known techniques such as, but not limited to, differential scanning calorimetry (DSC), thermogravimetry (TGA), X-ray powder diffractometry (XRPD), single crystal X-ray diffractometry, vibrational spectroscopy, solution calorimetry, solid-state nuclear magnetic resonance (NMR), infrared (IR) spectroscopy, Raman spectroscopy, hot stage optical microscopy, scanning electron microscopy (SEM), electron crystallography and quantitative analysis, particle size analysis (PSA), surface area analysis, solubility, and rate of dissolution.

Different solid-state forms can be characterized by scattering techniques, e.g., x-ray powder diffraction (XRPD) pattern, by spectroscopic methods, e.g., infrared absorption fingerprint, Raman absorption fingerprint, nuclear magnetic resonance (e.g., NMR, solid-state NMR) spectroscopy (e.g., $^{1}H$, $^{13}C$, $^{19}F$), and by thermal techniques, e.g., differential scanning calorimetry (DSC) or differential thermal analysis (TGA). Described herein are polymorphs (solid-state forms) of the compound represented by Formula (I). These solid-state forms and their distinct crystal structures and physical properties are characterized by TGA, DSC (measurement of melting point and thermal behavior), XRPD, and NMR such as proton NMR spectrum ($^{1}H$ NMR) and solid-state NMR spectrum (e.g., $^{13}C$ ssNMR).

As used herein, the compound represented by Formula (I) is 2-(isopropylamino)-3-methyl-5-(6-methyl-5-((2-(1-methyl-1H-pyrazol-4-yl)pyridin-4-yl)oxy)pyridin-2-yl)pyrimidin-4(3H)-one, and is also referred to herein as vimseltinib.

As used herein, the dihydrate form (e.g., crystalline dihydrate form) of the compound represented by Formula (I) is

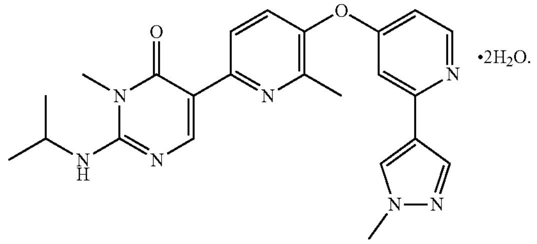 [SMILES: Cc1nc(-c2cnc(NC(C)C)n(C)c2=O)ccc1Oc1ccnc(-c2cnn(C)c2)c1]

As used herein to refer to the spectra or data presented in graphical form (e.g., XRPD, IR, Raman and NMR spectra), and unless otherwise indicated, the term "peak" refers to a peak or other special feature that one skilled in the art would recognize as not attributable to background noise.

Generally, a diffraction angle (2θ, "2 theta") in X-ray powder diffractometry may have a variation in the range of ±0.2°. Therefore, the aforementioned diffraction angle values should be understood as including values in the range of about ±0.2°. Accordingly, the solid-state forms described here includes not only crystals whose peak diffraction angles in powder X-ray diffractometry completely coincide with each other, but also crystals whose peak diffraction angles coincide with each other with an error of about ±0.0.2°. Therefore, in the present specification, the phrase "having a diffraction peak at a diffraction angle (2θ±0.2°) of 7.9°" means "having a diffraction peak at a diffraction angle (2θ) of 7.7° to 8.1°." Although the intensities of peaks in the x-ray powder diffraction patterns of different batches of a compound may vary slightly, the peak locations are characteristic for a specific polymorphic form. Alternatively, the term "about" means within an acceptable standard error of the mean, when considered by one of ordinary skill in the art. The relative intensities of the XRPD peaks can vary depending on the sample preparation technique, crystal size distribution, various filters used, the sample mounting procedure, and the particular instrument employed. Moreover, instrument variation and other factors can affect the 2-theta values. Therefore, the term "substantially" in the context of XRPD is meant to encompass that peak assignments can vary by plus or minus about 0.2 degree. Moreover, new peaks may be observed, or existing peaks may disappear, depending on the type of the machine or the settings (for example, whether a Ni filter is used or not).

In general, provided herein are solid-state forms of the compound represented by Formula (I) that are substantially free of any other solid-state forms whether as individual forms or mixtures of other forms, unless indicated otherwise. For example, the dihydrate form of the compound represented by Formula (I) will be substantially free of other forms of compound of formula (I) which may include the crystalline anhydrous form or other solid-state forms or mixtures thereof. As used herein, "substantially free of any solid-state forms" means that the solid-state form of the compound represented by Formula (I) contains about 20% or less, about 10% or less, about 5% or less, about 2% or less, or about 1% or less, of any other solid-state form of the compound represented by Formula (I) as measured, for example, by XRPD. In some embodiments, the solid-state form of the compound represented by Formula (I) contains less than about 20%, less than about 10%, less than about 5%, less than about 4%, less than about 3%, less than about 2%, or less than about 1% of any other solid-state forms of the compound represented by Formula (I) as measured, for example, by XRPD. Thus, a solid-state form of the compound represented by Formula (I) described herein as substantially free of any other solid-state forms would be understood to contain greater than 80% (w/w), greater than 90% (w/w), greater than 95% (w/w), greater than 98% (w/w), or greater than 99% (w/w) of the said solid-state forms of the compound represented by Formula (I). Accordingly, in some embodiments, the described solid-state forms of the compound represented by Formula (I) may contain from 1% to 20% (w/w), from 5% to 20% (w/w), or from 5% to 10% (w/w) of one or more other solid-state forms of the compound represented by Formula (I).

As used herein, "substantially free" means that the solid-state forms of the present disclosure contain 20% (w/w) or less of other polymorphs, or, alternatively, of a specified polymorph of the compound represented by Formula (I). According to some embodiments, the solid-state forms of the present disclosure contain 10% (w/w) or less, 5% (w/w) or less, 2% (w/w), 1% (w/w) or less of other polymorphs, or specified polymorphs of the compound represented by Formula (I). In other embodiments, solid-state forms of the compound represented by Formula (I) of the present disclosure contain from 1% to 20% (w/w), from 5% to 20% (w/w), or from 5% to 10% (w/w) of other solid-state forms, or of a specified polymorph of the compound represented by Formula (I).

As used herein and unless otherwise indicated, the term "substantially pure" when used to describe a polymorph of a compound means a solid form of the compound that comprises that polymorph and is substantially free of other polymorphs of the compound. For example, the dihydrate form of the compound represented by Formula (I) will be substantially pure of other forms of compound of formula (I) which may include the crystalline anhydrous form or other solid-state forms or mixtures thereof. A representative substantially pure polymorph comprises greater than about 80% by weight of one polymorphic form of the compound and less than about 20% by weight of other polymorphic forms of the compound. In some embodiments, a representative substantially pure polymorph comprises greater than about 90% by weight of one polymorphic form of the compound and less than about 10% by weight of the other polymorphic forms of the compound. In some embodiments, a representative substantially pure polymorph comprises greater than about 95% by weight of one polymorphic form of the compound and less than about 5% by weight of the other polymorphic forms of the compound. In some embodiments, a representative substantially pure polymorph comprises greater than about 97% by weight of one polymorphic form of the compound and less than about 3% by weight of the other polymorphic forms of the compound. In some embodiments, a representative substantially pure polymorph comprises greater than about 98% by weight of one polymorphic form of the compound and less than about 2% by weight of the other polymorphic forms of the compound. In some embodiments, a representative substantially pure polymorph comprises greater than about 99% by weight of one polymorphic form of the compound and less than about 1% by weight of the other polymorphic forms of the compound.

The content of solid-state forms is typically measured by any suitable method appreciated by a skilled person in the art, for example XRPD, solid-state NMR, IR, Raman, or DSC.

Crystalline and partially crystalline solid forms may be prepared by a variety of methods including, but not limited to, for example, crystallization or recrystallization from a suitable solvent mixture; sublimation; growth from a melt; solid-state transformation from another phase; crystallization from a supercritical fluid; antisolvent addition; slurrying at various temperatures (e.g., at room temperature, at 10° C., at 15° C., at 40° C., at 50° C., at 70° C.); solid vapor diffusion; liquid vapor diffusion; evaporation; slow cooling, polymer induced crystallization; milling; spray freezing; spray congealing; lyophilization; and humidity induced crystallization. Techniques for crystallization or recrystallization of crystalline and partially crystalline solid forms of a solvent mixture include, but are not limited to, for example, evaporation of the solvent; decreasing the temperature of the solvent mixture; crystal seeding of a supersaturated solvent mixture of the compound and/or salt thereof; crystal seeding a supersaturated solvent mixture of the compound and/or a salt from thereof; freeze drying the solvent mixture; temperature cycling; and adding anti-solvents (countersolvents) to the solvent mixture. As used herein, the term "anti-solvent" refers to a liquid that, when combined with a solution of the compound represented by Formula (I), reduces solubility of the compound represented by Formula (I) in the solution, causing crystallization or precipitation in some instances spontaneously, and in other instances with additional steps, such as seeding, cooling, scratching and/or concentrating. Crystals of drugs, including polymorphs, methods of preparation, and characterization of drug crystals, are discussed in Solid-State Chemistry of Drugs, S. R. Byrn, R. R. Pfeiffer, and J. G. Stowell, $2^{nd}$ Edition, SSCI, West Lafayette, Ind. (1999). In a crystallization technique in which solvent is employed, the solvent(s) are typically chosen based on one or more factors including, but not limited to, for example, solubility of the compound; crystallization technique utilized; and vapor pressure of the solvent. Combinations of solvents may be employed. For example, the compound may be solubilized in a first solvent to afford a solution to which antisolvent is then added to decrease the solubility of the compound represented by Formula (I) in the solution and precipitate the formation of crystals. An antisolvent is a solvent in which a compound has low solubility. In one method that can be used in preparing crystals, a compound can be suspended and/or stirred in a suitable solvent to afford a slurry, which may be heated to promote dissolution. A cooled crystallization mixture may be filtered under vacuum and the isolated solid product washed with a suitable solvent, such as, for example, cold recrystallization solvent. After being washed, the product may be dried under a nitrogen purge to afford the desired solid form. After being washed, the product may be dried under vacuum to afford the desired solid form.

As used herein, the term "based on the total weight of the pharmaceutically acceptable capsule" refers to the total weight of the compound of Formula (I), as a free base or a pharmaceutically acceptable salt thereof, or wherein the free base or a pharmaceutically acceptable salt thereof is in anhydrous or hydrate form (e.g., a crystalline dihydrate or crystalline anhydrous form of the compound of Formula (I)), and one or more pharmaceutically acceptable excipients (e.g., one or more fillers, and optionally one or more disintegrants and/or one or more lubricants), and does not include the weight of the empty capsule shell.

Formulations

The present disclosure encompasses formulations comprising a compound represented by Formula (I)

Formula (I)

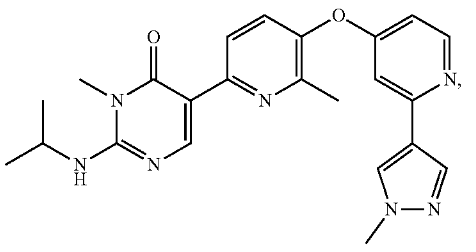

and one or more pharmaceutically acceptable excipients, wherein the compound is present in the pharmaceutically acceptable formulation as a free base, or a pharmaceutically acceptable salt of the compound.

The formulations provided herein can contain one or more fillers, which are added, for example, to increase the bulk weight of the blend resulting in a practical size for encapsulation or compression. Fillers that may be used include, but are not limited to, calcium phosphate, dicalcium phosphate, dicalcium phosphate dihydrate, calcium sulfate, calcium sulfate dihydrate, starch, calcium carbonate, magnesium carbonate, magnesium oxide, kaolin (natural hydrated aluminum silicate), sodium chloride, partially gelatinized starch, anhydrous lactose, lactose monohydrate, lactose dihydrate, trehalose dihydrate, spray dried lactose, sucrose, dextrose, dextrates, dextrin, cellulose, microcrystalline cellulose, silicified microcrystalline cellulose, powdered cellulose, partially depolymerized cellulose, mannitol, granulated mannitol, spray dried mannitol, maltodextrin, maltitol, confectioner's sugar, compressible sugar, sorbitol, starch and talc.

A disintegrant may be present in an amount necessary to expedite dissolution (e.g., increase the rate of tablet or capsule disintegration). The term "disintegrant" as used herein refers to an excipient which can oppose the physical forces of particle bonding in a tablet or capsule when the oral formulation is placed in an aqueous environment. Disintegrants include, but are not limited to, sodium starch glycolate, pregelatinized starch, clay, cellulose, alginic acid, alginate gum, polyvinylpyrrolidone, cross-linked polyvinylpyrrolidone, cross-linked calcium carboxymethylcellulose, cross-linked sodium carboxymethylcellulose, sodium croscarmellose, sodium carmellose, low substituted hydroxypropyl cellulose, low substituted hydroxypropyl cellulose sodium, guar gum, magnesium aluminum silicate, polacrilin potassium, powdered cellulose, sodium alginate and soy polysaccharide.

The formulations can also include a lubricant. The term "lubricant" as used herein is typically added to prevent the tablet or capsule materials from sticking to punches or pins, minimize friction during tablet compression or encapsulation, and to allow for removal of the compressed tablet from the die or improve flowability of blends in capsules for improved processing properties. Examples of lubricants include, but are not limited to, colloidal silica, magnesium trisilicate, talc, magnesium carbonate, magnesium oxide, glyceryl behaptate, mono, di and tri glyceryl behenate, bees wax, behenoyl polyoxyl-8 glycerides, hydrogenated vegetable oil, polyethylene glycol, ethylene oxide polymer, copolymer comprising poly(ethylene oxide) and poly(propylene oxide) (such as poloxomer 188), copolymer comprising polypropylene glycol and polyethylene glycol (such as poloxomer 407), sodium lauryl sulfate, magnesium stearate, aluminum stearate, calcium stearate, sodium stearyl fumarate, stearic acid, magnesium lauryl stearate, mixtures of magnesium stearate with sodium lauryl sulfate.

Flavoring agents and flavor enhancers may also be added for the dosage form to be more palatable to the patient. Common flavoring agents and flavor enhancers for pharmaceutical products that can be included in the formulation of the present disclosure include maltol, vanillin, ethyl vanillin, menthol, citric acid, fumaric acid, ethyl maltol, and tartaric acid.

Solid and liquid formulations can also be dyed using any pharmaceutically acceptable colorant to improve their appearance and/or facilitate patient identification of the product and unit dosage level.

In liquid formulations of the present disclosure, the active ingredient and any other solid excipients may be dissolved or suspended in a liquid carrier such as water, vegetable oil, alcohol, polyethylene glycol, propylene glycol, or glycerin.

Liquid formulations can contain emulsifying agents to disperse uniformly throughout the formulation an active ingredient or other excipient that is not soluble in the liquid carrier. Emulsifying agents that can be useful in liquid formulations of the present disclosure include, for example, gelatin, egg yolk, casein, cholesterol, acacia, tragacanth, chondrus, pectin, methyl cellulose, carbomer, cetostearyl alcohol, and cetyl alcohol.

Liquid formulations of the present disclosure can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as sorbitol, saccharin, sodium saccharin, sucrose, aspartame, fructose, mannitol, and invert sugar can be added to improve the taste.

Preservatives and chelating agents such as alcohol, sodium benzoate, butylated hydroxyl toluene, butylated hydroxyanisole, and ethylenediamine tetraacetic acid can be added at levels safe for ingestion to improve storage stability.

According to the present disclosure, a liquid formulation can also contain a buffer such as gluconic acid, lactic acid, citric acid, or acetic acid, sodium gluconate, sodium lactate, sodium citrate, or sodium acetate. Selection of excipients and the amounts used can be readily determined by the formulation scientist based upon experience and consideration of standard procedures and reference works in the field.

The solid formulations of the present disclosure include powders, granulates, aggregates, and compacted formulations. The dosages include dosages suitable for oral, buccal, rectal, parenteral (including subcutaneous, intramuscular, and intravenous), inhalant, and ophthalmic administration. Although the most suitable administration in any given case will depend on the nature and severity of the condition being treated, the most preferred route of the present disclosure is oral.

Diluents increase the bulk of a solid formulation and can make a pharmaceutical dosage form containing the formulation easier for the patient and caregiver to handle. Diluents for solid formulations include, for example, microcrystalline cellulose (e.g., Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., Eudragit®), potassium chloride, powdered cellulose, sodium chloride, sorbitol, and talc.

Solid formulations that are compacted into a dosage form, such as a tablet, can include excipients whose functions include helping to bind the active ingredient and other excipients together after compression. Binders for solid formulations include acacia, alginic acid, carbomer (e.g., Carbopol), carboxymethylcellulose sodium, dextrin, ethyl cellulose, gelatin, guar gum, hydrogenated vegetable oil, hydroxyethyl cellulose, hydroxypropyl cellulose (e.g., Klucel®), hydroxypropyl methyl cellulose (e.g., Methocel®), liquid glucose, magnesium aluminum silicate, maltodextrin, methylcellulose, polymethacrylates, povidone (e.g., Kollidon®, Plasdone®), pregelatinized starch, sodium alginate, and starch.

The dissolution rate of a compacted solid formulation in the patient's stomach can be increased by the addition of a disintegrant to the formulation. Disintegrants include alginic acid, carboxymethylcellulose calcium, carboxymethylcellulose sodium (e.g., Ac-Di-Sol®, Primellose®), colloidal silicon dioxide, croscarmellose sodium, Crospovidone (e.g., Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g., Explotab®), and starch.

Glidants can be added to improve the flowability of a non-compacted solid formulation and to improve the accuracy of dosing. Excipients that can function as glidants include colloidal silicon dioxide, magnesium trisilicate, powdered cellulose, starch, talc, and tribasic calcium phosphate.

When a dosage form such as a tablet is made by the compaction of a powdered formulation, the formulation is subjected to pressure from a punch and dye. Some excipients and active ingredients tend to adhere to the surfaces of the punch and dye, which can cause the product to have pitting and other surface irregularities. A lubricant can be added to the formulation to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

A formulation for tableting or capsule filling can be prepared by wet granulation. In wet granulation, some or all of the active ingredients and excipients in powder form are blended and then further mixed in the presence of a liquid, typically water, that causes the powders to clump into granules. The granulate is screened and/or milled, dried, and then screened and/or milled to the desired particle size. The granulate can then be tableted, or other excipients can be added prior to tableting, such as a glidant and/or a lubricant.

A tableting formulation can be prepared conventionally by dry blending. For example, the blended formulation of the actives and excipients can be compacted into a slug or a sheet and then comminuted into compacted granules. The compacted granules can subsequently be compressed into a tablet.

As an alternative to dry granulation, a blended formulation can be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

Dosage forms include solid dosage forms like tablets, powders, capsules, suppositories, sachets, troches, and lozenges, as well as liquid syrups, suspensions, and elixirs.

The dosage form of the present disclosure can be a capsule containing the formulation, such as a powdered or granulated solid formulation of the disclosure, within either a hard or soft shell. The shell can be made from gelatin and optionally contain a plasticizer such as glycerin and sorbitol, and an opacifying agent or colorant.

In further embodiments, a pharmaceutical formulation of the compound represented by Formula (I) is formulated for administration to a mammal, such as a human. The compound represented by Formula (I) can be formulated, for example, as a viscous liquid solution or suspension, such as a clear solution, for injection. The formulation can contain one or more solvents. A suitable solvent can be selected by considering the solvent's physical and chemical stability at various pH levels, viscosity (which would allow for syringe ability), fluidity, boiling point, miscibility, and purity. Suitable solvents include alcohol USP (United States Pharmacopeia), benzyl alcohol NF, benzyl benzoate USP, and Castor oil USP. Additional substances can be added to the formulation such as buffers, solubilizers, and antioxidants, among others. Ansel et al, Pharmaceutical Dosage Forms and Drug Delivery Systems, $7^{th}$ ed.

In some embodiments, provided herein are pharmaceutically acceptable formulations comprising a compound of Formula (I):

Formula (I)

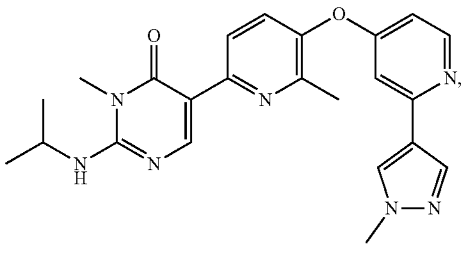

and one or more pharmaceutically acceptable excipients, wherein the compound is present in the pharmaceutically acceptable formulations as a free base, or a pharmaceutically acceptable salt of the compound, and wherein the free base or pharmaceutically acceptable salt is in anhydrous or hydrate form.

In some embodiments, the compound of Formula (I) is present in the pharmaceutically acceptable formulation as a hydrate form (the compound of Formula (I)·$nH_2O$). For example, the hydrate form is a hemihydrate form, a monohydrate form, a sesquihydrate form, a dihydrate form, a trihydrate form, a tetrahydrate form, a pentahydrate form, a hexahydrate form, a heptahydrate form, an octahydrate form, a nonahydrate form, or a decahydrate form. In some embodiments, the hydrate form is a hemihydrate form, a monohydrate form, a sesquihydrate form, a dihydrate form, a trihydrate form, or a tetrahydrate form. In some embodiments, the hydrate form is a hemihydrate form. In some embodiments, the hydrate form is a monohydrate form. In some embodiments, the hydrate form is a dihydrate form. In some embodiments, the compound of Formula (I) is present in the pharmaceutically acceptable formulation as a dihydrate form. In some embodiments, the compound of Formula (I) is present in the pharmaceutically acceptable formulation as an anhydrous form.

In some embodiments, the one or more pharmaceutically acceptable excipients is a filler. For example, the one or more pharmaceutically acceptable excipients is lactose, such as lactose monohydrate.

In some embodiments, the pharmaceutically acceptable formulations further comprise one or more disintegrants, one or more lubricants, or a combination thereof. For example, in some embodiments, the pharmaceutically acceptable formulations further comprise one or more disintegrants. In some embodiments, the pharmaceutically acceptable formulations further comprise one or more lubricants.

In some embodiments, provided herein are pharmaceutically acceptable unit formulations comprising a compound of Formula (I):

Formula (I)

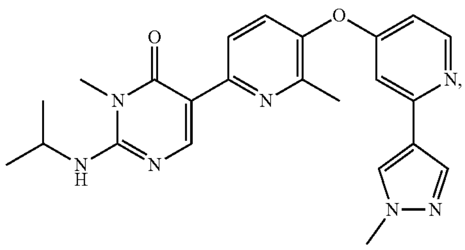

and one or more pharmaceutically acceptable excipients, wherein the compound is present in the pharmaceutically acceptable unit formulations as a free base, or a pharmaceutically acceptable salt of the compound, and wherein the free base or pharmaceutically acceptable salt is in anhydrous or hydrate form.

In some embodiments, the compound of Formula (I) is present in the pharmaceutically acceptable unit formulation as a hydrate form (the compound of Formula (I)·$nH_2O$). For example, the hydrate form is a hemihydrate form, a monohydrate form, a sesquihydrate form, a dihydrate form, a trihydrate form, a tetrahydrate form, a pentahydrate form, a hexahydrate form, a heptahydrate form, an octahydrate form, a nonahydrate form, or a decahydrate form. In some embodiments, the hydrate form is a hemihydrate form, a monohydrate form, a sesquihydrate form, a dihydrate form, a trihydrate form, or a tetrahydrate form. In some embodiments, the hydrate form is a hemihydrate form. In some embodiments, the hydrate form is a monohydrate form. In some embodiments, the hydrate form is a dihydrate form. In some embodiments, the compound of Formula (I) is present in the pharmaceutically acceptable unit formulation as a dihydrate form. In some embodiments, the compound of Formula (I) is present in the pharmaceutically acceptable unit formulation as an anhydrous form.

In some embodiments, the one or more pharmaceutically acceptable excipients is a filler. For example, the one or more pharmaceutically acceptable excipients is lactose, such as lactose monohydrate.

In some embodiments, the pharmaceutically acceptable unit formulations further comprise one or more disintegrants, one or more lubricants, or a combination thereof. For example, in some embodiments, the pharmaceutically acceptable unit formulations further comprise one or more disintegrants. In some embodiments, the pharmaceutically acceptable unit formulations further comprise one or more lubricants.

Also provided herein, in some embodiments, is a pharmaceutically acceptable unit formulation comprising:

(a) about 1% by weight to about 70% by weight, based on the weight of the pharmaceutically acceptable unit formulation, of a compound of Formula (I):

Formula (I)

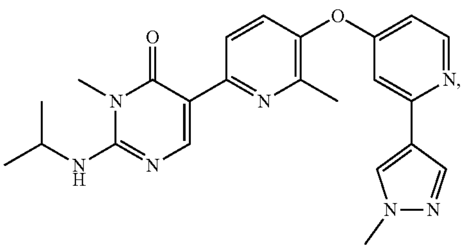

wherein the compound is present in the pharmaceutically acceptable unit formulation as a free base, or a pharmaceutically acceptable salt of the compound, and wherein the free base or pharmaceutically acceptable salt is in anhydrous or hydrate form, and one or more pharmaceutically acceptable excipients, wherein the one or more pharmaceutically acceptable excipients comprise:

(b) about 20% by weight to about 97% by weight of one or more fillers based on the weight of the pharmaceutically acceptable unit formulation;
(c) about 1% by weight to about 20% by weight of one or more disintegrants based on the weight of the pharmaceutically acceptable unit formulation; and
(d) about 0.1% by weight to about 10% by weight of one or more lubricants based on the weight of the pharmaceutically acceptable unit formulation.

Also provided herein, in some embodiments, is a pharmaceutically acceptable unit formulation comprising:

(a) about 10% by weight to about 30% by weight of the compound of Formula (I) based on the weight of the pharmaceutically acceptable unit formulation;
(b) about 70% by weight to about 90% by weight of one or more fillers based on the weight of the pharmaceutically acceptable unit formulation;
(c) about 1% by weight to about 10% by weight of one or more disintegrants based on the weight of the pharmaceutically acceptable unit formulation; and
(d) about 0.1% by weight to about 3% by weight of one or more lubricants based on the weight of the pharmaceutically acceptable unit formulation.

Also provided herein, in some embodiments, is a pharmaceutically acceptable unit formulation consisting essentially of:

(a) about 1% by weight to about 70% by weight, based on the weight of the pharmaceutically acceptable unit formulation, of a compound of Formula (I):

Formula (I)

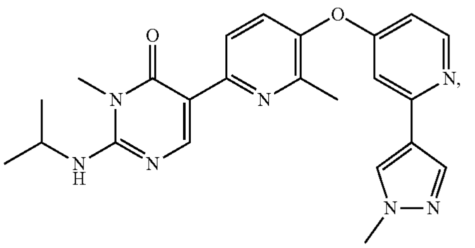

wherein the compound is present in the pharmaceutically acceptable unit formulation as a free base, or a pharmaceutically acceptable salt of the compound, and wherein the free base or pharmaceutically acceptable salt is in anhydrous or hydrate form, and one or more pharmaceutically acceptable excipients, wherein the one or more pharmaceutically acceptable excipients comprise:

(b) about 20% by weight to about 97% by weight of one or more fillers based on the weight of the pharmaceutically acceptable unit formulation;
(c) about 1% by weight to about 20% by weight of one or more disintegrants based on the weight of the pharmaceutically acceptable unit formulation; and
(d) about 0.1% by weight to about 10% by weight of one or more lubricants based on the weight of the pharmaceutically acceptable unit formulation.

Also provided herein, in some embodiments, is a pharmaceutically acceptable unit formulation consisting essentially of:

(a) about 1% by weight to about 30% by weight of a compound of Formula (I) based on the weight of the pharmaceutically acceptable unit formulation;
(b) about 20% by weight to about 90% by weight of one or more fillers based on the weight of the pharmaceutically acceptable unit formulation;
(c) about 1% by weight to about 20% by weight of one or more disintegrants based on the weight of the pharmaceutically acceptable unit formulation; and
(d) about 0.1% by weight to about 10% by weight of one or more lubricants based on the weight of the pharmaceutically acceptable unit formulation.

In some embodiments, the pharmaceutically acceptable unit formulation comprises about 1% by weight to about 60% by weight, based on the weight of the pharmaceutically acceptable unit formulation, of a compound of Formula (I), wherein the compound is present in the pharmaceutically acceptable formulation as a free base, or a pharmaceutically acceptable salt of the compound and wherein the free base or pharmaceutically acceptable salt is in anhydrous or hydrate form. In some embodiments, the pharmaceutically acceptable unit formulation comprises about 1% by weight to about 50% by weight, based on the weight of the pharmaceutically acceptable unit formulation, of a compound of Formula (I), wherein the compound is present in the pharmaceutically acceptable formulation as a free base, or a pharmaceutically acceptable salt of the compound and wherein the free base or pharmaceutically acceptable salt is in anhydrous or hydrate form. In some embodiments, the pharmaceutically acceptable unit formulation comprises about 1% by weight to about 40% by weight, based on the weight of the pharmaceutically acceptable unit formulation, of a compound of Formula (I), wherein the compound is present in the pharmaceutically acceptable formulation as a free base, or a pharmaceutically acceptable salt of the compound and wherein the free base or pharmaceutically acceptable salt is in anhydrous or hydrate form. In some embodiments, the pharmaceutically acceptable unit formulation comprises about 1% by weight to about 30% by weight, based on the weight of the pharmaceutically acceptable unit formulation, of a compound of Formula (I), wherein the compound is present in the pharmaceutically acceptable formulation as a free base, or a pharmaceutically acceptable salt of the compound and wherein the free base or pharmaceutically acceptable salt is in anhydrous or hydrate form. In some embodiments, the pharmaceutically acceptable unit formulation comprises about 1% by weight to about 20% by weight, based on the weight of the pharmaceutically acceptable unit formulation, of a compound of Formula (I), wherein the compound is present in the pharmaceutically acceptable formulation as a free base, or a pharmaceutically acceptable salt of the compound and wherein the free base or pharmaceutically acceptable salt is in anhydrous or hydrate form.

In some embodiments, the pharmaceutically acceptable unit formulation consists essentially of about 1% by weight to about 60% by weight, based on the weight of the pharmaceutically acceptable unit formulation, of a compound of Formula (I), wherein the compound is present in the pharmaceutically acceptable formulation as a free base, or a pharmaceutically acceptable salt of the compound and wherein the free base or pharmaceutically acceptable salt is in anhydrous or hydrate form. In some embodiments, the pharmaceutically acceptable unit formulation consists essentially of about 1% by weight to about 50% by weight, based on the weight of the pharmaceutically acceptable unit formulation, of a compound of Formula (I), wherein the compound is present in the pharmaceutically acceptable formulation as a free base, or a pharmaceutically acceptable salt of the compound and wherein the free base or pharmaceutically acceptable salt is in anhydrous or hydrate form. In some embodiments, the pharmaceutically acceptable unit formulation consists essentially of about 1% by weight to about 40% by weight, based on the weight of the pharmaceutically acceptable unit formulation, of a compound of Formula (I), wherein the compound is present in the pharmaceutically acceptable formulation as a free base, or a pharmaceutically acceptable salt of the compound and wherein the free base or pharmaceutically acceptable salt is in anhydrous or hydrate form. In some embodiments, the pharmaceutically acceptable unit formulation consists essentially of about 1% by weight to about 30% by weight, based on the weight of the pharmaceutically acceptable unit formulation, of a compound of Formula (I), wherein the compound is present in the pharmaceutically acceptable formulation as a free base, or a pharmaceutically acceptable salt of the compound and wherein the free base or pharmaceutically acceptable salt is in anhydrous or hydrate form. In some embodiments, the pharmaceutically acceptable unit formulation consists essentially of about 1% by weight to about 20% by weight, based on the weight of the pharmaceutically acceptable unit formulation, of a compound of Formula (I), wherein the compound is present in the pharmaceutically acceptable formulation as a free base, or a pharmaceutically acceptable salt of the compound and wherein the free base or pharmaceutically acceptable salt is in anhydrous or hydrate form.

In some embodiments, the pharmaceutically acceptable unit formulation comprises about 1% by weight to about 70% by weight of the compound of Formula (I) based on the weight of the pharmaceutically acceptable unit formulation. In some embodiments, the pharmaceutically acceptable unit formulation comprises about 1% by weight to about 65% by weight of the compound of Formula (I) based on the weight of the pharmaceutically acceptable unit formulation. In some embodiments, the pharmaceutically acceptable unit formulation comprises about 1% by weight to about 60% by weight of the compound of Formula (I) based on the weight of the pharmaceutically acceptable unit formulation. In some embodiments, the pharmaceutically acceptable unit formulation comprises about 1% by weight to about 55% by weight of the compound of Formula (I) based on the weight of the pharmaceutically acceptable unit formulation. In some embodiments, the pharmaceutically acceptable unit formulation comprises about 1% by weight to about 50% by weight of the compound of Formula (I) based on the weight of the pharmaceutically acceptable unit formulation. In some embodiments, the pharmaceutically acceptable unit formulation comprises about 1% by weight to about 45% by weight of the compound of Formula (I) based on the weight of the pharmaceutically acceptable unit formulation. In some embodiments, the pharmaceutically acceptable unit formulation comprises about 1% by weight to about 40% by weight of the compound of Formula (I) based on the weight of the pharmaceutically acceptable unit formulation. In some embodiments, the pharmaceutically acceptable unit formulation comprises about 1% by weight to about 35% by weight of the compound of Formula (I) based on the weight of the pharmaceutically acceptable unit formulation. In some embodiments, the pharmaceutically acceptable unit formulation comprises about 1% by weight to about 30% by weight of the compound of Formula (I) based on the weight of the pharmaceutically acceptable unit formulation. In some embodiments, the pharmaceutically acceptable unit formulation comprises about 1% by weight to about 25% by weight of the compound of Formula (I) based on the weight of the pharmaceutically acceptable unit formulation. In some embodiments, the pharmaceutically acceptable unit formulation comprises about 1% by weight to about 20% by weight of the compound of Formula (I) based on the weight of the pharmaceutically acceptable unit formulation. In some embodiments, the pharmaceutically acceptable unit formulation comprises about 1% by weight to about 15% by weight of the compound of Formula (I) based on the weight of the pharmaceutically acceptable unit formulation. In some embodiments, the pharmaceutically acceptable unit formulation comprises about 1% by weight to about 10% by weight of the compound of Formula (I) based on the weight of the pharmaceutically acceptable unit formulation.

In some embodiments, the pharmaceutically acceptable unit formulation consists essentially of about 1% by weight to about 70% by weight of the compound of Formula (I) based on the weight of the pharmaceutically acceptable unit formulation. In some embodiments, the pharmaceutically acceptable unit formulation consists essentially of about 1% by weight to about 65% by weight of the compound of Formula (I) based on the weight of the pharmaceutically acceptable unit formulation. In some embodiments, the pharmaceutically acceptable unit formulation consists essentially of about 1% by weight to about 60% by weight of the compound of Formula (I) based on the weight of the pharmaceutically acceptable unit formulation. In some embodiments, the pharmaceutically acceptable unit formulation consists essentially of about 1% by weight to about 55% by weight of the compound of Formula (I) based on the weight of the pharmaceutically acceptable unit formulation. In some embodiments, the pharmaceutically acceptable unit formulation consists essentially of about 1% by weight to about 50% by weight of the compound of Formula (I) based on the weight of the pharmaceutically acceptable unit formulation. In some embodiments, the pharmaceutically acceptable unit formulation consists essentially of about 1% by weight to about 45% by weight of the compound of Formula (I) based on the weight of the pharmaceutically acceptable unit formulation. In some embodiments, the pharmaceutically acceptable unit formulation consists essentially of about 1% by weight to about 40% by weight of the compound of Formula (I) based on the weight of the pharmaceutically acceptable unit formulation. In some embodiments, the pharmaceutically acceptable unit formulation consists essentially of about 1% by weight to about 35% by weight of the compound of Formula (I) based on the weight of the pharmaceutically acceptable unit formulation. In some embodiments, the pharmaceutically acceptable unit formulation consists essentially of about 1% by weight to about 30% by weight of the compound of Formula (I) based on the weight of the pharmaceutically acceptable unit formulation. In some embodiments, the pharmaceutically acceptable unit formulation consists essentially of about 1% by weight to about 25% by weight of the compound of Formula (I) based on the weight of the pharmaceutically acceptable unit formulation. In some embodiments, the pharmaceutically acceptable unit formulation consists essentially of about 1% by weight to about 20% by weight of the compound of Formula (I) based on the weight of the pharmaceutically acceptable unit formulation. In some embodiments, the pharmaceutically acceptable unit formulation consists essentially of about 1% by weight to about 15% by weight of the compound of Formula (I) based on the weight of the pharmaceutically acceptable unit formulation. In some embodiments, the pharmaceutically acceptable unit formulation consists essentially of about 1% by weight to about 10% by weight of the compound of Formula (I) based on the weight of the pharmaceutically acceptable unit formulation.

In some embodiments, the pharmaceutically acceptable unit formulation comprises about 5% by weight to about 30% by weight of the compound of Formula (I) based on the weight of the pharmaceutically acceptable unit formulation. In some embodiments, the pharmaceutically acceptable unit formulation comprises about 5% by weight to about 25% by weight of the compound of Formula (I) based on the weight of the pharmaceutically acceptable unit formulation. In some embodiments, the pharmaceutically acceptable unit formulation comprises about 5% by weight to about 20% by weight of the compound of Formula (I) based on the weight of the pharmaceutically acceptable unit formulation. In some embodiments, the pharmaceutically acceptable unit formulation comprises about 5% by weight to about 15% by weight of the compound of Formula (I) based on the weight of the pharmaceutically acceptable unit formulation. In some embodiments, the pharmaceutically acceptable unit formulation comprises about 5% by weight to about 10% by weight of the compound of Formula (I) based on the weight of the pharmaceutically acceptable unit formulation.

In some embodiments, the pharmaceutically acceptable unit formulation consists essentially of about 5% by weight to about 30% by weight of the compound of Formula (I) based on the weight of the pharmaceutically acceptable unit formulation. In some embodiments, the pharmaceutically acceptable unit formulation consists essentially of about 5% by weight to about 25% by weight of the compound of Formula (I) based on the weight of the pharmaceutically acceptable unit formulation. In some embodiments, the pharmaceutically acceptable unit formulation consists essentially of about 5% by weight to about 20% by weight of the compound of Formula (I) based on the weight of the pharmaceutically acceptable unit formulation. In some embodiments, the pharmaceutically acceptable unit formulation consists essentially of about 5% by weight to about 15% by weight of the compound of Formula (I) based on the weight of the pharmaceutically acceptable unit formulation. In some embodiments, the pharmaceutically acceptable unit formulation consists essentially of about 5% by weight to about 10% by weight of the compound of Formula (I) based on the weight of the pharmaceutically acceptable unit formulation.

In some embodiments, the pharmaceutically acceptable unit formulation comprises about 10% to about 30% of the compound of Formula (I) based on the weight of the pharmaceutically acceptable unit formulation. In some embodiments, the pharmaceutically acceptable unit formulation comprises about 10% to about 25% of the compound of Formula (I) based on the weight of the pharmaceutically acceptable unit formulation. In some embodiments, the pharmaceutically acceptable unit formulation comprises about 10% to about 20% of the compound of Formula (I) based on the weight of the pharmaceutically acceptable unit formulation. In some embodiments, the pharmaceutically acceptable unit formulation comprises about 10% by weight to about 15% by weight of the compound of Formula (I) based on the weight of the pharmaceutically acceptable unit formulation.

In some embodiments, the pharmaceutically acceptable unit formulation consists essentially of about 10% to about 30% of the compound of Formula (I) based on the weight of the pharmaceutically acceptable unit formulation. In some embodiments, the pharmaceutically acceptable unit formulation consists essentially of about 10% to about 25% of the compound of Formula (I) based on the weight of the pharmaceutically acceptable unit formulation. In some embodiments, the pharmaceutically acceptable unit formulation consists essentially of about 10% to about 20% of the compound of Formula (I) based on the weight of the pharmaceutically acceptable unit formulation. In some embodiments, the pharmaceutically acceptable unit formulation consists essentially of about 10% by weight to about 15% by weight of the compound of Formula (I) based on the weight of the pharmaceutically acceptable unit formulation.

In some embodiments, the pharmaceutically acceptable unit formulation comprises about 1% by weight to about 30% by weight of the compound of Formula (I) based on the weight of the pharmaceutically acceptable unit formulation. In some embodiments, the pharmaceutically acceptable unit formulation comprises about 1% by weight to about 10% by weight of the compound of Formula (I) based on the weight of the pharmaceutically acceptable unit formulation. In some embodiments, the pharmaceutically acceptable unit formulation comprises about 10% to about 20% of the compound of Formula (I) based on the weight of the pharmaceutically acceptable unit formulation. In some embodiments, the pharmaceutically acceptable unit formulation comprises about 10% by weight to about 15% by weight of the compound of Formula (I) based on the weight of the pharmaceutically acceptable unit formulation.

In some embodiments, the pharmaceutically acceptable unit formulation consists essentially of about 1% by weight to about 30% by weight of the compound of Formula (I) based on the weight of the pharmaceutically acceptable unit formulation. In some embodiments, the pharmaceutically acceptable unit formulation consists essentially of about 1% by weight to about 10% by weight of the compound of Formula (I) based on the weight of the pharmaceutically acceptable unit formulation. In some embodiments, the pharmaceutically acceptable unit formulation consists essentially of about 10% to about 20% of the compound of Formula (I) based on the weight of the pharmaceutically acceptable unit formulation. In some embodiments, the pharmaceutically acceptable unit formulation consists essentially of about 10% by weight to about 15% by weight of the compound of Formula (I) based on the weight of the pharmaceutically acceptable unit formulation.

In some embodiments, the one or more pharmaceutically acceptable excipients comprise about 20% by weight to about 90% by weight of one or more fillers based on the weight of the pharmaceutically acceptable unit formulation. In some embodiments, the one or more pharmaceutically acceptable excipients comprise about 20% by weight to about 85% by weight of one or more fillers based on the weight of the pharmaceutically acceptable unit formulation. In some embodiments, the one or more pharmaceutically acceptable excipients comprise about 20% by weight to about 80% by weight of one or more fillers based on the weight of the pharmaceutically acceptable unit formulation. In some embodiments, the one or more pharmaceutically acceptable excipients comprise about 20% by weight to about 75% by weight of one or more fillers based on the weight of the pharmaceutically acceptable unit formulation. In some embodiments, the one or more pharmaceutically acceptable excipients comprise about 20% by weight to about 70% by weight of one or more fillers based on the weight of the pharmaceutically acceptable unit formulation. In some embodiments, the one or more pharmaceutically acceptable excipients comprise about 20% by weight to about 65% by weight of one or more fillers based on the weight of the pharmaceutically acceptable unit formulation. In some embodiments, the one or more pharmaceutically acceptable excipients comprise about 20% by weight to about 60% by weight of one or more fillers based on the weight of the pharmaceutically acceptable unit formulation. In some embodiments, the one or more pharmaceutically acceptable excipients comprise about 20% by weight to about 55% by weight of one or more fillers based on the weight of the pharmaceutically acceptable unit formulation. In some embodiments, the one or more pharmaceutically acceptable excipients comprise about 20% by weight to about 50% by weight of one or more fillers based on the weight of the pharmaceutically acceptable unit formulation. In some embodiments, the one or more pharmaceutically acceptable excipients comprise about 20% by weight to about 45% by weight of one or more fillers based on the weight of the pharmaceutically acceptable unit formulation. In some embodiments, the one or more pharmaceutically acceptable excipients comprise about 20% by weight to about 40% by weight of one or more fillers based on the weight of the pharmaceutically acceptable unit formulation. In some embodiments, the one or more pharmaceutically acceptable excipients comprise about 20% by weight to about 35% by weight of one or more fillers based on the weight of the pharmaceutically acceptable unit formulation. In some embodiments, the one or more pharmaceutically acceptable excipients comprise about 20% by weight to about 30% by weight of one or more fillers based on the weight of the pharmaceutically acceptable unit formulation. In some embodiments, the one or more pharmaceutically acceptable excipients comprise about 20% by weight to about 25% by weight of one or more fillers based on the weight of the pharmaceutically acceptable unit formulation.

In some embodiments, the one or more pharmaceutically acceptable excipients comprise about 30% by weight to about 90% by weight of one or more fillers based on the weight of the pharmaceutically acceptable unit formulation. In some embodiments, the one or more pharmaceutically acceptable excipients comprise about 30% by weight to about 80% by weight of one or more fillers based on the weight of the pharmaceutically acceptable unit formulation. In some embodiments, the one or more pharmaceutically acceptable excipients comprise about 30% by weight to about 70% by weight of one or more fillers based on the weight of the pharmaceutically acceptable unit formulation. In some embodiments, the one or more pharmaceutically acceptable excipients comprise about 30% by weight to about 60% by weight of one or more fillers based on the weight of the pharmaceutically acceptable unit formulation. In some embodiments, the one or more pharmaceutically acceptable excipients comprise about 30% by weight to about 50% by weight of one or more fillers based on the weight of the pharmaceutically acceptable unit formulation. In some embodiments, the one or more pharmaceutically acceptable excipients comprise about 30% by weight to about 40% by weight of one or more fillers based on the weight of the pharmaceutically acceptable unit formulation.

In some embodiments, the one or more pharmaceutically acceptable excipients comprise about 40% by weight to about 90% by weight of one or more fillers based on the weight of the pharmaceutically acceptable unit formulation. In some embodiments, the one or more pharmaceutically acceptable excipients comprise about 40% by weight to about 80% by weight of one or more fillers based on the weight of the pharmaceutically acceptable unit formulation. In some embodiments, the one or more pharmaceutically acceptable excipients comprise about 40% by weight to about 70% by weight of one or more fillers based on the weight of the pharmaceutically acceptable unit formulation. In some embodiments, the one or more pharmaceutically acceptable excipients comprise about 40% by weight to about 60% by weight of one or more fillers based on the weight of the pharmaceutically acceptable unit formulation. In some embodiments, the one or more pharmaceutically acceptable excipients comprise about 40% by weight to about 50% by weight of one or more fillers based on the weight of the pharmaceutically acceptable unit formulation.

In some embodiments, the one or more pharmaceutically acceptable excipients comprise about 50% by weight to about 90% by weight of one or more fillers based on the weight of the pharmaceutically acceptable unit formulation. In some embodiments, the one or more pharmaceutically acceptable excipients comprise about 50% by weight to about 80% by weight of one or more fillers based on the weight of the pharmaceutically acceptable unit formulation. In some embodiments, the one or more pharmaceutically acceptable excipients comprise about 50% by weight to about 70% by weight of one or more fillers based on the weight of the pharmaceutically acceptable unit formulation. In some embodiments, the one or more pharmaceutically acceptable excipients comprise about 50% by weight to about 60% by weight of one or more fillers based on the weight of the pharmaceutically acceptable unit formulation.

In some embodiments, the one or more pharmaceutically acceptable excipients comprise about 60% by weight to about 90% by weight of one or more fillers based on the weight of the pharmaceutically acceptable unit formulation. In some embodiments, the one or more pharmaceutically acceptable excipients comprise about 60% by weight to about 80% by weight of one or more fillers based on the weight of the pharmaceutically acceptable unit formulation. In some embodiments, the one or more pharmaceutically acceptable excipients comprise about 60% by weight to about 70% by weight of one or more fillers based on the weight of the pharmaceutically acceptable unit formulation.

In some embodiments, the one or more pharmaceutically acceptable excipients comprise about 70% by weight to about 90% by weight of one or more fillers based on the weight of the pharmaceutically acceptable unit formulation. In some embodiments, the one or more pharmaceutically acceptable excipients comprise about 70% by weight to about 80% by weight of one or more fillers based on the weight of the pharmaceutically acceptable unit formulation.

In some embodiments, the one or more pharmaceutically acceptable excipients comprise about 80% by weight to about 90% by weight of one or more fillers based on the weight of the pharmaceutically acceptable unit formulation.

In some embodiments, the one or more pharmaceutically acceptable excipients comprise about 1% by weight to about 20% by weight of one or more disintegrants based on the weight of the pharmaceutically acceptable unit formulation. In some embodiments, the one or more pharmaceutically acceptable excipients comprise about 1% by weight to about 15% by weight of one or more disintegrants based on the weight of the pharmaceutically acceptable unit formulation. In some embodiments, the one or more pharmaceutically acceptable excipients comprise about 1% by weight to about 14% by weight of one or more disintegrants based on the weight of the pharmaceutically acceptable unit formulation. In some embodiments, the one or more pharmaceutically acceptable excipients comprise about 1% by weight to about 13% by weight of one or more disintegrants based on the weight of the pharmaceutically acceptable unit formulation. In some embodiments, the one or more pharmaceutically acceptable excipients comprise about 1% by weight to about 12% by weight of one or more disintegrants based on the weight of the pharmaceutically acceptable unit formulation. In some embodiments, the one or more pharmaceutically acceptable excipients comprise about 1% by weight to about 11% by weight of one or more disintegrants based on the weight of the pharmaceutically acceptable unit formulation. In some embodiments, the one or more pharmaceutically acceptable excipients comprise about 1% by weight to about 10% by weight of one or more disintegrants based on the weight of the pharmaceutically acceptable unit formulation. In some embodiments, the one or more pharmaceutically acceptable excipients comprise about 1% by weight to about 9% by weight of one or more disintegrants based on the weight of the pharmaceutically acceptable unit formulation. In some embodiments, the one or more pharmaceutically acceptable excipients comprise about 1% by weight to about 8% by weight of one or more disintegrants based on the weight of the pharmaceutically acceptable unit formulation. In some embodiments, the one or more pharmaceutically acceptable excipients comprise about 1% by weight to about 7% by weight of one or more disintegrants based on the weight of the pharmaceutically acceptable unit formulation. In some embodiments, the one or more pharmaceutically acceptable excipients comprise about 1% by weight to about 6% by weight of one or more disintegrants based on the weight of the pharmaceutically acceptable unit formulation. In some embodiments, the one or more pharmaceutically acceptable excipients comprise about 1% by weight to about 5% by weight of one or more disintegrants based on the weight of the pharmaceutically acceptable unit formulation. In some embodiments, the one or more pharmaceutically acceptable excipients comprise about 1% by weight to about 4% by weight of one or more disintegrants based on the weight of the pharmaceutically acceptable unit formulation. In some embodiments, the one or more pharmaceutically acceptable excipients comprise about 1% by weight to about 3% by weight of one or more disintegrants based on the weight of the pharmaceutically acceptable unit formulation.

In some embodiments, the one or more pharmaceutically acceptable excipients comprise about 1% by weight of one or more disintegrants based on the weight of the pharmaceutically acceptable unit formulation. In some embodiments, the one or more pharmaceutically acceptable excipients comprise about 2% by weight of one or more disintegrants based on the weight of the pharmaceutically acceptable unit formulation. In some embodiments, the one or more pharmaceutically acceptable excipients comprise about 3% by weight of one or more disintegrants based on the weight of the pharmaceutically acceptable unit formulation. In some embodiments, the one or more pharmaceutically acceptable excipients comprise about 4% by weight of one or more disintegrants based on the weight of the pharmaceutically acceptable unit formulation. In some embodiments, the one or more pharmaceutically acceptable excipients comprise about 5% by weight of one or more disintegrants based on the weight of the pharmaceutically acceptable unit formulation. In some embodiments, the one or more pharmaceutically acceptable excipients comprise about 6% by weight of one or more disintegrants based on the weight of the pharmaceutically acceptable unit formulation. In some embodiments, the one or more pharmaceutically acceptable excipients comprise about 7% by weight of one or more disintegrants based on the weight of the pharmaceutically acceptable unit formulation. In some embodiments, the one or more pharmaceutically acceptable excipients comprise about 8% by weight of one or more disintegrants based on the weight of the pharmaceutically acceptable unit formulation. In some embodiments, the one or more pharmaceutically acceptable excipients comprise about 9% by weight of one or more disintegrants based on the weight of the pharmaceutically acceptable unit formulation. In some embodiments, the one or more pharmaceutically acceptable excipients comprise about 10% by weight of one or more disintegrants based on the weight of the pharmaceutically acceptable unit formulation. In some embodiments, the one or more pharmaceutically acceptable excipients comprise about 11% by weight of one or more disintegrants based on the weight of the pharmaceutically acceptable unit formulation. In some embodiments, the one or more pharmaceutically acceptable excipients comprise about 12% by weight of one or more disintegrants based on the weight of the pharmaceutically acceptable unit formulation. In some embodiments, the one or more pharmaceutically acceptable excipients comprise about 13% by weight of one or more disintegrants based on the weight of the pharmaceutically acceptable unit formulation. In some embodiments, the one or more pharmaceutically acceptable excipients comprise about 14% by weight of one or more disintegrants based on the weight of the pharmaceutically acceptable unit formulation. In some embodiments, the one or more pharmaceutically acceptable excipients comprise about 15% by weight of one or more disintegrants based on the weight of the pharmaceutically acceptable unit formulation.

In some embodiments, the one or more pharmaceutically acceptable excipients comprise about 0.1% by weight to about 10% by weight of one or more lubricants based on the weight of the pharmaceutically acceptable unit formulation. In some embodiments, the one or more pharmaceutically acceptable excipients comprise about 0.1% by weight to about 9% by weight of one or more lubricants based on the weight of the pharmaceutically acceptable unit formulation. In some embodiments, the one or more pharmaceutically acceptable excipients comprise about 0.1% by weight to about 8% by weight of one or more lubricants based on the weight of the pharmaceutically acceptable unit formulation. In some embodiments, the one or more pharmaceutically acceptable excipients comprise about 0.1% by weight to about 7% by weight of one or more lubricants based on the weight of the pharmaceutically acceptable unit formulation. In some embodiments, the one or more pharmaceutically acceptable excipients comprise about 0.1% by weight to about 6% by weight of one or more lubricants based on the weight of the pharmaceutically acceptable unit formulation. In some embodiments, the one or more pharmaceutically acceptable excipients comprise about 0.1% by weight to about 5% by weight of one or more lubricants based on the weight of the pharmaceutically acceptable unit formulation. In some embodiments, the one or more pharmaceutically acceptable excipients comprise about 0.1% by weight to about 4% by weight of one or more lubricants based on the weight of the pharmaceutically acceptable unit formulation. In some embodiments, the one or more pharmaceutically acceptable excipients comprise about 0.1% by weight to about 3% by weight of one or more lubricants based on the weight of the pharmaceutically acceptable unit formulation. In some embodiments, the one or more pharmaceutically acceptable excipients comprise about 0.1% by weight to about 2% by weight of one or more lubricants based on the weight of the pharmaceutically acceptable unit formulation.

In some embodiments, the one or more pharmaceutically acceptable excipients comprise about 0.1% by weight to about 1.9% by weight of one or more lubricants based on the weight of the pharmaceutically acceptable unit formulation. In some embodiments, the one or more pharmaceutically acceptable excipients comprise about 0.1% by weight to about 1.8% by weight of one or more lubricants based on the weight of the pharmaceutically acceptable unit formulation. In some embodiments, the one or more pharmaceutically acceptable excipients comprise about 0.1% by weight to about 1.7% by weight of one or more lubricants based on the weight of the pharmaceutically acceptable unit formulation. In some embodiments, the one or more pharmaceutically acceptable excipients comprise about 0.1% by weight to about 1.6% by weight of one or more lubricants based on the weight of the pharmaceutically acceptable unit formulation. In some embodiments, the one or more pharmaceutically acceptable excipients comprise about 0.1% by weight to about 1.5% by weight of one or more lubricants based on the weight of the pharmaceutically acceptable unit formulation. In some embodiments, the one or more pharmaceutically acceptable excipients comprise about 0.1% by weight to about 1.4% by weight of one or more lubricants based on the weight of the pharmaceutically acceptable unit formulation. In some embodiments, the one or more pharmaceutically acceptable excipients comprise about 0.1% by weight to about 1.3% by weight of one or more lubricants based on the weight of the pharmaceutically acceptable unit formulation. In some embodiments, the one or more pharmaceutically acceptable excipients comprise about 0.1% by weight to about 1.2% by weight of one or more lubricants based on the weight of the pharmaceutically acceptable unit formulation. In some embodiments, the one or more pharmaceutically acceptable excipients comprise about 0.1% by weight to about 1.1% by weight of one or more lubricants based on the weight of the pharmaceutically acceptable unit formulation. In some embodiments, the one or more pharmaceutically acceptable excipients comprise about 0.1% by weight to about 1.0% by weight of one or more lubricants based on the weight of the pharmaceutically acceptable unit formulation. In some embodiments, the one or more pharmaceutically acceptable excipients comprise about 0.1% by weight to about 0.9% by weight of one or more lubricants based on the weight of the pharmaceutically acceptable unit formulation. In some embodiments, the one or more pharmaceutically acceptable excipients comprise about 0.1% by weight to about 0.8% by weight of one or more lubricants based on the weight of the pharmaceutically acceptable unit formulation. In some embodiments, the one or more pharmaceutically acceptable excipients comprise about 0.1% by weight to about 0.7% by weight of one or more lubricants based on the weight of the pharmaceutically acceptable unit formulation. In some embodiments, the one or more pharmaceutically acceptable excipients comprise about 0.1% by weight to about 0.6% by weight of one or more lubricants based on the weight of the pharmaceutically acceptable unit formulation. In some embodiments, the one or more pharmaceutically acceptable excipients comprise about 0.1% by weight to about 0.5% by weight of one or more lubricants based on the weight of the pharmaceutically acceptable unit formulation. In some embodiments, the one or more pharmaceutically acceptable excipients comprise about 0.1% by weight to about 0.4% by weight of one or more lubricants based on the weight of the pharmaceutically acceptable unit formulation. In some embodiments, the one or more pharmaceutically acceptable excipients comprise about 0.1% by weight to about 0.3% by weight of one or more lubricants based on the weight of the pharmaceutically acceptable unit formulation. In some embodiments, the one or more pharmaceutically acceptable excipients comprise about 0.1% by weight to about 0.2% by weight of one or more lubricants based on the weight of the pharmaceutically acceptable unit formulation.

In some embodiments, the one or more pharmaceutically acceptable excipients comprise about 0.1% by weight of one or more lubricants based on the weight of the pharmaceutically acceptable unit formulation. In some embodiments, the one or more pharmaceutically acceptable excipients comprise about 0.2% by weight of one or more lubricants based on the weight of the pharmaceutically acceptable unit formulation. In some embodiments, the one or more pharmaceutically acceptable excipients comprise about 0.3% by weight of one or more lubricants based on the weight of the pharmaceutically acceptable unit formulation. In some embodiments, the one or more pharmaceutically acceptable excipients comprise about 0.4% by weight of one or more lubricants based on the weight of the pharmaceutically acceptable unit formulation. In some embodiments, the one or more pharmaceutically acceptable excipients comprise about 0.5% by weight of one or more lubricants based on the weight of the pharmaceutically acceptable unit formulation. In some embodiments, the one or more pharmaceutically acceptable excipients comprise about 0.6% by weight of one or more lubricants based on the weight of the pharmaceutically acceptable unit formulation. In some embodiments, the one or more pharmaceutically acceptable excipients comprise about 0.7% by weight of one or more lubricants based on the weight of the pharmaceutically acceptable unit formulation. In some embodiments, the one or more pharmaceutically acceptable excipients comprise about 0.8% by weight of one or more lubricants based on the weight of the pharmaceutically acceptable unit formulation. In some embodiments, the one or more pharmaceutically acceptable excipients comprise about 0.9% by weight of one or more lubricants based on the weight of the pharmaceutically acceptable unit formulation. In some embodiments, the one or more pharmaceutically acceptable excipients comprise about 1.0% by weight of one or more lubricants based on the weight of the pharmaceutically acceptable unit formulation.

In some embodiments, the pharmaceutically acceptable unit formulation comprises: (a) about 1% by weight to about 30% by weight of the compound of Formula (I) based on the weight of the pharmaceutically acceptable unit formulation; (b) about 20% by weight to about 90% by weight of one or more fillers based on the weight of the pharmaceutically acceptable unit formulation; (c) about 1% by weight to about 20% by weight of one or more disintegrants based on the weight of the pharmaceutically acceptable unit formulation; and (d) about 0.1% by weight to about 10% by weight of one or more lubricants based on the weight of the pharmaceutically acceptable unit formulation.

In some embodiments, the pharmaceutically acceptable unit formulation consists essentially of: (a) about 1% by weight to about 30% by weight of the compound of Formula (I) based on the weight of the pharmaceutically acceptable unit formulation; (b) about 20% by weight to about 90% by weight of one or more fillers based on the weight of the pharmaceutically acceptable unit formulation; (c) about 1% by weight to about 20% by weight of one or more disintegrants based on the weight of the pharmaceutically acceptable unit formulation; and (d) about 0.1% by weight to about 10% by weight of one or more lubricants based on the weight of the pharmaceutically acceptable unit formulation.

In some embodiments, the pharmaceutically acceptable unit formulation comprises (a) about 5% by weight to about 25% by weight of the compound of Formula (I) based on the weight of the pharmaceutically acceptable unit formulation; (b) about 60% by weight to about 90% by weight of one or more fillers based on the weight of the pharmaceutically acceptable unit formulation; (c) about 1% by weight to about 15% by weight of one or more disintegrants based on the weight of the pharmaceutically acceptable unit formulation; and (d) about 0.1% by weight to about 4% by weight of one or more lubricants based on the weight of the pharmaceutically acceptable unit formulation.

In some embodiments, the pharmaceutically acceptable unit formulation consists essentially of: (a) about 5% by weight to about 25% by weight of the compound of Formula (I) based on the weight of the pharmaceutically acceptable unit formulation; (b) about 60% by weight to about 90% by weight of one or more fillers based on the weight of the pharmaceutically acceptable unit formulation; (c) about 1% by weight to about 15% by weight of one or more disintegrants based on the weight of the pharmaceutically acceptable unit formulation; and (d) about 0.1% by weight to about 4% by weight of one or more lubricants based on the weight of the pharmaceutically acceptable unit formulation.

In some embodiments, the pharmaceutically acceptable unit formulation comprises (a) about 10% by weight to about 30% by weight of the compound of Formula (I) based on the weight of the pharmaceutically acceptable unit formulation; (b) about 70% by weight to about 90% by weight of one or more fillers based on the weight of the pharmaceutically acceptable unit formulation; (c) about 1% by weight to about 10% by weight of one or more disintegrants based on the weight of the pharmaceutically acceptable unit formulation; and (d) about 0.1% by weight to about 3% by weight of one or more lubricants based on the weight of the pharmaceutically acceptable unit formulation.

In some embodiments, the pharmaceutically acceptable unit formulation consists essentially of: (a) about 10% by weight to about 30% by weight of the compound of Formula (I) based on the weight of the pharmaceutically acceptable unit formulation; (b) about 70% by weight to about 90% by weight of one or more fillers based on the weight of the pharmaceutically acceptable unit formulation; (c) about 1% by weight to about 10% by weight of one or more disintegrants based on the weight of the pharmaceutically acceptable unit formulation; and (d) about 0.1% by weight to about 3% by weight of one or more lubricants based on the weight of the pharmaceutically acceptable unit formulation.

In some embodiments, the one or more pharmaceutically acceptable excipients is one or more fillers selected from the group consisting of calcium phosphate, dicalcium phosphate, dicalcium phosphate dihydrate, calcium sulfate, calcium sulfate dihydrate, starch, calcium carbonate, magnesium carbonate, magnesium oxide, kaolin (natural hydrated aluminum silicate), sodium chloride, partially gelatinized starch, anhydrous lactose, lactose monohydrate, lactose dihydrate, trehalose dihydrate, spray dried lactose, sucrose, dextrose, dextrates, dextrin, cellulose, microcrystalline cellulose, silicified microcrystalline cellulose, powdered cellulose, partially depolymerized cellulose, mannitol, granulated mannitol, spray dried mannitol, maltodextrin, maltitol, confectioner's sugar, compressible sugar, sorbitol, starch and talc. In some embodiments, the one or more fillers is lactose monohydrate.

In some embodiments, the one or more disintegrants is one or more disintegrants selected from the group consisting of sodium starch glycolate, pregelatinized starch, clay, cellulose, alginic acid, alginate gum, polyvinylpyrrolidone, cross-linked polyvinylpyrrolidone, cross-linked calcium carboxymethylcellulose, cross-linked sodium carboxymethylcellulose, sodium croscarmellose, sodium carmellose, low substituted hydroxypropyl cellulose, low substituted hydroxypropyl cellulose sodium, guar gum, magnesium aluminum silicate, polacrilin potassium, powdered cellulose, sodium alginate and soy polysaccharides. In some embodiments, the one or more disintegrants is cross-linked polyvinylpyrrolidone (also referred to as crospovidone).

In some embodiments, the one or more lubricants is one or more lubricants selected from the group consisting of colloidal silica, magnesium trisilicate, talc, magnesium carbonate, magnesium oxide, glyceryl behaptate, mono, di and tri glyceryl behenate, bees wax, behenoyl polyoxyl-8 glycerides, hydrogenated vegetable oil, polyethylene glycol, ethylene oxide polymer, copolymer comprising poly(ethylene oxide) and poly(propylene oxide) (such as poloxomer 188), copolymer comprising polypropylene glycol and polyethylene glycol (such as poloxomer 407), sodium lauryl sulfate, magnesium stearate, aluminum stearate, calcium stearate, sodium stearyl fumarate, stearic acid, magnesium lauryl stearate, mixtures of magnesium stearate with sodium lauryl sulfate. In some embodiments, the one or more lubricants is magnesium stearate.

In some embodiments, the pharmaceutically acceptable unit formulation further comprises cross-linked polyvinylpyrrolidone and magnesium stearate. In some embodiments, the one or more pharmaceutically acceptable excipients is lactose monohydrate and the formulation further comprises cross-linked polyvinylpyrrolidone and magnesium stearate.

In some embodiments, the pharmaceutically acceptable unit formulation is for oral administration.

In some embodiments, the pharmaceutically acceptable unit formulation is a solid dosage form.

In some embodiments, the pharmaceutically acceptable unit formulation is a tablet or capsule. In some embodiments, the pharmaceutically acceptable unit formulation is a tablet. In some embodiments, the pharmaceutically acceptable unit formulation is a capsule. In some embodiments, the pharmaceutically acceptable unit formulation is a sachet. In some embodiments, the pharmaceutically acceptable unit formulation is a powder in a packet.

In some embodiments, the pharmaceutically acceptable unit formulation comprises about 1 mg to about 40 mg of the compound of Formula (I). In some embodiments, the pharmaceutically acceptable unit formulation comprises about 1 mg to about 30 mg of the compound of Formula (I). In some embodiments, the pharmaceutically acceptable unit formulation comprises about 1 mg to about 20 mg of the compound of Formula (I). In some embodiments, the pharmaceutically acceptable unit formulation comprises about 1 mg to about 15 mg of the compound of Formula (I). In some embodiments, the pharmaceutically acceptable unit formulation comprises about 5 mg to about 40 mg of the compound of Formula (I). In some embodiments, the pharmaceutically acceptable unit formulation comprises about 5 mg to about 30 mg of the compound of Formula (I). In some embodiments, the pharmaceutically acceptable unit formulation comprises about 5 mg to about 20 mg of the compound of Formula (I). In some embodiments, the pharmaceutically acceptable unit formulation comprises about 5 mg to about 15 mg of the compound of Formula (I). In some embodiments, the pharmaceutically acceptable unit formulation comprises about 10 mg to about 40 mg of the compound of Formula (I). In some embodiments, the pharmaceutically acceptable unit formulation comprises about 10 mg to about 30 mg of the compound of Formula (I). In some embodiments, the pharmaceutically acceptable unit formulation comprises about 10 mg to about 20 mg of the compound of Formula (I). In some embodiments, the pharmaceutically acceptable unit formulation comprises about 10 mg to about 15 mg of the compound of Formula (I).

In some embodiments, the pharmaceutically acceptable unit formulation consists essentially of about 1 mg to about 40 mg of the compound of Formula (I). In some embodiments, the pharmaceutically acceptable unit formulation consists essentially of about 1 mg to about 30 mg of the compound of Formula (I). In some embodiments, the pharmaceutically acceptable unit formulation consists essentially of about 1 mg to about 20 mg of the compound of Formula (I). In some embodiments, the pharmaceutically acceptable unit formulation consists essentially of about 1 mg to about 15 mg of the compound of Formula (I). In some embodiments, the pharmaceutically acceptable unit formulation consists essentially of about 5 mg to about 40 mg of the compound of Formula (I). In some embodiments, the pharmaceutically acceptable unit formulation consists essentially of about 5 mg to about 30 mg of the compound of Formula (I). In some embodiments, the pharmaceutically acceptable unit formulation consists essentially of about 5 mg to about 20 mg of the compound of Formula (I). In some embodiments, the pharmaceutically acceptable unit formulation consists essentially of about 5 mg to about 15 mg of the compound of Formula (I). In some embodiments, the pharmaceutically acceptable unit formulation consists essentially of about 10 mg to about 40 mg of the compound of Formula (I). In some embodiments, the pharmaceutically acceptable unit formulation consists essentially of about 10 mg to about 30 mg of the compound of Formula (I). In some embodiments, the pharmaceutically acceptable unit formulation consists essentially of about 10 mg to about 20 mg of the compound of Formula (I). In some embodiments, the pharmaceutically acceptable unit formulation consists essentially of about 10 mg to about 15 mg of the compound of Formula (I).

In some embodiments, compound of Formula (I) is present in the pharmaceutically acceptable unit formulation as a cocrystal. In some embodiments, compound of Formula (I) is present in the pharmaceutically acceptable unit formulation as a channel crystal. In some embodiments, compound of Formula (I) is present in the pharmaceutically acceptable unit formulation as a crystalline dihydrate form. In some embodiments, the compound of Formula (I) is present in the pharmaceutically acceptable unit formulation as a crystalline anhydrous form. In some embodiments, compound of Formula (I) is present in the pharmaceutically acceptable unit formulation as a solvate.

In some embodiments, the pharmaceutically acceptable unit formulation comprises about 0.5 mg to about 5 mg, about 6 mg to about 14 mg, about 11 mg to about 19 mg, about 17 mg to about 25 mg, or about 28 mg to about 36 mg of the compound of Formula (I) as a crystalline dihydrate form. In some embodiments, the pharmaceutically acceptable unit formulation comprises about 1 mg to about 4 mg, about 8 mg to about 12 mg, about 13 mg to about 17 mg, about 19 mg to about 23 mg, or about 30 mg to about 34 mg of the compound of Formula (I) as a crystalline dihydrate form. In some embodiments, the pharmaceutically acceptable unit formulation comprises about 2.2 mg, about 10.8 mg, about 15.2 mg, about 21.7 mg, or about 32.5 mg of the compound of Formula (I) as a crystalline dihydrate form.

In some embodiments, the pharmaceutically acceptable unit formulation consists essentially of about 0.5 mg to about 5 mg, about 6 mg to about 14 mg, about 11 mg to about 19 mg, about 17 mg to about 25 mg, or about 28 mg to about 36 mg of the compound of Formula (I) as a crystalline dihydrate form. In some embodiments, the pharmaceutically acceptable unit formulation consists essentially of about 1 mg to about 4 mg, about 8 mg to about 12 mg, about 13 mg to about 17 mg, about 19 mg to about 23 mg, or about 30 mg to about 34 mg of the compound of Formula (I) as a crystalline dihydrate form. In some embodiments, the pharmaceutically acceptable unit formulation consists essentially of about 2.2 mg, about 10.8 mg, about 15.2 mg, about 21.7 mg, or about 32.5 mg of the compound of Formula (I) as a crystalline dihydrate form.

In some embodiments, the pharmaceutically acceptable unit formulation has an acceptance value of less than about 15 as determined by USP Uniformity of Dosage Unit <905>. In some embodiments, the pharmaceutically acceptable unit formulation has a maximum acceptance value of equal to or less than about 15 as determined by USP Uniformity of Dosage Unit <905>.

In some embodiments, the uniformity of the pharmaceutically acceptable formulation represents the degree of uniformity in the amount of the compound of Formula (I) in the pharmaceutically acceptable formulation.

In some embodiments, the uniformity of the oral dosage form represents the degree of uniformity in the amount of the compound of Formula (I) in the oral dosage form.

In some embodiments, the uniformity of the pharmaceutically acceptable capsule represents the degree of uniformity in the amount of the compound of Formula (I) in the pharmaceutically acceptable capsule.

Also provided herein, in some embodiments, are pharmaceutically acceptable formulations comprising the crystalline dihydrate form of a compound of Formula (I):

Formula (I)

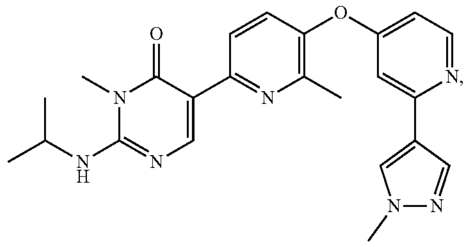

and one or more pharmaceutically acceptable excipients.

Also provided herein, in some embodiments, are pharmaceutically acceptable formulations consisting essentially of the crystalline dihydrate form of a compound of Formula (I):

Formula (I)

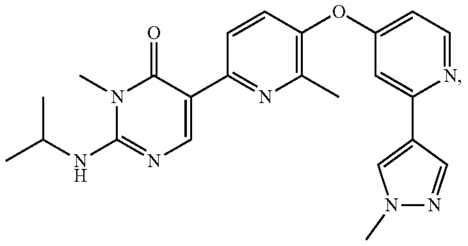

and one or more pharmaceutically acceptable excipients.

Also provided herein, in some embodiments, are pharmaceutically acceptable unit formulations comprising the crystalline dihydrate form of a compound of Formula (I):

Formula (I)

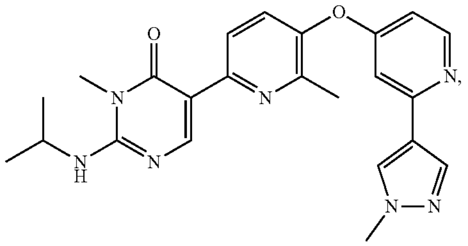

and one or more pharmaceutically acceptable excipients.

Also provided herein, in some embodiments, are pharmaceutically acceptable unit formulations consisting essentially of the crystalline dihydrate form of a compound of Formula (I):

Formula (I)

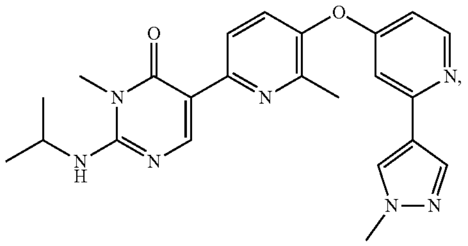

and one or more pharmaceutically acceptable excipients.

In some embodiments, the crystalline dihydrate form of the compound represented by Formula (I) has an XRPD pattern comprising a peak, in terms of 2-theta, at about 10.9° as measured by CuKα radiation.

In some embodiments, the crystalline dihydrate form of the compound represented by Formula (I) has an XRPD pattern comprising peaks, in terms of 2-theta, at about 10.9°, about 16.8°, and about 27.10 as measured by CuKα radiation.

In some embodiments, the crystalline dihydrate form of the compound of Formula (I) has an X-ray powder diffraction pattern comprising peaks, in terms of 2-theta, at about 5.9°, about 10.9°, about 11.9°, about 13.7°, about 16.8°, and about 27.1° as measured by CuKα radiation.

In some embodiments, the crystalline dihydrate form of the compound represented by Formula (I) has an XRPD pattern comprising peaks, in terms of 2-theta, at about 5.9°, about 10.9°, about 11.9°, about 13.7°, about 16.8°, about 27.10, about 28.3° and about 28.7° as measured by CuKα radiation.

In some embodiments, the one or more pharmaceutically acceptable excipients is a filler. For example, the one or more pharmaceutically acceptable excipients is lactose, such as lactose monohydrate.

In some embodiments, the pharmaceutically acceptable unit formulations further comprise one or more disintegrants, one or more lubricants, or a combination thereof. For example, in some embodiments, the pharmaceutically acceptable unit formulations further comprise one or more disintegrants. In some embodiments, the pharmaceutically acceptable unit formulations further comprise one or more lubricants.

Also provided herein, in some embodiments, is a pharmaceutically acceptable unit formulation comprising:

(a) about 1% by weight to about 70% by weight, based on the weight of the pharmaceutically acceptable unit formulation, of a crystalline dihydrate form of a compound of Formula (I):

Formula (I)

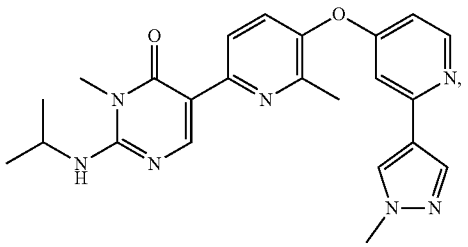

and one or more pharmaceutically acceptable excipients, wherein the one or more pharmaceutically acceptable excipients comprise:

(b) about 20% by weight to about 97% by weight of one or more fillers based on the weight of the pharmaceutically acceptable unit formulation;

(c) about 1% by weight to about 20% by weight of one or more disintegrants based on the weight of the pharmaceutically acceptable unit formulation; and (d) about 0.1% by weight to about 10% by weight of one or more lubricants based on the weight of the pharmaceutically acceptable unit formulation.

Also provided herein, in some embodiments, is a pharmaceutically acceptable unit formulation comprising:

(a) about 1% by weight to about 30% by weight of a crystalline dihydrate form of a compound of Formula (I) based on the weight of the pharmaceutically acceptable unit formulation;

(b) about 20% by weight to about 90% by weight of one or more fillers based on the weight of the pharmaceutically acceptable unit formulation;

(c) about 1% by weight to about 20% by weight of one or more disintegrants based on the weight of the pharmaceutically acceptable unit formulation; and (d) about 0.1% by weight to about 10% by weight of one or more lubricants based on the weight of the pharmaceutically acceptable unit formulation.

Also provided herein, in some embodiments, is a pharmaceutically acceptable unit formulation consisting essentially of:

(a) about 1% by weight to about 70% by weight, based on the weight of the pharmaceutically acceptable unit formulation, of a crystalline dihydrate form of a compound of Formula (I):

Formula (I)

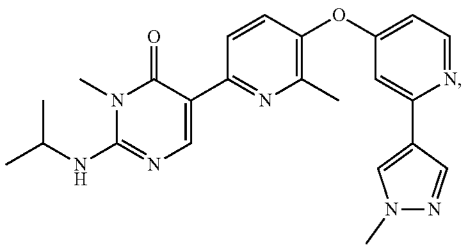

and one or more pharmaceutically acceptable excipients, wherein the one or more pharmaceutically acceptable excipients comprise:

(b) about 20% by weight to about 97% by weight of one or more fillers based on the weight of the pharmaceutically acceptable unit formulation;

(c) about 1% by weight to about 20% by weight of one or more disintegrants based on the weight of the pharmaceutically acceptable unit formulation; and (d) about 0.1% by weight to about 10% by weight of one or more lubricants based on the weight of the pharmaceutically acceptable unit formulation.

Also provided herein, in some embodiments, is a pharmaceutically acceptable unit formulation consisting essentially of:

(a) about 1% by weight to about 30% by weight of a crystalline dihydrate form of a compound of Formula (I) based on the weight of the pharmaceutically acceptable unit formulation;

(b) about 20% by weight to about 90% by weight of one or more fillers based on the weight of the pharmaceutically acceptable unit formulation;

(c) about 1% by weight to about 20% by weight of one or more disintegrants based on the weight of the pharmaceutically acceptable unit formulation; and (d) about 0.1% by weight to about 10% by weight of one or more lubricants based on the weight of the pharmaceutically acceptable unit formulation.

In some embodiments, the pharmaceutically acceptable unit formulation comprising the crystalline dihydrate form of the compound represented by Formula (I), has no more than about 10 mol %, no more than about 5 mol %, no more than about 3 mol %, or no more than about 1 mol % of other solid-state forms of the compound represented by Formula (I). In some embodiments, the pharmaceutically acceptable unit formulation comprising the crystalline dihydrate forms of the compound represented by Formula (I), has no more than about 10 mol % of other solid-state forms of the compound represented by Formula (I). In some embodiments, the pharmaceutically acceptable unit formulation comprising the crystalline dihydrate forms of the compound represented by Formula (I), has no more than about 9 mol % of other solid-state forms of the compound represented by Formula (I). In some embodiments, the pharmaceutically acceptable unit formulation comprising the crystalline dihydrate forms of the compound represented by Formula (I), has no more than about 8 mol % of other solid-state forms of the compound represented by Formula (I). In some embodiments, the pharmaceutically acceptable unit formulation comprising the crystalline dihydrate forms of the compound represented by Formula (I), has no more than about 7 mol % of other solid-state forms of the compound represented by Formula (I). In some embodiments, the pharmaceutically acceptable unit formulation comprising the crystalline dihydrate forms of the compound represented by Formula (I), has no more than about 6 mol % of other solid-state forms of the compound represented by Formula (I). In some embodiments, the pharmaceutically acceptable unit formulation comprising the crystalline dihydrate forms of the compound represented by Formula (I), has no more than about 5 mol % of other solid-state forms of the compound represented by Formula (I). In some embodiments, the pharmaceutically acceptable unit formulation comprising the crystalline dihydrate forms of the compound represented by Formula (I), has no more than about 4 mol % of other solid-state forms of the compound represented by Formula (I). In some embodiments, the pharmaceutically acceptable unit formulation comprising the crystalline dihydrate forms of the compound represented by Formula (I), has no more than about 3 mol % of other solid-state forms of the compound represented by Formula (I). In some embodiments, the pharmaceutically acceptable unit formulation comprising the crystalline dihydrate forms of the compound represented by Formula (I), has no more than about 2 mol % of other solid-state forms of the compound represented by Formula (I). In some embodiments, the pharmaceutically acceptable unit formulation comprising the crystalline dihydrate forms of the compound represented by Formula (I), has no more than about 1 mol % of other solid-state forms of the compound represented by Formula (I).

In some embodiments, the pharmaceutically acceptable unit formulation comprises about 1% by weight to about 60% by weight, based on the weight of the pharmaceutically acceptable unit formulation, of a crystalline dihydrate form of a compound of Formula (I). In some embodiments, the pharmaceutically acceptable unit formulation comprises about 1% by weight to about 50% by weight, based on the weight of the pharmaceutically acceptable unit formulation, of a crystalline dihydrate form of a compound of Formula (I). In some embodiments, the pharmaceutically acceptable unit formulation comprises about 1% by weight to about 40% by weight, based on the weight of the pharmaceutically acceptable unit formulation, of a crystalline dihydrate form of a compound of Formula (I). In some embodiments, the pharmaceutically acceptable unit formulation comprises about 1% by weight to about 30% by weight, based on the weight of the pharmaceutically acceptable unit formulation, of a crystalline dihydrate form of a compound of Formula (I). In some embodiments, the pharmaceutically acceptable unit formulation comprises about 1% by weight to about 20% by weight, based on the weight of the pharmaceutically acceptable unit formulation, of a crystalline dihydrate form of a compound of Formula (I).

In some embodiments, the pharmaceutically acceptable unit formulation consists essentially of about 1% by weight to about 60% by weight, based on the weight of the pharmaceutically acceptable unit formulation, of a crystalline dihydrate form of a compound of Formula (I). In some embodiments, the pharmaceutically acceptable unit formulation consists essentially of about 1% by weight to about 50% by weight, based on the weight of the pharmaceutically acceptable unit formulation, of a crystalline dihydrate form of a compound of Formula (I). In some embodiments, the pharmaceutically acceptable unit formulation consists essentially of about 1% by weight to about 40% by weight, based on the weight of the pharmaceutically acceptable unit formulation, of a crystalline dihydrate form of a compound of Formula (I). In some embodiments, the pharmaceutically acceptable unit formulation consists essentially of about 1% by weight to about 30% by weight, based on the weight of the pharmaceutically acceptable unit formulation, of a crystalline dihydrate form of a compound of Formula (I). In some embodiments, the pharmaceutically acceptable unit formulation consists essentially of about 1% by weight to about 20% by weight, based on the weight of the pharmaceutically acceptable unit formulation, of a crystalline dihydrate form of a compound of Formula (I).

In some embodiments, the pharmaceutically acceptable unit formulation comprises about 1% by weight to about 70% by weight of the crystalline dihydrate form of the compound of Formula (I) based on the weight of the pharmaceutically acceptable unit formulation. In some embodiments, the pharmaceutically acceptable unit formulation comprises about 1% by weight to about 65% by weight of the crystalline dihydrate form of the compound of Formula (I) based on the weight of the pharmaceutically acceptable unit formulation. In some embodiments, the pharmaceutically acceptable unit formulation comprises about 1% by weight to about 60% by weight of the crystalline dihydrate form of the compound of Formula (I) based on the weight of the pharmaceutically acceptable unit formulation. In some embodiments, the pharmaceutically acceptable unit formulation comprises about 1% by weight to about 55% by weight of the crystalline dihydrate form of the compound of Formula (I) based on the weight of the pharmaceutically acceptable unit formulation. In some embodiments, the pharmaceutically acceptable unit formulation comprises about 1% by weight to about 50% by weight of the crystalline dihydrate form of the compound of Formula (I) based on the weight of the pharmaceutically acceptable unit formulation. In some embodiments, the pharmaceutically acceptable unit formulation comprises about 1% by weight to about 45% by weight of the crystalline dihydrate form of the compound of Formula (I) based on the weight of the pharmaceutically acceptable unit formulation. In some embodiments, the pharmaceutically acceptable unit formulation comprises about 1% by weight to about 40% by weight of the crystalline dihydrate form of the compound of Formula (I) based on the weight of the pharmaceutically acceptable unit formulation. In some embodiments, the pharmaceutically acceptable unit formulation comprises about 1% by weight to about 35% by weight of the crystalline dihydrate form of the compound of Formula (I) based on the weight of the pharmaceutically acceptable unit formulation. In some embodiments, the pharmaceutically acceptable unit formulation comprises about 1% by weight to about 30% by weight of the crystalline dihydrate form of the compound of Formula (I) based on the weight of the pharmaceutically acceptable unit formulation. In some embodiments, the pharmaceutically acceptable unit formulation comprises about 1% by weight to about 25% by weight of the crystalline dihydrate form of the compound of Formula (I) based on the weight of the pharmaceutically acceptable unit formulation. In some embodiments, the pharmaceutically acceptable unit formulation comprises about 1% by weight to about 20% by weight of the crystalline dihydrate form of the compound of Formula (I) based on the weight of the pharmaceutically acceptable unit formulation. In some embodiments, the pharmaceutically acceptable unit formulation comprises about 1% by weight to about 15% by weight of the crystalline dihydrate form of the compound of Formula (I) based on the weight of the pharmaceutically acceptable unit formulation. In some embodiments, the pharmaceutically acceptable unit formulation comprises about 1% by weight to about 10% by weight of the crystalline dihydrate form of the compound of Formula (I) based on the weight of the pharmaceutically acceptable unit formulation.

In some embodiments, the pharmaceutically acceptable unit formulation consists essentially of about 1% by weight to about 70% by weight of the crystalline dihydrate form of the compound of Formula (I) based on the weight of the pharmaceutically acceptable unit formulation. In some embodiments, the pharmaceutically acceptable unit formulation consists essentially of about 1% by weight to about 65% by weight of the crystalline dihydrate form of the compound of Formula (I) based on the weight of the pharmaceutically acceptable unit formulation. In some embodiments, the pharmaceutically acceptable unit formulation consists essentially of about 1% by weight to about 60% by weight of the crystalline dihydrate form of the compound of Formula (I) based on the weight of the pharmaceutically acceptable unit formulation. In some embodiments, the pharmaceutically acceptable unit formulation consists essentially of about 1% by weight to about 55% by weight of the crystalline dihydrate form of the compound of Formula (I) based on the weight of the pharmaceutically acceptable unit formulation. In some embodiments, the pharmaceutically acceptable unit formulation consists essentially of about 1% by weight to about 50% by weight of the crystalline dihydrate form of the compound of Formula (I) based on the weight of the pharmaceutically acceptable unit formulation. In some embodiments, the pharmaceutically acceptable unit formulation consists essentially of about 1% by weight to about 45% by weight of the crystalline dihydrate form of the compound of Formula (I) based on the weight of the pharmaceutically acceptable unit formulation. In some embodiments, the pharmaceutically acceptable unit formulation consists essentially of about 1% by weight to about 40% by weight of the crystalline dihydrate form of the compound of Formula (I) based on the weight of the pharmaceutically acceptable unit formulation. In some embodiments, the pharmaceutically acceptable unit formulation consists essentially of about 1% by weight to about 35% by weight of the crystalline dihydrate form of the compound of Formula (I) based on the weight of the pharmaceutically acceptable unit formulation. In some embodiments, the pharmaceutically acceptable unit formulation consists essentially of about 1% by weight to about 30% by weight of the crystalline dihydrate form of the compound of Formula (I) based on the weight of the pharmaceutically acceptable unit formulation. In some embodiments, the pharmaceutically acceptable unit formulation consists essentially of about 1% by weight to about 25% by weight of the crystalline dihydrate form of the compound of Formula (I) based on the weight of the pharmaceutically acceptable unit formulation. In some embodiments, the pharmaceutically acceptable unit formulation consists essentially of about 1% by weight to about 20% by weight of the crystalline dihydrate form of the compound of Formula (I) based on the weight of the pharmaceutically acceptable unit formulation. In some embodiments, the pharmaceutically acceptable unit formulation consists essentially of about 1% by weight to about 15% by weight of the crystalline dihydrate form of the compound of Formula (I) based on the weight of the pharmaceutically acceptable unit formulation. In some embodiments, the pharmaceutically acceptable unit formulation consists essentially of about 1% by weight to about 10% by weight of the crystalline dihydrate form of the compound of Formula (I) based on the weight of the pharmaceutically acceptable unit formulation.

In some embodiments, the pharmaceutically acceptable unit formulation comprises about 5% by weight to about 30% by weight of the crystalline dihydrate form of the compound of Formula (I) based on the weight of the pharmaceutically acceptable unit formulation. In some embodiments, the pharmaceutically acceptable unit formulation comprises about 5% by weight to about 25% by weight of the crystalline dihydrate form of the compound of Formula (I) based on the weight of the pharmaceutically acceptable unit formulation. In some embodiments, the pharmaceutically acceptable unit formulation comprises about 5% by weight to about 20% by weight of the crystalline dihydrate form of the compound of Formula (I) based on the weight of the pharmaceutically acceptable unit formulation. In some embodiments, the pharmaceutically acceptable unit formulation comprises about 5% by weight to about 15% by weight of the crystalline dihydrate form of the compound of Formula (I) based on the weight of the pharmaceutically acceptable unit formulation. In some embodiments, the pharmaceutically acceptable unit formulation comprises about 5% by weight to about 10% by weight of the crystalline dihydrate form of the compound of Formula (I) based on the weight of the pharmaceutically acceptable unit formulation.

In some embodiments, the pharmaceutically acceptable unit formulation consists essentially of about 5% by weight to about 30% by weight of the crystalline dihydrate form of the compound of Formula (I) based on the weight of the pharmaceutically acceptable unit formulation. In some embodiments, the pharmaceutically acceptable unit formulation consists essentially of about 5% by weight to about 25% by weight of the crystalline dihydrate form of the compound of Formula (I) based on the weight of the pharmaceutically acceptable unit formulation. In some embodiments, the pharmaceutically acceptable unit formulation consists essentially of about 5% by weight to about 20% by weight of the crystalline dihydrate form of the compound of Formula (I) based on the weight of the pharmaceutically acceptable unit formulation. In some embodiments, the pharmaceutically acceptable unit formulation consists essentially of about 5% by weight to about 15% by weight of the crystalline dihydrate form of the compound of Formula (I) based on the weight of the pharmaceutically acceptable unit formulation. In some embodiments, the pharmaceutically acceptable unit formulation consists essentially of about 5% by weight to about 10% by weight of the crystalline dihydrate form of the compound of Formula (I) based on the weight of the pharmaceutically acceptable unit formulation.

In some embodiments, the pharmaceutically acceptable unit formulation comprises about 10% to about 30% of the compound of Formula (I) based on the weight of the pharmaceutically acceptable unit formulation. In some embodiments, the pharmaceutically acceptable unit formulation comprises about 10% to about 25% of the compound of Formula (I) based on the weight of the pharmaceutically acceptable unit formulation. In some embodiments, the pharmaceutically acceptable unit formulation comprises about 10% to about 20% of the compound of Formula (I) based on the weight of the pharmaceutically acceptable unit formulation. In some embodiments, the pharmaceutically acceptable unit formulation comprises about 10% by weight to about 15% by weight of the crystalline dihydrate form of the compound of Formula (I) based on the weight of the pharmaceutically acceptable unit formulation.

In some embodiments, the pharmaceutically acceptable unit formulation consists essentially of about 10% to about 30% of the crystalline dihydrate form of the compound of Formula (I) based on the weight of the pharmaceutically acceptable unit formulation. In some embodiments, the pharmaceutically acceptable unit formulation consists essentially of about 10% to about 25% of the crystalline dihydrate form of the compound of Formula (I) based on the weight of the pharmaceutically acceptable unit formulation. In some embodiments, the pharmaceutically acceptable unit formulation consists essentially of about 10% to about 20% of the crystalline dihydrate form of the compound of Formula (I) based on the weight of the pharmaceutically acceptable unit formulation. In some embodiments, the pharmaceutically acceptable unit formulation consists essentially of about 10% by weight to about 15% by weight of the crystalline dihydrate form of the compound of Formula (I) based on the weight of the pharmaceutically acceptable unit formulation.

In some embodiments, the pharmaceutically acceptable unit formulation comprises about 1% by weight to about 30% by weight of the crystalline dihydrate form of the compound of Formula (I) based on the weight of the pharmaceutically acceptable unit formulation. In some embodiments, the pharmaceutically acceptable unit formulation comprises about 1% by weight to about 10% by weight of the crystalline dihydrate form of the compound of Formula (I) based on the weight of the pharmaceutically acceptable unit formulation. In some embodiments, the pharmaceutically acceptable unit formulation comprises about 10% to about 20% of the compound of Formula (I) based on the weight of the pharmaceutically acceptable unit formulation. In some embodiments, the pharmaceutically acceptable unit formulation comprises about 10% by weight to about 15% by weight of the crystalline dihydrate form of the compound of Formula (I) based on the weight of the pharmaceutically acceptable unit formulation.

In some embodiments, the pharmaceutically acceptable unit formulation consists essentially of about 1% by weight to about 30% by weight of the crystalline dihydrate form of the compound of Formula (I) based on the weight of the pharmaceutically acceptable unit formulation. In some embodiments, the pharmaceutically acceptable unit formulation consists essentially of about 1% by weight to about 10% by weight of the crystalline dihydrate form of the compound of Formula (I) based on the weight of the pharmaceutically acceptable unit formulation. In some embodiments, the pharmaceutically acceptable unit formulation consists essentially of about 10% to about 20% of the crystalline dihydrate form of the compound of Formula (I) based on the weight of the pharmaceutically acceptable unit formulation. In some embodiments, the pharmaceutically acceptable unit formulation consists essentially of about 10% by weight to about 15% by weight of the crystalline dihydrate form of the compound of Formula (I) based on the weight of the pharmaceutically acceptable unit formulation.

In some embodiments, the one or more pharmaceutically acceptable excipients comprise about 20% by weight to about 90% by weight of one or more fillers based on the weight of the pharmaceutically acceptable unit formulation. In some embodiments, the one or more pharmaceutically acceptable excipients comprise about 20% by weight to about 85% by weight of one or more fillers based on the weight of the pharmaceutically acceptable unit formulation. In some embodiments, the one or more pharmaceutically acceptable excipients comprise about 20% by weight to about 80% by weight of one or more fillers based on the weight of the pharmaceutically acceptable unit formulation. In some embodiments, the one or more pharmaceutically acceptable excipients comprise about 20% by weight to about 75% by weight of one or more fillers based on the weight of the pharmaceutically acceptable unit formulation. In some embodiments, the one or more pharmaceutically acceptable excipients comprise about 20% by weight to about 70% by weight of one or more fillers based on the weight of the pharmaceutically acceptable unit formulation. In some embodiments, the one or more pharmaceutically acceptable excipients comprise about 20% by weight to about 65% by weight of one or more fillers based on the weight of the pharmaceutically acceptable unit formulation. In some embodiments, the one or more pharmaceutically acceptable excipients comprise about 20% by weight to about 60% by weight of one or more fillers based on the weight of the pharmaceutically acceptable unit formulation. In some embodiments, the one or more pharmaceutically acceptable excipients comprise about 20% by weight to about 55% by weight of one or more fillers based on the weight of the pharmaceutically acceptable unit formulation. In some embodiments, the one or more pharmaceutically acceptable excipients comprise about 20% by weight to about 50% by weight of one or more fillers based on the weight of the pharmaceutically acceptable unit formulation. In some embodiments, the one or more pharmaceutically acceptable excipients comprise about 20% by weight to about 45% by weight of one or more fillers based on the weight of the pharmaceutically acceptable unit formulation. In some embodiments, the one or more pharmaceutically acceptable excipients comprise about 20% by weight to about 40% by weight of one or more fillers based on the weight of the pharmaceutically acceptable unit formulation. In some embodiments, the one or more pharmaceutically acceptable excipients comprise about 20% by weight to about 35% by weight of one or more fillers based on the weight of the pharmaceutically acceptable unit formulation. In some embodiments, the one or more pharmaceutically acceptable excipients comprise about 20% by weight to about 30% by weight of one or more fillers based on the weight of the pharmaceutically acceptable unit formulation. In some embodiments, the one or more pharmaceutically acceptable excipients comprise about 20% by weight to about 25% by weight of one or more fillers based on the weight of the pharmaceutically acceptable unit formulation.

In some embodiments, the one or more pharmaceutically acceptable excipients comprise about 30% by weight to about 90% by weight of one or more fillers based on the weight of the pharmaceutically acceptable unit formulation. In some embodiments, the one or more pharmaceutically acceptable excipients comprise about 30% by weight to about 80% by weight of one or more fillers based on the weight of the pharmaceutically acceptable unit formulation. In some embodiments, the one or more pharmaceutically acceptable excipients comprise about 30% by weight to about 70% by weight of one or more fillers based on the weight of the pharmaceutically acceptable unit formulation. In some embodiments, the one or more pharmaceutically acceptable excipients comprise about 30% by weight to about 60% by weight of one or more fillers based on the weight of the pharmaceutically acceptable unit formulation. In some embodiments, the one or more pharmaceutically acceptable excipients comprise about 30% by weight to about 50% by weight of one or more fillers based on the weight of the pharmaceutically acceptable unit formulation. In some embodiments, the one or more pharmaceutically acceptable excipients comprise about 30% by weight to about 40% by weight of one or more fillers based on the weight of the pharmaceutically acceptable unit formulation.

In some embodiments, the one or more pharmaceutically acceptable excipients comprise about 40% by weight to about 90% by weight of one or more fillers based on the weight of the pharmaceutically acceptable unit formulation. In some embodiments, the one or more pharmaceutically acceptable excipients comprise about 40% by weight to about 80% by weight of one or more fillers based on the weight of the pharmaceutically acceptable unit formulation. In some embodiments, the one or more pharmaceutically acceptable excipients comprise about 40% by weight to about 70% by weight of one or more fillers based on the weight of the pharmaceutically acceptable unit formulation. In some embodiments, the one or more pharmaceutically acceptable excipients comprise about 40% by weight to about 60% by weight of one or more fillers based on the weight of the pharmaceutically acceptable unit formulation. In some embodiments, the one or more pharmaceutically acceptable excipients comprise about 40% by weight to about 50% by weight of one or more fillers based on the weight of the pharmaceutically acceptable unit formulation.

In some embodiments, the one or more pharmaceutically acceptable excipients comprise about 50% by weight to about 90% by weight of one or more fillers based on the weight of the pharmaceutically acceptable unit formulation. In some embodiments, the one or more pharmaceutically acceptable excipients comprise about 50% by weight to about 80% by weight of one or more fillers based on the weight of the pharmaceutically acceptable unit formulation. In some embodiments, the one or more pharmaceutically acceptable excipients comprise about 50% by weight to about 70% by weight of one or more fillers based on the weight of the pharmaceutically acceptable unit formulation. In some embodiments, the one or more pharmaceutically acceptable excipients comprise about 50% by weight to about 60% by weight of one or more fillers based on the weight of the pharmaceutically acceptable unit formulation.

In some embodiments, the one or more pharmaceutically acceptable excipients comprise about 60% by weight to about 90% by weight of one or more fillers based on the weight of the pharmaceutically acceptable unit formulation. In some embodiments, the one or more pharmaceutically acceptable excipients comprise about 60% by weight to about 80% by weight of one or more fillers based on the weight of the pharmaceutically acceptable unit formulation. In some embodiments, the one or more pharmaceutically acceptable excipients comprise about 60% by weight to about 70% by weight of one or more fillers based on the weight of the pharmaceutically acceptable unit formulation.

In some embodiments, the one or more pharmaceutically acceptable excipients comprise about 70% by weight to about 90% by weight of one or more fillers based on the weight of the pharmaceutically acceptable unit formulation. In some embodiments, the one or more pharmaceutically acceptable excipients comprise about 70% by weight to about 80% by weight of one or more fillers based on the weight of the pharmaceutically acceptable unit formulation.

In some embodiments, the one or more pharmaceutically acceptable excipients comprise about 80% by weight to about 90% by weight of one or more fillers based on the weight of the pharmaceutically acceptable unit formulation.

In some embodiments, the one or more pharmaceutically acceptable excipients comprise about 1% by weight to about 20% by weight of one or more disintegrants based on the weight of the pharmaceutically acceptable unit formulation. In some embodiments, the one or more pharmaceutically acceptable excipients comprise about 1% by weight to about 15% by weight of one or more disintegrants based on the weight of the pharmaceutically acceptable unit formulation. In some embodiments, the one or more pharmaceutically acceptable excipients comprise about 1% by weight to about 14% by weight of one or more disintegrants based on the weight of the pharmaceutically acceptable unit formulation. In some embodiments, the one or more pharmaceutically acceptable excipients comprise about 1% by weight to about 13% by weight of one or more disintegrants based on the weight of the pharmaceutically acceptable unit formulation. In some embodiments, the one or more pharmaceutically acceptable excipients comprise about 1% by weight to about 12% by weight of one or more disintegrants based on the weight of the pharmaceutically acceptable unit formulation. In some embodiments, the one or more pharmaceutically acceptable excipients comprise about 1% by weight to about 11% by weight of one or more disintegrants based on the weight of the pharmaceutically acceptable unit formulation. In some embodiments, the one or more pharmaceutically acceptable excipients comprise about 1% by weight to about 10% by weight of one or more disintegrants based on the weight of the pharmaceutically acceptable unit formulation. In some embodiments, the one or more pharmaceutically acceptable excipients comprise about 1% by weight to about 9% by weight of one or more disintegrants based on the weight of the pharmaceutically acceptable unit formulation. In some embodiments, the one or more pharmaceutically acceptable excipients comprise about 1% by weight to about 8% by weight of one or more disintegrants based on the weight of the pharmaceutically acceptable unit formulation. In some embodiments, the one or more pharmaceutically acceptable excipients comprise about 1% by weight to about 7% by weight of one or more disintegrants based on the weight of the pharmaceutically acceptable unit formulation. In some embodiments, the one or more pharmaceutically acceptable excipients comprise about 1% by weight to about 6% by weight of one or more disintegrants based on the weight of the pharmaceutically acceptable unit formulation. In some embodiments, the one or more pharmaceutically acceptable excipients comprise about 1% by weight to about 5% by weight of one or more disintegrants based on the weight of the pharmaceutically acceptable unit formulation. In some embodiments, the one or more pharmaceutically acceptable excipients comprise about 1% by weight to about 4% by weight of one or more disintegrants based on the weight of the pharmaceutically acceptable unit formulation. In some embodiments, the one or more pharmaceutically acceptable excipients comprise about 1% by weight to about 3% by weight of one or more disintegrants based on the weight of the pharmaceutically acceptable unit formulation.

In some embodiments, the one or more pharmaceutically acceptable excipients comprise about 1% by weight of one or more disintegrants based on the weight of the pharmaceutically acceptable unit formulation. In some embodiments, the one or more pharmaceutically acceptable excipients comprise about 2% by weight of one or more disintegrants based on the weight of the pharmaceutically acceptable unit formulation. In some embodiments, the one or more pharmaceutically acceptable excipients comprise about 3% by weight of one or more disintegrants based on the weight of the pharmaceutically acceptable unit formulation. In some embodiments, the one or more pharmaceutically acceptable excipients comprise about 4% by weight of one or more disintegrants based on the weight of the pharmaceutically acceptable unit formulation. In some embodiments, the one or more pharmaceutically acceptable excipients comprise about 5% by weight of one or more disintegrants based on the weight of the pharmaceutically acceptable unit formulation. In some embodiments, the one or more pharmaceutically acceptable excipients comprise about 6% by weight of one or more disintegrants based on the weight of the pharmaceutically acceptable unit formulation. In some embodiments, the one or more pharmaceutically acceptable excipients comprise about 7% by weight of one or more disintegrants based on the weight of the pharmaceutically acceptable unit formulation. In some embodiments, the one or more pharmaceutically acceptable excipients comprise about 8% by weight of one or more disintegrants based on the weight of the pharmaceutically acceptable unit formulation. In some embodiments, the one or more pharmaceutically acceptable excipients comprise about 9% by weight of one or more disintegrants based on the weight of the pharmaceutically acceptable unit formulation. In some embodiments, the one or more pharmaceutically acceptable excipients comprise about 10% by weight of one or more disintegrants based on the weight of the pharmaceutically acceptable unit formulation. In some embodiments, the one or more pharmaceutically acceptable excipients comprise about 11% by weight of one or more disintegrants based on the weight of the pharmaceutically acceptable unit formulation. In some embodiments, the one or more pharmaceutically acceptable excipients comprise about 12% by weight of one or more disintegrants based on the weight of the pharmaceutically acceptable unit formulation. In some embodiments, the one or more pharmaceutically acceptable excipients comprise about 13% by weight of one or more disintegrants based on the weight of the pharmaceutically acceptable unit formulation. In some embodiments, the one or more pharmaceutically acceptable excipients comprise about 14% by weight of one or more disintegrants based on the weight of the pharmaceutically acceptable unit formulation. In some embodiments, the one or more pharmaceutically acceptable excipients comprise about 15% by weight of one or more disintegrants based on the weight of the pharmaceutically acceptable unit formulation.

In some embodiments, the one or more pharmaceutically acceptable excipients comprise about 0.1% by weight to about 10% by weight of one or more lubricants based on the weight of the pharmaceutically acceptable unit formulation. In some embodiments, the one or more pharmaceutically acceptable excipients comprise about 0.1% by weight to about 9% by weight of one or more lubricants based on the weight of the pharmaceutically acceptable unit formulation. In some embodiments, the one or more pharmaceutically acceptable excipients comprise about 0.1% by weight to about 8% by weight of one or more lubricants based on the weight of the pharmaceutically acceptable unit formulation. In some embodiments, the one or more pharmaceutically acceptable excipients comprise about 0.1% by weight to about 7% by weight of one or more lubricants based on the weight of the pharmaceutically acceptable unit formulation. In some embodiments, the one or more pharmaceutically acceptable excipients comprise about 0.1% by weight to about 6% by weight of one or more lubricants based on the weight of the pharmaceutically acceptable unit formulation. In some embodiments, the one or more pharmaceutically acceptable excipients comprise about 0.1% by weight to about 5% by weight of one or more lubricants based on the weight of the pharmaceutically acceptable unit formulation. In some embodiments, the one or more pharmaceutically acceptable excipients comprise about 0.1% by weight to about 4% by weight of one or more lubricants based on the weight of the pharmaceutically acceptable unit formulation. In some embodiments, the one or more pharmaceutically acceptable excipients comprise about 0.1% by weight to about 3% by weight of one or more lubricants based on the weight of the pharmaceutically acceptable unit formulation. In some embodiments, the one or more pharmaceutically acceptable excipients comprise about 0.1% by weight to about 2% by weight of one or more lubricants based on the weight of the pharmaceutically acceptable unit formulation.

In some embodiments, the one or more pharmaceutically acceptable excipients comprise about 0.1% by weight to about 1.9% by weight of one or more lubricants based on the weight of the pharmaceutically acceptable unit formulation. In some embodiments, the one or more pharmaceutically acceptable excipients comprise about 0.1% by weight to about 1.8% by weight of one or more lubricants based on the weight of the pharmaceutically acceptable unit formulation. In some embodiments, the one or more pharmaceutically acceptable excipients comprise about 0.1% by weight to about 1.7% by weight of one or more lubricants based on the weight of the pharmaceutically acceptable unit formulation. In some embodiments, the one or more pharmaceutically acceptable excipients comprise about 0.1% by weight to about 1.6% by weight of one or more lubricants based on the weight of the pharmaceutically acceptable unit formulation. In some embodiments, the one or more pharmaceutically acceptable excipients comprise about 0.1% by weight to about 1.5% by weight of one or more lubricants based on the weight of the pharmaceutically acceptable unit formulation. In some embodiments, the one or more pharmaceutically acceptable excipients comprise about 0.1% by weight to about 1.4% by weight of one or more lubricants based on the weight of the pharmaceutically acceptable unit formulation. In some embodiments, the one or more pharmaceutically acceptable excipients comprise about 0.1% by weight to about 1.3% by weight of one or more lubricants based on the weight of the pharmaceutically acceptable unit formulation. In some embodiments, the one or more pharmaceutically acceptable excipients comprise about 0.1% by weight to about 1.2% by weight of one or more lubricants based on the weight of the pharmaceutically acceptable unit formulation. In some embodiments, the one or more pharmaceutically acceptable excipients comprise about 0.1% by weight to about 1.1% by weight of one or more lubricants based on the weight of the pharmaceutically acceptable unit formulation. In some embodiments, the one or more pharmaceutically acceptable excipients comprise about 0.1% by weight to about 1.0% by weight of one or more lubricants based on the weight of the pharmaceutically acceptable unit formulation. In some embodiments, the one or more pharmaceutically acceptable excipients comprise about 0.1% by weight to about 0.9% by weight of one or more lubricants based on the weight of the pharmaceutically acceptable unit formulation. In some embodiments, the one or more pharmaceutically acceptable excipients comprise about 0.1% by weight to about 0.8% by weight of one or more lubricants based on the weight of the pharmaceutically acceptable unit formulation. In some embodiments, the one or more pharmaceutically acceptable excipients comprise about 0.1% by weight to about 0.7% by weight of one or more lubricants based on the weight of the pharmaceutically acceptable unit formulation. In some embodiments, the one or more pharmaceutically acceptable excipients comprise about 0.1% by weight to about 0.6% by weight of one or more lubricants based on the weight of the pharmaceutically acceptable unit formulation. In some embodiments, the one or more pharmaceutically acceptable excipients comprise about 0.1% by weight to about 0.5% by weight of one or more lubricants based on the weight of the pharmaceutically acceptable unit formulation. In some embodiments, the one or more pharmaceutically acceptable excipients comprise about 0.1% by weight to about 0.4% by weight of one or more lubricants based on the weight of the pharmaceutically acceptable unit formulation. In some embodiments, the one or more pharmaceutically acceptable excipients comprise about 0.1% by weight to about 0.3% by weight of one or more lubricants based on the weight of the pharmaceutically acceptable unit formulation. In some embodiments, the one or more pharmaceutically acceptable excipients comprise about 0.1% by weight to about 0.2% by weight of one or more lubricants based on the weight of the pharmaceutically acceptable unit formulation.

In some embodiments, the one or more pharmaceutically acceptable excipients comprise about 0.1% by weight of one or more lubricants based on the weight of the pharmaceutically acceptable unit formulation. In some embodiments, the one or more pharmaceutically acceptable excipients comprise about 0.2% by weight of one or more lubricants based on the weight of the pharmaceutically acceptable unit formulation. In some embodiments, the one or more pharmaceutically acceptable excipients comprise about 0.3% by weight of one or more lubricants based on the weight of the pharmaceutically acceptable unit formulation. In some embodiments, the one or more pharmaceutically acceptable excipients comprise about 0.4% by weight of one or more lubricants based on the weight of the pharmaceutically acceptable unit formulation. In some embodiments, the one or more pharmaceutically acceptable excipients comprise about 0.5% by weight of one or more lubricants based on the weight of the pharmaceutically acceptable unit formulation. In some embodiments, the one or more pharmaceutically acceptable excipients comprise about 0.6% by weight of one or more lubricants based on the weight of the pharmaceutically acceptable unit formulation. In some embodiments, the one or more pharmaceutically acceptable excipients comprise about 0.7% by weight of one or more lubricants based on the weight of the pharmaceutically acceptable unit formulation. In some embodiments, the one or more pharmaceutically acceptable excipients comprise about 0.8% by weight of one or more lubricants based on the weight of the pharmaceutically acceptable unit formulation. In some embodiments, the one or more pharmaceutically acceptable excipients comprise about 0.9% by weight of one or more lubricants based on the weight of the pharmaceutically acceptable unit formulation. In some embodiments, the one or more pharmaceutically acceptable excipients comprise about 1.0% by weight of one or more lubricants based on the weight of the pharmaceutically acceptable unit formulation.

In some embodiments, the pharmaceutically acceptable unit formulation comprises: (a) about 1% by weight to about 30% by weight of the compound of Formula (I) based on the weight of the pharmaceutically acceptable unit formulation; (b) about 20% by weight to about 90% by weight of one or more fillers based on the weight of the pharmaceutically acceptable unit formulation; (c) about 1% by weight to about 20% by weight of one or more disintegrants based on the weight of the pharmaceutically acceptable unit formulation; and (d) about 0.1% by weight to about 10% by weight of one or more lubricants based on the weight of the pharmaceutically acceptable unit formulation.

In some embodiments, the pharmaceutically acceptable unit formulation consists essentially of: (a) about 1% by weight to about 30% by weight of the compound of Formula (I) based on the weight of the pharmaceutically acceptable unit formulation; (b) about 20% by weight to about 90% by weight of one or more fillers based on the weight of the pharmaceutically acceptable unit formulation; (c) about 1% by weight to about 20% by weight of one or more disintegrants based on the weight of the pharmaceutically acceptable unit formulation; and (d) about 0.1% by weight to about 10% by weight of one or more lubricants based on the weight of the pharmaceutically acceptable unit formulation.

In some embodiments, the pharmaceutically acceptable unit formulation comprises (a) about 5% by weight to about 25% by weight of the crystalline dihydrate form of the compound of Formula (I) based on the weight of the pharmaceutically acceptable unit formulation; (b) about 60% by weight to about 90% by weight of one or more fillers based on the weight of the pharmaceutically acceptable unit formulation; (c) about 1% by weight to about 15% by weight of one or more disintegrants based on the weight of the pharmaceutically acceptable unit formulation; and (d) about 0.1% by weight to about 4% by weight of one or more lubricants based on the weight of the pharmaceutically acceptable unit formulation.

In some embodiments, the pharmaceutically acceptable unit formulation consists essentially of: (a) about 5% by weight to about 25% by weight of the crystalline dihydrate form of the compound of Formula (I) based on the weight of the pharmaceutically acceptable unit formulation; (b) about 60% by weight to about 90% by weight of one or more fillers based on the weight of the pharmaceutically acceptable unit formulation; (c) about 1% by weight to about 15% by weight of one or more disintegrants based on the weight of the pharmaceutically acceptable unit formulation; and (d) about 0.1% by weight to about 4% by weight of one or more lubricants based on the weight of the pharmaceutically acceptable unit formulation.

In some embodiments, the pharmaceutically acceptable unit formulation comprises (a) about 10% by weight to about 30% by weight of the crystalline dihydrate form of the compound of Formula (I) based on the weight of the pharmaceutically acceptable unit formulation; (b) about 70% by weight to about 90% by weight of one or more fillers based on the weight of the pharmaceutically acceptable unit formulation; (c) about 1% by weight to about 10% by weight of one or more disintegrants based on the weight of the pharmaceutically acceptable unit formulation; and (d) about 0.1% by weight to about 3% by weight of one or more lubricants based on the weight of the pharmaceutically acceptable unit formulation.

In some embodiments, the pharmaceutically acceptable unit formulation consists essentially of: (a) about 10% by weight to about 30% by weight of the crystalline dihydrate form of the compound of Formula (I) based on the weight of the pharmaceutically acceptable unit formulation; (b) about 70% by weight to about 90% by weight of one or more fillers based on the weight of the pharmaceutically acceptable unit formulation; (c) about 1% by weight to about 10% by weight of one or more disintegrants based on the weight of the pharmaceutically acceptable unit formulation; and (d) about 0.1% by weight to about 3% by weight of one or more lubricants based on the weight of the pharmaceutically acceptable unit formulation.

In some embodiments, the one or more pharmaceutically acceptable excipients is one or more fillers selected from the group consisting of calcium phosphate, dicalcium phosphate, dicalcium phosphate dihydrate, calcium sulfate, calcium sulfate dihydrate, starch, calcium carbonate, magnesium carbonate, magnesium oxide, kaolin (natural hydrated aluminum silicate), sodium chloride, partially gelatinized starch, anhydrous lactose, lactose monohydrate, lactose dihydrate, trehalose dihydrate, spray dried lactose, sucrose, dextrose, dextrates, dextrin, cellulose, microcrystalline cellulose, silicified microcrystalline cellulose, powdered cellulose, partially depolymerized cellulose, mannitol, granulated mannitol, spray dried mannitol, maltodextrin, maltitol, confectioner's sugar, compressible sugar, sorbitol, starch and talc. In some embodiments, the one or more fillers is lactose monohydrate.

In some embodiments, the one or more disintegrants is one or more disintegrants selected from the group consisting of sodium starch glycolate, pregelatinized starch, clay, cellulose, alginic acid, alginate gum, polyvinylpyrrolidone, cross-linked polyvinylpyrrolidone, cross-linked calcium carboxymethylcellulose, cross-linked sodium carboxymethylcellulose, sodium croscarmellose, sodium carmellose, low substituted hydroxypropyl cellulose, low substituted hydroxypropyl cellulose sodium, guar gum, magnesium aluminum silicate, polacrilin potassium, powdered cellulose, sodium alginate and soy polysaccharides. In some embodiments, the one or more disintegrants is cross-linked polyvinylpyrrolidone (also referred to as crospovidone).

In some embodiments, the one or more lubricants is one or more lubricants selected from the group consisting of colloidal silica, magnesium trisilicate, talc, magnesium carbonate, magnesium oxide, glyceryl behaptate, mono, di and tri glyceryl behenate, bees wax, behenoyl polyoxyl-8 glycerides, hydrogenated vegetable oil, polyethylene glycol, ethylene oxide polymer, copolymer comprising poly(ethylene oxide) and poly(propylene oxide) (such as poloxomer 188), copolymer comprising polypropylene glycol and polyethylene glycol (such as poloxomer 407), sodium lauryl sulfate, magnesium stearate, aluminum stearate, calcium stearate, sodium stearyl fumarate, stearic acid, magnesium lauryl stearate, mixtures of magnesium stearate with sodium lauryl sulfate. In some embodiments, the one or more lubricants is magnesium stearate.

In some embodiments, the one or more disintegrants is selected from the group consisting of cross-linked polyvinylpyrrolidone, croscarmellose sodium, and sodium starch glycolate; and the one or more lubricants is selected from the group consisting of sodium stearyl fumarate, stearic acid, talc, calcium stearate, magnesium stearate, solid polyethylene glycols, and sodium lauryl sulfate. In some embodiments, the pharmaceutically acceptable unit formulation comprises cross-linked polyvinylpyrrolidone and magnesium stearate. In some embodiments, the one or more pharmaceutically acceptable excipients is lactose monohydrate and the pharmaceutically acceptable unit formulation further comprises cross-linked polyvinylpyrrolidone and magnesium stearate.

In some embodiments, the pharmaceutically acceptable unit formulation is for oral administration.

In some embodiments, the pharmaceutically acceptable unit formulation is a solid dosage form.

In some embodiments, the pharmaceutically acceptable unit formulation is a tablet or capsule. In some embodiments, the pharmaceutically acceptable unit formulation is a tablet. In some embodiments, the pharmaceutically acceptable unit formulation is a capsule. In some embodiments, the pharmaceutically acceptable unit formulation is a sachet. In some embodiments, the pharmaceutically acceptable unit formulation is a powder in a packet.

In some embodiments, the pharmaceutically acceptable unit formulation comprises about 1 mg to about 40 mg of the crystalline dihydrate form of the compound of Formula (I).

In some embodiments, the pharmaceutically acceptable unit formulation comprises about 5 mg to about 35 mg of the crystalline dihydrate form of the compound of Formula (I). In some embodiments, the pharmaceutically acceptable unit formulation comprises about 10 mg to about 35 mg of the crystalline dihydrate form of the compound of Formula (I). In some embodiments, the pharmaceutically acceptable unit formulation comprises about 0.5 mg to about 5 mg, about 6 mg to about 14 mg, about 11 mg to about 19 mg, about 17 mg to about 25 mg, or about 28 mg to about 36 mg of the crystalline dihydrate form of the compound of Formula (I). In some embodiments, the pharmaceutically acceptable unit formulation comprises about 1 mg to about 4 mg, about 8 mg to about 12 mg, about 13 mg to about 17 mg, about 19 mg to about 23 mg, or about 30 mg to about 34 mg of the crystalline dihydrate form of the compound of Formula (I). In some embodiments, the pharmaceutically acceptable unit formulation comprises about 2.2 mg, about 10.8 mg, about 15.2 mg, about 21.7 mg, or about 32.5 mg of the crystalline dihydrate form of the compound of Formula (I). In some embodiments, the crystalline dihydrate form of the compound of Formula (I) is present in an amount of about 2.2 mg. In some embodiments, the crystalline dihydrate form of the compound of Formula (I) is present in an amount of about 10.8 mg. In some embodiments, the crystalline dihydrate form of the compound of Formula (I) is present in an amount of about 15.2 mg. In some embodiments, the crystalline dihydrate form of the compound of Formula (I) is present in an amount of about 21.7 mg. In some embodiments, the crystalline dihydrate form of the compound of Formula (I) is present in an amount of about 32.5 mg.

In some embodiments, the pharmaceutically acceptable unit formulation consists essentially of about 1 mg to about 40 mg of the crystalline dihydrate form of the compound of Formula (I). In some embodiments, the pharmaceutically acceptable unit formulation consists essentially of about 5 mg to about 35 mg of the crystalline dihydrate form of the compound of Formula (I). In some embodiments, the pharmaceutically acceptable unit formulation consists essentially of about 10 mg to about 35 mg of the crystalline dihydrate form of the compound of Formula (I). In some embodiments, the pharmaceutically acceptable unit formulation consists essentially of about 0.5 mg to about 5 mg, about 6 mg to about 14 mg, about 11 mg to about 19 mg, about 17 mg to about 25 mg, or about 28 mg to about 36 mg of the crystalline dihydrate form of the compound of Formula (I). In some embodiments, the pharmaceutically acceptable unit formulation consists essentially of about 1 mg to about 4 mg, about 8 mg to about 12 mg, about 13 mg to about 17 mg, about 19 mg to about 23 mg, or about 30 mg to about 34 mg of the crystalline dihydrate form of the compound of Formula (I). In some embodiments, the pharmaceutically acceptable unit formulation consists essentially of about 2.2 mg, about 10.8 mg, about 15.2 mg, about 21.7 mg, or about 32.5 mg of the crystalline dihydrate form of the compound of Formula (I). In some embodiments, the crystalline dihydrate form of the compound of Formula (I) is present in an amount of about 2.2 mg. In some embodiments, the crystalline dihydrate form of the compound of Formula (I) is present in an amount of about 10.8 mg. In some embodiments, the crystalline dihydrate form of the compound of Formula (I) is present in an amount of about 15.2 mg. In some embodiments, the crystalline dihydrate form of the compound of Formula (I) is present in an amount of about 21.7 mg. In some embodiments, the crystalline dihydrate form of the compound of Formula (I) is present in an amount of about 32.5 mg.

In some embodiments, the pharmaceutically acceptable unit formulation has an acceptance value of less than about 15 as determined by USP Uniformity of Dosage Unit <905>. In some embodiments, the pharmaceutically acceptable unit formulation has a maximum acceptance value of equal to or less than about 15 as determined by USP Uniformity of Dosage Unit <905>.

In some embodiments, the uniformity of the pharmaceutically acceptable formulation represents the degree of uniformity in the amount of the compound of Formula (I) in the pharmaceutically acceptable formulation.

In some embodiments, the uniformity of the oral dosage form represents the degree of uniformity in the amount of the compound of Formula (I) in the oral dosage form.

In some embodiments, the uniformity of the pharmaceutically acceptable capsule represents the degree of uniformity in the amount of the compound of Formula (I) in the pharmaceutically acceptable capsule.

Also provided herein, in some embodiments, are oral dosage forms comprising a compound of Formula (I):

Formula (I)

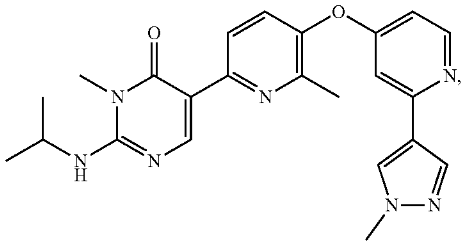

and one or more pharmaceutically acceptable excipients, wherein the compound is present in the oral dosage forms as a free base, or a pharmaceutically acceptable salt of the compound, and wherein the free base or pharmaceutically acceptable salt is in anhydrous or hydrate form.

In some embodiments, the compound of Formula (I) is present in the oral dosage form as a hydrate form (the compound of Formula (I)$\cdot$n$H_2O$). For example, the hydrate form is a hemihydrate form, a monohydrate form, a sesquihydrate form, a dihydrate form, a trihydrate form, a tetrahydrate form, a pentahydrate form, a hexahydrate form, a heptahydrate form, an octahydrate form, a nonahydrate form, or a decahydrate form. In some embodiments, the hydrate form is a hemihydrate form, a monohydrate form, a sesquihydrate form, a dihydrate form, a trihydrate form, or a tetrahydrate form. In some embodiments, the hydrate form is a hemihydrate form. In some embodiments, the hydrate form is a monohydrate form. In some embodiments, the hydrate form is a dihydrate form. In some embodiments, the compound of Formula (I) is present in the oral dosage form as a dihydrate form. In some embodiments, the compound of Formula (I) is present in the oral dosage form as an anhydrous form.

In some embodiments, the one or more pharmaceutically acceptable excipients is a filler. For example, the one or more pharmaceutically acceptable excipients is lactose, such as lactose monohydrate.

In some embodiments, the oral dosage forms further comprise one or more disintegrants, one or more lubricants, or a combination thereof. For example, in some embodiments, the oral dosage forms further comprise one or more disintegrants. In some embodiments, the oral dosage forms further comprise one or more lubricants.

Also provided herein, in some embodiments, is an oral dosage form comprising:

(a) about 1% by weight to about 70% by weight, based on the total weight of the oral dosage form, of a compound of Formula (I):

Formula (I)

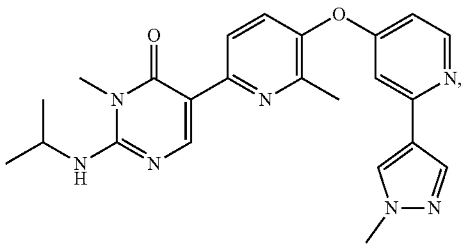

wherein the compound is present in the oral dosage form as a free base, or a pharmaceutically acceptable salt of the compound and wherein the free base or pharmaceutically acceptable salt is in anhydrous or hydrate form, and one or more pharmaceutically acceptable excipients, wherein the one or more pharmaceutically acceptable excipients comprise:

(b) about 20% by weight to about 97% by weight of one or more fillers based on the total weight of the oral dosage form;

(c) about 1% by weight to about 20% by weight of one or more disintegrants based on the total weight of the oral dosage form; and (d) about 0.1% by weight to about 10% by weight of one or more lubricants based on the total weight of the oral dosage form.

Also provided herein, in some embodiments, is an oral dosage form comprising:

(a) about 10% by weight to about 30% by weight of the compound of Formula (I) based on the total weight of the oral dosage form;

(b) about 70% by weight to about 90% by weight of one or more fillers based on the total weight of the oral dosage form;

(c) about 1% by weight to about 10% by weight of one or more disintegrants based on the total weight of the oral dosage form; and (d) about 0.1% by weight to about 3% by weight of one or more lubricants based on the total weight of the oral dosage form.

Also provided herein, in some embodiments, is an oral dosage form consisting essentially of:

(a) about 1% by weight to about 70% by weight, based on the total weight of the oral dosage form, of a compound of Formula (I):

Formula (I)

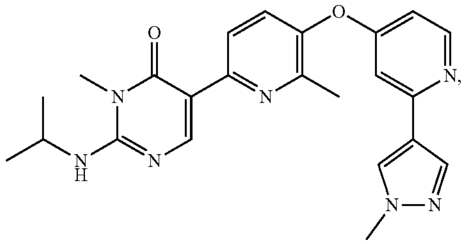

wherein the compound is present in the oral dosage form as a free base, or a pharmaceutically acceptable salt of the compound and wherein the free base or pharmaceutically acceptable salt is in anhydrous or hydrate form, and one or more pharmaceutically acceptable excipients, wherein the one or more pharmaceutically acceptable excipients comprise:

(b) about 20% by weight to about 97% by weight of one or more fillers based on the total weight of the oral dosage form;

(c) about 1% by weight to about 20% by weight of one or more disintegrants based on the total weight of the oral dosage form; and (d) about 0.1% by weight to about 10% by weight of one or more lubricants based on the total weight of the oral dosage form.

Also provided herein, in some embodiments, is an oral dosage form consisting essentially of:

(a) about 1% by weight to about 30% by weight of a compound of Formula (I) based on the total weight of the oral dosage form;

(b) about 20% by weight to about 90% by weight of one or more fillers based on the total weight of the oral dosage form;

(c) about 1% by weight to about 20% by weight of one or more disintegrants based on the total weight of the oral dosage form; and (d) about 0.1% by weight to about 10% by weight of one or more lubricants based on the total weight of the oral dosage form.

In some embodiments, the oral dosage form comprises about 1% by weight to about 60% by weight, based on the total weight of the oral dosage form, of a compound of Formula (I), wherein the compound is present in the oral dosage form as a free base, or a pharmaceutically acceptable salt of the compound and wherein the free base or pharmaceutically acceptable salt is in anhydrous or hydrate form. In some embodiments, the oral dosage form comprises about 1% by weight to about 50% by weight, based on the total weight of the oral dosage form, of a compound of Formula (I), wherein the compound is present in the oral dosage form as a free base, or a pharmaceutically acceptable salt of the compound and wherein the free base or pharmaceutically acceptable salt is in anhydrous or hydrate form. In some embodiments, the oral dosage form comprises about 1% by weight to about 40% by weight, based on the total weight of the oral dosage form, of a compound of Formula (I), wherein the compound is present in the oral dosage form as a free base, or a pharmaceutically acceptable salt of the compound and wherein the free base or pharmaceutically acceptable salt is in anhydrous or hydrate form. In some embodiments, the oral dosage form comprises about 1% by weight to about 30% by weight, based on the total weight of the oral dosage form, of a compound of Formula (I), wherein the compound is present in the oral dosage form as a free base, or a pharmaceutically acceptable salt of the compound and wherein the free base or pharmaceutically acceptable salt is in anhydrous or hydrate form. In some embodiments, the oral dosage form comprises about 1% by weight to about 20% by weight, based on the total weight of the oral dosage form, of a compound of Formula (I), wherein the compound is present in the oral dosage form as a free base, or a pharmaceutically acceptable salt of the compound and wherein the free base or pharmaceutically acceptable salt is in anhydrous or hydrate form.

In some embodiments, the oral dosage form consists essentially of about 1% by weight to about 60% by weight, based on the total weight of the oral dosage form, of a compound of Formula (I), wherein the compound is present in the oral dosage form as a free base, or a pharmaceutically acceptable salt of the compound and wherein the free base or pharmaceutically acceptable salt is in anhydrous or hydrate form. In some embodiments, the oral dosage form consists essentially of about 1% by weight to about 50% by weight, based on the total weight of the oral dosage form, of a compound of Formula (I), wherein the compound is present in the oral dosage form as a free base, or a pharmaceutically acceptable salt of the compound and wherein the free base or pharmaceutically acceptable salt is in anhydrous or hydrate form. In some embodiments, the oral dosage form consists essentially of about 1% by weight to about 40% by weight, based on the total weight of the oral dosage form, of a compound of Formula (I), wherein the compound is present in the oral dosage form as a free base, or a pharmaceutically acceptable salt of the compound and wherein the free base or pharmaceutically acceptable salt is in anhydrous or hydrate form. In some embodiments, the oral dosage form consists essentially of about 1% by weight to about 30% by weight, based on the total weight of the oral dosage form, of a compound of Formula (I), wherein the compound is present in the oral dosage form as a free base, or a pharmaceutically acceptable salt of the compound and wherein the free base or pharmaceutically acceptable salt is in anhydrous or hydrate form. In some embodiments, the oral dosage form consists essentially of about 1% by weight to about 20% by weight, based on the total weight of the oral dosage form, of a compound of Formula (I), wherein the compound is present in the oral dosage form as a free base, or a pharmaceutically acceptable salt of the compound and wherein the free base or pharmaceutically acceptable salt is in anhydrous or hydrate form.

In some embodiments, the oral dosage form comprises about 1% by weight to about 70% by weight of the compound of Formula (I) based on the total weight of the oral dosage form. In some embodiments, the oral dosage form comprises about 1% by weight to about 65% by weight of the compound of Formula (I) based on the total weight of the oral dosage form. In some embodiments, the oral dosage form comprises about 1% by weight to about 60% by weight of the compound of Formula (I) based on the total weight of the oral dosage form. In some embodiments, the oral dosage form comprises about 1% by weight to about 55% by weight of the compound of Formula (I) based on the total weight of the oral dosage form. In some embodiments, the oral dosage form comprises about 1% by weight to about 50% by weight of the compound of Formula (I) based on the total weight of the oral dosage form. In some embodiments, the oral dosage form comprises about 1% by weight to about 45% by weight of the compound of Formula (I) based on the total weight of the oral dosage form. In some embodiments, the oral dosage form comprises about 1% by weight to about 40% by weight of the compound of Formula (I) based on the total weight of the oral dosage form. In some embodiments, the oral dosage form comprises about 1% by weight to about 35% by weight of the compound of Formula (I) based on the total weight of the oral dosage form. In some embodiments, the oral dosage form comprises about 1% by weight to about 30% by weight of the compound of Formula (I) based on the total weight of the oral dosage form. In some embodiments, the oral dosage form comprises about 1% by weight to about 25% by weight of the compound of Formula (I) based on the total weight of the oral dosage form. In some embodiments, the oral dosage form comprises about 1% by weight to about 20% by weight of the compound of Formula (I) based on the total weight of the oral dosage form. In some embodiments, the oral dosage form comprises about 1% by weight to about 15% by weight of the compound of Formula (I) based on the total weight of the oral dosage form. In some embodiments, the oral dosage form comprises about 1% by weight to about 10% by weight of the compound of Formula (I) based on the total weight of the oral dosage form.

In some embodiments, the oral dosage form consists essentially of about 1% by weight to about 70% by weight of the compound of Formula (I) based on the total weight of the oral dosage form. In some embodiments, the oral dosage form consists essentially of about 1% by weight to about 65% by weight of the compound of Formula (I) based on the total weight of the oral dosage form. In some embodiments, the oral dosage form consists essentially of about 1% by weight to about 60% by weight of the compound of Formula (I) based on the total weight of the oral dosage form. In some embodiments, the oral dosage form consists essentially of about 1% by weight to about 55% by weight of the compound of Formula (I) based on the total weight of the oral dosage form. In some embodiments, the oral dosage form consists essentially of about 1% by weight to about 50% by weight of the compound of Formula (I) based on the total weight of the oral dosage form. In some embodiments, the oral dosage form consists essentially of about 1% by weight to about 45% by weight of the compound of Formula (I) based on the total weight of the oral dosage form. In some embodiments, the oral dosage form consists essentially of about 1% by weight to about 40% by weight of the compound of Formula (I) based on the total weight of the oral dosage form. In some embodiments, the oral dosage form consists essentially of about 1% by weight to about 35% by weight of the compound of Formula (I) based on the total weight of the oral dosage form. In some embodiments, the oral dosage form consists essentially of about 1% by weight to about 30% by weight of the compound of Formula (I) based on the total weight of the oral dosage form. In some embodiments, the oral dosage form consists essentially of about 1% by weight to about 25% by weight of the compound of Formula (I) based on the total weight of the oral dosage form. In some embodiments, the oral dosage form consists essentially of about 1% by weight to about 20% by weight of the compound of Formula (I) based on the total weight of the oral dosage form. In some embodiments, the oral dosage form consists essentially of about 1% by weight to about 15% by weight of the compound of Formula (I) based on the total weight of the oral dosage form. In some embodiments, the oral dosage form consists essentially of about 1% by weight to about 10% by weight of the compound of Formula (I) based on the total weight of the oral dosage form.

In some embodiments, the oral dosage form comprises about 5% by weight to about 30% by weight of the compound of Formula (I) based on the total weight of the oral dosage form. In some embodiments, the oral dosage form comprises about 5% by weight to about 25% by weight of the compound of Formula (I) based on the total weight of the oral dosage form. In some embodiments, the oral dosage form comprises about 5% by weight to about 20% by weight of the compound of Formula (I) based on the total weight of the oral dosage form. In some embodiments, the oral dosage form comprises about 5% by weight to about 15% by weight of the compound of Formula (I) based on the total weight of the oral dosage form. In some embodiments, the oral dosage form comprises about 5% by weight to about 10% by weight of the compound of Formula (I) based on the total weight of the oral dosage form.

In some embodiments, the oral dosage form consists essentially of about 5% by weight to about 30% by weight of the compound of Formula (I) based on the total weight of the oral dosage form. In some embodiments, the oral dosage form consists essentially of about 5% by weight to about 25% by weight of the compound of Formula (I) based on the total weight of the oral dosage form. In some embodiments, the oral dosage form consists essentially of about 5% by weight to about 20% by weight of the compound of Formula (I) based on the total weight of the oral dosage form. In some embodiments, the oral dosage form consists essentially of about 5% by weight to about 15% by weight of the compound of Formula (I) based on the total weight of the oral dosage form. In some embodiments, the oral dosage form consists essentially of about 5% by weight to about 10% by weight of the compound of Formula (I) based on the total weight of the oral dosage form.

In some embodiments, the oral dosage form comprises about 10% to about 30% of the compound of Formula (I) based on the total weight of the oral dosage form. In some embodiments, the oral dosage form comprises about 10% to about 25% of the compound of Formula (I) based on the total weight of the oral dosage form. In some embodiments, the oral dosage form comprises about 10% to about 20% of the compound of Formula (I) based on the total weight of the oral dosage form. In some embodiments, the oral dosage form comprises about 10% by weight to about 15% by weight of the compound of Formula (I) based on the total weight of the oral dosage form.

In some embodiments, the oral dosage form consists essentially of about 10% to about 30% of the compound of Formula (I) based on the total weight of the oral dosage form. In some embodiments, the oral dosage form consists essentially of about 10% to about 25% of the compound of Formula (I) based on the total weight of the oral dosage form. In some embodiments, the oral dosage form consists essentially of about 10% to about 20% of the compound of Formula (I) based on the total weight of the oral dosage form. In some embodiments, the oral dosage form consists essentially of about 10% by weight to about 15% by weight of the compound of Formula (I) based on the total weight of the oral dosage form.

In some embodiments, the oral dosage form comprises about 1% by weight to about 30% by weight of the compound of Formula (I) based on the total weight of the oral dosage form. In some embodiments, the oral dosage form comprises about 1% by weight to about 10% by weight of the compound of Formula (I) based on the total weight of the oral dosage form. In some embodiments, the oral dosage form comprises about 10% to about 20% of the compound of Formula (I) based on the total weight of the oral dosage form. In some embodiments, the oral dosage form comprises about 10% by weight to about 15% by weight of the compound of Formula (I) based on the total weight of the oral dosage form.

In some embodiments, the oral dosage form consists essentially of about 1% by weight to about 30% by weight of the compound of Formula (I) based on the total weight of the oral dosage form. In some embodiments, the oral dosage form consists essentially of about 1% by weight to about 10% by weight of the compound of Formula (I) based on the total weight of the oral dosage form. In some embodiments, the oral dosage form consists essentially of about 10% to about 20% of the compound of Formula (I) based on the total weight of the oral dosage form. In some embodiments, the oral dosage form consists essentially of about 10% by weight to about 15% by weight of the compound of Formula (I) based on the total weight of the oral dosage form.

In some embodiments, the one or more pharmaceutically acceptable excipients comprise about 20% by weight to about 90% by weight of one or more fillers based on the total weight of the oral dosage form. In some embodiments, the one or more pharmaceutically acceptable excipients comprise about 20% by weight to about 85% by weight of one or more fillers based on the total weight of the oral dosage form. In some embodiments, the one or more pharmaceutically acceptable excipients comprise about 20% by weight to about 80% by weight of one or more fillers based on the total weight of the oral dosage form. In some embodiments, the one or more pharmaceutically acceptable excipients comprise about 20% by weight to about 75% by weight of one or more fillers based on the total weight of the oral dosage form. In some embodiments, the one or more pharmaceutically acceptable excipients comprise about 20% by weight to about 70% by weight of one or more fillers based on the total weight of the oral dosage form. In some embodiments, the one or more pharmaceutically acceptable excipients comprise about 20% by weight to about 65% by weight of one or more fillers based on the total weight of the oral dosage form. In some embodiments, the one or more pharmaceutically acceptable excipients comprise about 20% by weight to about 60% by weight of one or more fillers based on the total weight of the oral dosage form. In some embodiments, the one or more pharmaceutically acceptable excipients comprise about 20% by weight to about 55% by weight of one or more fillers based on the total weight of the oral dosage form. In some embodiments, the one or more pharmaceutically acceptable excipients comprise about 20% by weight to about 50% by weight of one or more fillers based on the total weight of the oral dosage form. In some embodiments, the one or more pharmaceutically acceptable excipients comprise about 20% by weight to about 45% by weight of one or more fillers based on the total weight of the oral dosage form. In some embodiments, the one or more pharmaceutically acceptable excipients comprise about 20% by weight to about 40% by weight of one or more fillers based on the total weight of the oral dosage form. In some embodiments, the one or more pharmaceutically acceptable excipients comprise about 20% by weight to about 35% by weight of one or more fillers based on the total weight of the oral dosage form. In some embodiments, the one or more pharmaceutically acceptable excipients comprise about 20% by weight to about 30% by weight of one or more fillers based on the total weight of the oral dosage form. In some embodiments, the one or more pharmaceutically acceptable excipients comprise about 20% by weight to about 25% by weight of one or more fillers based on the total weight of the oral dosage form.

In some embodiments, the one or more pharmaceutically acceptable excipients comprise about 30% by weight to about 90% by weight of one or more fillers based on the total weight of the oral dosage form. In some embodiments, the one or more pharmaceutically acceptable excipients comprise about 30% by weight to about 80% by weight of one or more fillers based on the total weight of the oral dosage form. In some embodiments, the one or more pharmaceutically acceptable excipients comprise about 30% by weight to about 70% by weight of one or more fillers based on the total weight of the oral dosage form. In some embodiments, the one or more pharmaceutically acceptable excipients comprise about 30% by weight to about 60% by weight of one or more fillers based on the total weight of the oral dosage form. In some embodiments, the one or more pharmaceutically acceptable excipients comprise about 30% by weight to about 50% by weight of one or more fillers based on the total weight of the oral dosage form. In some embodiments, the one or more pharmaceutically acceptable excipients comprise about 30% by weight to about 40% by weight of one or more fillers based on the total weight of the oral dosage form.

In some embodiments, the one or more pharmaceutically acceptable excipients comprise about 40% by weight to about 90% by weight of one or more fillers based on the total weight of the oral dosage form. In some embodiments, the one or more pharmaceutically acceptable excipients comprise about 40% by weight to about 80% by weight of one or more fillers based on the total weight of the oral dosage form. In some embodiments, the one or more pharmaceutically acceptable excipients comprise about 40% by weight to about 70% by weight of one or more fillers based on the total weight of the oral dosage form. In some embodiments, the one or more pharmaceutically acceptable excipients comprise about 40% by weight to about 60% by weight of one or more fillers based on the total weight of the oral dosage form. In some embodiments, the one or more pharmaceutically acceptable excipients comprise about 40% by weight to about 50% by weight of one or more fillers based on the total weight of the oral dosage form.

In some embodiments, the one or more pharmaceutically acceptable excipients comprise about 50% by weight to about 90% by weight of one or more fillers based on the total weight of the oral dosage form. In some embodiments, the one or more pharmaceutically acceptable excipients comprise about 50% by weight to about 80% by weight of one or more fillers based on the total weight of the oral dosage form. In some embodiments, the one or more pharmaceutically acceptable excipients comprise about 50% by weight to about 70% by weight of one or more fillers based on the total weight of the oral dosage form. In some embodiments, the one or more pharmaceutically acceptable excipients comprise about 50% by weight to about 60% by weight of one or more fillers based on the total weight of the oral dosage form.

In some embodiments, the one or more pharmaceutically acceptable excipients comprise about 60% by weight to about 90% by weight of one or more fillers based on the total weight of the oral dosage form. In some embodiments, the one or more pharmaceutically acceptable excipients comprise about 60% by weight to about 80% by weight of one or more fillers based on the total weight of the oral dosage form. In some embodiments, the one or more pharmaceutically acceptable excipients comprise about 60% by weight to about 70% by weight of one or more fillers based on the total weight of the oral dosage form.

In some embodiments, the one or more pharmaceutically acceptable excipients comprise about 70% by weight to about 90% by weight of one or more fillers based on the total weight of the oral dosage form. In some embodiments, the one or more pharmaceutically acceptable excipients comprise about 70% by weight to about 80% by weight of one or more fillers based on the total weight of the oral dosage form.

In some embodiments, the one or more pharmaceutically acceptable excipients comprise about 80% by weight to about 90% by weight of one or more fillers based on the total weight of the oral dosage form.

In some embodiments, the one or more pharmaceutically acceptable excipients comprise about 1% by weight to about 20% by weight of one or more disintegrants based on the total weight of the oral dosage form. In some embodiments, the one or more pharmaceutically acceptable excipients comprise about 1% by weight to about 15% by weight of one or more disintegrants based on the total weight of the oral dosage form. In some embodiments, the one or more pharmaceutically acceptable excipients comprise about 1% by weight to about 14% by weight of one or more disintegrants based on the total weight of the oral dosage form. In some embodiments, the one or more pharmaceutically acceptable excipients comprise about 1% by weight to about 13% by weight of one or more disintegrants based on the total weight of the oral dosage form. In some embodiments, the one or more pharmaceutically acceptable excipients comprise about 1% by weight to about 12% by weight of one or more disintegrants based on the total weight of the oral dosage form. In some embodiments, the one or more pharmaceutically acceptable excipients comprise about 1% by weight to about 11% by weight of one or more disintegrants based on the total weight of the oral dosage form. In some embodiments, the one or more pharmaceutically acceptable excipients comprise about 1% by weight to about 10% by weight of one or more disintegrants based on the total weight of the oral dosage form. In some embodiments, the one or more pharmaceutically acceptable excipients comprise about 1% by weight to about 9% by weight of one or more disintegrants based on the total weight of the oral dosage form. In some embodiments, the one or more pharmaceutically acceptable excipients comprise about 1% by weight to about 8% by weight of one or more disintegrants based on the total weight of the oral dosage form. In some embodiments, the one or more pharmaceutically acceptable excipients comprise about 1% by weight to about 7% by weight of one or more disintegrants based on the total weight of the oral dosage form. In some embodiments, the one or more pharmaceutically acceptable excipients comprise about 1% by weight to about 6% by weight of one or more disintegrants based on the total weight of the oral dosage form. In some embodiments, the one or more pharmaceutically acceptable excipients comprise about 1% by weight to about 5% by weight of one or more disintegrants based on the total weight of the oral dosage form. In some embodiments, the one or more pharmaceutically acceptable excipients comprise about 1% by weight to about 4% by weight of one or more disintegrants based on the total weight of the oral dosage form. In some embodiments, the one or more pharmaceutically acceptable excipients comprise about 1% by weight to about 3% by weight of one or more disintegrants based on the total weight of the oral dosage form.

In some embodiments, the one or more pharmaceutically acceptable excipients comprise about 1% by weight of one or more disintegrants based on the total weight of the oral dosage form. In some embodiments, the one or more pharmaceutically acceptable excipients comprise about 2% by weight of one or more disintegrants based on the total weight of the oral dosage form. In some embodiments, the one or more pharmaceutically acceptable excipients comprise about 3% by weight of one or more disintegrants based on the total weight of the oral dosage form. In some embodiments, the one or more pharmaceutically acceptable excipients comprise about 4% by weight of one or more disintegrants based on the total weight of the oral dosage form. In some embodiments, the one or more pharmaceutically acceptable excipients comprise about 5% by weight of one or more disintegrants based on the total weight of the oral dosage form. In some embodiments, the one or more pharmaceutically acceptable excipients comprise about 6% by weight of one or more disintegrants based on the total weight of the oral dosage form. In some embodiments, the one or more pharmaceutically acceptable excipients comprise about 7% by weight of one or more disintegrants based on the total weight of the oral dosage form. In some embodiments, the one or more pharmaceutically acceptable excipients comprise about 8% by weight of one or more disintegrants based on the total weight of the oral dosage form. In some embodiments, the one or more pharmaceutically acceptable excipients comprise about 9% by weight of one or more disintegrants based on the total weight of the oral dosage form. In some embodiments, the one or more pharmaceutically acceptable excipients comprise about 10% by weight of one or more disintegrants based on the total weight of the oral dosage form. In some embodiments, the one or more pharmaceutically acceptable excipients comprise about 11% by weight of one or more disintegrants based on the total weight of the oral dosage form. In some embodiments, the one or more pharmaceutically acceptable excipients comprise about 12% by weight of one or more disintegrants based on the total weight of the oral dosage form. In some embodiments, the one or more pharmaceutically acceptable excipients comprise about 13% by weight of one or more disintegrants based on the total weight of the oral dosage form. In some embodiments, the one or more pharmaceutically acceptable excipients comprise about 14% by weight of one or more disintegrants based on the total weight of the oral dosage form. In some embodiments, the one or more pharmaceutically acceptable excipients comprise about 15% by weight of one or more disintegrants based on the total weight of the oral dosage form.

In some embodiments, the one or more pharmaceutically acceptable excipients comprise about 0.1% by weight to about 10% by weight of one or more lubricants based on the total weight of the oral dosage form. In some embodiments, the one or more pharmaceutically acceptable excipients comprise about 0.1% by weight to about 9% by weight of one or more lubricants based on the total weight of the oral dosage form. In some embodiments, the one or more pharmaceutically acceptable excipients comprise about 0.1% by weight to about 8% by weight of one or more lubricants based on the total weight of the oral dosage form. In some embodiments, the one or more pharmaceutically acceptable excipients comprise about 0.1% by weight to about 7% by weight of one or more lubricants based on the total weight of the oral dosage form. In some embodiments, the one or more pharmaceutically acceptable excipients comprise about 0.1% by weight to about 6% by weight of one or more lubricants based on the total weight of the oral dosage form. In some embodiments, the one or more pharmaceutically acceptable excipients comprise about 0.1% by weight to about 5% by weight of one or more lubricants based on the total weight of the oral dosage form. In some embodiments, the one or more pharmaceutically acceptable excipients comprise about 0.1% by weight to about 4% by weight of one or more lubricants based on the total weight of the oral dosage form. In some embodiments, the one or more pharmaceutically acceptable excipients comprise about 0.1% by weight to about 3% by weight of one or more lubricants based on the total weight of the oral dosage form. In some embodiments, the one or more pharmaceutically acceptable excipients comprise about 0.1% by weight to about 2% by weight of one or more lubricants based on the total weight of the oral dosage form.

In some embodiments, the one or more pharmaceutically acceptable excipients comprise about 0.1% by weight to about 1.9% by weight of one or more lubricants based on the total weight of the oral dosage form. In some embodiments, the one or more pharmaceutically acceptable excipients comprise about 0.1% by weight to about 1.8% by weight of one or more lubricants based on the total weight of the oral dosage form. In some embodiments, the one or more pharmaceutically acceptable excipients comprise about 0.1% by weight to about 1.7% by weight of one or more lubricants based on the total weight of the oral dosage form. In some embodiments, the one or more pharmaceutically acceptable excipients comprise about 0.1% by weight to about 1.6% by weight of one or more lubricants based on the total weight of the oral dosage form. In some embodiments, the one or more pharmaceutically acceptable excipients comprise about 0.1% by weight to about 1.5% by weight of one or more lubricants based on the total weight of the oral dosage form. In some embodiments, the one or more pharmaceutically acceptable excipients comprise about 0.1% by weight to about 1.4% by weight of one or more lubricants based on the total weight of the oral dosage form. In some embodiments, the one or more pharmaceutically acceptable excipients comprise about 0.1% by weight to about 1.3% by weight of one or more lubricants based on the total weight of the oral dosage form. In some embodiments, the one or more pharmaceutically acceptable excipients comprise about 0.1% by weight to about 1.2% by weight of one or more lubricants based on the total weight of the oral dosage form. In some embodiments, the one or more pharmaceutically acceptable excipients comprise about 0.1% by weight to about 1.1% by weight of one or more lubricants based on the total weight of the oral dosage form. In some embodiments, the one or more pharmaceutically acceptable excipients comprise about 0.1% by weight to about 1.0% by weight of one or more lubricants based on the total weight of the oral dosage form. In some embodiments, the one or more pharmaceutically acceptable excipients comprise about 0.1% by weight to about 0.9% by weight of one or more lubricants based on the total weight of the oral dosage form. In some embodiments, the one or more pharmaceutically acceptable excipients comprise about 0.1% by weight to about 0.8% by weight of one or more lubricants based on the total weight of the oral dosage form. In some embodiments, the one or more pharmaceutically acceptable excipients comprise about 0.1% by weight to about 0.7% by weight of one or more lubricants based on the total weight of the oral dosage form. In some embodiments, the one or more pharmaceutically acceptable excipients comprise about 0.1% by weight to about 0.6% by weight of one or more lubricants based on the total weight of the oral dosage form. In some embodiments, the one or more pharmaceutically acceptable excipients comprise about 0.1% by weight to about 0.5% by weight of one or more lubricants based on the total weight of the oral dosage form. In some embodiments, the one or more pharmaceutically acceptable excipients comprise about 0.1% by weight to about 0.4% by weight of one or more lubricants based on the total weight of the oral dosage form. In some embodiments, the one or more pharmaceutically acceptable excipients comprise about 0.1% by weight to about 0.3% by weight of one or more lubricants based on the total weight of the oral dosage form. In some embodiments, the one or more pharmaceutically acceptable excipients comprise about 0.1% by weight to about 0.2% by weight of one or more lubricants based on the total weight of the oral dosage form.

In some embodiments, the one or more pharmaceutically acceptable excipients comprise about 0.1% by weight of one or more lubricants based on the total weight of the oral dosage form. In some embodiments, the one or more pharmaceutically acceptable excipients comprise about 0.2% by weight of one or more lubricants based on the total weight of the oral dosage form. In some embodiments, the one or more pharmaceutically acceptable excipients comprise about 0.3% by weight of one or more lubricants based on the total weight of the oral dosage form. In some embodiments, the one or more pharmaceutically acceptable excipients comprise about 0.4% by weight of one or more lubricants based on the total weight of the oral dosage form. In some embodiments, the one or more pharmaceutically acceptable excipients comprise about 0.5% by weight of one or more lubricants based on the total weight of the oral dosage form. In some embodiments, the one or more pharmaceutically acceptable excipients comprise about 0.6% by weight of one or more lubricants based on the total weight of the oral dosage form. In some embodiments, the one or more pharmaceutically acceptable excipients comprise about 0.7% by weight of one or more lubricants based on the total weight of the oral dosage form. In some embodiments, the one or more pharmaceutically acceptable excipients comprise about 0.8% by weight of one or more lubricants based on the total weight of the oral dosage form. In some embodiments, the one or more pharmaceutically acceptable excipients comprise about 0.9% by weight of one or more lubricants based on the total weight of the oral dosage form. In some embodiments, the one or more pharmaceutically acceptable excipients comprise about 1.0% by weight of one or more lubricants based on the total weight of the oral dosage form.

In some embodiments, the oral dosage form comprises: (a) about 1% by weight to about 30% by weight of the compound of Formula (I) based on the total weight of the oral dosage form; (b) about 20% by weight to about 90% by weight of one or more fillers based on the total weight of the oral dosage form; (c) about 1% by weight to about 20% by weight of one or more disintegrants based on the total weight of the oral dosage form; and (d) about 0.1% by weight to about 10% by weight of one or more lubricants based on the total weight of the oral dosage form.

In some embodiments, the oral dosage form consists essentially of: (a) about 1% by weight to about 30% by weight of the compound of Formula (I) based on the total weight of the oral dosage form; (b) about 20% by weight to about 90% by weight of one or more fillers based on the total weight of the oral dosage form; (c) about 1% by weight to about 20% by weight of one or more disintegrants based on the total weight of the oral dosage form; and (d) about 0.1% by weight to about 10% by weight of one or more lubricants based on the total weight of the oral dosage form.

In some embodiments, the oral dosage form comprises (a) about 5% by weight to about 25% by weight of the compound of Formula (I) based on the total weight of the oral dosage form; (b) about 60% by weight to about 90% by weight of one or more fillers based on the total weight of the oral dosage form; (c) about 1% by weight to about 15% by weight of one or more disintegrants based on the total weight of the oral dosage form; and (d) about 0.1% by weight to about 4% by weight of one or more lubricants based on the total weight of the oral dosage form.

In some embodiments, the oral dosage form consists essentially of: (a) about 5% by weight to about 25% by weight of the compound of Formula (I) based on the total weight of the oral dosage form; (b) about 60% by weight to about 90% by weight of one or more fillers based on the total weight of the oral dosage form; (c) about 1% by weight to about 15% by weight of one or more disintegrants based on the total weight of the oral dosage form; and (d) about 0.1% by weight to about 4% by weight of one or more lubricants based on the total weight of the oral dosage form.

In some embodiments, the oral dosage form comprises (a) about 10% by weight to about 30% by weight of the compound of Formula (I) based on the total weight of the oral dosage form; (b) about 70% by weight to about 90% by weight of one or more fillers based on the total weight of the oral dosage form; (c) about 1% by weight to about 10% by weight of one or more disintegrants based on the total weight of the oral dosage form; and (d) about 0.1% by weight to about 3% by weight of one or more lubricants based on the total weight of the oral dosage form.

In some embodiments, the oral dosage form consists essentially of: (a) about 10% by weight to about 30% by weight of the compound of Formula (I) based on the total weight of the oral dosage form; (b) about 70% by weight to about 90% by weight of one or more fillers based on the total weight of the oral dosage form; (c) about 1% by weight to about 10% by weight of one or more disintegrants based on the total weight of the oral dosage form; and (d) about 0.1% by weight to about 3% by weight of one or more lubricants based on the total weight of the oral dosage form.

In some embodiments, the one or more pharmaceutically acceptable excipients is one or more fillers selected from the group consisting of calcium phosphate, dicalcium phosphate, dicalcium phosphate dihydrate, calcium sulfate, calcium sulfate dihydrate, starch, calcium carbonate, magnesium carbonate, magnesium oxide, kaolin (natural hydrated aluminum silicate), sodium chloride, partially gelatinized starch, anhydrous lactose, lactose monohydrate, lactose dihydrate, trehalose dihydrate, spray dried lactose, sucrose, dextrose, dextrates, dextrin, cellulose, microcrystalline cellulose, silicified microcrystalline cellulose, powdered cellulose, partially depolymerized cellulose, mannitol, granulated mannitol, spray dried mannitol, maltodextrin, maltitol, confectioner's sugar, compressible sugar, sorbitol, starch and talc. In some embodiments, the one or more fillers is lactose monohydrate.

In some embodiments, the one or more disintegrants is one or more disintegrants selected from the group consisting of sodium starch glycolate, pregelatinized starch, clay, cellulose, alginic acid, alginate gum, polyvinylpyrrolidone, cross-linked polyvinylpyrrolidone, cross-linked calcium carboxymethylcellulose, cross-linked sodium carboxymethylcellulose, sodium croscarmellose, sodium carmellose, low substituted hydroxypropyl cellulose, low substituted hydroxypropyl cellulose sodium, guar gum, magnesium aluminum silicate, polacrilin potassium, powdered cellulose, sodium alginate and soy polysaccharides. In some embodiments, the one or more disintegrants is cross-linked polyvinylpyrrolidone (also referred to as crospovidone).

In some embodiments, the one or more lubricants is one or more lubricants selected from the group consisting of colloidal silica, magnesium trisilicate, talc, magnesium carbonate, magnesium oxide, glyceryl behaptate, mono, di and tri glyceryl behenate, bees wax, behenoyl polyoxyl-8 glycerides, hydrogenated vegetable oil, polyethylene glycol, ethylene oxide polymer, copolymer comprising poly(ethylene oxide) and poly(propylene oxide) (such as poloxomer 188), copolymer comprising polypropylene glycol and polyethylene glycol (such as poloxomer 407), sodium lauryl sulfate, magnesium stearate, aluminum stearate, calcium stearate, sodium stearyl fumarate, stearic acid, magnesium lauryl stearate, mixtures of magnesium stearate with sodium lauryl sulfate. In some embodiments, the one or more lubricants is magnesium stearate.

In some embodiments, the oral dosage form further comprises cross-linked polyvinylpyrrolidone and magnesium stearate. In some embodiments, the one or more pharmaceutically acceptable excipients is lactose monohydrate and the oral dosage form further comprises cross-linked polyvinylpyrrolidone and magnesium stearate.

In some embodiments, the oral dosage form is a tablet or capsule. In some embodiments, the oral dosage form is a tablet. In some embodiments, the oral dosage form is a capsule. In some embodiments, the oral dosage form is a sachet. In some embodiments, the oral dosage form is a powder in a packet.

In some embodiments, the oral dosage form comprises about 1 mg to about 40 mg of the compound of Formula (I). In some embodiments, the oral dosage form comprises about 1 mg to about 30 mg of the compound of Formula (I). In some embodiments, the oral dosage form comprises about 1 mg to about 20 mg of the compound of Formula (I). In some embodiments, the oral dosage form comprises about 1 mg to about 15 mg of the compound of Formula (I). In some embodiments, the oral dosage form comprises about 5 mg to about 40 mg of the compound of Formula (I). In some embodiments, the oral dosage form comprises about 5 mg to about 30 mg of the compound of Formula (I). In some embodiments, the oral dosage form comprises about 5 mg to about 20 mg of the compound of Formula (I). In some embodiments, the oral dosage form comprises about 5 mg to about 15 mg of the compound of Formula (I). In some embodiments, the oral dosage form comprises about 10 mg to about 40 mg of the compound of Formula (I). In some embodiments, the oral dosage form comprises about 10 mg to about 30 mg of the compound of Formula (I). In some embodiments, the oral dosage form comprises about 10 mg to about 20 mg of the compound of Formula (I). In some embodiments, the oral dosage form comprises about 10 mg to about 15 mg of the compound of Formula (I).

In some embodiments, the oral dosage form consists essentially of about 1 mg to about 40 mg of the compound of Formula (I). In some embodiments, the oral dosage form consists essentially of about 1 mg to about 30 mg of the compound of Formula (I). In some embodiments, the oral dosage form consists essentially of about 1 mg to about 20 mg of the compound of Formula (I). In some embodiments, the oral dosage form consists essentially of about 1 mg to about 15 mg of the compound of Formula (I). In some embodiments, the oral dosage form consists essentially of about 5 mg to about 40 mg of the compound of Formula (I). In some embodiments, the oral dosage form consists essentially of about 5 mg to about 30 mg of the compound of Formula (I). In some embodiments, the oral dosage form consists essentially of about 5 mg to about 20 mg of the compound of Formula (I). In some embodiments, the oral dosage form consists essentially of about 5 mg to about 15 mg of the compound of Formula (I). In some embodiments, the oral dosage form consists essentially of about 10 mg to about 40 mg of the compound of Formula (I). In some embodiments, the oral dosage form consists essentially of about 10 mg to about 30 mg of the compound of Formula (I). In some embodiments, the oral dosage form consists essentially of about 10 mg to about 20 mg of the compound of Formula (I). In some embodiments, the oral dosage form consists essentially of about 10 mg to about 15 mg of the compound of Formula (I).

In some embodiments, compound of Formula (I) is present in the oral dosage form as a cocrystal. In some embodiments, compound of Formula (I) is present in the oral dosage form as a channel crystal. In some embodiments, compound of Formula (I) is present in the oral dosage form as a crystalline dihydrate form. In some embodiments, the compound of Formula (I) is present in the oral dosage form as a crystalline anhydrous form. In some embodiments, compound of Formula (I) is present in the oral dosage form as a solvate.

In some embodiments, the oral dosage form comprises about 0.5 mg to about 5 mg, about 6 mg to about 14 mg, about 11 mg to about 19 mg, about 17 mg to about 25 mg, or about 28 mg to about 36 mg of the compound of Formula (I) as a crystalline dihydrate form. In some embodiments, the oral dosage form comprises about 1 mg to about 4 mg, about 8 mg to about 12 mg, about 13 mg to about 17 mg, about 19 mg to about 23 mg, or about 30 mg to about 34 mg of the compound of Formula (I) as a crystalline dihydrate form. In some embodiments, the oral dosage form comprises about 2.2 mg, about 10.8 mg, about 15.2 mg, about 21.7 mg, or about 32.5 mg of the compound of Formula (I) as a crystalline dihydrate form.

In some embodiments, the oral dosage form consists essentially of about 0.5 mg to about 5 mg, about 6 mg to about 14 mg, about 11 mg to about 19 mg, about 17 mg to about 25 mg, or about 28 mg to about 36 mg of the compound of Formula (I) as a crystalline dihydrate form. In some embodiments, the oral dosage form consists essentially of about 1 mg to about 4 mg, about 8 mg to about 12 mg, about 13 mg to about 17 mg, about 19 mg to about 23 mg, or about 30 mg to about 34 mg of the compound of Formula (I) as a crystalline dihydrate form. In some embodiments, the oral dosage form consists essentially of about 2.2 mg, about 10.8 mg, about 15.2 mg, about 21.7 mg, or about 32.5 mg of the compound of Formula (I) as a crystalline dihydrate form.

Also provided herein, in some embodiments, are oral dosage forms comprising the crystalline dihydrate form of a compound of Formula (I):

Formula (I)

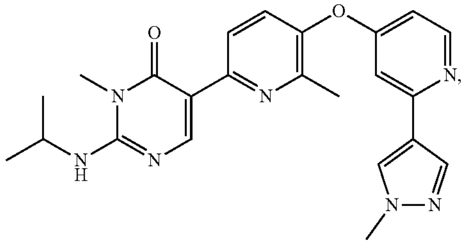

and one or more pharmaceutically acceptable excipients.

Also provided herein, in some embodiments, are oral dosage forms consisting essentially of the crystalline dihydrate form of a compound of Formula (I):

Formula (I)

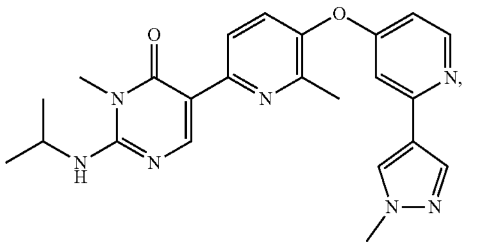

and one or more pharmaceutically acceptable excipients.

In some embodiments, the crystalline dihydrate form of the compound represented by Formula (I) has an XRPD pattern comprising a peak, in terms of 2-theta, at about 10.9° as measured by CuKα radiation.

In some embodiments, the crystalline dihydrate form of the compound represented by Formula (I) has an XRPD pattern comprising peaks, in terms of 2-theta, at about 10.9°, about 16.8°, and about 27.10 as measured by CuKα radiation.

In some embodiments, the crystalline dihydrate form of the compound of Formula (I) has an X-ray powder diffraction pattern comprising peaks, in terms of 2-theta, at about 5.9°, about 10.9°, about 11.9°, about 13.7°, about 16.8°, and about 27.10 as measured by CuKα radiation.

In some embodiments, the crystalline dihydrate form of the compound represented by Formula (I) has an XRPD pattern comprising peaks, in terms of 2-theta, at about 5.9°, about 10.9°, about 11.9°, about 13.7°, about 16.8°, about 27.10, about 28.3° and about 28.7° as measured by CuKα radiation.

In some embodiments, the one or more pharmaceutically acceptable excipients is a filler. For example, the one or more pharmaceutically acceptable excipients is lactose, such as lactose monohydrate.

In some embodiments, the oral dosage forms further comprise one or more disintegrants, one or more lubricants, or a combination thereof. For example, in some embodiments, the oral dosage forms further comprise one or more disintegrants. In some embodiments, the oral dosage forms further comprise one or more lubricants.

Also provided herein, in some embodiments, is an oral dosage form comprising:

(a) about 1% by weight to about 70% by weight, based on the total weight of the oral dosage form, of a crystalline dihydrate form of a compound of Formula (I):

Formula (I)

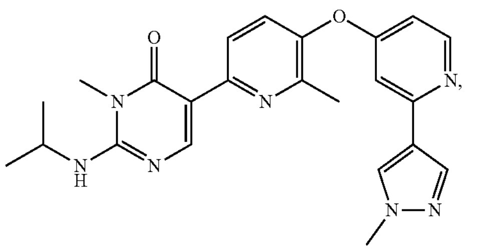

and one or more pharmaceutically acceptable excipients, wherein the one or more pharmaceutically acceptable excipients comprise:

(b) about 20% by weight to about 97% by weight of one or more fillers based on the total weight of the oral dosage form;

(c) about 1% by weight to about 20% by weight of one or more disintegrants based on the total weight of the oral dosage form; and (d) about 0.1% by weight to about 10% by weight of one or more lubricants based on the total weight of the oral dosage form.

Also provided herein, in some embodiments, is an oral dosage form comprising:

(a) about 1% by weight to about 30% by weight of a crystalline dihydrate form of a compound of Formula (I) based on the total weight of the oral dosage form;

(b) about 20% by weight to about 90% by weight of one or more fillers based on the total weight of the oral dosage form;

(c) about 1% by weight to about 20% by weight of one or more disintegrants based on the total weight of the oral dosage form; and (d) about 0.1% by weight to about 10% by weight of one or more lubricants based on the total weight of the oral dosage form.

Also provided herein, in some embodiments, is an oral dosage form consisting essentially of:

(a) about 1% by weight to about 70% by weight, based on the total weight of the oral dosage form, of a crystalline dihydrate form of a compound of Formula (I):

Formula (I)

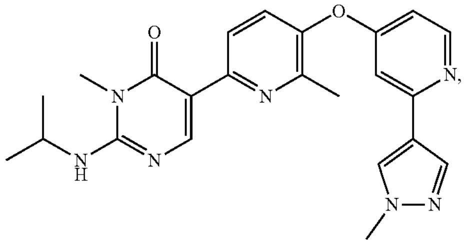

and one or more pharmaceutically acceptable excipients, wherein the one or more pharmaceutically acceptable excipients comprise:

(b) about 20% by weight to about 97% by weight of one or more fillers based on the total weight of the oral dosage form;

(c) about 1% by weight to about 20% by weight of one or more disintegrants based on the total weight of the oral dosage form; and (d) about 0.1% by weight to about 10% by weight of one or more lubricants based on the total weight of the oral dosage form.

Also provided herein, in some embodiments, is an oral dosage form consisting essentially of:

(a) about 1% by weight to about 30% by weight of a crystalline dihydrate form of a compound of Formula (I) based on the total weight of the oral dosage form;

(b) about 20% by weight to about 90% by weight of one or more fillers based on the total weight of the oral dosage form;

(c) about 1% by weight to about 20% by weight of one or more disintegrants based on the total weight of the oral dosage form; and (d) about 0.1% by weight to about 10% by weight of one or more lubricants based on the total weight of the oral dosage form.

In some embodiments, the oral dosage form comprising the crystalline dihydrate form of the compound represented by Formula (I), has no more than about 10 mol %, no more than about 5 mol %, no more than about 3 mol %, or no more than about 1 mol % of other solid-state forms of the compound represented by Formula (I). In some embodiments, the oral dosage form comprising the crystalline dihydrate forms of the compound represented by Formula (I), has no more than about 10 mol % of other solid-state forms of the compound represented by Formula (I). In some embodiments, the oral dosage form comprising the crystalline dihydrate forms of the compound represented by Formula (I), has no more than about 9 mol % of other solid-state forms of the compound represented by Formula (I). In some embodiments, the oral dosage form comprising the crystalline dihydrate forms of the compound represented by Formula (I), has no more than about 8 mol % of other solid-state forms of the compound represented by Formula (I). In some embodiments, the oral dosage form comprising the crystalline dihydrate forms of the compound represented by Formula (I), has no more than about 7 mol % of other solid-state forms of the compound represented by Formula (I). In some embodiments, the oral dosage form comprising the crystalline dihydrate forms of the compound represented by Formula (I), has no more than about 6 mol % of other solid-state forms of the compound represented by Formula (I). In some embodiments, the oral dosage form comprising the crystalline dihydrate forms of the compound represented by Formula (I), has no more than about 5 mol % of other solid-state forms of the compound represented by Formula (I). In some embodiments, the oral dosage form comprising the crystalline dihydrate forms of the compound represented by Formula (I), has no more than about 4 mol % of other solid-state forms of the compound represented by Formula (I). In some embodiments, the oral dosage form comprising the crystalline dihydrate forms of the compound represented by Formula (I), has no more than about 3 mol % of other solid-state forms of the compound represented by Formula (I). In some embodiments, the oral dosage form comprising the crystalline dihydrate forms of the compound represented by Formula (I), has no more than about 2 mol % of other solid-state forms of the compound represented by Formula (I). In some embodiments, the oral dosage form comprising the crystalline dihydrate forms of the compound represented by Formula (I), has no more than about 1 mol % of other solid-state forms of the compound represented by Formula (I).

In some embodiments, the oral dosage form comprises about 1% by weight to about 60% by weight, based on the total weight of the oral dosage form, of a crystalline dihydrate form of a compound of Formula (I). In some embodiments, the oral dosage form comprises about 1% by weight to about 50% by weight, based on the total weight of the oral dosage form, of a crystalline dihydrate form of a compound of Formula (I). In some embodiments, the oral dosage form comprises about 1% by weight to about 40% by weight, based on the total weight of the oral dosage form, of a crystalline dihydrate form of a compound of Formula (I). In some embodiments, the oral dosage form comprises about 1% by weight to about 30% by weight, based on the total weight of the oral dosage form, of a crystalline dihydrate form of a compound of Formula (I). In some embodiments, the oral dosage form comprises about 1% by weight to about 20% by weight, based on the total weight of the oral dosage form, of a crystalline dihydrate form of a compound of Formula (I).

In some embodiments, the oral dosage form consists essentially of about 1% by weight to about 60% by weight, based on the total weight of the oral dosage form, of a crystalline dihydrate form of a compound of Formula (I). In some embodiments, the oral dosage form consists essentially of about 1% by weight to about 50% by weight, based on the total weight of the oral dosage form, of a crystalline dihydrate form of a compound of Formula (I). In some embodiments, the oral dosage form consists essentially of about 1% by weight to about 40% by weight, based on the total weight of the oral dosage form, of a crystalline dihydrate form of a compound of Formula (I). In some embodiments, the oral dosage form consists essentially of about 1% by weight to about 30% by weight, based on the total weight of the oral dosage form, of a crystalline dihydrate form of a compound of Formula (I). In some embodiments, the oral dosage form consists essentially of about 1% by weight to about 20% by weight, based on the total weight of the oral dosage form, of a crystalline dihydrate form of a compound of Formula (I).

In some embodiments, the oral dosage form comprises about 1% by weight to about 70% by weight of the crystalline dihydrate form of the compound of Formula (I) based on the total weight of the oral dosage form. In some embodiments, the oral dosage form comprises about 1% by weight to about 65% by weight of the crystalline dihydrate form of the compound of Formula (I) based on the total weight of the oral dosage form. In some embodiments, the oral dosage form comprises about 1% by weight to about 60% by weight of the crystalline dihydrate form of the compound of Formula (I) based on the total weight of the oral dosage form. In some embodiments, the oral dosage form comprises about 1% by weight to about 55% by weight of the crystalline dihydrate form of the compound of Formula (I) based on the total weight of the oral dosage form. In some embodiments, the oral dosage form comprises about 1% by weight to about 50% by weight of the crystalline dihydrate form of the compound of Formula (I) based on the total weight of the oral dosage form. In some embodiments, the oral dosage form comprises about 1% by weight to about 45% by weight of the crystalline dihydrate form of the compound of Formula (I) based on the total weight of the oral dosage form. In some embodiments, the oral dosage form comprises about 1% by weight to about 40% by weight of the crystalline dihydrate form of the compound of Formula (I) based on the total weight of the oral dosage form. In some embodiments, the oral dosage form comprises about 1% by weight to about 35% by weight of the crystalline dihydrate form of the compound of Formula (I) based on the total weight of the oral dosage form. In some embodiments, the oral dosage form comprises about 1% by weight to about 30% by weight of the crystalline dihydrate form of the compound of Formula (I) based on the total weight of the oral dosage form. In some embodiments, the oral dosage form comprises about 1% by weight to about 25% by weight of the crystalline dihydrate form of the compound of Formula (I) based on the total weight of the oral dosage form. In some embodiments, the oral dosage form comprises about 1% by weight to about 20% by weight of the crystalline dihydrate form of the compound of Formula (I) based on the total weight of the oral dosage form. In some embodiments, the oral dosage form comprises about 1% by weight to about 15% by weight of the crystalline dihydrate form of the compound of Formula (I) based on the total weight of the oral dosage form. In some embodiments, the oral dosage form comprises about 1% by weight to about 10% by weight of the crystalline dihydrate form of the compound of Formula (I) based on the total weight of the oral dosage form.

In some embodiments, the oral dosage form consists essentially of about 1% by weight to about 70% by weight of the crystalline dihydrate form of the compound of Formula (I) based on the total weight of the oral dosage form. In some embodiments, the oral dosage form consists essentially of about 1% by weight to about 65% by weight of the crystalline dihydrate form of the compound of Formula (I) based on the total weight of the oral dosage form. In some embodiments, the oral dosage form consists essentially of about 1% by weight to about 60% by weight of the crystalline dihydrate form of the compound of Formula (I) based on the total weight of the oral dosage form. In some embodiments, the oral dosage form consists essentially of about 1% by weight to about 55% by weight of the crystalline dihydrate form of the compound of Formula (I) based on the total weight of the oral dosage form. In some embodiments, the oral dosage form consists essentially of about 1% by weight to about 50% by weight of the crystalline dihydrate form of the compound of Formula (I) based on the total weight of the oral dosage form. In some embodiments, the oral dosage form consists essentially of about 1% by weight to about 45% by weight of the crystalline dihydrate form of the compound of Formula (I) based on the total weight of the oral dosage form. In some embodiments, the oral dosage form consists essentially of about 1% by weight to about 40% by weight of the crystalline dihydrate form of the compound of Formula (I) based on the total weight of the oral dosage form. In some embodiments, the oral dosage form consists essentially of about 1% by weight to about 35% by weight of the crystalline dihydrate form of the compound of Formula (I) based on the total weight of the oral dosage form. In some embodiments, the oral dosage form consists essentially of about 1% by weight to about 30% by weight of the crystalline dihydrate form of the compound of Formula (I) based on the total weight of the oral dosage form. In some embodiments, the oral dosage form consists essentially of about 1% by weight to about 25% by weight of the crystalline dihydrate form of the compound of Formula (I) based on the total weight of the oral dosage form. In some embodiments, the oral dosage form consists essentially of about 1% by weight to about 20% by weight of the crystalline dihydrate form of the compound of Formula (I) based on the total weight of the oral dosage form. In some embodiments, the oral dosage form consists essentially of about 1% by weight to about 15% by weight of the crystalline dihydrate form of the compound of Formula (I) based on the total weight of the oral dosage form. In some embodiments, the oral dosage form consists essentially of about 1% by weight to about 10% by weight of the crystalline dihydrate form of the compound of Formula (I) based on the total weight of the oral dosage form.

In some embodiments, the oral dosage form comprises about 5% by weight to about 30% by weight of the crystalline dihydrate form of the compound of Formula (I) based on the total weight of the oral dosage form. In some embodiments, the oral dosage form comprises about 5% by weight to about 25% by weight of the crystalline dihydrate form of the compound of Formula (I) based on the total weight of the oral dosage form. In some embodiments, the oral dosage form comprises about 5% by weight to about 20% by weight of the crystalline dihydrate form of the compound of Formula (I) based on the total weight of the oral dosage form. In some embodiments, the oral dosage form comprises about 5% by weight to about 15% by weight of the crystalline dihydrate form of the compound of Formula (I) based on the total weight of the oral dosage form. In some embodiments, the oral dosage form comprises about 5% by weight to about 10% by weight of the crystalline dihydrate form of the compound of Formula (I) based on the total weight of the oral dosage form.

In some embodiments, the oral dosage form consists essentially of about 5% by weight to about 30% by weight of the crystalline dihydrate form of the compound of Formula (I) based on the total weight of the oral dosage form. In some embodiments, the oral dosage form consists essentially of about 5% by weight to about 25% by weight of the crystalline dihydrate form of the compound of Formula (I) based on the total weight of the oral dosage form. In some embodiments, the oral dosage form consists essentially of about 5% by weight to about 20% by weight of the crystalline dihydrate form of the compound of Formula (I) based on the total weight of the oral dosage form. In some embodiments, the oral dosage form consists essentially of about 5% by weight to about 15% by weight of the crystalline dihydrate form of the compound of Formula (I) based on the total weight of the oral dosage form. In some embodiments, the oral dosage form consists essentially of about 5% by weight to about 10% by weight of the crystalline dihydrate form of the compound of Formula (I) based on the total weight of the oral dosage form.

In some embodiments, the oral dosage form comprises about 10% to about 30% of the compound of Formula (I) based on the total weight of the oral dosage form. In some embodiments, the oral dosage form comprises about 10% to about 25% of the compound of Formula (I) based on the total weight of the oral dosage form. In some embodiments, the oral dosage form comprises about 10% to about 20% of the compound of Formula (I) based on the total weight of the oral dosage form. In some embodiments, the oral dosage form comprises about 10% by weight to about 15% by weight of the crystalline dihydrate form of the compound of Formula (I) based on the total weight of the oral dosage form.

In some embodiments, the oral dosage form consists essentially of about 10% to about 30% of the crystalline dihydrate form of the compound of Formula (I) based on the total weight of the oral dosage form. In some embodiments, the oral dosage form consists essentially of about 10% to about 25% of the crystalline dihydrate form of the compound of Formula (I) based on the total weight of the oral dosage form. In some embodiments, the oral dosage form consists essentially of about 10% to about 20% of the crystalline dihydrate form of the compound of Formula (I) based on the total weight of the oral dosage form. In some embodiments, the oral dosage form consists essentially of about 10% by weight to about 15% by weight of the crystalline dihydrate form of the compound of Formula (I) based on the total weight of the oral dosage form.

In some embodiments, the oral dosage form comprises about 1% by weight to about 30% by weight of the crystalline dihydrate form of the compound of Formula (I) based on the total weight of the oral dosage form. In some embodiments, the oral dosage form comprises about 1% by weight to about 10% by weight of the crystalline dihydrate form of the compound of Formula (I) based on the total weight of the oral dosage form. In some embodiments, the oral dosage form comprises about 10% to about 20% of the compound of Formula (I) based on the total weight of the oral dosage form. In some embodiments, the oral dosage form comprises about 10% by weight to about 15% by weight of the crystalline dihydrate form of the compound of Formula (I) based on the total weight of the oral dosage form.

In some embodiments, the oral dosage form consists essentially of about 1% by weight to about 30% by weight of the crystalline dihydrate form of the compound of Formula (I) based on the total weight of the oral dosage form. In some embodiments, the oral dosage form consists essentially of about 1% by weight to about 10% by weight of the crystalline dihydrate form of the compound of Formula (I) based on the total weight of the oral dosage form. In some embodiments, the oral dosage form consists essentially of about 10% to about 20% of the crystalline dihydrate form of the compound of Formula (I) based on the total weight of the oral dosage form. In some embodiments, the oral dosage form consists essentially of about 10% by weight to about 15% by weight of the crystalline dihydrate form of the compound of Formula (I) based on the total weight of the oral dosage form.

In some embodiments, the one or more pharmaceutically acceptable excipients comprise about 20% by weight to about 90% by weight of one or more fillers based on the total weight of the oral dosage form. In some embodiments, the one or more pharmaceutically acceptable excipients comprise about 20% by weight to about 85% by weight of one or more fillers based on the total weight of the oral dosage form. In some embodiments, the one or more pharmaceutically acceptable excipients comprise about 20% by weight to about 80% by weight of one or more fillers based on the total weight of the oral dosage form. In some embodiments, the one or more pharmaceutically acceptable excipients comprise about 20% by weight to about 75% by weight of one or more fillers based on the total weight of the oral dosage form. In some embodiments, the one or more pharmaceutically acceptable excipients comprise about 20% by weight to about 70% by weight of one or more fillers based on the total weight of the oral dosage form. In some embodiments, the one or more pharmaceutically acceptable excipients comprise about 20% by weight to about 65% by weight of one or more fillers based on the total weight of the oral dosage form. In some embodiments, the one or more pharmaceutically acceptable excipients comprise about 20% by weight to about 60% by weight of one or more fillers based on the total weight of the oral dosage form. In some embodiments, the one or more pharmaceutically acceptable excipients comprise about 20% by weight to about 55% by weight of one or more fillers based on the total weight of the oral dosage form. In some embodiments, the one or more pharmaceutically acceptable excipients comprise about 20% by weight to about 50% by weight of one or more fillers based on the total weight of the oral dosage form. In some embodiments, the one or more pharmaceutically acceptable excipients comprise about 20% by weight to about 45% by weight of one or more fillers based on the total weight of the oral dosage form. In some embodiments, the one or more pharmaceutically acceptable excipients comprise about 20% by weight to about 40% by weight of one or more fillers based on the total weight of the oral dosage form. In some embodiments, the one or more pharmaceutically acceptable excipients comprise about 20% by weight to about 35% by weight of one or more fillers based on the total weight of the oral dosage form. In some embodiments, the one or more pharmaceutically acceptable excipients comprise about 20% by weight to about 30% by weight of one or more fillers based on the total weight of the oral dosage form. In some embodiments, the one or more pharmaceutically acceptable excipients comprise about 20% by weight to about 25% by weight of one or more fillers based on the total weight of the oral dosage form.

In some embodiments, the one or more pharmaceutically acceptable excipients comprise about 30% by weight to about 90% by weight of one or more fillers based on the total weight of the oral dosage form. In some embodiments, the one or more pharmaceutically acceptable excipients comprise about 30% by weight to about 80% by weight of one or more fillers based on the total weight of the oral dosage form. In some embodiments, the one or more pharmaceutically acceptable excipients comprise about 30% by weight to about 70% by weight of one or more fillers based on the total weight of the oral dosage form. In some embodiments, the one or more pharmaceutically acceptable excipients comprise about 30% by weight to about 60% by weight of one or more fillers based on the total weight of the oral dosage form. In some embodiments, the one or more pharmaceutically acceptable excipients comprise about 30% by weight to about 50% by weight of one or more fillers based on the total weight of the oral dosage form. In some embodiments, the one or more pharmaceutically acceptable excipients comprise about 30% by weight to about 40% by weight of one or more fillers based on the total weight of the oral dosage form.

In some embodiments, the one or more pharmaceutically acceptable excipients comprise about 40% by weight to about 90% by weight of one or more fillers based on the total weight of the oral dosage form. In some embodiments, the one or more pharmaceutically acceptable excipients comprise about 40% by weight to about 80% by weight of one or more fillers based on the total weight of the oral dosage form. In some embodiments, the one or more pharmaceutically acceptable excipients comprise about 40% by weight to about 70% by weight of one or more fillers based on the total weight of the oral dosage form. In some embodiments, the one or more pharmaceutically acceptable excipients comprise about 40% by weight to about 60% by weight of one or more fillers based on the total weight of the oral dosage form. In some embodiments, the one or more pharmaceutically acceptable excipients comprise about 40% by weight to about 50% by weight of one or more fillers based on the total weight of the oral dosage form.

In some embodiments, the one or more pharmaceutically acceptable excipients comprise about 50% by weight to about 90% by weight of one or more fillers based on the total weight of the oral dosage form. In some embodiments, the one or more pharmaceutically acceptable excipients comprise about 50% by weight to about 80% by weight of one or more fillers based on the total weight of the oral dosage form. In some embodiments, the one or more pharmaceutically acceptable excipients comprise about 50% by weight to about 70% by weight of one or more fillers based on the total weight of the oral dosage form. In some embodiments, the one or more pharmaceutically acceptable excipients comprise about 50% by weight to about 60% by weight of one or more fillers based on the total weight of the oral dosage form.

In some embodiments, the one or more pharmaceutically acceptable excipients comprise about 60% by weight to about 90% by weight of one or more fillers based on the total weight of the oral dosage form. In some embodiments, the one or more pharmaceutically acceptable excipients comprise about 60% by weight to about 80% by weight of one or more fillers based on the total weight of the oral dosage form. In some embodiments, the one or more pharmaceutically acceptable excipients comprise about 60% by weight to about 70% by weight of one or more fillers based on the total weight of the oral dosage form.

In some embodiments, the one or more pharmaceutically acceptable excipients comprise about 70% by weight to about 90% by weight of one or more fillers based on the total weight of the oral dosage form. In some embodiments, the one or more pharmaceutically acceptable excipients comprise about 70% by weight to about 80% by weight of one or more fillers based on the total weight of the oral dosage form.

In some embodiments, the one or more pharmaceutically acceptable excipients comprise about 80% by weight to about 90% by weight of one or more fillers based on the total weight of the oral dosage form.

In some embodiments, the one or more pharmaceutically acceptable excipients comprise about 1% by weight to about 20% by weight of one or more disintegrants based on the total weight of the oral dosage form. In some embodiments, the one or more pharmaceutically acceptable excipients comprise about 1% by weight to about 15% by weight of one or more disintegrants based on the total weight of the oral dosage form. In some embodiments, the one or more pharmaceutically acceptable excipients comprise about 1% by weight to about 14% by weight of one or more disintegrants based on the total weight of the oral dosage form. In some embodiments, the one or more pharmaceutically acceptable excipients comprise about 1% by weight to about 13% by weight of one or more disintegrants based on the total weight of the oral dosage form. In some embodiments, the one or more pharmaceutically acceptable excipients comprise about 1% by weight to about 12% by weight of one or more disintegrants based on the total weight of the oral dosage form. In some embodiments, the one or more pharmaceutically acceptable excipients comprise about 1% by weight to about 11% by weight of one or more disintegrants based on the total weight of the oral dosage form. In some embodiments, the one or more pharmaceutically acceptable excipients comprise about 1% by weight to about 10% by weight of one or more disintegrants based on the total weight of the oral dosage form. In some embodiments, the one or more pharmaceutically acceptable excipients comprise about 1% by weight to about 9% by weight of one or more disintegrants based on the total weight of the oral dosage form. In some embodiments, the one or more pharmaceutically acceptable excipients comprise about 1% by weight to about 8% by weight of one or more disintegrants based on the total weight of the oral dosage form. In some embodiments, the one or more pharmaceutically acceptable excipients comprise about 1% by weight to about 7% by weight of one or more disintegrants based on the total weight of the oral dosage form. In some embodiments, the one or more pharmaceutically acceptable excipients comprise about 1% by weight to about 6% by weight of one or more disintegrants based on the total weight of the oral dosage form. In some embodiments, the one or more pharmaceutically acceptable excipients comprise about 1% by weight to about 5% by weight of one or more disintegrants based on the total weight of the oral dosage form. In some embodiments, the one or more pharmaceutically acceptable excipients comprise about 1% by weight to about 4% by weight of one or more disintegrants based on the total weight of the oral dosage form. In some embodiments, the one or more pharmaceutically acceptable excipients comprise about 1% by weight to about 3% by weight of one or more disintegrants based on the total weight of the oral dosage form.

In some embodiments, the one or more pharmaceutically acceptable excipients comprise about 1% by weight of one or more disintegrants based on the total weight of the oral dosage form. In some embodiments, the one or more pharmaceutically acceptable excipients comprise about 2% by weight of one or more disintegrants based on the total weight of the oral dosage form. In some embodiments, the one or more pharmaceutically acceptable excipients comprise about 3% by weight of one or more disintegrants based on the total weight of the oral dosage form. In some embodiments, the one or more pharmaceutically acceptable excipients comprise about 4% by weight of one or more disintegrants based on the total weight of the oral dosage form. In some embodiments, the one or more pharmaceutically acceptable excipients comprise about 5% by weight of one or more disintegrants based on the total weight of the oral dosage form. In some embodiments, the one or more pharmaceutically acceptable excipients comprise about 6% by weight of one or more disintegrants based on the total weight of the oral dosage form. In some embodiments, the one or more pharmaceutically acceptable excipients comprise about 7% by weight of one or more disintegrants based on the total weight of the oral dosage form. In some embodiments, the one or more pharmaceutically acceptable excipients comprise about 8% by weight of one or more disintegrants based on the total weight of the oral dosage form. In some embodiments, the one or more pharmaceutically acceptable excipients comprise about 9% by weight of one or more disintegrants based on the total weight of the oral dosage form. In some embodiments, the one or more pharmaceutically acceptable excipients comprise about 10% by weight of one or more disintegrants based on the total weight of the oral dosage form. In some embodiments, the one or more pharmaceutically acceptable excipients comprise about 11% by weight of one or more disintegrants based on the total weight of the oral dosage form. In some embodiments, the one or more pharmaceutically acceptable excipients comprise about 12% by weight of one or more disintegrants based on the total weight of the oral dosage form. In some embodiments, the one or more pharmaceutically acceptable excipients comprise about 13% by weight of one or more disintegrants based on the total weight of the oral dosage form. In some embodiments, the one or more pharmaceutically acceptable excipients comprise about 14% by weight of one or more disintegrants based on the total weight of the oral dosage form. In some embodiments, the one or more pharmaceutically acceptable excipients comprise about 15% by weight of one or more disintegrants based on the total weight of the oral dosage form.

In some embodiments, the one or more pharmaceutically acceptable excipients comprise about 0.1% by weight to about 10% by weight of one or more lubricants based on the total weight of the oral dosage form. In some embodiments, the one or more pharmaceutically acceptable excipients comprise about 0.1% by weight to about 9% by weight of one or more lubricants based on the total weight of the oral dosage form. In some embodiments, the one or more pharmaceutically acceptable excipients comprise about 0.1% by weight to about 8% by weight of one or more lubricants based on the total weight of the oral dosage form. In some embodiments, the one or more pharmaceutically acceptable excipients comprise about 0.1% by weight to about 7% by weight of one or more lubricants based on the total weight of the oral dosage form. In some embodiments, the one or more pharmaceutically acceptable excipients comprise about 0.1% by weight to about 6% by weight of one or more lubricants based on the total weight of the oral dosage form. In some embodiments, the one or more pharmaceutically acceptable excipients comprise about 0.1% by weight to about 5% by weight of one or more lubricants based on the total weight of the oral dosage form. In some embodiments, the one or more pharmaceutically acceptable excipients comprise about 0.1% by weight to about 4% by weight of one or more lubricants based on the total weight of the oral dosage form. In some embodiments, the one or more pharmaceutically acceptable excipients comprise about 0.1% by weight to about 3% by weight of one or more lubricants based on the total weight of the oral dosage form. In some embodiments, the one or more pharmaceutically acceptable excipients comprise about 0.1% by weight to about 2% by weight of one or more lubricants based on the total weight of the oral dosage form.

In some embodiments, the one or more pharmaceutically acceptable excipients comprise about 0.1% by weight to about 1.9% by weight of one or more lubricants based on the total weight of the oral dosage form. In some embodiments, the one or more pharmaceutically acceptable excipients comprise about 0.1% by weight to about 1.8% by weight of one or more lubricants based on the total weight of the oral dosage form. In some embodiments, the one or more pharmaceutically acceptable excipients comprise about 0.1% by weight to about 1.7% by weight of one or more lubricants based on the total weight of the oral dosage form. In some embodiments, the one or more pharmaceutically acceptable excipients comprise about 0.1% by weight to about 1.6% by weight of one or more lubricants based on the total weight of the oral dosage form. In some embodiments, the one or more pharmaceutically acceptable excipients comprise about 0.1% by weight to about 1.5% by weight of one or more lubricants based on the total weight of the oral dosage form. In some embodiments, the one or more pharmaceutically acceptable excipients comprise about 0.1% by weight to about 1.4% by weight of one or more lubricants based on the total weight of the oral dosage form. In some embodiments, the one or more pharmaceutically acceptable excipients comprise about 0.1% by weight to about 1.3% by weight of one or more lubricants based on the total weight of the oral dosage form. In some embodiments, the one or more pharmaceutically acceptable excipients comprise about 0.1% by weight to about 1.2% by weight of one or more lubricants based on the total weight of the oral dosage form. In some embodiments, the one or more pharmaceutically acceptable excipients comprise about 0.1% by weight to about 1.1% by weight of one or more lubricants based on the total weight of the oral dosage form. In some embodiments, the one or more pharmaceutically acceptable excipients comprise about 0.1% by weight to about 1.0% by weight of one or more lubricants based on the total weight of the oral dosage form. In some embodiments, the one or more pharmaceutically acceptable excipients comprise about 0.1% by weight to about 0.9% by weight of one or more lubricants based on the total weight of the oral dosage form. In some embodiments, the one or more pharmaceutically acceptable excipients comprise about 0.1% by weight to about 0.8% by weight of one or more lubricants based on the total weight of the oral dosage form. In some embodiments, the one or more pharmaceutically acceptable excipients comprise about 0.1% by weight to about 0.7% by weight of one or more lubricants based on the total weight of the oral dosage form. In some embodiments, the one or more pharmaceutically acceptable excipients comprise about 0.1% by weight to about 0.6% by weight of one or more lubricants based on the total weight of the oral dosage form. In some embodiments, the one or more pharmaceutically acceptable excipients comprise about 0.1% by weight to about 0.5% by weight of one or more lubricants based on the total weight of the oral dosage form. In some embodiments, the one or more pharmaceutically acceptable excipients comprise about 0.1% by weight to about 0.4% by weight of one or more lubricants based on the total weight of the oral dosage form. In some embodiments, the one or more pharmaceutically acceptable excipients comprise about 0.1% by weight to about 0.3% by weight of one or more lubricants based on the total weight of the oral dosage form. In some embodiments, the one or more pharmaceutically acceptable excipients comprise about 0.1% by weight to about 0.2% by weight of one or more lubricants based on the total weight of the oral dosage form.

In some embodiments, the one or more pharmaceutically acceptable excipients comprise about 0.1% by weight of one or more lubricants based on the total weight of the oral dosage form. In some embodiments, the one or more pharmaceutically acceptable excipients comprise about 0.2% by weight of one or more lubricants based on the total weight of the oral dosage form. In some embodiments, the one or more pharmaceutically acceptable excipients comprise about 0.3% by weight of one or more lubricants based on the total weight of the oral dosage form. In some embodiments, the one or more pharmaceutically acceptable excipients comprise about 0.4% by weight of one or more lubricants based on the total weight of the oral dosage form. In some embodiments, the one or more pharmaceutically acceptable excipients comprise about 0.5% by weight of one or more lubricants based on the total weight of the oral dosage form. In some embodiments, the one or more pharmaceutically acceptable excipients comprise about 0.6% by weight of one or more lubricants based on the total weight of the oral dosage form. In some embodiments, the one or more pharmaceutically acceptable excipients comprise about 0.7% by weight of one or more lubricants based on the total weight of the oral dosage form. In some embodiments, the one or more pharmaceutically acceptable excipients comprise about 0.8% by weight of one or more lubricants based on the total weight of the oral dosage form. In some embodiments, the one or more pharmaceutically acceptable excipients comprise about 0.9% by weight of one or more lubricants based on the total weight of the oral dosage form. In some embodiments, the one or more pharmaceutically acceptable excipients comprise about 1.0% by weight of one or more lubricants based on the total weight of the oral dosage form.

In some embodiments, the oral dosage form comprises: (a) about 1% by weight to about 30% by weight of the compound of Formula (I) based on the total weight of the oral dosage form; (b) about 20% by weight to about 90% by weight of one or more fillers based on the total weight of the oral dosage form; (c) about 1% by weight to about 20% by weight of one or more disintegrants based on the total weight of the oral dosage form; and (d) about 0.1% by weight to about 10% by weight of one or more lubricants based on the total weight of the oral dosage form.

In some embodiments, the oral dosage form consists essentially of: (a) about 1% by weight to about 30% by weight of the compound of Formula (I) based on the total weight of the oral dosage form; (b) about 20% by weight to about 90% by weight of one or more fillers based on the total weight of the oral dosage form; (c) about 1% by weight to about 20% by weight of one or more disintegrants based on the total weight of the oral dosage form; and (d) about 0.1% by weight to about 10% by weight of one or more lubricants based on the total weight of the oral dosage form.

In some embodiments, the oral dosage form comprises (a) about 5% by weight to about 25% by weight of the crystalline dihydrate form of the compound of Formula (I) based on the total weight of the oral dosage form; (b) about 60% by weight to about 90% by weight of one or more fillers based on the total weight of the oral dosage form; (c) about 1% by weight to about 15% by weight of one or more disintegrants based on the total weight of the oral dosage form; and (d) about 0.1% by weight to about 4% by weight of one or more lubricants based on the total weight of the oral dosage form.

In some embodiments, the oral dosage form consists essentially of: (a) about 5% by weight to about 25% by weight of the crystalline dihydrate form of the compound of Formula (I) based on the total weight of the oral dosage form; (b) about 60% by weight to about 90% by weight of one or more fillers based on the total weight of the oral dosage form; (c) about 1% by weight to about 15% by weight of one or more disintegrants based on the total weight of the oral dosage form; and (d) about 0.1% by weight to about 4% by weight of one or more lubricants based on the total weight of the oral dosage form.

In some embodiments, the oral dosage form comprises (a) about 10% by weight to about 30% by weight of the crystalline dihydrate form of the compound of Formula (I) based on the total weight of the oral dosage form; (b) about 70% by weight to about 90% by weight of one or more fillers based on the total weight of the oral dosage form; (c) about 1% by weight to about 10% by weight of one or more disintegrants based on the total weight of the oral dosage form; and (d) about 0.1% by weight to about 3% by weight of one or more lubricants based on the total weight of the oral dosage form.

In some embodiments, the oral dosage form consists essentially of: (a) about 10% by weight to about 30% by weight of the crystalline dihydrate form of the compound of Formula (I) based on the total weight of the oral dosage form; (b) about 70% by weight to about 90% by weight of one or more fillers based on the total weight of the oral dosage form; (c) about 1% by weight to about 10% by weight of one or more disintegrants based on the total weight of the oral dosage form; and (d) about 0.1% by weight to about 3% by weight of one or more lubricants based on the total weight of the oral dosage form.

In some embodiments, the one or more pharmaceutically acceptable excipients is one or more fillers selected from the group consisting of calcium phosphate, dicalcium phosphate, dicalcium phosphate dihydrate, calcium sulfate, calcium sulfate dihydrate, starch, calcium carbonate, magnesium carbonate, magnesium oxide, kaolin (natural hydrated aluminum silicate), sodium chloride, partially gelatinized starch, anhydrous lactose, lactose monohydrate, lactose dihydrate, trehalose dihydrate, spray dried lactose, sucrose, dextrose, dextrates, dextrin, cellulose, microcrystalline cellulose, silicified microcrystalline cellulose, powdered cellulose, partially depolymerized cellulose, mannitol, granulated mannitol, spray dried mannitol, maltodextrin, maltitol, confectioner's sugar, compressible sugar, sorbitol, starch and talc. In some embodiments, the one or more fillers is lactose monohydrate.

In some embodiments, the one or more disintegrants is one or more disintegrants selected from the group consisting of sodium starch glycolate, pregelatinized starch, clay, cellulose, alginic acid, alginate gum, polyvinylpyrrolidone, cross-linked polyvinylpyrrolidone, cross-linked calcium carboxymethylcellulose, cross-linked sodium carboxymethylcellulose, sodium croscarmellose, sodium carmellose, low substituted hydroxypropyl cellulose, low substituted hydroxypropyl cellulose sodium, guar gum, magnesium aluminum silicate, polacrilin potassium, powdered cellulose, sodium alginate and soy polysaccharides. In some embodiments, the one or more disintegrants is cross-linked polyvinylpyrrolidone (also referred to as crospovidone).

In some embodiments, the one or more lubricants is one or more lubricants selected from the group consisting of colloidal silica, magnesium trisilicate, talc, magnesium carbonate, magnesium oxide, glyceryl behaptate, mono, di and tri glyceryl behenate, bees wax, behenoyl polyoxyl-8 glycerides, hydrogenated vegetable oil, polyethylene glycol, ethylene oxide polymer, copolymer comprising poly(ethylene oxide) and poly(propylene oxide) (such as poloxomer 188), copolymer comprising polypropylene glycol and polyethylene glycol (such as poloxomer 407), sodium lauryl sulfate, magnesium stearate, aluminum stearate, calcium stearate, sodium stearyl fumarate, stearic acid, magnesium lauryl stearate, mixtures of magnesium stearate with sodium lauryl sulfate. In some embodiments, the one or more lubricants is magnesium stearate.

In some embodiments, the one or more disintegrants is selected from the group consisting of cross-linked polyvinylpyrrolidone, croscarmellose sodium, and sodium starch glycolate; and the one or more lubricants is selected from the group consisting of sodium stearyl fumarate, stearic acid, talc, calcium stearate, magnesium stearate, solid polyethylene glycols, and sodium lauryl sulfate. In some embodiments, the oral dosage form comprises cross-linked polyvinylpyrrolidone and magnesium stearate. In some embodiments, the one or more pharmaceutically acceptable excipients is lactose monohydrate and the oral dosage form further comprises cross-linked polyvinylpyrrolidone and magnesium stearate.

In some embodiments, the oral dosage form is a tablet or capsule. In some embodiments, the oral dosage form is a tablet. In some embodiments, the oral dosage form is a capsule. In some embodiments, the oral dosage form is a sachet. In some embodiments, the oral dosage form is a powder in a packet.

In some embodiments, the oral dosage form comprises about 1 mg to about 40 mg of the crystalline dihydrate form of the compound of Formula (I). In some embodiments, the oral dosage form comprises about 5 mg to about 35 mg of the crystalline dihydrate form of the compound of Formula (I). In some embodiments, the oral dosage form comprises about 10 mg to about 35 mg of the crystalline dihydrate form of the compound of Formula (I). In some embodiments, the oral dosage form comprises about 0.5 mg to about 5 mg, about 6 mg to about 14 mg, about 11 mg to about 19 mg, about 17 mg to about 25 mg, or about 28 mg to about 36 mg of the crystalline dihydrate form of the compound of Formula (I). In some embodiments, the oral dosage form comprises about 1 mg to about 4 mg, about 8 mg to about 12 mg, about 13 mg to about 17 mg, about 19 mg to about 23 mg, or about 30 mg to about 34 mg of the crystalline dihydrate form of the compound of Formula (I). In some embodiments, the oral dosage form comprises about 2.2 mg, about 10.8 mg, about 15.2 mg, about 21.7 mg, or about 32.5 mg of the crystalline dihydrate form of the compound of Formula (I). In some embodiments, the crystalline dihydrate form of the compound of Formula (I) is present in an amount of about 2.2 mg. In some embodiments, the crystalline dihydrate form of the compound of Formula (I) is present in an amount of about 10.8 mg. In some embodiments, the crystalline dihydrate form of the compound of Formula (I) is present in an amount of about 15.2 mg. In some embodiments, the crystalline dihydrate form of the compound of Formula (I) is present in an amount of about 21.7 mg. In some embodiments, the crystalline dihydrate form of the compound of Formula (I) is present in an amount of about 32.5 mg.

In some embodiments, the oral dosage form consists essentially of about 1 mg to about 40 mg of the crystalline dihydrate form of the compound of Formula (I). In some embodiments, the oral dosage form consists essentially of about 5 mg to about 35 mg of the crystalline dihydrate form of the compound of Formula (I). In some embodiments, the oral dosage form consists essentially of about 10 mg to about 35 mg of the crystalline dihydrate form of the compound of Formula (I). In some embodiments, the oral dosage form consists essentially of about 0.5 mg to about 5 mg, about 6 mg to about 14 mg, about 11 mg to about 19 mg, about 17 mg to about 25 mg, or about 28 mg to about 36 mg of the crystalline dihydrate form of the compound of Formula (I). In some embodiments, the oral dosage form consists essentially of about 1 mg to about 4 mg, about 8 mg to about 12 mg, about 13 mg to about 17 mg, about 19 mg to about 23 mg, or about 30 mg to about 34 mg of the crystalline dihydrate form of the compound of Formula (I). In some embodiments, the oral dosage form consists essentially of about 2.2 mg, about 10.8 mg, about 15.2 mg, about 21.7 mg, or about 32.5 mg of the crystalline dihydrate form of the compound of Formula (I). In some embodiments, the crystalline dihydrate form of the compound of Formula (I) is present in an amount of about 2.2 mg. In some embodiments, the crystalline dihydrate form of the compound of Formula (I) is present in an amount of about 10.8 mg. In some embodiments, the crystalline dihydrate form of the compound of Formula (I) is present in an amount of about 15.2 mg. In some embodiments, the crystalline dihydrate form of the compound of Formula (I) is present in an amount of about 21.7 mg. In some embodiments, the crystalline dihydrate form of the compound of Formula (I) is present in an amount of about 32.5 mg.

Also provided herein, in some embodiments, are pharmaceutically acceptable capsules comprising a compound of Formula (I):

Formula (I)

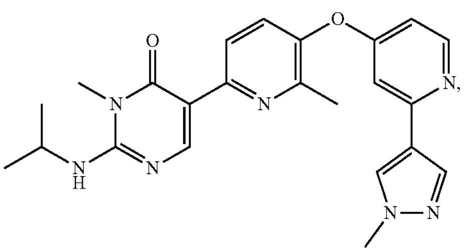

and one or more pharmaceutically acceptable excipients, wherein the compound is present in the pharmaceutically acceptable capsules as a free base, or a pharmaceutically acceptable salt of the compound, and wherein the free base or pharmaceutically acceptable salt is in anhydrous or hydrate form.

Also provided herein, in some embodiments, are pharmaceutically acceptable capsules consisting essentially of a compound of Formula (I):

Formula (I)

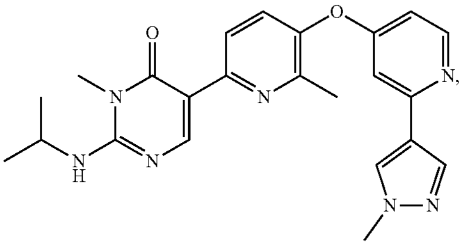

and one or more pharmaceutically acceptable excipients, wherein the compound is present in the pharmaceutically acceptable capsules as a free base, or a pharmaceutically acceptable salt of the compound, and wherein the free base or pharmaceutically acceptable salt is in anhydrous or hydrate form.

In some embodiments, the compound of Formula (I) is present in the pharmaceutically acceptable capsule as a hydrate form (the compound of Formula (I)·$nH_2O$). For example, the hydrate form is a hemihydrate form, a monohydrate form, a sesquihydrate form, a dihydrate form, a trihydrate form, a tetrahydrate form, a pentahydrate form, a hexahydrate form, a heptahydrate form, an octahydrate form, a nonahydrate form, or a decahydrate form. In some embodiments, the hydrate form is a hemihydrate form, a monohydrate form, a sesquihydrate form, a dihydrate form, a trihydrate form, or a tetrahydrate form. In some embodiments, the hydrate form is a hemihydrate form. In some embodiments, the hydrate form is a monohydrate form. In some embodiments, the hydrate form is a dihydrate form. In some embodiments, the compound of Formula (I) is present in the pharmaceutically acceptable capsule as a dihydrate form. In some embodiments, the compound of Formula (I) is present in the pharmaceutically acceptable capsule as an anhydrous form.

In some embodiments, the one or more pharmaceutically acceptable excipients is a filler. For example, the one or more pharmaceutically acceptable excipients is lactose, such as lactose monohydrate.

In some embodiments, the pharmaceutically acceptable capsules further comprise one or more disintegrants, one or more lubricants, or a combination thereof. For example, in some embodiments, the pharmaceutically acceptable capsules further comprise one or more disintegrants. In some embodiments, the pharmaceutically acceptable capsules further comprise one or more lubricants.

Also provided herein, in some embodiments, is a pharmaceutically acceptable capsule comprising:

(a) about 1% by weight to about 70% by weight, based on the total weight of the pharmaceutically acceptable capsule, of a compound of Formula (I):

Formula (I)

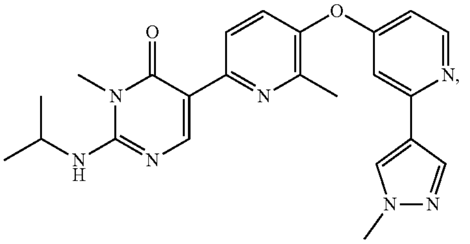

wherein the compound is present in the pharmaceutically acceptable capsule as a free base, or a pharmaceutically acceptable salt of the compound, and wherein the free base or pharmaceutically acceptable salt is in anhydrous or hydrate form, and one or more pharmaceutically acceptable excipients, wherein the one or more pharmaceutically acceptable excipients comprise:

(b) about 20% by weight to about 97% by weight of one or more fillers based on the total weight of the pharmaceutically acceptable capsule;

(c) about 1% by weight to about 20% by weight of one or more disintegrants based on the total weight of the pharmaceutically acceptable capsule; and (d) about 0.1% by weight to about 10% by weight of one or more lubricants based on the total weight of the pharmaceutically acceptable capsule.

Also provided herein, in some embodiments, is a pharmaceutically acceptable capsule comprising:

(a) about 1% by weight to about 30% by weight, based on the total weight of the pharmaceutically acceptable capsule, of a compound of Formula (I) based on the total weight of the pharmaceutically acceptable capsule;

(b) about 20% by weight to about 90% by weight of one or more fillers based on the total weight of the pharmaceutically acceptable capsule;

(c) about 1% by weight to about 20% by weight of one or more disintegrants based on the total weight of the pharmaceutically acceptable capsule; and (d) about 0.1% by weight to about 10% by weight of one or more lubricants based on the total weight of the pharmaceutically acceptable capsule.

Also provided herein, in some embodiments, is a pharmaceutically acceptable capsule consisting essentially of:

(a) about 1% by weight to about 70% by weight, based on the total weight of the pharmaceutically acceptable capsule, of a compound of Formula (I):

Formula (I)

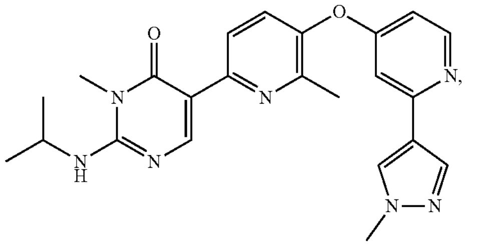

wherein the compound is present in the pharmaceutically acceptable capsule as a free base, or a pharmaceutically acceptable salt of the compound and wherein the free base or pharmaceutically acceptable salt is in anhydrous or hydrate form, and one or more pharmaceutically acceptable excipients, wherein the one or more pharmaceutically acceptable excipients comprise:

(b) about 20% by weight to about 97% by weight of one or more fillers based on the total weight of the pharmaceutically acceptable capsule;

(c) about 1% by weight to about 20% by weight of one or more disintegrants based on the total weight of the pharmaceutically acceptable capsule; and (d) about 0.1% by weight to about 10% by weight of one or more lubricants based on the total weight of the pharmaceutically acceptable capsule.

Also provided herein, in some embodiments, is a pharmaceutically acceptable capsule consisting essentially of:

(a) about 1% by weight to about 30% by weight, based on the total weight of the pharmaceutically acceptable capsule, of a compound of Formula (I) based on the total weight of the pharmaceutically acceptable capsule;

(b) about 20% by weight to about 90% by weight of one or more fillers based on the total weight of the pharmaceutically acceptable capsule;

(c) about 1% by weight to about 20% by weight of one or more disintegrants based on the total weight of the pharmaceutically acceptable capsule; and (d) about 0.1% by weight to about 10% by weight of one or more lubricants based on the total weight of the pharmaceutically acceptable capsule.

In some embodiments, the pharmaceutically acceptable capsule comprises about 1% by weight to about 60% by weight, based on the total weight of the pharmaceutically acceptable capsule, of a compound of Formula (I), wherein the compound is present in the pharmaceutically acceptable capsule as a free base, or a pharmaceutically acceptable salt of the compound and wherein the free base or pharmaceutically acceptable salt is in anhydrous or hydrate form. In some embodiments, the pharmaceutically acceptable capsule comprises about 1% by weight to about 50% by weight, based on the total weight of the pharmaceutically acceptable capsule, of a compound of Formula (I), wherein the compound is present in the pharmaceutically acceptable capsule as a free base, or a pharmaceutically acceptable salt of the compound and wherein the free base or pharmaceutically acceptable salt is in anhydrous or hydrate form. In some embodiments, the pharmaceutically acceptable capsule comprises about 1% by weight to about 40% by weight, based on the total weight of the pharmaceutically acceptable capsule, of a compound of Formula (I), wherein the compound is present in the pharmaceutically acceptable capsule as a free base, or a pharmaceutically acceptable salt of the compound and wherein the free base or pharmaceutically acceptable salt is in anhydrous or hydrate form. In some embodiments, the pharmaceutically acceptable capsule comprises about 1% by weight to about 30% by weight, based on the total weight of the pharmaceutically acceptable capsule, of a compound of Formula (I), wherein the compound is present in the pharmaceutically acceptable capsule as a free base, or a pharmaceutically acceptable salt of the compound and wherein the free base or pharmaceutically acceptable salt is in anhydrous or hydrate form. In some embodiments, the pharmaceutically acceptable capsule comprises about 1% by weight to about 20% by weight, based on the total weight of the pharmaceutically acceptable capsule, of a compound of Formula (I), wherein the compound is present in the pharmaceutically acceptable capsule as a free base, or a pharmaceutically acceptable salt of the compound and wherein the free base or pharmaceutically acceptable salt is in anhydrous or hydrate form.

In some embodiments, the pharmaceutically acceptable capsule consists essentially of about 1% by weight to about 60% by weight, based on the total weight of the pharmaceutically acceptable capsule, of a compound of Formula (I), wherein the compound is present in the pharmaceutically acceptable formulation as a free base, or a pharmaceutically acceptable salt of the compound and wherein the free base or pharmaceutically acceptable salt is in anhydrous or hydrate form. In some embodiments, the pharmaceutically acceptable capsule consists essentially of about 1% by weight to about 50% by weight, based on the total weight of the pharmaceutically acceptable capsule, of a compound of Formula (I), wherein the compound is present in the pharmaceutically acceptable formulation as a free base, or a pharmaceutically acceptable salt of the compound and wherein the free base or pharmaceutically acceptable salt is in anhydrous or hydrate form. In some embodiments, the pharmaceutically acceptable capsule consists essentially of about 1% by weight to about 40% by weight, based on the total weight of the pharmaceutically acceptable capsule, of a compound of Formula (I), wherein the compound is present in the pharmaceutically acceptable formulation as a free base, or a pharmaceutically acceptable salt of the compound and wherein the free base or pharmaceutically acceptable salt is in anhydrous or hydrate form. In some embodiments, the pharmaceutically acceptable capsule consists essentially of about 1% by weight to about 30% by weight, based on the total weight of the pharmaceutically acceptable capsule, of a compound of Formula (I), wherein the compound is present in the pharmaceutically acceptable formulation as a free base, or a pharmaceutically acceptable salt of the compound and wherein the free base or pharmaceutically acceptable salt is in anhydrous or hydrate form. In some embodiments, the pharmaceutically acceptable capsule consists essentially of about 1% by weight to about 20% by weight, based on the total weight of the pharmaceutically acceptable capsule, of a compound of Formula (I), wherein the compound is present in the pharmaceutically acceptable formulation as a free base, or a pharmaceutically acceptable salt of the compound and wherein the free base or pharmaceutically acceptable salt is in anhydrous or hydrate form.

In some embodiments, the pharmaceutically acceptable capsule comprises about 1% by weight to about 70% by weight of the compound of Formula (I) based on the total weight of the pharmaceutically acceptable capsule. In some embodiments, the pharmaceutically acceptable capsule comprises about 1% by weight to about 65% by weight of the compound of Formula (I) based on the total weight of the pharmaceutically acceptable capsule. In some embodiments, the pharmaceutically acceptable capsule comprises about 1% by weight to about 60% by weight of the compound of Formula (I) based on the total weight of the pharmaceutically acceptable capsule. In some embodiments, the pharmaceutically acceptable capsule comprises about 1% by weight to about 55% by weight of the compound of Formula (I) based on the total weight of the pharmaceutically acceptable capsule. In some embodiments, the pharmaceutically acceptable capsule comprises about 1% by weight to about 50% by weight of the compound of Formula (I) based on the total weight of the pharmaceutically acceptable capsule. In some embodiments, the pharmaceutically acceptable capsule comprises about 1% by weight to about 45% by weight of the compound of Formula (I) based on the total weight of the pharmaceutically acceptable capsule. In some embodiments, the pharmaceutically acceptable capsule comprises about 1% by weight to about 40% by weight of the compound of Formula (I) based on the total weight of the pharmaceutically acceptable capsule. In some embodiments, the pharmaceutically acceptable capsule comprises about 1% by weight to about 35% by weight of the compound of Formula (I) based on the total weight of the pharmaceutically acceptable capsule. In some embodiments, the pharmaceutically acceptable capsule comprises about 1% by weight to about 30% by weight of the compound of Formula (I) based on the total weight of the pharmaceutically acceptable capsule. In some embodiments, the pharmaceutically acceptable capsule comprises about 1% by weight to about 25% by weight of the compound of Formula (I) based on the total weight of the pharmaceutically acceptable capsule. In some embodiments, the pharmaceutically acceptable capsule comprises about 1% by weight to about 20% by weight of the compound of Formula (I) based on the total weight of the pharmaceutically acceptable capsule. In some embodiments, the pharmaceutically acceptable capsule comprises about 1% by weight to about 15% by weight of the compound of Formula (I) based on the total weight of the pharmaceutically acceptable capsule. In some embodiments, the pharmaceutically acceptable capsule comprises about 1% by weight to about 10% by weight of the compound of Formula (I) based on the total weight of the pharmaceutically acceptable capsule.

In some embodiments, the pharmaceutically acceptable capsule consists essentially of about 1% by weight to about 70% by weight of the compound of Formula (I) based on the total weight of the pharmaceutically acceptable capsule. In some embodiments, the pharmaceutically acceptable capsule consists essentially of about 1% by weight to about 65% by weight of the compound of Formula (I) based on the total weight of the pharmaceutically acceptable capsule. In some embodiments, the pharmaceutically acceptable capsule consists essentially of about 1% by weight to about 60% by weight of the compound of Formula (I) based on the total weight of the pharmaceutically acceptable capsule. In some embodiments, the pharmaceutically acceptable capsule consists essentially of about 1% by weight to about 55% by weight of the compound of Formula (I) based on the total weight of the pharmaceutically acceptable capsule. In some embodiments, the pharmaceutically acceptable capsule consists essentially of about 1% by weight to about 50% by weight of the compound of Formula (I) based on the total weight of the pharmaceutically acceptable capsule. In some embodiments, the pharmaceutically acceptable capsule consists essentially of about 1% by weight to about 45% by weight of the compound of Formula (I) based on the total weight of the pharmaceutically acceptable capsule. In some embodiments, the pharmaceutically acceptable capsule consists essentially of about 1% by weight to about 40% by weight of the compound of Formula (I) based on the total weight of the pharmaceutically acceptable capsule. In some embodiments, the pharmaceutically acceptable capsule consists essentially of about 1% by weight to about 35% by weight of the compound of Formula (I) based on the total weight of the pharmaceutically acceptable capsule. In some embodiments, the pharmaceutically acceptable capsule consists essentially of about 1% by weight to about 30% by weight of the compound of Formula (I) based on the total weight of the pharmaceutically acceptable capsule. In some embodiments, the pharmaceutically acceptable capsule consists essentially of about 1% by weight to about 25% by weight of the compound of Formula (I) based on the total weight of the pharmaceutically acceptable capsule. In some embodiments, the pharmaceutically acceptable capsule consists essentially of about 1% by weight to about 20% by weight of the compound of Formula (I) based on the total weight of the pharmaceutically acceptable capsule. In some embodiments, the pharmaceutically acceptable capsule consists essentially of about 1% by weight to about 15% by weight of the compound of Formula (I) based on the total weight of the pharmaceutically acceptable capsule. In some embodiments, the pharmaceutically acceptable capsule consists essentially of about 1% by weight to about 10% by weight of the compound of Formula (I) based on the total weight of the pharmaceutically acceptable capsule.

In some embodiments, the pharmaceutically acceptable capsule comprises about 5% by weight to about 30% by weight of the compound of Formula (I) based on the total weight of the pharmaceutically acceptable capsule. In some embodiments, the pharmaceutically acceptable capsule comprises about 5% by weight to about 25% by weight of the compound of Formula (I) based on the total weight of the pharmaceutically acceptable capsule. In some embodiments, the pharmaceutically acceptable capsule comprises about 5% by weight to about 20% by weight of the compound of Formula (I) based on the total weight of the pharmaceutically acceptable capsule. In some embodiments, the pharmaceutically acceptable capsule comprises about 5% by weight to about 15% by weight of the compound of Formula (I) based on the total weight of the pharmaceutically acceptable capsule. In some embodiments, the pharmaceutically acceptable capsule comprises about 5% by weight to about 10% by weight of the compound of Formula (I) based on the total weight of the pharmaceutically acceptable capsule.

In some embodiments, the pharmaceutically acceptable capsule consists essentially of about 5% by weight to about 30% by weight of the compound of Formula (I) based on the total weight of the pharmaceutically acceptable capsule. In some embodiments, the pharmaceutically acceptable capsule consists essentially of about 5% by weight to about 25% by weight of the compound of Formula (I) based on the total weight of the pharmaceutically acceptable capsule. In some embodiments, the pharmaceutically acceptable capsule consists essentially of about 5% by weight to about 20% by weight of the compound of Formula (I) based on the total weight of the pharmaceutically acceptable capsule. In some embodiments, the pharmaceutically acceptable capsule consists essentially of about 5% by weight to about 15% by weight of the compound of Formula (I) based on the total weight of the pharmaceutically acceptable capsule. In some embodiments, the pharmaceutically acceptable capsule consists essentially of about 5% by weight to about 10% by weight of the compound of Formula (I) based on the total weight of the pharmaceutically acceptable capsule.

In some embodiments, the pharmaceutically acceptable capsule comprises about 10% to about 30% of the compound of Formula (I) based on the total weight of the pharmaceutically acceptable capsule. In some embodiments, the pharmaceutically acceptable capsule comprises about 10% to about 25% of the compound of Formula (I) based on the total weight of the pharmaceutically acceptable capsule. In some embodiments, the pharmaceutically acceptable capsule comprises about 10% to about 20% of the compound of Formula (I) based on the total weight of the pharmaceutically acceptable capsule. In some embodiments, the pharmaceutically acceptable capsule comprises about 10% by weight to about 15% by weight of the compound of Formula (I) based on the total weight of the pharmaceutically acceptable capsule.

In some embodiments, the pharmaceutically acceptable capsule consists essentially of about 10% to about 30% of the compound of Formula (I) based on the total weight of the pharmaceutically acceptable capsule. In some embodiments, the pharmaceutically acceptable capsule consists essentially of about 10% to about 25% of the compound of Formula (I) based on the total weight of the pharmaceutically acceptable capsule. In some embodiments, the pharmaceutically acceptable capsule consists essentially of about 10% to about 20% of the compound of Formula (I) based on the total weight of the pharmaceutically acceptable capsule. In some embodiments, the pharmaceutically acceptable capsule consists essentially of about 10% by weight to about 15% by weight of the compound of Formula (I) based on the total weight of the pharmaceutically acceptable capsule.

In some embodiments, the pharmaceutically acceptable capsule comprises about 1% by weight to about 30% by weight of the compound of Formula (I) based on the total weight of the pharmaceutically acceptable capsule. In some embodiments, the pharmaceutically acceptable capsule comprises about 1% by weight to about 10% by weight of the compound of Formula (I) based on the total weight of the pharmaceutically acceptable capsule. In some embodiments, the pharmaceutically acceptable capsule comprises about 10% to about 20% of the compound of Formula (I) based on the total weight of the pharmaceutically acceptable capsule. In some embodiments, the pharmaceutically acceptable capsule comprises about 10% by weight to about 15% by weight of the compound of Formula (I) based on the total weight of the pharmaceutically acceptable capsule.

In some embodiments, the pharmaceutically acceptable capsule consists essentially of about 1% by weight to about 30% by weight of the compound of Formula (I) based on the total weight of the pharmaceutically acceptable capsule. In some embodiments, the pharmaceutically acceptable capsule consists essentially of about 1% by weight to about 10% by weight of the compound of Formula (I) based on the total weight of the pharmaceutically acceptable capsule. In some embodiments, the pharmaceutically acceptable capsule consists essentially of about 10% to about 20% of the compound of Formula (I) based on the total weight of the pharmaceutically acceptable capsule. In some embodiments, the pharmaceutically acceptable capsule consists essentially of about 10% by weight to about 15% by weight of the compound of Formula (I) based on the total weight of the pharmaceutically acceptable capsule.

In some embodiments, the one or more pharmaceutically acceptable excipients comprise about 20% by weight to about 90% by weight of one or more fillers based on the total weight of the pharmaceutically acceptable capsule. In some embodiments, the one or more pharmaceutically acceptable excipients comprise about 20% by weight to about 85% by weight of one or more fillers based on the total weight of the pharmaceutically acceptable capsule. In some embodiments, the one or more pharmaceutically acceptable excipients comprise about 20% by weight to about 80% by weight of one or more fillers based on the total weight of the pharmaceutically acceptable capsule. In some embodiments, the one or more pharmaceutically acceptable excipients comprise about 20% by weight to about 75% by weight of one or more fillers based on the total weight of the pharmaceutically acceptable capsule. In some embodiments, the one or more pharmaceutically acceptable excipients comprise about 20% by weight to about 70% by weight of one or more fillers based on the total weight of the pharmaceutically acceptable capsule. In some embodiments, the one or more pharmaceutically acceptable excipients comprise about 20% by weight to about 65% by weight of one or more fillers based on the total weight of the pharmaceutically acceptable capsule. In some embodiments, the one or more pharmaceutically acceptable excipients comprise about 20% by weight to about 60% by weight of one or more fillers based on the total weight of the pharmaceutically acceptable capsule. In some embodiments, the one or more pharmaceutically acceptable excipients comprise about 20% by weight to about 55% by weight of one or more fillers based on the total weight of the pharmaceutically acceptable capsule. In some embodiments, the one or more pharmaceutically acceptable excipients comprise about 20% by weight to about 50% by weight of one or more fillers based on the total weight of the pharmaceutically acceptable capsule. In some embodiments, the one or more pharmaceutically acceptable excipients comprise about 20% by weight to about 45% by weight of one or more fillers based on the total weight of the pharmaceutically acceptable capsule. In some embodiments, the one or more pharmaceutically acceptable excipients comprise about 20% by weight to about 40% by weight of one or more fillers based on the total weight of the pharmaceutically acceptable capsule. In some embodiments, the one or more pharmaceutically acceptable excipients comprise about 20% by weight to about 35% by weight of one or more fillers based on the total weight of the pharmaceutically acceptable capsule. In some embodiments, the one or more pharmaceutically acceptable excipients comprise about 20% by weight to about 30% by weight of one or more fillers based on the total weight of the pharmaceutically acceptable capsule. In some embodiments, the one or more pharmaceutically acceptable excipients comprise about 20% by weight to about 25% by weight of one or more fillers based on the total weight of the pharmaceutically acceptable capsule.

In some embodiments, the one or more pharmaceutically acceptable excipients comprise about 30% by weight to about 90% by weight of one or more fillers based on the total weight of the pharmaceutically acceptable capsule. In some embodiments, the one or more pharmaceutically acceptable excipients comprise about 30% by weight to about 80% by weight of one or more fillers based on the total weight of the pharmaceutically acceptable capsule. In some embodiments, the one or more pharmaceutically acceptable excipients comprise about 30% by weight to about 70% by weight of one or more fillers based on the total weight of the pharmaceutically acceptable capsule. In some embodiments, the one or more pharmaceutically acceptable excipients comprise about 30% by weight to about 60% by weight of one or more fillers based on the total weight of the pharmaceutically acceptable capsule. In some embodiments, the one or more pharmaceutically acceptable excipients comprise about 30% by weight to about 50% by weight of one or more fillers based on the total weight of the pharmaceutically acceptable capsule. In some embodiments, the one or more pharmaceutically acceptable excipients comprise about 30% by weight to about 40% by weight of one or more fillers based on the total weight of the pharmaceutically acceptable capsule.

In some embodiments, the one or more pharmaceutically acceptable excipients comprise about 40% by weight to about 90% by weight of one or more fillers based on the total weight of the pharmaceutically acceptable capsule. In some embodiments, the one or more pharmaceutically acceptable excipients comprise about 40% by weight to about 80% by weight of one or more fillers based on the total weight of the pharmaceutically acceptable capsule. In some embodiments, the one or more pharmaceutically acceptable excipients comprise about 40% by weight to about 70% by weight of one or more fillers based on the total weight of the pharmaceutically acceptable capsule. In some embodiments, the one or more pharmaceutically acceptable excipients comprise about 40% by weight to about 60% by weight of one or more fillers based on the total weight of the pharmaceutically acceptable capsule. In some embodiments, the one or more pharmaceutically acceptable excipients comprise about 40% by weight to about 50% by weight of one or more fillers based on the total weight of the pharmaceutically acceptable capsule.

In some embodiments, the one or more pharmaceutically acceptable excipients comprise about 50% by weight to about 90% by weight of one or more fillers based on the total weight of the pharmaceutically acceptable capsule. In some embodiments, the one or more pharmaceutically acceptable excipients comprise about 50% by weight to about 80% by weight of one or more fillers based on the total weight of the pharmaceutically acceptable capsule. In some embodiments, the one or more pharmaceutically acceptable excipients comprise about 50% by weight to about 70% by weight of one or more fillers based on the total weight of the pharmaceutically acceptable capsule. In some embodiments, the one or more pharmaceutically acceptable excipients comprise about 50% by weight to about 60% by weight of one or more fillers based on the total weight of the pharmaceutically acceptable capsule.

In some embodiments, the one or more pharmaceutically acceptable excipients comprise about 60% by weight to about 90% by weight of one or more fillers based on the total weight of the pharmaceutically acceptable capsule. In some embodiments, the one or more pharmaceutically acceptable excipients comprise about 60% by weight to about 80% by weight of one or more fillers based on the total weight of the pharmaceutically acceptable capsule. In some embodiments, the one or more pharmaceutically acceptable excipients comprise about 60% by weight to about 70% by weight of one or more fillers based on the total weight of the pharmaceutically acceptable capsule.

In some embodiments, the one or more pharmaceutically acceptable excipients comprise about 70% by weight to about 90% by weight of one or more fillers based on the total weight of the pharmaceutically acceptable capsule. In some embodiments, the one or more pharmaceutically acceptable excipients comprise about 70% by weight to about 80% by weight of one or more fillers based on the total weight of the pharmaceutically acceptable capsule.

In some embodiments, the one or more pharmaceutically acceptable excipients comprise about 80% by weight to about 90% by weight of one or more fillers based on the total weight of the pharmaceutically acceptable capsule.

In some embodiments, the one or more pharmaceutically acceptable excipients comprise about 1% by weight to about 20% by weight of one or more disintegrants based on the total weight of the pharmaceutically acceptable capsule. In some embodiments, the one or more pharmaceutically acceptable excipients comprise about 1% by weight to about 15% by weight of one or more disintegrants based on the total weight of the pharmaceutically acceptable capsule. In some embodiments, the one or more pharmaceutically acceptable excipients comprise about 1% by weight to about 14% by weight of one or more disintegrants based on the total weight of the pharmaceutically acceptable capsule. In some embodiments, the one or more pharmaceutically acceptable excipients comprise about 1% by weight to about 13% by weight of one or more disintegrants based on the total weight of the pharmaceutically acceptable capsule. In some embodiments, the one or more pharmaceutically acceptable excipients comprise about 1% by weight to about 12% by weight of one or more disintegrants based on the total weight of the pharmaceutically acceptable capsule. In some embodiments, the one or more pharmaceutically acceptable excipients comprise about 1% by weight to about 11% by weight of one or more disintegrants based on the total weight of the pharmaceutically acceptable capsule. In some embodiments, the one or more pharmaceutically acceptable excipients comprise about 1% by weight to about 10% by weight of one or more disintegrants based on the total weight of the pharmaceutically acceptable capsule. In some embodiments, the one or more pharmaceutically acceptable excipients comprise about 1% by weight to about 9% by weight of one or more disintegrants based on the total weight of the pharmaceutically acceptable capsule. In some embodiments, the one or more pharmaceutically acceptable excipients comprise about 1% by weight to about 8% by weight of one or more disintegrants based on the total weight of the pharmaceutically acceptable capsule. In some embodiments, the one or more pharmaceutically acceptable excipients comprise about 1% by weight to about 7% by weight of one or more disintegrants based on the total weight of the pharmaceutically acceptable capsule. In some embodiments, the one or more pharmaceutically acceptable excipients comprise about 1% by weight to about 6% by weight of one or more disintegrants based on the total weight of the pharmaceutically acceptable capsule. In some embodiments, the one or more pharmaceutically acceptable excipients comprise about 1% by weight to about 5% by weight of one or more disintegrants based on the total weight of the pharmaceutically acceptable capsule. In some embodiments, the one or more pharmaceutically acceptable excipients comprise about 1% by weight to about 4% by weight of one or more disintegrants based on the total weight of the pharmaceutically acceptable capsule. In some embodiments, the one or more pharmaceutically acceptable excipients comprise about 1% by weight to about 3% by weight of one or more disintegrants based on the total weight of the pharmaceutically acceptable capsule.

In some embodiments, the one or more pharmaceutically acceptable excipients comprise about 1% by weight of one or more disintegrants based on the total weight of the pharmaceutically acceptable capsule. In some embodiments, the one or more pharmaceutically acceptable excipients comprise about 2% by weight of one or more disintegrants based on the total weight of the pharmaceutically acceptable capsule. In some embodiments, the one or more pharmaceutically acceptable excipients comprise about 3% by weight of one or more disintegrants based on the total weight of the pharmaceutically acceptable capsule. In some embodiments, the one or more pharmaceutically acceptable excipients comprise about 4% by weight of one or more disintegrants based on the total weight of the pharmaceutically acceptable capsule. In some embodiments, the one or more pharmaceutically acceptable excipients comprise about 5% by weight of one or more disintegrants based on the total weight of the pharmaceutically acceptable capsule. In some embodiments, the one or more pharmaceutically acceptable excipients comprise about 6% by weight of one or more disintegrants based on the total weight of the pharmaceutically acceptable capsule. In some embodiments, the one or more pharmaceutically acceptable excipients comprise about 7% by weight of one or more disintegrants based on the total weight of the pharmaceutically acceptable capsule. In some embodiments, the one or more pharmaceutically acceptable excipients comprise about 8% by weight of one or more disintegrants based on the total weight of the pharmaceutically acceptable capsule. In some embodiments, the one or more pharmaceutically acceptable excipients comprise about 9% by weight of one or more disintegrants based on the total weight of the pharmaceutically acceptable capsule. In some embodiments, the one or more pharmaceutically acceptable excipients comprise about 10% by weight of one or more disintegrants based on the total weight of the pharmaceutically acceptable capsule. In some embodiments, the one or more pharmaceutically acceptable excipients comprise about 11% by weight of one or more disintegrants based on the total weight of the pharmaceutically acceptable capsule. In some embodiments, the one or more pharmaceutically acceptable excipients comprise about 12% by weight of one or more disintegrants based on the total weight of the pharmaceutically acceptable capsule. In some embodiments, the one or more pharmaceutically acceptable excipients comprise about 13% by weight of one or more disintegrants based on the total weight of the pharmaceutically acceptable capsule. In some embodiments, the one or more pharmaceutically acceptable excipients comprise about 14% by weight of one or more disintegrants based on the total weight of the pharmaceutically acceptable capsule. In some embodiments, the one or more pharmaceutically acceptable excipients comprise about 15% by weight of one or more disintegrants based on the total weight of the pharmaceutically acceptable capsule.

In some embodiments, the one or more pharmaceutically acceptable excipients comprise about 0.1% by weight to about 10% by weight of one or more lubricants based on the total weight of the pharmaceutically acceptable capsule. In some embodiments, the one or more pharmaceutically acceptable excipients comprise about 0.1% by weight to about 9% by weight of one or more lubricants based on the total weight of the pharmaceutically acceptable capsule. In some embodiments, the one or more pharmaceutically acceptable excipients comprise about 0.1% by weight to about 8% by weight of one or more lubricants based on the total weight of the pharmaceutically acceptable capsule. In some embodiments, the one or more pharmaceutically acceptable excipients comprise about 0.1% by weight to about 7% by weight of one or more lubricants based on the total weight of the pharmaceutically acceptable capsule. In some embodiments, the one or more pharmaceutically acceptable excipients comprise about 0.1% by weight to about 6% by weight of one or more lubricants based on the total weight of the pharmaceutically acceptable capsule. In some embodiments, the one or more pharmaceutically acceptable excipients comprise about 0.1% by weight to about 5% by weight of one or more lubricants based on the total weight of the pharmaceutically acceptable capsule. In some embodiments, the one or more pharmaceutically acceptable excipients comprise about 0.1% by weight to about 4% by weight of one or more lubricants based on the total weight of the pharmaceutically acceptable capsule. In some embodiments, the one or more pharmaceutically acceptable excipients comprise about 0.1% by weight to about 3% by weight of one or more lubricants based on the total weight of the pharmaceutically acceptable capsule. In some embodiments, the one or more pharmaceutically acceptable excipients comprise about 0.1% by weight to about 2% by weight of one or more lubricants based on the total weight of the pharmaceutically acceptable capsule.

In some embodiments, the one or more pharmaceutically acceptable excipients comprise about 0.1% by weight to about 1.9% by weight of one or more lubricants based on the total weight of the pharmaceutically acceptable capsule. In some embodiments, the one or more pharmaceutically acceptable excipients comprise about 0.1% by weight to about 1.8% by weight of one or more lubricants based on the total weight of the pharmaceutically acceptable capsule. In some embodiments, the one or more pharmaceutically acceptable excipients comprise about 0.1% by weight to about 1.7% by weight of one or more lubricants based on the total weight of the pharmaceutically acceptable capsule. In some embodiments, the one or more pharmaceutically acceptable excipients comprise about 0.1% by weight to about 1.6% by weight of one or more lubricants based on the total weight of the pharmaceutically acceptable capsule. In some embodiments, the one or more pharmaceutically acceptable excipients comprise about 0.1% by weight to about 1.5% by weight of one or more lubricants based on the total weight of the pharmaceutically acceptable capsule. In some embodiments, the one or more pharmaceutically acceptable excipients comprise about 0.1% by weight to about 1.4% by weight of one or more lubricants based on the total weight of the pharmaceutically acceptable capsule. In some embodiments, the one or more pharmaceutically acceptable excipients comprise about 0.1% by weight to about 1.3% by weight of one or more lubricants based on the total weight of the pharmaceutically acceptable capsule. In some embodiments, the one or more pharmaceutically acceptable excipients comprise about 0.1% by weight to about 1.2% by weight of one or more lubricants based on the total weight of the pharmaceutically acceptable capsule. In some embodiments, the one or more pharmaceutically acceptable excipients comprise about 0.1% by weight to about 1.1% by weight of one or more lubricants based on the total weight of the pharmaceutically acceptable capsule. In some embodiments, the one or more pharmaceutically acceptable excipients comprise about 0.1% by weight to about 1.0% by weight of one or more lubricants based on the total weight of the pharmaceutically acceptable capsule. In some embodiments, the one or more pharmaceutically acceptable excipients comprise about 0.1% by weight to about 0.9% by weight of one or more lubricants based on the total weight of the pharmaceutically acceptable capsule. In some embodiments, the one or more pharmaceutically acceptable excipients comprise about 0.1% by weight to about 0.8% by weight of one or more lubricants based on the total weight of the pharmaceutically acceptable capsule. In some embodiments, the one or more pharmaceutically acceptable excipients comprise about 0.1% by weight to about 0.7% by weight of one or more lubricants based on the total weight of the pharmaceutically acceptable capsule. In some embodiments, the one or more pharmaceutically acceptable excipients comprise about 0.1% by weight to about 0.6% by weight of one or more lubricants based on the total weight of the pharmaceutically acceptable capsule. In some embodiments, the one or more pharmaceutically acceptable excipients comprise about 0.1% by weight to about 0.5% by weight of one or more lubricants based on the total weight of the pharmaceutically acceptable capsule. In some embodiments, the one or more pharmaceutically acceptable excipients comprise about 0.1% by weight to about 0.4% by weight of one or more lubricants based on the total weight of the pharmaceutically acceptable capsule. In some embodiments, the one or more pharmaceutically acceptable excipients comprise about 0.1% by weight to about 0.3% by weight of one or more lubricants based on the total weight of the pharmaceutically acceptable capsule. In some embodiments, the one or more pharmaceutically acceptable excipients comprise about 0.1% by weight to about 0.2% by weight of one or more lubricants based on the total weight of the pharmaceutically acceptable capsule.

In some embodiments, the one or more pharmaceutically acceptable excipients comprise about 0.1% by weight of one or more lubricants based on the total weight of the pharmaceutically acceptable capsule. In some embodiments, the one or more pharmaceutically acceptable excipients comprise about 0.2% by weight of one or more lubricants based on the total weight of the pharmaceutically acceptable capsule. In some embodiments, the one or more pharmaceutically acceptable excipients comprise about 0.3% by weight of one or more lubricants based on the total weight of the pharmaceutically acceptable capsule. In some embodiments, the one or more pharmaceutically acceptable excipients comprise about 0.4% by weight of one or more lubricants based on the total weight of the pharmaceutically acceptable capsule. In some embodiments, the one or more pharmaceutically acceptable excipients comprise about 0.5% by weight of one or more lubricants based on the total weight of the pharmaceutically acceptable capsule. In some embodiments, the one or more pharmaceutically acceptable excipients comprise about 0.6% by weight of one or more lubricants based on the total weight of the pharmaceutically acceptable capsule. In some embodiments, the one or more pharmaceutically acceptable excipients comprise about 0.7% by weight of one or more lubricants based on the total weight of the pharmaceutically acceptable capsule. In some embodiments, the one or more pharmaceutically acceptable excipients comprise about 0.8% by weight of one or more lubricants based on the total weight of the pharmaceutically acceptable capsule. In some embodiments, the one or more pharmaceutically acceptable excipients comprise about 0.9% by weight of one or more lubricants based on the total weight of the pharmaceutically acceptable capsule. In some embodiments, the one or more pharmaceutically acceptable excipients comprise about 1.0% by weight of one or more lubricants based on the total weight of the pharmaceutically acceptable capsule.

In some embodiments, the pharmaceutically acceptable capsule comprises: (a) about 1% by weight to about 30% by weight of the compound of Formula (I) based on the total weight of the pharmaceutically acceptable capsule; (b) about 20% by weight to about 90% by weight of one or more fillers based on the total weight of the pharmaceutically acceptable capsule; (c) about 1% by weight to about 20% by weight of one or more disintegrants based on the total weight of the pharmaceutically acceptable capsule; and (d) about 0.1% by weight to about 10% by weight of one or more lubricants based on the total weight of the pharmaceutically acceptable capsule.

In some embodiments, the pharmaceutically acceptable capsule consists essentially of: (a) about 1% by weight to about 30% by weight of the compound of Formula (I) based on the total weight of the pharmaceutically acceptable capsule; (b) about 20% by weight to about 90% by weight of one or more fillers based on the total weight of the pharmaceutically acceptable capsule; (c) about 1% by weight to about 20% by weight of one or more disintegrants based on the total weight of the pharmaceutically acceptable capsule; and (d) about 0.1% by weight to about 10% by weight of one or more lubricants based on the total weight of the pharmaceutically acceptable capsule.

In some embodiments, the pharmaceutically acceptable capsule comprises (a) about 5% by weight to about 25% by weight of the compound of Formula (I) based on the total weight of the pharmaceutically acceptable capsule; (b) about 60% by weight to about 90% by weight of one or more fillers based on the total weight of the pharmaceutically acceptable capsule; (c) about 1% by weight to about 15% by weight of one or more disintegrants based on the total weight of the pharmaceutically acceptable capsule; and (d) about 0.1% by weight to about 4% by weight of one or more lubricants based on the total weight of the pharmaceutically acceptable capsule.

In some embodiments, the pharmaceutically acceptable capsule consists essentially of (a) about 5% by weight to about 25% by weight of the compound of Formula (I) based on the total weight of the pharmaceutically acceptable capsule; (b) about 60% by weight to about 90% by weight of one or more fillers based on the total weight of the pharmaceutically acceptable capsule; (c) about 1% by weight to about 15% by weight of one or more disintegrants based on the total weight of the pharmaceutically acceptable capsule; and (d) about 0.1% by weight to about 4% by weight of one or more lubricants based on the total weight of the pharmaceutically acceptable capsule.

In some embodiments, the pharmaceutically acceptable capsule comprises (a) about 10% by weight to about 30% by weight of the compound of Formula (I) based on the total weight of the pharmaceutically acceptable capsule; (b) about 70% by weight to about 90% by weight of one or more fillers based on the total weight of the pharmaceutically acceptable capsule; (c) about 1% by weight to about 10% by weight of one or more disintegrants based on the total weight of the pharmaceutically acceptable capsule; and (d) about 0.1% by weight to about 3% by weight of one or more lubricants based on the total weight of the pharmaceutically acceptable capsule.

In some embodiments, the pharmaceutically acceptable capsule consists essentially of (a) about 10% by weight to about 30% by weight of the compound of Formula (I) based on the total weight of the pharmaceutically acceptable capsule; (b) about 70% by weight to about 90% by weight of one or more fillers based on the total weight of the pharmaceutically acceptable capsule; (c) about 1% by weight to about 10% by weight of one or more disintegrants based on the total weight of the pharmaceutically acceptable capsule; and (d) about 0.1% by weight to about 3% by weight of one or more lubricants based on the total weight of the pharmaceutically acceptable capsule.

In some embodiments, the one or more pharmaceutically acceptable excipients is one or more fillers selected from the group consisting of calcium phosphate, dicalcium phosphate, dicalcium phosphate dihydrate, calcium sulfate, calcium sulfate dihydrate, starch, calcium carbonate, magnesium carbonate, magnesium oxide, kaolin (natural hydrated aluminum silicate), sodium chloride, partially gelatinized starch, anhydrous lactose, lactose monohydrate, lactose dihydrate, trehalose dihydrate, spray dried lactose, sucrose, dextrose, dextrates, dextrin, cellulose, microcrystalline cellulose, silicified microcrystalline cellulose, powdered cellulose, partially depolymerized cellulose, mannitol, granulated mannitol, spray dried mannitol, maltodextrin, maltitol, confectioner's sugar, compressible sugar, sorbitol, starch and talc. In some embodiments, the one or more fillers is lactose monohydrate.

In some embodiments, the one or more disintegrants is one or more disintegrants selected from the group consisting of sodium starch glycolate, pregelatinized starch, clay, cellulose, alginic acid, alginate gum, polyvinylpyrrolidone, cross-linked polyvinylpyrrolidone, cross-linked calcium carboxymethylcellulose, cross-linked sodium carboxymethylcellulose, sodium croscarmellose, sodium carmellose, low substituted hydroxypropyl cellulose, low substituted hydroxypropyl cellulose sodium, guar gum, magnesium aluminum silicate, polacrilin potassium, powdered cellulose, sodium alginate and soy polysaccharides. In some embodiments, the one or more disintegrants is cross-linked polyvinylpyrrolidone (also referred to as crospovidone).

In some embodiments, the one or more lubricants is one or more lubricants selected from the group consisting of colloidal silica, magnesium trisilicate, talc, magnesium carbonate, magnesium oxide, glyceryl behaptate, mono, di and tri glyceryl behenate, bees wax, behenoyl polyoxyl-8 glycerides, hydrogenated vegetable oil, polyethylene glycol, ethylene oxide polymer, copolymer comprising poly(ethylene oxide) and poly(propylene oxide) (such as poloxomer 188), copolymer comprising polypropylene glycol and polyethylene glycol (such as poloxomer 407), sodium lauryl sulfate, magnesium stearate, aluminum stearate, calcium stearate, sodium stearyl fumarate, stearic acid, magnesium lauryl stearate, mixtures of magnesium stearate with sodium lauryl sulfate. In some embodiments, the one or more lubricants is magnesium stearate.

In some embodiments, the pharmaceutically acceptable capsule further comprises cross-linked polyvinylpyrrolidone and magnesium stearate. In some embodiments, the one or more pharmaceutically acceptable excipients is lactose monohydrate and the pharmaceutically acceptable capsule further comprises cross-linked polyvinylpyrrolidone and magnesium stearate.

In some embodiments, the pharmaceutically acceptable capsule is for oral administration.

In some embodiments, the pharmaceutically acceptable capsule is a solid dosage form.

In some embodiments, the pharmaceutically acceptable capsule comprises about 1 mg to about 40 mg of the compound of Formula (I). In some embodiments, the pharmaceutically acceptable capsule comprises about 1 mg to about 30 mg of the compound of Formula (I). In some embodiments, the pharmaceutically acceptable capsule comprises about 1 mg to about 20 mg of the compound of Formula (I). In some embodiments, the pharmaceutically acceptable capsule comprises about 1 mg to about 15 mg of the compound of Formula (I). In some embodiments, the pharmaceutically acceptable capsule comprises about 5 mg to about 40 mg of the compound of Formula (I). In some embodiments, the pharmaceutically acceptable capsule comprises about 5 mg to about 30 mg of the compound of Formula (I). In some embodiments, the pharmaceutically acceptable capsule comprises about 5 mg to about 20 mg of the compound of Formula (I). In some embodiments, the pharmaceutically acceptable capsule comprises about 5 mg to about 15 mg of the compound of Formula (I). In some embodiments, the pharmaceutically acceptable capsule comprises about 10 mg to about 40 mg of the compound of Formula (I). In some embodiments, the pharmaceutically acceptable capsule comprises about 10 mg to about 30 mg of the compound of Formula (I). In some embodiments, the pharmaceutically acceptable capsule comprises about 10 mg to about 20 mg of the compound of Formula (I). In some embodiments, the pharmaceutically acceptable capsule comprises about 10 mg to about 15 mg of the compound of Formula (I).

In some embodiments, the pharmaceutically acceptable capsule consists essentially of about 1 mg to about 40 mg of the compound of Formula (I). In some embodiments, the pharmaceutically acceptable capsule consists essentially of about 1 mg to about 30 mg of the compound of Formula (I). In some embodiments, the pharmaceutically acceptable capsule consists essentially of about 1 mg to about 20 mg of the compound of Formula (I). In some embodiments, the pharmaceutically acceptable capsule consists essentially of about 1 mg to about 15 mg of the compound of Formula (I). In some embodiments, the pharmaceutically acceptable capsule consists essentially of about 5 mg to about 40 mg of the compound of Formula (I). In some embodiments, the pharmaceutically acceptable capsule consists essentially of about 5 mg to about 30 mg of the compound of Formula (I). In some embodiments, the pharmaceutically acceptable capsule consists essentially of about 5 mg to about 20 mg of the compound of Formula (I). In some embodiments, the pharmaceutically acceptable capsule consists essentially of about 5 mg to about 15 mg of the compound of Formula (I). In some embodiments, the pharmaceutically acceptable capsule consists essentially of about 10 mg to about 40 mg of the compound of Formula (I). In some embodiments, the pharmaceutically acceptable capsule consists essentially of about 10 mg to about 30 mg of the compound of Formula (I). In some embodiments, the pharmaceutically acceptable capsule consists essentially of about 10 mg to about 20 mg of the compound of Formula (I). In some embodiments, the pharmaceutically acceptable capsule consists essentially of about 10 mg to about 15 mg of the compound of Formula (I).

In some embodiments, compound of Formula (I) is present in the pharmaceutically acceptable capsule as a cocrystal. In some embodiments, compound of Formula (I) is present in the pharmaceutically acceptable capsule as a channel crystal. In some embodiments, compound of Formula (I) is present in the pharmaceutically acceptable capsule as a crystalline dihydrate form. In some embodiments, the compound of Formula (I) is present in the pharmaceutically acceptable capsule as a crystalline anhydrous form. In some embodiments, compound of Formula (I) is present in the pharmaceutically acceptable capsule as a solvate.

In some embodiments, the pharmaceutically acceptable capsule comprises about 0.5 mg to about 5 mg, about 6 mg to about 14 mg, about 11 mg to about 19 mg, about 17 mg to about 25 mg, or about 28 mg to about 36 mg of the compound of Formula (I) as a crystalline dihydrate form. In some embodiments, the pharmaceutically acceptable capsule comprises about 1 mg to about 4 mg, about 8 mg to about 12 mg, about 13 mg to about 17 mg, about 19 mg to about 23 mg, or about 30 mg to about 34 mg of the compound of Formula (I) as a crystalline dihydrate form. In some embodiments, the pharmaceutically acceptable capsule comprises about 2.2 mg, about 10.8 mg, about 15.2 mg, about 21.7 mg, or about 32.5 mg of the compound of Formula (I) as a crystalline dihydrate form.

In some embodiments, the pharmaceutically acceptable capsule consists essentially of about 0.5 mg to about 5 mg, about 6 mg to about 14 mg, about 11 mg to about 19 mg, about 17 mg to about 25 mg, or about 28 mg to about 36 mg of the compound of Formula (I) as a crystalline dihydrate form. In some embodiments, the pharmaceutically acceptable capsule consists essentially of about 1 mg to about 4 mg, about 8 mg to about 12 mg, about 13 mg to about 17 mg, about 19 mg to about 23 mg, or about 30 mg to about 34 mg of the compound of Formula (I) as a crystalline dihydrate form. In some embodiments, the pharmaceutically acceptable capsule consists essentially of about 2.2 mg, about 10.8 mg, about 15.2 mg, about 21.7 mg, or about 32.5 mg of the compound of Formula (I) as a crystalline dihydrate form.

Also provided herein, in some embodiments, are pharmaceutically acceptable capsules comprising a crystalline dihydrate form of a compound of Formula (I):

Formula (I)

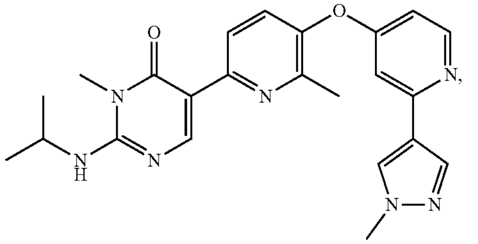

and one or more pharmaceutically acceptable excipients.

Also provided herein, in some embodiments, are pharmaceutically acceptable capsules consisting essentially of a crystalline dihydrate form of a compound of Formula (I):

Formula (I)

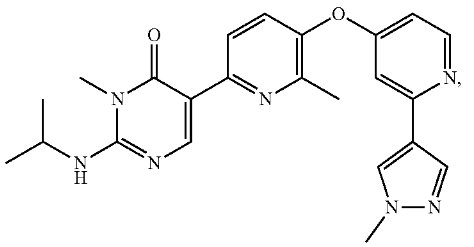

and one or more pharmaceutically acceptable excipients.

In some embodiments, the crystalline dihydrate form of the compound represented by Formula (I) has an XRPD pattern comprising a peak, in terms of 2-theta, at about 10.9° as measured by CuKα radiation.

In some embodiments, the crystalline dihydrate form of the compound represented by Formula (I) has an XRPD pattern comprising peaks, in terms of 2-theta, at about 10.9°, about 16.8°, and about 27.10 as measured by CuKα radiation.

In some embodiments, the crystalline dihydrate form of the compound of Formula (I) has an X-ray powder diffraction pattern comprising peaks, in terms of 2-theta, at about 5.9°, about 10.9°, about 11.9°, about 13.7°, about 16.8°, and about 27.10 as measured by CuKα radiation.

In some embodiments, the crystalline dihydrate form of the compound represented by Formula (I) has an XRPD pattern comprising peaks, in terms of 2-theta, at about 5.9°, about 10.9°, about 11.9°, about 13.7°, about 16.8°, about 27.1°, about 28.3° and about 28.7° as measured by CuKα radiation.

In some embodiments, the one or more pharmaceutically acceptable excipients is a filler. For example, the one or more pharmaceutically acceptable excipients is lactose, such as lactose monohydrate.

In some embodiments, the pharmaceutically acceptable capsules further comprise one or more disintegrants, one or more lubricants, or a combination thereof. For example, in some embodiments, the pharmaceutically acceptable capsules further comprise one or more disintegrants. In some embodiments, the pharmaceutically acceptable capsules further comprise one or more lubricants.

Also provided herein, in some embodiments, is a pharmaceutically acceptable capsule comprising:

(a) about 1% by weight to about 70% by weight, based on the total weight of the pharmaceutically acceptable capsule, of a crystalline dihydrate form of a compound of Formula (I):

Formula (I)

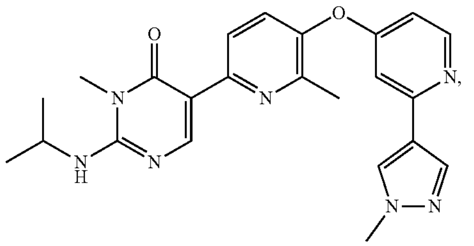

and one or more pharmaceutically acceptable excipients, wherein the one or more pharmaceutically acceptable excipients comprise:

(b) about 20% by weight to about 97% by weight of one or more fillers based on the total weight of the pharmaceutically acceptable capsule;

(c) about 1% by weight to about 20% by weight of one or more disintegrants based on the total weight of the pharmaceutically acceptable capsule; and (d) about 0.1% by weight to about 10% by weight of one or more lubricants based on the total weight of the pharmaceutically acceptable capsule.

Also provided herein, in some embodiments, is a pharmaceutically acceptable capsule comprising:

(a) about 1% by weight to about 30% by weight of a crystalline dihydrate form of a compound of Formula (I) based on the total weight of the pharmaceutically acceptable capsule;

(b) about 20% by weight to about 90% by weight of one or more fillers based on the total weight of the pharmaceutically acceptable capsule;

(c) about 1% by weight to about 20% by weight of one or more disintegrants based on the total weight of the pharmaceutically acceptable capsule; and (d) about 0.1% by weight to about 10% by weight of one or more lubricants based on the total weight of the pharmaceutically acceptable capsule.

Also provided herein, in some embodiments, is a pharmaceutically acceptable capsule consisting essentially of:

(a) about 1% by weight to about 70% by weight, based on the total weight of the pharmaceutically acceptable capsule, of a crystalline dihydrate form of a compound of Formula (I):

Formula (I)

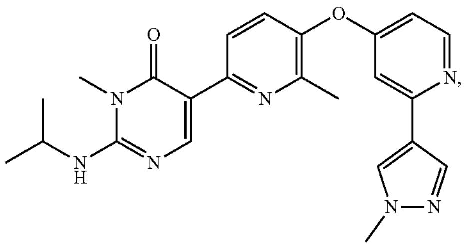

and one or more pharmaceutically acceptable excipients, wherein the one or more pharmaceutically acceptable excipients comprise:

(b) about 20% by weight to about 97% by weight of one or more fillers based on the total weight of the pharmaceutically acceptable capsule;

(c) about 1% by weight to about 20% by weight of one or more disintegrants based on the total weight of the pharmaceutically acceptable capsule; and (d) about 0.1% by weight to about 10% by weight of one or more lubricants based on the total weight of the pharmaceutically acceptable capsule.

Also provided herein, in some embodiments, is a pharmaceutically acceptable capsule consisting essentially of:

(a) about 1% by weight to about 30% by weight of a crystalline dihydrate form of a compound of Formula (I): based on the total weight of the pharmaceutically acceptable capsule;

(b) about 20% by weight to about 90% by weight of one or more fillers based on the total weight of the pharmaceutically acceptable capsule;

(c) about 1% by weight to about 20% by weight of one or more disintegrants based on the total weight of the pharmaceutically acceptable capsule; and (d) about 0.1% by weight to about 10% by weight of one or more lubricants based on the total weight of the pharmaceutically acceptable capsule.

In some embodiments, the pharmaceutically acceptable capsule comprising the crystalline dihydrate form of the compound represented by Formula (I), has no more than about 10 mol %, no more than about 5 mol %, no more than about 3 mol %, or no more than about 1 mol % of other solid-state forms of the compound represented by Formula (I). In some embodiments, the pharmaceutically acceptable capsule comprising the crystalline dihydrate forms of the compound represented by Formula (I), has no more than about 10 mol % of other solid-state forms of the compound represented by Formula (I). In some embodiments, the pharmaceutically acceptable capsule comprising the crystalline dihydrate forms of the compound represented by Formula (I), has no more than about 9 mol % of other solid-state forms of the compound represented by Formula (I). In some embodiments, the pharmaceutically acceptable capsule comprising the crystalline dihydrate forms of the compound represented by Formula (I), has no more than about 8 mol % of other solid-state forms of the compound represented by Formula (I). In some embodiments, the pharmaceutically acceptable capsule comprising the crystalline dihydrate forms of the compound represented by Formula (I), has no more than about 7 mol % of other solid-state forms of the compound represented by Formula (I). In some embodiments, the pharmaceutically acceptable capsule comprising the crystalline dihydrate forms of the compound represented by Formula (I), has no more than about 6 mol % of other solid-state forms of the compound represented by Formula (I). In some embodiments, the pharmaceutically acceptable capsule comprising the crystalline dihydrate forms of the compound represented by Formula (I), has no more than about 5 mol % of other solid-state forms of the compound represented by Formula (I). In some embodiments, the pharmaceutically acceptable capsule comprising the crystalline dihydrate forms of the compound represented by Formula (I), has no more than about 4 mol % of other solid-state forms of the compound represented by Formula (I). In some embodiments, the pharmaceutically acceptable capsule comprising the crystalline dihydrate forms of the compound represented by Formula (I), has no more than about 3 mol % of other solid-state forms of the compound represented by Formula (I). In some embodiments, the pharmaceutically acceptable capsule comprising the crystalline dihydrate forms of the compound represented by Formula (I), has no more than about 2 mol % of other solid-state forms of the compound represented by Formula (I). In some embodiments, the pharmaceutically acceptable capsule comprising the crystalline dihydrate forms of the compound represented by Formula (I), has no more than about 1 mol % of other solid-state forms of the compound represented by Formula (I).

In some embodiments, the pharmaceutically acceptable capsule comprises about 1% by weight to about 60% by weight, based on the total weight of the pharmaceutically acceptable capsule, of a crystalline dihydrate form of a compound of Formula (I). In some embodiments, the pharmaceutically acceptable capsule comprises about 1% by weight to about 50% by weight, based on the total weight of the pharmaceutically acceptable capsule, of a crystalline dihydrate form of a compound of Formula (I). In some embodiments, the pharmaceutically acceptable capsule comprises about 1% by weight to about 40% by weight, based on the total weight of the pharmaceutically acceptable capsule, of a crystalline dihydrate form of a compound of Formula (I). In some embodiments, the pharmaceutically acceptable capsule comprises about 1% by weight to about 30% by weight, based on the total weight of the pharmaceutically acceptable capsule, of a crystalline dihydrate form of a compound of Formula (I). In some embodiments, the pharmaceutically acceptable capsule comprises about 1% by weight to about 20% by weight, based on the total weight of the pharmaceutically acceptable capsule, of a crystalline dihydrate form of a compound of Formula (I).

In some embodiments, the pharmaceutically acceptable capsule consists essentially of about 1% by weight to about 60% by weight, based on the total weight of the pharmaceutically acceptable capsule, of a crystalline dihydrate form of a compound of Formula (I). In some embodiments, the pharmaceutically acceptable capsule consists essentially of about 1% by weight to about 50% by weight, based on the total weight of the pharmaceutically acceptable capsule, of a crystalline dihydrate form of a compound of Formula (I). In some embodiments, the pharmaceutically acceptable capsule consists essentially of about 1% by weight to about 40% by weight, based on the total weight of the pharmaceutically acceptable capsule, of a crystalline dihydrate form of a compound of Formula (I). In some embodiments, the pharmaceutically acceptable capsule consists essentially of about 1% by weight to about 30% by weight, based on the total weight of the pharmaceutically acceptable capsule, of a crystalline dihydrate form of a compound of Formula (I). In some embodiments, the pharmaceutically acceptable capsule consists essentially of about 1% by weight to about 20% by weight, based on the total weight of the pharmaceutically acceptable capsule, of a crystalline dihydrate form of a compound of Formula (I).

In some embodiments, the pharmaceutically acceptable capsule comprises about 1% by weight to about 70% by weight of the compound of Formula (I) based on the total weight of the pharmaceutically acceptable capsule. In some embodiments, the pharmaceutically acceptable capsule comprises about 1% by weight to about 65% by weight of the compound of Formula (I) based on the total weight of the pharmaceutically acceptable capsule. In some embodiments, the pharmaceutically acceptable capsule comprises about 1% by weight to about 60% by weight of the compound of Formula (I) based on the total weight of the pharmaceutically acceptable capsule. In some embodiments, the pharmaceutically acceptable capsule comprises about 1% by weight to about 55% by weight of the compound of Formula (I) based on the total weight of the pharmaceutically acceptable capsule. In some embodiments, the pharmaceutically acceptable capsule comprises about 1% by weight to about 50% by weight of the compound of Formula (I) based on the total weight of the pharmaceutically acceptable capsule. In some embodiments, the pharmaceutically acceptable capsule comprises about 1% by weight to about 45% by weight of the compound of Formula (I) based on the total weight of the pharmaceutically acceptable capsule. In some embodiments, the pharmaceutically acceptable capsule comprises about 1% by weight to about 40% by weight of the compound of Formula (I) based on the total weight of the pharmaceutically acceptable capsule. In some embodiments, the pharmaceutically acceptable capsule comprises about 1% by weight to about 35% by weight of the compound of Formula (I) based on the total weight of the pharmaceutically acceptable capsule. In some embodiments, the pharmaceutically acceptable capsule comprises about 1% by weight to about 30% by weight of the crystalline dihydrate form of the compound of Formula (I) based on the total weight of the pharmaceutically acceptable capsule. In some embodiments, the pharmaceutically acceptable capsule comprises about 1% by weight to about 25% by weight of the crystalline dihydrate form of the compound of Formula (I) based on the total weight of the pharmaceutically acceptable capsule. In some embodiments, the pharmaceutically acceptable capsule comprises about 1% by weight to about 20% by weight of the crystalline dihydrate form of the compound of Formula (I) based on the total weight of the pharmaceutically acceptable capsule. In some embodiments, the pharmaceutically acceptable capsule comprises about 1% by weight to about 15% by weight of the crystalline dihydrate form of the compound of Formula (I) based on the total weight of the pharmaceutically acceptable capsule. In some embodiments, the pharmaceutically acceptable capsule comprises about 1% by weight to about 10% by weight of the crystalline dihydrate form of the compound of Formula (I) based on the total weight of the pharmaceutically acceptable capsule.

In some embodiments, the pharmaceutically acceptable capsule consists essentially of about 1% by weight to about 70% by weight of the crystalline dihydrate form of the compound of Formula (I) based on the total weight of the pharmaceutically acceptable capsule. In some embodiments, the pharmaceutically acceptable capsule consists essentially of about 1% by weight to about 65% by weight of the crystalline dihydrate form of the compound of Formula (I) based on the total weight of the pharmaceutically acceptable capsule. In some embodiments, the pharmaceutically acceptable capsule consists essentially of about 1% by weight to about 60% by weight of the crystalline dihydrate form of the compound of Formula (I) based on the total weight of the pharmaceutically acceptable capsule. In some embodiments, the pharmaceutically acceptable capsule consists essentially of about 1% by weight to about 55% by weight of the crystalline dihydrate form of the compound of Formula (I) based on the total weight of the pharmaceutically acceptable capsule. In some embodiments, the pharmaceutically acceptable capsule consists essentially of about 1% by weight to about 50% by weight of the crystalline dihydrate form of the compound of Formula (I) based on the total weight of the pharmaceutically acceptable capsule. In some embodiments, the pharmaceutically acceptable capsule consists essentially of about 1% by weight to about 45% by weight of the crystalline dihydrate form of the compound of Formula (I) based on the total weight of the pharmaceutically acceptable capsule. In some embodiments, the pharmaceutically acceptable capsule consists essentially of about 1% by weight to about 40% by weight of the crystalline dihydrate form of the compound of Formula (I) based on the total weight of the pharmaceutically acceptable capsule. In some embodiments, the pharmaceutically acceptable capsule consists essentially of about 1% by weight to about 35% by weight of the crystalline dihydrate form of the compound of Formula (I) based on the total weight of the pharmaceutically acceptable capsule. In some embodiments, the pharmaceutically acceptable capsule consists essentially of about 1% by weight to about 30% by weight of the crystalline dihydrate form of the compound of Formula (I) based on the total weight of the pharmaceutically acceptable capsule. In some embodiments, the pharmaceutically acceptable capsule consists essentially of about 1% by weight to about 25% by weight of the crystalline dihydrate form of the compound of Formula (I) based on the total weight of the pharmaceutically acceptable capsule. In some embodiments, the pharmaceutically acceptable capsule consists essentially of about 1% by weight to about 20% by weight of the crystalline dihydrate form of the compound of Formula (I) based on the total weight of the pharmaceutically acceptable capsule. In some embodiments, the pharmaceutically acceptable capsule consists essentially of about 1% by weight to about 15% by weight of the crystalline dihydrate form of the compound of Formula (I) based on the total weight of the pharmaceutically acceptable capsule. In some embodiments, the pharmaceutically acceptable capsule consists essentially of about 1% by weight to about 10% by weight of the crystalline dihydrate form of the compound of Formula (I) based on the total weight of the pharmaceutically acceptable capsule.

In some embodiments, the pharmaceutically acceptable capsule comprises about 5% by weight to about 30% by weight of the crystalline dihydrate form of the compound of Formula (I) based on the total weight of the pharmaceutically acceptable capsule. In some embodiments, the pharmaceutically acceptable capsule comprises about 5% by weight to about 25% by weight of the crystalline dihydrate form of the compound of Formula (I) based on the total weight of the pharmaceutically acceptable capsule. In some embodiments, the pharmaceutically acceptable capsule comprises about 5% by weight to about 20% by weight of the crystalline dihydrate form of the compound of Formula (I) based on the total weight of the pharmaceutically acceptable capsule. In some embodiments, the pharmaceutically acceptable capsule comprises about 5% by weight to about 15% by weight of the crystalline dihydrate form of the compound of Formula (I) based on the total weight of the pharmaceutically acceptable capsule. In some embodiments, the pharmaceutically acceptable capsule comprises about 5% by weight to about 10% by weight of the crystalline dihydrate form of the compound of Formula (I) based on the total weight of the pharmaceutically acceptable capsule.

In some embodiments, the pharmaceutically acceptable capsule consists essentially of about 5% by weight to about 30% by weight of the crystalline dihydrate form of the compound of Formula (I) based on the total weight of the pharmaceutically acceptable capsule. In some embodiments, the pharmaceutically acceptable capsule consists essentially of about 5% by weight to about 25% by weight of the crystalline dihydrate form of the compound of Formula (I) based on the total weight of the pharmaceutically acceptable capsule. In some embodiments, the pharmaceutically acceptable capsule consists essentially of about 5% by weight to about 20% by weight of the crystalline dihydrate form of the compound of Formula (I) based on the total weight of the pharmaceutically acceptable capsule. In some embodiments, the pharmaceutically acceptable capsule consists essentially of about 5% by weight to about 15% by weight of the crystalline dihydrate form of the compound of Formula (I) based on the total weight of the pharmaceutically acceptable capsule. In some embodiments, the pharmaceutically acceptable capsule consists essentially of about 5% by weight to about 10% by weight of the crystalline dihydrate form of the compound of Formula (I) based on the total weight of the pharmaceutically acceptable capsule.

In some embodiments, the pharmaceutically acceptable capsule comprises about 10% to about 30% of the compound of Formula (I) based on the total weight of the pharmaceutically acceptable capsule. In some embodiments, the pharmaceutically acceptable capsule comprises about 10% to about 25% of the compound of Formula (I) based on the total weight of the pharmaceutically acceptable capsule. In some embodiments, the pharmaceutically acceptable capsule comprises about 10% to about 20% of the compound of Formula (I) based on the total weight of the pharmaceutically acceptable capsule. In some embodiments, the pharmaceutically acceptable capsule comprises about 10% by weight to about 15% by weight of the crystalline dihydrate form of the compound of Formula (I) based on the total weight of the pharmaceutically acceptable capsule.

In some embodiments, the pharmaceutically acceptable capsule consists essentially of about 10% to about 30% of the compound of Formula (I) based on the total weight of the pharmaceutically acceptable capsule. In some embodiments, the pharmaceutically acceptable capsule consists essentially of about 10% to about 25% of the compound of Formula (I) based on the total weight of the pharmaceutically acceptable capsule. In some embodiments, the pharmaceutically acceptable capsule consists essentially of about 10% to about 20% of the compound of Formula (I) based on the total weight of the pharmaceutically acceptable capsule. In some embodiments, the pharmaceutically acceptable capsule consists essentially of about 10% by weight to about 15% by weight of the crystalline dihydrate form of the compound of Formula (I) based on the total weight of the pharmaceutically acceptable capsule.

In some embodiments, the pharmaceutically acceptable capsule comprises about 1% by weight to about 30% by weight of the crystalline dihydrate form of the compound of Formula (I) based on the total weight of the pharmaceutically acceptable capsule. In some embodiments, the pharmaceutically acceptable capsule comprises about 1% by weight to about 10% by weight of the crystalline dihydrate form of the compound of Formula (I) based on the total weight of the pharmaceutically acceptable capsule. In some embodiments, the pharmaceutically acceptable capsule comprises about 10% to about 20% of the compound of Formula (I) based on the total weight of the pharmaceutically acceptable capsule. In some embodiments, the pharmaceutically acceptable capsule comprises about 10% by weight to about 15% by weight of the crystalline dihydrate form of the compound of Formula (I) based on the total weight of the pharmaceutically acceptable capsule.

In some embodiments, the pharmaceutically acceptable capsule consists essentially of about 1% by weight to about 30% by weight of the crystalline dihydrate form of the compound of Formula (I) based on the total weight of the pharmaceutically acceptable capsule. In some embodiments, the pharmaceutically acceptable capsule consists essentially of about 1% by weight to about 10% by weight of the crystalline dihydrate form of the compound of Formula (I) based on the total weight of the pharmaceutically acceptable capsule. In some embodiments, the pharmaceutically acceptable capsule consists essentially of about 10% to about 20% of the compound of Formula (I) based on the total weight of the pharmaceutically acceptable capsule. In some embodiments, the pharmaceutically acceptable capsule consists essentially of about 10% by weight to about 15% by weight of the crystalline dihydrate form of the compound of Formula (I) based on the total weight of the pharmaceutically acceptable capsule.

In some embodiments, the one or more pharmaceutically acceptable excipients comprise about 20% by weight to about 90% by weight of one or more fillers based on the total weight of the pharmaceutically acceptable capsule. In some embodiments, the one or more pharmaceutically acceptable excipients comprise about 20% by weight to about 85% by weight of one or more fillers based on the total weight of the pharmaceutically acceptable capsule. In some embodiments, the one or more pharmaceutically acceptable excipients comprise about 20% by weight to about 80% by weight of one or more fillers based on the total weight of the pharmaceutically acceptable capsule. In some embodiments, the one or more pharmaceutically acceptable excipients comprise about 20% by weight to about 75% by weight of one or more fillers based on the total weight of the pharmaceutically acceptable capsule. In some embodiments, the one or more pharmaceutically acceptable excipients comprise about 20% by weight to about 70% by weight of one or more fillers based on the total weight of the pharmaceutically acceptable capsule. In some embodiments, the one or more pharmaceutically acceptable excipients comprise about 20% by weight to about 65% by weight of one or more fillers based on the total weight of the pharmaceutically acceptable capsule. In some embodiments, the one or more pharmaceutically acceptable excipients comprise about 20% by weight to about 60% by weight of one or more fillers based on the total weight of the pharmaceutically acceptable capsule. In some embodiments, the one or more pharmaceutically acceptable excipients comprise about 20% by weight to about 55% by weight of one or more fillers based on the total weight of the pharmaceutically acceptable capsule. In some embodiments, the one or more pharmaceutically acceptable excipients comprise about 20% by weight to about 50% by weight of one or more fillers based on the total weight of the pharmaceutically acceptable capsule. In some embodiments, the one or more pharmaceutically acceptable excipients comprise about 20% by weight to about 45% by weight of one or more fillers based on the total weight of the pharmaceutically acceptable capsule. In some embodiments, the one or more pharmaceutically acceptable excipients comprise about 20% by weight to about 40% by weight of one or more fillers based on the total weight of the pharmaceutically acceptable capsule. In some embodiments, the one or more pharmaceutically acceptable excipients comprise about 20% by weight to about 35% by weight of one or more fillers based on the total weight of the pharmaceutically acceptable capsule. In some embodiments, the one or more pharmaceutically acceptable excipients comprise about 20% by weight to about 30% by weight of one or more fillers based on the total weight of the pharmaceutically acceptable capsule. In some embodiments, the one or more pharmaceutically acceptable excipients comprise about 20% by weight to about 25% by weight of one or more fillers based on the total weight of the pharmaceutically acceptable capsule.

In some embodiments, the one or more pharmaceutically acceptable excipients comprise about 30% by weight to about 90% by weight of one or more fillers based on the total weight of the pharmaceutically acceptable capsule. In some embodiments, the one or more pharmaceutically acceptable excipients comprise about 30% by weight to about 80% by weight of one or more fillers based on the total weight of the pharmaceutically acceptable capsule. In some embodiments, the one or more pharmaceutically acceptable excipients comprise about 30% by weight to about 70% by weight of one or more fillers based on the total weight of the pharmaceutically acceptable capsule. In some embodiments, the one or more pharmaceutically acceptable excipients comprise about 30% by weight to about 60% by weight of one or more fillers based on the total weight of the pharmaceutically acceptable capsule. In some embodiments, the one or more pharmaceutically acceptable excipients comprise about 30% by weight to about 50% by weight of one or more fillers based on the total weight of the pharmaceutically acceptable capsule. In some embodiments, the one or more pharmaceutically acceptable excipients comprise about 30% by weight to about 40% by weight of one or more fillers based on the total weight of the pharmaceutically acceptable capsule.

In some embodiments, the one or more pharmaceutically acceptable excipients comprise about 40% by weight to about 90% by weight of one or more fillers based on the total weight of the pharmaceutically acceptable capsule. In some embodiments, the one or more pharmaceutically acceptable excipients comprise about 40% by weight to about 80% by weight of one or more fillers based on the total weight of the pharmaceutically acceptable capsule. In some embodiments, the one or more pharmaceutically acceptable excipients comprise about 40% by weight to about 70% by weight of one or more fillers based on the total weight of the pharmaceutically acceptable capsule. In some embodiments, the one or more pharmaceutically acceptable excipients comprise about 40% by weight to about 60% by weight of one or more fillers based on the total weight of the pharmaceutically acceptable capsule. In some embodiments, the one or more pharmaceutically acceptable excipients comprise about 40% by weight to about 50% by weight of one or more fillers based on the total weight of the pharmaceutically acceptable capsule.

In some embodiments, the one or more pharmaceutically acceptable excipients comprise about 50% by weight to about 90% by weight of one or more fillers based on the total weight of the pharmaceutically acceptable capsule. In some embodiments, the one or more pharmaceutically acceptable excipients comprise about 50% by weight to about 80% by weight of one or more fillers based on the total weight of the pharmaceutically acceptable capsule. In some embodiments, the one or more pharmaceutically acceptable excipients comprise about 50% by weight to about 70% by weight of one or more fillers based on the total weight of the pharmaceutically acceptable capsule. In some embodiments, the one or more pharmaceutically acceptable excipients comprise about 50% by weight to about 60% by weight of one or more fillers based on the total weight of the pharmaceutically acceptable capsule.

In some embodiments, the one or more pharmaceutically acceptable excipients comprise about 60% by weight to about 90% by weight of one or more fillers based on the total weight of the pharmaceutically acceptable capsule. In some embodiments, the one or more pharmaceutically acceptable excipients comprise about 60% by weight to about 80% by weight of one or more fillers based on the total weight of the pharmaceutically acceptable capsule. In some embodiments, the one or more pharmaceutically acceptable excipients comprise about 60% by weight to about 70% by weight of one or more fillers based on the total weight of the pharmaceutically acceptable capsule.

In some embodiments, the one or more pharmaceutically acceptable excipients comprise about 70% by weight to about 90% by weight of one or more fillers based on the total weight of the pharmaceutically acceptable capsule. In some embodiments, the one or more pharmaceutically acceptable excipients comprise about 70% by weight to about 80% by weight of one or more fillers based on the total weight of the pharmaceutically acceptable capsule.

In some embodiments, the one or more pharmaceutically acceptable excipients comprise about 80% by weight to about 90% by weight of one or more fillers based on the total weight of the pharmaceutically acceptable capsule.

In some embodiments, the one or more pharmaceutically acceptable excipients comprise about 1% by weight to about 20% by weight of one or more disintegrants based on the total weight of the pharmaceutically acceptable capsule. In some embodiments, the one or more pharmaceutically acceptable excipients comprise about 1% by weight to about 15% by weight of one or more disintegrants based on the total weight of the pharmaceutically acceptable capsule. In some embodiments, the one or more pharmaceutically acceptable excipients comprise about 1% by weight to about 14% by weight of one or more disintegrants based on the total weight of the pharmaceutically acceptable capsule. In some embodiments, the one or more pharmaceutically acceptable excipients comprise about 1% by weight to about 13% by weight of one or more disintegrants based on the total weight of the pharmaceutically acceptable capsule. In some embodiments, the one or more pharmaceutically acceptable excipients comprise about 1% by weight to about 12% by weight of one or more disintegrants based on the total weight of the pharmaceutically acceptable capsule. In some embodiments, the one or more pharmaceutically acceptable excipients comprise about 1% by weight to about 11% by weight of one or more disintegrants based on the total weight of the pharmaceutically acceptable capsule. In some embodiments, the one or more pharmaceutically acceptable excipients comprise about 1% by weight to about 10% by weight of one or more disintegrants based on the total weight of the pharmaceutically acceptable capsule. In some embodiments, the one or more pharmaceutically acceptable excipients comprise about 1% by weight to about 9% by weight of one or more disintegrants based on the total weight of the pharmaceutically acceptable capsule. In some embodiments, the one or more pharmaceutically acceptable excipients comprise about 1% by weight to about 8% by weight of one or more disintegrants based on the total weight of the pharmaceutically acceptable capsule. In some embodiments, the one or more pharmaceutically acceptable excipients comprise about 1% by weight to about 7% by weight of one or more disintegrants based on the total weight of the pharmaceutically acceptable capsule. In some embodiments, the one or more pharmaceutically acceptable excipients comprise about 1% by weight to about 6% by weight of one or more disintegrants based on the total weight of the pharmaceutically acceptable capsule. In some embodiments, the one or more pharmaceutically acceptable excipients comprise about 1% by weight to about 5% by weight of one or more disintegrants based on the total weight of the pharmaceutically acceptable capsule. In some embodiments, the one or more pharmaceutically acceptable excipients comprise about 1% by weight to about 4% by weight of one or more disintegrants based on the total weight of the pharmaceutically acceptable capsule. In some embodiments, the one or more pharmaceutically acceptable excipients comprise about 1% by weight to about 3% by weight of one or more disintegrants based on the total weight of the pharmaceutically acceptable capsule.

In some embodiments, the one or more pharmaceutically acceptable excipients comprise about 1% by weight of one or more disintegrants based on the total weight of the pharmaceutically acceptable capsule. In some embodiments, the one or more pharmaceutically acceptable excipients comprise about 2% by weight of one or more disintegrants based on the total weight of the pharmaceutically acceptable capsule. In some embodiments, the one or more pharmaceutically acceptable excipients comprise about 3% by weight of one or more disintegrants based on the total weight of the pharmaceutically acceptable capsule. In some embodiments, the one or more pharmaceutically acceptable excipients comprise about 4% by weight of one or more disintegrants based on the total weight of the pharmaceutically acceptable capsule. In some embodiments, the one or more pharmaceutically acceptable excipients comprise about 5% by weight of one or more disintegrants based on the total weight of the pharmaceutically acceptable capsule. In some embodiments, the one or more pharmaceutically acceptable excipients comprise about 6% by weight of one or more disintegrants based on the total weight of the pharmaceutically acceptable capsule. In some embodiments, the one or more pharmaceutically acceptable excipients comprise about 7% by weight of one or more disintegrants based on the total weight of the pharmaceutically acceptable capsule. In some embodiments, the one or more pharmaceutically acceptable excipients comprise about 8% by weight of one or more disintegrants based on the total weight of the pharmaceutically acceptable capsule. In some embodiments, the one or more pharmaceutically acceptable excipients comprise about 9% by weight of one or more disintegrants based on the total weight of the pharmaceutically acceptable capsule. In some embodiments, the one or more pharmaceutically acceptable excipients comprise about 10% by weight of one or more disintegrants based on the total weight of the pharmaceutically acceptable capsule. In some embodiments, the one or more pharmaceutically acceptable excipients comprise about 11% by weight of one or more disintegrants based on the total weight of the pharmaceutically acceptable capsule. In some embodiments, the one or more pharmaceutically acceptable excipients comprise about 12% by weight of one or more disintegrants based on the total weight of the pharmaceutically acceptable capsule. In some embodiments, the one or more pharmaceutically acceptable excipients comprise about 13% by weight of one or more disintegrants based on the total weight of the pharmaceutically acceptable capsule. In some embodiments, the one or more pharmaceutically acceptable excipients comprise about 14% by weight of one or more disintegrants based on the total weight of the pharmaceutically acceptable capsule. In some embodiments, the one or more pharmaceutically acceptable excipients comprise about 15% by weight of one or more disintegrants based on the total weight of the pharmaceutically acceptable capsule.

In some embodiments, the one or more pharmaceutically acceptable excipients comprise about 0.1% by weight to about 10% by weight of one or more lubricants based on the total weight of the pharmaceutically acceptable capsule. In some embodiments, the one or more pharmaceutically acceptable excipients comprise about 0.1% by weight to about 9% by weight of one or more lubricants based on the total weight of the pharmaceutically acceptable capsule. In some embodiments, the one or more pharmaceutically acceptable excipients comprise about 0.1% by weight to about 8% by weight of one or more lubricants based on the total weight of the pharmaceutically acceptable capsule. In some embodiments, the one or more pharmaceutically acceptable excipients comprise about 0.1% by weight to about 7% by weight of one or more lubricants based on the total weight of the pharmaceutically acceptable capsule. In some embodiments, the one or more pharmaceutically acceptable excipients comprise about 0.1% by weight to about 6% by weight of one or more lubricants based on the total weight of the pharmaceutically acceptable capsule. In some embodiments, the one or more pharmaceutically acceptable excipients comprise about 0.1% by weight to about 5% by weight of one or more lubricants based on the total weight of the pharmaceutically acceptable capsule. In some embodiments, the one or more pharmaceutically acceptable excipients comprise about 0.1% by weight to about 4% by weight of one or more lubricants based on the total weight of the pharmaceutically acceptable capsule. In some embodiments, the one or more pharmaceutically acceptable excipients comprise about 0.1% by weight to about 3% by weight of one or more lubricants based on the total weight of the pharmaceutically acceptable capsule. In some embodiments, the one or more pharmaceutically acceptable excipients comprise about 0.1% by weight to about 2% by weight of one or more lubricants based on the total weight of the pharmaceutically acceptable capsule.

In some embodiments, the one or more pharmaceutically acceptable excipients comprise about 0.1% by weight to about 1.9% by weight of one or more lubricants based on the total weight of the pharmaceutically acceptable capsule. In some embodiments, the one or more pharmaceutically acceptable excipients comprise about 0.1% by weight to about 1.8% by weight of one or more lubricants based on the total weight of the pharmaceutically acceptable capsule. In some embodiments, the one or more pharmaceutically acceptable excipients comprise about 0.1% by weight to about 1.7% by weight of one or more lubricants based on the total weight of the pharmaceutically acceptable capsule. In some embodiments, the one or more pharmaceutically acceptable excipients comprise about 0.1% by weight to about 1.6% by weight of one or more lubricants based on the total weight of the pharmaceutically acceptable capsule. In some embodiments, the one or more pharmaceutically acceptable excipients comprise about 0.1% by weight to about 1.5% by weight of one or more lubricants based on the total weight of the pharmaceutically acceptable capsule. In some embodiments, the one or more pharmaceutically acceptable excipients comprise about 0.1% by weight to about 1.4% by weight of one or more lubricants based on the total weight of the pharmaceutically acceptable capsule. In some embodiments, the one or more pharmaceutically acceptable excipients comprise about 0.1% by weight to about 1.3% by weight of one or more lubricants based on the total weight of the pharmaceutically acceptable capsule. In some embodiments, the one or more pharmaceutically acceptable excipients comprise about 0.1% by weight to about 1.2% by weight of one or more lubricants based on the total weight of the pharmaceutically acceptable capsule. In some embodiments, the one or more pharmaceutically acceptable excipients comprise about 0.1% by weight to about 1.1% by weight of one or more lubricants based on the total weight of the pharmaceutically acceptable capsule. In some embodiments, the one or more pharmaceutically acceptable excipients comprise about 0.1% by weight to about 1.0% by weight of one or more lubricants based on the total weight of the pharmaceutically acceptable capsule. In some embodiments, the one or more pharmaceutically acceptable excipients comprise about 0.1% by weight to about 0.9% by weight of one or more lubricants based on the total weight of the pharmaceutically acceptable capsule. In some embodiments, the one or more pharmaceutically acceptable excipients comprise about 0.1% by weight to about 0.8% by weight of one or more lubricants based on the total weight of the pharmaceutically acceptable capsule. In some embodiments, the one or more pharmaceutically acceptable excipients comprise about 0.1% by weight to about 0.7% by weight of one or more lubricants based on the total weight of the pharmaceutically acceptable capsule. In some embodiments, the one or more pharmaceutically acceptable excipients comprise about 0.1% by weight to about 0.6% by weight of one or more lubricants based on the total weight of the pharmaceutically acceptable capsule. In some embodiments, the one or more pharmaceutically acceptable excipients comprise about 0.1% by weight to about 0.5% by weight of one or more lubricants based on the total weight of the pharmaceutically acceptable capsule. In some embodiments, the one or more pharmaceutically acceptable excipients comprise about 0.1% by weight to about 0.4% by weight of one or more lubricants based on the total weight of the pharmaceutically acceptable capsule. In some embodiments, the one or more pharmaceutically acceptable excipients comprise about 0.1% by weight to about 0.3% by weight of one or more lubricants based on the total weight of the pharmaceutically acceptable capsule. In some embodiments, the one or more pharmaceutically acceptable excipients comprise about 0.1% by weight to about 0.2% by weight of one or more lubricants based on the total weight of the pharmaceutically acceptable capsule.

In some embodiments, the one or more pharmaceutically acceptable excipients comprise about 0.1% by weight of one or more lubricants based on the total weight of the pharmaceutically acceptable capsule. In some embodiments, the one or more pharmaceutically acceptable excipients comprise about 0.2% by weight of one or more lubricants based on the total weight of the pharmaceutically acceptable capsule. In some embodiments, the one or more pharmaceutically acceptable excipients comprise about 0.3% by weight of one or more lubricants based on the total weight of the pharmaceutically acceptable capsule. In some embodiments, the one or more pharmaceutically acceptable excipients comprise about 0.4% by weight of one or more lubricants based on the total weight of the pharmaceutically acceptable capsule. In some embodiments, the one or more pharmaceutically acceptable excipients comprise about 0.5% by weight of one or more lubricants based on the total weight of the pharmaceutically acceptable capsule. In some embodiments, the one or more pharmaceutically acceptable excipients comprise about 0.6% by weight of one or more lubricants based on the total weight of the pharmaceutically acceptable capsule. In some embodiments, the one or more pharmaceutically acceptable excipients comprise about 0.7% by weight of one or more lubricants based on the total weight of the pharmaceutically acceptable capsule. In some embodiments, the one or more pharmaceutically acceptable excipients comprise about 0.8% by weight of one or more lubricants based on the total weight of the pharmaceutically acceptable capsule. In some embodiments, the one or more pharmaceutically acceptable excipients comprise about 0.9% by weight of one or more lubricants based on the total weight of the pharmaceutically acceptable capsule. In some embodiments, the one or more pharmaceutically acceptable excipients comprise about 1.0% by weight of one or more lubricants based on the total weight of the pharmaceutically acceptable capsule.

In some embodiments, the pharmaceutically acceptable capsule comprises: (a) about 1% by weight to about 30% by weight of the crystalline dihydrate form of the compound of Formula (I) based on the total weight of the pharmaceutically acceptable capsule; (b) about 20% by weight to about 90% by weight of one or more fillers based on the total weight of the pharmaceutically acceptable capsule; (c) about 1% by weight to about 20% by weight of one or more disintegrants based on the total weight of the pharmaceutically acceptable capsule; and (d) about 0.1% by weight to about 10% by weight of one or more lubricants based on the total weight of the pharmaceutically acceptable capsule.

In some embodiments, the pharmaceutically acceptable capsule consists essentially of: (a) about 1% by weight to about 30% by weight of the crystalline dihydrate form of the compound of Formula (I) based on the total weight of the pharmaceutically acceptable capsule; (b) about 20% by weight to about 90% by weight of one or more fillers based on the total weight of the pharmaceutically acceptable capsule; (c) about 1% by weight to about 20% by weight of one or more disintegrants based on the total weight of the pharmaceutically acceptable capsule; and (d) about 0.1% by weight to about 10% by weight of one or more lubricants based on the total weight of the pharmaceutically acceptable capsule.

In some embodiments, the pharmaceutically acceptable capsule comprises (a) about 5% by weight to about 25% by weight of the crystalline dihydrate form of the compound of Formula (I) based on the total weight of the pharmaceutically acceptable capsule; (b) about 60% by weight to about 90% by weight of one or more fillers based on the total weight of the pharmaceutically acceptable capsule; (c) about 1% by weight to about 15% by weight of one or more disintegrants based on the total weight of the pharmaceutically acceptable capsule; and (d) about 0.1% by weight to about 4% by weight of one or more lubricants based on the total weight of the pharmaceutically acceptable capsule.

In some embodiments, the pharmaceutically acceptable capsule consists essentially of (a) about 5% by weight to about 25% by weight of the crystalline dihydrate form of the compound of Formula (I) based on the total weight of the pharmaceutically acceptable capsule; (b) about 60% by weight to about 90% by weight of one or more fillers based on the total weight of the pharmaceutically acceptable capsule; (c) about 1% by weight to about 15% by weight of one or more disintegrants based on the total weight of the pharmaceutically acceptable capsule; and (d) about 0.1% by weight to about 4% by weight of one or more lubricants based on the total weight of the pharmaceutically acceptable capsule.

In some embodiments, the pharmaceutically acceptable capsule comprises (a) about 10% by weight to about 30% by weight of the crystalline dihydrate form of the compound of Formula (I) based on the total weight of the pharmaceutically acceptable capsule; (b) about 70% by weight to about 90% by weight of one or more fillers based on the total weight of the pharmaceutically acceptable capsule; (c) about 1% by weight to about 10% by weight of one or more disintegrants based on the total weight of the pharmaceutically acceptable capsule; and (d) about 0.1% by weight to about 3% by weight of one or more lubricants based on the total weight of the pharmaceutically acceptable capsule.

In some embodiments, the pharmaceutically acceptable capsule consists essentially of (a) about 10% by weight to about 30% by weight of the crystalline dihydrate form of the compound of Formula (I) based on the total weight of the pharmaceutically acceptable capsule; (b) about 70% by weight to about 90% by weight of one or more fillers based on the total weight of the pharmaceutically acceptable capsule; (c) about 1% by weight to about 10% by weight of one or more disintegrants based on the total weight of the pharmaceutically acceptable capsule; and (d) about 0.1% by weight to about 3% by weight of one or more lubricants based on the total weight of the pharmaceutically acceptable capsule.

In some embodiments, the one or more pharmaceutically acceptable excipients is one or more fillers selected from the group consisting of calcium phosphate, dicalcium phosphate, dicalcium phosphate dihydrate, calcium sulfate, calcium sulfate dihydrate, starch, calcium carbonate, magnesium carbonate, magnesium oxide, kaolin (natural hydrated aluminum silicate), sodium chloride, partially gelatinized starch, anhydrous lactose, lactose monohydrate, lactose dihydrate, trehalose dihydrate, spray dried lactose, sucrose, dextrose, dextrates, dextrin, cellulose, microcrystalline cellulose, silicified microcrystalline cellulose, powdered cellulose, partially depolymerized cellulose, mannitol, granulated mannitol, spray dried mannitol, maltodextrin, maltitol, confectioner's sugar, compressible sugar, sorbitol, starch and talc. In some embodiments, the one or more fillers is lactose monohydrate.

In some embodiments, the one or more disintegrants is one or more disintegrants selected from the group consisting of sodium starch glycolate, pregelatinized starch, clay, cellulose, alginic acid, alginate gum, polyvinylpyrrolidone, cross-linked polyvinylpyrrolidone, cross-linked calcium carboxymethylcellulose, cross-linked sodium carboxymethylcellulose, sodium croscarmellose, sodium carmellose, low substituted hydroxypropyl cellulose, low substituted hydroxypropyl cellulose sodium, guar gum, magnesium aluminum silicate, polacrilin potassium, powdered cellulose, sodium alginate and soy polysaccharides. In some embodiments, the one or more disintegrants is cross-linked polyvinylpyrrolidone (also referred to as crospovidone).

In some embodiments, the one or more lubricants is one or more lubricants selected from the group consisting of colloidal silica, magnesium trisilicate, talc, magnesium carbonate, magnesium oxide, glyceryl behaptate, mono, di and tri glyceryl behenate, bees wax, behenoyl polyoxyl-8 glycerides, hydrogenated vegetable oil, polyethylene glycol, ethylene oxide polymer, copolymer comprising poly(ethylene oxide) and poly(propylene oxide) (such as poloxomer 188), copolymer comprising polypropylene glycol and polyethylene glycol (such as poloxomer 407), sodium lauryl sulfate, magnesium stearate, aluminum stearate, calcium stearate, sodium stearyl fumarate, stearic acid, magnesium lauryl stearate, mixtures of magnesium stearate with sodium lauryl sulfate. In some embodiments, the one or more lubricants is magnesium stearate.

In some embodiments, the one or more disintegrants is selected from the group consisting of cross-linked polyvinylpyrrolidone, croscarmellose sodium, and sodium starch glycolate; and the one or more lubricants is selected from the group consisting of sodium stearyl fumarate, stearic acid, talc, calcium stearate, magnesium stearate, solid polyethylene glycols, and sodium lauryl sulfate. In some embodiments, the pharmaceutically acceptable capsule comprises cross-linked polyvinylpyrrolidone and magnesium stearate. In some embodiments, the one or more pharmaceutically acceptable excipients is lactose monohydrate and the pharmaceutically acceptable capsule further comprises cross-linked polyvinylpyrrolidone and magnesium stearate.

In some embodiments, the pharmaceutically acceptable capsule is for oral administration.

In some embodiments, the pharmaceutically acceptable capsule is a solid dosage form.

In some embodiments, the pharmaceutically acceptable capsule comprises about 1 mg to about 40 mg of the crystalline dihydrate form of the compound of Formula (I). In some embodiments, the pharmaceutically acceptable capsule comprises about 5 mg to about 35 mg of the crystalline dihydrate form of the compound of Formula (I). In some embodiments, the pharmaceutically acceptable capsule comprises about 10 mg to about 35 mg of the crystalline dihydrate form of the compound of Formula (I). In some embodiments, the pharmaceutically acceptable capsule comprises about 0.5 mg to about 5 mg, about 6 mg to about 14 mg, about 11 mg to about 19 mg, about 17 mg to about 25 mg, or about 28 mg to about 36 mg of the crystalline dihydrate form of the compound of Formula (I). In some embodiments, the pharmaceutically acceptable capsule comprises about 1 mg to about 4 mg, about 8 mg to about 12 mg, about 13 mg to about 17 mg, about 19 mg to about 23 mg, or about 30 mg to about 34 mg of the crystalline dihydrate form of the compound of Formula (I). In some embodiments, the pharmaceutically acceptable capsule comprises about 2.2 mg, about 10.8 mg, about 15.2 mg, about 21.7 mg, or about 32.5 mg of the crystalline dihydrate form of the compound of Formula (I). In some embodiments, the crystalline dihydrate form of the compound of Formula (I) is present in an amount of about 2.2 mg. In some embodiments, the crystalline dihydrate form of the compound of Formula (I) is present in an amount of about 10.8 mg. In some embodiments, the crystalline dihydrate form of the compound of Formula (I) is present in an amount of about 15.2 mg. In some embodiments, the crystalline dihydrate form of the compound of Formula (I) is present in an amount of about 21.7 mg. In some embodiments, the crystalline dihydrate form of the compound of Formula (I) is present in an amount of about 32.5 mg.

In some embodiments, the pharmaceutically acceptable capsule consists essentially of about 1 mg to about 40 mg of the crystalline dihydrate form of the compound of Formula (I). In some embodiments, the pharmaceutically acceptable capsule consists essentially of about 5 mg to about 35 mg of the crystalline dihydrate form of the compound of Formula (I). In some embodiments, the pharmaceutically acceptable capsule consists essentially of about 10 mg to about 35 mg of the crystalline dihydrate form of the compound of Formula (I). In some embodiments, the pharmaceutically acceptable capsule consists essentially of about 0.5 mg to about 5 mg, about 6 mg to about 14 mg, about 11 mg to about 19 mg, about 17 mg to about 25 mg, or about 28 mg to about 36 mg of the crystalline dihydrate form of the compound of Formula (I). In some embodiments, the pharmaceutically acceptable capsule consists essentially of about 1 mg to about 4 mg, about 8 mg to about 12 mg, about 13 mg to about 17 mg, about 19 mg to about 23 mg, or about 30 mg to about 34 mg of the crystalline dihydrate form of the compound of Formula (I). In some embodiments, the pharmaceutically acceptable capsule consists essentially of about 2.2 mg, about 10.8 mg, about 15.2 mg, about 21.7 mg, or about 32.5 mg of the crystalline dihydrate form of the compound of Formula (I). In some embodiments, the crystalline dihydrate form of the compound of Formula (I) is present in an amount of about 2.2 mg. In some embodiments, the crystalline dihydrate form of the compound of Formula (I) is present in an amount of about 10.8 mg. In some embodiments, the crystalline dihydrate form of the compound of Formula (I) is present in an amount of about 15.2 mg. In some embodiments, the crystalline dihydrate form of the compound of Formula (I) is present in an amount of about 21.7 mg. In some embodiments, the crystalline dihydrate form of the compound of Formula (I) is present in an amount of about 32.5 mg.

In some embodiments, the pharmaceutically acceptable capsule is a size 4 hard gelatin capsule. In some embodiments, the pharmaceutically acceptable capsule is a size 2 hard gelatin capsule. In some embodiments, the pharmaceutically acceptable capsule is a size 1 hard gelatin capsule. In some embodiments, the pharmaceutically acceptable capsule further comprises one more colorants selected from the group consisting of FD&C Blue #1(E133), FD&C Red #40 (E129), Titanium Dioxide (E171) United States Pharmacopeia—National Formulary (USP/NF) or European Pharmacopeia (Ph. Eur.), and Gelatin USP/NF or Ph. Eur.

In some embodiments, the pharmaceutically acceptable capsule comprises about 1.55% of the crystalline dihydrate form by weight, based on the weight of the formulation blend, about 95.95% of lactose monohydrate by weight, based on the weight of the formulation blend, about 2.00% of cross-linked polyvinylpyrrolidone by weight, based on the weight of the formulation blend, and about 0.50% of magnesium stearate by weight, based on the weight of the formulation blend. In some embodiments, the pharmaceutically acceptable capsule is a size 4 hard gelatin capsule.

In some embodiments, the pharmaceutically acceptable capsule comprises about 10.84% of the crystalline dihydrate form by weight, based on the weight of the formulation blend, about 86.66% of lactose monohydrate by weight, based on the weight of the formulation blend, about 2.00% of cross-linked polyvinylpyrrolidone by weight, based on the weight of the formulation blend, and about 0.50% of magnesium stearate by weight, based on the weight of the formulation blend. In some embodiments, the pharmaceutically acceptable capsule is a size 4 hard gelatin capsule.

In some embodiments, the pharmaceutically acceptable capsule comprises about 10.84% of the crystalline dihydrate form by weight, based on the weight of the formulation blend, about 86.66% of lactose monohydrate by weight, based on the weight of the formulation blend, about 2.00% of cross-linked polyvinylpyrrolidone by weight, based on the weight of the formulation blend, and about 0.50% of magnesium stearate by weight, based on the weight of the formulation blend. In some embodiments, the pharmaceutically acceptable capsule is a size 2 hard gelatin capsule.

In some embodiments, the pharmaceutically acceptable capsule comprises about 10.84% of the crystalline dihydrate form by weight, based on the weight of the formulation blend, about 86.66% of lactose monohydrate by weight, based on the weight of the formulation blend, about 2.00% of cross-linked polyvinylpyrrolidone by weight, based on the weight of the formulation blend, and about 0.50% of magnesium stearate by weight, based on the weight of the formulation blend. In some embodiments, the pharmaceutically acceptable capsule is a size 1 hard gelatin capsule.

In some embodiments, the pharmaceutically acceptable capsule consists essentially of about 10.84% of the crystalline dihydrate form by weight, based on the weight of the formulation blend, about 86.66% of lactose monohydrate by weight, based on the weight of the formulation blend, about 2.00% of cross-linked polyvinylpyrrolidone by weight, based on the weight of the formulation blend, and about 0.50% of magnesium stearate by weight, based on the weight of the formulation blend. In some embodiments, the pharmaceutically acceptable capsule is a size 4 hard gelatin capsule.

In some embodiments, the pharmaceutically acceptable capsule consists essentially of about 10.84% of the crystalline dihydrate form by weight, based on the weight of the formulation blend, about 86.66% of lactose monohydrate by weight, based on the weight of the formulation blend, about 2.00% of cross-linked polyvinylpyrrolidone by weight, based on the weight of the formulation blend, and about 0.50% of magnesium stearate by weight, based on the weight of the formulation blend. In some embodiments, the pharmaceutically acceptable capsule is a size 2 hard gelatin capsule.

In some embodiments, the pharmaceutically acceptable capsule consists essentially of about 10.84% of the crystalline dihydrate form by weight, based on the weight of the formulation blend, about 86.66% of lactose monohydrate by weight, based on the weight of the formulation blend, about 2.00% of cross-linked polyvinylpyrrolidone by weight, based on the weight of the formulation blend, and about 0.50% of magnesium stearate by weight, based on the weight of the formulation blend. In some embodiments, the pharmaceutically acceptable capsule is a size 1 hard gelatin capsule.

Also provided herein, in some embodiments, are pharmaceutically acceptable formulations comprising the crystalline anhydrous form of a compound of Formula (I):

Formula (I)

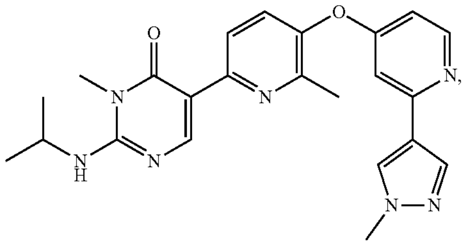

and one or more pharmaceutically acceptable excipients.

Also provided herein, in some embodiments, are pharmaceutically acceptable formulations consisting essentially of the crystalline anhydrous form of a compound of Formula (I):

Formula (I)

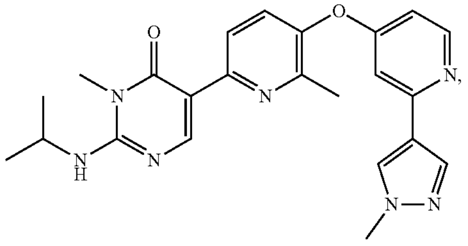

and one or more pharmaceutically acceptable excipients.

Also provided herein, in some embodiments, are pharmaceutically acceptable unit formulations comprising the crystalline anhydrous form of a compound of Formula (I):

Formula (I)

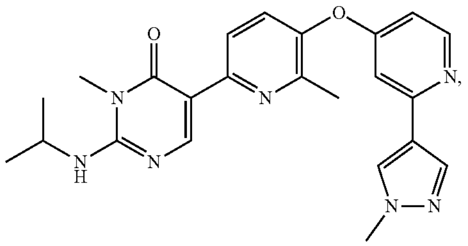

and one or more pharmaceutically acceptable excipients.

Also provided herein, in some embodiments, are pharmaceutically acceptable unit formulations consisting essentially of the crystalline anhydrous form of a compound of Formula (I):

Formula (I)

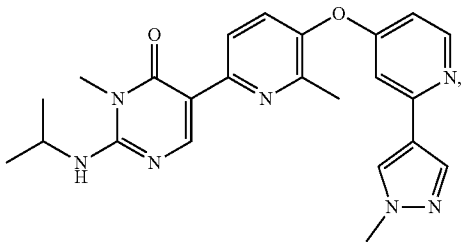

and one or more pharmaceutically acceptable excipients.

In some embodiments, the crystalline anhydrous form of the compound represented by Formula (I) has an XRPD pattern comprising a peak, in terms of 2-theta, at about 11.4° as measured by CuKα radiation.

In some embodiments, the crystalline anhydrous form of the compound represented by Formula (I) has an XRPD pattern comprising two or more of the characteristic peaks, in terms of 2-theta, at about 11.4°, about 14.7°, about 17.1°, and about 21.3° as measured by CuKα radiation.

In some embodiments, the crystalline anhydrous form of the compound represented by Formula (I) has an XRPD pattern comprising two or more of the characteristic peaks, in terms of 2-theta, at about 11.4°, about 14.7°, about 17.1°, about 20.10, about 21.3°, and about 29.10 as measured by CuKα radiation.

In some embodiments, the crystalline anhydrous form of the compound represented by Formula (I) has an XRPD pattern comprising two or more of the characteristic peaks, in terms of 2-theta, at about 10.2°, about 10.5°, about 11.4°, about 14.7°, about 17.1°, about 20.10, about 21.3°, and about 29.10 as measured by CuKα radiation.

In some embodiments, the one or more pharmaceutically acceptable excipients is a filler. For example, the one or more pharmaceutically acceptable excipients is lactose, such as lactose monohydrate.

In some embodiments, the pharmaceutically acceptable unit formulations further comprise one or more disintegrants, one or more lubricants, or a combination thereof. For example, in some embodiments, the pharmaceutically acceptable unit formulations further comprise one or more disintegrants. In some embodiments, the pharmaceutically acceptable unit formulations further comprise one or more lubricants.

Also provided herein, in some embodiments, is a pharmaceutically acceptable unit formulation comprising:

(a) about 1% by weight to about 70% by weight, based on the weight of the pharmaceutically acceptable unit formulation, of a crystalline anhydrous form of a compound of Formula (I):

Formula (I)

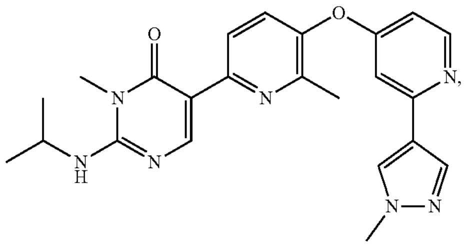

and one or more pharmaceutically acceptable excipients, wherein the one or more pharmaceutically acceptable excipients comprise:

(b) about 20% by weight to about 97% by weight of one or more fillers based on the weight of the pharmaceutically acceptable unit formulation;

(c) about 1% by weight to about 20% by weight of one or more disintegrants based on the weight of the pharmaceutically acceptable unit formulation; and (d) about 0.1% by weight to about 10% by weight of one or more lubricants based on the weight of the pharmaceutically acceptable unit formulation.

Also provided herein, in some embodiments, is a pharmaceutically acceptable unit formulation comprising:

(a) about 1% by weight to about 30% by weight of a crystalline anhydrous form of a compound of Formula (I) based on the weight of the pharmaceutically acceptable unit formulation;

(b) about 20% by weight to about 90% by weight of one or more fillers based on the weight of the pharmaceutically acceptable unit formulation;

(c) about 1% by weight to about 20% by weight of one or more disintegrants based on the weight of the pharmaceutically acceptable unit formulation; and (d) about 0.1% by weight to about 10% by weight of one or more lubricants based on the weight of the pharmaceutically acceptable unit formulation.

Also provided herein, in some embodiments, is a pharmaceutically acceptable unit formulation consisting essentially of:

(a) about 1% by weight to about 70% by weight, based on the weight of the pharmaceutically acceptable unit formulation, of a crystalline anhydrous form of a compound of Formula (I):

Formula (I)

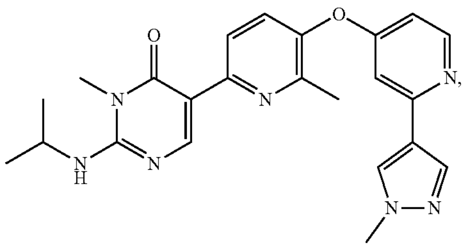

and one or more pharmaceutically acceptable excipients, wherein the one or more pharmaceutically acceptable excipients comprise:

(b) about 20% by weight to about 97% by weight of one or more fillers based on the weight of the pharmaceutically acceptable unit formulation;

(c) about 1% by weight to about 20% by weight of one or more disintegrants based on the weight of the pharmaceutically acceptable unit formulation; and (d) about 0.1% by weight to about 10% by weight of one or more lubricants based on the weight of the pharmaceutically acceptable unit formulation.

Also provided herein, in some embodiments, is a pharmaceutically acceptable unit formulation consisting essentially of:

(a) about 1% by weight to about 30% by weight of a crystalline anhydrous form of a compound of Formula (I) based on the weight of the pharmaceutically acceptable unit formulation;

(b) about 20% by weight to about 90% by weight of one or more fillers based on the weight of the pharmaceutically acceptable unit formulation;

(c) about 1% by weight to about 20% by weight of one or more disintegrants based on the weight of the pharmaceutically acceptable unit formulation; and (d) about 0.1% by weight to about 10% by weight of one or more lubricants based on the weight of the pharmaceutically acceptable unit formulation.

In some embodiments, the pharmaceutically acceptable unit formulation comprising the crystalline anhydrous form of the compound represented by Formula (I), has no more than about 10 mol %, no more than about 5 mol %, no more than about 3 mol %, or no more than about 1 mol % of other solid-state forms of the compound represented by Formula (I). In some embodiments, the pharmaceutically acceptable unit formulation comprising the crystalline anhydrous forms of the compound represented by Formula (I), has no more than about 10 mol % of other solid-state forms of the compound represented by Formula (I). In some embodiments, the pharmaceutically acceptable unit formulation comprising the crystalline anhydrous forms of the compound represented by Formula (I), has no more than about 9 mol % of other solid-state forms of the compound represented by Formula (I). In some embodiments, the pharmaceutically acceptable unit formulation comprising the crystalline anhydrous forms of the compound represented by Formula (I), has no more than about 8 mol % of other solid-state forms of the compound represented by Formula (I). In some embodiments, the pharmaceutically acceptable unit formulation comprising the crystalline anhydrous forms of the compound represented by Formula (I), has no more than about 7 mol % of other solid-state forms of the compound represented by Formula (I). In some embodiments, the pharmaceutically acceptable unit formulation comprising the crystalline anhydrous forms of the compound represented by Formula (I), has no more than about 6 mol % of other solid-state forms of the compound represented by Formula (I). In some embodiments, the pharmaceutically acceptable unit formulation comprising the crystalline anhydrous forms of the compound represented by Formula (I), has no more than about 5 mol % of other solid-state forms of the compound represented by Formula (I). In some embodiments, the pharmaceutically acceptable unit formulation comprising the crystalline anhydrous forms of the compound represented by Formula (I), has no more than about 4 mol % of other solid-state forms of the compound represented by Formula (I). In some embodiments, the pharmaceutically acceptable unit formulation comprising the crystalline anhydrous forms of the compound represented by Formula (I), has no more than about 3 mol % of other solid-state forms of the compound represented by Formula (I). In some embodiments, the pharmaceutically acceptable unit formulation comprising the crystalline anhydrous forms of the compound represented by Formula (I), has no more than about 2 mol % of other solid-state forms of the compound represented by Formula (I). In some embodiments, the pharmaceutically acceptable unit formulation comprising the crystalline anhydrous forms of the compound represented by Formula (I), has no more than about 1 mol % of other solid-state forms of the compound represented by Formula (I).

In some embodiments, the pharmaceutically acceptable unit formulation comprises about 1% by weight to about 60% by weight, based on the weight of the pharmaceutically acceptable unit formulation, of a crystalline anhydrous form of a compound of Formula (I). In some embodiments, the pharmaceutically acceptable unit formulation comprises about 1% by weight to about 50% by weight, based on the weight of the pharmaceutically acceptable unit formulation, of a crystalline anhydrous form of a compound of Formula (I). In some embodiments, the pharmaceutically acceptable unit formulation comprises about 1% by weight to about 40% by weight, based on the weight of the pharmaceutically acceptable unit formulation, of a crystalline anhydrous form of a compound of Formula (I). In some embodiments, the pharmaceutically acceptable unit formulation comprises about 1% by weight to about 30% by weight, based on the weight of the pharmaceutically acceptable unit formulation, of a crystalline anhydrous form of a compound of Formula (I). In some embodiments, the pharmaceutically acceptable unit formulation comprises about 1% by weight to about 20% by weight, based on the weight of the pharmaceutically acceptable unit formulation, of a crystalline anhydrous form of a compound of Formula (I).

In some embodiments, the pharmaceutically acceptable unit formulation consists essentially of about 1% by weight to about 60% by weight, based on the weight of the pharmaceutically acceptable unit formulation, of a crystalline anhydrous form of a compound of Formula (I). In some embodiments, the pharmaceutically acceptable unit formulation consists essentially of about 1% by weight to about 50% by weight, based on the weight of the pharmaceutically acceptable unit formulation, of a crystalline anhydrous form of a compound of Formula (I). In some embodiments, the pharmaceutically acceptable unit formulation consists essentially of about 1% by weight to about 40% by weight, based on the weight of the pharmaceutically acceptable unit formulation, of a crystalline anhydrous form of a compound of Formula (I). In some embodiments, the pharmaceutically acceptable unit formulation consists essentially of about 1% by weight to about 30% by weight, based on the weight of the pharmaceutically acceptable unit formulation, of a crystalline anhydrous form of a compound of Formula (I). In some embodiments, the pharmaceutically acceptable unit formulation consists essentially of about 1% by weight to about 20% by weight, based on the weight of the pharmaceutically acceptable unit formulation, of a crystalline anhydrous form of a compound of Formula (I).

In some embodiments, the pharmaceutically acceptable unit formulation comprises about 1% by weight to about 70% by weight of the crystalline anhydrous form of the compound of Formula (I) based on the weight of the pharmaceutically acceptable unit formulation. In some embodiments, the pharmaceutically acceptable unit formulation comprises about 1% by weight to about 65% by weight of the crystalline anhydrous form of the compound of Formula (I) based on the weight of the pharmaceutically acceptable unit formulation. In some embodiments, the pharmaceutically acceptable unit formulation comprises about 1% by weight to about 60% by weight of the crystalline anhydrous form of the compound of Formula (I) based on the weight of the pharmaceutically acceptable unit formulation. In some embodiments, the pharmaceutically acceptable unit formulation comprises about 1% by weight to about 55% by weight of the crystalline anhydrous form of the compound of Formula (I) based on the weight of the pharmaceutically acceptable unit formulation. In some embodiments, the pharmaceutically acceptable unit formulation comprises about 1% by weight to about 50% by weight of the crystalline anhydrous form of the compound of Formula (I) based on the weight of the pharmaceutically acceptable unit formulation. In some embodiments, the pharmaceutically acceptable unit formulation comprises about 1% by weight to about 45% by weight of the crystalline anhydrous form of the compound of Formula (I) based on the weight of the pharmaceutically acceptable unit formulation. In some embodiments, the pharmaceutically acceptable unit formulation comprises about 1% by weight to about 40% by weight of the crystalline anhydrous form of the compound of Formula (I) based on the weight of the pharmaceutically acceptable unit formulation. In some embodiments, the pharmaceutically acceptable unit formulation comprises about 1% by weight to about 35% by weight of the crystalline anhydrous form of the compound of Formula (I) based on the weight of the pharmaceutically acceptable unit formulation. In some embodiments, the pharmaceutically acceptable unit formulation comprises about 1% by weight to about 30% by weight of the crystalline anhydrous form of the compound of Formula (I) based on the weight of the pharmaceutically acceptable unit formulation. In some embodiments, the pharmaceutically acceptable unit formulation comprises about 1% by weight to about 25% by weight of the crystalline anhydrous form of the compound of Formula (I) based on the weight of the pharmaceutically acceptable unit formulation. In some embodiments, the pharmaceutically acceptable unit formulation comprises about 1% by weight to about 20% by weight of the crystalline anhydrous form of the compound of Formula (I) based on the weight of the pharmaceutically acceptable unit formulation. In some embodiments, the pharmaceutically acceptable unit formulation comprises about 1% by weight to about 15% by weight of the crystalline anhydrous form of the compound of Formula (I) based on the weight of the pharmaceutically acceptable unit formulation. In some embodiments, the pharmaceutically acceptable unit formulation comprises about 1% by weight to about 10% by weight of the crystalline anhydrous form of the compound of Formula (I) based on the weight of the pharmaceutically acceptable unit formulation.

In some embodiments, the pharmaceutically acceptable unit formulation consists essentially of about 1% by weight to about 70% by weight of the crystalline anhydrous form of the compound of Formula (I) based on the weight of the pharmaceutically acceptable unit formulation. In some embodiments, the pharmaceutically acceptable unit formulation consists essentially of about 1% by weight to about 65% by weight of the crystalline anhydrous form of the compound of Formula (I) based on the weight of the pharmaceutically acceptable unit formulation. In some embodiments, the pharmaceutically acceptable unit formulation consists essentially of about 1% by weight to about 60% by weight of the crystalline anhydrous form of the compound of Formula (I) based on the weight of the pharmaceutically acceptable unit formulation. In some embodiments, the pharmaceutically acceptable unit formulation consists essentially of about 1% by weight to about 55% by weight of the crystalline anhydrous form of the compound of Formula (I) based on the weight of the pharmaceutically acceptable unit formulation. In some embodiments, the pharmaceutically acceptable unit formulation consists essentially of about 1% by weight to about 50% by weight of the crystalline anhydrous form of the compound of Formula (I) based on the weight of the pharmaceutically acceptable unit formulation. In some embodiments, the pharmaceutically acceptable unit formulation consists essentially of about 1% by weight to about 45% by weight of the crystalline anhydrous form of the compound of Formula (I) based on the weight of the pharmaceutically acceptable unit formulation. In some embodiments, the pharmaceutically acceptable unit formulation consists essentially of about 1% by weight to about 40% by weight of the crystalline anhydrous form of the compound of Formula (I) based on the weight of the pharmaceutically acceptable unit formulation. In some embodiments, the pharmaceutically acceptable unit formulation consists essentially of about 1% by weight to about 35% by weight of the crystalline anhydrous form of the compound of Formula (I) based on the weight of the pharmaceutically acceptable unit formulation. In some embodiments, the pharmaceutically acceptable unit formulation consists essentially of about 1% by weight to about 30% by weight of the crystalline anhydrous form of the compound of Formula (I) based on the weight of the pharmaceutically acceptable unit formulation. In some embodiments, the pharmaceutically acceptable unit formulation consists essentially of about 1% by weight to about 25% by weight of the crystalline anhydrous form of the compound of Formula (I) based on the weight of the pharmaceutically acceptable unit formulation. In some embodiments, the pharmaceutically acceptable unit formulation consists essentially of about 1% by weight to about 20% by weight of the crystalline anhydrous form of the compound of Formula (I) based on the weight of the pharmaceutically acceptable unit formulation. In some embodiments, the pharmaceutically acceptable unit formulation consists essentially of about 1% by weight to about 15% by weight of the crystalline anhydrous form of the compound of Formula (I) based on the weight of the pharmaceutically acceptable unit formulation. In some embodiments, the pharmaceutically acceptable unit formulation consists essentially of about 1% by weight to about 10% by weight of the crystalline anhydrous form of the compound of Formula (I) based on the weight of the pharmaceutically acceptable unit formulation.

In some embodiments, the pharmaceutically acceptable unit formulation comprises about 5% by weight to about 30% by weight of the crystalline anhydrous form of the compound of Formula (I) based on the weight of the pharmaceutically acceptable unit formulation. In some embodiments, the pharmaceutically acceptable unit formulation comprises about 5% by weight to about 25% by weight of the crystalline anhydrous form of the compound of Formula (I) based on the weight of the pharmaceutically acceptable unit formulation. In some embodiments, the pharmaceutically acceptable unit formulation comprises about 5% by weight to about 20% by weight of the crystalline anhydrous form of the compound of Formula (I) based on the weight of the pharmaceutically acceptable unit formulation. In some embodiments, the pharmaceutically acceptable unit formulation comprises about 5% by weight to about 15% by weight of the crystalline anhydrous form of the compound of Formula (I) based on the weight of the pharmaceutically acceptable unit formulation. In some embodiments, the pharmaceutically acceptable unit formulation comprises about 5% by weight to about 10% by weight of the crystalline anhydrous form of the compound of Formula (I) based on the weight of the pharmaceutically acceptable unit formulation.

In some embodiments, the pharmaceutically acceptable unit formulation consists essentially of about 5% by weight to about 30% by weight of the crystalline anhydrous form of the compound of Formula (I) based on the weight of the pharmaceutically acceptable unit formulation. In some embodiments, the pharmaceutically acceptable unit formulation consists essentially of about 5% by weight to about 25% by weight of the crystalline anhydrous form of the compound of Formula (I) based on the weight of the pharmaceutically acceptable unit formulation. In some embodiments, the pharmaceutically acceptable unit formulation consists essentially of about 5% by weight to about 20% by weight of the crystalline anhydrous form of the compound of Formula (I) based on the weight of the pharmaceutically acceptable unit formulation. In some embodiments, the pharmaceutically acceptable unit formulation consists essentially of about 5% by weight to about 15% by weight of the crystalline anhydrous form of the compound of Formula (I) based on the weight of the pharmaceutically acceptable unit formulation. In some embodiments, the pharmaceutically acceptable unit formulation consists essentially of about 5% by weight to about 10% by weight of the crystalline anhydrous form of the compound of Formula (I) based on the weight of the pharmaceutically acceptable unit formulation.

In some embodiments, the pharmaceutically acceptable unit formulation comprises about 10% to about 30% of the compound of Formula (I) based on the weight of the pharmaceutically acceptable unit formulation. In some embodiments, the pharmaceutically acceptable unit formulation comprises about 10% to about 25% of the compound of Formula (I) based on the weight of the pharmaceutically acceptable unit formulation. In some embodiments, the pharmaceutically acceptable unit formulation comprises about 10% to about 20% of the compound of Formula (I) based on the weight of the pharmaceutically acceptable unit formulation. In some embodiments, the pharmaceutically acceptable unit formulation comprises about 10% by weight to about 15% by weight of the crystalline anhydrous form of the compound of Formula (I) based on the weight of the pharmaceutically acceptable unit formulation.

In some embodiments, the pharmaceutically acceptable unit formulation consists essentially of about 10% to about 30% of the crystalline anhydrous form of the compound of Formula (I) based on the weight of the pharmaceutically acceptable unit formulation. In some embodiments, the pharmaceutically acceptable unit formulation consists essentially of about 10% to about 25% of the crystalline anhydrous form of the compound of Formula (I) based on the weight of the pharmaceutically acceptable unit formulation. In some embodiments, the pharmaceutically acceptable unit formulation consists essentially of about 10% to about 20% of the crystalline anhydrous form of the compound of Formula (I) based on the weight of the pharmaceutically acceptable unit formulation. In some embodiments, the pharmaceutically acceptable unit formulation consists essentially of about 10% by weight to about 15% by weight of the crystalline anhydrous form of the compound of Formula (I) based on the weight of the pharmaceutically acceptable unit formulation.

In some embodiments, the pharmaceutically acceptable unit formulation comprises about 1% by weight to about 30% by weight of the crystalline anhydrous form of the compound of Formula (I) based on the weight of the pharmaceutically acceptable unit formulation. In some embodiments, the pharmaceutically acceptable unit formulation comprises about 1% by weight to about 10% by weight of the crystalline anhydrous form of the compound of Formula (I) based on the weight of the pharmaceutically acceptable unit formulation. In some embodiments, the pharmaceutically acceptable unit formulation comprises about 10% to about 20% of the compound of Formula (I) based on the weight of the pharmaceutically acceptable unit formulation. In some embodiments, the pharmaceutically acceptable unit formulation comprises about 10% by weight to about 15% by weight of the crystalline anhydrous form of the compound of Formula (I) based on the weight of the pharmaceutically acceptable unit formulation.

In some embodiments, the pharmaceutically acceptable unit formulation consists essentially of about 1% by weight to about 30% by weight of the crystalline anhydrous form of the compound of Formula (I) based on the weight of the pharmaceutically acceptable unit formulation. In some embodiments, the pharmaceutically acceptable unit formulation consists essentially of about 1% by weight to about 10% by weight of the crystalline anhydrous form of the compound of Formula (I) based on the weight of the pharmaceutically acceptable unit formulation. In some embodiments, the pharmaceutically acceptable unit formulation consists essentially of about 10% to about 20% of the crystalline anhydrous form of the compound of Formula (I) based on the weight of the pharmaceutically acceptable unit formulation. In some embodiments, the pharmaceutically acceptable unit formulation consists essentially of about 10% by weight to about 15% by weight of the crystalline anhydrous form of the compound of Formula (I) based on the weight of the pharmaceutically acceptable unit formulation.

In some embodiments, the one or more pharmaceutically acceptable excipients comprise about 20% by weight to about 90% by weight of one or more fillers based on the weight of the pharmaceutically acceptable unit formulation. In some embodiments, the one or more pharmaceutically acceptable excipients comprise about 20% by weight to about 85% by weight of one or more fillers based on the weight of the pharmaceutically acceptable unit formulation. In some embodiments, the one or more pharmaceutically acceptable excipients comprise about 20% by weight to about 80% by weight of one or more fillers based on the weight of the pharmaceutically acceptable unit formulation. In some embodiments, the one or more pharmaceutically acceptable excipients comprise about 20% by weight to about 75% by weight of one or more fillers based on the weight of the pharmaceutically acceptable unit formulation. In some embodiments, the one or more pharmaceutically acceptable excipients comprise about 20% by weight to about 70% by weight of one or more fillers based on the weight of the pharmaceutically acceptable unit formulation. In some embodiments, the one or more pharmaceutically acceptable excipients comprise about 20% by weight to about 65% by weight of one or more fillers based on the weight of the pharmaceutically acceptable unit formulation. In some embodiments, the one or more pharmaceutically acceptable excipients comprise about 20% by weight to about 60% by weight of one or more fillers based on the weight of the pharmaceutically acceptable unit formulation. In some embodiments, the one or more pharmaceutically acceptable excipients comprise about 20% by weight to about 55% by weight of one or more fillers based on the weight of the pharmaceutically acceptable unit formulation. In some embodiments, the one or more pharmaceutically acceptable excipients comprise about 20% by weight to about 50% by weight of one or more fillers based on the weight of the pharmaceutically acceptable unit formulation. In some embodiments, the one or more pharmaceutically acceptable excipients comprise about 20% by weight to about 45% by weight of one or more fillers based on the weight of the pharmaceutically acceptable unit formulation. In some embodiments, the one or more pharmaceutically acceptable excipients comprise about 20% by weight to about 40% by weight of one or more fillers based on the weight of the pharmaceutically acceptable unit formulation. In some embodiments, the one or more pharmaceutically acceptable excipients comprise about 20% by weight to about 35% by weight of one or more fillers based on the weight of the pharmaceutically acceptable unit formulation. In some embodiments, the one or more pharmaceutically acceptable excipients comprise about 20% by weight to about 30% by weight of one or more fillers based on the weight of the pharmaceutically acceptable unit formulation. In some embodiments, the one or more pharmaceutically acceptable excipients comprise about 20% by weight to about 25% by weight of one or more fillers based on the weight of the pharmaceutically acceptable unit formulation.

In some embodiments, the one or more pharmaceutically acceptable excipients comprise about 30% by weight to about 90% by weight of one or more fillers based on the weight of the pharmaceutically acceptable unit formulation. In some embodiments, the one or more pharmaceutically acceptable excipients comprise about 30% by weight to about 80% by weight of one or more fillers based on the weight of the pharmaceutically acceptable unit formulation. In some embodiments, the one or more pharmaceutically acceptable excipients comprise about 30% by weight to about 70% by weight of one or more fillers based on the weight of the pharmaceutically acceptable unit formulation. In some embodiments, the one or more pharmaceutically acceptable excipients comprise about 30% by weight to about 60% by weight of one or more fillers based on the weight of the pharmaceutically acceptable unit formulation. In some embodiments, the one or more pharmaceutically acceptable excipients comprise about 30% by weight to about 50% by weight of one or more fillers based on the weight of the pharmaceutically acceptable unit formulation. In some embodiments, the one or more pharmaceutically acceptable excipients comprise about 30% by weight to about 40% by weight of one or more fillers based on the weight of the pharmaceutically acceptable unit formulation.

In some embodiments, the one or more pharmaceutically acceptable excipients comprise about 40% by weight to about 90% by weight of one or more fillers based on the weight of the pharmaceutically acceptable unit formulation. In some embodiments, the one or more pharmaceutically acceptable excipients comprise about 40% by weight to about 80% by weight of one or more fillers based on the weight of the pharmaceutically acceptable unit formulation. In some embodiments, the one or more pharmaceutically acceptable excipients comprise about 40% by weight to about 70% by weight of one or more fillers based on the weight of the pharmaceutically acceptable unit formulation. In some embodiments, the one or more pharmaceutically acceptable excipients comprise about 40% by weight to about 60% by weight of one or more fillers based on the weight of the pharmaceutically acceptable unit formulation. In some embodiments, the one or more pharmaceutically acceptable excipients comprise about 40% by weight to about 50% by weight of one or more fillers based on the weight of the pharmaceutically acceptable unit formulation.

In some embodiments, the one or more pharmaceutically acceptable excipients comprise about 50% by weight to about 90% by weight of one or more fillers based on the weight of the pharmaceutically acceptable unit formulation. In some embodiments, the one or more pharmaceutically acceptable excipients comprise about 50% by weight to about 80% by weight of one or more fillers based on the weight of the pharmaceutically acceptable unit formulation. In some embodiments, the one or more pharmaceutically acceptable excipients comprise about 50% by weight to about 70% by weight of one or more fillers based on the weight of the pharmaceutically acceptable unit formulation.

In some embodiments, the one or more pharmaceutically acceptable excipients comprise about 50% by weight to about 60% by weight of one or more fillers based on the weight of the pharmaceutically acceptable unit formulation.

In some embodiments, the one or more pharmaceutically acceptable excipients comprise about 60% by weight to about 90% by weight of one or more fillers based on the weight of the pharmaceutically acceptable unit formulation. In some embodiments, the one or more pharmaceutically acceptable excipients comprise about 60% by weight to about 80% by weight of one or more fillers based on the weight of the pharmaceutically acceptable unit formulation. In some embodiments, the one or more pharmaceutically acceptable excipients comprise about 60% by weight to about 70% by weight of one or more fillers based on the weight of the pharmaceutically acceptable unit formulation.

In some embodiments, the one or more pharmaceutically acceptable excipients comprise about 70% by weight to about 90% by weight of one or more fillers based on the weight of the pharmaceutically acceptable unit formulation. In some embodiments, the one or more pharmaceutically acceptable excipients comprise about 70% by weight to about 80% by weight of one or more fillers based on the weight of the pharmaceutically acceptable unit formulation.

In some embodiments, the one or more pharmaceutically acceptable excipients comprise about 80% by weight to about 90% by weight of one or more fillers based on the weight of the pharmaceutically acceptable unit formulation.

In some embodiments, the one or more pharmaceutically acceptable excipients comprise about 1% by weight to about 20% by weight of one or more disintegrants based on the weight of the pharmaceutically acceptable unit formulation. In some embodiments, the one or more pharmaceutically acceptable excipients comprise about 1% by weight to about 15% by weight of one or more disintegrants based on the weight of the pharmaceutically acceptable unit formulation. In some embodiments, the one or more pharmaceutically acceptable excipients comprise about 1% by weight to about 14% by weight of one or more disintegrants based on the weight of the pharmaceutically acceptable unit formulation. In some embodiments, the one or more pharmaceutically acceptable excipients comprise about 1% by weight to about 13% by weight of one or more disintegrants based on the weight of the pharmaceutically acceptable unit formulation. In some embodiments, the one or more pharmaceutically acceptable excipients comprise about 1% by weight to about 12% by weight of one or more disintegrants based on the weight of the pharmaceutically acceptable unit formulation. In some embodiments, the one or more pharmaceutically acceptable excipients comprise about 1% by weight to about 11% by weight of one or more disintegrants based on the weight of the pharmaceutically acceptable unit formulation. In some embodiments, the one or more pharmaceutically acceptable excipients comprise about 1% by weight to about 10% by weight of one or more disintegrants based on the weight of the pharmaceutically acceptable unit formulation. In some embodiments, the one or more pharmaceutically acceptable excipients comprise about 1% by weight to about 9% by weight of one or more disintegrants based on the weight of the pharmaceutically acceptable unit formulation. In some embodiments, the one or more pharmaceutically acceptable excipients comprise about 1% by weight to about 8% by weight of one or more disintegrants based on the weight of the pharmaceutically acceptable unit formulation. In some embodiments, the one or more pharmaceutically acceptable excipients comprise about 1% by weight to about 7% by weight of one or more disintegrants based on the weight of the pharmaceutically acceptable unit formulation. In some embodiments, the one or more pharmaceutically acceptable excipients comprise about 1% by weight to about 6% by weight of one or more disintegrants based on the weight of the pharmaceutically acceptable unit formulation. In some embodiments, the one or more pharmaceutically acceptable excipients comprise about 1% by weight to about 5% by weight of one or more disintegrants based on the weight of the pharmaceutically acceptable unit formulation. In some embodiments, the one or more pharmaceutically acceptable excipients comprise about 1% by weight to about 4% by weight of one or more disintegrants based on the weight of the pharmaceutically acceptable unit formulation. In some embodiments, the one or more pharmaceutically acceptable excipients comprise about 1% by weight to about 3% by weight of one or more disintegrants based on the weight of the pharmaceutically acceptable unit formulation.

In some embodiments, the one or more pharmaceutically acceptable excipients comprise about 1% by weight of one or more disintegrants based on the weight of the pharmaceutically acceptable unit formulation. In some embodiments, the one or more pharmaceutically acceptable excipients comprise about 2% by weight of one or more disintegrants based on the weight of the pharmaceutically acceptable unit formulation. In some embodiments, the one or more pharmaceutically acceptable excipients comprise about 3% by weight of one or more disintegrants based on the weight of the pharmaceutically acceptable unit formulation. In some embodiments, the one or more pharmaceutically acceptable excipients comprise about 4% by weight of one or more disintegrants based on the weight of the pharmaceutically acceptable unit formulation. In some embodiments, the one or more pharmaceutically acceptable excipients comprise about 5% by weight of one or more disintegrants based on the weight of the pharmaceutically acceptable unit formulation. In some embodiments, the one or more pharmaceutically acceptable excipients comprise about 6% by weight of one or more disintegrants based on the weight of the pharmaceutically acceptable unit formulation. In some embodiments, the one or more pharmaceutically acceptable excipients comprise about 7% by weight of one or more disintegrants based on the weight of the pharmaceutically acceptable unit formulation. In some embodiments, the one or more pharmaceutically acceptable excipients comprise about 8% by weight of one or more disintegrants based on the weight of the pharmaceutically acceptable unit formulation. In some embodiments, the one or more pharmaceutically acceptable excipients comprise about 9% by weight of one or more disintegrants based on the weight of the pharmaceutically acceptable unit formulation. In some embodiments, the one or more pharmaceutically acceptable excipients comprise about 10% by weight of one or more disintegrants based on the weight of the pharmaceutically acceptable unit formulation. In some embodiments, the one or more pharmaceutically acceptable excipients comprise about 11% by weight of one or more disintegrants based on the weight of the pharmaceutically acceptable unit formulation. In some embodiments, the one or more pharmaceutically acceptable excipients comprise about 12% by weight of one or more disintegrants based on the weight of the pharmaceutically acceptable unit formulation. In some embodiments, the one or more pharmaceutically acceptable excipients comprise about 13% by weight of one or more disintegrants based on the weight of the pharmaceutically acceptable unit formulation. In some embodiments, the one or more pharmaceutically acceptable excipients comprise about 14% by weight of one or more disintegrants based on the weight of the pharmaceutically acceptable unit formulation. In some embodiments, the one or more pharmaceutically acceptable excipients comprise about 15% by weight of one or more disintegrants based on the weight of the pharmaceutically acceptable unit formulation.

In some embodiments, the one or more pharmaceutically acceptable excipients comprise about 0.1% by weight to about 10% by weight of one or more lubricants based on the weight of the pharmaceutically acceptable unit formulation. In some embodiments, the one or more pharmaceutically acceptable excipients comprise about 0.1% by weight to about 9% by weight of one or more lubricants based on the weight of the pharmaceutically acceptable unit formulation. In some embodiments, the one or more pharmaceutically acceptable excipients comprise about 0.1% by weight to about 8% by weight of one or more lubricants based on the weight of the pharmaceutically acceptable unit formulation. In some embodiments, the one or more pharmaceutically acceptable excipients comprise about 0.1% by weight to about 7% by weight of one or more lubricants based on the weight of the pharmaceutically acceptable unit formulation. In some embodiments, the one or more pharmaceutically acceptable excipients comprise about 0.1% by weight to about 6% by weight of one or more lubricants based on the weight of the pharmaceutically acceptable unit formulation. In some embodiments, the one or more pharmaceutically acceptable excipients comprise about 0.1% by weight to about 5% by weight of one or more lubricants based on the weight of the pharmaceutically acceptable unit formulation. In some embodiments, the one or more pharmaceutically acceptable excipients comprise about 0.1% by weight to about 4% by weight of one or more lubricants based on the weight of the pharmaceutically acceptable unit formulation. In some embodiments, the one or more pharmaceutically acceptable excipients comprise about 0.1% by weight to about 3% by weight of one or more lubricants based on the weight of the pharmaceutically acceptable unit formulation. In some embodiments, the one or more pharmaceutically acceptable excipients comprise about 0.1% by weight to about 2% by weight of one or more lubricants based on the weight of the pharmaceutically acceptable unit formulation.

In some embodiments, the one or more pharmaceutically acceptable excipients comprise about 0.1% by weight to about 1.9% by weight of one or more lubricants based on the weight of the pharmaceutically acceptable unit formulation. In some embodiments, the one or more pharmaceutically acceptable excipients comprise about 0.1% by weight to about 1.8% by weight of one or more lubricants based on the weight of the pharmaceutically acceptable unit formulation. In some embodiments, the one or more pharmaceutically acceptable excipients comprise about 0.1% by weight to about 1.7% by weight of one or more lubricants based on the weight of the pharmaceutically acceptable unit formulation. In some embodiments, the one or more pharmaceutically acceptable excipients comprise about 0.1% by weight to about 1.6% by weight of one or more lubricants based on the weight of the pharmaceutically acceptable unit formulation. In some embodiments, the one or more pharmaceutically acceptable excipients comprise about 0.1% by weight to about 1.5% by weight of one or more lubricants based on the weight of the pharmaceutically acceptable unit formulation. In some embodiments, the one or more pharmaceutically acceptable excipients comprise about 0.1% by weight to about 1.4% by weight of one or more lubricants based on the weight of the pharmaceutically acceptable unit formulation. In some embodiments, the one or more pharmaceutically acceptable excipients comprise about 0.1% by weight to about 1.3% by weight of one or more lubricants based on the weight of the pharmaceutically acceptable unit formulation. In some embodiments, the one or more pharmaceutically acceptable excipients comprise about 0.1% by weight to about 1.2% by weight of one or more lubricants based on the weight of the pharmaceutically acceptable unit formulation. In some embodiments, the one or more pharmaceutically acceptable excipients comprise about 0.1% by weight to about 1.1% by weight of one or more lubricants based on the weight of the pharmaceutically acceptable unit formulation. In some embodiments, the one or more pharmaceutically acceptable excipients comprise about 0.1% by weight to about 1.0% by weight of one or more lubricants based on the weight of the pharmaceutically acceptable unit formulation. In some embodiments, the one or more pharmaceutically acceptable excipients comprise about 0.1% by weight to about 0.9% by weight of one or more lubricants based on the weight of the pharmaceutically acceptable unit formulation. In some embodiments, the one or more pharmaceutically acceptable excipients comprise about 0.1% by weight to about 0.8% by weight of one or more lubricants based on the weight of the pharmaceutically acceptable unit formulation. In some embodiments, the one or more pharmaceutically acceptable excipients comprise about 0.1% by weight to about 0.7% by weight of one or more lubricants based on the weight of the pharmaceutically acceptable unit formulation. In some embodiments, the one or more pharmaceutically acceptable excipients comprise about 0.1% by weight to about 0.6% by weight of one or more lubricants based on the weight of the pharmaceutically acceptable unit formulation. In some embodiments, the one or more pharmaceutically acceptable excipients comprise about 0.1% by weight to about 0.5% by weight of one or more lubricants based on the weight of the pharmaceutically acceptable unit formulation. In some embodiments, the one or more pharmaceutically acceptable excipients comprise about 0.1% by weight to about 0.4% by weight of one or more lubricants based on the weight of the pharmaceutically acceptable unit formulation. In some embodiments, the one or more pharmaceutically acceptable excipients comprise about 0.1% by weight to about 0.3% by weight of one or more lubricants based on the weight of the pharmaceutically acceptable unit formulation. In some embodiments, the one or more pharmaceutically acceptable excipients comprise about 0.1% by weight to about 0.2% by weight of one or more lubricants based on the weight of the pharmaceutically acceptable unit formulation.

In some embodiments, the one or more pharmaceutically acceptable excipients comprise about 0.1% by weight of one or more lubricants based on the weight of the pharmaceutically acceptable unit formulation. In some embodiments, the one or more pharmaceutically acceptable excipients comprise about 0.2% by weight of one or more lubricants based on the weight of the pharmaceutically acceptable unit formulation. In some embodiments, the one or more pharmaceutically acceptable excipients comprise about 0.3% by weight of one or more lubricants based on the weight of the pharmaceutically acceptable unit formulation. In some embodiments, the one or more pharmaceutically acceptable excipients comprise about 0.4% by weight of one or more lubricants based on the weight of the pharmaceutically acceptable unit formulation. In some embodiments, the one or more pharmaceutically acceptable excipients comprise about 0.5% by weight of one or more lubricants based on the weight of the pharmaceutically acceptable unit formulation. In some embodiments, the one or more pharmaceutically acceptable excipients comprise about 0.6% by weight of one or more lubricants based on the weight of the pharmaceutically acceptable unit formulation. In some embodiments, the one or more pharmaceutically acceptable excipients comprise about 0.7% by weight of one or more lubricants based on the weight of the pharmaceutically acceptable unit formulation. In some embodiments, the one or more pharmaceutically acceptable excipients comprise about 0.8% by weight of one or more lubricants based on the weight of the pharmaceutically acceptable unit formulation. In some embodiments, the one or more pharmaceutically acceptable excipients comprise about 0.9% by weight of one or more lubricants based on the weight of the pharmaceutically acceptable unit formulation. In some embodiments, the one or more pharmaceutically acceptable excipients comprise about 1.0% by weight of one or more lubricants based on the weight of the pharmaceutically acceptable unit formulation.

In some embodiments, the pharmaceutically acceptable unit formulation comprises: (a) about 1% by weight to about 30% by weight of the compound of Formula (I) based on the weight of the pharmaceutically acceptable unit formulation; (b) about 20% by weight to about 90% by weight of one or more fillers based on the weight of the pharmaceutically acceptable unit formulation; (c) about 1% by weight to about 20% by weight of one or more disintegrants based on the weight of the pharmaceutically acceptable unit formulation; and (d) about 0.1% by weight to about 10% by weight of one or more lubricants based on the weight of the pharmaceutically acceptable unit formulation.

In some embodiments, the pharmaceutically acceptable unit formulation consists essentially of: (a) about 1% by weight to about 30% by weight of the compound of Formula (I) based on the weight of the pharmaceutically acceptable unit formulation; (b) about 20% by weight to about 90% by weight of one or more fillers based on the weight of the pharmaceutically acceptable unit formulation; (c) about 1% by weight to about 20% by weight of one or more disintegrants based on the weight of the pharmaceutically acceptable unit formulation; and (d) about 0.1% by weight to about 10% by weight of one or more lubricants based on the weight of the pharmaceutically acceptable unit formulation.

In some embodiments, the pharmaceutically acceptable unit formulation comprises (a) about 5% by weight to about 25% by weight of the crystalline anhydrous form of the compound of Formula (I) based on the weight of the pharmaceutically acceptable unit formulation; (b) about 60% by weight to about 90% by weight of one or more fillers based on the weight of the pharmaceutically acceptable unit formulation; (c) about 1% by weight to about 15% by weight of one or more disintegrants based on the weight of the pharmaceutically acceptable unit formulation; and (d) about 0.1% by weight to about 4% by weight of one or more lubricants based on the weight of the pharmaceutically acceptable unit formulation.

In some embodiments, the pharmaceutically acceptable unit formulation consists essentially of: (a) about 5% by weight to about 25% by weight of the crystalline anhydrous form of the compound of Formula (I) based on the weight of the pharmaceutically acceptable unit formulation; (b) about 60% by weight to about 90% by weight of one or more fillers based on the weight of the pharmaceutically acceptable unit formulation; (c) about 1% by weight to about 15% by weight of one or more disintegrants based on the weight of the pharmaceutically acceptable unit formulation; and (d) about 0.1% by weight to about 4% by weight of one or more lubricants based on the weight of the pharmaceutically acceptable unit formulation.

In some embodiments, the pharmaceutically acceptable unit formulation comprises (a) about 10% by weight to about 30% by weight of the crystalline anhydrous form of the compound of Formula (I) based on the weight of the pharmaceutically acceptable unit formulation; (b) about 70% by weight to about 90% by weight of one or more fillers based on the weight of the pharmaceutically acceptable unit formulation; (c) about 1% by weight to about 10% by weight of one or more disintegrants based on the weight of the pharmaceutically acceptable unit formulation; and (d) about 0.1% by weight to about 3% by weight of one or more lubricants based on the weight of the pharmaceutically acceptable unit formulation.

In some embodiments, the pharmaceutically acceptable unit formulation consists essentially of: (a) about 10% by weight to about 30% by weight of the crystalline anhydrous form of the compound of Formula (I) based on the weight of the pharmaceutically acceptable unit formulation; (b) about 70% by weight to about 90% by weight of one or more fillers based on the weight of the pharmaceutically acceptable unit formulation; (c) about 1% by weight to about 10% by weight of one or more disintegrants based on the weight of the pharmaceutically acceptable unit formulation; and (d) about 0.1% by weight to about 3% by weight of one or more lubricants based on the weight of the pharmaceutically acceptable unit formulation.

In some embodiments, the one or more pharmaceutically acceptable excipients is one or more fillers selected from the group consisting of calcium phosphate, dicalcium phosphate, dicalcium phosphate dihydrate, calcium sulfate, calcium sulfate dihydrate, starch, calcium carbonate, magnesium carbonate, magnesium oxide, kaolin (natural hydrated aluminum silicate), sodium chloride, partially gelatinized starch, anhydrous lactose, lactose monohydrate, lactose dihydrate, trehalose dihydrate, spray dried lactose, sucrose, dextrose, dextrates, dextrin, cellulose, microcrystalline cellulose, silicified microcrystalline cellulose, powdered cellulose, partially depolymerized cellulose, mannitol, granulated mannitol, spray dried mannitol, maltodextrin, maltitol, confectioner's sugar, compressible sugar, sorbitol, starch and talc. In some embodiments, the one or more fillers is lactose monohydrate.

In some embodiments, the one or more disintegrants is one or more disintegrants selected from the group consisting of sodium starch glycolate, pregelatinized starch, clay, cellulose, alginic acid, alginate gum, polyvinylpyrrolidone, cross-linked polyvinylpyrrolidone, cross-linked calcium carboxymethylcellulose, cross-linked sodium carboxymethylcellulose, sodium croscarmellose, sodium carmellose, low substituted hydroxypropyl cellulose, low substituted hydroxypropyl cellulose sodium, guar gum, magnesium aluminum silicate, polacrilin potassium, powdered cellulose, sodium alginate and soy polysaccharides. In some embodiments, the one or more disintegrants is cross-linked polyvinylpyrrolidone (also referred to as crospovidone).

In some embodiments, the one or more lubricants is one or more lubricants selected from the group consisting of colloidal silica, magnesium trisilicate, talc, magnesium carbonate, magnesium oxide, glyceryl behaptate, mono, di and tri glyceryl behenate, bees wax, behenoyl polyoxyl-8 glycerides, hydrogenated vegetable oil, polyethylene glycol, ethylene oxide polymer, copolymer comprising poly(ethylene oxide) and poly(propylene oxide) (such as poloxomer 188), copolymer comprising polypropylene glycol and polyethylene glycol (such as poloxomer 407), sodium lauryl sulfate, magnesium stearate, aluminum stearate, calcium stearate, sodium stearyl fumarate, stearic acid, magnesium lauryl stearate, mixtures of magnesium stearate with sodium lauryl sulfate. In some embodiments, the one or more lubricants is magnesium stearate.

In some embodiments, the one or more disintegrants is selected from the group consisting of cross-linked polyvinylpyrrolidone, croscarmellose sodium, and sodium starch glycolate; and the one or more lubricants is selected from the group consisting of sodium stearyl fumarate, stearic acid, talc, calcium stearate, magnesium stearate, solid polyethylene glycols, and sodium lauryl sulfate. In some embodiments, the pharmaceutically acceptable unit formulation comprises cross-linked polyvinylpyrrolidone and magnesium stearate. In some embodiments, the one or more pharmaceutically acceptable excipients is lactose monohydrate and the pharmaceutically acceptable unit formulation further comprises cross-linked polyvinylpyrrolidone and magnesium stearate.

In some embodiments, the pharmaceutically acceptable unit formulation is for oral administration.

In some embodiments, the pharmaceutically acceptable unit formulation is a solid dosage form.

In some embodiments, the pharmaceutically acceptable unit formulation is a tablet or capsule. In some embodiments, the pharmaceutically acceptable unit formulation is a tablet. In some embodiments, the pharmaceutically acceptable unit formulation is a capsule. In some embodiments, the pharmaceutically acceptable unit formulation is a sachet. In some embodiments, the pharmaceutically acceptable unit formulation is a powder in a packet.

In some embodiments, the pharmaceutically acceptable unit formulation comprises about 1 mg to about 40 mg of the crystalline anhydrous form of the compound of Formula (I). In some embodiments, the pharmaceutically acceptable unit formulation comprises about 5 mg to about 35 mg of the crystalline anhydrous form of the compound of Formula (I). In some embodiments, the pharmaceutically acceptable unit formulation comprises about 10 mg to about 35 mg of the crystalline anhydrous form of the compound of Formula (I). In some embodiments, the pharmaceutically acceptable unit formulation comprises about 0.5 mg to about 5 mg, about 6 mg to about 14 mg, about 10 mg to about 18 mg, about 16 mg to about 24 mg, or about 26 mg to about 34 mg of the crystalline anhydrous form of the compound of Formula (I). In some embodiments, the pharmaceutically acceptable unit formulation comprises about 1 mg to about 3 mg, about 8 mg to about 12 mg, about 12 mg to about 16 mg, about 18 mg to about 22 mg, or about 28 mg to about 32 mg of the crystalline anhydrous form of the compound of Formula (I). In some embodiments, the pharmaceutically acceptable unit formulation comprises about 2 mg, about 10 mg, about 14 mg, about 20 mg, or about 30 mg of the crystalline anhydrous form of the compound of Formula (I). In some embodiments, the crystalline anhydrous form of the compound of Formula (I) is present in an amount of about 2 mg. In some embodiments, the crystalline anhydrous form of the compound of Formula (I) is present in an amount of about 10 mg. In some embodiments, the crystalline anhydrous form of the compound of Formula (I) is present in an amount of about 14 mg. In some embodiments, the crystalline anhydrous form of the compound of Formula (I) is present in an amount of about 20 mg. In some embodiments, the crystalline anhydrous form of the compound of Formula (I) is present in an amount of about 30 mg.

In some embodiments, the pharmaceutically acceptable unit formulation consists essentially of about 1 mg to about 40 mg of the crystalline anhydrous form of the compound of Formula (I). In some embodiments, the pharmaceutically acceptable unit formulation consists essentially of about 5 mg to about 35 mg of the crystalline anhydrous form of the compound of Formula (I). In some embodiments, the pharmaceutically acceptable unit formulation consists essentially of about 10 mg to about 35 mg of the crystalline anhydrous form of the compound of Formula (I). In some embodiments, the pharmaceutically acceptable unit formulation consists essentially of about 0.5 mg to about 5 mg, about 6 mg to about 14 mg, about 10 mg to about 18 mg, about 16 mg to about 24 mg, or about 26 mg to about 34 mg of the crystalline anhydrous form of the compound of Formula (I). In some embodiments, the pharmaceutically acceptable unit formulation consists essentially of about 1 mg to about 3 mg, about 8 mg to about 12 mg, about 12 mg to about 16 mg, about 18 mg to about 22 mg, or about 28 mg to about 32 mg of the crystalline anhydrous form of the compound of Formula (I). In some embodiments, the pharmaceutically acceptable unit formulation consists essentially of about 2 mg, about 10 mg, about 14 mg, about 20 mg, or about 30 mg of the crystalline anhydrous form of the compound of Formula (I). In some embodiments, the crystalline anhydrous form of the compound of Formula (I) is present in an amount of about 2 mg. In some embodiments, the crystalline anhydrous form of the compound of Formula (I) is present in an amount of about 10 mg. In some embodiments, the crystalline anhydrous form of the compound of Formula (I) is present in an amount of about 14 mg. In some embodiments, the crystalline anhydrous form of the compound of Formula (I) is present in an amount of about 20 mg. In some embodiments, the crystalline anhydrous form of the compound of Formula (I) is present in an amount of about 30 mg.

In some embodiments, the pharmaceutically acceptable unit formulation has an acceptance value of less than about 15 as determined by USP Uniformity of Dosage Unit <905>. In some embodiments, the pharmaceutically acceptable unit formulation has a maximum acceptance value of equal to or less than about 15 as determined by USP Uniformity of Dosage Unit <905>.

In some embodiments, the uniformity of the pharmaceutically acceptable formulation represents the degree of uniformity in the amount of the compound of Formula (I) in the pharmaceutically acceptable formulation.

In some embodiments, the uniformity of the oral dosage form represents the degree of uniformity in the amount of the compound of Formula (I) in the oral dosage form.

In some embodiments, the uniformity of the pharmaceutically acceptable capsule represents the degree of uniformity in the amount of the compound of Formula (I) in the pharmaceutically acceptable capsule.

Also provided herein, in some embodiments, are oral dosage forms comprising the crystalline anhydrous form of a compound of Formula (I):

Formula (I)

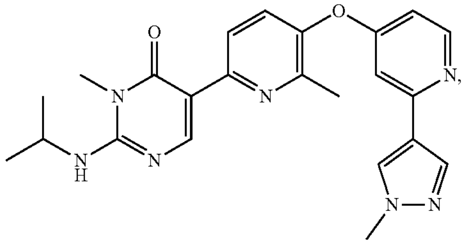

, and one or more pharmaceutically acceptable excipients.

Also provided herein, in some embodiments, are oral dosage forms consisting essentially of the crystalline anhydrous form of a compound of Formula (I):

Formula (I)

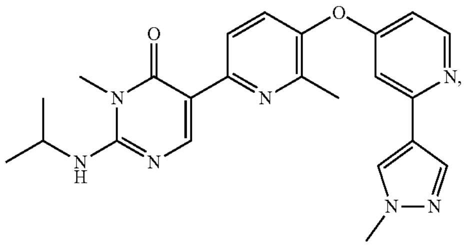

and one or more pharmaceutically acceptable excipients.

In some embodiments, the crystalline anhydrous form of the compound represented by Formula (I) has an XRPD pattern comprising a peak, in terms of 2-theta, at about 11.4° as measured by CuKα radiation.

In some embodiments, the crystalline anhydrous form of the compound represented by Formula (I) has an XRPD pattern comprising two or more of the characteristic peaks, in terms of 2-theta, at about 11.4°, about 14.7°, about 17.1°, and about 21.3° as measured by CuKα radiation.

In some embodiments, the crystalline anhydrous form of the compound represented by Formula (I) has an XRPD pattern comprising two or more of the characteristic peaks, in terms of 2-theta, at about 11.4°, about 14.7°, about 17.10, about 20.10, about 21.3°, and about 29.10 as measured by CuKα radiation.

In some embodiments, the crystalline anhydrous form of the compound represented by Formula (I) has an XRPD pattern comprising two or more of the characteristic peaks, in terms of 2-theta, at about 10.2°, about 10.5°, about 11.4°, about 14.7°, about 17.1°, about 20.10, about 21.3°, and about 29.10 as measured by CuKα radiation.

In some embodiments, the one or more pharmaceutically acceptable excipients is a filler. For example, the one or more pharmaceutically acceptable excipients is lactose, such as lactose monohydrate.

In some embodiments, the oral dosage forms further comprise one or more disintegrants, one or more lubricants, or a combination thereof. For example, in some embodiments, the oral dosage forms further comprise one or more disintegrants. In some embodiments, the oral dosage forms further comprise one or more lubricants.

Also provided herein, in some embodiments, is an oral dosage form comprising:

(a) about 1% by weight to about 70% by weight, based on the total weight of the oral dosage form, of a crystalline anhydrous form of a compound of Formula (I):

Formula (I)

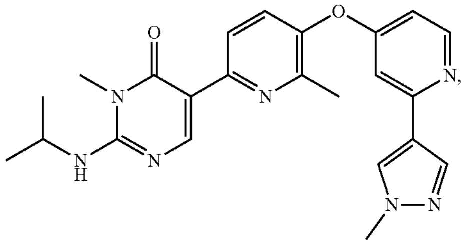

and one or more pharmaceutically acceptable excipients, wherein the one or more pharmaceutically acceptable excipients comprise:

(b) about 20% by weight to about 97% by weight of one or more fillers based on the total weight of the oral dosage form;

(c) about 1% by weight to about 20% by weight of one or more disintegrants based on the total weight of the oral dosage form; and (d) about 0.1% by weight to about 10% by weight of one or more lubricants based on the total weight of the oral dosage form.

Also provided herein, in some embodiments, is an oral dosage form comprising:

(a) about 1% by weight to about 30% by weight of a crystalline anhydrous form of a compound of Formula (I) based on the total weight of the oral dosage form;

(b) about 20% by weight to about 90% by weight of one or more fillers based on the total weight of the oral dosage form;

(c) about 1% by weight to about 20% by weight of one or more disintegrants based on the total weight of the oral dosage form; and (d) about 0.1% by weight to about 10% by weight of one or more lubricants based on the total weight of the oral dosage form.

Also provided herein, in some embodiments, is an oral dosage form consisting essentially of:

(a) about 1% by weight to about 70% by weight, based on the total weight of the oral dosage form, of a crystalline anhydrous form of a compound of Formula (I):

Formula (I)

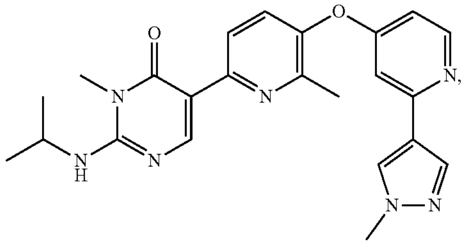

and one or more pharmaceutically acceptable excipients, wherein the one or more pharmaceutically acceptable excipients comprise:

(b) about 20% by weight to about 97% by weight of one or more fillers based on the total weight of the oral dosage form;

(c) about 1% by weight to about 20% by weight of one or more disintegrants based on the total weight of the oral dosage form; and (d) about 0.1% by weight to about 10% by weight of one or more lubricants based on the total weight of the oral dosage form.

Also provided herein, in some embodiments, is an oral dosage form consisting essentially of:

(a) about 1% by weight to about 30% by weight of a crystalline anhydrous form of a compound of Formula (I) based on the total weight of the oral dosage form;

(b) about 20% by weight to about 90% by weight of one or more fillers based on the total weight of the oral dosage form;

(c) about 1% by weight to about 20% by weight of one or more disintegrants based on the total weight of the oral dosage form; and (d) about 0.1% by weight to about 10% by weight of one or more lubricants based on the total weight of the oral dosage form.

In some embodiments, the oral dosage form comprising the crystalline anhydrous form of the compound represented by Formula (I), has no more than about 10 mol %, no more than about 5 mol %, no more than about 3 mol %, or no more than about 1 mol % of other solid-state forms of the compound represented by Formula (I). In some embodiments, the oral dosage form comprising the crystalline anhydrous forms of the compound represented by Formula (I), has no more than about 10 mol % of other solid-state forms of the compound represented by Formula (I). In some embodiments, the oral dosage form comprising the crystalline anhydrous forms of the compound represented by Formula (I), has no more than about 9 mol % of other solid-state forms of the compound represented by Formula (I). In some embodiments, the oral dosage form comprising the crystalline anhydrous forms of the compound represented by Formula (I), has no more than about 8 mol % of other solid-state forms of the compound represented by Formula (I). In some embodiments, the oral dosage form comprising the crystalline anhydrous forms of the compound represented by Formula (I), has no more than about 7 mol % of other solid-state forms of the compound represented by Formula (I). In some embodiments, the oral dosage form comprising the crystalline anhydrous forms of the compound represented by Formula (I), has no more than about 6 mol % of other solid-state forms of the compound represented by Formula (I). In some embodiments, the oral dosage form comprising the crystalline anhydrous forms of the compound represented by Formula (I), has no more than about 5 mol % of other solid-state forms of the compound represented by Formula (I). In some embodiments, the oral dosage form comprising the crystalline anhydrous forms of the compound represented by Formula (I), has no more than about 4 mol % of other solid-state forms of the compound represented by Formula (I). In some embodiments, the oral dosage form comprising the crystalline anhydrous forms of the compound represented by Formula (I), has no more than about 3 mol % of other solid-state forms of the compound represented by Formula (I). In some embodiments, the oral dosage form comprising the crystalline anhydrous forms of the compound represented by Formula (I), has no more than about 2 mol % of other solid-state forms of the compound represented by Formula (I). In some embodiments, the oral dosage form comprising the crystalline anhydrous forms of the compound represented by Formula (I), has no more than about 1 mol % of other solid-state forms of the compound represented by Formula (I).

In some embodiments, the oral dosage form comprises about 1% by weight to about 60% by weight, based on the total weight of the oral dosage form, of a crystalline anhydrous form of a compound of Formula (I). In some embodiments, the oral dosage form comprises about 1% by weight to about 50% by weight, based on the total weight of the oral dosage form, of a crystalline anhydrous form of a compound of Formula (I). In some embodiments, the oral dosage form comprises about 1% by weight to about 40% by weight, based on the total weight of the oral dosage form, of a crystalline anhydrous form of a compound of Formula (I). In some embodiments, the oral dosage form comprises about 1% by weight to about 30% by weight, based on the total weight of the oral dosage form, of a crystalline anhydrous form of a compound of Formula (I). In some embodiments, the oral dosage form comprises about 1% by weight to about 20% by weight, based on the total weight of the oral dosage form, of a crystalline anhydrous form of a compound of Formula (I).

In some embodiments, the oral dosage form consists essentially of about 1% by weight to about 60% by weight, based on the total weight of the oral dosage form, of a crystalline anhydrous form of a compound of Formula (I). In some embodiments, the oral dosage form consists essentially of about 1% by weight to about 50% by weight, based on the total weight of the oral dosage form, of a crystalline anhydrous form of a compound of Formula (I). In some embodiments, the oral dosage form consists essentially of about 1% by weight to about 40% by weight, based on the total weight of the oral dosage form, of a crystalline anhydrous form of a compound of Formula (I). In some embodiments, the oral dosage form consists essentially of about 1% by weight to about 30% by weight, based on the total weight of the oral dosage form, of a crystalline anhydrous form of a compound of Formula (I). In some embodiments, the oral dosage form consists essentially of about 1% by weight to about 20% by weight, based on the total weight of the oral dosage form, of a crystalline anhydrous form of a compound of Formula of:

In some embodiments, the oral dosage form comprises about 1% by weight to about 70% by weight of crystalline anhydrous form of the compound of Formula (I) based on the total weight of the oral dosage form. In some embodiments, the oral dosage form comprises about 1% by weight to about 65% by weight of crystalline anhydrous form of the compound of Formula (I) based on the total weight of the oral dosage form. In some embodiments, the oral dosage form comprises about 1% by weight to about 60% by weight of crystalline anhydrous form of the compound of Formula (I) based on the total weight of the oral dosage form. In some embodiments, the oral dosage form comprises about 1% by weight to about 55% by weight of crystalline anhydrous form of the compound of Formula (I) based on the total weight of the oral dosage form. In some embodiments, the oral dosage form comprises about 1% by weight to about 50% by weight of crystalline anhydrous form of the compound of Formula (I) based on the total weight of the oral dosage form. In some embodiments, the oral dosage form comprises about 1% by weight to about 45% by weight of crystalline anhydrous form of the compound of Formula (I) based on the total weight of the oral dosage form. In some embodiments, the oral dosage form comprises about 1% by weight to about 40% by weight of crystalline anhydrous form of the compound of Formula (I) based on the total weight of the oral dosage form. In some embodiments, the oral dosage form comprises about 1% by weight to about 35% by weight of crystalline anhydrous form of the compound of Formula (I) based on the total weight of the oral dosage form. In some embodiments, the oral dosage form comprises about 1% by weight to about 30% by weight of the crystalline anhydrous form of the compound of Formula (I) based on the total weight of the oral dosage form. In some embodiments, the oral dosage form comprises about 1% by weight to about 25% by weight of the crystalline anhydrous form of the compound of Formula (I) based on the total weight of the oral dosage form. In some embodiments, the oral dosage form comprises about 1% by weight to about 20% by weight of the crystalline anhydrous form of the compound of Formula (I) based on the total weight of the oral dosage form. In some embodiments, the oral dosage form comprises about 1% by weight to about 15% by weight of the crystalline anhydrous form of the compound of Formula (I) based on the total weight of the oral dosage form. In some embodiments, the oral dosage form comprises about 1% by weight to about 10% by weight of the crystalline anhydrous form of the compound of Formula (I) based on the total weight of the oral dosage form.

In some embodiments, the oral dosage form consists essentially of about 1% by weight to about 70% by weight of crystalline anhydrous form of the compound of Formula (I) based on the total weight of the oral dosage form. In some embodiments, the oral dosage form consists essentially of about 1% by weight to about 65% by weight of crystalline anhydrous form of the compound of Formula (I) based on the total weight of the oral dosage form. In some embodiments, the oral dosage form consists essentially of about 1% by weight to about 60% by weight of crystalline anhydrous form of the compound of Formula (I) based on the total weight of the oral dosage form. In some embodiments, the oral dosage form consists essentially of about 1% by weight to about 55% by weight of crystalline anhydrous form of the compound of Formula (I) based on the total weight of the oral dosage form. In some embodiments, the oral dosage form consists essentially of about 1% by weight to about 50% by weight of crystalline anhydrous form of the compound of Formula (I) based on the total weight of the oral dosage form. In some embodiments, the oral dosage form consists essentially of about 1% by weight to about 45% by weight of crystalline anhydrous form of the compound of Formula (I) based on the total weight of the oral dosage form. In some embodiments, the oral dosage form consists essentially of about 1% by weight to about 40% by weight of crystalline anhydrous form of the compound of Formula (I) based on the total weight of the oral dosage form. In some embodiments, the oral dosage form consists essentially of about 1% by weight to about 35% by weight of crystalline anhydrous form of the compound of Formula (I) based on the total weight of the oral dosage form. In some embodiments, the oral dosage form consists essentially of about 1% by weight to about 30% by weight of the crystalline anhydrous form of the compound of Formula (I) based on the total weight of the oral dosage form. In some embodiments, the oral dosage form consists essentially of about 1% by weight to about 25% by weight of the crystalline anhydrous form of the compound of Formula (I) based on the total weight of the oral dosage form. In some embodiments, the oral dosage form consists essentially of about 1% by weight to about 20% by weight of the crystalline anhydrous form of the compound of Formula (I) based on the total weight of the oral dosage form. In some embodiments, the oral dosage form consists essentially of about 1% by weight to about 15% by weight of the crystalline anhydrous form of the compound of Formula (I) based on the total weight of the oral dosage form. In some embodiments, the oral dosage form consists essentially of about 1% by weight to about 10% by weight of the crystalline anhydrous form of the compound of Formula (I) based on the total weight of the oral dosage form.

In some embodiments, the oral dosage form comprises about 5% by weight to about 30% by weight of the crystalline anhydrous form of the compound of Formula (I) based on the total weight of the oral dosage form. In some embodiments, the oral dosage form comprises about 5% by weight to about 25% by weight of the crystalline anhydrous form of the compound of Formula (I) based on the total weight of the oral dosage form. In some embodiments, the oral dosage form comprises about 5% by weight to about 20% by weight of the crystalline anhydrous form of the compound of Formula (I) based on the total weight of the oral dosage form. In some embodiments, the oral dosage form comprises about 5% by weight to about 15% by weight of the crystalline anhydrous form of the compound of Formula (I) based on the total weight of the oral dosage form. In some embodiments, the oral dosage form comprises about 5% by weight to about 10% by weight of the crystalline anhydrous form of the compound of Formula (I) based on the total weight of the oral dosage form.

In some embodiments, the oral dosage form consists essentially of about 5% by weight to about 30% by weight of the crystalline anhydrous form of the compound of Formula (I) based on the total weight of the oral dosage form. In some embodiments, the oral dosage form consists essentially of about 5% by weight to about 25% by weight of the crystalline anhydrous form of the compound of Formula (I) based on the total weight of the oral dosage form. In some embodiments, the oral dosage form consists essentially of about 5% by weight to about 20% by weight of the crystalline anhydrous form of the compound of Formula (I) based on the total weight of the oral dosage form. In some embodiments, the oral dosage form consists essentially of about 5% by weight to about 15% by weight of the crystalline anhydrous form of the compound of Formula (I) based on the total weight of the oral dosage form. In some embodiments, the oral dosage form consists essentially of about 5% by weight to about 10% by weight of the crystalline anhydrous form of the compound of Formula (I) based on the total weight of the oral dosage form.

In some embodiments, the oral dosage form comprises about 10% to about 30% of the compound of Formula (I) based on the total weight of the oral dosage form. In some embodiments, the oral dosage form comprises about 10% to about 25% of the compound of Formula (I) based on the total weight of the oral dosage form. In some embodiments, the oral dosage form comprises about 10% to about 20% of the compound of Formula (I) based on the total weight of the oral dosage form. In some embodiments, the oral dosage form comprises about 10% by weight to about 15% by weight of the crystalline anhydrous form of the compound of Formula (I) based on the total weight of the oral dosage form.

In some embodiments, the oral dosage form consists essentially of about 10% to about 30% of the compound of Formula (I) based on the total weight of the oral dosage form. In some embodiments, the oral dosage form consists essentially of about 10% to about 25% of the compound of Formula (I) based on the total weight of the oral dosage form. In some embodiments, the oral dosage form consists essentially of about 10% to about 20% of the compound of Formula (I) based on the total weight of the oral dosage form. In some embodiments, the oral dosage form consists essentially of about 10% by weight to about 15% by weight of the crystalline anhydrous form of the compound of Formula (I) based on the total weight of the oral dosage form.

In some embodiments, the oral dosage form comprises about 1% by weight to about 30% by weight of the crystalline anhydrous form of the compound of Formula (I) based on the total weight of the oral dosage form. In some embodiments, the oral dosage form comprises about 1% by weight to about 10% by weight of the crystalline anhydrous form of the compound of Formula (I) based on the total weight of the oral dosage form. In some embodiments, the oral dosage form comprises about 10% to about 20% of the compound of Formula (I) based on the total weight of the oral dosage form. In some embodiments, the oral dosage form comprises about 10% by weight to about 15% by weight of the crystalline anhydrous form of the compound of Formula (I) based on the total weight of the oral dosage form.

In some embodiments, the oral dosage form consists essentially of about 1% by weight to about 30% by weight of the crystalline anhydrous form of the compound of Formula (I) based on the total weight of the oral dosage form. In some embodiments, the oral dosage form consists essentially of about 1% by weight to about 10% by weight of the crystalline anhydrous form of the compound of Formula (I) based on the total weight of the oral dosage form. In some embodiments, the oral dosage form consists essentially of about 10% to about 20% of the compound of Formula (I) based on the total weight of the oral dosage form. In some embodiments, the oral dosage form consists essentially of about 10% by weight to about 15% by weight of the crystalline anhydrous form of the compound of Formula (I) based on the total weight of the oral dosage form.

In some embodiments, the one or more pharmaceutically acceptable excipients comprise about 20% by weight to about 90% by weight of one or more fillers based on the total weight of the oral dosage form. In some embodiments, the one or more pharmaceutically acceptable excipients comprise about 20% by weight to about 85% by weight of one or more fillers based on the total weight of the oral dosage form. In some embodiments, the one or more pharmaceutically acceptable excipients comprise about 20% by weight to about 80% by weight of one or more fillers based on the total weight of the oral dosage form. In some embodiments, the one or more pharmaceutically acceptable excipients comprise about 20% by weight to about 75% by weight of one or more fillers based on the total weight of the oral dosage form. In some embodiments, the one or more pharmaceutically acceptable excipients comprise about 20% by weight to about 70% by weight of one or more fillers based on the total weight of the oral dosage form. In some embodiments, the one or more pharmaceutically acceptable excipients comprise about 20% by weight to about 65% by weight of one or more fillers based on the total weight of the oral dosage form. In some embodiments, the one or more pharmaceutically acceptable excipients comprise about 20% by weight to about 60% by weight of one or more fillers based on the total weight of the oral dosage form. In some embodiments, the one or more pharmaceutically acceptable excipients comprise about 20% by weight to about 55% by weight of one or more fillers based on the total weight of the oral dosage form. In some embodiments, the one or more pharmaceutically acceptable excipients comprise about 20% by weight to about 50% by weight of one or more fillers based on the total weight of the oral dosage form. In some embodiments, the one or more pharmaceutically acceptable excipients comprise about 20% by weight to about 45% by weight of one or more fillers based on the total weight of the oral dosage form. In some embodiments, the one or more pharmaceutically acceptable excipients comprise about 20% by weight to about 40% by weight of one or more fillers based on the total weight of the oral dosage form. In some embodiments, the one or more pharmaceutically acceptable excipients comprise about 20% by weight to about 35% by weight of one or more fillers based on the total weight of the oral dosage form. In some embodiments, the one or more pharmaceutically acceptable excipients comprise about 20% by weight to about 30% by weight of one or more fillers based on the total weight of the oral dosage form. In some embodiments, the one or more pharmaceutically acceptable excipients comprise about 20% by weight to about 25% by weight of one or more fillers based on the total weight of the oral dosage form.

In some embodiments, the one or more pharmaceutically acceptable excipients comprise about 30% by weight to about 90% by weight of one or more fillers based on the total weight of the oral dosage form. In some embodiments, the one or more pharmaceutically acceptable excipients comprise about 30% by weight to about 80% by weight of one or more fillers based on the total weight of the oral dosage form. In some embodiments, the one or more pharmaceutically acceptable excipients comprise about 30% by weight to about 70% by weight of one or more fillers based on the total weight of the oral dosage form. In some embodiments, the one or more pharmaceutically acceptable excipients comprise about 30% by weight to about 60% by weight of one or more fillers based on the total weight of the oral dosage form. In some embodiments, the one or more pharmaceutically acceptable excipients comprise about 30% by weight to about 50% by weight of one or more fillers based on the total weight of the oral dosage form. In some embodiments, the one or more pharmaceutically acceptable excipients comprise about 30% by weight to about 40% by weight of one or more fillers based on the total weight of the oral dosage form.

In some embodiments, the one or more pharmaceutically acceptable excipients comprise about 40% by weight to about 90% by weight of one or more fillers based on the total weight of the oral dosage form. In some embodiments, the one or more pharmaceutically acceptable excipients comprise about 40% by weight to about 80% by weight of one or more fillers based on the total weight of the oral dosage form. In some embodiments, the one or more pharmaceutically acceptable excipients comprise about 40% by weight to about 70% by weight of one or more fillers based on the total weight of the oral dosage form. In some embodiments, the one or more pharmaceutically acceptable excipients comprise about 40% by weight to about 60% by weight of one or more fillers based on the total weight of the oral dosage form. In some embodiments, the one or more pharmaceutically acceptable excipients comprise about 40% by weight to about 50% by weight of one or more fillers based on the total weight of the oral dosage form.

In some embodiments, the one or more pharmaceutically acceptable excipients comprise about 50% by weight to about 90% by weight of one or more fillers based on the total weight of the oral dosage form. In some embodiments, the one or more pharmaceutically acceptable excipients comprise about 50% by weight to about 80% by weight of one or more fillers based on the total weight of the oral dosage form. In some embodiments, the one or more pharmaceutically acceptable excipients comprise about 50% by weight to about 70% by weight of one or more fillers based on the total weight of the oral dosage form. In some embodiments, the one or more pharmaceutically acceptable excipients comprise about 50% by weight to about 60% by weight of one or more fillers based on the total weight of the oral dosage form.

In some embodiments, the one or more pharmaceutically acceptable excipients comprise about 60% by weight to about 90% by weight of one or more fillers based on the total weight of the oral dosage form. In some embodiments, the one or more pharmaceutically acceptable excipients comprise about 60% by weight to about 80% by weight of one or more fillers based on the total weight of the oral dosage form. In some embodiments, the one or more pharmaceutically acceptable excipients comprise about 60% by weight to about 70% by weight of one or more fillers based on the total weight of the oral dosage form.

In some embodiments, the one or more pharmaceutically acceptable excipients comprise about 70% by weight to about 90% by weight of one or more fillers based on the total weight of the oral dosage form. In some embodiments, the one or more pharmaceutically acceptable excipients comprise about 70% by weight to about 80% by weight of one or more fillers based on the total weight of the oral dosage form.

In some embodiments, the one or more pharmaceutically acceptable excipients comprise about 80% by weight to about 90% by weight of one or more fillers based on the total weight of the oral dosage form.

In some embodiments, the one or more pharmaceutically acceptable excipients comprise about 1% by weight to about 20% by weight of one or more disintegrants based on the total weight of the oral dosage form. In some embodiments, the one or more pharmaceutically acceptable excipients comprise about 1% by weight to about 15% by weight of one or more disintegrants based on the total weight of the oral dosage form. In some embodiments, the one or more pharmaceutically acceptable excipients comprise about 1% by weight to about 14% by weight of one or more disintegrants based on the total weight of the oral dosage form. In some embodiments, the one or more pharmaceutically acceptable excipients comprise about 1% by weight to about 13% by weight of one or more disintegrants based on the total weight of the oral dosage form. In some embodiments, the one or more pharmaceutically acceptable excipients comprise about 1% by weight to about 12% by weight of one or more disintegrants based on the total weight of the oral dosage form. In some embodiments, the one or more pharmaceutically acceptable excipients comprise about 1% by weight to about 11% by weight of one or more disintegrants based on the total weight of the oral dosage form. In some embodiments, the one or more pharmaceutically acceptable excipients comprise about 1% by weight to about 10% by weight of one or more disintegrants based on the total weight of the oral dosage form. In some embodiments, the one or more pharmaceutically acceptable excipients comprise about 1% by weight to about 9% by weight of one or more disintegrants based on the total weight of the oral dosage form. In some embodiments, the one or more pharmaceutically acceptable excipients comprise about 1% by weight to about 8% by weight of one or more disintegrants based on the total weight of the oral dosage form. In some embodiments, the one or more pharmaceutically acceptable excipients comprise about 1% by weight to about 7% by weight of one or more disintegrants based on the total weight of the oral dosage form. In some embodiments, the one or more pharmaceutically acceptable excipients comprise about 1% by weight to about 6% by weight of one or more disintegrants based on the total weight of the oral dosage form. In some embodiments, the one or more pharmaceutically acceptable excipients comprise about 1% by weight to about 5% by weight of one or more disintegrants based on the total weight of the oral dosage form. In some embodiments, the one or more pharmaceutically acceptable excipients comprise about 1% by weight to about 4% by weight of one or more disintegrants based on the total weight of the oral dosage form. In some embodiments, the one or more pharmaceutically acceptable excipients comprise about 1% by weight to about 3% by weight of one or more disintegrants based on the total weight of the oral dosage form.

In some embodiments, the one or more pharmaceutically acceptable excipients comprise about 1% by weight of one or more disintegrants based on the total weight of the oral dosage form. In some embodiments, the one or more pharmaceutically acceptable excipients comprise about 2% by weight of one or more disintegrants based on the total weight of the oral dosage form. In some embodiments, the one or more pharmaceutically acceptable excipients comprise about 3% by weight of one or more disintegrants based on the total weight of the oral dosage form. In some embodiments, the one or more pharmaceutically acceptable excipients comprise about 4% by weight of one or more disintegrants based on the total weight of the oral dosage form. In some embodiments, the one or more pharmaceutically acceptable excipients comprise about 5% by weight of one or more disintegrants based on the total weight of the oral dosage form. In some embodiments, the one or more pharmaceutically acceptable excipients comprise about 6% by weight of one or more disintegrants based on the total weight of the oral dosage form. In some embodiments, the one or more pharmaceutically acceptable excipients comprise about 7% by weight of one or more disintegrants based on the total weight of the oral dosage form. In some embodiments, the one or more pharmaceutically acceptable excipients comprise about 8% by weight of one or more disintegrants based on the total weight of the oral dosage form. In some embodiments, the one or more pharmaceutically acceptable excipients comprise about 9% by weight of one or more disintegrants based on the total weight of the oral dosage form. In some embodiments, the one or more pharmaceutically acceptable excipients comprise about 10% by weight of one or more disintegrants based on the total weight of the oral dosage form. In some embodiments, the one or more pharmaceutically acceptable excipients comprise about 11% by weight of one or more disintegrants based on the total weight of the oral dosage form. In some embodiments, the one or more pharmaceutically acceptable excipients comprise about 12% by weight of one or more disintegrants based on the total weight of the oral dosage form. In some embodiments, the one or more pharmaceutically acceptable excipients comprise about 13% by weight of one or more disintegrants based on the total weight of the oral dosage form. In some embodiments, the one or more pharmaceutically acceptable excipients comprise about 14% by weight of one or more disintegrants based on the total weight of the oral dosage form. In some embodiments, the one or more pharmaceutically acceptable excipients comprise about 15% by weight of one or more disintegrants based on the total weight of the oral dosage form.

In some embodiments, the one or more pharmaceutically acceptable excipients comprise about 0.1% by weight to about 10% by weight of one or more lubricants based on the total weight of the oral dosage form. In some embodiments, the one or more pharmaceutically acceptable excipients comprise about 0.1% by weight to about 9% by weight of one or more lubricants based on the total weight of the oral dosage form. In some embodiments, the one or more pharmaceutically acceptable excipients comprise about 0.1% by weight to about 8% by weight of one or more lubricants based on the total weight of the oral dosage form. In some embodiments, the one or more pharmaceutically acceptable excipients comprise about 0.1% by weight to about 7% by weight of one or more lubricants based on the total weight of the oral dosage form. In some embodiments, the one or more pharmaceutically acceptable excipients comprise about 0.1% by weight to about 6% by weight of one or more lubricants based on the total weight of the oral dosage form. In some embodiments, the one or more pharmaceutically acceptable excipients comprise about 0.1% by weight to about 5% by weight of one or more lubricants based on the total weight of the oral dosage form. In some embodiments, the one or more pharmaceutically acceptable excipients comprise about 0.1% by weight to about 4% by weight of one or more lubricants based on the total weight of the oral dosage form. In some embodiments, the one or more pharmaceutically acceptable excipients comprise about 0.1% by weight to about 3% by weight of one or more lubricants based on the total weight of the oral dosage form. In some embodiments, the one or more pharmaceutically acceptable excipients comprise about 0.1% by weight to about 2% by weight of one or more lubricants based on the total weight of the oral dosage form.

In some embodiments, the one or more pharmaceutically acceptable excipients comprise about 0.1% by weight to about 1.9% by weight of one or more lubricants based on the total weight of the oral dosage form. In some embodiments, the one or more pharmaceutically acceptable excipients comprise about 0.1% by weight to about 1.8% by weight of one or more lubricants based on the total weight of the oral dosage form. In some embodiments, the one or more pharmaceutically acceptable excipients comprise about 0.1% by weight to about 1.7% by weight of one or more lubricants based on the total weight of the oral dosage form. In some embodiments, the one or more pharmaceutically acceptable excipients comprise about 0.1% by weight to about 1.6% by weight of one or more lubricants based on the total weight of the oral dosage form. In some embodiments, the one or more pharmaceutically acceptable excipients comprise about 0.1% by weight to about 1.5% by weight of one or more lubricants based on the total weight of the oral dosage form. In some embodiments, the one or more pharmaceutically acceptable excipients comprise about 0.1% by weight to about 1.4% by weight of one or more lubricants based on the total weight of the oral dosage form. In some embodiments, the one or more pharmaceutically acceptable excipients comprise about 0.1% by weight to about 1.3% by weight of one or more lubricants based on the total weight of the oral dosage form. In some embodiments, the one or more pharmaceutically acceptable excipients comprise about 0.1% by weight to about 1.2% by weight of one or more lubricants based on the total weight of the oral dosage form. In some embodiments, the one or more pharmaceutically acceptable excipients comprise about 0.1% by weight to about 1.1% by weight of one or more lubricants based on the total weight of the oral dosage form. In some embodiments, the one or more pharmaceutically acceptable excipients comprise about 0.1% by weight to about 1.0% by weight of one or more lubricants based on the total weight of the oral dosage form. In some embodiments, the one or more pharmaceutically acceptable excipients comprise about 0.1% by weight to about 0.9% by weight of one or more lubricants based on the total weight of the oral dosage form. In some embodiments, the one or more pharmaceutically acceptable excipients comprise about 0.1% by weight to about 0.8% by weight of one or more lubricants based on the total weight of the oral dosage form. In some embodiments, the one or more pharmaceutically acceptable excipients comprise about 0.1% by weight to about 0.7% by weight of one or more lubricants based on the total weight of the oral dosage form. In some embodiments, the one or more pharmaceutically acceptable excipients comprise about 0.1% by weight to about 0.6% by weight of one or more lubricants based on the total weight of the oral dosage form. In some embodiments, the one or more pharmaceutically acceptable excipients comprise about 0.1% by weight to about 0.5% by weight of one or more lubricants based on the total weight of the oral dosage form. In some embodiments, the one or more pharmaceutically acceptable excipients comprise about 0.1% by weight to about 0.4% by weight of one or more lubricants based on the total weight of the oral dosage form. In some embodiments, the one or more pharmaceutically acceptable excipients comprise about 0.1% by weight to about 0.3% by weight of one or more lubricants based on the total weight of the oral dosage form. In some embodiments, the one or more pharmaceutically acceptable excipients comprise about 0.1% by weight to about 0.2% by weight of one or more lubricants based on the total weight of the oral dosage form.

In some embodiments, the one or more pharmaceutically acceptable excipients comprise about 0.1% by weight of one or more lubricants based on the total weight of the oral dosage form. In some embodiments, the one or more pharmaceutically acceptable excipients comprise about 0.2% by weight of one or more lubricants based on the total weight of the oral dosage form. In some embodiments, the one or more pharmaceutically acceptable excipients comprise about 0.3% by weight of one or more lubricants based on the total weight of the oral dosage form. In some embodiments, the one or more pharmaceutically acceptable excipients comprise about 0.4% by weight of one or more lubricants based on the total weight of the oral dosage form. In some embodiments, the one or more pharmaceutically acceptable excipients comprise about 0.5% by weight of one or more lubricants based on the total weight of the oral dosage form. In some embodiments, the one or more pharmaceutically acceptable excipients comprise about 0.6% by weight of one or more lubricants based on the total weight of the oral dosage form. In some embodiments, the one or more pharmaceutically acceptable excipients comprise about 0.7% by weight of one or more lubricants based on the total weight of the oral dosage form. In some embodiments, the one or more pharmaceutically acceptable excipients comprise about 0.8% by weight of one or more lubricants based on the total weight of the oral dosage form. In some embodiments, the one or more pharmaceutically acceptable excipients comprise about 0.9% by weight of one or more lubricants based on the total weight of the oral dosage form. In some embodiments, the one or more pharmaceutically acceptable excipients comprise about 1.0% by weight of one or more lubricants based on the total weight of the oral dosage form.

In some embodiments, the oral dosage form comprises: (a) about 1% by weight to about 30% by weight of the crystalline anhydrous form of the compound of Formula (I) based on the total the weight of the oral dosage form; (b) about 20% by weight to about 90% by weight of one or more fillers based on the total weight of the oral dosage form; (c) about 1% by weight to about 20% by weight of one or more disintegrants based on the total weight of the oral dosage form; and (d) about 0.1% by weight to about 10% by weight of one or more lubricants based on the total weight of the oral dosage form.

In some embodiments, the oral dosage form consists essentially of: (a) about 1% by weight to about 30% by weight of the crystalline anhydrous form of the compound of Formula (I) based on the total weight of the oral dosage form; (b) about 20% by weight to about 90% by weight of one or more fillers based on the total weight of the oral dosage form; (c) about 1% by weight to about 20% by weight of one or more disintegrants based on the total weight of the oral dosage form; and (d) about 0.1% by weight to about 10% by weight of one or more lubricants based on the total weight of the oral dosage form.

In some embodiments, the oral dosage form comprises (a) about 5% by weight to about 25% by weight of the crystalline anhydrous form of the compound of Formula (I) based on the total weight of the oral dosage form; (b) about 60% by weight to about 90% by weight of one or more fillers based on the total weight of the oral dosage form; (c) about 1% by weight to about 15% by weight of one or more disintegrants based on the total weight of the oral dosage form; and (d) about 0.1% by weight to about 4% by weight of one or more lubricants based on the total weight of the oral dosage form.

In some embodiments, the oral dosage form consists essentially of (a) about 5% by weight to about 25% by weight of the crystalline anhydrous form of the compound of Formula (I) based on the total weight of the oral dosage form; (b) about 60% by weight to about 90% by weight of one or more fillers based on the total weight of the oral dosage form; (c) about 1% by weight to about 15% by weight of one or more disintegrants based on the total weight of the oral dosage form; and (d) about 0.1% by weight to about 4% by weight of one or more lubricants based on the total weight of the oral dosage form.

In some embodiments, the oral dosage form comprises (a) about 10% by weight to about 30% by weight of the crystalline anhydrous form of the compound of Formula (I) based on the total weight of the oral dosage form; (b) about 70% by weight to about 90% by weight of one or more fillers based on the total weight of the oral dosage form; (c) about 1% by weight to about 10% by weight of one or more disintegrants based on the total weight of the oral dosage form; and (d) about 0.1% by weight to about 3% by weight of one or more lubricants based on the total weight of the oral dosage form.

In some embodiments, the oral dosage form consists essentially of (a) about 10% by weight to about 30% by weight of the crystalline anhydrous form of the compound of Formula (I) based on the total weight of the oral dosage form; (b) about 70% by weight to about 90% by weight of one or more fillers based on the total weight of the oral dosage form; (c) about 1% by weight to about 10% by weight of one or more disintegrants based on the total weight of the oral dosage form; and (d) about 0.1% by weight to about 3% by weight of one or more lubricants based on the total weight of the oral dosage form.

In some embodiments, the one or more pharmaceutically acceptable excipients is one or more fillers selected from the group consisting of calcium phosphate, dicalcium phosphate, dicalcium phosphate anhydrous, calcium sulfate, calcium sulfate anhydrous, starch, calcium carbonate, magnesium carbonate, magnesium oxide, kaolin (natural hydrated aluminum silicate), sodium chloride, partially gelatinized starch, anhydrous lactose, lactose monohydrate, lactose dihydrate, trehalose dihydrate, spray dried lactose, sucrose, dextrose, dextrates, dextrin, cellulose, microcrystalline cellulose, silicified microcrystalline cellulose, powdered cellulose, partially depolymerized cellulose, mannitol, granulated mannitol, spray dried mannitol, maltodextrin, maltitol, confectioner's sugar, compressible sugar, sorbitol, starch and talc. In some embodiments, the one or more fillers is lactose monohydrate.

In some embodiments, the one or more disintegrants is one or more disintegrants selected from the group consisting of sodium starch glycolate, pregelatinized starch, clay, cellulose, alginic acid, alginate gum, polyvinylpyrrolidone, cross-linked polyvinylpyrrolidone, cross-linked calcium carboxymethylcellulose, cross-linked sodium carboxymethylcellulose, sodium croscarmellose, sodium carmellose, low substituted hydroxypropyl cellulose, low substituted hydroxypropyl cellulose sodium, guar gum, magnesium aluminum silicate, polacrilin potassium, powdered cellulose, sodium alginate and soy polysaccharides. In some embodiments, the one or more disintegrants is cross-linked polyvinylpyrrolidone (also referred to as crospovidone).

In some embodiments, the one or more lubricants is one or more lubricants selected from the group consisting of colloidal silica, magnesium trisilicate, talc, magnesium carbonate, magnesium oxide, glyceryl behaptate, mono, di and tri glyceryl behenate, bees wax, behenoyl polyoxyl-8 glycerides, hydrogenated vegetable oil, polyethylene glycol, ethylene oxide polymer, copolymer comprising poly(ethylene oxide) and poly(propylene oxide) (such as poloxomer 188), copolymer comprising polypropylene glycol and polyethylene glycol (such as poloxomer 407), sodium lauryl sulfate, magnesium stearate, aluminum stearate, calcium stearate, sodium stearyl fumarate, stearic acid, magnesium lauryl stearate, mixtures of magnesium stearate with sodium lauryl sulfate. In some embodiments, the one or more lubricants is magnesium stearate.

In some embodiments, the one or more disintegrants is selected from the group consisting of cross-linked polyvinylpyrrolidone, croscarmellose sodium, and sodium starch glycolate; and the one or more lubricants is selected from the group consisting of sodium stearyl fumarate, stearic acid, talc, calcium stearate, magnesium stearate, solid polyethylene glycols, and sodium lauryl sulfate. In some embodiments, the oral dosage form comprises cross-linked polyvinylpyrrolidone and magnesium stearate. In some embodiments, the one or more pharmaceutically acceptable excipients is lactose monohydrate and the oral dosage form further comprises cross-linked polyvinylpyrrolidone and magnesium stearate.

In some embodiments, the oral dosage form is a tablet or capsule. In some embodiments, the oral dosage form is a tablet. In some embodiments, the oral dosage form is a capsule. In some embodiments, the oral dosage form is a sachet. In some embodiments, the oral dosage form is a powder in a packet.

In some embodiments, the oral dosage form comprises about 1 mg to about 40 mg of the crystalline anhydrous form of the compound of Formula (I). In some embodiments, the oral dosage form comprises about 5 mg to about 35 mg of the crystalline anhydrous form of the compound of Formula (I). In some embodiments, the oral dosage form comprises about 10 mg to about 35 mg of the crystalline anhydrous form of the compound of Formula (I). In some embodiments, the oral dosage form comprises about 0.5 mg to about 5 mg, about 6 mg to about 14 mg, about 10 mg to about 18 mg, about 16 mg to about 24 mg, or about 26 mg to about 34 mg of the crystalline anhydrous form of the compound of Formula (I). In some embodiments, the oral dosage form comprises about 1 mg to about 3 mg, about 8 mg to about 12 mg, about 12 mg to about 16 mg, about 18 mg to about 22 mg, or about 28 mg to about 32 mg of the crystalline anhydrous form of the compound of Formula (I). In some embodiments, the oral dosage form comprises about 2 mg, about 10 mg, about 14 mg, about 20 mg, or about 30 mg of the crystalline anhydrous form of the compound of Formula (I). In some embodiments, the crystalline anhydrous form of the compound of Formula (I) is present in an amount of about 2 mg. In some embodiments, the crystalline anhydrous form of the compound of Formula (I) is present in an amount of about 10 mg. In some embodiments, the crystalline anhydrous form of the compound of Formula (I) is present in an amount of about 14 mg. In some embodiments, the crystalline anhydrous form of the compound of Formula (I) is present in an amount of about 20 mg. In some embodiments, the crystalline anhydrous form of the compound of Formula (I) is present in an amount of about 30 mg.

In some embodiments, the oral dosage form consists essentially of about 1 mg to about 40 mg of the crystalline anhydrous form of the compound of Formula (I). In some embodiments, the oral dosage form consists essentially of about 5 mg to about 35 mg of the crystalline anhydrous form of the compound of Formula (I). In some embodiments, the oral dosage form consists essentially of about 10 mg to about 35 mg of the crystalline anhydrous form of the compound of Formula (I). In some embodiments, the oral dosage form consists essentially of about 0.5 mg to about 5 mg, about 6 mg to about 14 mg, about 10 mg to about 18 mg, about 16 mg to about 24 mg, or about 26 mg to about 34 mg of the crystalline anhydrous form of the compound of Formula (I). In some embodiments, the oral dosage form consists essentially of about 1 mg to about 3 mg, about 8 mg to about 12 mg, about 12 mg to about 16 mg, about 18 mg to about 22 mg, or about 28 mg to about 32 mg of the crystalline anhydrous form of the compound of Formula (I). In some embodiments, the oral dosage form consists essentially of about 2 mg, about 10 mg, about 14 mg, about 20 mg, or about 30 mg of the crystalline anhydrous form of the compound of Formula (I). In some embodiments, the crystalline anhydrous form of the compound of Formula (I) is present in an amount of about 2 mg. In some embodiments, the crystalline anhydrous form of the compound of Formula (I) is present in an amount of about 10 mg. In some embodiments, the crystalline anhydrous form of the compound of Formula (I) is present in an amount of about 14 mg. In some embodiments, the crystalline anhydrous form of the compound of Formula (I) is present in an amount of about 20 mg. In some embodiments, the crystalline anhydrous form of the compound of Formula (I) is present in an amount of about 30 mg.

Also provided herein, in some embodiments, are pharmaceutically acceptable capsules comprising a crystalline anhydrous form of a compound of Formula (I):

Formula (I)

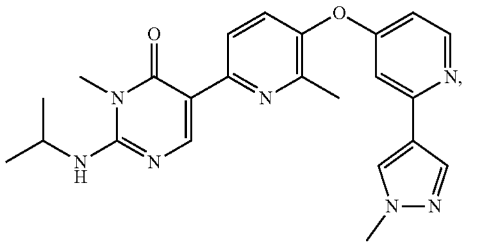

and one or more pharmaceutically acceptable excipients.

Also provided herein, in some embodiments, are pharmaceutically acceptable capsules consisting essentially of a crystalline anhydrous form of a compound of Formula (I):

Formula (I)

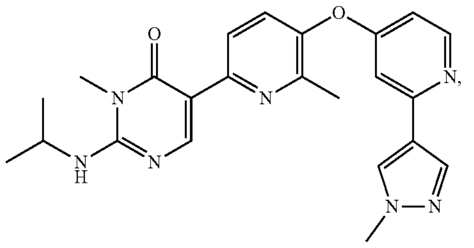

and one or more pharmaceutically acceptable excipients.

In some embodiments, the crystalline anhydrous form of the compound represented by Formula (I) has an XRPD pattern comprising a peak, in terms of 2-theta, at about 11.4° as measured by CuKα radiation.

In some embodiments, the crystalline anhydrous form of the compound represented by Formula (I) has an XRPD pattern comprising two or more of the characteristic peaks, in terms of 2-theta, at about 11.4°, about 14.7°, about 17.1°, and about 21.3° as measured by CuKα radiation.

In some embodiments, the crystalline anhydrous form of the compound represented by Formula (I) has an XRPD pattern comprising two or more of the characteristic peaks, in terms of 2-theta, at about 11.4°, about 14.7°, about 17.10, about 20.10, about 21.3°, and about 29.10 as measured by CuKα radiation.

In some embodiments, the crystalline anhydrous form of the compound represented by Formula (I) has an XRPD pattern comprising two or more of the characteristic peaks, in terms of 2-theta, at about 10.2°, about 10.5°, about 11.4°, about 14.7°, about 17.1°, about 20.10, about 21.3°, and about 29.10 as measured by CuKα radiation.

In some embodiments, the one or more pharmaceutically acceptable excipients is a filler. For example, the one or more pharmaceutically acceptable excipients is lactose, such as lactose monohydrate.

In some embodiments, the pharmaceutically acceptable capsules further comprise one or more disintegrants, one or more lubricants, or a combination thereof. For example, in some embodiments, the pharmaceutically acceptable capsules further comprise one or more disintegrants. In some embodiments, the pharmaceutically acceptable capsules further comprise one or more lubricants.

Also provided herein, in some embodiments, is a pharmaceutically acceptable capsule comprising:

(a) about 1% by weight to about 70% by weight, based on the total weight of the pharmaceutically acceptable capsule, of a crystalline anhydrous form of a compound of Formula (I):

Formula (I)

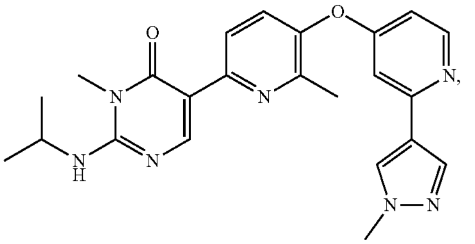

and one or more pharmaceutically acceptable excipients, wherein the one or more pharmaceutically acceptable excipients comprise:

(b) about 20% by weight to about 97% by weight of one or more fillers based on the total weight of the pharmaceutically acceptable capsule;
(c) about 1% by weight to about 20% by weight of one or more disintegrants based on the total weight of the pharmaceutically acceptable capsule; and
(d) about 0.1% by weight to about 10% by weight of one or more lubricants based on the total weight of the pharmaceutically acceptable capsule.

Also provided herein, in some embodiments, is a pharmaceutically acceptable capsule comprising:

(a) about 1% by weight to about 30% by weight of a crystalline anhydrous form of a compound of Formula (I) based on the total weight of the pharmaceutically acceptable capsule;
(b) about 20% by weight to about 90% by weight of one or more fillers based on the total weight of the pharmaceutically acceptable capsule;
(c) about 1% by weight to about 20% by weight of one or more disintegrants based on the total weight of the pharmaceutically acceptable capsule; and
(d) about 0.1% by weight to about 10% by weight of one or more lubricants based on the total weight of the pharmaceutically acceptable capsule.

Also provided herein, in some embodiments, is a pharmaceutically acceptable capsule consisting essentially of:

(a) about 1% by weight to about 70% by weight, based on the total weight of the pharmaceutically acceptable capsule, of a crystalline anhydrous form of a compound of Formula (I):

Formula (I)

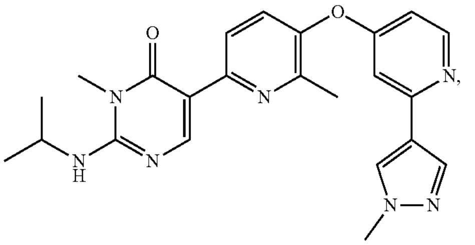

and one or more pharmaceutically acceptable excipients, wherein the one or more pharmaceutically acceptable excipients comprise:

(b) about 20% by weight to about 97% by weight of one or more fillers based on the total weight of the pharmaceutically acceptable capsule;
(c) about 1% by weight to about 20% by weight of one or more disintegrants based on the total weight of the pharmaceutically acceptable capsule; and
(d) about 0.1% by weight to about 10% by weight of one or more lubricants based on the total weight of the pharmaceutically acceptable capsule.

Also provided herein, in some embodiments, is a pharmaceutically acceptable capsule consisting essentially of:

(a) about 1% by weight to about 30% by weight of a crystalline anhydrous form of a compound of Formula (I) based on the total weight of the pharmaceutically acceptable capsule;
(b) about 20% by weight to about 90% by weight of one or more fillers based on the total weight of the pharmaceutically acceptable capsule;
(c) about 1% by weight to about 20% by weight of one or more disintegrants based on the total weight of the pharmaceutically acceptable capsule; and
(d) about 0.1% by weight to about 10% by weight of one or more lubricants based on the total weight of the pharmaceutically acceptable capsule.

In some embodiments, the pharmaceutically acceptable capsule comprising the crystalline anhydrous form of the compound represented by Formula (I), has no more than about 10 mol %, no more than about 5 mol %, no more than about 3 mol %, or no more than about 1 mol % of other solid-state forms of the compound represented by Formula (I). In some embodiments, the pharmaceutically acceptable capsule comprising the crystalline anhydrous forms of the compound represented by Formula (I), has no more than about 10 mol % of other solid-state forms of the compound represented by Formula (I). In some embodiments, the pharmaceutically acceptable capsule comprising the crystalline anhydrous forms of the compound represented by Formula (I), has no more than about 9 mol % of other solid-state forms of the compound represented by Formula (I). In some embodiments, the pharmaceutically acceptable capsule comprising the crystalline anhydrous forms of the compound represented by Formula (I), has no more than about 8 mol % of other solid-state forms of the compound represented by Formula (I). In some embodiments, the pharmaceutically acceptable capsule comprising the crystalline anhydrous forms of the compound represented by Formula (I), has no more than about 7 mol % of other solid-state forms of the compound represented by Formula (I). In some embodiments, the pharmaceutically acceptable capsule comprising the crystalline anhydrous forms of the compound represented by Formula (I), has no more than about 6 mol % of other solid-state forms of the compound represented by Formula (I). In some embodiments, the pharmaceutically acceptable capsule comprising the crystalline anhydrous forms of the compound represented by Formula (I), has no more than about 5 mol % of other solid-state forms of the compound represented by Formula (I). In some embodiments, the pharmaceutically acceptable capsule comprising the crystalline anhydrous forms of the compound represented by Formula (I), has no more than about 4 mol % of other solid-state forms of the compound represented by Formula (I). In some embodiments, the pharmaceutically acceptable capsule comprising the crystalline anhydrous forms of the compound represented by Formula (I), has no more than about 3 mol % of other solid-state forms of the compound represented by Formula (I). In some embodiments, the pharmaceutically acceptable capsule comprising the crystalline anhydrous forms of the compound represented by Formula (I), has no more than about 2 mol % of other solid-state forms of the compound represented by Formula (I). In some embodiments, the pharmaceutically acceptable capsule comprising the crystalline anhydrous forms of the compound represented by Formula (I), has no more than about 1 mol % of other solid-state forms of the compound represented by Formula (I).

In some embodiments, the pharmaceutically acceptable capsule comprises about 1% by weight to about 60% by weight, based on the total weight of the pharmaceutically acceptable capsule, of a crystalline anhydrous form of a compound of Formula (I). In some embodiments, the pharmaceutically acceptable capsule comprises about 1% by weight to about 50% by weight, based on the total weight of the pharmaceutically acceptable capsule, of a crystalline anhydrous form of a compound of Formula (I). In some embodiments, the pharmaceutically acceptable capsule comprises about 1% by weight to about 40% by weight, based on the total weight of the pharmaceutically acceptable capsule, of a crystalline anhydrous form of a compound of Formula (I). In some embodiments, the pharmaceutically acceptable capsule comprises about 1% by weight to about 30% by weight, based on the total weight of the pharmaceutically acceptable capsule, of a crystalline anhydrous form of a compound of Formula (I). In some embodiments, the pharmaceutically acceptable capsule comprises about 1% by weight to about 20% by weight, based on the total weight of the pharmaceutically acceptable capsule, of a crystalline anhydrous form of a compound of Formula (I).

In some embodiments, the pharmaceutically acceptable capsule consists essentially of about 1% by weight to about 60% by weight, based on the total weight of the pharmaceutically acceptable capsule, of a crystalline anhydrous form of a compound of Formula (I). In some embodiments, the pharmaceutically acceptable capsule consists essentially of about 1% by weight to about 50% by weight, based on the total weight of the pharmaceutically acceptable capsule, of a crystalline anhydrous form of a compound of Formula (I). In some embodiments, the pharmaceutically acceptable capsule consists essentially of about 1% by weight to about 40% by weight, based on the total weight of the pharmaceutically acceptable capsule, of a crystalline anhydrous form of a compound of Formula (I). In some embodiments, the pharmaceutically acceptable capsule consists essentially of about 1% by weight to about 30% by weight, based on the total weight of the pharmaceutically acceptable capsule, of a crystalline anhydrous form of a compound of Formula (I). In some embodiments, the pharmaceutically acceptable capsule consists essentially of about 1% by weight to about 20% by weight, based on the total weight of the pharmaceutically acceptable capsule, of a crystalline anhydrous form of a compound of Formula (I).

In some embodiments, the pharmaceutically acceptable capsule comprises about 1% by weight to about 70% by weight of crystalline anhydrous form of the compound of Formula (I) based on the total weight of the pharmaceutically acceptable capsule. In some embodiments, the pharmaceutically acceptable capsule comprises about 1% by weight to about 65% by weight of crystalline anhydrous form of the compound of Formula (I) based on the total weight of the pharmaceutically acceptable capsule. In some embodiments, the pharmaceutically acceptable capsule comprises about 1% by weight to about 60% by weight of crystalline anhydrous form of the compound of Formula (I) based on the total weight of the pharmaceutically acceptable capsule. In some embodiments, the pharmaceutically acceptable capsule comprises about 1% by weight to about 55% by weight of crystalline anhydrous form of the compound of Formula (I) based on the total weight of the pharmaceutically acceptable capsule. In some embodiments, the pharmaceutically acceptable capsule comprises about 1% by weight to about 50% by weight of crystalline anhydrous form of the compound of Formula (I) based on the total weight of the pharmaceutically acceptable capsule. In some embodiments, the pharmaceutically acceptable capsule comprises about 1% by weight to about 45% by weight of crystalline anhydrous form of the compound of Formula (I) based on the total weight of the pharmaceutically acceptable capsule. In some embodiments, the pharmaceutically acceptable capsule comprises about 1% by weight to about 40% by weight of crystalline anhydrous form of the compound of Formula (I) based on the total weight of the pharmaceutically acceptable capsule. In some embodiments, the pharmaceutically acceptable capsule comprises about 1% by weight to about 35% by weight of crystalline anhydrous form of the compound of Formula (I) based on the total weight of the pharmaceutically acceptable capsule. In some embodiments, the pharmaceutically acceptable capsule comprises about 1% by weight to about 30% by weight of the crystalline anhydrous form of the compound of Formula (I) based on the total weight of the pharmaceutically acceptable capsule. In some embodiments, the pharmaceutically acceptable capsule comprises about 1% by weight to about 25% by weight of the crystalline anhydrous form of the compound of Formula (I) based on the total weight of the pharmaceutically acceptable capsule. In some embodiments, the pharmaceutically acceptable capsule comprises about 1% by weight to about 20% by weight of the crystalline anhydrous form of the compound of Formula (I) based on the total weight of the pharmaceutically acceptable capsule. In some embodiments, the pharmaceutically acceptable capsule comprises about 1% by weight to about 15% by weight of the crystalline anhydrous form of the compound of Formula (I) based on the total weight of the pharmaceutically acceptable capsule. In some embodiments, the pharmaceutically acceptable capsule comprises about 1% by weight to about 10% by weight of the crystalline anhydrous form of the compound of Formula (I) based on the total weight of the pharmaceutically acceptable capsule.

In some embodiments, the pharmaceutically acceptable capsule consists essentially of about 1% by weight to about 70% by weight of crystalline anhydrous form of the compound of Formula (I) based on the total weight of the pharmaceutically acceptable capsule. In some embodiments, the pharmaceutically acceptable capsule consists essentially of about 1% by weight to about 65% by weight of crystalline anhydrous form of the compound of Formula (I) based on the total weight of the pharmaceutically acceptable capsule. In some embodiments, the pharmaceutically acceptable capsule consists essentially of about 1% by weight to about 60% by weight of crystalline anhydrous form of the compound of Formula (I) based on the total weight of the pharmaceutically acceptable capsule. In some embodiments, the pharmaceutically acceptable capsule consists essentially of about 1% by weight to about 55% by weight of crystalline anhydrous form of the compound of Formula (I) based on the total weight of the pharmaceutically acceptable capsule. In some embodiments, the pharmaceutically acceptable capsule consists essentially of about 1% by weight to about 50% by weight of crystalline anhydrous form of the compound of Formula (I) based on the total weight of the pharmaceutically acceptable capsule. In some embodiments, the pharmaceutically acceptable capsule consists essentially of about 1% by weight to about 45% by weight of crystalline anhydrous form of the compound of Formula (I) based on the total weight of the pharmaceutically acceptable capsule. In some embodiments, the pharmaceutically acceptable capsule consists essentially of about 1% by weight to about 40% by weight of crystalline anhydrous form of the compound of Formula (I) based on the total weight of the pharmaceutically acceptable capsule. In some embodiments, the pharmaceutically acceptable capsule consists essentially of about 1% by weight to about 35% by weight of crystalline anhydrous form of the compound of Formula (I) based on the total weight of the pharmaceutically acceptable capsule. In some embodiments, the pharmaceutically acceptable capsule consists essentially of about 1% by weight to about 30% by weight of the crystalline anhydrous form of the compound of Formula (I) based on the total weight of the pharmaceutically acceptable capsule. In some embodiments, the pharmaceutically acceptable capsule consists essentially of about 1% by weight to about 25% by weight of the crystalline anhydrous form of the compound of Formula (I) based on the total weight of the pharmaceutically acceptable capsule. In some embodiments, the pharmaceutically acceptable capsule consists essentially of about 1% by weight to about 20% by weight of the crystalline anhydrous form of the compound of Formula (I) based on the total weight of the pharmaceutically acceptable capsule. In some embodiments, the pharmaceutically acceptable capsule consists essentially of about 1% by weight to about 15% by weight of the crystalline anhydrous form of the compound of Formula (I) based on the total weight of the pharmaceutically acceptable capsule. In some embodiments, the pharmaceutically acceptable capsule consists essentially of about 1% by weight to about 10% by weight of the crystalline anhydrous form of the compound of Formula (I) based on the total weight of the pharmaceutically acceptable capsule.

In some embodiments, the pharmaceutically acceptable capsule comprises about 5% by weight to about 30% by weight of the crystalline anhydrous form of the compound of Formula (I) based on the total weight of the pharmaceutically acceptable capsule. In some embodiments, the pharmaceutically acceptable capsule comprises about 5% by weight to about 25% by weight of the crystalline anhydrous form of the compound of Formula (I) based on the total weight of the pharmaceutically acceptable capsule. In some embodiments, the pharmaceutically acceptable capsule comprises about 5% by weight to about 20% by weight of the crystalline anhydrous form of the compound of Formula (I) based on the total weight of the pharmaceutically acceptable capsule. In some embodiments, the pharmaceutically acceptable capsule comprises about 5% by weight to about 15% by weight of the crystalline anhydrous form of the compound of Formula (I) based on the total weight of the pharmaceutically acceptable capsule. In some embodiments, the pharmaceutically acceptable capsule comprises about 5% by weight to about 10% by weight of the crystalline anhydrous form of the compound of Formula (I) based on the total weight of the pharmaceutically acceptable capsule.

In some embodiments, the pharmaceutically acceptable capsule consists essentially of about 5% by weight to about 30% by weight of the crystalline anhydrous form of the compound of Formula (I) based on the total weight of the pharmaceutically acceptable capsule. In some embodiments, the pharmaceutically acceptable capsule consists essentially of about 5% by weight to about 25% by weight of the crystalline anhydrous form of the compound of Formula (I) based on the total weight of the pharmaceutically acceptable capsule. In some embodiments, the pharmaceutically acceptable capsule consists essentially of about 5% by weight to about 20% by weight of the crystalline anhydrous form of the compound of Formula (I) based on the total weight of the pharmaceutically acceptable capsule. In some embodiments, the pharmaceutically acceptable capsule consists essentially of about 5% by weight to about 15% by weight of the crystalline anhydrous form of the compound of Formula (I) based on the total weight of the pharmaceutically acceptable capsule. In some embodiments, the pharmaceutically acceptable capsule consists essentially of about 5% by weight to about 10% by weight of the crystalline anhydrous form of the compound of Formula (I) based on the total weight of the pharmaceutically acceptable capsule.

In some embodiments, the pharmaceutically acceptable capsule comprises about 10% to about 30% of the compound of Formula (I) based on the total weight of the pharmaceutically acceptable capsule. In some embodiments, the pharmaceutically acceptable capsule comprises about 10% to about 25% of the compound of Formula (I) based on the total weight of the pharmaceutically acceptable capsule. In some embodiments, the pharmaceutically acceptable capsule comprises about 10% to about 20% of the compound of Formula (I) based on the total weight of the pharmaceutically acceptable capsule. In some embodiments, the pharmaceutically acceptable capsule comprises about 10% by weight to about 15% by weight of the crystalline anhydrous form of the compound of Formula (I) based on the total weight of the pharmaceutically acceptable capsule.

In some embodiments, the pharmaceutically acceptable capsule consists essentially of about 10% to about 30% of the compound of Formula (I) based on the total weight of the pharmaceutically acceptable capsule. In some embodiments, the pharmaceutically acceptable capsule consists essentially of about 10% to about 25% of the compound of Formula (I) based on the total weight of the pharmaceutically acceptable capsule. In some embodiments, the pharmaceutically acceptable capsule consists essentially of about 10% to about 20% of the compound of Formula (I) based on the total weight of the pharmaceutically acceptable capsule. In some embodiments, the pharmaceutically acceptable capsule consists essentially of about 10% by weight to about 15% by weight of the crystalline anhydrous form of the compound of Formula (I) based on the total weight of the pharmaceutically acceptable capsule.

In some embodiments, the pharmaceutically acceptable capsule comprises about 1% by weight to about 30% by weight of the crystalline anhydrous form of the compound of Formula (I) based on the total weight of the pharmaceutically acceptable capsule. In some embodiments, the pharmaceutically acceptable capsule comprises about 1% by weight to about 10% by weight of the crystalline anhydrous form of the compound of Formula (I) based on the total weight of the pharmaceutically acceptable capsule. In some embodiments, the pharmaceutically acceptable capsule comprises about 10% to about 20% of the compound of Formula (I) based on the total weight of the pharmaceutically acceptable capsule. In some embodiments, the pharmaceutically acceptable capsule comprises about 10% by weight to about 15% by weight of the crystalline anhydrous form of the compound of Formula (I) based on the total weight of the pharmaceutically acceptable capsule.

In some embodiments, the pharmaceutically acceptable capsule consists essentially of about 1% by weight to about 30% by weight of the crystalline anhydrous form of the compound of Formula (I) based on the total weight of the pharmaceutically acceptable capsule. In some embodiments, the pharmaceutically acceptable capsule consists essentially of about 1% by weight to about 10% by weight of the crystalline anhydrous form of the compound of Formula (I)

based on the total weight of the pharmaceutically acceptable capsule. In some embodiments, the pharmaceutically acceptable capsule consists essentially of about 10% to about 20% of the compound of Formula (I) based on the total weight of the pharmaceutically acceptable capsule. In some embodiments, the pharmaceutically acceptable capsule consists essentially of about 10% by weight to about 15% by weight of the crystalline anhydrous form of the compound of Formula (I) based on the total weight of the pharmaceutically acceptable capsule.

In some embodiments, the one or more pharmaceutically acceptable excipients comprise about 20% by weight to about 90% by weight of one or more fillers based on the total weight of the pharmaceutically acceptable capsule. In some embodiments, the one or more pharmaceutically acceptable excipients comprise about 20% by weight to about 85% by weight of one or more fillers based on the total weight of the pharmaceutically acceptable capsule. In some embodiments, the one or more pharmaceutically acceptable excipients comprise about 20% by weight to about 80% by weight of one or more fillers based on the total weight of the pharmaceutically acceptable capsule. In some embodiments, the one or more pharmaceutically acceptable excipients comprise about 20% by weight to about 75% by weight of one or more fillers based on the total weight of the pharmaceutically acceptable capsule. In some embodiments, the one or more pharmaceutically acceptable excipients comprise about 20% by weight to about 70% by weight of one or more fillers based on the total weight of the pharmaceutically acceptable capsule. In some embodiments, the one or more pharmaceutically acceptable excipients comprise about 20% by weight to about 65% by weight of one or more fillers based on the total weight of the pharmaceutically acceptable capsule. In some embodiments, the one or more pharmaceutically acceptable excipients comprise about 20% by weight to about 60% by weight of one or more fillers based on the total weight of the pharmaceutically acceptable capsule. In some embodiments, the one or more pharmaceutically acceptable excipients comprise about 20% by weight to about 55% by weight of one or more fillers based on the total weight of the pharmaceutically acceptable capsule. In some embodiments, the one or more pharmaceutically acceptable excipients comprise about 20% by weight to about 50% by weight of one or more fillers based on the total weight of the pharmaceutically acceptable capsule. In some embodiments, the one or more pharmaceutically acceptable excipients comprise about 20% by weight to about 45% by weight of one or more fillers based on the total weight of the pharmaceutically acceptable capsule. In some embodiments, the one or more pharmaceutically acceptable excipients comprise about 20% by weight to about 40% by weight of one or more fillers based on the total weight of the pharmaceutically acceptable capsule. In some embodiments, the one or more pharmaceutically acceptable excipients comprise about 20% by weight to about 35% by weight of one or more fillers based on the total weight of the pharmaceutically acceptable capsule. In some embodiments, the one or more pharmaceutically acceptable excipients comprise about 20% by weight to about 30% by weight of one or more fillers based on the total weight of the pharmaceutically acceptable capsule. In some embodiments, the one or more pharmaceutically acceptable excipients comprise about 20% by weight to about 25% by weight of one or more fillers based on the total weight of the pharmaceutically acceptable capsule.

In some embodiments, the one or more pharmaceutically acceptable excipients comprise about 30% by weight to about 90% by weight of one or more fillers based on the total weight of the pharmaceutically acceptable capsule. In some embodiments, the one or more pharmaceutically acceptable excipients comprise about 30% by weight to about 80% by weight of one or more fillers based on the total weight of the pharmaceutically acceptable capsule. In some embodiments, the one or more pharmaceutically acceptable excipients comprise about 30% by weight to about 70% by weight of one or more fillers based on the total weight of the pharmaceutically acceptable capsule. In some embodiments, the one or more pharmaceutically acceptable excipients comprise about 30% by weight to about 60% by weight of one or more fillers based on the total weight of the pharmaceutically acceptable capsule. In some embodiments, the one or more pharmaceutically acceptable excipients comprise about 30% by weight to about 50% by weight of one or more fillers based on the total weight of the pharmaceutically acceptable capsule. In some embodiments, the one or more pharmaceutically acceptable excipients comprise about 30% by weight to about 40% by weight of one or more fillers based on the total weight of the pharmaceutically acceptable capsule.

In some embodiments, the one or more pharmaceutically acceptable excipients comprise about 40% by weight to about 90% by weight of one or more fillers based on the total weight of the pharmaceutically acceptable capsule. In some embodiments, the one or more pharmaceutically acceptable excipients comprise about 40% by weight to about 80% by weight of one or more fillers based on the total weight of the pharmaceutically acceptable capsule. In some embodiments, the one or more pharmaceutically acceptable excipients comprise about 40% by weight to about 70% by weight of one or more fillers based on the total weight of the pharmaceutically acceptable capsule. In some embodiments, the one or more pharmaceutically acceptable excipients comprise about 40% by weight to about 60% by weight of one or more fillers based on the total weight of the pharmaceutically acceptable capsule. In some embodiments, the one or more pharmaceutically acceptable excipients comprise about 40% by weight to about 50% by weight of one or more fillers based on the total weight of the pharmaceutically acceptable capsule.

In some embodiments, the one or more pharmaceutically acceptable excipients comprise about 50% by weight to about 90% by weight of one or more fillers based on the total weight of the pharmaceutically acceptable capsule. In some embodiments, the one or more pharmaceutically acceptable excipients comprise about 50% by weight to about 80% by weight of one or more fillers based on the total weight of the pharmaceutically acceptable capsule. In some embodiments, the one or more pharmaceutically acceptable excipients comprise about 50% by weight to about 70% by weight of one or more fillers based on the total weight of the pharmaceutically acceptable capsule. In some embodiments, the one or more pharmaceutically acceptable excipients comprise about 50% by weight to about 60% by weight of one or more fillers based on the total weight of the pharmaceutically acceptable capsule.

In some embodiments, the one or more pharmaceutically acceptable excipients comprise about 60% by weight to about 90% by weight of one or more fillers based on the total weight of the pharmaceutically acceptable capsule. In some embodiments, the one or more pharmaceutically acceptable excipients comprise about 60% by weight to about 80% by weight of one or more fillers based on the total weight of the pharmaceutically acceptable capsule. In some embodiments, the one or more pharmaceutically acceptable excipients comprise about 60% by weight to about 70% by weight of one or more fillers based on the total weight of the pharmaceutically acceptable capsule.

In some embodiments, the one or more pharmaceutically acceptable excipients comprise about 70% by weight to about 90% by weight of one or more fillers based on the total weight of the pharmaceutically acceptable capsule. In some embodiments, the one or more pharmaceutically acceptable excipients comprise about 70% by weight to about 80% by weight of one or more fillers based on the total weight of the pharmaceutically acceptable capsule.

In some embodiments, the one or more pharmaceutically acceptable excipients comprise about 80% by weight to about 90% by weight of one or more fillers based on the total weight of the pharmaceutically acceptable capsule.

In some embodiments, the one or more pharmaceutically acceptable excipients comprise about 1% by weight to about 20% by weight of one or more disintegrants based on the total weight of the pharmaceutically acceptable capsule. In some embodiments, the one or more pharmaceutically acceptable excipients comprise about 1% by weight to about 15% by weight of one or more disintegrants based on the total weight of the pharmaceutically acceptable capsule. In some embodiments, the one or more pharmaceutically acceptable excipients comprise about 1% by weight to about 14% by weight of one or more disintegrants based on the total weight of the pharmaceutically acceptable capsule. In some embodiments, the one or more pharmaceutically acceptable excipients comprise about 1% by weight to about 13% by weight of one or more disintegrants based on the total weight of the pharmaceutically acceptable capsule. In some embodiments, the one or more pharmaceutically acceptable excipients comprise about 1% by weight to about 12% by weight of one or more disintegrants based on the total weight of the pharmaceutically acceptable capsule. In some embodiments, the one or more pharmaceutically acceptable excipients comprise about 1% by weight to about 11% by weight of one or more disintegrants based on the total weight of the pharmaceutically acceptable capsule. In some embodiments, the one or more pharmaceutically acceptable excipients comprise about 1% by weight to about 10% by weight of one or more disintegrants based on the total weight of the pharmaceutically acceptable capsule. In some embodiments, the one or more pharmaceutically acceptable excipients comprise about 1% by weight to about 9% by weight of one or more disintegrants based on the total weight of the pharmaceutically acceptable capsule. In some embodiments, the one or more pharmaceutically acceptable excipients comprise about 1% by weight to about 8% by weight of one or more disintegrants based on the total weight of the pharmaceutically acceptable capsule. In some embodiments, the one or more pharmaceutically acceptable excipients comprise about 1% by weight to about 7% by weight of one or more disintegrants based on the total weight of the pharmaceutically acceptable capsule. In some embodiments, the one or more pharmaceutically acceptable excipients comprise about 1% by weight to about 6% by weight of one or more disintegrants based on the total weight of the pharmaceutically acceptable capsule. In some embodiments, the one or more pharmaceutically acceptable excipients comprise about 1% by weight to about 5% by weight of one or more disintegrants based on the total weight of the pharmaceutically acceptable capsule. In some embodiments, the one or more pharmaceutically acceptable excipients comprise about 1% by weight to about 4% by weight of one or more disintegrants based on the total weight of the pharmaceutically acceptable capsule. In some embodiments, the one or more pharmaceutically acceptable excipients comprise about 1% by weight to about 3% by weight of one or more disintegrants based on the total weight of the pharmaceutically acceptable capsule.

In some embodiments, the one or more pharmaceutically acceptable excipients comprise about 1% by weight of one or more disintegrants based on the total weight of the pharmaceutically acceptable capsule. In some embodiments, the one or more pharmaceutically acceptable excipients comprise about 2% by weight of one or more disintegrants based on the total weight of the pharmaceutically acceptable capsule. In some embodiments, the one or more pharmaceutically acceptable excipients comprise about 3% by weight of one or more disintegrants based on the total weight of the pharmaceutically acceptable capsule. In some embodiments, the one or more pharmaceutically acceptable excipients comprise about 4% by weight of one or more disintegrants based on the total weight of the pharmaceutically acceptable capsule. In some embodiments, the one or more pharmaceutically acceptable excipients comprise about 5% by weight of one or more disintegrants based on the total weight of the pharmaceutically acceptable capsule. In some embodiments, the one or more pharmaceutically acceptable excipients comprise about 6% by weight of one or more disintegrants based on the total weight of the pharmaceutically acceptable capsule. In some embodiments, the one or more pharmaceutically acceptable excipients comprise about 7% by weight of one or more disintegrants based on the total weight of the pharmaceutically acceptable capsule. In some embodiments, the one or more pharmaceutically acceptable excipients comprise about 8% by weight of one or more disintegrants based on the total weight of the pharmaceutically acceptable capsule. In some embodiments, the one or more pharmaceutically acceptable excipients comprise about 9% by weight of one or more disintegrants based on the total weight of the pharmaceutically acceptable capsule. In some embodiments, the one or more pharmaceutically acceptable excipients comprise about 10% by weight of one or more disintegrants based on the total weight of the pharmaceutically acceptable capsule. In some embodiments, the one or more pharmaceutically acceptable excipients comprise about 11% by weight of one or more disintegrants based on the total weight of the pharmaceutically acceptable capsule. In some embodiments, the one or more pharmaceutically acceptable excipients comprise about 12% by weight of one or more disintegrants based on the total weight of the pharmaceutically acceptable capsule. In some embodiments, the one or more pharmaceutically acceptable excipients comprise about 13% by weight of one or more disintegrants based on the total weight of the pharmaceutically acceptable capsule. In some embodiments, the one or more pharmaceutically acceptable excipients comprise about 14% by weight of one or more disintegrants based on the total weight of the pharmaceutically acceptable capsule. In some embodiments, the one or more pharmaceutically acceptable excipients comprise about 15% by weight of one or more disintegrants based on the total weight of the pharmaceutically acceptable capsule.

In some embodiments, the one or more pharmaceutically acceptable excipients comprise about 0.1% by weight to about 10% by weight of one or more lubricants based on the total weight of the pharmaceutically acceptable capsule. In some embodiments, the one or more pharmaceutically acceptable excipients comprise about 0.1% by weight to about 9% by weight of one or more lubricants based on the total weight of the pharmaceutically acceptable capsule. In some embodiments, the one or more pharmaceutically acceptable excipients comprise about 0.1% by weight to about 8% by weight of one or more lubricants based on the total weight of the pharmaceutically acceptable capsule. In some embodiments, the one or more pharmaceutically acceptable excipients comprise about 0.1% by weight to about 7% by weight of one or more lubricants based on the total weight of the pharmaceutically acceptable capsule. In some embodiments, the one or more pharmaceutically acceptable excipients comprise about 0.1% by weight to about 6% by weight of one or more lubricants based on the total weight of the pharmaceutically acceptable capsule. In some embodiments, the one or more pharmaceutically acceptable excipients comprise about 0.1% by weight to about 5% by weight of one or more lubricants based on the total weight of the pharmaceutically acceptable capsule. In some embodiments, the one or more pharmaceutically acceptable excipients comprise about 0.1% by weight to about 4% by weight of one or more lubricants based on the total weight of the pharmaceutically acceptable capsule. In some embodiments, the one or more pharmaceutically acceptable excipients comprise about 0.1% by weight to about 3% by weight of one or more lubricants based on the total weight of the pharmaceutically acceptable capsule. In some embodiments, the one or more pharmaceutically acceptable excipients comprise about 0.1% by weight to about 2% by weight of one or more lubricants based on the total weight of the pharmaceutically acceptable capsule.

In some embodiments, the one or more pharmaceutically acceptable excipients comprise about 0.1% by weight to about 1.9% by weight of one or more lubricants based on the total weight of the pharmaceutically acceptable capsule. In some embodiments, the one or more pharmaceutically acceptable excipients comprise about 0.1% by weight to about 1.8% by weight of one or more lubricants based on the total weight of the pharmaceutically acceptable capsule. In some embodiments, the one or more pharmaceutically acceptable excipients comprise about 0.1% by weight to about 1.7% by weight of one or more lubricants based on the total weight of the pharmaceutically acceptable capsule. In some embodiments, the one or more pharmaceutically acceptable excipients comprise about 0.1% by weight to about 1.6% by weight of one or more lubricants based on the total weight of the pharmaceutically acceptable capsule. In some embodiments, the one or more pharmaceutically acceptable excipients comprise about 0.1% by weight to about 1.5% by weight of one or more lubricants based on the total weight of the pharmaceutically acceptable capsule. In some embodiments, the one or more pharmaceutically acceptable excipients comprise about 0.1% by weight to about 1.4% by weight of one or more lubricants based on the total weight of the pharmaceutically acceptable capsule. In some embodiments, the one or more pharmaceutically acceptable excipients comprise about 0.1% by weight to about 1.3% by weight of one or more lubricants based on the total weight of the pharmaceutically acceptable capsule. In some embodiments, the one or more pharmaceutically acceptable excipients comprise about 0.1% by weight to about 1.2% by weight of one or more lubricants based on the total weight of the pharmaceutically acceptable capsule. In some embodiments, the one or more pharmaceutically acceptable excipients comprise about 0.1% by weight to about 1.1% by weight of one or more lubricants based on the total weight of the pharmaceutically acceptable capsule. In some embodiments, the one or more pharmaceutically acceptable excipients comprise about 0.1% by weight to about 1.0% by weight of one or more lubricants based on the total weight of the pharmaceutically acceptable capsule. In some embodiments, the one or more pharmaceutically acceptable excipients comprise about 0.1% by weight to about 0.9% by weight of one or more lubricants based on the total weight of the pharmaceutically acceptable capsule. In some embodiments, the one or more pharmaceutically acceptable excipients comprise about 0.1% by weight to about 0.8% by weight of one or more lubricants based on the total weight of the pharmaceutically acceptable capsule. In some embodiments, the one or more pharmaceutically acceptable excipients comprise about 0.1% by weight to about 0.7% by weight of one or more lubricants based on the total weight of the pharmaceutically acceptable capsule. In some embodiments, the one or more pharmaceutically acceptable excipients comprise about 0.1% by weight to about 0.6% by weight of one or more lubricants based on the total weight of the pharmaceutically acceptable capsule. In some embodiments, the one or more pharmaceutically acceptable excipients comprise about 0.1% by weight to about 0.5% by weight of one or more lubricants based on the total weight of the pharmaceutically acceptable capsule. In some embodiments, the one or more pharmaceutically acceptable excipients comprise about 0.1% by weight to about 0.4% by weight of one or more lubricants based on the total weight of the pharmaceutically acceptable capsule. In some embodiments, the one or more pharmaceutically acceptable excipients comprise about 0.1% by weight to about 0.3% by weight of one or more lubricants based on the total weight of the pharmaceutically acceptable capsule. In some embodiments, the one or more pharmaceutically acceptable excipients comprise about 0.1% by weight to about 0.2% by weight of one or more lubricants based on the total weight of the pharmaceutically acceptable capsule.

In some embodiments, the one or more pharmaceutically acceptable excipients comprise about 0.1% by weight of one or more lubricants based on the total weight of the pharmaceutically acceptable capsule. In some embodiments, the one or more pharmaceutically acceptable excipients comprise about 0.2% by weight of one or more lubricants based on the total weight of the pharmaceutically acceptable capsule. In some embodiments, the one or more pharmaceutically acceptable excipients comprise about 0.3% by weight of one or more lubricants based on the total weight of the pharmaceutically acceptable capsule. In some embodiments, the one or more pharmaceutically acceptable excipients comprise about 0.4% by weight of one or more lubricants based on the total weight of the pharmaceutically acceptable capsule. In some embodiments, the one or more pharmaceutically acceptable excipients comprise about 0.5% by weight of one or more lubricants based on the total weight of the pharmaceutically acceptable capsule. In some embodiments, the one or more pharmaceutically acceptable excipients comprise about 0.6% by weight of one or more lubricants based on the total weight of the pharmaceutically acceptable capsule. In some embodiments, the one or more pharmaceutically acceptable excipients comprise about 0.7% by weight of one or more lubricants based on the total weight of the pharmaceutically acceptable capsule. In some embodiments, the one or more pharmaceutically acceptable excipients comprise about 0.8% by weight of one or more lubricants based on the total weight of the pharmaceutically acceptable capsule. In some embodiments, the one or more pharmaceutically acceptable excipients comprise about 0.9% by weight of one or more lubricants based on the total weight of the pharmaceutically acceptable capsule. In some embodiments, the one or more pharmaceutically acceptable excipients comprise about 1.0% by weight of one or more lubricants based on the total weight of the pharmaceutically acceptable capsule.

In some embodiments, the pharmaceutically acceptable capsule comprises: (a) about 1% by weight to about 30% by weight of the crystalline anhydrous form of the compound of Formula (I) based on the total weight of the pharmaceutically acceptable capsule; (b) about 20% by weight to about 90% by weight of one or more fillers based on the total weight of the pharmaceutically acceptable capsule; (c) about 1% by weight to about 20% by weight of one or more disintegrants based on the total weight of the pharmaceutically acceptable capsule; and (d) about 0.1% by weight to about 10% by weight of one or more lubricants based on the total weight of the pharmaceutically acceptable capsule.

In some embodiments, the pharmaceutically acceptable capsule consists essentially of: (a) about 1% by weight to about 30% by weight of the crystalline anhydrous form of the compound of Formula (I) based on the total weight of the pharmaceutically acceptable capsule; (b) about 20% by weight to about 90% by weight of one or more fillers based on the total weight of the pharmaceutically acceptable capsule; (c) about 1% by weight to about 20% by weight of one or more disintegrants based on the total weight of the pharmaceutically acceptable capsule; and (d) about 0.1% by weight to about 10% by weight of one or more lubricants based on the total weight of the pharmaceutically acceptable capsule.

In some embodiments, the pharmaceutically acceptable capsule comprises (a) about 5% by weight to about 25% by weight of the crystalline anhydrous form of the compound of Formula (I) based on the total weight of the pharmaceutically acceptable capsule; (b) about 60% by weight to about 90% by weight of one or more fillers based on the total weight of the pharmaceutically acceptable capsule; (c) about 1% by weight to about 15% by weight of one or more disintegrants based on the total weight of the pharmaceutically acceptable capsule; and (d) about 0.1% by weight to about 4% by weight of one or more lubricants based on the total weight of the pharmaceutically acceptable capsule.

In some embodiments, the pharmaceutically acceptable capsule consists essentially of (a) about 5% by weight to about 25% by weight of the crystalline anhydrous form of the compound of Formula (I) based on the total weight of the pharmaceutically acceptable capsule; (b) about 60% by weight to about 90% by weight of one or more fillers based on the total weight of the pharmaceutically acceptable capsule; (c) about 1% by weight to about 15% by weight of one or more disintegrants based on the total weight of the pharmaceutically acceptable capsule; and (d) about 0.1% by weight to about 4% by weight of one or more lubricants based on the total weight of the pharmaceutically acceptable capsule.

In some embodiments, the pharmaceutically acceptable capsule comprises (a) about 10% by weight to about 30% by weight of the crystalline anhydrous form of the compound of Formula (I) based on the total weight of the pharmaceutically acceptable capsule; (b) about 70% by weight to about 90% by weight of one or more fillers based on the total weight of the pharmaceutically acceptable capsule; (c) about 1% by weight to about 10% by weight of one or more disintegrants based on the total weight of the pharmaceutically acceptable capsule; and (d) about 0.1% by weight to about 3% by weight of one or more lubricants based on the total weight of the pharmaceutically acceptable capsule.

In some embodiments, the pharmaceutically acceptable capsule consists essentially of (a) about 10% by weight to about 30% by weight of the crystalline anhydrous form of the compound of Formula (I) based on the total weight of the pharmaceutically acceptable capsule; (b) about 70% by weight to about 90% by weight of one or more fillers based on the total weight of the pharmaceutically acceptable capsule; (c) about 1% by weight to about 10% by weight of one or more disintegrants based on the total weight of the pharmaceutically acceptable capsule; and (d) about 0.1% by weight to about 3% by weight of one or more lubricants based on the total weight of the pharmaceutically acceptable capsule.

In some embodiments, the one or more pharmaceutically acceptable excipients is one or more fillers selected from the group consisting of calcium phosphate, dicalcium phosphate, dicalcium phosphate anhydrous, calcium sulfate, calcium sulfate anhydrous, starch, calcium carbonate, magnesium carbonate, magnesium oxide, kaolin (natural hydrated aluminum silicate), sodium chloride, partially gelatinized starch, anhydrous lactose, lactose monohydrate, lactose dihydrate, trehalose dihydrate, spray dried lactose, sucrose, dextrose, dextrates, dextrin, cellulose, microcrystalline cellulose, silicified microcrystalline cellulose, powdered cellulose, partially depolymerized cellulose, mannitol, granulated mannitol, spray dried mannitol, maltodextrin, maltitol, confectioner's sugar, compressible sugar, sorbitol, starch and talc. In some embodiments, the one or more fillers is lactose monohydrate.

In some embodiments, the one or more disintegrants is one or more disintegrants selected from the group consisting of sodium starch glycolate, pregelatinized starch, clay, cellulose, alginic acid, alginate gum, polyvinylpyrrolidone, cross-linked polyvinylpyrrolidone, cross-linked calcium carboxymethylcellulose, cross-linked sodium carboxymethylcellulose, sodium croscarmellose, sodium carmellose, low substituted hydroxypropyl cellulose, low substituted hydroxypropyl cellulose sodium, guar gum, magnesium aluminum silicate, polacrilin potassium, powdered cellulose, sodium alginate and soy polysaccharides. In some embodiments, the one or more disintegrants is cross-linked polyvinylpyrrolidone (also referred to as crospovidone).

In some embodiments, the one or more lubricants is one or more lubricants selected from the group consisting of colloidal silica, magnesium trisilicate, talc, magnesium carbonate, magnesium oxide, glyceryl behaptate, mono, di and tri glyceryl behenate, bees wax, behenoyl polyoxyl-8 glycerides, hydrogenated vegetable oil, polyethylene glycol, ethylene oxide polymer, copolymer comprising poly(ethylene oxide) and poly(propylene oxide) (such as poloxomer 188), copolymer comprising polypropylene glycol and polyethylene glycol (such as poloxomer 407), sodium lauryl sulfate, magnesium stearate, aluminum stearate, calcium stearate, sodium stearyl fumarate, stearic acid, magnesium lauryl stearate, mixtures of magnesium stearate with sodium lauryl sulfate. In some embodiments, the one or more lubricants is magnesium stearate.

In some embodiments, the one or more disintegrants is selected from the group consisting of cross-linked polyvinylpyrrolidone, croscarmellose sodium, and sodium starch glycolate; and the one or more lubricants is selected from the group consisting of sodium stearyl fumarate, stearic acid, talc, calcium stearate, magnesium stearate, solid polyethylene glycols, and sodium lauryl sulfate. In some embodiments, the pharmaceutically acceptable capsule comprises cross-linked polyvinylpyrrolidone and magnesium stearate. In some embodiments, the one or more pharmaceutically acceptable excipients is lactose monohydrate and the pharmaceutically acceptable capsule further comprises cross-linked polyvinylpyrrolidone and magnesium stearate.

In some embodiments, the pharmaceutically acceptable capsule is for oral administration.

In some embodiments, the pharmaceutically acceptable capsule is a solid dosage form.

In some embodiments, the pharmaceutically acceptable capsule comprises about 1 mg to about 40 mg of the crystalline anhydrous form of the compound of Formula (I). In some embodiments, the pharmaceutically acceptable capsule comprises about 5 mg to about 35 mg of the crystalline anhydrous form of the compound of Formula (I). In some embodiments, the pharmaceutically acceptable capsule comprises about 10 mg to about 35 mg of the crystalline anhydrous form of the compound of Formula (I). In some embodiments, the pharmaceutically acceptable capsule comprises about 0.5 mg to about 5 mg, about 6 mg to about 14 mg, about 10 mg to about 18 mg, about 16 mg to about 24 mg, or about 26 mg to about 34 mg of the crystalline anhydrous form of the compound of Formula (I). In some embodiments, the pharmaceutically acceptable capsule comprises about 1 mg to about 3 mg, about 8 mg to about 12 mg, about 12 mg to about 16 mg, about 18 mg to about 22 mg, or about 28 mg to about 32 mg of the crystalline anhydrous form of the compound of Formula (I). In some embodiments, the pharmaceutically acceptable capsule comprises about 2 mg, about 10 mg, about 14 mg, about 20 mg, or about 30 mg of the crystalline anhydrous form of the compound of Formula (I). In some embodiments, the crystalline anhydrous form of the compound of Formula (I) is present in an amount of about 2 mg. In some embodiments, the crystalline anhydrous form of the compound of Formula (I) is present in an amount of about 10 mg. In some embodiments, the crystalline anhydrous form of the compound of Formula (I) is present in an amount of about 14 mg. In some embodiments, the crystalline anhydrous form of the compound of Formula (I) is present in an amount of about 20 mg. In some embodiments, the crystalline anhydrous form of the compound of Formula (I) is present in an amount of about 30 mg.

In some embodiments, the pharmaceutically acceptable capsule consists essentially of about 1 mg to about 40 mg of the crystalline anhydrous form of the compound of Formula (I). In some embodiments, the pharmaceutically acceptable capsule consists essentially of about 5 mg to about 35 mg of the crystalline anhydrous form of the compound of Formula (I). In some embodiments, the pharmaceutically acceptable capsule consists essentially of about 10 mg to about 35 mg of the crystalline anhydrous form of the compound of Formula (I). In some embodiments, the pharmaceutically acceptable capsule consists essentially of about 0.5 mg to about 5 mg, about 6 mg to about 14 mg, about 10 mg to about 18 mg, about 16 mg to about 24 mg, or about 26 mg to about 34 mg of the crystalline anhydrous form of the compound of Formula (I). In some embodiments, the pharmaceutically acceptable capsule consists essentially of about 1 mg to about 3 mg, about 8 mg to about 12 mg, about 12 mg to about 16 mg, about 18 mg to about 22 mg, or about 28 mg to about 32 mg of the crystalline anhydrous form of the compound of Formula (I). In some embodiments, the pharmaceutically acceptable capsule consists essentially of about 2 mg, about 10 mg, about 14 mg, about 20 mg, or about 30 mg of the crystalline anhydrous form of the compound of Formula (I). In some embodiments, the crystalline anhydrous form of the compound of Formula (I) is present in an amount of about 2 mg. In some embodiments, the crystalline anhydrous form of the compound of Formula (I) is present in an amount of about 10 mg. In some embodiments, the crystalline anhydrous form of the compound of Formula (I) is present in an amount of about 14 mg. In some embodiments, the crystalline anhydrous form of the compound of Formula (I) is present in an amount of about 20 mg. In some embodiments, the crystalline anhydrous form of the compound of Formula (I) is present in an amount of about 30 mg.

In some embodiments, the pharmaceutically acceptable capsule is a size 4 hard gelatin capsule. In some embodiments, the pharmaceutically acceptable capsule is a size 2 hard gelatin capsule. In some embodiments, the pharmaceutically acceptable capsule is a size 1 hard gelatin capsule. In some embodiments, the pharmaceutically acceptable capsule further comprises one more colorants selected from the group consisting of FD&C Blue #1(E133), FD&C Red #40 (E129), Titanium Dioxide (E171) USP/NF or Ph. Eur., and Gelatin USP/NF or Ph. Eur.

Stability of Crystalline Solid-State Forms

Crystalline solid-state forms of the compound represented by Formula (I) are highly stable. The term "stable form" when used herein refers to solid-state forms of the compound of Formula (I) following storage comprises at least 75% (w/v or w/w), 80% (w/v or w/w), 85% (w/v or w/w), 90% (w/v or w/w), 95% (w/v or w/w), 96% (w/v or w/w), 97% (w/v or w/w), 98% (w/v or w/w), or 99% (w/v or w/w) of said particular solid-state forms after static storage (e.g., after static storage for at least 4 weeks at about 25° C. to about 40° C. at about 0-97% relative humidity). In some embodiments, storage conditions for stability testing are about 25° C. at about 60% relative humidity, such as about 25° C. at about 60% relative humidity of at least 1 year, 2 years, 3 years, 4 years, or 5 years. In some embodiments, the storage conditions for stability testing are about 25° C. and about 0-97% relative humidity for at least 4 weeks, such as about 25° C. and about 0% relative humidity for at least 4 weeks or about 25° C. and about 97% relative humidity for at least 4 weeks. In some embodiments, storage conditions for stability testing are about 40° C. and about 0-75% relative humidity for at least 4 weeks, such as about 40° C. and about 0% relative humidity for at least 4 weeks or about 40° C. and about 75% relative humidity for at least 4 weeks.

In some embodiments, the stability of the particular solid-state form of compound of Formula (I) requires at least 75% (w/v or w/w), 80% (w/v or w/w), 85% (w/v or w/w), 90% (w/v or w/w), 95% (w/v or w/w), 96% (w/v or w/w), 97% (w/v or w/w), 98% (w/v or w/w), or 99% (w/v or w/w) of said form remaining as said form at the end of the storage period, e.g., without converting to another form of the compound of Formula (I).

In some embodiments, the crystalline dihydrate form of the compound of Formula (I) is stable upon static storage at about 25° C. at about 60% relative humidity for at least 1 year. In some embodiments, the crystalline dihydrate form of the compound of Formula (I) is stable upon static storage at about 25° C. at about 60% relative humidity for at least 2 years. In some embodiments, the crystalline dihydrate form of the compound of Formula (I) is stable upon static storage at about 25° C. at about 60% relative humidity for at least 3 years. In some embodiments, the crystalline dihydrate form of the compound of Formula (I) is stable upon static storage at about 25° C. at about 60% relative humidity for at least 4 years. In some embodiments, the crystalline dihydrate form of the compound of Formula (I) is stable upon static storage at about 25° C. at about 60% relative humidity for at least 5 years.

In some embodiments, the crystalline dihydrate form of the compound of Formula (I) is stable upon static storage at about 25° C. at about 97% relative humidity for at least 1 week. In some embodiments, the crystalline dihydrate form of the compound of Formula (I) is stable upon static storage at about 25° C. at about 97% relative humidity for at least 2 weeks. In some embodiments, the crystalline dihydrate form of the compound of Formula (I) is stable upon static storage at about 25° C. at about 97% relative humidity for at least 3 weeks. In some embodiments, the crystalline dihydrate form of the compound of Formula (I) is stable upon static storage at about 25° C. at about 97% relative humidity for at least 4 weeks. In some embodiments, the crystalline dihydrate form of the compound of Formula (I) is stable upon static storage at about 25° C. at about 97% relative humidity for at least 1 month. In some embodiments, the crystalline dihydrate form of the compound of Formula (I) is stable upon static storage at about 25° C. at about 97% relative humidity for at least 2 months. In some embodiments, the crystalline dihydrate form of the compound of Formula (I) is stable upon static storage at about 25° C. at about 97% relative humidity for at least 3 months. In some embodiments, the crystalline dihydrate form of the compound of Formula (I) is stable upon static storage at about 25° C. at about 97% relative humidity for at least 4 months. In some embodiments, the crystalline dihydrate form of the compound of Formula (I) is stable upon static storage at about 25° C. at about 97% relative humidity for at least 5 months. In some embodiments, the crystalline dihydrate form of the compound of Formula (I) is stable upon static storage at about 25° C. at about 97% relative humidity for at least 6 months. In some embodiments, the crystalline dihydrate form of the compound of Formula (I) is stable upon static storage at about 25° C. at about 97% relative humidity for at least 12 months. In some embodiments, the crystalline dihydrate form of the compound of Formula (I) is stable upon static storage at about 25° C. at about 97% relative humidity for at least 24 months.

In some embodiments, the crystalline dihydrate form of the compound of Formula (I) is stable upon static storage at about 40° C. at about 75% relative humidity for at least 1 week. In some embodiments, the crystalline dihydrate form of the compound of Formula (I) is stable upon static storage at about 40° C. at about 75% relative humidity for at least 2 weeks. In some embodiments, the crystalline dihydrate form of the compound of Formula (I) is stable upon static storage at about 40° C. at about 75% relative humidity for at least 3 weeks. In some embodiments, the crystalline dihydrate form of the compound of Formula (I) is stable upon static storage at about 40° C. at about 75% relative humidity for at least 4 weeks. In some embodiments, the crystalline dihydrate form of the compound of Formula (I) is stable upon static storage at about 40° C. at about 75% relative humidity for at least 1 month. In some embodiments, the crystalline dihydrate form of the compound of Formula (I) is stable upon static storage at about 40° C. at about 75% relative humidity for at least 2 months. In some embodiments, the crystalline dihydrate form of the compound of Formula (I) is stable upon static storage at about 40° C. at about 75% relative humidity for at least 3 months. In some embodiments, the crystalline dihydrate form of the compound of Formula (I) is stable upon static storage at about 40° C. at about 75% relative humidity for at least 4 months. In some embodiments, the crystalline dihydrate form of the compound of Formula (I) is stable upon static storage at about 40° C. at about 75% relative humidity for at least 5 months. In some embodiments, the crystalline dihydrate form of the compound of Formula (I) is stable upon static storage at about 40° C. at about 75% relative humidity for at least 6 months. In some embodiments, the crystalline dihydrate form of the compound of Formula (I) is stable upon static storage at about 40° C. at about 75% relative humidity for at least 12 months. In some embodiments, the crystalline dihydrate form of the compound of Formula (I) is stable upon static storage at about 40° C. at about 75% relative humidity for at least 24 months.

In some embodiments, the crystalline anhydrous form of the compound of Formula (I) is stable upon static storage at about 25° C. at about 97% relative humidity for at least 1 week. In some embodiments, the crystalline anhydrous form of the compound of Formula (I) is stable upon static storage at about 25° C. at about 97% relative humidity for at least 2 weeks. In some embodiments, the crystalline anhydrous form of the compound of Formula (I) is stable upon static storage at about 25° C. at about 97% relative humidity for at least 3 weeks. In some embodiments, the crystalline anhydrous form of the compound of Formula (I) is stable upon static storage at about 25° C. at about 97% relative humidity for at least 4 weeks. In some embodiments, the crystalline anhydrous form of the compound of Formula (I) is stable upon static storage at about 25° C. at about 97% relative humidity for at least 1 month. In some embodiments, the crystalline anhydrous form of the compound of Formula (I) is stable upon static storage at about 25° C. at about 97% relative humidity for at least 2 months. In some embodiments, the crystalline anhydrous form of the compound of Formula (I) is stable upon static storage at about 25° C. at about 97% relative humidity for at least 3 months. In some embodiments, the crystalline anhydrous form of the compound of Formula (I) is stable upon static storage at about 25° C. at about 97% relative humidity for at least 4 months. In some embodiments, the crystalline anhydrous form of the compound of Formula (I) is stable upon static storage at about 25° C. at about 97% relative humidity for at least 5 months. In some embodiments, the crystalline anhydrous form of the compound of Formula (I) is stable upon static storage at about 25° C. at about 97% relative humidity for at least 6 months. In some embodiments, the crystalline anhydrous form of the compound of Formula (I) is stable upon static storage at about 25° C. at about 97% relative humidity for at least 12 months. In some embodiments, the crystalline anhydrous form of the compound of Formula (I) is stable upon static storage at about 25° C. at about 97% relative humidity for at least 24 months.

In some embodiments, the crystalline anhydrous form of the compound of Formula (I) is stable upon static storage at about 40° C. at about 75% relative humidity for at least 1 week. In some embodiments, the crystalline anhydrous form of the compound of Formula (I) is stable upon static storage at about 40° C. at about 75% relative humidity for at least 2 weeks. In some embodiments, the crystalline anhydrous form of the compound of Formula (I) is stable upon static storage at about 40° C. at about 75% relative humidity for at least 3 weeks. In some embodiments, the crystalline anhydrous form of the compound of Formula (I) is stable upon static storage at about 40° C. at about 75% relative humidity for at least 4 weeks. In some embodiments, the crystalline anhydrous form of the compound of Formula (I) is stable upon static storage at about 40° C. at about 75% relative humidity for at least 1 month. In some embodiments, the crystalline anhydrous form of the compound of Formula (I) is stable upon static storage at about 40° C. at about 75% relative humidity for at least 2 months. In some embodiments, the crystalline anhydrous form of the compound of Formula (I) is stable upon static storage at about 40° C. at about 75% relative humidity for at least 3 months. In some embodiments, the crystalline anhydrous form of the compound of Formula (I) is stable upon static storage at about 40° C. at about 75% relative humidity for at least 4 months. In some embodiments, the crystalline anhydrous form of the compound of Formula (I) is stable upon static storage at about 40° C. at about 75% relative humidity for at least 5 months. In some embodiments, the crystalline anhydrous form of the compound of Formula (I) is stable upon static storage at about 40° C. at about 75% relative humidity for at least 6 months. In some embodiments, the crystalline anhydrous form of the compound of Formula (I) is stable upon static storage at about 40° C. at about 75% relative humidity for at least 12 months. In some embodiments, the crystalline anhydrous form of the compound of Formula (I) is stable upon static storage at about 40° C. at about 75% relative humidity for at least 24 months.

In some embodiments, provided herein is a stable pharmaceutically acceptable unit formulation comprising the crystalline dihydrate form of the compound of Formula (I) and one or more pharmaceutically acceptable excipients.

In another embodiment, provided herein is a stable pharmaceutically acceptable unit formulation comprising the crystalline anhydrous form of the compound of Formula (I) and one or more pharmaceutically acceptable excipients.

In some embodiments, provided herein is a stable pharmaceutically acceptable unit formulation consisting essentially of the crystalline dihydrate form of the compound of Formula (I) and one or more pharmaceutically acceptable excipients.

In another embodiment, provided herein is a stable pharmaceutically acceptable unit formulation consisting essentially of the crystalline anhydrous form of the compound of Formula (I) and one or more pharmaceutically acceptable excipients.

In some embodiments, provided herein is a stable oral dosage form comprising the crystalline dihydrate form of the compound of Formula (I) and one or more pharmaceutically acceptable excipients.

In another embodiment, provided herein is a stable oral dosage form comprising the crystalline anhydrous form of the compound of Formula (I) and one or more pharmaceutically acceptable excipients.

In some embodiments, provided herein is a stable oral dosage form consisting essentially of the crystalline dihydrate form of the compound of Formula (I) and one or more pharmaceutically acceptable excipients.

In another embodiment, provided herein is a stable oral dosage form consisting essentially of the crystalline anhydrous form of the compound of Formula (I) and one or more pharmaceutically acceptable excipients.

In some embodiments, provided herein is a stable pharmaceutically acceptable capsule comprising the crystalline dihydrate form of the compound of Formula (I) and one or more pharmaceutically acceptable excipients.

In another embodiment, provided herein is a stable pharmaceutically acceptable capsule comprising the crystalline anhydrous form of the compound of Formula (I) and one or more pharmaceutically acceptable excipients.

In some embodiments, provided herein is a stable pharmaceutically acceptable capsule consisting essentially of the crystalline dihydrate form of the compound of Formula (I) and one or more pharmaceutically acceptable excipients.

In another embodiment, provided herein is a stable pharmaceutically acceptable capsule consisting essentially of the crystalline anhydrous form of the compound of Formula (I) and one or more pharmaceutically acceptable excipients.

Also provided herein is a pharmaceutically acceptable unit formulation, the pharmaceutically acceptable unit formulation comprising:

(a) about 1% by weight to about 70% by weight, based on the weight of the pharmaceutically acceptable unit formulation, of a compound of Formula (I):

Formula (I)

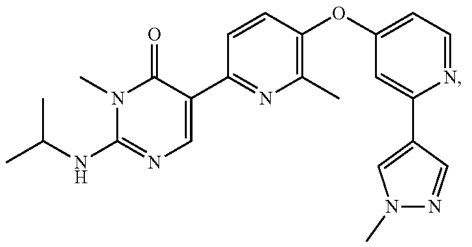

wherein the compound is present in the pharmaceutically acceptable formulation as a free base, a pharmaceutically acceptable salt of the compound and wherein the free base or pharmaceutically acceptable salt is in anhydrous or hydrate form, and one or more pharmaceutically acceptable excipients, wherein the one or more pharmaceutically acceptable excipients comprise:

(b) about 20% by weight to about 97% by weight of one or more fillers, based on the weight of the pharmaceutically acceptable unit formulation;

(c) about 1% by weight to about 20% by weight of one or more disintegrants, based on the weight of the pharmaceutically acceptable unit formulation; and (d) about 0.1% by weight to about 10% by weight of one or more lubricants, based on the weight of the pharmaceutically acceptable unit formulation, made by the process comprising:

(i) blending the compound represented by Formula (I) with the one or more fillers and one or more disintegrants to produce a first blend; and (ii) blending the first blend with the one or more lubricants, thereby preparing the pharmaceutically acceptable unit formulation.

Also provided herein is a pharmaceutically acceptable unit formulation, the pharmaceutically acceptable unit formulation consisting essentially of:

(a) about 1% by weight to about 70% by weight, based on the weight of the pharmaceutically acceptable unit formulation, of a compound of Formula (I):

Formula (I)

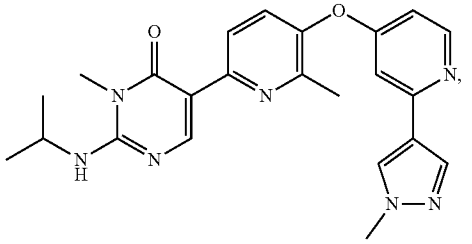

wherein the compound is present in the pharmaceutically acceptable formulation as a free base, a pharmaceutically acceptable salt of the compound and wherein the free base or pharmaceutically acceptable salt is in anhydrous or hydrate form, and one or more pharmaceutically acceptable excipients, wherein the one or more pharmaceutically acceptable excipients comprise:

(b) about 20% by weight to about 97% by weight of one or more fillers, based on the weight of the pharmaceutically acceptable unit formulation;

(c) about 1% by weight to about 20% by weight of one or more disintegrants, based on the weight of the pharmaceutically acceptable unit formulation; and (d) about 0.1% by weight to about 10% by weight of one or more lubricants, based on the weight of the pharmaceutically acceptable unit formulation, made by the process comprising:

(i) blending the compound represented by Formula (I) with the one or more fillers and one or more disintegrants to produce a first blend; and (ii) blending the first blend with the one or more lubricants, thereby preparing the pharmaceutically acceptable unit formulation.

Also provided herein is a pharmaceutically acceptable unit formulation, the pharmaceutically acceptable unit formulation comprising:

(a) about 1% by weight to about 70% by weight, based on the weight of the pharmaceutically acceptable unit formulation, of a compound of Formula (I):

Formula (I)

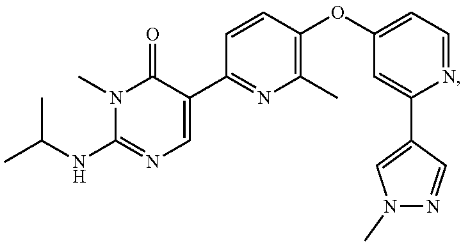

wherein the compound is present in the pharmaceutically acceptable formulation as a free base, a pharmaceutically acceptable salt of the compound and wherein the free base or pharmaceutically acceptable salt is in anhydrous or hydrate form, and one or more pharmaceutically acceptable excipients, wherein the one or more pharmaceutically acceptable excipients comprise:

(b) about 20% by weight to about 97% by weight of one or more fillers, based on the weight of the pharmaceutically acceptable unit formulation;

(c) about 1% by weight to about 20% by weight of one or more disintegrants, based on the weight of the pharmaceutically acceptable unit formulation; and (d) about 0.1% by weight to about 10% by weight of one or more lubricants, based on the weight of the pharmaceutically acceptable unit formulation, made by the process comprising:

(i) blending the compound represented by Formula (I) with the one or more fillers to produce a first blend;

(ii) blending the first blend with one or more disintegrants to produce a second blend; and (iii) blending the second blend with the one or more lubricants, thereby preparing the pharmaceutically acceptable unit formulation.

Also provided herein is a pharmaceutically acceptable unit formulation, the pharmaceutically acceptable unit formulation consisting essentially of:

(a) about 1% by weight to about 70% by weight, based on the weight of the pharmaceutically acceptable unit formulation, of a compound of Formula (I):

Formula (I)

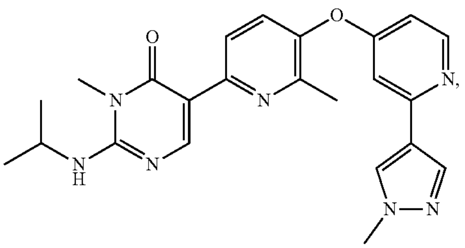

wherein the compound is present in the pharmaceutically acceptable formulation as a free base, a pharmaceutically acceptable salt of the compound and wherein the free base or pharmaceutically acceptable salt is in anhydrous or hydrate form, and one or more pharmaceutically acceptable excipients, wherein the one or more pharmaceutically acceptable excipients comprise:

(b) about 20% by weight to about 97% by weight of one or more fillers, based on the weight of the pharmaceutically acceptable unit formulation;

(c) about 1% by weight to about 20% by weight of one or more disintegrants, based on the weight of the pharmaceutically acceptable unit formulation; and (d) about 0.1% by weight to about 10% by weight of one or more lubricants, based on the weight of the pharmaceutically acceptable unit formulation, made by the process comprising:

(i) blending the compound represented by Formula (I) with the one or more fillers to produce a first blend;

(ii) blending the first blend with one or more disintegrants to produce a second blend; and (iii) blending the second blend with the one or more lubricants, thereby preparing the pharmaceutically acceptable unit formulation.

Also provided herein is a pharmaceutically acceptable unit formulation, the pharmaceutically acceptable unit formulation comprising:

(a) about 1% by weight to about 70% by weight, based on the weight of the pharmaceutically acceptable unit formulation of a compound of Formula (I):

Formula (I)

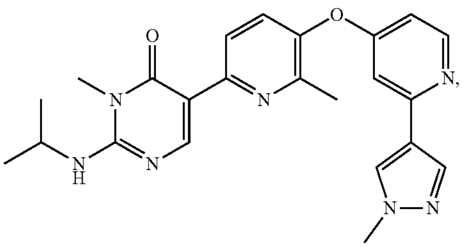

wherein the compound is present in the pharmaceutically acceptable formulation as a free base, a pharmaceutically acceptable salt of the compound and wherein the free base or pharmaceutically acceptable salt is in anhydrous or hydrate form, and one or more pharmaceutically acceptable excipients, wherein the one or more pharmaceutically acceptable excipients comprise:

(b) about 20% by weight to about 97% by weight of one or more fillers, based on the weight of the pharmaceutically acceptable unit formulation;

(c) about 1% by weight to about 20% by weight of one or more disintegrants, based on the weight of the pharmaceutically acceptable unit formulation; and (d) about 0.1% by weight to about 10% by weight of one or more lubricants, based on the weight of the pharmaceutically acceptable unit formulation, made by the process comprising:

(i) blending the compound represented by Formula (I) with the one or more fillers to produce a first blend;

(ii) blending the first blend with a second blend comprising one or more disintegrants and one or more fillers and optionally a third blend comprising one or more fillers to produce a fourth blend; and (iii) blending the fourth blend with the one or more lubricants, thereby preparing the pharmaceutically acceptable unit formulation.

Also provided herein is a pharmaceutically acceptable unit formulation, the pharmaceutically acceptable unit formulation consisting essentially of:

(a) about 1% by weight to about 70% by weight, based on the weight of the pharmaceutically acceptable unit formulation of a compound of Formula (I):

Formula (I)

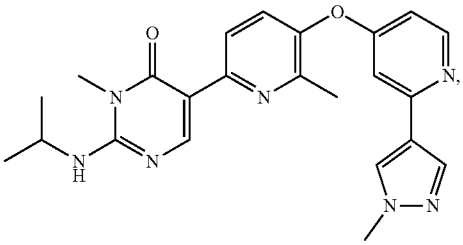

wherein the compound is present in the pharmaceutically acceptable formulation as a free base, a pharmaceutically acceptable salt of the compound and wherein the free base or pharmaceutically acceptable salt is in anhydrous or hydrate form, and one or more pharmaceutically acceptable excipients, wherein the one or more pharmaceutically acceptable excipients comprise:

(b) about 20% by weight to about 97% by weight of one or more fillers, based on the weight of the pharmaceutically acceptable unit formulation;

(c) about 1% by weight to about 20% by weight of one or more disintegrants, based on the weight of the pharmaceutically acceptable unit formulation; and (d) about 0.1% by weight to about 10% by weight of one or more lubricants, based on the weight of the pharmaceutically acceptable unit formulation, made by the process comprising:

(i) blending the compound represented by Formula (I) with the one or more fillers to produce a first blend;

(ii) blending the first blend with a second blend comprising one or more disintegrants and one or more fillers and optionally a third blend comprising one or more fillers to produce a fourth blend; and (iii) blending the fourth blend with the one or more lubricants, thereby preparing the pharmaceutically acceptable unit formulation.

Also provided herein is a pharmaceutically acceptable unit formulation, the pharmaceutically acceptable unit formulation comprising:

(a) about 1% by weight to about 70% by weight, based on the weight of the pharmaceutically acceptable unit formulation, of a crystalline dihydrate form of a compound of Formula (I):

Formula (I)

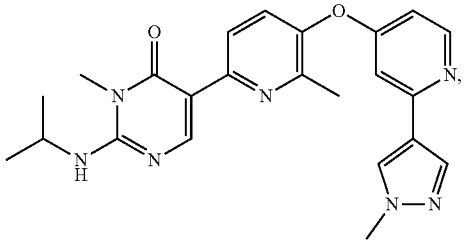

and one or more pharmaceutically acceptable excipients, wherein the one or more pharmaceutically acceptable excipients comprise:

(b) about 20% by weight to about 97% by weight of one or more fillers, based on the weight of the pharmaceutically acceptable unit formulation;

(c) about 1% by weight to about 20% by weight of one or more disintegrants, based on the weight of the pharmaceutically acceptable unit formulation; and (d) about 0.1% by weight to about 10% by weight of one or more lubricants, based on the weight of the pharmaceutically acceptable unit formulation, made by the process comprising:

(i) blending the crystalline dihydrate form of a compound represented by Formula (I) with the one or more fillers and one or more disintegrants to produce a first blend; and (ii) blending the first blend with the one or more lubricants, thereby preparing the pharmaceutically acceptable unit formulation.

Also provided herein is a pharmaceutically acceptable unit formulation, the pharmaceutically acceptable unit formulation consisting essentially of:

(a) about 1% by weight to about 70% by weight, based on the weight of the pharmaceutically acceptable unit formulation, of a crystalline dihydrate form of a compound of Formula (I):

Formula (I)

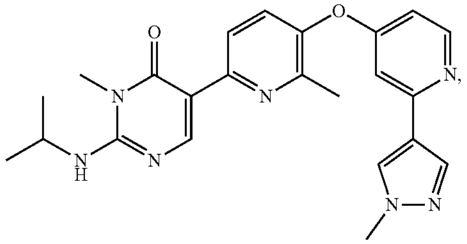

and one or more pharmaceutically acceptable excipients, wherein the one or more pharmaceutically acceptable excipients comprise:

(b) about 20% by weight to about 97% by weight of one or more fillers, based on the weight of the pharmaceutically acceptable unit formulation;
(c) about 1% by weight to about 20% by weight of one or more disintegrants, based on the weight of the pharmaceutically acceptable unit formulation; and
(d) about 0.1% by weight to about 10% by weight of one or more lubricants, based on the weight of the pharmaceutically acceptable unit formulation, made by the process comprising:
(i) blending the crystalline dihydrate form of a compound represented by Formula (I) with the one or more fillers and one or more disintegrants to produce a first blend; and
(ii) blending the first blend with the one or more lubricants, thereby preparing the pharmaceutically acceptable unit formulation.

Also provided herein is a pharmaceutically acceptable unit formulation, the pharmaceutically acceptable unit formulation comprising:
(a) about 1% by weight to about 70% by weight, based on the weight of the pharmaceutically acceptable unit formulation of a crystalline dihydrate form of a compound of Formula (I):

Formula (I)

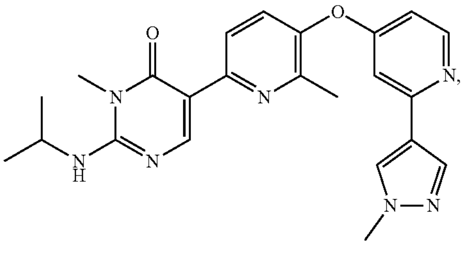

and one or more pharmaceutically acceptable excipients, wherein the one or more pharmaceutically acceptable excipients comprise:
(b) about 20% by weight to about 97% by weight of one or more fillers, based on the weight of the pharmaceutically acceptable unit formulation;
(c) about 1% by weight to about 20% by weight of one or more disintegrants, based on the weight of the pharmaceutically acceptable unit formulation; and
(d) about 0.1% by weight to about 10% by weight of one or more lubricants, based on the weight of the pharmaceutically acceptable unit formulation, made by the process comprising:
(i) blending the crystalline dihydrate form of a compound represented by Formula (I) with the one or more fillers to produce a first blend;
(ii) blending the first blend with one or more disintegrants to produce a second blend; and
(iii) blending the second blend with the one or more lubricants, thereby preparing the pharmaceutically acceptable unit formulation.

Also provided herein is a pharmaceutically acceptable unit formulation, the pharmaceutically acceptable unit formulation consisting essentially of:
(a) about 1% by weight to about 70% by weight, based on the weight of the pharmaceutically acceptable unit formulation of a crystalline dihydrate form of a compound of Formula (I):

Formula (I)

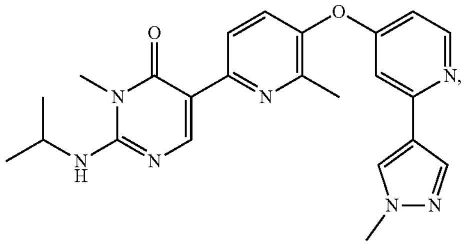

and one or more pharmaceutically acceptable excipients, wherein the one or more pharmaceutically acceptable excipients comprise:
(b) about 20% by weight to about 97% by weight of one or more fillers, based on the weight of the pharmaceutically acceptable unit formulation;
(c) about 1% by weight to about 20% by weight of one or more disintegrants, based on the weight of the pharmaceutically acceptable unit formulation; and
(d) about 0.1% by weight to about 10% by weight of one or more lubricants, based on the weight of the pharmaceutically acceptable unit formulation, made by the process comprising:
(i) blending the crystalline dihydrate form of a compound represented by Formula (I) with the one or more fillers to produce a first blend;
(ii) blending the first blend with one or more disintegrants to produce a second blend; and
(iii) blending the second blend with the one or more lubricants, thereby preparing the pharmaceutically acceptable unit formulation.

Also provided herein is a pharmaceutically acceptable unit formulation, the pharmaceutically acceptable unit formulation comprising:
(a) about 1% by weight to about 70% by weight, based on the weight of the pharmaceutically acceptable unit formulation of a crystalline dihydrate form of a compound of Formula (I):

Formula (I)

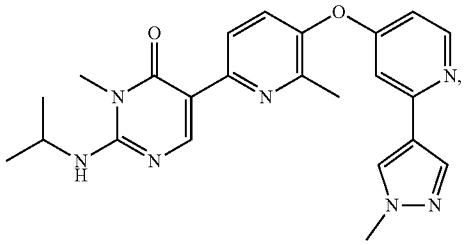

and one or more pharmaceutically acceptable excipients, wherein the one or more pharmaceutically acceptable excipients comprise:
(b) about 20% by weight to about 97% by weight of one or more fillers, based on the weight of the pharmaceutically acceptable unit formulation;
(c) about 1% by weight to about 20% by weight of one or more disintegrants, based on the weight of the pharmaceutically acceptable unit formulation; and
(d) about 0.1% by weight to about 10% by weight of one or more lubricants, based on the weight of the pharmaceutically acceptable unit formulation, made by the process comprising:

(i) blending the crystalline dihydrate form of a compound represented by Formula (I) with the one or more fillers to produce a first blend;

(ii) blending the first blend with a second blend comprising one or more disintegrants and one or more fillers and optionally a third blend comprising one or more fillers to produce a fourth blend; and (iii) blending the fourth blend with the one or more lubricants, thereby preparing the pharmaceutically acceptable unit formulation.

Also provided herein is a pharmaceutically acceptable unit formulation, the pharmaceutically acceptable unit formulation consisting essentially of:

(a) about 1% by weight to about 70% by weight, based on the weight of the pharmaceutically acceptable unit formulation of a crystalline dihydrate form of a compound of Formula (I):

Formula (I)

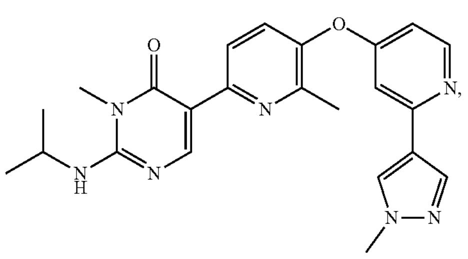

and one or more pharmaceutically acceptable excipients, wherein the one or more pharmaceutically acceptable excipients comprise:

(b) about 20% by weight to about 97% by weight of one or more fillers, based on the weight of the pharmaceutically acceptable unit formulation;

(c) about 1% by weight to about 20% by weight of one or more disintegrants, based on the weight of the pharmaceutically acceptable unit formulation; and (d) about 0.1% by weight to about 10% by weight of one or more lubricants, based on the weight of the pharmaceutically acceptable unit formulation, made by the process comprising:

(i) blending the crystalline dihydrate form of a compound represented by Formula (I) with the one or more fillers to produce a first blend;

(ii) blending the first blend with a second blend comprising one or more disintegrants and one or more fillers and optionally a third blend comprising one or more fillers to produce a fourth blend; and (iii) blending the fourth blend with the one or more lubricants, thereby preparing the pharmaceutically acceptable unit formulation.

Also provided herein is an oral dosage form, the oral dosage form comprising:

(a) about 1% by weight to about 70% by weight, based on the total weight of the oral dosage form, of a compound of Formula (I):

Formula (I)

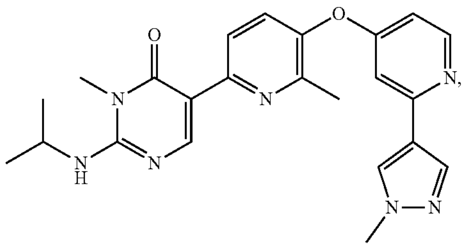

wherein the compound is present in the oral dosage form as a free base, a pharmaceutically acceptable salt of the compound and wherein the free base or pharmaceutically acceptable salt is in anhydrous or hydrate form, and one or more pharmaceutically acceptable excipients, wherein the one or more pharmaceutically acceptable excipients comprise:

(b) about 20% by weight to about 97% by weight of one or more fillers, based on the total weight of the oral dosage form;

(c) about 1% by weight to about 20% by weight of one or more disintegrants, based on the total weight of the oral dosage form; and (d) about 0.1% by weight to about 10% by weight of one or more lubricants, based on the total weight of the oral dosage form, made by the process comprising:

(i) blending the compound represented by Formula (I) with the one or more fillers and one or more disintegrants to produce a first blend; and (ii) blending the first blend with the one or more lubricants, thereby preparing the oral dosage form.

Also provided herein is an oral dosage form, the oral dosage form consisting essentially of:

(a) about 1% by weight to about 70% by weight, based on the total weight of the oral dosage form, of a compound of Formula (I):

Formula (I)

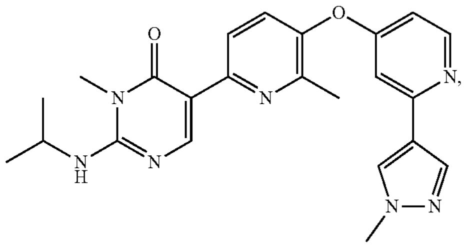

wherein the compound is present in the oral dosage form as a free base, a pharmaceutically acceptable salt of the compound and wherein the free base or pharmaceutically acceptable salt is in anhydrous or hydrate form, and one or more pharmaceutically acceptable excipients, wherein the one or more pharmaceutically acceptable excipients comprise:

(b) about 20% by weight to about 97% by weight of one or more fillers, based on the total weight of the oral dosage form;

(c) about 1% by weight to about 20% by weight of one or more disintegrants, based on the total weight of the oral dosage form; and (d) about 0.1% by weight to about 10% by weight of one or more lubricants, based on the total weight of the oral dosage form, made by the process comprising:

(i) blending the compound represented by Formula (I) with the one or more fillers and one or more disintegrants to produce a first blend; and (ii) blending the first blend with the one or more lubricants, thereby preparing the oral dosage form.

Also provided herein is an oral dosage form, the oral dosage form comprising:

(a) about 1% by weight to about 70% by weight, based on the total weight of the oral dosage form, of a compound of Formula (I):

Formula (I)

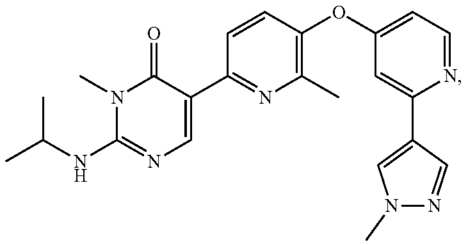

wherein the compound is present in the oral dosage form as a free base, a pharmaceutically acceptable salt of the compound and wherein the free base or pharmaceutically acceptable salt is in anhydrous or hydrate form, and one or more pharmaceutically acceptable excipients, wherein the one or more pharmaceutically acceptable excipients comprise:

(b) about 20% by weight to about 97% by weight of one or more fillers, based on the total weight of the oral dosage form;

(c) about 1% by weight to about 20% by weight of one or more disintegrants, based on the total weight of the oral dosage form; and (d) about 0.1% by weight to about 10% by weight of one or more lubricants, based on the total weight of the oral dosage form, made by the process comprising:

(i) blending the compound represented by Formula (I) with the one or more fillers to produce a first blend;

(ii) blending the first blend with one or more disintegrants to produce a second blend; and (iii) blending the second blend with the one or more lubricants, thereby preparing the oral dosage form.

Also provided herein is an oral dosage form, the oral dosage form consisting essentially of:

(a) about 1% by weight to about 70% by weight, based on the total weight of the oral dosage form, of a compound of Formula (I):

Formula (I)

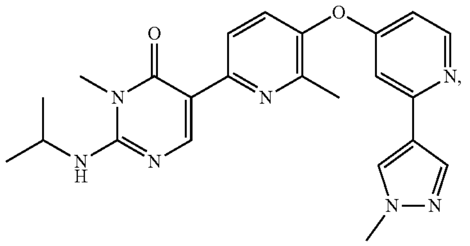

wherein the compound is present in the oral dosage form as a free base, a pharmaceutically acceptable salt of the compound and wherein the free base or pharmaceutically acceptable salt is in anhydrous or hydrate form, and one or more pharmaceutically acceptable excipients, wherein the one or more pharmaceutically acceptable excipients comprise:

(b) about 20% by weight to about 97% by weight of one or more fillers, based on the total weight of the oral dosage form;

(c) about 1% by weight to about 20% by weight of one or more disintegrants, based on the total weight of the oral dosage form; and (d) about 0.1% by weight to about 10% by weight of one or more lubricants, based on the total weight of the oral dosage form, made by the process comprising:

(i) blending the compound represented by Formula (I) with the one or more fillers to produce a first blend;

(ii) blending the first blend with one or more disintegrants to produce a second blend; and (iii) blending the second blend with the one or more lubricants, thereby preparing the oral dosage form.

Also provided herein is an oral dosage form, the oral dosage form comprising:

(a) about 1% by weight to about 70% by weight, based on the total weight of the oral dosage form of a compound of Formula (I):

Formula (I)

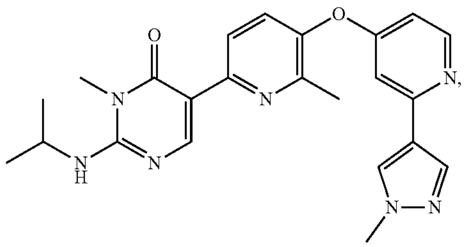

wherein the compound is present in the oral dosage form as a free base, a pharmaceutically acceptable salt of the compound and wherein the free base or pharmaceutically acceptable salt is in anhydrous or hydrate form, and one or more pharmaceutically acceptable excipients, wherein the one or more pharmaceutically acceptable excipients comprise:

(b) about 20% by weight to about 97% by weight of one or more fillers, based on the total weight of the oral dosage form;

(c) about 1% by weight to about 20% by weight of one or more disintegrants, based on the total weight of the oral dosage form; and (d) about 0.1% by weight to about 10% by weight of one or more lubricants, based on the total weight of the oral dosage form, made by the process comprising:

(i) blending the compound represented by Formula (I) with the one or more fillers to produce a first blend;

(ii) blending the first blend with a second blend comprising one or more disintegrants and one or more fillers and optionally a third blend comprising one or more fillers to produce a fourth blend; and (iii) blending the fourth blend with the one or more lubricants, thereby preparing the oral dosage form.

Also provided herein is an oral dosage form, the oral dosage form consisting essentially of:

(a) about 1% by weight to about 70% by weight, based on the total weight of the oral dosage form of a compound of Formula (I):

Formula (I)

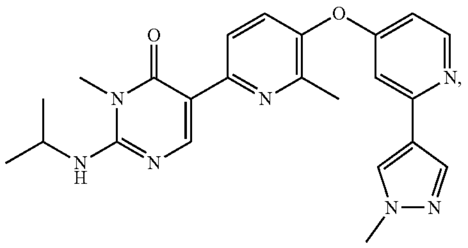

wherein the compound is present in the oral dosage form as a free base, a pharmaceutically acceptable salt of the compound and wherein the free base or pharmaceutically acceptable salt is in anhydrous or hydrate form, and one or more pharmaceutically acceptable excipients, wherein the one or more pharmaceutically acceptable excipients comprise:

(b) about 20% by weight to about 97% by weight of one or more fillers, based on the total weight of the oral dosage form;

(c) about 1% by weight to about 20% by weight of one or more disintegrants, based on the total weight of the oral dosage form; and (d) about 0.1% by weight to about 10% by weight of one or more lubricants, based on the total weight of the oral dosage form, made by the process comprising:

(i) blending the compound represented by Formula (I) with the one or more fillers to produce a first blend;

(ii) blending the first blend with a second blend comprising one or more disintegrants and one or more fillers and optionally a third blend comprising one or more fillers to produce a fourth blend; and (iii) blending the fourth blend with the one or more lubricants, thereby preparing the oral dosage form.

Also provided herein is an oral dosage form, the oral dosage form comprising:

(a) about 1% by weight to about 70% by weight, based on the total weight of the oral dosage form, of a crystalline dihydrate form of a compound of Formula (I):

Formula (I)

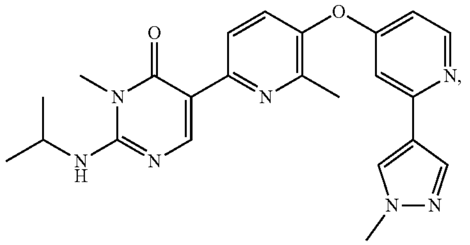

and one or more pharmaceutically acceptable excipients, wherein the one or more pharmaceutically acceptable excipients comprise:

(b) about 20% by weight to about 97% by weight of one or more fillers, based on the total weight of the oral dosage form;

(c) about 1% by weight to about 20% by weight of one or more disintegrants, based on the total weight of the oral dosage form; and (d) about 0.1% by weight to about 10% by weight of one or more lubricants, based on the total weight of the oral dosage form, made by the process comprising:

(i) blending the crystalline dihydrate form of a compound represented by Formula (I) with the one or more fillers and one or more disintegrants to produce a first blend; and (ii) blending the first blend with the one or more lubricants, thereby preparing the oral dosage form.

Also provided herein is an oral dosage form, the oral dosage form consisting essentially of:

(a) about 1% by weight to about 70% by weight, based on the total weight of the oral dosage form, of a crystalline dihydrate form of a compound of Formula (I):

Formula (I)

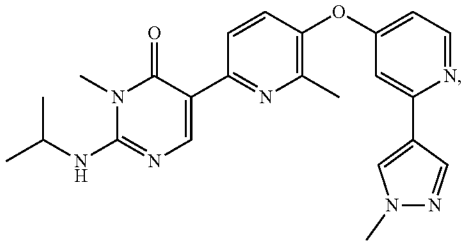

and one or more pharmaceutically acceptable excipients, wherein the one or more pharmaceutically acceptable excipients comprise:

(b) about 20% by weight to about 97% by weight of one or more fillers, based on the total weight of the oral dosage form;

(c) about 1% by weight to about 20% by weight of one or more disintegrants, based on the total weight of the oral dosage form; and (d) about 0.1% by weight to about 10% by weight of one or more lubricants, based on the total weight of the oral dosage form, made by the process comprising:

(i) blending the crystalline dihydrate form of a compound represented by Formula (I) with the one or more fillers and one or more disintegrants to produce a first blend; and (ii) blending the first blend with the one or more lubricants, thereby preparing the oral dosage form.

Also provided herein is an oral dosage form, the oral dosage form comprising:

(a) about 1% by weight to about 70% by weight, based on the total weight of the oral dosage form of a crystalline dihydrate form of a compound of Formula (I):

Formula (I)

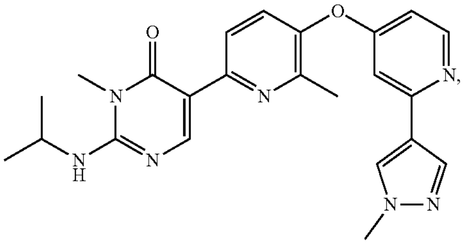

and one or more pharmaceutically acceptable excipients, wherein the one or more pharmaceutically acceptable excipients comprise:

(b) about 20% by weight to about 97% by weight of one or more fillers, based on the total weight of the oral dosage form;

(c) about 1% by weight to about 20% by weight of one or more disintegrants, based on the total weight of the oral dosage form; and (d) about 0.1% by weight to about 10% by weight of one or more lubricants, based on the total weight of the oral dosage form, made by the process comprising:

(i) blending the crystalline dihydrate form of a compound represented by Formula (I) with the one or more fillers to produce a first blend;

(ii) blending the first blend with one or more disintegrants to produce a second blend; and (iii) blending the second blend with the one or more lubricants, thereby preparing the oral dosage form.

Also provided herein is an oral dosage form, the oral dosage form consisting essentially of:

(a) about 1% by weight to about 70% by weight, based on the total weight of the oral dosage form of a crystalline dihydrate form of a compound of Formula (I):

Formula (I)

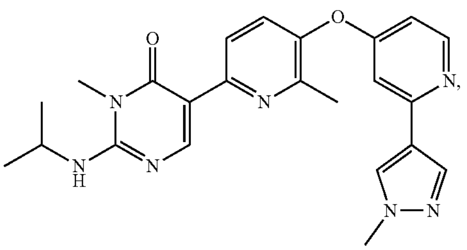

and one or more pharmaceutically acceptable excipients, wherein the one or more pharmaceutically acceptable excipients comprise:

(b) about 20% by weight to about 97% by weight of one or more fillers, based on the total weight of the oral dosage form;

(c) about 1% by weight to about 20% by weight of one or more disintegrants, based on the total weight of the oral dosage form; and (d) about 0.1% by weight to about 10% by weight of one or more lubricants, based on the total weight of the oral dosage form, made by the process comprising:

(i) blending the crystalline dihydrate form of a compound represented by Formula (I) with the one or more fillers to produce a first blend;

(ii) blending the first blend with one or more disintegrants to produce a second blend; and (iii) blending the second blend with the one or more lubricants, thereby preparing the oral dosage form.

Also provided herein is an oral dosage form, the oral dosage form comprising:

(a) about 1% by weight to about 70% by weight, based on the total weight of the oral dosage form of a crystalline dihydrate form of a compound of Formula (I):

Formula (I)

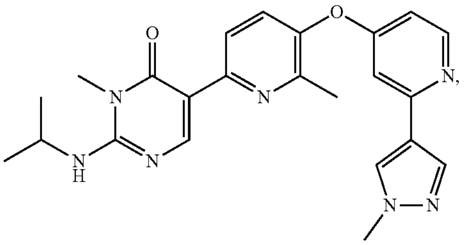

and one or more pharmaceutically acceptable excipients, wherein the one or more pharmaceutically acceptable excipients comprise:

(b) about 20% by weight to about 97% by weight of one or more fillers, based on the total weight of the oral dosage form;

(c) about 1% by weight to about 20% by weight of one or more disintegrants, based on the total weight of the oral dosage form; and (d) about 0.1% by weight to about 10% by weight of one or more lubricants, based on the total weight of the oral dosage form, made by the process comprising:

(i) blending the crystalline dihydrate form of a compound represented by Formula (I) with the one or more fillers to produce a first blend;

(ii) blending the first blend with a second blend comprising one or more disintegrants and one or more fillers and optionally a third blend comprising one or more fillers to produce a fourth blend; and (iii) blending the fourth blend with the one or more lubricants, thereby preparing the oral dosage form.

Also provided herein is an oral dosage form, the oral dosage form consisting essentially of:

(a) about 1% by weight to about 70% by weight, based on the total weight of the oral dosage form of a crystalline dihydrate form of a compound of Formula (I):

Formula (I)

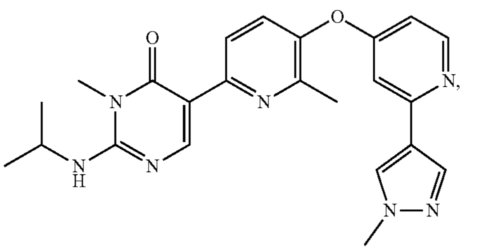

and one or more pharmaceutically acceptable excipients, wherein the one or more pharmaceutically acceptable excipients comprise:

(b) about 20% by weight to about 97% by weight of one or more fillers, based on the total weight of the oral dosage form;
(c) about 1% by weight to about 20% by weight of one or more disintegrants, based on the total weight of the oral dosage form; and
(d) about 0.1% by weight to about 10% by weight of one or more lubricants, based on the total weight of the oral dosage form, made by the process comprising:

(i) blending the crystalline dihydrate form of a compound represented by Formula (I) with the one or more fillers to produce a first blend;
(ii) blending the first blend with a second blend comprising one or more disintegrants and one or more fillers and optionally a third blend comprising one or more fillers to produce a fourth blend; and
(iii) blending the fourth blend with the one or more lubricants, thereby preparing the oral dosage form.

Also provided herein, in some embodiments, is a pharmaceutically acceptable capsule, the pharmaceutically acceptable capsule comprising:

(a) about 1% to about 70%, based on the total weight of the pharmaceutically acceptable capsule, of a compound of Formula (I):

Formula (I)

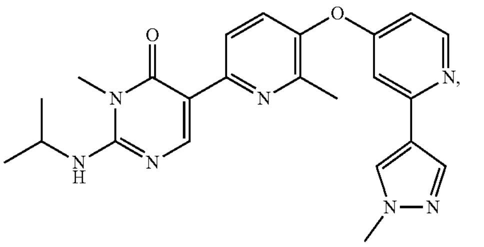

wherein the compound is present in the pharmaceutically acceptable capsule as a free base, or a pharmaceutically acceptable salt of the compound and wherein the free base or pharmaceutically acceptable salt is in anhydrous or hydrate form, and one or more pharmaceutically acceptable excipients, wherein the one or more pharmaceutically acceptable excipients comprise:

(b) about 20% by weight to about 97% by weight of one or more fillers, based on the total weight of the pharmaceutically acceptable capsule;
(c) about 1% by weight to about 20% by weight of one or more disintegrants, based on the total weight of the pharmaceutically acceptable capsule; and
(d) about 0.1% by weight to about 10% by weight of one or more lubricants, based on the total weight of the pharmaceutically acceptable capsule;

made by the process comprising:

(i) blending the compound represented by Formula (I) with the one or more fillers and one or more disintegrants to produce a first blend;
(ii) blending the first blend with the one or more lubricants to form a second blend; and
(iii) dispensing the second blend into an empty pharmaceutically acceptable capsule, thereby forming the pharmaceutically acceptable capsule.

Also provided herein, in some embodiments, is a pharmaceutically acceptable capsule, the pharmaceutically acceptable capsule consisting essentially of:

(a) about 1% to about 70%, based on the total weight of the pharmaceutically acceptable capsule, of a compound of Formula (I):

Formula (I)

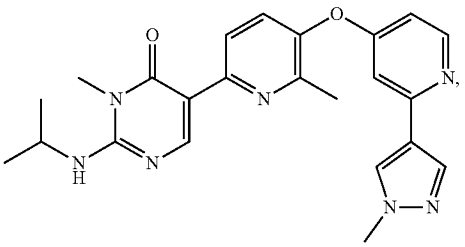

wherein the compound is present in the pharmaceutically acceptable capsule as a free base, or a pharmaceutically acceptable salt of the compound and wherein the free base or pharmaceutically acceptable salt is in anhydrous or hydrate form, and one or more pharmaceutically acceptable excipients, wherein the one or more pharmaceutically acceptable excipients comprise:

(b) about 20% by weight to about 97% by weight of one or more fillers, based on the total weight of the pharmaceutically acceptable capsule;
(c) about 1% by weight to about 20% by weight of one or more disintegrants, based on the total weight of the pharmaceutically acceptable capsule; and
(d) about 0.1% by weight to about 10% by weight of one or more lubricants, based on the total weight of the pharmaceutically acceptable capsule;

made by the process comprising:

(i) blending the compound represented by Formula (I) with the one or more fillers and one or more disintegrants to produce a first blend;
(ii) blending the first blend with the one or more lubricants to form a second blend; and
(iii) dispensing the second blend into an empty pharmaceutically acceptable capsule, thereby forming the pharmaceutically acceptable capsule.

Also provided herein, in some embodiments, is a pharmaceutically acceptable capsule, the pharmaceutically acceptable capsule comprising:

(a) about 1% to about 70%, based on the total weight of the pharmaceutically acceptable capsule, of a compound of Formula (I):

Formula (I)

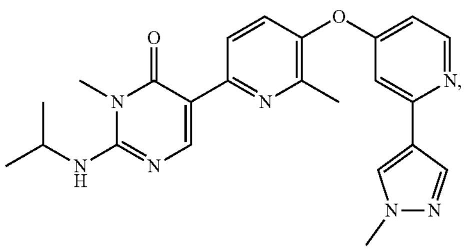

wherein the compound is present in the pharmaceutically acceptable capsule as a free base, or a pharmaceutically acceptable salt of the compound and wherein the free base or pharmaceutically acceptable salt is in anhydrous or hydrate form, and one or more pharmaceutically acceptable excipients, wherein the one or more pharmaceutically acceptable excipients comprise:

(b) about 20% by weight to about 97% by weight of one or more fillers, based on the total weight of the pharmaceutically acceptable capsule;

(c) about 1% by weight to about 20% by weight of one or more disintegrants, based on the total weight of the pharmaceutically acceptable capsule; and (d) about 0.1% by weight to about 10% by weight of one or more lubricants, based on the total weight of the pharmaceutically acceptable capsule;

made by the process comprising:

(i) blending the compound represented by Formula (I) with the one or more fillers to produce a first blend;

(ii) blending the first blend with the one or more disintegrants to form a second blend;

(iii) blending the second blend with the one or more lubricants to form a third blend; and (iv) dispensing the third blend into an empty pharmaceutically acceptable capsule, thereby forming the pharmaceutically acceptable capsule.

Also provided herein, in some embodiments, is a pharmaceutically acceptable capsule, the pharmaceutically acceptable capsule consisting essentially of:

(a) about 1% to about 70%, based on the total weight of the pharmaceutically acceptable capsule, of a compound of Formula (I):

Formula (I)

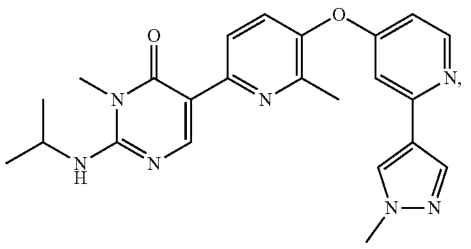

wherein the compound is present in the pharmaceutically acceptable capsule as a free base, or a pharmaceutically acceptable salt of the compound and wherein the free base or pharmaceutically acceptable salt is in anhydrous or hydrate form, and one or more pharmaceutically acceptable excipients, wherein the one or more pharmaceutically acceptable excipients comprise:

(b) about 20% by weight to about 97% by weight of one or more fillers, based on the total weight of the pharmaceutically acceptable capsule;

(c) about 1% by weight to about 20% by weight of one or more disintegrants, based on the total weight of the pharmaceutically acceptable capsule; and (d) about 0.1% by weight to about 10% by weight of one or more lubricants, based on the total weight of the pharmaceutically acceptable capsule;

made by the process comprising:

(i) blending the compound represented by Formula (I) with the one or more fillers to produce a first blend;

(ii) blending the first blend with the one or more disintegrants to form a second blend;

(iii) blending the second blend with the one or more lubricants to form a third blend; and (iv) dispensing the third blend into an empty pharmaceutically acceptable capsule, thereby forming the pharmaceutically acceptable capsule.

Also provided herein, in some embodiments, is a pharmaceutically acceptable capsule, the pharmaceutically acceptable capsule comprising:

(a) about 1% to about 70%, based on the total weight of the pharmaceutically acceptable capsule, of a compound of Formula (I):

Formula (I)

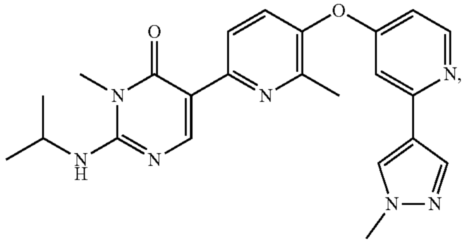

wherein the compound is present in the pharmaceutically acceptable capsule as a free base, or a pharmaceutically acceptable salt of the compound and wherein the free base or pharmaceutically acceptable salt is in anhydrous or hydrate form, and one or more pharmaceutically acceptable excipients, wherein the one or more pharmaceutically acceptable excipients comprise:

(b) about 20% by weight to about 97% by weight of one or more fillers, based on the total weight of the pharmaceutically acceptable capsule;

(c) about 1% by weight to about 20% by weight of one or more disintegrants, based on the total weight of the pharmaceutically acceptable capsule; and (d) about 0.1% by weight to about 10% by weight of one or more lubricants, based on the total weight of the pharmaceutically acceptable capsule;

made by the process comprising:

(i) blending the compound represented by Formula (I) with the one or more fillers to produce a first blend;

(ii) blending the first blend with a second blend comprising one or more disintegrants and one or more fillers and optionally a third blend comprising one or more fillers to form a fourth blend;

(iii) blending the fourth blend with the one or more lubricants to form a fifth blend; and (iv) dispensing the fifth blend into an empty pharmaceutically acceptable capsule, thereby forming the pharmaceutically acceptable capsule.

Also provided herein, in some embodiments, is a pharmaceutically acceptable capsule, the pharmaceutically acceptable capsule consisting essentially of:

(a) about 1% to about 70%, based on the total weight of the pharmaceutically acceptable capsule, of a compound of Formula (I):

Formula (I)

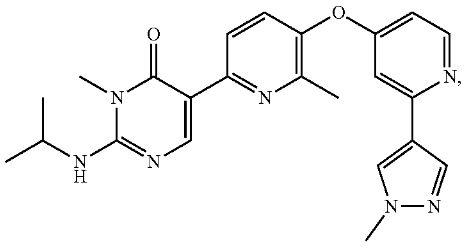

wherein the compound is present in the pharmaceutically acceptable capsule as a free base, or a pharmaceutically acceptable salt of the compound and wherein the free base or pharmaceutically acceptable salt is in anhydrous or hydrate form, and one or more pharmaceutically acceptable excipients, wherein the one or more pharmaceutically acceptable excipients comprise:

(b) about 20% by weight to about 97% by weight of one or more fillers, based on the total weight of the pharmaceutically acceptable capsule;

(c) about 1% by weight to about 20% by weight of one or more disintegrants, based on the total weight of the pharmaceutically acceptable capsule; and (d) about 0.1% by weight to about 10% by weight of one or more lubricants, based on the total weight of the pharmaceutically acceptable capsule;

made by the process comprising:

(i) blending the compound represented by Formula (I) with the one or more fillers to produce a first blend;

(ii) blending the first blend with a second blend comprising one or more disintegrants and one or more fillers and optionally a third blend comprising one or more fillers to form a fourth blend;

(iii) blending the fourth blend with the one or more lubricants to form a fifth blend; and (iv) dispensing the fifth blend into an empty pharmaceutically acceptable capsule, thereby forming the pharmaceutically acceptable capsule.

Also provided herein, in some embodiments, is a pharmaceutically acceptable capsule, the pharmaceutically acceptable capsule comprising:

(a) about 1% to about 70%, based on the total weight of the pharmaceutically acceptable capsule, of a crystalline dihydrate form of a compound of Formula (I):

Formula (I)

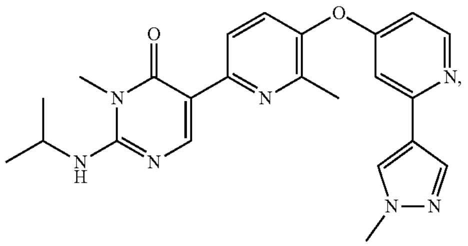

and one or more pharmaceutically acceptable excipients, wherein the one or more pharmaceutically acceptable excipients comprise:

(b) about 20% by weight to about 97% by weight of one or more fillers, based on the total weight of the pharmaceutically acceptable capsule;

(c) about 1% by weight to about 20% by weight of one or more disintegrants, based on the total weight of the pharmaceutically acceptable capsule; and (d) about 0.1% by weight to about 10% by weight of one or more lubricants, based on the total weight of the pharmaceutically acceptable capsule;

made by the process comprising:

(i) blending the crystalline dihydrate form of a compound represented by Formula (I) with the one or more fillers and one or more disintegrants to produce a first blend;

(ii) blending the first blend with the one or more lubricants to form a second blend; and (iii) dispensing the second blend into an empty pharmaceutically acceptable capsule, thereby forming the pharmaceutically acceptable capsule.

Also provided herein, in some embodiments, is a pharmaceutically acceptable capsule, the pharmaceutically acceptable capsule consisting essentially of:

(a) about 1% to about 70%, based on the total weight of the pharmaceutically acceptable capsule, of a crystalline dihydrate form of a compound of Formula (I):

Formula (I)

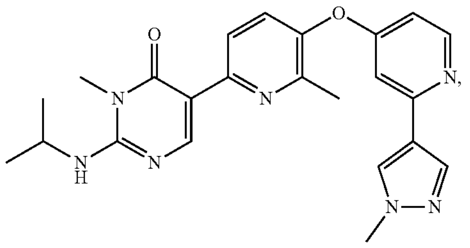

and one or more pharmaceutically acceptable excipients, wherein the one or more pharmaceutically acceptable excipients comprise:

(b) about 20% by weight to about 97% by weight of one or more fillers, based on the total weight of the pharmaceutically acceptable capsule;

(c) about 1% by weight to about 20% by weight of one or more disintegrants, based on the total weight of the pharmaceutically acceptable capsule; and (d) about 0.1% by weight to about 10% by weight of one or more lubricants, based on the total weight of the pharmaceutically acceptable capsule;

made by the process comprising:

(i) blending the crystalline dihydrate form of a compound represented by Formula (I) with the one or more fillers and one or more disintegrants to produce a first blend;

ii) blending the first blend with the one or more lubricants to form a second blend; and (iii) dispensing the second blend into an empty pharmaceutically acceptable capsule, thereby forming the pharmaceutically acceptable capsule.

Also provided herein, in some embodiments, is a pharmaceutically acceptable capsule, the pharmaceutically acceptable capsule comprising:

(a) about 1% to about 70%, based on the total weight of the pharmaceutically acceptable capsule, of a crystalline dihydrate form of a compound of Formula (I):

Formula (I)

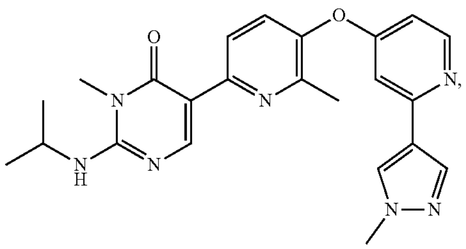

and one or more pharmaceutically acceptable excipients, wherein the one or more pharmaceutically acceptable excipients comprise:

(b) about 20% by weight to about 97% by weight of one or more fillers, based on the total weight of the pharmaceutically acceptable capsule;

(c) about 1% by weight to about 20% by weight of one or more disintegrants, based on the total weight of the pharmaceutically acceptable capsule; and (d) about 0.1% by weight to about 10% by weight of one or more lubricants, based on the total weight of the pharmaceutically acceptable capsule;

made by the process comprising:

(i) blending the crystalline dihydrate form of a compound represented by Formula (I) with the one or more fillers to produce a first blend;

(ii) blending the first blend with the one or more disintegrants to form a second blend;

(iii) blending the second blend with the one or more lubricants to form a third blend; and (iv) dispensing the third blend into an empty pharmaceutically acceptable capsule, thereby forming the pharmaceutically acceptable capsule.

Also provided herein, in some embodiments, is a pharmaceutically acceptable capsule, the pharmaceutically acceptable capsule consisting essentially of:

(a) about 1% to about 70%, based on the total weight of the pharmaceutically acceptable capsule, of a crystalline dihydrate form of a compound of Formula (I):

Formula (I)

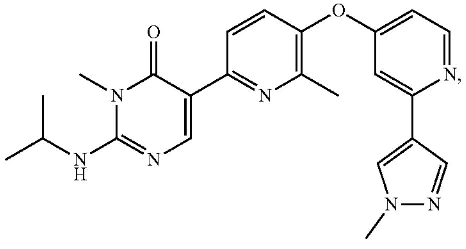

and one or more pharmaceutically acceptable excipients, wherein the one or more pharmaceutically acceptable excipients comprise:

(b) about 20% by weight to about 97% by weight of one or more fillers, based on the total weight of the pharmaceutically acceptable capsule;

(c) about 1% by weight to about 20% by weight of one or more disintegrants, based on the total weight of the pharmaceutically acceptable capsule; and (d) about 0.1% by weight to about 10% by weight of one or more lubricants, based on the total weight of the pharmaceutically acceptable capsule;

made by the process comprising:

(i) blending the crystalline dihydrate form of a compound represented by Formula (I) with the one or more fillers to produce a first blend;

(ii) blending the first blend with the one or more disintegrants to form a second blend;

(iii) blending the second blend with the one or more lubricants to form a third blend; and (iv) dispensing the third blend into an empty pharmaceutically acceptable capsule, thereby forming the pharmaceutically acceptable capsule.

Also provided herein, in some embodiments, is a pharmaceutically acceptable capsule, the pharmaceutically acceptable capsule comprising:

(a) about 1% to about 70%, based on the total weight of the pharmaceutically acceptable capsule, of a crystalline dihydrate form of a compound of Formula (I):

Formula (I)

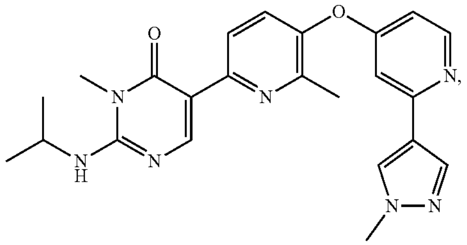

and one or more pharmaceutically acceptable excipients, wherein the one or more pharmaceutically acceptable excipients comprise:

(b) about 20% by weight to about 97% by weight of one or more fillers, based on the total weight of the pharmaceutically acceptable capsule;

(c) about 1% by weight to about 20% by weight of one or more disintegrants, based on the total weight of the pharmaceutically acceptable capsule; and (d) about 0.1% by weight to about 10% by weight of one or more lubricants, based on the total weight of the pharmaceutically acceptable capsule;

made by the process comprising:

(i) blending the crystalline dihydrate form of a compound represented by Formula (I) with the one or more fillers to produce a first blend;

(ii) blending the first blend with a second blend comprising one or more disintegrants and one or more fillers and optionally a third blend comprising one or more fillers to form a fourth blend;

(iii) blending the fourth blend with the one or more lubricants to form a fifth blend; and (iv) dispensing the fifth blend into an empty pharmaceutically acceptable capsule, thereby forming the pharmaceutically acceptable capsule.

Also provided herein, in some embodiments, is a pharmaceutically acceptable capsule, the pharmaceutically acceptable capsule consisting essentially of:

(a) about 1% to about 70%, based on the total weight of the pharmaceutically acceptable capsule, of a crystalline dihydrate form of a compound of Formula (I):

Formula (I)

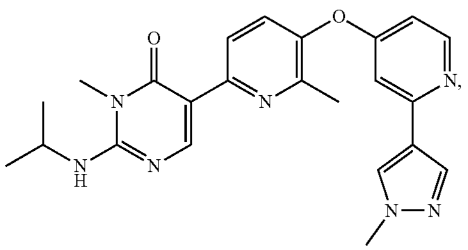

and one or more pharmaceutically acceptable excipients, wherein the one or more pharmaceutically acceptable excipients comprise:

(b) about 20% by weight to about 97% by weight of one or more fillers, based on the total weight of the pharmaceutically acceptable capsule;

(c) about 1% by weight to about 20% by weight of one or more disintegrants, based on the total weight of the pharmaceutically acceptable capsule; and (d) about 0.1% by weight to about 10% by weight of one or more lubricants, based on the total weight of the pharmaceutically acceptable capsule;

made by the process comprising:

(i) blending the crystalline dihydrate form of a compound represented by Formula (I) with the one or more fillers to produce a first blend;

(ii) blending the first blend with a second blend comprising one or more disintegrants and one or more fillers and optionally a third blend comprising one or more fillers to form a fourth blend;

(iii) blending the fourth blend with the one or more lubricants to form a fifth blend; and (iv) dispensing the fifth blend into an empty pharmaceutically acceptable capsule, thereby forming the pharmaceutically acceptable capsule.

Also provided herein is a pharmaceutically acceptable unit formulation, the pharmaceutically acceptable unit formulation comprising:

(a) about 1% by weight to about 70% by weight, based on the weight of the pharmaceutically acceptable unit formulation, of a crystalline anhydrous form of a compound of Formula (I):

Formula (I)

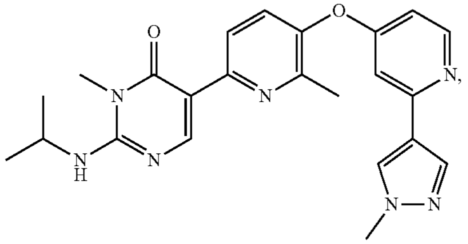

and one or more pharmaceutically acceptable excipients, wherein the one or more pharmaceutically acceptable excipients comprise:

(b) about 20% by weight to about 97% by weight of one or more fillers, based on the weight of the pharmaceutically acceptable unit formulation;

(c) about 1% by weight to about 20% by weight of one or more disintegrants, based on the weight of the pharmaceutically acceptable unit formulation; and (d) about 0.1% by weight to about 10% by weight of one or more lubricants, based on the weight of the pharmaceutically acceptable unit formulation, made by the process comprising:

(i) blending the crystalline anhydrous form of a compound represented by Formula (I) with the one or more fillers and one or more disintegrants to produce a first blend; and (ii) blending the first blend with the one or more lubricants, thereby preparing the pharmaceutically acceptable unit formulation.

Also provided herein is a pharmaceutically acceptable unit formulation, the pharmaceutically acceptable unit formulation consisting essentially of:

(a) about 1% by weight to about 70% by weight, based on the weight of the pharmaceutically acceptable unit formulation, of a crystalline anhydrous form of a compound of Formula (I):

Formula (I)

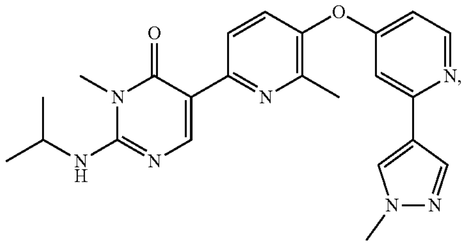

and one or more pharmaceutically acceptable excipients, wherein the one or more pharmaceutically acceptable excipients comprise:

(b) about 20% by weight to about 97% by weight of one or more fillers, based on the weight of the pharmaceutically acceptable unit formulation;

(c) about 1% by weight to about 20% by weight of one or more disintegrants, based on the weight of the pharmaceutically acceptable unit formulation; and (d) about 0.1% by weight to about 10% by weight of one or more lubricants, based on the weight of the pharmaceutically acceptable unit formulation, made by the process comprising:

(i) blending the crystalline anhydrous form of a compound represented by Formula (I) with the one or more fillers and one or more disintegrants to produce a first blend; and (ii) blending the first blend with the one or more lubricants, thereby preparing the pharmaceutically acceptable unit formulation.

Also provided herein is a pharmaceutically acceptable unit formulation, the pharmaceutically acceptable unit formulation comprising:

(a) about 1% by weight to about 70% by weight, based on the weight of the pharmaceutically acceptable unit formulation of a crystalline anhydrous form of a compound of Formula (I):

Formula (I)

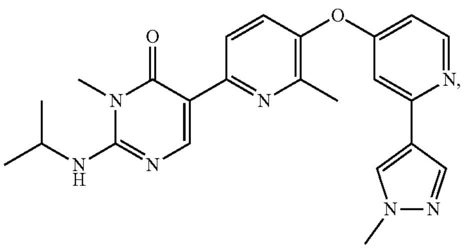

and one or more pharmaceutically acceptable excipients, wherein the one or more pharmaceutically acceptable excipients comprise:

(b) about 20% by weight to about 97% by weight of one or more fillers, based on the weight of the pharmaceutically acceptable unit formulation;

(c) about 1% by weight to about 20% by weight of one or more disintegrants, based on the weight of the pharmaceutically acceptable unit formulation; and (d) about 0.1% by weight to about 10% by weight of one or more lubricants, based on the weight of the pharmaceutically acceptable unit formulation, made by the process comprising:

(i) blending the crystalline anhydrous form of a compound represented by Formula (I) with the one or more fillers to produce a first blend;

(ii) blending the first blend with one or more disintegrants to produce a second blend; and (iii) blending the second blend with the one or more lubricants, thereby preparing the pharmaceutically acceptable unit formulation.

Also provided herein is a pharmaceutically acceptable unit formulation, the pharmaceutically acceptable unit formulation consisting essentially of:

(a) about 1% by weight to about 70% by weight, based on the weight of the pharmaceutically acceptable unit formulation of a crystalline anhydrous form of a compound of Formula (I):

Formula (I)

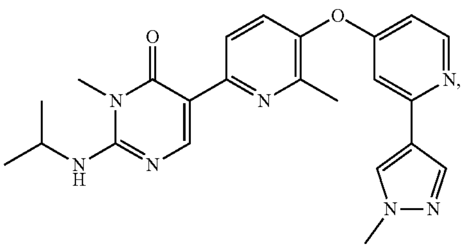

and one or more pharmaceutically acceptable excipients, wherein the one or more pharmaceutically acceptable excipients comprise:

(b) about 20% by weight to about 97% by weight of one or more fillers, based on the weight of the pharmaceutically acceptable unit formulation;

(c) about 1% by weight to about 20% by weight of one or more disintegrants, based on the weight of the pharmaceutically acceptable unit formulation; and (d) about 0.1% by weight to about 10% by weight of one or more lubricants, based on the weight of the pharmaceutically acceptable unit formulation made by the process comprising:

(i) blending the crystalline anhydrous form of a compound represented by Formula (I) with the one or more fillers to produce a first blend;

(ii) blending the first blend with one or more disintegrants to produce a second blend; and (iii) blending the second blend with the one or more lubricants, thereby preparing the pharmaceutically acceptable unit formulation.

Also provided herein is a pharmaceutically acceptable unit formulation, the pharmaceutically acceptable unit formulation comprising:

(a) about 1% by weight to about 70% by weight, based on the weight of the pharmaceutically acceptable unit formulation of a crystalline anhydrous form of a compound of Formula (I):

Formula (I)

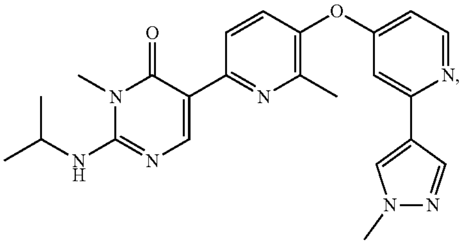

and one or more pharmaceutically acceptable excipients, wherein the one or more pharmaceutically acceptable excipients comprise:

(b) about 20% by weight to about 97% by weight of one or more fillers, based on the weight of the pharmaceutically acceptable unit formulation;

(c) about 1% by weight to about 20% by weight of one or more disintegrants, based on the weight of the pharmaceutically acceptable unit formulation; and (d) about 0.1% by weight to about 10% by weight of one or more lubricants, based on the weight of the pharmaceutically acceptable unit formulation made by the process comprising:

(i) blending the crystalline anhydrous form of a compound represented by Formula (I) with the one or more fillers to produce a first blend;

(ii) blending the first blend with a second blend comprising one or more disintegrants and one or more fillers and optionally a third blend comprising one or more fillers to produce a fourth blend; and (iii) blending the fourth blend with the one or more lubricants, thereby preparing the pharmaceutically acceptable unit formulation.

Also provided herein is a pharmaceutically acceptable unit formulation, the pharmaceutically acceptable unit formulation consisting essentially of:

(a) about 1% by weight to about 70% by weight, based on the weight of the pharmaceutically acceptable unit formulation of a crystalline anhydrous form of a compound of Formula (I):

Formula (I)

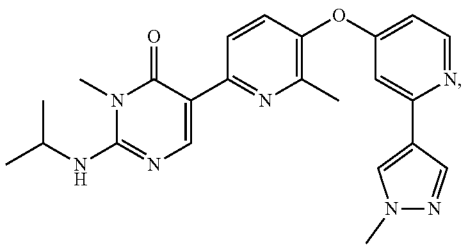

and one or more pharmaceutically acceptable excipients, wherein the one or more pharmaceutically acceptable excipients comprise:

(b) about 20% by weight to about 97% by weight of one or more fillers, based on the weight of the pharmaceutically acceptable unit formulation;

(c) about 1% by weight to about 20% by weight of one or more disintegrants, based on the weight of the pharmaceutically acceptable unit formulation; and (d) about 0.1% by weight to about 10% by weight of one or more lubricants, based on the weight of the pharmaceutically acceptable unit formulation made by the process comprising:

(i) blending the crystalline anhydrous form of a compound represented by Formula (I) with the one or more fillers to produce a first blend;

(ii) blending the first blend with a second blend comprising one or more disintegrants and one or more fillers and optionally a third blend comprising one or more fillers to produce a fourth blend; and (iii) blending the fourth blend with the one or more lubricants, thereby preparing the pharmaceutically acceptable unit formulation.

Also provided herein is an oral dosage form, the oral dosage form comprising:

(a) about 1% by weight to about 70% by weight, based on the total weight of the oral dosage form, of a crystalline anhydrous form of a compound of Formula (I):

Formula (I)

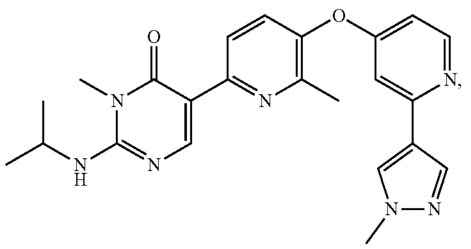

and one or more pharmaceutically acceptable excipients, wherein the one or more pharmaceutically acceptable excipients comprise:

(b) about 20% by weight to about 97% by weight of one or more fillers, based on the total weight of the oral dosage form;

(c) about 1% by weight to about 20% by weight of one or more disintegrants, based on the total weight of the oral dosage form; and (d) about 0.1% by weight to about 10% by weight of one or more lubricants, based on the total weight of the oral dosage form, made by the process comprising:

(i) blending the crystalline anhydrous form of a compound represented by Formula (I) with the one or more fillers and one or more disintegrants to produce a first blend; and (ii) blending the first blend with the one or more lubricants, thereby preparing the oral dosage form.

Also provided herein is an oral dosage form, the oral dosage form consisting essentially of:

(a) about 1% by weight to about 70% by weight, based on the total weight of the oral dosage form, of a crystalline anhydrous form of a compound of Formula (I):

Formula (I)

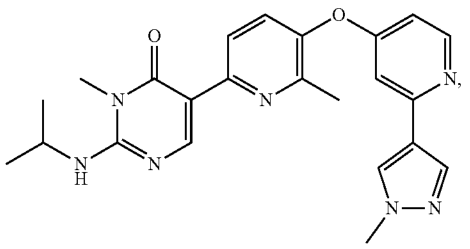

and one or more pharmaceutically acceptable excipients, wherein the one or more pharmaceutically acceptable excipients comprise:

(b) about 20% by weight to about 97% by weight of one or more fillers, based on the total weight of the oral dosage form;

(c) about 1% by weight to about 20% by weight of one or more disintegrants, based on the total weight of the oral dosage form; and (d) about 0.1% by weight to about 10% by weight of one or more lubricants, based on the total weight of the oral dosage form, made by the process comprising:

(i) blending the crystalline anhydrous form of a compound represented by Formula (I) with the one or more fillers and one or more disintegrants to produce a first blend; and (ii) blending the first blend with the one or more lubricants, thereby preparing the oral dosage form.

Also provided herein is an oral dosage form, the oral dosage form comprising:

(a) about 1% by weight to about 70% by weight, based on the total weight of the oral dosage form of a crystalline anhydrous form of a compound of Formula (I):

Formula (I)

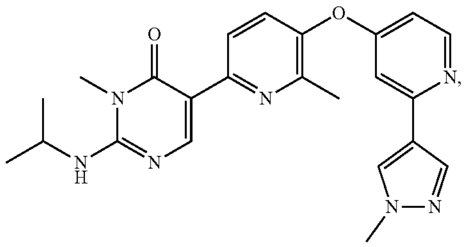

and one or more pharmaceutically acceptable excipients, wherein the one or more pharmaceutically acceptable excipients comprise:

(b) about 20% by weight to about 97% by weight of one or more fillers, based on the total weight of the oral dosage form;

(c) about 1% by weight to about 20% by weight of one or more disintegrants, based on the total weight of the oral dosage form; and (d) about 0.1% by weight to about 10% by weight of one or more lubricants, based on the total weight of the oral dosage form, made by the process comprising:

(i) blending the crystalline anhydrous form of a compound represented by Formula (I) with the one or more fillers to produce a first blend;

(ii) blending the first blend with one or more disintegrants to produce a second blend; and (iii) blending the second blend with the one or more lubricants, thereby preparing the oral dosage form.

Also provided herein is an oral dosage form, the oral dosage form consisting essentially of:

(a) about 1% by weight to about 70% by weight, based on the total weight of the oral dosage form of a crystalline anhydrous form of a compound of Formula (I):

Formula (I)

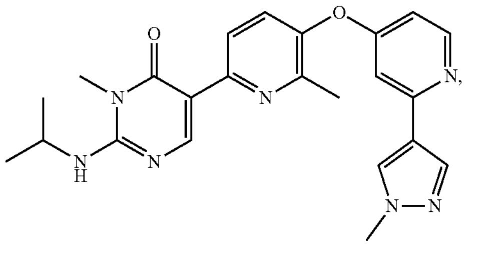

and one or more pharmaceutically acceptable excipients, wherein the one or more pharmaceutically acceptable excipients comprise:

(b) about 20% by weight to about 97% by weight of one or more fillers, based on the total weight of the oral dosage form;

(c) about 1% by weight to about 20% by weight of one or more disintegrants, based on the total weight of the oral dosage form; and (d) about 0.1% by weight to about 10% by weight of one or more lubricants, based on the total weight of the oral dosage form, made by the process comprising:

(i) blending the crystalline anhydrous form of a compound represented by Formula (I) with the one or more fillers to produce a first blend;

(ii) blending the first blend with one or more disintegrants to produce a second blend; and (iii) blending the second blend with the one or more lubricants, thereby preparing the oral dosage form.

Also provided herein is an oral dosage form, the oral dosage form comprising:

(a) about 1% by weight to about 70% by weight, based on the total weight of the oral dosage form of a crystalline anhydrous form of a compound of Formula (I):

Formula (I)

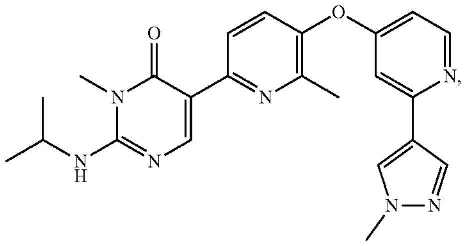

and one or more pharmaceutically acceptable excipients, wherein the one or more pharmaceutically acceptable excipients comprise:

(b) about 20% by weight to about 97% by weight of one or more fillers, based on the total weight of the oral dosage form;

(c) about 1% by weight to about 20% by weight of one or more disintegrants, based on the total weight of the oral dosage form; and (d) about 0.1% by weight to about 10% by weight of one or more lubricants, based on the total weight of the oral dosage form, made by the process comprising:

(i) blending the crystalline anhydrous form of a compound represented by Formula (I) with the one or more fillers to produce a first blend;

(ii) blending the first blend with a second blend comprising one or more disintegrants and one or more fillers and optionally a third blend comprising one or more fillers to produce a fourth blend; and (iii) blending the fourth blend with the one or more lubricants, thereby preparing the oral dosage form.

Also provided herein is an oral dosage form, the oral dosage form consisting essentially of:

(a) about 1% by weight to about 70% by weight, based on the total weight of the oral dosage form of a crystalline anhydrous form of a compound of Formula (I):

Formula (I)

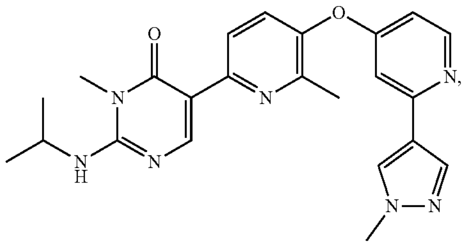

and one or more pharmaceutically acceptable excipients, wherein the one or more pharmaceutically acceptable excipients comprise:

(b) about 20% by weight to about 97% by weight of one or more fillers, based on the total weight of the oral dosage form;

(c) about 1% by weight to about 20% by weight of one or more disintegrants, based on the total weight of the oral dosage form; and (d) about 0.1% by weight to about 10% by weight of one or more lubricants, based on the total weight of the oral dosage form, made by the process comprising:

(i) blending the crystalline anhydrous form of a compound represented by Formula (I) with the one or more fillers to produce a first blend;

(ii) blending the first blend with a second blend comprising one or more disintegrants and one or more fillers and optionally a third blend comprising one or more fillers to produce a fourth blend; and (iii) blending the fourth blend with the one or more lubricants, thereby preparing the oral dosage form.

Also provided herein, in some embodiments, is a pharmaceutically acceptable capsule, the pharmaceutically acceptable capsule comprising:

(a) about 1% to about 70%, based on the total weight of the pharmaceutically acceptable capsule, of a crystalline anhydrous form of a compound of Formula (I):

Formula (I)

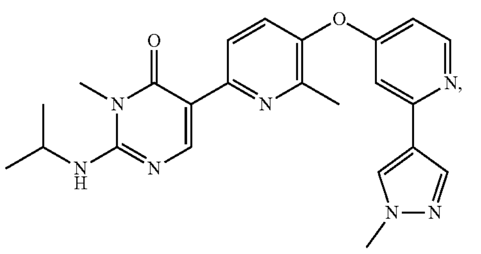

and one or more pharmaceutically acceptable excipients, wherein the one or more pharmaceutically acceptable excipients comprise:

(b) about 20% by weight to about 97% by weight of one or more fillers, based on the total weight of the pharmaceutically acceptable capsule;

(c) about 1% by weight to about 20% by weight of one or more disintegrants, based on the total weight of the pharmaceutically acceptable capsule; and (d) about 0.1% by weight to about 10% by weight of one or more lubricants, based on the total weight of the pharmaceutically acceptable capsule;

made by the process comprising:

(i) blending the crystalline anhydrous form of a compound represented by Formula (I) with the one or more fillers and one or more disintegrants to produce a first blend;

(ii) blending the first blend with the one or more lubricants to form a second blend; and (iii) dispensing the second blend into an empty pharmaceutically acceptable capsule, thereby forming the pharmaceutically acceptable capsule.

Also provided herein, in some embodiments, is a pharmaceutically acceptable capsule, the pharmaceutically acceptable capsule consisting essentially of:

(a) about 1% to about 70%, based on the total weight of the pharmaceutically acceptable capsule, of a crystalline anhydrous form of a compound of Formula (I):

Formula (I)

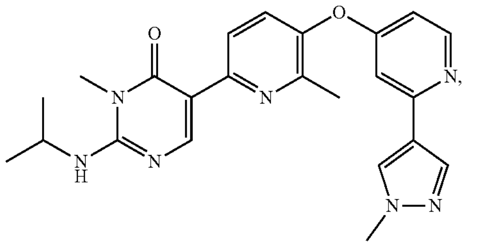

and one or more pharmaceutically acceptable excipients, wherein the one or more pharmaceutically acceptable excipients comprise:

(b) about 20% by weight to about 97% by weight of one or more fillers, based on the total weight of the pharmaceutically acceptable capsule;

(c) about 1% by weight to about 20% by weight of one or more disintegrants, based on the total weight of the pharmaceutically acceptable capsule; and (d) about 0.1% by weight to about 10% by weight of one or more lubricants, based on the total weight of the pharmaceutically acceptable capsule;

made by the process comprising:

(i) blending the crystalline anhydrous form of a compound represented by Formula (I) with the one or more fillers and one or more disintegrants to produce a first blend;

(ii) blending the first blend with the one or more lubricants to form a second blend; and (iii) dispensing the second blend into an empty pharmaceutically acceptable capsule, thereby forming the pharmaceutically acceptable capsule.

Also provided herein, in some embodiments, is a pharmaceutically acceptable capsule, the pharmaceutically acceptable capsule comprising:

(a) about 1% to about 70%, based on the total weight of the pharmaceutically acceptable capsule, of a crystalline anhydrous form of a compound of Formula (I):

Formula (I)

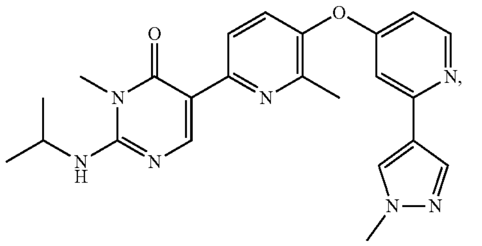

and one or more pharmaceutically acceptable excipients, wherein the one or more pharmaceutically acceptable excipients comprise:

(b) about 20% by weight to about 97% by weight of one or more fillers, based on the total weight of the pharmaceutically acceptable capsule;

(c) about 1% by weight to about 20% by weight of one or more disintegrants, based on the total weight of the pharmaceutically acceptable capsule; and (d) about 0.1% by weight to about 10% by weight of one or more lubricants, based on the total weight of the pharmaceutically acceptable capsule;

made by the process comprising:

(i) blending the crystalline anhydrous form of a compound represented by Formula (I) with the one or more fillers to produce a first blend;

(ii) blending the first blend with the one or more disintegrants to form a second blend;

(iii) blending the second blend with the one or more lubricants to form a third blend; and (iv) dispensing the third blend into an empty pharmaceutically acceptable capsule, thereby forming the pharmaceutically acceptable capsule.

Also provided herein, in some embodiments, is a pharmaceutically acceptable capsule, the pharmaceutically acceptable capsule consisting essentially of:

(a) about 1% to about 70%, based on the total weight of the pharmaceutically acceptable capsule, of a crystalline anhydrous form of a compound of Formula (I):

Formula (I)

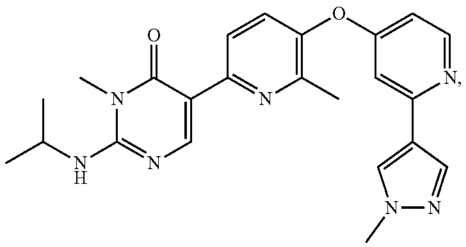

and one or more pharmaceutically acceptable excipients, wherein the one or more pharmaceutically acceptable excipients comprise:

(b) about 20% by weight to about 97% by weight of one or more fillers, based on the total weight of the pharmaceutically acceptable capsule;

(c) about 1% by weight to about 20% by weight of one or more disintegrants, based on the total weight of the pharmaceutically acceptable capsule; and (d) about 0.1% by weight to about 10% by weight of one or more lubricants, based on the total weight of the pharmaceutically acceptable capsule;

made by the process comprising:

(i) blending the crystalline anhydrous form of a compound represented by Formula (I) with the one or more fillers to produce a first blend;

(ii) blending the first blend with the one or more disintegrants to form a second blend;

(iii) blending the second blend with the one or more lubricants to form a third blend; and (iv) dispensing the third blend into an empty pharmaceutically acceptable capsule, thereby forming the pharmaceutically acceptable capsule.

Also provided herein, in some embodiments, is a pharmaceutically acceptable capsule, the pharmaceutically acceptable capsule comprising:

(a) about 1% to about 70%, based on the total weight of the pharmaceutically acceptable capsule, of a crystalline anhydrous form of a compound of Formula (I):

Formula (I)

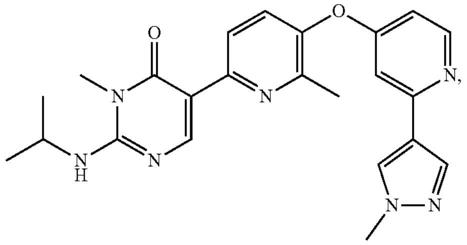

and one or more pharmaceutically acceptable excipients, wherein the one or more pharmaceutically acceptable excipients comprise:

(b) about 20% by weight to about 97% by weight of one or more fillers, based on the total weight of the pharmaceutically acceptable capsule;

(c) about 1% by weight to about 20% by weight of one or more disintegrants, based on the total weight of the pharmaceutically acceptable capsule; and (d) about 0.1% by weight to about 10% by weight of one or more lubricants, based on the total weight of the pharmaceutically acceptable capsule;

made by the process comprising:

(i) blending the crystalline anhydrous form of a compound represented by Formula (I) with the one or more fillers to produce a first blend;

(ii) blending the first blend with a second blend comprising one or more disintegrants and one or more fillers and optionally a third blend comprising one or more fillers to form a fourth blend;

(iii) blending the fourth blend with the one or more lubricants to form a fifth blend; and (iv) dispensing the fifth blend into an empty pharmaceutically acceptable capsule, thereby forming the pharmaceutically acceptable capsule.

Also provided herein, in some embodiments, is a pharmaceutically acceptable capsule, the pharmaceutically acceptable capsule consisting essentially of:

(a) about 1% to about 70%, based on the total weight of the pharmaceutically acceptable capsule, of a crystalline anhydrous form of a compound of Formula (I):

Formula (I)

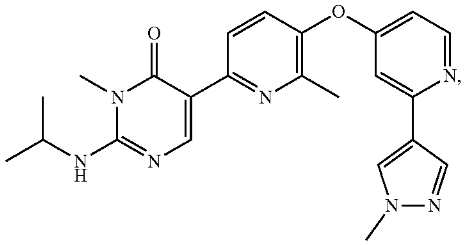

and one or more pharmaceutically acceptable excipients, wherein the one or more pharmaceutically acceptable excipients comprise:

(b) about 20% by weight to about 97% by weight of one or more fillers, based on the total weight of the pharmaceutically acceptable capsule;

(c) about 1% by weight to about 20% by weight of one or more disintegrants, based on the total weight of the pharmaceutically acceptable capsule; and (d) about 0.1% by weight to about 10% by weight of one or more lubricants, based on the total weight of the pharmaceutically acceptable capsule;

made by the process comprising:

(i) blending the crystalline anhydrous form of a compound represented by Formula (I) with the one or more fillers to produce a first blend;

(ii) blending the first blend with a second blend comprising one or more disintegrants and one or more fillers and optionally a third blend comprising one or more fillers to form a fourth blend;

(iii) blending the fourth blend with the one or more lubricants to form a fifth blend; and (iv) dispensing the fifth blend into an empty pharmaceutically acceptable capsule, thereby forming the pharmaceutically acceptable capsule.

Process of Preparation

Also provided herein is a process of preparing a pharmaceutically acceptable unit formulation, the pharmaceutically acceptable unit formulation comprising:

(a) about 1% by weight to about 70% by weight, based on the weight of the pharmaceutically acceptable unit formulation, of a compound of Formula (I):

Formula (I)

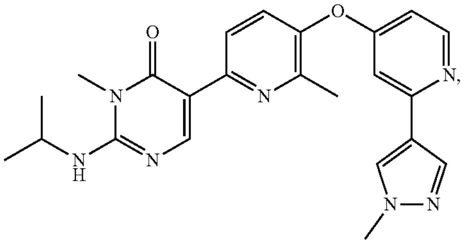

wherein the compound is present in the pharmaceutically acceptable formulation as a free base, a pharmaceutically acceptable salt of the compound and wherein the free base or pharmaceutically acceptable salt is in anhydrous or hydrate form, and one or more pharmaceutically acceptable excipients, wherein the one or more pharmaceutically acceptable excipients comprise:

(b) about 20% by weight to about 97% by weight of one or more fillers, based on the weight of the pharmaceutically acceptable unit formulation;

(c) about 1% by weight to about 20% by weight of one or more disintegrants, based on the weight of the pharmaceutically acceptable unit formulation; and (d) about 0.1% by weight to about 10% by weight of one or more lubricants, based on the weight of the pharmaceutically acceptable unit formulation the process comprising:

(i) blending the compound represented by Formula (I) with the one or more fillers and one or more disintegrants to produce a first blend; and (ii) blending the first blend with the one or more lubricants, thereby preparing the pharmaceutically acceptable unit formulation.

Also provided herein is a process of preparing a pharmaceutically acceptable unit formulation, the pharmaceutically acceptable unit formulation consisting essentially of:

(a) about 1% by weight to about 70% by weight, based on the weight of the pharmaceutically acceptable unit formulation, of a compound of Formula (I):

Formula (I)

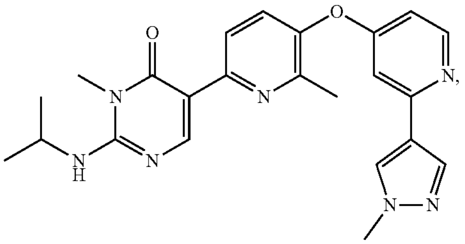

wherein the compound is present in the pharmaceutically acceptable formulation as a free base, a pharmaceutically acceptable salt of the compound and wherein the free base or pharmaceutically acceptable salt is in anhydrous or hydrate form, and one or more pharmaceutically acceptable excipients, wherein the one or more pharmaceutically acceptable excipients comprise:

(b) about 20% by weight to about 97% by weight of one or more fillers, based on the weight of the pharmaceutically acceptable unit formulation;

(c) about 1% by weight to about 20% by weight of one or more disintegrants, based on the weight of the pharmaceutically acceptable unit formulation; and (d) about 0.1% by weight to about 10% by weight of one or more lubricants, based on the weight of the pharmaceutically acceptable unit formulation the process comprising:

(i) blending the compound represented by Formula (I) with the one or more fillers and one or more disintegrants to produce a first blend; and (ii) blending the first blend with the one or more lubricants, thereby preparing the pharmaceutically acceptable unit formulation.

Also provided herein is a process of preparing a pharmaceutically acceptable unit formulation, the pharmaceutically acceptable unit formulation comprising:

(a) about 1% by weight to about 70% by weight, based on the weight of the pharmaceutically acceptable unit formulation, of a compound of Formula (I):

Formula (I)

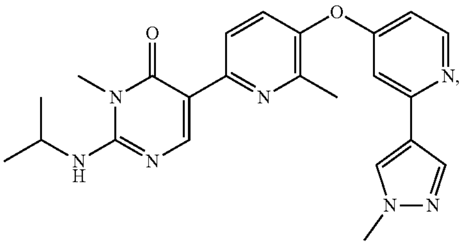

wherein the compound is present in the pharmaceutically acceptable formulation as a free base, a pharmaceutically acceptable salt of the compound and wherein the free base or pharmaceutically acceptable salt is in anhydrous or hydrate form, and one or more pharmaceutically acceptable excipients, wherein the one or more pharmaceutically acceptable excipients comprise:

(b) about 20% by weight to about 97% by weight of one or more fillers, based on the weight of the pharmaceutically acceptable unit formulation;

(c) about 1% by weight to about 20% by weight of one or more disintegrants, based on the weight of the pharmaceutically acceptable unit formulation; and (d) about 0.1% by weight to about 10% by weight of one or more lubricants, based on the weight of the pharmaceutically acceptable unit formulation the process comprising:

(i) blending the compound represented by Formula (I) with the one or more fillers to produce a first blend;

(ii) blending the first blend with one or more disintegrants to produce a second blend; and (iii) blending the second blend with the one or more lubricants, thereby preparing the pharmaceutically acceptable unit formulation.

Also provided herein is a process of preparing a pharmaceutically acceptable unit formulation, the pharmaceutically acceptable unit formulation consisting essentially of:

(a) about 1% by weight to about 70% by weight, based on the weight of the pharmaceutically acceptable unit formulation, of a compound of Formula (I):

Formula (I)

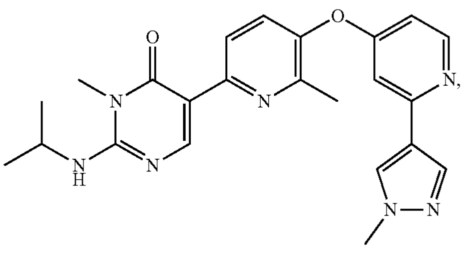

wherein the compound is present in the pharmaceutically acceptable formulation as a free base, a pharmaceutically acceptable salt of the compound and wherein the free base or pharmaceutically acceptable salt is in anhydrous or hydrate form, and one or more pharmaceutically acceptable excipients, wherein the one or more pharmaceutically acceptable excipients comprise:

(b) about 20% by weight to about 97% by weight of one or more fillers, based on the weight of the pharmaceutically acceptable unit formulation;

(c) about 1% by weight to about 20% by weight of one or more disintegrants, based on the weight of the pharmaceutically acceptable unit formulation; and (d) about 0.1% by weight to about 10% by weight of one or more lubricants, based on the weight of the pharmaceutically acceptable unit formulation the process comprising:

(i) blending the compound represented by Formula (I) with the one or more fillers to produce a first blend;

(ii) blending the first blend with one or more disintegrants to produce a second blend; and (iii) blending the second blend with the one or more lubricants, thereby preparing the pharmaceutically acceptable unit formulation.

Also provided herein is a process of preparing a pharmaceutically acceptable unit formulation, the pharmaceutically acceptable unit formulation comprising:

(a) about 1% by weight to about 70% by weight, based on the weight of the pharmaceutically acceptable unit formulation of a compound of Formula (I):

Formula (I)

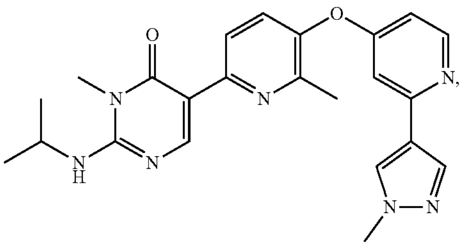

wherein the compound is present in the pharmaceutically acceptable formulation as a free base, a pharmaceutically acceptable salt of the compound and wherein the free base or pharmaceutically acceptable salt is in anhydrous or hydrate form, and one or more pharmaceutically acceptable excipients, wherein the one or more pharmaceutically acceptable excipients comprise:

(b) about 20% by weight to about 97% by weight of one or more fillers, based on the weight of the pharmaceutically acceptable unit formulation;

(c) about 1% by weight to about 20% by weight of one or more disintegrants, based on the weight of the pharmaceutically acceptable unit formulation; and (d) about 0.1% by weight to about 10% by weight of one or more lubricants, based on the weight of the pharmaceutically acceptable unit formulation the process comprising:

(i) blending the compound represented by Formula (I) with the one or more fillers to produce a first blend;

(ii) blending the first blend with a second blend comprising one or more disintegrants and one or more fillers and optionally a third blend comprising one or more fillers to produce a fourth blend; and (iii) blending the fourth blend with the one or more lubricants, thereby preparing the pharmaceutically acceptable unit formulation.

Also provided herein is a process of preparing a pharmaceutically acceptable unit formulation, the pharmaceutically acceptable unit formulation consisting essentially of:

(a) about 1% by weight to about 70% by weight, based on the weight of the pharmaceutically acceptable unit formulation of a compound of Formula (I):

Formula (I)

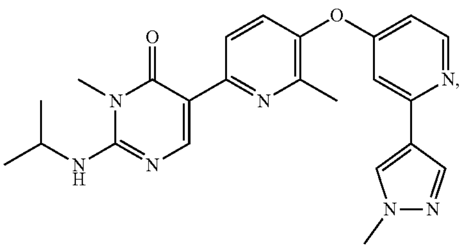

wherein the compound is present in the pharmaceutically acceptable formulation as a free base, a pharmaceutically acceptable salt of the compound and wherein the free base or pharmaceutically acceptable salt is in anhydrous or hydrate form, and one or more pharmaceutically acceptable excipients, wherein the one or more pharmaceutically acceptable excipients comprise:

(b) about 20% by weight to about 97% by weight of one or more fillers, based on the weight of the pharmaceutically acceptable unit formulation;

(c) about 1% by weight to about 20% by weight of one or more disintegrants, based on the weight of the pharmaceutically acceptable unit formulation; and (d) about 0.1% by weight to about 10% by weight of one or more lubricants, based on the weight of the pharmaceutically acceptable unit formulation the process comprising:

(i) blending the compound represented by Formula (I) with the one or more fillers to produce a first blend;

(ii) blending the first blend with a second blend comprising one or more disintegrants and one or more fillers and optionally a third blend comprising one or more fillers to produce a fourth blend; and (iii) blending the fourth blend with the one or more lubricants, thereby preparing the pharmaceutically acceptable unit formulation.

In some embodiments, the pharmaceutically acceptable unit formulation comprises about 1% by weight to about 60% by weight, based on the weight of the pharmaceutically acceptable unit formulation, of a compound of Formula (I), wherein the compound is present in the pharmaceutically acceptable formulation as a free base, or a pharmaceutically acceptable salt of the compound and wherein the free base or pharmaceutically acceptable salt is in anhydrous or hydrate form. In some embodiments, the pharmaceutically acceptable unit formulation comprises about 1% by weight to about 50% by weight, based on the weight of the pharmaceutically acceptable unit formulation, of a compound of Formula (I), wherein the compound is present in the pharmaceutically acceptable formulation as a free base, or a pharmaceutically acceptable salt of the compound and wherein the free base or pharmaceutically acceptable salt is in anhydrous or hydrate form. In some embodiments, the pharmaceutically acceptable unit formulation comprises about 1% by weight to about 40% by weight, based on the weight of the pharmaceutically acceptable unit formulation, of a compound of Formula (I), wherein the compound is present in the pharmaceutically acceptable formulation as a free base, or a pharmaceutically acceptable salt of the compound and wherein the free base or pharmaceutically acceptable salt is in anhydrous or hydrate form. In some embodiments, the pharmaceutically acceptable unit formulation comprises about 1% by weight to about 30% by weight, based on the weight of the pharmaceutically acceptable unit formulation, of a compound of Formula (I), wherein the compound is present in the pharmaceutically acceptable formulation as a free base, or a pharmaceutically acceptable salt of the compound and wherein the free base or pharmaceutically acceptable salt is in anhydrous or hydrate form. In some embodiments, the pharmaceutically acceptable unit formulation comprises about 1% by weight to about 20% by weight, based on the weight of the pharmaceutically acceptable unit formulation, of a compound of Formula (I), wherein the compound is present in the pharmaceutically acceptable formulation as a free base, or a pharmaceutically acceptable salt of the compound and wherein the free base or pharmaceutically acceptable salt is in anhydrous or hydrate form.

In some embodiments, the pharmaceutically acceptable unit formulation consists essentially of about 1% by weight to about 60% by weight, based on the weight of the pharmaceutically acceptable unit formulation, of a compound of Formula (I), wherein the compound is present in the pharmaceutically acceptable formulation as a free base, or a pharmaceutically acceptable salt of the compound and wherein the free base or pharmaceutically acceptable salt is in anhydrous or hydrate form. In some embodiments, the pharmaceutically acceptable unit formulation consists essentially of about 1% by weight to about 50% by weight, based on the weight of the pharmaceutically acceptable unit formulation, of a compound of Formula (I), wherein the compound is present in the pharmaceutically acceptable formulation as a free base, or a pharmaceutically acceptable salt of the compound and wherein the free base or pharmaceutically acceptable salt is in anhydrous or hydrate form. In some embodiments, the pharmaceutically acceptable unit formulation consists essentially of about 1% by weight to about 40% by weight, based on the weight of the pharmaceutically acceptable unit formulation, of a compound of Formula (I), wherein the compound is present in the pharmaceutically acceptable formulation as a free base, or a pharmaceutically acceptable salt of the compound and wherein the free base or pharmaceutically acceptable salt is in anhydrous or hydrate form. In some embodiments, the pharmaceutically acceptable unit formulation consists essentially of about 1% by weight to about 30% by weight, based on the weight of the pharmaceutically acceptable unit formulation, of a compound of Formula (I), wherein the compound is present in the pharmaceutically acceptable formulation as a free base, or a pharmaceutically acceptable salt of the compound and wherein the free base or pharmaceutically acceptable salt is in anhydrous or hydrate form. In some embodiments, the pharmaceutically acceptable unit formulation consists essentially of about 1% by weight to about 20% by weight, based on the weight of the pharmaceutically acceptable unit formulation, of a compound of Formula (I), wherein the compound is present in the pharmaceutically acceptable formulation as a free base, or a pharmaceutically acceptable salt of the compound and wherein the free base or pharmaceutically acceptable salt is in anhydrous or hydrate form.

In some embodiments, the pharmaceutically acceptable unit formulation comprises about 1% by weight to about 70% by weight of the compound of Formula (I) based on the weight of the pharmaceutically acceptable unit formulation. In some embodiments, the pharmaceutically acceptable unit formulation comprises about 1% by weight to about 65% by weight of the compound of Formula (I) based on the weight of the pharmaceutically acceptable unit formulation. In some embodiments, the pharmaceutically acceptable unit formulation comprises about 1% by weight to about 60% by weight of the compound of Formula (I) based on the weight of the pharmaceutically acceptable unit formulation. In some embodiments, the pharmaceutically acceptable unit formulation comprises about 1% by weight to about 55% by weight of the compound of Formula (I) based on the weight of the pharmaceutically acceptable unit formulation. In some embodiments, the pharmaceutically acceptable unit formulation comprises about 1% by weight to about 50% by weight of the compound of Formula (I) based on the weight of the pharmaceutically acceptable unit formulation. In some embodiments, the pharmaceutically acceptable unit formulation comprises about 1% by weight to about 45% by weight of the compound of Formula (I) based on the weight of the pharmaceutically acceptable unit formulation. In some embodiments, the pharmaceutically acceptable unit formulation comprises about 1% by weight to about 40% by weight of the compound of Formula (I) based on the weight of the pharmaceutically acceptable unit formulation. In some embodiments, the pharmaceutically acceptable unit formulation comprises about 1% by weight to about 35% by weight of the compound of Formula (I) based on the weight of the pharmaceutically acceptable unit formulation. In some embodiments, the pharmaceutically acceptable unit formulation comprises about 1% by weight to about 30% by weight of the compound of Formula (I) based on the weight of the pharmaceutically acceptable unit formulation. In some embodiments, the pharmaceutically acceptable unit formulation comprises about 1% by weight to about 25% by weight of the compound of Formula (I) based on the weight of the pharmaceutically acceptable unit formulation. In some embodiments, the pharmaceutically acceptable unit formulation comprises about 1% by weight to about 20% by weight of the compound of Formula (I) based on the weight of the pharmaceutically acceptable unit formulation. In some embodiments, the pharmaceutically acceptable unit formulation comprises about 1% by weight to about 15% by weight of the compound of Formula (I) based on the weight of the pharmaceutically acceptable unit formulation. In some embodiments, the pharmaceutically acceptable unit formulation comprises about 1% by weight to about 10% by weight of the compound of Formula (I) based on the weight of the pharmaceutically acceptable unit formulation.

In some embodiments, the pharmaceutically acceptable unit formulation consists essentially of about 1% by weight to about 70% by weight of the compound of Formula (I) based on the weight of the pharmaceutically acceptable unit formulation. In some embodiments, the pharmaceutically acceptable unit formulation consists essentially of about 1% by weight to about 65% by weight of the compound of Formula (I) based on the weight of the pharmaceutically acceptable unit formulation. In some embodiments, the pharmaceutically acceptable unit formulation consists essentially of about 1% by weight to about 60% by weight of the compound of Formula (I) based on the weight of the pharmaceutically acceptable unit formulation. In some embodiments, the pharmaceutically acceptable unit formulation consists essentially of about 1% by weight to about 55% by weight of the compound of Formula (I) based on the weight of the pharmaceutically acceptable unit formulation. In some embodiments, the pharmaceutically acceptable unit formulation consists essentially of about 1% by weight to about 50% by weight of the compound of Formula (I) based on the weight of the pharmaceutically acceptable unit formulation. In some embodiments, the pharmaceutically acceptable unit formulation consists essentially of about 1% by weight to about 45% by weight of the compound of Formula (I) based on the weight of the pharmaceutically acceptable unit formulation. In some embodiments, the pharmaceutically acceptable unit formulation consists essentially of about 1% by weight to about 40% by weight of the compound of Formula (I) based on the weight of the pharmaceutically acceptable unit formulation. In some embodiments, the pharmaceutically acceptable unit formulation consists essentially of about 1% by weight to about 35% by weight of the compound of Formula (I) based on the weight of the pharmaceutically acceptable unit formulation. In some embodiments, the pharmaceutically acceptable unit formulation consists essentially of about 1% by weight to about 30% by weight of the compound of Formula (I) based on the weight of the pharmaceutically acceptable unit formulation. In some embodiments, the pharmaceutically acceptable unit formulation consists essentially of about 1% by weight to about 25% by weight of the compound of Formula (I) based on the weight of the pharmaceutically acceptable unit formulation. In some embodiments, the pharmaceutically acceptable unit formulation consists essentially of about 1% by weight to about 20% by weight of the compound of Formula (I) based on the weight of the pharmaceutically acceptable unit formulation. In some embodiments, the pharmaceutically acceptable unit formulation consists essentially of about 1% by weight to about 15% by weight of the compound of Formula (I) based on the weight of the pharmaceutically acceptable unit formulation. In some embodiments, the pharmaceutically acceptable unit formulation consists essentially of about 1% by weight to about 10% by weight of the compound of Formula (I) based on the weight of the pharmaceutically acceptable unit formulation.

In some embodiments, the pharmaceutically acceptable unit formulation comprises about 5% by weight to about 30% by weight of the compound of Formula (I) based on the weight of the pharmaceutically acceptable unit formulation. In some embodiments, the pharmaceutically acceptable unit formulation comprises about 5% by weight to about 25% by weight of the compound of Formula (I) based on the weight of the pharmaceutically acceptable unit formulation. In some embodiments, the pharmaceutically acceptable unit formulation comprises about 5% by weight to about 20% by weight of the compound of Formula (I) based on the weight of the pharmaceutically acceptable unit formulation. In some embodiments, the pharmaceutically acceptable unit formulation comprises about 5% by weight to about 15% by weight of the compound of Formula (I) based on the weight of the pharmaceutically acceptable unit formulation. In some embodiments, the pharmaceutically acceptable unit formulation comprises about 5% by weight to about 10% by weight of the compound of Formula (I) based on the weight of the pharmaceutically acceptable unit formulation.

In some embodiments, the pharmaceutically acceptable unit formulation consists essentially of about 5% by weight to about 30% by weight of the compound of Formula (I) based on the weight of the pharmaceutically acceptable unit formulation. In some embodiments, the pharmaceutically acceptable unit formulation consists essentially of about 5% by weight to about 25% by weight of the compound of Formula (I) based on the weight of the pharmaceutically acceptable unit formulation. In some embodiments, the pharmaceutically acceptable unit formulation consists essentially of about 5% by weight to about 20% by weight of the compound of Formula (I) based on the weight of the pharmaceutically acceptable unit formulation. In some embodiments, the pharmaceutically acceptable unit formulation consists essentially of about 5% by weight to about 15% by weight of the compound of Formula (I) based on the weight of the pharmaceutically acceptable unit formulation. In some embodiments, the pharmaceutically acceptable unit formulation consists essentially of about 5% by weight to about 10% by weight of the compound of Formula (I) based on the weight of the pharmaceutically acceptable unit formulation.

In some embodiments, the pharmaceutically acceptable unit formulation comprises about 10% to about 30% of the compound of Formula (I) based on the weight of the pharmaceutically acceptable unit formulation. In some embodiments, the pharmaceutically acceptable unit formulation comprises about 10% to about 25% of the compound of Formula (I) based on the weight of the pharmaceutically acceptable unit formulation. In some embodiments, the pharmaceutically acceptable unit formulation comprises about 10% to about 20% of the compound of Formula (I) based on the weight of the pharmaceutically acceptable unit formulation. In some embodiments, the pharmaceutically acceptable unit formulation comprises about 10% by weight to about 15% by weight of the compound of Formula (I) based on the weight of the pharmaceutically acceptable unit formulation.

In some embodiments, the pharmaceutically acceptable unit formulation consists essentially of about 10% to about 30% of the compound of Formula (I) based on the weight of the pharmaceutically acceptable unit formulation. In some embodiments, the pharmaceutically acceptable unit formulation consists essentially of about 10% to about 25% of the compound of Formula (I) based on the weight of the pharmaceutically acceptable unit formulation. In some embodiments, the pharmaceutically acceptable unit formulation consists essentially of about 10% to about 20% of the compound of Formula (I) based on the weight of the pharmaceutically acceptable unit formulation. In some embodiments, the pharmaceutically acceptable unit formulation consists essentially of about 10% by weight to about 15% by weight of the compound of Formula (I) based on the weight of the pharmaceutically acceptable unit formulation.

In some embodiments, the pharmaceutically acceptable unit formulation comprises about 1% by weight to about 30% by weight of the compound of Formula (I) based on the weight of the pharmaceutically acceptable unit formulation. In some embodiments, the pharmaceutically acceptable unit formulation comprises about 1% by weight to about 10% by weight of the compound of Formula (I) based on the weight of the pharmaceutically acceptable unit formulation. In some embodiments, the pharmaceutically acceptable unit formulation comprises about 10% to about 20% of the compound of Formula (I) based on the weight of the pharmaceutically acceptable unit formulation. In some embodiments, the pharmaceutically acceptable unit formulation comprises about 10% by weight to about 15% by weight of the compound of Formula (I) based on the weight of the pharmaceutically acceptable unit formulation.

In some embodiments, the pharmaceutically acceptable unit formulation consists essentially of about 1% by weight to about 30% by weight of the compound of Formula (I) based on the weight of the pharmaceutically acceptable unit formulation. In some embodiments, the pharmaceutically acceptable unit formulation consists essentially of about 1% by weight to about 10% by weight of the compound of Formula (I) based on the weight of the pharmaceutically acceptable unit formulation. In some embodiments, the pharmaceutically acceptable unit formulation consists essentially of about 10% to about 20% of the compound of Formula (I) based on the weight of the pharmaceutically acceptable unit formulation. In some embodiments, the pharmaceutically acceptable unit formulation consists essentially of about 10% by weight to about 15% by weight of the compound of Formula (I) based on the weight of the pharmaceutically acceptable unit formulation.

In some embodiments, the one or more pharmaceutically acceptable excipients comprise about 20% by weight to about 90% by weight of one or more fillers based on the weight of the pharmaceutically acceptable unit formulation. In some embodiments, the one or more pharmaceutically acceptable excipients comprise about 20% by weight to about 85% by weight of one or more fillers based on the weight of the pharmaceutically acceptable unit formulation. In some embodiments, the one or more pharmaceutically acceptable excipients comprise about 20% by weight to about 80% by weight of one or more fillers based on the weight of the pharmaceutically acceptable unit formulation. In some embodiments, the one or more pharmaceutically acceptable excipients comprise about 20% by weight to about 75% by weight of one or more fillers based on the weight of the pharmaceutically acceptable unit formulation. In some embodiments, the one or more pharmaceutically acceptable excipients comprise about 20% by weight to about 70% by weight of one or more fillers based on the weight of the pharmaceutically acceptable unit formulation. In some embodiments, the one or more pharmaceutically acceptable excipients comprise about 20% by weight to about 65% by weight of one or more fillers based on the weight of the pharmaceutically acceptable unit formulation. In some embodiments, the one or more pharmaceutically acceptable excipients comprise about 20% by weight to about 60% by weight of one or more fillers based on the weight of the pharmaceutically acceptable unit formulation. In some embodiments, the one or more pharmaceutically acceptable excipients comprise about 20% by weight to about 55% by weight of one or more fillers based on the weight of the pharmaceutically acceptable unit formulation. In some embodiments, the one or more pharmaceutically acceptable excipients comprise about 20% by weight to about 50% by weight of one or more fillers based on the weight of the pharmaceutically acceptable unit formulation. In some embodiments, the one or more pharmaceutically acceptable excipients comprise about 20% by weight to about 45% by weight of one or more fillers based on the weight of the pharmaceutically acceptable unit formulation. In some embodiments, the one or more pharmaceutically acceptable excipients comprise about 20% by weight to about 40% by weight of one or more fillers based on the weight of the pharmaceutically acceptable unit formulation. In some embodiments, the one or more pharmaceutically acceptable excipients comprise about 20% by weight to about 35% by weight of one or more fillers based on the weight of the pharmaceutically acceptable unit formulation. In some embodiments, the one or more pharmaceutically acceptable excipients comprise about 20% by weight to about 30% by weight of one or more fillers based on the weight of the pharmaceutically acceptable unit formulation. In some embodiments, the one or more pharmaceutically acceptable excipients comprise about 20% by weight to about 25% by weight of one or more fillers based on the weight of the pharmaceutically acceptable unit formulation.

In some embodiments, the one or more pharmaceutically acceptable excipients comprise about 30% by weight to about 90% by weight of one or more fillers based on the weight of the pharmaceutically acceptable unit formulation. In some embodiments, the one or more pharmaceutically acceptable excipients comprise about 30% by weight to about 80% by weight of one or more fillers based on the weight of the pharmaceutically acceptable unit formulation. In some embodiments, the one or more pharmaceutically acceptable excipients comprise about 30% by weight to about 70% by weight of one or more fillers based on the weight of the pharmaceutically acceptable unit formulation. In some embodiments, the one or more pharmaceutically acceptable excipients comprise about 30% by weight to about 60% by weight of one or more fillers based on the weight of the pharmaceutically acceptable unit formulation. In some embodiments, the one or more pharmaceutically acceptable excipients comprise about 30% by weight to about 50% by weight of one or more fillers based on the weight of the pharmaceutically acceptable unit formulation. In some embodiments, the one or more pharmaceutically acceptable excipients comprise about 30% by weight to about 40% by weight of one or more fillers based on the weight of the pharmaceutically acceptable unit formulation.

In some embodiments, the one or more pharmaceutically acceptable excipients comprise about 40% by weight to about 90% by weight of one or more fillers based on the weight of the pharmaceutically acceptable unit formulation. In some embodiments, the one or more pharmaceutically acceptable excipients comprise about 40% by weight to about 80% by weight of one or more fillers based on the weight of the pharmaceutically acceptable unit formulation. In some embodiments, the one or more pharmaceutically acceptable excipients comprise about 40% by weight to about 70% by weight of one or more fillers based on the weight of the pharmaceutically acceptable unit formulation. In some embodiments, the one or more pharmaceutically acceptable excipients comprise about 40% by weight to about 60% by weight of one or more fillers based on the weight of the pharmaceutically acceptable unit formulation. In some embodiments, the one or more pharmaceutically acceptable excipients comprise about 40% by weight to about 50% by weight of one or more fillers based on the weight of the pharmaceutically acceptable unit formulation.

In some embodiments, the one or more pharmaceutically acceptable excipients comprise about 50% by weight to about 90% by weight of one or more fillers based on the weight of the pharmaceutically acceptable unit formulation. In some embodiments, the one or more pharmaceutically acceptable excipients comprise about 50% by weight to about 80% by weight of one or more fillers based on the weight of the pharmaceutically acceptable unit formulation. In some embodiments, the one or more pharmaceutically acceptable excipients comprise about 50% by weight to about 70% by weight of one or more fillers based on the weight of the pharmaceutically acceptable unit formulation. In some embodiments, the one or more pharmaceutically acceptable excipients comprise about 50% by weight to about 60% by weight of one or more fillers based on the weight of the pharmaceutically acceptable unit formulation.

In some embodiments, the one or more pharmaceutically acceptable excipients comprise about 60% by weight to about 90% by weight of one or more fillers based on the weight of the pharmaceutically acceptable unit formulation. In some embodiments, the one or more pharmaceutically acceptable excipients comprise about 60% by weight to about 80% by weight of one or more fillers based on the weight of the pharmaceutically acceptable unit formulation. In some embodiments, the one or more pharmaceutically acceptable excipients comprise about 60% by weight to about 70% by weight of one or more fillers based on the weight of the pharmaceutically acceptable unit formulation.

In some embodiments, the one or more pharmaceutically acceptable excipients comprise about 70% by weight to about 90% by weight of one or more fillers based on the weight of the pharmaceutically acceptable unit formulation. In some embodiments, the one or more pharmaceutically acceptable excipients comprise about 70% by weight to about 80% by weight of one or more fillers based on the weight of the pharmaceutically acceptable unit formulation.

In some embodiments, the one or more pharmaceutically acceptable excipients comprise about 80% by weight to about 90% by weight of one or more fillers based on the weight of the pharmaceutically acceptable unit formulation.

In some embodiments, the one or more pharmaceutically acceptable excipients comprise about 1% by weight to about 20% by weight of one or more disintegrants based on the weight of the pharmaceutically acceptable unit formulation. In some embodiments, the one or more pharmaceutically acceptable excipients comprise about 1% by weight to about 15% by weight of one or more disintegrants based on the weight of the pharmaceutically acceptable unit formulation. In some embodiments, the one or more pharmaceutically acceptable excipients comprise about 1% by weight to about 14% by weight of one or more disintegrants based on the weight of the pharmaceutically acceptable unit formulation. In some embodiments, the one or more pharmaceutically acceptable excipients comprise about 1% by weight to about 13% by weight of one or more disintegrants based on the weight of the pharmaceutically acceptable unit formulation. In some embodiments, the one or more pharmaceutically acceptable excipients comprise about 1% by weight to about 12% by weight of one or more disintegrants based on the weight of the pharmaceutically acceptable unit formulation. In some embodiments, the one or more pharmaceutically acceptable excipients comprise about 1% by weight to about 11% by weight of one or more disintegrants based on the weight of the pharmaceutically acceptable unit formulation. In some embodiments, the one or more pharmaceutically acceptable excipients comprise about 1% by weight to about 10% by weight of one or more disintegrants based on the weight of the pharmaceutically acceptable unit formulation. In some embodiments, the one or more pharmaceutically acceptable excipients comprise about 1% by weight to about 9% by weight of one or more disintegrants based on the weight of the pharmaceutically acceptable unit formulation. In some embodiments, the one or more pharmaceutically acceptable excipients comprise about 1% by weight to about 8% by weight of one or more disintegrants based on the weight of the pharmaceutically acceptable unit formulation. In some embodiments, the one or more pharmaceutically acceptable excipients comprise about 1% by weight to about 7% by weight of one or more disintegrants based on the weight of the pharmaceutically acceptable unit formulation. In some embodiments, the one or more pharmaceutically acceptable excipients comprise about 1% by weight to about 6% by weight of one or more disintegrants based on the weight of the pharmaceutically acceptable unit formulation. In some embodiments, the one or more pharmaceutically acceptable excipients comprise about 1% by weight to about 5% by weight of one or more disintegrants based on the weight of the pharmaceutically acceptable unit formulation. In some embodiments, the one or more pharmaceutically acceptable excipients comprise about 1% by weight to about 4% by weight of one or more disintegrants based on the weight of the pharmaceutically acceptable unit formulation. In some embodiments, the one or more pharmaceutically acceptable excipients comprise about 1% by weight to about 3% by weight of one or more disintegrants based on the weight of the pharmaceutically acceptable unit formulation.

In some embodiments, the one or more pharmaceutically acceptable excipients comprise about 1% by weight of one or more disintegrants based on the weight of the pharmaceutically acceptable unit formulation. In some embodiments, the one or more pharmaceutically acceptable excipients comprise about 2% by weight of one or more disintegrants based on the weight of the pharmaceutically acceptable unit formulation. In some embodiments, the one or more pharmaceutically acceptable excipients comprise about 3% by weight of one or more disintegrants based on the weight of the pharmaceutically acceptable unit formulation. In some embodiments, the one or more pharmaceutically acceptable excipients comprise about 4% by weight of one or more disintegrants based on the weight of the pharmaceutically acceptable unit formulation. In some embodiments, the one or more pharmaceutically acceptable excipients comprise about 5% by weight of one or more disintegrants based on the weight of the pharmaceutically acceptable unit formulation. In some embodiments, the one or more pharmaceutically acceptable excipients comprise about 6% by weight of one or more disintegrants based on the weight of the pharmaceutically acceptable unit formulation. In some embodiments, the one or more pharmaceutically acceptable excipients comprise about 7% by weight of one or more disintegrants based on the weight of the pharmaceutically acceptable unit formulation. In some embodiments, the one or more pharmaceutically acceptable excipients comprise about 8% by weight of one or more disintegrants based on the weight of the pharmaceutically acceptable unit formulation. In some embodiments, the one or more pharmaceutically acceptable excipients comprise about 9% by weight of one or more disintegrants based on the weight of the pharmaceutically acceptable unit formulation. In some embodiments, the one or more pharmaceutically acceptable excipients comprise about 10% by weight of one or more disintegrants based on the weight of the pharmaceutically acceptable unit formulation. In some embodiments, the one or more pharmaceutically acceptable excipients comprise about 11% by weight of one or more disintegrants based on the weight of the pharmaceutically acceptable unit formulation. In some embodiments, the one or more pharmaceutically acceptable excipients comprise about 12% by weight of one or more disintegrants based on the weight of the pharmaceutically acceptable unit formulation. In some embodiments, the one or more pharmaceutically acceptable excipients comprise about 13% by weight of one or more disintegrants based on the weight of the pharmaceutically acceptable unit formulation. In some embodiments, the one or more pharmaceutically acceptable excipients comprise about 14% by weight of one or more disintegrants based on the weight of the pharmaceutically acceptable unit formulation. In some embodiments, the one or more pharmaceutically acceptable excipients comprise about 15% by weight of one or more disintegrants based on the weight of the pharmaceutically acceptable unit formulation.

In some embodiments, the one or more pharmaceutically acceptable excipients comprise about 0.1% by weight to about 10% by weight of one or more lubricants based on the weight of the pharmaceutically acceptable unit formulation. In some embodiments, the one or more pharmaceutically acceptable excipients comprise about 0.1% by weight to about 9% by weight of one or more lubricants based on the weight of the pharmaceutically acceptable unit formulation. In some embodiments, the one or more pharmaceutically acceptable excipients comprise about 0.1% by weight to about 8% by weight of one or more lubricants based on the weight of the pharmaceutically acceptable unit formulation. In some embodiments, the one or more pharmaceutically acceptable excipients comprise about 0.1% by weight to about 7% by weight of one or more lubricants based on the weight of the pharmaceutically acceptable unit formulation. In some embodiments, the one or more pharmaceutically acceptable excipients comprise about 0.1% by weight to about 6% by weight of one or more lubricants based on the weight of the pharmaceutically acceptable unit formulation. In some embodiments, the one or more pharmaceutically acceptable excipients comprise about 0.1% by weight to about 5% by weight of one or more lubricants based on the weight of the pharmaceutically acceptable unit formulation. In some embodiments, the one or more pharmaceutically acceptable excipients comprise about 0.1% by weight to about 4% by weight of one or more lubricants based on the weight of the pharmaceutically acceptable unit formulation. In some embodiments, the one or more pharmaceutically acceptable excipients comprise about 0.1% by weight to about 3% by weight of one or more lubricants based on the weight of the pharmaceutically acceptable unit formulation. In some embodiments, the one or more pharmaceutically acceptable excipients comprise about 0.1% by weight to about 2% by weight of one or more lubricants based on the weight of the pharmaceutically acceptable unit formulation.

In some embodiments, the one or more pharmaceutically acceptable excipients comprise about 0.1% by weight to about 1.9% by weight of one or more lubricants based on the weight of the pharmaceutically acceptable unit formulation. In some embodiments, the one or more pharmaceutically acceptable excipients comprise about 0.1% by weight to about 1.8% by weight of one or more lubricants based on the weight of the pharmaceutically acceptable unit formulation. In some embodiments, the one or more pharmaceutically acceptable excipients comprise about 0.1% by weight to about 1.7% by weight of one or more lubricants based on the weight of the pharmaceutically acceptable unit formulation. In some embodiments, the one or more pharmaceutically acceptable excipients comprise about 0.1% by weight to about 1.6% by weight of one or more lubricants based on the weight of the pharmaceutically acceptable unit formulation. In some embodiments, the one or more pharmaceutically acceptable excipients comprise about 0.1% by weight to about 1.5% by weight of one or more lubricants based on the weight of the pharmaceutically acceptable unit formulation. In some embodiments, the one or more pharmaceutically acceptable excipients comprise about 0.1% by weight to about 1.4% by weight of one or more lubricants based on the weight of the pharmaceutically acceptable unit formulation. In some embodiments, the one or more pharmaceutically acceptable excipients comprise about 0.1% by weight to about 1.3% by weight of one or more lubricants based on the weight of the pharmaceutically acceptable unit formulation. In some embodiments, the one or more pharmaceutically acceptable excipients comprise about 0.1% by weight to about 1.2% by weight of one or more lubricants based on the weight of the pharmaceutically acceptable unit formulation. In some embodiments, the one or more pharmaceutically acceptable excipients comprise about 0.1% by weight to about 1.1% by weight of one or more lubricants based on the weight of the pharmaceutically acceptable unit formulation. In some embodiments, the one or more pharmaceutically acceptable excipients comprise about 0.1% by weight to about 1.0% by weight of one or more lubricants based on the weight of the pharmaceutically acceptable unit formulation. In some embodiments, the one or more pharmaceutically acceptable excipients comprise about 0.1% by weight to about 0.9% by weight of one or more lubricants based on the weight of the pharmaceutically acceptable unit formulation. In some embodiments, the one or more pharmaceutically acceptable excipients comprise about 0.1% by weight to about 0.8% by weight of one or more lubricants based on the weight of the pharmaceutically acceptable unit formulation. In some embodiments, the one or more pharmaceutically acceptable excipients comprise about 0.1% by weight to about 0.7% by weight of one or more lubricants based on the weight of the pharmaceutically acceptable unit formulation. In some embodiments, the one or more pharmaceutically acceptable excipients comprise about 0.1% by weight to about 0.6% by weight of one or more lubricants based on the weight of the pharmaceutically acceptable unit formulation. In some embodiments, the one or more pharmaceutically acceptable excipients comprise about 0.1% by weight to about 0.5% by weight of one or more lubricants based on the weight of the pharmaceutically acceptable unit formulation. In some embodiments, the one or more pharmaceutically acceptable excipients comprise about 0.1% by weight to about 0.4% by weight of one or more lubricants based on the weight of the pharmaceutically acceptable unit formulation. In some embodiments, the one or more pharmaceutically acceptable excipients comprise about 0.1% by weight to about 0.3% by weight of one or more lubricants based on the weight of the pharmaceutically acceptable unit formulation. In some embodiments, the one or more pharmaceutically acceptable excipients comprise about 0.1% by weight to about 0.2% by weight of one or more lubricants based on the weight of the pharmaceutically acceptable unit formulation.

In some embodiments, the pharmaceutically acceptable unit formulation comprises: (a) about 1% by weight to about 30% by weight of the compound of Formula (I) based on the weight of the pharmaceutically acceptable unit formulation; (b) about 20% by weight to about 90% by weight of one or more fillers based on the weight of the pharmaceutically acceptable unit formulation; (c) about 1% by weight to about 20% by weight of one or more disintegrants based on the weight of the pharmaceutically acceptable unit formulation; and (d) about 0.1% by weight to about 10% by weight of one or more lubricants based on the weight of the pharmaceutically acceptable unit formulation.

In some embodiments, the pharmaceutically acceptable unit formulation consists essentially of: (a) about 1% by weight to about 30% by weight of the compound of Formula (I) based on the weight of the pharmaceutically acceptable unit formulation; (b) about 20% by weight to about 90% by weight of one or more fillers based on the weight of the pharmaceutically acceptable unit formulation; (c) about 1% by weight to about 20% by weight of one or more disintegrants based on the weight of the pharmaceutically acceptable unit formulation; and (d) about 0.1% by weight to about 10% by weight of one or more lubricants based on the weight of the pharmaceutically acceptable unit formulation.

In some embodiments, the pharmaceutically acceptable unit formulation comprises (a) about 5% by weight to about 25% by weight of the compound of Formula (I) based on the weight of the pharmaceutically acceptable unit formulation; (b) about 60% by weight to about 90% by weight of one or more fillers based on the weight of the pharmaceutically acceptable unit formulation; (c) about 1% by weight to about 15% by weight of one or more disintegrants based on the weight of the pharmaceutically acceptable unit formulation; and (d) about 0.1% by weight to about 4% by weight of one or more lubricants based on the weight of the pharmaceutically acceptable unit formulation.

In some embodiments, the pharmaceutically acceptable unit formulation consists essentially of: (a) about 5% by weight to about 25% by weight of the compound of Formula (I) based on the weight of the pharmaceutically acceptable unit formulation; (b) about 60% by weight to about 90% by weight of one or more fillers based on the weight of the pharmaceutically acceptable unit formulation; (c) about 1% by weight to about 15% by weight of one or more disintegrants based on the weight of the pharmaceutically acceptable unit formulation; and (d) about 0.1% by weight to about 4% by weight of one or more lubricants based on the weight of the pharmaceutically acceptable unit formulation.

In some embodiments, the pharmaceutically acceptable unit formulation comprises: (a) about 10% by weight to about 30% by weight of the compound of Formula (I) based on the weight of the pharmaceutically acceptable unit formulation; (b) about 70% by weight to about 90% by weight of one or more fillers based on the weight of the pharmaceutically acceptable unit formulation; (c) about 1% by weight to about 10% by weight of one or more disintegrants based on the weight of the pharmaceutically acceptable unit formulation; and (d) about 0.1% by weight to about 3% by weight of one or more lubricants based on the weight of the pharmaceutically acceptable unit formulation.

In some embodiments, the pharmaceutically acceptable unit formulation consists essentially of: (a) about 10% by weight to about 30% by weight of the compound of Formula (I) based on the weight of the pharmaceutically acceptable unit formulation; (b) about 70% by weight to about 90% by weight of one or more fillers based on the weight of the pharmaceutically acceptable unit formulation; (c) about 1% by weight to about 10% by weight of one or more disintegrants based on the weight of the pharmaceutically acceptable unit formulation; and (d) about 0.1% by weight to about 3% by weight of one or more lubricants based on the weight of the pharmaceutically acceptable unit formulation.

In some embodiments, the one or more pharmaceutically acceptable excipients is one or more fillers selected from the group consisting of calcium phosphate, dicalcium phosphate, dicalcium phosphate dihydrate, calcium sulfate, calcium sulfate dihydrate, starch, calcium carbonate, magnesium carbonate, magnesium oxide, kaolin (natural hydrated aluminum silicate), sodium chloride, partially gelatinized starch, anhydrous lactose, lactose monohydrate, lactose dihydrate, trehalose dihydrate, spray dried lactose, sucrose, dextrose, dextrates, dextrin, cellulose, microcrystalline cellulose, silicified microcrystalline cellulose, powdered cellulose, partially depolymerized cellulose, mannitol, granulated mannitol, spray dried mannitol, maltodextrin, maltitol, confectioner's sugar, compressible sugar, sorbitol, starch and talc. In some embodiments, the one or more fillers is lactose monohydrate.

In some embodiments, the one or more disintegrants is one or more disintegrants selected from the group consisting of sodium starch glycolate, pregelatinized starch, clay, cellulose, alginic acid, alginate gum, polyvinylpyrrolidone, cross-linked polyvinylpyrrolidone, cross-linked calcium carboxymethylcellulose, cross-linked sodium carboxymethylcellulose, sodium croscarmellose, sodium carmellose, low substituted hydroxypropyl cellulose, low substituted hydroxypropyl cellulose sodium, guar gum, magnesium aluminum silicate, polacrilin potassium, powdered cellulose, sodium alginate and soy polysaccharides. In some embodiments, the one or more disintegrants is cross-linked polyvinylpyrrolidone (also referred to as crospovidone).

In some embodiments, the one or more lubricants is one or more lubricants selected from the group consisting of colloidal silica, magnesium trisilicate, talc, magnesium carbonate, magnesium oxide, glyceryl behaptate, mono, di and tri glyceryl behenate, bees wax, behenoyl polyoxyl-8 glycerides, hydrogenated vegetable oil, polyethylene glycol, ethylene oxide polymer, copolymer comprising poly(ethylene oxide) and poly(propylene oxide) (such as poloxomer 188), copolymer comprising polypropylene glycol and polyethylene glycol (such as poloxomer 407), sodium lauryl sulfate, magnesium stearate, aluminum stearate, calcium stearate, sodium stearyl fumarate, stearic acid, magnesium lauryl stearate, mixtures of magnesium stearate with sodium lauryl sulfate. In some embodiments, the one or more lubricants is magnesium stearate.

In some embodiments, the pharmaceutically acceptable unit formulation further comprises cross-linked polyvinylpyrrolidone and magnesium stearate. In some embodiments, the one or more pharmaceutically acceptable excipients is lactose monohydrate and the pharmaceutically acceptable unit formulation further comprises cross-linked polyvinylpyrrolidone and magnesium stearate.

In some embodiments, the pharmaceutically acceptable unit formulation is for oral administration.

In some embodiments, the pharmaceutically acceptable unit formulation is a solid dosage form.

In some embodiments, the pharmaceutically acceptable unit formulation is a tablet or a capsule. In some embodiments, the pharmaceutically acceptable unit formulation is a tablet. In some embodiments, the pharmaceutically acceptable unit formulation is a capsule. In some embodiments, the pharmaceutically acceptable unit formulation is a sachet. In some embodiments, the pharmaceutically acceptable unit formulation is a powder in a packet.

In some embodiments, the pharmaceutically acceptable unit formulation comprises about 1 mg to about 40 mg of the compound of Formula (I). In some embodiments, the pharmaceutically acceptable unit formulation comprises about 1 mg to about 30 mg of the compound of Formula (I). In some embodiments, the pharmaceutically acceptable unit formulation comprises about 1 mg to about 20 mg of the compound of Formula (I). In some embodiments, the pharmaceutically acceptable unit formulation comprises about 1 mg to about 15 mg of the compound of Formula (I). In some embodiments, the pharmaceutically acceptable unit formulation comprises about 5 mg to about 40 mg of the compound of Formula (I). In some embodiments, the pharmaceutically acceptable unit formulation comprises about 5 mg to about 30 mg of the compound of Formula (I). In some embodiments, the pharmaceutically acceptable unit formulation comprises about 5 mg to about 20 mg of the compound of Formula (I). In some embodiments, the pharmaceutically acceptable unit formulation comprises about 5 mg to about 15 mg of the compound of Formula (I). In some embodiments, the pharmaceutically acceptable unit formulation comprises about 10 mg to about 40 mg of the compound of Formula (I). In some embodiments, the pharmaceutically acceptable unit formulation comprises about 10 mg to about 30 mg of the compound of Formula (I). In some embodiments, the pharmaceutically acceptable unit formulation comprises about 10 mg to about 20 mg of the compound of Formula (I). In some embodiments, the pharmaceutically acceptable unit formulation comprises about 10 mg to about 15 mg of the compound of Formula (I).

In some embodiments, the pharmaceutically acceptable unit formulation consists essentially of about 1 mg to about 40 mg of the compound of Formula (I). In some embodiments, the pharmaceutically acceptable unit formulation consists essentially of about 1 mg to about 30 mg of the compound of Formula (I). In some embodiments, the pharmaceutically acceptable unit formulation consists essentially of about 1 mg to about 20 mg of the compound of Formula (I). In some embodiments, the pharmaceutically acceptable unit formulation consists essentially of about 1 mg to about 15 mg of the compound of Formula (I). In some embodiments, the pharmaceutically acceptable unit formulation consists essentially of about 5 mg to about 40 mg of the compound of Formula (I). In some embodiments, the pharmaceutically acceptable unit formulation consists essentially of about 5 mg to about 30 mg of the compound of Formula (I). In some embodiments, the pharmaceutically acceptable unit formulation consists essentially of about 5 mg to about 20 mg of the compound of Formula (I). In some embodiments, the pharmaceutically acceptable unit formulation consists essentially of about 5 mg to about 15 mg of the compound of Formula (I). In some embodiments, the pharmaceutically acceptable unit formulation consists essentially of about 10 mg to about 40 mg of the compound of Formula (I). In some embodiments, the pharmaceutically acceptable unit formulation consists essentially of about 10 mg to about 30 mg of the compound of Formula (I). In some embodiments, the pharmaceutically acceptable unit formulation consists essentially of about 10 mg to about 20 mg of the compound of Formula (I). In some embodiments, the pharmaceutically acceptable unit formulation consists essentially of about 10 mg to about 15 mg of the compound of Formula (I).

In some embodiments, compound of Formula (I) is present in the pharmaceutically acceptable unit formulation as a cocrystal. In some embodiments, compound of Formula (I) is present in the pharmaceutically acceptable unit formulation as a channel crystal. In some embodiments, compound of Formula (I) is present in the pharmaceutically acceptable unit formulation as a crystalline dihydrate form. In some embodiments, the compound of Formula (I) is present in the pharmaceutically acceptable unit formulation as a crystalline anhydrous form. In some embodiments, compound of Formula (I) is present in the pharmaceutically acceptable unit formulation as a solvate.

In some embodiments, the pharmaceutically acceptable unit formulation comprises about 0.5 mg to about 5 mg, about 6 mg to about 14 mg, about 11 mg to about 19 mg, about 17 mg to about 25 mg, or about 28 mg to about 36 mg of the compound of Formula (I) as a crystalline dihydrate form. In some embodiments, the pharmaceutically acceptable unit formulation comprises about 1 mg to about 4 mg, about 8 mg to about 12 mg, about 13 mg to about 17 mg, about 19 mg to about 23 mg, or about 30 mg to about 34 mg of the compound of Formula (I) as a crystalline dihydrate form. In some embodiments, the pharmaceutically acceptable unit formulation comprises about 2.2 mg, about 10.8 mg, about 15.2 mg, about 21.7 mg, or about 32.5 mg of the compound of Formula (I) as a crystalline dihydrate form.

In some embodiments, the pharmaceutically acceptable unit formulation consists essentially of about 0.5 mg to about 5 mg, about 6 mg to about 14 mg, about 11 mg to about 19 mg, about 17 mg to about 25 mg, or about 28 mg to about 36 mg of the compound of Formula (I) as a crystalline dihydrate form. In some embodiments, the pharmaceutically acceptable unit formulation consists essentially of about 1 mg to about 4 mg, about 8 mg to about 12 mg, about 13 mg to about 17 mg, about 19 mg to about 23 mg, or about 30 mg to about 34 mg of the compound of Formula (I) as a crystalline dihydrate form. In some embodiments, the pharmaceutically acceptable unit formulation consists essentially of about 2.2 mg, about 10.8 mg, about 15.2 mg, about 21.7 mg, or about 32.5 mg of the compound of Formula (I) as a crystalline dihydrate form.

In some embodiments, the pharmaceutically acceptable unit formulation has an acceptance value of less than about 15 as determined by USP Uniformity of Dosage Unit <905>. In some embodiments, the pharmaceutically acceptable unit formulation has a maximum acceptance value of equal to or less than about 15 as determined by USP Uniformity of Dosage Unit <905>.

In some embodiments, the uniformity of the pharmaceutically acceptable formulation represents the degree of uniformity in the amount of the compound of Formula (I) in the pharmaceutically acceptable formulation.

In some embodiments, the uniformity of the oral dosage form represents the degree of uniformity in the amount of the compound of Formula (I) in the oral dosage form.

In some embodiments, the uniformity of the pharmaceutically acceptable capsule represents the degree of uniformity in the amount of the compound of Formula (I) in the pharmaceutically acceptable capsule.

Also provided herein is a process of preparing a pharmaceutically acceptable unit formulation, the pharmaceutically acceptable unit formulation comprising:

(a) about 1% by weight to about 70% by weight, based on the weight of the pharmaceutically acceptable unit formulation, of a crystalline dihydrate form of a compound of Formula (I):

Formula (I)

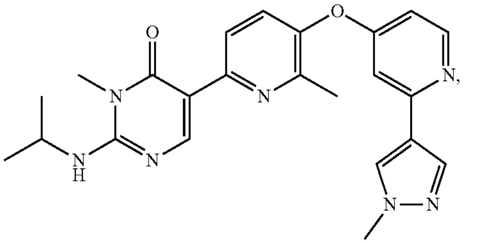

and one or more pharmaceutically acceptable excipients, wherein the one or more pharmaceutically acceptable excipients comprise:

(b) about 20% by weight to about 97% by weight of one or more fillers, based on the weight of the pharmaceutically acceptable unit formulation;

(c) about 1% by weight to about 20% by weight of one or more disintegrants, based on the weight of the pharmaceutically acceptable unit formulation; and (d) about 0.1% by weight to about 10% by weight of one or more lubricants, based on the weight of the pharmaceutically acceptable unit formulation the process comprising:

(i) blending the crystalline dihydrate form of a compound represented by Formula (I) with the one or more fillers and one or more disintegrants to produce a first blend; and (ii) blending the first blend with the one or more lubricants, thereby preparing the pharmaceutically acceptable unit formulation.

Also provided herein is a process of preparing a pharmaceutically acceptable unit formulation, the pharmaceutically acceptable unit formulation consisting essentially of:

(a) about 1% by weight to about 70% by weight, based on the weight of the pharmaceutically acceptable unit formulation, of a crystalline dihydrate form of a compound of Formula (I):

Formula (I)

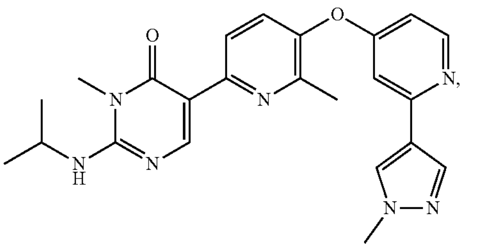

and one or more pharmaceutically acceptable excipients, wherein the one or more pharmaceutically acceptable excipients comprise:

(b) about 20% by weight to about 97% by weight of one or more fillers, based on the weight of the pharmaceutically acceptable unit formulation;

(c) about 1% by weight to about 20% by weight of one or more disintegrants, based on the weight of the pharmaceutically acceptable unit formulation; and (d) about 0.1% by weight to about 10% by weight of one or more lubricants, based on the weight of the pharmaceutically acceptable unit formulation the process comprising:

(i) blending the crystalline dihydrate form of a compound represented by Formula (I) with the one or more fillers and one or more disintegrants to produce a first blend; and (ii) blending the first blend with the one or more lubricants, thereby preparing the pharmaceutically acceptable unit formulation.

Also provided herein is a process of preparing a pharmaceutically acceptable unit formulation, the pharmaceutically acceptable unit formulation comprising:

(a) about 1% by weight to about 70% by weight, based on the weight of the pharmaceutically acceptable unit formulation of a crystalline dihydrate form of a compound of Formula (I):

Formula (I)

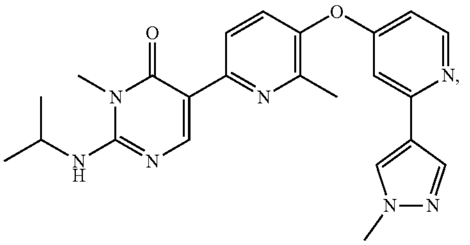

and one or more pharmaceutically acceptable excipients, wherein the one or more pharmaceutically acceptable excipients comprise:

(b) about 20% by weight to about 97% by weight of one or more fillers, based on the weight of the pharmaceutically acceptable unit formulation;

(c) about 1% by weight to about 20% by weight of one or more disintegrants, based on the weight of the pharmaceutically acceptable unit formulation; and (d) about 0.1% by weight to about 10% by weight of one or more lubricants, based on the weight of the pharmaceutically acceptable unit formulation the process comprising:

(i) blending the crystalline dihydrate form of a compound represented by Formula (I) with the one or more fillers to produce a first blend;

(ii) blending the first blend with one or more disintegrants to produce a second blend; and (iii) blending the second blend with the one or more lubricants, thereby preparing the pharmaceutically acceptable unit formulation.

Also provided herein is a process of preparing a pharmaceutically acceptable unit formulation, the pharmaceutically acceptable unit formulation consisting essentially of:

(a) about 1% by weight to about 70% by weight, based on the weight of the pharmaceutically acceptable unit formulation of a crystalline dihydrate form of a compound of Formula (I):

Formula (I)

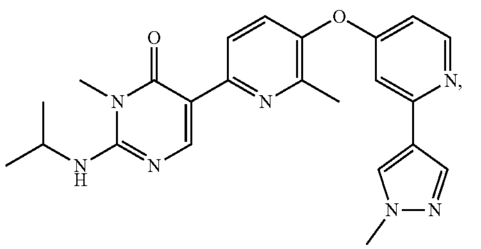

and one or more pharmaceutically acceptable excipients, wherein the one or more pharmaceutically acceptable excipients comprise:

(b) about 20% by weight to about 97% by weight of one or more fillers, based on the weight of the pharmaceutically acceptable unit formulation;

(c) about 1% by weight to about 20% by weight of one or more disintegrants, based on the weight of the pharmaceutically acceptable unit formulation; and (d) about 0.1% by weight to about 10% by weight of one or more lubricants, based on the weight of the pharmaceutically acceptable unit formulation the process comprising:

(i) blending the crystalline dihydrate form of a compound represented by Formula (I) with the one or more fillers to produce a first blend;

(ii) blending the first blend with one or more disintegrants to produce a second blend; and (iii) blending the second blend with the one or more lubricants, thereby preparing the pharmaceutically acceptable unit formulation.

Also provided herein is a process of preparing a pharmaceutically acceptable unit formulation, the pharmaceutically acceptable unit formulation comprising:

(a) about 1% by weight to about 70% by weight, based on the weight of the pharmaceutically acceptable unit formulation of a crystalline dihydrate form of a compound of Formula (I):

Formula (I)

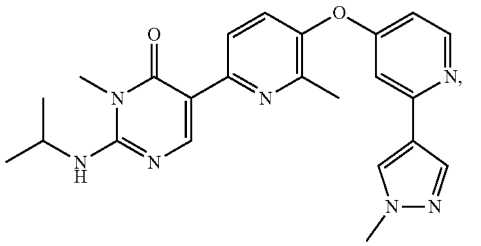

and one or more pharmaceutically acceptable excipients, wherein the one or more pharmaceutically acceptable excipients comprise:

(b) about 20% by weight to about 97% by weight of one or more fillers, based on the weight of the pharmaceutically acceptable unit formulation;

(c) about 1% by weight to about 20% by weight of one or more disintegrants, based on the weight of the pharmaceutically acceptable unit formulation; and (d) about 0.1% by weight to about 10% by weight of one or more lubricants, based on the weight of the pharmaceutically acceptable unit formulation the process comprising:

(i) blending the crystalline dihydrate form of a compound represented by Formula (I) with the one or more fillers to produce a first blend;

(ii) blending the first blend with a second blend comprising one or more disintegrants and one or more fillers and optionally a third blend comprising one or more fillers to produce a fourth blend; and (iii) blending the fourth blend with the one or more lubricants, thereby preparing the pharmaceutically acceptable unit formulation.

Also provided herein is a process of preparing a pharmaceutically acceptable unit formulation, the pharmaceutically acceptable unit formulation consisting essentially of:

(a) about 1% by weight to about 70% by weight, based on the weight of the pharmaceutically acceptable unit formulation of a crystalline dihydrate form of a compound of Formula (I):

Formula (I)

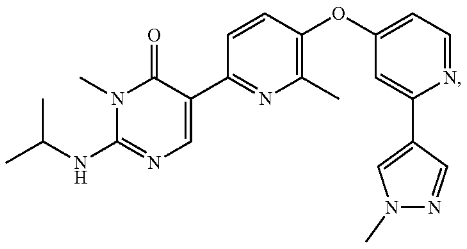

and one or more pharmaceutically acceptable excipients, wherein the one or more pharmaceutically acceptable excipients comprise:

(b) about 20% by weight to about 97% by weight of one or more fillers, based on the weight of the pharmaceutically acceptable unit formulation;

(c) about 1% by weight to about 20% by weight of one or more disintegrants, based on the weight of the pharmaceutically acceptable unit formulation; and (d) about 0.1% by weight to about 10% by weight of one or more lubricants, based on the weight of the pharmaceutically acceptable unit formulation the process comprising:

(i) blending the crystalline dihydrate form of a compound represented by Formula (I) with the one or more fillers to produce a first blend;

(ii) blending the first blend with a second blend comprising one or more disintegrants and one or more fillers and optionally a third blend comprising one or more fillers to produce a fourth blend; and (iii) blending the fourth blend with the one or more lubricants, thereby preparing the pharmaceutically acceptable unit formulation.

In some embodiments, the pharmaceutically acceptable unit formulation comprising the crystalline dihydrate form of the compound represented by Formula (I), has no more than about 10 mol %, no more than about 5 mol %, no more than about 3 mol %, or no more than about 1 mol % of other solid-state forms of the compound represented by Formula (I). In some embodiments, the pharmaceutically acceptable unit formulation comprising the crystalline dihydrate forms of the compound represented by Formula (I), has no more than about 10 mol % of other solid-state forms of the compound represented by Formula (I). In some embodiments, the pharmaceutically acceptable unit formulation comprising the crystalline dihydrate forms of the compound represented by Formula (I), has no more than about 9 mol % of other solid-state forms of the compound represented by Formula (I). In some embodiments, the pharmaceutically acceptable unit formulation comprising the crystalline dihydrate forms of the compound represented by Formula (I), has no more than about 8 mol % of other solid-state forms of the compound represented by Formula (I). In some embodiments, the pharmaceutically acceptable unit formulation comprising the crystalline dihydrate forms of the compound represented by Formula (I), has no more than about 7 mol % of other solid-state forms of the compound represented by Formula (I). In some embodiments, the pharmaceutically acceptable unit formulation comprising the crystalline dihydrate forms of the compound represented by Formula (I), has no more than about 6 mol % of other solid-state forms of the compound represented by Formula (I). In some embodiments, the pharmaceutically acceptable unit formulation comprising the crystalline dihydrate forms of the compound represented by Formula (I), has no more than about 5 mol % of other solid-state forms of the compound represented by Formula (I). In some embodiments, the pharmaceutically acceptable unit formulation comprising the crystalline dihydrate forms of the compound represented by Formula (I), has no more than about 4 mol % of other solid-state forms of the compound represented by Formula (I). In some embodiments, the pharmaceutically acceptable unit formulation comprising the crystalline dihydrate forms of the compound represented by Formula (I), has no more than about 3 mol % of other solid-state forms of the compound represented by Formula (I). In some embodiments, the pharmaceutically acceptable unit formulation comprising the crystalline dihydrate forms of the compound represented by Formula (I), has no more than about 2 mol % of other solid-state forms of the compound represented by Formula (I). In some embodiments, the pharmaceutically acceptable unit formulation comprising the crystalline dihydrate forms of the compound represented by Formula (I), has no more than about 1 mol % of other solid-state forms of the compound represented by Formula (I).

In some embodiments, the pharmaceutically acceptable unit formulation comprises about 1% by weight to about 60% by weight, based on the weight of the pharmaceutically acceptable unit formulation, of a crystalline dihydrate form of a compound of Formula (I). In some embodiments, the pharmaceutically acceptable unit formulation comprises about 1% by weight to about 50% by weight, based on the weight of the pharmaceutically acceptable unit formulation, of a crystalline dihydrate form of a compound of Formula (I). In some embodiments, the pharmaceutically acceptable unit formulation comprises about 1% by weight to about 40% by weight, based on the weight of the pharmaceutically acceptable unit formulation, of a crystalline dihydrate form of a compound of Formula (I). In some embodiments, the pharmaceutically acceptable unit formulation comprises about 1% by weight to about 30% by weight, based on the weight of the pharmaceutically acceptable unit formulation, of a crystalline dihydrate form of a compound of Formula (I). In some embodiments, the pharmaceutically acceptable unit formulation comprises about 1% by weight to about 20% by weight, based on the weight of the pharmaceutically acceptable unit formulation, of a crystalline dihydrate form of a compound of Formula (I).

In some embodiments, the pharmaceutically acceptable unit formulation consists essentially of about 1% by weight to about 60% by weight, based on the weight of the pharmaceutically acceptable unit formulation, of a crystalline dihydrate form of a compound of Formula (I). In some embodiments, the pharmaceutically acceptable unit formulation consists essentially of about 1% by weight to about 50% by weight, based on the weight of the pharmaceutically acceptable unit formulation, of a crystalline dihydrate form of a compound of Formula (I). In some embodiments, the pharmaceutically acceptable unit formulation consists essentially of about 1% by weight to about 40% by weight, based on the weight of the pharmaceutically acceptable unit formulation, of a crystalline dihydrate form of a compound of Formula (I). In some embodiments, the pharmaceutically acceptable unit formulation consists essentially of about 1% by weight to about 30% by weight, based on the weight of the pharmaceutically acceptable unit formulation, of a crystalline dihydrate form of a compound of Formula (I). In some embodiments, the pharmaceutically acceptable unit formulation consists essentially of about 1% by weight to about 20% by weight, based on the weight of the pharmaceutically acceptable unit formulation, of a crystalline dihydrate form of a compound of Formula (I).

In some embodiments, the pharmaceutically acceptable unit formulation comprises about 1% by weight to about 70% by weight of the crystalline dihydrate form of the compound of Formula (I) based on the weight of the pharmaceutically acceptable unit formulation. In some embodiments, the pharmaceutically acceptable unit formulation comprises about 1% by weight to about 65% by weight of the crystalline dihydrate form of the compound of Formula (I) based on the weight of the pharmaceutically acceptable unit formulation. In some embodiments, the pharmaceutically acceptable unit formulation comprises about 1% by weight to about 60% by weight of the crystalline dihydrate form of the compound of Formula (I) based on the weight of the pharmaceutically acceptable unit formulation. In some embodiments, the pharmaceutically acceptable unit formulation comprises about 1% by weight to about 55% by weight of the crystalline dihydrate form of the compound of Formula (I) based on the weight of the pharmaceutically acceptable unit formulation. In some embodiments, the pharmaceutically acceptable unit formulation comprises about 1% by weight to about 50% by weight of the crystalline dihydrate form of the compound of Formula (I) based on the weight of the pharmaceutically acceptable unit formulation. In some embodiments, the pharmaceutically acceptable unit formulation comprises about 1% by weight to about 45% by weight of the crystalline dihydrate form of the compound of Formula (I) based on the weight of the pharmaceutically acceptable unit formulation. In some embodiments, the pharmaceutically acceptable unit formulation comprises about 1% by weight to about 40% by weight of the crystalline dihydrate form of the compound of Formula (I) based on the weight of the pharmaceutically acceptable unit formulation. In some embodiments, the pharmaceutically acceptable unit formulation comprises about 1% by weight to about 35% by weight of the crystalline dihydrate form of the compound of Formula (I) based on the weight of the pharmaceutically acceptable unit formulation. In some embodiments, the pharmaceutically acceptable unit formulation comprises about 1% by weight to about 30% by weight of the crystalline dihydrate form of the compound of Formula (I) based on the weight of the pharmaceutically acceptable unit formulation. In some embodiments, the pharmaceutically acceptable unit formulation comprises about 1% by weight to about 25% by weight of the crystalline dihydrate form of the compound of Formula (I) based on the weight of the pharmaceutically acceptable unit formulation. In some embodiments, the pharmaceutically acceptable unit formulation comprises about 1% by weight to about 20% by weight of the crystalline dihydrate form of the compound of Formula (I) based on the weight of the pharmaceutically acceptable unit formulation. In some embodiments, the pharmaceutically acceptable unit formulation comprises about 1% by weight to about 15% by weight of the crystalline dihydrate form of the compound of Formula (I) based on the weight of the pharmaceutically acceptable unit formulation. In some embodiments, the pharmaceutically acceptable unit formulation comprises about 1% by weight to about 10% by weight of the crystalline dihydrate form of the compound of Formula (I) based on the weight of the pharmaceutically acceptable unit formulation.

In some embodiments, the pharmaceutically acceptable unit formulation consists essentially of about 1% by weight to about 70% by weight of the crystalline dihydrate form of the compound of Formula (I) based on the weight of the pharmaceutically acceptable unit formulation. In some embodiments, the pharmaceutically acceptable unit formulation consists essentially of about 1% by weight to about 65% by weight of the crystalline dihydrate form of the compound of Formula (I) based on the weight of the pharmaceutically acceptable unit formulation. In some embodiments, the pharmaceutically acceptable unit formulation consists essentially of about 1% by weight to about 60% by weight of the crystalline dihydrate form of the compound of Formula (I) based on the weight of the pharmaceutically acceptable unit formulation. In some embodiments, the pharmaceutically acceptable unit formulation consists essentially of about 1% by weight to about 55% by weight of the crystalline dihydrate form of the compound of Formula (I) based on the weight of the pharmaceutically acceptable unit formulation. In some embodiments, the pharmaceutically acceptable unit formulation consists essentially of about 1% by weight to about 50% by weight of the crystalline dihydrate form of the compound of Formula (I) based on the weight of the pharmaceutically acceptable unit formulation. In some embodiments, the pharmaceutically acceptable unit formulation consists essentially of about 1% by weight to about 45% by weight of the crystalline dihydrate form of the compound of Formula (I) based on the weight of the pharmaceutically acceptable unit formulation. In some embodiments, the pharmaceutically acceptable unit formulation consists essentially of about 1% by weight to about 40% by weight of the crystalline dihydrate form of the compound of Formula (I) based on the weight of the pharmaceutically acceptable unit formulation. In some embodiments, the pharmaceutically acceptable unit formulation consists essentially of about 1% by weight to about 35% by weight of the crystalline dihydrate form of the compound of Formula (I) based on the weight of the pharmaceutically acceptable unit formulation. In some embodiments, the pharmaceutically acceptable unit formulation consists essentially of about 1% by weight to about 30% by weight of the crystalline dihydrate form of the compound of Formula (I) based on the weight of the pharmaceutically acceptable unit formulation. In some embodiments, the pharmaceutically acceptable unit formulation consists essentially of about 1% by weight to about 25% by weight of the crystalline dihydrate form of the compound of Formula (I) based on the weight of the pharmaceutically acceptable unit formulation. In some embodiments, the pharmaceutically acceptable unit formulation consists essentially of about 1% by weight to about 20% by weight of the crystalline dihydrate form of the compound of Formula (I) based on the weight of the pharmaceutically acceptable unit formulation. In some embodiments, the pharmaceutically acceptable unit formulation consists essentially of about 1% by weight to about 15% by weight of the crystalline dihydrate form of the compound of Formula (I) based on the weight of the pharmaceutically acceptable unit formulation. In some embodiments, the pharmaceutically acceptable unit formulation consists essentially of about 1% by weight to about 10% by weight of the crystalline dihydrate form of the compound of Formula (I) based on the weight of the pharmaceutically acceptable unit formulation.

In some embodiments, the pharmaceutically acceptable unit formulation comprises about 5% by weight to about 30% by weight of the crystalline dihydrate form of the compound of Formula (I) based on the weight of the pharmaceutically acceptable unit formulation. In some embodiments, the pharmaceutically acceptable unit formulation comprises about 5% by weight to about 25% by weight of the crystalline dihydrate form of the compound of Formula (I) based on the weight of the pharmaceutically acceptable unit formulation. In some embodiments, the pharmaceutically acceptable unit formulation comprises about 5% by weight to about 20% by weight of the crystalline dihydrate form of the compound of Formula (I) based on the weight of the pharmaceutically acceptable unit formulation. In some embodiments, the pharmaceutically acceptable unit formulation comprises about 5% by weight to about 15% by weight of the crystalline dihydrate form of the compound of Formula (I) based on the weight of the pharmaceutically acceptable unit formulation. In some embodiments, the pharmaceutically acceptable unit formulation comprises about 5% by weight to about 10% by weight of the crystalline dihydrate form of the compound of Formula (I) based on the weight of the pharmaceutically acceptable unit formulation.

In some embodiments, the pharmaceutically acceptable unit formulation consists essentially of about 5% by weight to about 30% by weight of the crystalline dihydrate form of the compound of Formula (I) based on the weight of the pharmaceutically acceptable unit formulation. In some embodiments, the pharmaceutically acceptable unit formulation consists essentially of about 5% by weight to about 25% by weight of the crystalline dihydrate form of the compound of Formula (I) based on the weight of the pharmaceutically acceptable unit formulation. In some embodiments, the pharmaceutically acceptable unit formulation consists essentially of about 5% by weight to about 20% by weight of the crystalline dihydrate form of the compound of Formula (I) based on the weight of the pharmaceutically acceptable unit formulation. In some embodiments, the pharmaceutically acceptable unit formulation consists essentially of about 5% by weight to about 15% by weight of the crystalline dihydrate form of the compound of Formula (I) based on the weight of the pharmaceutically acceptable unit formulation. In some embodiments, the pharmaceutically acceptable unit formulation consists essentially of about 5% by weight to about 10% by weight of the crystalline dihydrate form of the compound of Formula (I) based on the weight of the pharmaceutically acceptable unit formulation.

In some embodiments, the pharmaceutically acceptable unit formulation comprises about 10% to about 30% of the compound of Formula (I) based on the weight of the pharmaceutically acceptable unit formulation. In some embodiments, the pharmaceutically acceptable unit formulation comprises about 10% to about 25% of the compound of Formula (I) based on the weight of the pharmaceutically acceptable unit formulation. In some embodiments, the pharmaceutically acceptable unit formulation comprises about 10% to about 20% of the compound of Formula (I) based on the weight of the pharmaceutically acceptable unit formulation. In some embodiments, the pharmaceutically acceptable unit formulation comprises about 10% by weight to about 15% by weight of the crystalline dihydrate form of the compound of Formula (I) based on the weight of the pharmaceutically acceptable unit formulation.

In some embodiments, the pharmaceutically acceptable unit formulation consists essentially of about 10% to about 30% of the crystalline dihydrate form of the compound of Formula (I) based on the weight of the pharmaceutically acceptable unit formulation. In some embodiments, the pharmaceutically acceptable unit formulation consists essentially of about 10% to about 25% of the crystalline dihydrate form of the compound of Formula (I) based on the weight of the pharmaceutically acceptable unit formulation. In some embodiments, the pharmaceutically acceptable unit formulation consists essentially of about 10% to about 20% of the crystalline dihydrate form of the compound of Formula (I) based on the weight of the pharmaceutically acceptable unit formulation. In some embodiments, the pharmaceutically acceptable unit formulation consists essentially of about 10% by weight to about 15% by weight of the crystalline dihydrate form of the compound of Formula (I) based on the weight of the pharmaceutically acceptable unit formulation.

In some embodiments, the pharmaceutically acceptable unit formulation comprises about 1% by weight to about 30% by weight of the crystalline dihydrate form of the compound of Formula (I) based on the weight of the pharmaceutically acceptable unit formulation. In some embodiments, the pharmaceutically acceptable unit formulation comprises about 1% by weight to about 10% by weight of the crystalline dihydrate form of the compound of Formula (I) based on the weight of the pharmaceutically acceptable unit formulation. In some embodiments, the pharmaceutically acceptable unit formulation comprises about 10% to about 20% of the compound of Formula (I) based on the weight of the pharmaceutically acceptable unit formulation. In some embodiments, the pharmaceutically acceptable unit formulation comprises about 10% by weight to about 15% by weight of the crystalline dihydrate form of the compound of Formula (I) based on the weight of the pharmaceutically acceptable unit formulation.

In some embodiments, the pharmaceutically acceptable unit formulation consists essentially of about 1% by weight to about 30% by weight of the crystalline dihydrate form of the compound of Formula (I) based on the weight of the pharmaceutically acceptable unit formulation. In some embodiments, the pharmaceutically acceptable unit formulation consists essentially of about 1% by weight to about 10% by weight of the crystalline dihydrate form of the compound of Formula (I) based on the weight of the pharmaceutically acceptable unit formulation. In some embodiments, the pharmaceutically acceptable unit formulation consists essentially of about 10% to about 20% of the crystalline dihydrate form of the compound of Formula (I) based on the weight of the pharmaceutically acceptable unit formulation. In some embodiments, the pharmaceutically acceptable unit formulation consists essentially of about 10% by weight to about 15% by weight of the crystalline dihydrate form of the compound of Formula (I) based on the weight of the pharmaceutically acceptable unit formulation.

In some embodiments, the one or more pharmaceutically acceptable excipients comprise about 20% by weight to about 90% by weight of one or more fillers based on the weight of the pharmaceutically acceptable unit formulation. In some embodiments, the one or more pharmaceutically acceptable excipients comprise about 20% by weight to about 85% by weight of one or more fillers based on the weight of the pharmaceutically acceptable unit formulation. In some embodiments, the one or more pharmaceutically acceptable excipients comprise about 20% by weight to about 80% by weight of one or more fillers based on the weight of the pharmaceutically acceptable unit formulation. In some embodiments, the one or more pharmaceutically acceptable excipients comprise about 20% by weight to about 75% by weight of one or more fillers based on the weight of the pharmaceutically acceptable unit formulation. In some embodiments, the one or more pharmaceutically acceptable excipients comprise about 20% by weight to about 70% by weight of one or more fillers based on the weight of the pharmaceutically acceptable unit formulation. In some embodiments, the one or more pharmaceutically acceptable excipients comprise about 20% by weight to about 65% by weight of one or more fillers based on the weight of the pharmaceutically acceptable unit formulation. In some embodiments, the one or more pharmaceutically acceptable excipients comprise about 20% by weight to about 60% by weight of one or more fillers based on the weight of the pharmaceutically acceptable unit formulation. In some embodiments, the one or more pharmaceutically acceptable excipients comprise about 20% by weight to about 55% by weight of one or more fillers based on the weight of the pharmaceutically acceptable unit formulation. In some embodiments, the one or more pharmaceutically acceptable excipients comprise about 20% by weight to about 50% by weight of one or more fillers based on the weight of the pharmaceutically acceptable unit formulation. In some embodiments, the one or more pharmaceutically acceptable excipients comprise about 20% by weight to about 45% by weight of one or more fillers based on the weight of the pharmaceutically acceptable unit formulation. In some embodiments, the one or more pharmaceutically acceptable excipients comprise about 20% by weight to about 40% by weight of one or more fillers based on the weight of the pharmaceutically acceptable unit formulation. In some embodiments, the one or more pharmaceutically acceptable excipients comprise about 20% by weight to about 35% by weight of one or more fillers based on the weight of the pharmaceutically acceptable unit formulation. In some embodiments, the one or more pharmaceutically acceptable excipients comprise about 20% by weight to about 30% by weight of one or more fillers based on the weight of the pharmaceutically acceptable unit formulation. In some embodiments, the one or more pharmaceutically acceptable excipients comprise about 20% by weight to about 25% by weight of one or more fillers based on the weight of the pharmaceutically acceptable unit formulation.

In some embodiments, the one or more pharmaceutically acceptable excipients comprise about 30% by weight to about 90% by weight of one or more fillers based on the weight of the pharmaceutically acceptable unit formulation. In some embodiments, the one or more pharmaceutically acceptable excipients comprise about 30% by weight to about 80% by weight of one or more fillers based on the weight of the pharmaceutically acceptable unit formulation. In some embodiments, the one or more pharmaceutically acceptable excipients comprise about 30% by weight to about 70% by weight of one or more fillers based on the weight of the pharmaceutically acceptable unit formulation. In some embodiments, the one or more pharmaceutically acceptable excipients comprise about 30% by weight to about 60% by weight of one or more fillers based on the weight of the pharmaceutically acceptable unit formulation. In some embodiments, the one or more pharmaceutically acceptable excipients comprise about 30% by weight to about 50% by weight of one or more fillers based on the weight of the pharmaceutically acceptable unit formulation. In some embodiments, the one or more pharmaceutically acceptable excipients comprise about 30% by weight to about 40% by weight of one or more fillers based on the weight of the pharmaceutically acceptable unit formulation.

In some embodiments, the one or more pharmaceutically acceptable excipients comprise about 40% by weight to about 90% by weight of one or more fillers based on the weight of the pharmaceutically acceptable unit formulation. In some embodiments, the one or more pharmaceutically acceptable excipients comprise about 40% by weight to about 80% by weight of one or more fillers based on the weight of the pharmaceutically acceptable unit formulation. In some embodiments, the one or more pharmaceutically acceptable excipients comprise about 40% by weight to about 70% by weight of one or more fillers based on the weight of the pharmaceutically acceptable unit formulation. In some embodiments, the one or more pharmaceutically acceptable excipients comprise about 40% by weight to about 60% by weight of one or more fillers based on the weight of the pharmaceutically acceptable unit formulation. In some embodiments, the one or more pharmaceutically acceptable excipients comprise about 40% by weight to about 50% by weight of one or more fillers based on the weight of the pharmaceutically acceptable unit formulation.

In some embodiments, the one or more pharmaceutically acceptable excipients comprise about 50% by weight to about 90% by weight of one or more fillers based on the weight of the pharmaceutically acceptable unit formulation. In some embodiments, the one or more pharmaceutically acceptable excipients comprise about 50% by weight to about 80% by weight of one or more fillers based on the weight of the pharmaceutically acceptable unit formulation. In some embodiments, the one or more pharmaceutically acceptable excipients comprise about 50% by weight to about 70% by weight of one or more fillers based on the weight of the pharmaceutically acceptable unit formulation. In some embodiments, the one or more pharmaceutically acceptable excipients comprise about 50% by weight to about 60% by weight of one or more fillers based on the weight of the pharmaceutically acceptable unit formulation.

In some embodiments, the one or more pharmaceutically acceptable excipients comprise about 60% by weight to about 90% by weight of one or more fillers based on the weight of the pharmaceutically acceptable unit formulation. In some embodiments, the one or more pharmaceutically acceptable excipients comprise about 60% by weight to about 80% by weight of one or more fillers based on the weight of the pharmaceutically acceptable unit formulation. In some embodiments, the one or more pharmaceutically acceptable excipients comprise about 60% by weight to about 70% by weight of one or more fillers based on the weight of the pharmaceutically acceptable unit formulation.

In some embodiments, the one or more pharmaceutically acceptable excipients comprise about 70% by weight to about 90% by weight of one or more fillers based on the weight of the pharmaceutically acceptable unit formulation. In some embodiments, the one or more pharmaceutically acceptable excipients comprise about 70% by weight to about 80% by weight of one or more fillers based on the weight of the pharmaceutically acceptable unit formulation.

In some embodiments, the one or more pharmaceutically acceptable excipients comprise about 80% by weight to about 90% by weight of one or more fillers based on the weight of the pharmaceutically acceptable unit formulation.

In some embodiments, the one or more pharmaceutically acceptable excipients comprise about 1% by weight to about 20% by weight of one or more disintegrants based on the weight of the pharmaceutically acceptable unit formulation. In some embodiments, the one or more pharmaceutically acceptable excipients comprise about 1% by weight to about 15% by weight of one or more disintegrants based on the weight of the pharmaceutically acceptable unit formulation. In some embodiments, the one or more pharmaceutically acceptable excipients comprise about 1% by weight to about 14% by weight of one or more disintegrants based on the weight of the pharmaceutically acceptable unit formulation. In some embodiments, the one or more pharmaceutically acceptable excipients comprise about 1% by weight to about 13% by weight of one or more disintegrants based on the weight of the pharmaceutically acceptable unit formulation. In some embodiments, the one or more pharmaceutically acceptable excipients comprise about 1% by weight to about 12% by weight of one or more disintegrants based on the weight of the pharmaceutically acceptable unit formulation. In some embodiments, the one or more pharmaceutically acceptable excipients comprise about 1% by weight to about 11% by weight of one or more disintegrants based on the weight of the pharmaceutically acceptable unit formulation. In some embodiments, the one or more pharmaceutically acceptable excipients comprise about 1% by weight to about 10% by weight of one or more disintegrants based on the weight of the pharmaceutically acceptable unit formulation. In some embodiments, the one or more pharmaceutically acceptable excipients comprise about 1% by weight to about 9% by weight of one or more disintegrants based on the weight of the pharmaceutically acceptable unit formulation. In some embodiments, the one or more pharmaceutically acceptable excipients comprise about 1% by weight to about 8% by weight of one or more disintegrants based on the weight of the pharmaceutically acceptable unit formulation. In some embodiments, the one or more pharmaceutically acceptable excipients comprise about 1% by weight to about 7% by weight of one or more disintegrants based on the weight of the pharmaceutically acceptable unit formulation. In some embodiments, the one or more pharmaceutically acceptable excipients comprise about 1% by weight to about 6% by weight of one or more disintegrants based on the weight of the pharmaceutically acceptable unit formulation. In some embodiments, the one or more pharmaceutically acceptable excipients comprise about 1% by weight to about 5% by weight of one or more disintegrants based on the weight of the pharmaceutically acceptable unit formulation. In some embodiments, the one or more pharmaceutically acceptable excipients comprise about 1% by weight to about 4% by weight of one or more disintegrants based on the weight of the pharmaceutically acceptable unit formulation. In some embodiments, the one or more pharmaceutically acceptable excipients comprise about 1% by weight to about 3% by weight of one or more disintegrants based on the weight of the pharmaceutically acceptable unit formulation.

In some embodiments, the one or more pharmaceutically acceptable excipients comprise about 1% by weight of one or more disintegrants based on the weight of the pharmaceutically acceptable unit formulation. In some embodiments, the one or more pharmaceutically acceptable excipients comprise about 2% by weight of one or more disintegrants based on the weight of the pharmaceutically acceptable unit formulation. In some embodiments, the one or more pharmaceutically acceptable excipients comprise about 3% by weight of one or more disintegrants based on the weight of the pharmaceutically acceptable unit formulation. In some embodiments, the one or more pharmaceutically acceptable excipients comprise about 4% by weight of one or more disintegrants based on the weight of the pharmaceutically acceptable unit formulation. In some embodiments, the one or more pharmaceutically acceptable excipients comprise about 5% by weight of one or more disintegrants based on the weight of the pharmaceutically acceptable unit formulation. In some embodiments, the one or more pharmaceutically acceptable excipients comprise about 6% by weight of one or more disintegrants based on the weight of the pharmaceutically acceptable unit formulation. In some embodiments, the one or more pharmaceutically acceptable excipients comprise about 7% by weight of one or more disintegrants based on the weight of the pharmaceutically acceptable unit formulation. In some embodiments, the one or more pharmaceutically acceptable excipients comprise about 8% by weight of one or more disintegrants based on the weight of the pharmaceutically acceptable unit formulation. In some embodiments, the one or more pharmaceutically acceptable excipients comprise about 9% by weight of one or more disintegrants based on the weight of the pharmaceutically acceptable unit formulation. In some embodiments, the one or more pharmaceutically acceptable excipients comprise about 10% by weight of one or more disintegrants based on the weight of the pharmaceutically acceptable unit formulation. In some embodiments, the one or more pharmaceutically acceptable excipients comprise about 11% by weight of one or more disintegrants based on the weight of the pharmaceutically acceptable unit formulation. In some embodiments, the one or more pharmaceutically acceptable excipients comprise about 12% by weight of one or more disintegrants based on the weight of the pharmaceutically acceptable unit formulation. In some embodiments, the one or more pharmaceutically acceptable excipients comprise about 13% by weight of one or more disintegrants based on the weight of the pharmaceutically acceptable unit formulation. In some embodiments, the one or more pharmaceutically acceptable excipients comprise about 14% by weight of one or more disintegrants based on the weight of the pharmaceutically acceptable unit formulation. In some embodiments, the one or more pharmaceutically acceptable excipients comprise about 15% by weight of one or more disintegrants based on the weight of the pharmaceutically acceptable unit formulation.

In some embodiments, the one or more pharmaceutically acceptable excipients comprise about 0.1% by weight to about 10% by weight of one or more lubricants based on the weight of the pharmaceutically acceptable unit formulation. In some embodiments, the one or more pharmaceutically acceptable excipients comprise about 0.1% by weight to about 9% by weight of one or more lubricants based on the weight of the pharmaceutically acceptable unit formulation. In some embodiments, the one or more pharmaceutically acceptable excipients comprise about 0.1% by weight to about 8% by weight of one or more lubricants based on the weight of the pharmaceutically acceptable unit formulation. In some embodiments, the one or more pharmaceutically acceptable excipients comprise about 0.1% by weight to about 7% by weight of one or more lubricants based on the weight of the pharmaceutically acceptable unit formulation. In some embodiments, the one or more pharmaceutically acceptable excipients comprise about 0.1% by weight to about 6% by weight of one or more lubricants based on the weight of the pharmaceutically acceptable unit formulation. In some embodiments, the one or more pharmaceutically acceptable excipients comprise about 0.1% by weight to about 5% by weight of one or more lubricants based on the weight of the pharmaceutically acceptable unit formulation. In some embodiments, the one or more pharmaceutically acceptable excipients comprise about 0.1% by weight to about 4% by weight of one or more lubricants based on the weight of the pharmaceutically acceptable unit formulation. In some embodiments, the one or more pharmaceutically acceptable excipients comprise about 0.1% by weight to about 3% by weight of one or more lubricants based on the weight of the pharmaceutically acceptable unit formulation. In some embodiments, the one or more pharmaceutically acceptable excipients comprise about 0.1% by weight to about 2% by weight of one or more lubricants based on the weight of the pharmaceutically acceptable unit formulation.

In some embodiments, the one or more pharmaceutically acceptable excipients comprise about 0.1% by weight to about 1.9% by weight of one or more lubricants based on the weight of the pharmaceutically acceptable unit formulation. In some embodiments, the one or more pharmaceutically acceptable excipients comprise about 0.1% by weight to about 1.8% by weight of one or more lubricants based on the weight of the pharmaceutically acceptable unit formulation. In some embodiments, the one or more pharmaceutically acceptable excipients comprise about 0.1% by weight to about 1.7% by weight of one or more lubricants based on the weight of the pharmaceutically acceptable unit formulation. In some embodiments, the one or more pharmaceutically acceptable excipients comprise about 0.1% by weight to about 1.6% by weight of one or more lubricants based on the weight of the pharmaceutically acceptable unit formulation. In some embodiments, the one or more pharmaceutically acceptable excipients comprise about 0.1% by weight to about 1.5% by weight of one or more lubricants based on the weight of the pharmaceutically acceptable unit formulation. In some embodiments, the one or more pharmaceutically acceptable excipients comprise about 0.1% by weight to about 1.4% by weight of one or more lubricants based on the weight of the pharmaceutically acceptable unit formulation. In some embodiments, the one or more pharmaceutically acceptable excipients comprise about 0.1% by weight to about 1.3% by weight of one or more lubricants based on the weight of the pharmaceutically acceptable unit formulation. In some embodiments, the one or more pharmaceutically acceptable excipients comprise about 0.1% by weight to about 1.2% by weight of one or more lubricants based on the weight of the pharmaceutically acceptable unit formulation. In some embodiments, the one or more pharmaceutically acceptable excipients comprise about 0.1% by weight to about 1.1% by weight of one or more lubricants based on the weight of the pharmaceutically acceptable unit formulation. In some embodiments, the one or more pharmaceutically acceptable excipients comprise about 0.1% by weight to about 1.0% by weight of one or more lubricants based on the weight of the pharmaceutically acceptable unit formulation. In some embodiments, the one or more pharmaceutically acceptable excipients comprise about 0.1% by weight to about 0.9% by weight of one or more lubricants based on the weight of the pharmaceutically acceptable unit formulation. In some embodiments, the one or more pharmaceutically acceptable excipients comprise about 0.1% by weight to about 0.8% by weight of one or more lubricants based on the weight of the pharmaceutically acceptable unit formulation. In some embodiments, the one or more pharmaceutically acceptable excipients comprise about 0.1% by weight to about 0.7% by weight of one or more lubricants based on the weight of the pharmaceutically acceptable unit formulation. In some embodiments, the one or more pharmaceutically acceptable excipients comprise about 0.1% by weight to about 0.6% by weight of one or more lubricants based on the weight of the pharmaceutically acceptable unit formulation. In some embodiments, the one or more pharmaceutically acceptable excipients comprise about 0.1% by weight to about 0.5% by weight of one or more lubricants based on the weight of the pharmaceutically acceptable unit formulation. In some embodiments, the one or more pharmaceutically acceptable excipients comprise about 0.1% by weight to about 0.4% by weight of one or more lubricants based on the weight of the pharmaceutically acceptable unit formulation. In some embodiments, the one or more pharmaceutically acceptable excipients comprise about 0.1% by weight to about 0.3% by weight of one or more lubricants based on the weight of the pharmaceutically acceptable unit formulation. In some embodiments, the one or more pharmaceutically acceptable excipients comprise about 0.1% by weight to about 0.2% by weight of one or more lubricants based on the weight of the pharmaceutically acceptable unit formulation.

In some embodiments, the one or more pharmaceutically acceptable excipients comprise about 0.1% by weight of one or more lubricants based on the weight of the pharmaceutically acceptable unit formulation. In some embodiments, the one or more pharmaceutically acceptable excipients comprise about 0.2% by weight of one or more lubricants based on the weight of the pharmaceutically acceptable unit formulation. In some embodiments, the one or more pharmaceutically acceptable excipients comprise about 0.3% by weight of one or more lubricants based on the weight of the pharmaceutically acceptable unit formulation. In some embodiments, the one or more pharmaceutically acceptable excipients comprise about 0.4% by weight of one or more lubricants based on the weight of the pharmaceutically acceptable unit formulation. In some embodiments, the one or more pharmaceutically acceptable excipients comprise about 0.5% by weight of one or more lubricants based on the weight of the pharmaceutically acceptable unit formulation. In some embodiments, the one or more pharmaceutically acceptable excipients comprise about 0.6% by weight of one or more lubricants based on the weight of the pharmaceutically acceptable unit formulation. In some embodiments, the one or more pharmaceutically acceptable excipients comprise about 0.7% by weight of one or more lubricants based on the weight of the pharmaceutically acceptable unit formulation. In some embodiments, the one or more pharmaceutically acceptable excipients comprise about 0.8% by weight of one or more lubricants based on the weight of the pharmaceutically acceptable unit formulation. In some embodiments, the one or more pharmaceutically acceptable excipients comprise about 0.9% by weight of one or more lubricants based on the weight of the pharmaceutically acceptable unit formulation. In some embodiments, the one or more pharmaceutically acceptable excipients comprise about 1.0% by weight of one or more lubricants based on the weight of the pharmaceutically acceptable unit formulation.

In some embodiments, the pharmaceutically acceptable unit formulation comprises: (a) about 1% by weight to about 30% by weight of the compound of Formula (I) based on the weight of the pharmaceutically acceptable unit formulation; (b) about 20% by weight to about 90% by weight of one or more fillers based on the weight of the pharmaceutically acceptable unit formulation; (c) about 1% by weight to about 20% by weight of one or more disintegrants based on the weight of the pharmaceutically acceptable unit formulation; and (d) about 0.1% by weight to about 10% by weight of one or more lubricants based on the weight of the pharmaceutically acceptable unit formulation.

In some embodiments, the pharmaceutically acceptable unit formulation consists essentially of: (a) about 1% by weight to about 30% by weight of the compound of Formula (I) based on the weight of the pharmaceutically acceptable unit formulation; (b) about 20% by weight to about 90% by weight of one or more fillers based on the weight of the pharmaceutically acceptable unit formulation; (c) about 1% by weight to about 20% by weight of one or more disintegrants based on the weight of the pharmaceutically acceptable unit formulation; and (d) about 0.1% by weight to about 10% by weight of one or more lubricants based on the weight of the pharmaceutically acceptable unit formulation.

In some embodiments, the pharmaceutically acceptable unit formulation comprises (a) about 5% by weight to about 25% by weight of the crystalline dihydrate form of the compound of Formula (I) based on the weight of the pharmaceutically acceptable unit formulation; (b) about 60% by weight to about 90% by weight of one or more fillers based on the weight of the pharmaceutically acceptable unit formulation; (c) about 1% by weight to about 15% by weight of one or more disintegrants based on the weight of the pharmaceutically acceptable unit formulation; and (d) about 0.1% by weight to about 4% by weight of one or more lubricants based on the weight of the pharmaceutically acceptable unit formulation.

In some embodiments, the pharmaceutically acceptable unit formulation consists essentially of: (a) about 5% by weight to about 25% by weight of the crystalline dihydrate form of the compound of Formula (I) based on the weight of the pharmaceutically acceptable unit formulation; (b) about 60% by weight to about 90% by weight of one or more fillers based on the weight of the pharmaceutically acceptable unit formulation; (c) about 1% by weight to about 15% by weight of one or more disintegrants based on the weight of the pharmaceutically acceptable unit formulation; and (d) about 0.1% by weight to about 4% by weight of one or more lubricants based on the weight of the pharmaceutically acceptable unit formulation.

In some embodiments, the pharmaceutically acceptable unit formulation comprises (a) about 10% by weight to about 30% by weight of the crystalline dihydrate form of the compound of Formula (I) based on the weight of the pharmaceutically acceptable unit formulation; (b) about 70% by weight to about 90% by weight of one or more fillers based on the weight of the pharmaceutically acceptable unit formulation; (c) about 1% by weight to about 10% by weight of one or more disintegrants based on the weight of the pharmaceutically acceptable unit formulation; and (d) about 0.1% by weight to about 3% by weight of one or more lubricants based on the weight of the pharmaceutically acceptable unit formulation.

In some embodiments, the pharmaceutically acceptable unit formulation consists essentially of: (a) about 10% by weight to about 30% by weight of the crystalline dihydrate form of the compound of Formula (I) based on the weight of the pharmaceutically acceptable unit formulation; (b) about 70% by weight to about 90% by weight of one or more fillers based on the weight of the pharmaceutically acceptable unit formulation; (c) about 1% by weight to about 10% by weight of one or more disintegrants based on the weight of the pharmaceutically acceptable unit formulation; and (d) about 0.1% by weight to about 3% by weight of one or more lubricants based on the weight of the pharmaceutically acceptable unit formulation.

In some embodiments, the one or more pharmaceutically acceptable excipients is one or more fillers selected from the group consisting of calcium phosphate, dicalcium phosphate, dicalcium phosphate dihydrate, calcium sulfate, calcium sulfate dihydrate, starch, calcium carbonate, magnesium carbonate, magnesium oxide, kaolin (natural hydrated aluminum silicate), sodium chloride, partially gelatinized starch, anhydrous lactose, lactose monohydrate, lactose dihydrate, trehalose dihydrate, spray dried lactose, sucrose, dextrose, dextrates, dextrin, cellulose, microcrystalline cellulose, silicified microcrystalline cellulose, powdered cellulose, partially depolymerized cellulose, mannitol, granulated mannitol, spray dried mannitol, maltodextrin, maltitol, confectioner's sugar, compressible sugar, sorbitol, starch and talc. In some embodiments, the one or more fillers is lactose monohydrate.

In some embodiments, the one or more disintegrants is one or more disintegrants selected from the group consisting of sodium starch glycolate, pregelatinized starch, clay, cellulose, alginic acid, alginate gum, polyvinylpyrrolidone, cross-linked polyvinylpyrrolidone, cross-linked calcium carboxymethylcellulose, cross-linked sodium carboxymethylcellulose, sodium croscarmellose, sodium carmellose, low substituted hydroxypropyl cellulose, low substituted hydroxypropyl cellulose sodium, guar gum, magnesium aluminum silicate, polacrilin potassium, powdered cellulose, sodium alginate and soy polysaccharides. In some embodiments, the one or more disintegrants is cross-linked polyvinylpyrrolidone (also referred to as crospovidone).

In some embodiments, the one or more lubricants is one or more lubricants selected from the group consisting of colloidal silica, magnesium trisilicate, talc, magnesium carbonate, magnesium oxide, glyceryl behaptate, mono, di and tri glyceryl behenate, bees wax, behenoyl polyoxyl-8 glycerides, hydrogenated vegetable oil, polyethylene glycol, ethylene oxide polymer, copolymer comprising poly(ethylene oxide) and poly(propylene oxide) (such as poloxomer 188), copolymer comprising polypropylene glycol and polyethylene glycol (such as poloxomer 407), sodium lauryl sulfate, magnesium stearate, aluminum stearate, calcium stearate, sodium stearyl fumarate, stearic acid, magnesium lauryl stearate, mixtures of magnesium stearate with sodium lauryl sulfate. In some embodiments, the one or more lubricants is magnesium stearate.

In some embodiments, the one or more disintegrants is selected from the group consisting of cross-linked polyvinylpyrrolidone, croscarmellose sodium, and sodium starch glycolate; and the one or more lubricants is selected from the group consisting of sodium stearyl fumarate, stearic acid, talc, calcium stearate, magnesium stearate, solid polyethylene glycols, and sodium lauryl sulfate. In some embodiments, the pharmaceutically acceptable unit formulation comprises cross-linked polyvinylpyrrolidone and magnesium stearate. In some embodiments, the one or more pharmaceutically acceptable excipients is lactose monohydrate and the pharmaceutically acceptable unit formulation further comprises cross-linked polyvinylpyrrolidone and magnesium stearate.

In some embodiments, the pharmaceutically acceptable unit formulation is for oral administration.

In some embodiments, the pharmaceutically acceptable unit formulation is a solid dosage form.

In some embodiments, the pharmaceutically acceptable unit formulation is a tablet or capsule. In some embodiments, the pharmaceutically acceptable unit formulation is a tablet. In some embodiments, the pharmaceutically acceptable unit formulation is a capsule. In some embodiments, the pharmaceutically acceptable unit formulation is a sachet. In some embodiments, the pharmaceutically acceptable unit formulation is a powder in a packet.

In some embodiments, the pharmaceutically acceptable unit formulation comprises about 1 mg to about 40 mg of the crystalline dihydrate form of the compound of Formula (I). In some embodiments, the pharmaceutically acceptable unit formulation comprises about 5 mg to about 35 mg of the crystalline dihydrate form of the compound of Formula (I). In some embodiments, the pharmaceutically acceptable unit formulation comprises about 10 mg to about 35 mg of the crystalline dihydrate form of the compound of Formula (I). In some embodiments, the pharmaceutically acceptable unit formulation comprises about 0.5 mg to about 5 mg, about 6 mg to about 14 mg, about 11 mg to about 19 mg, about 17 mg to about 25 mg, or about 28 mg to about 36 mg of the crystalline dihydrate form of the compound of Formula (I). In some embodiments, the pharmaceutically acceptable unit formulation comprises about 1 mg to about 4 mg, about 8 mg to about 12 mg, about 13 mg to about 17 mg, about 19 mg to about 23 mg, or about 30 mg to about 34 mg of the crystalline dihydrate form of the compound of Formula (I). In some embodiments, the pharmaceutically acceptable unit formulation comprises about 2.2 mg, about 10.8 mg, about 15.2 mg, about 21.7 mg, or about 32.5 mg of the crystalline dihydrate form of the compound of Formula (I). In some embodiments, the crystalline dihydrate form of the compound of Formula (I) is present in an amount of about 2.2 mg. In some embodiments, the crystalline dihydrate form of the compound of Formula (I) is present in an amount of about 10.8 mg. In some embodiments, the crystalline dihydrate form of the compound of Formula (I) is present in an amount of about 15.2 mg. In some embodiments, the crystalline dihydrate form of the compound of Formula (I) is present in an amount of about 21.7 mg. In some embodiments, the crystalline dihydrate form of the compound of Formula (I) is present in an amount of about 32.5 mg.

In some embodiments, the pharmaceutically acceptable unit formulation consists essentially of about 1 mg to about 40 mg of the crystalline dihydrate form of the compound of Formula (I). In some embodiments, the pharmaceutically acceptable unit formulation consists essentially of about 5 mg to about 35 mg of the crystalline dihydrate form of the compound of Formula (I). In some embodiments, the pharmaceutically acceptable unit formulation consists essentially of about 10 mg to about 35 mg of the crystalline dihydrate form of the compound of Formula (I). In some embodiments, the pharmaceutically acceptable unit formulation consists essentially of about 0.5 mg to about 5 mg, about 6 mg to about 14 mg, about 11 mg to about 19 mg, about 17 mg to about 25 mg, or about 28 mg to about 36 mg of the crystalline dihydrate form of the compound of Formula (I). In some embodiments, the pharmaceutically acceptable unit formulation consists essentially of about 1 mg to about 4 mg, about 8 mg to about 12 mg, about 13 mg to about 17 mg, about 19 mg to about 23 mg, or about 30 mg to about 34 mg of the crystalline dihydrate form of the compound of Formula (I). In some embodiments, the pharmaceutically acceptable unit formulation consists essentially of about 2.2 mg, about 10.8 mg, about 15.2 mg, about 21.7 mg, or about 32.5 mg of the crystalline dihydrate form of the compound of Formula (I). In some embodiments, the crystalline dihydrate form of the compound of Formula (I) is present in an amount of about 2.2 mg. In some embodiments, the crystalline dihydrate form of the compound of Formula (I) is present in an amount of about 10.8 mg. In some embodiments, the crystalline dihydrate form of the compound of Formula (I) is present in an amount of about 15.2 mg. In some embodiments, the crystalline dihydrate form of the compound of Formula (I) is present in an amount of about 21.7 mg. In some embodiments, the crystalline dihydrate form of the compound of Formula (I) is present in an amount of about 32.5 mg.

In some embodiments, the pharmaceutically acceptable unit formulation has an acceptance value of less than about 15 as determined by USP Uniformity of Dosage Unit <905>. In some embodiments, the pharmaceutically acceptable unit formulation has a maximum acceptance value of equal to or less than about 15 as determined by USP Uniformity of Dosage Unit <905>.

In some embodiments, the uniformity of the pharmaceutically acceptable formulation represents the degree of uniformity in the amount of the compound of Formula (I) in the pharmaceutically acceptable formulation.

In some embodiments, the uniformity of the oral dosage form represents the degree of uniformity in the amount of the compound of Formula (I) in the oral dosage form.

In some embodiments, the uniformity of the pharmaceutically acceptable capsule represents the degree of uniformity in the amount of the compound of Formula (I) in the pharmaceutically acceptable capsule.

Also provided herein is a process of preparing an oral dosage form, the oral dosage form comprising:

(a) about 1% by weight to about 70% by weight, based on the total weight of the oral dosage form, of a compound of Formula (I):

Formula (I)

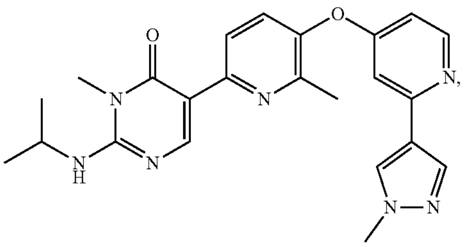

wherein the compound is present in the oral dosage form as a free base, a pharmaceutically acceptable salt of the compound and wherein the free base or pharmaceutically acceptable salt is in anhydrous or hydrate form, and one or more pharmaceutically acceptable excipients, wherein the one or more pharmaceutically acceptable excipients comprise:

(b) about 20% by weight to about 97% by weight of one or more fillers, based on the total weight of the oral dosage form;

(c) about 1% by weight to about 20% by weight of one or more disintegrants, based on the total weight of the oral dosage form; and (d) about 0.1% by weight to about 10% by weight of one or more lubricants, based on the total weight of the oral dosage form the process comprising:

(i) blending the compound represented by Formula (I) with the one or more fillers and one or more disintegrants to produce a first blend; and (ii) blending the first blend with the one or more lubricants, thereby preparing the oral dosage form.

Also provided herein is a process of preparing an oral dosage form, the oral dosage form consisting essentially of:

(a) about 1% by weight to about 70% by weight, based on the total weight of the oral dosage form, of a compound of Formula (I):

Formula (I)

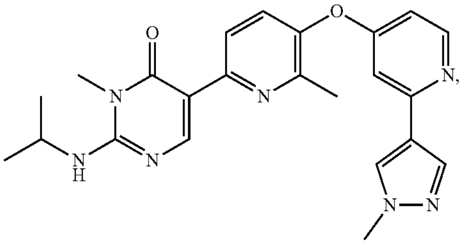

wherein the compound is present in the oral dosage form as a free base, a pharmaceutically acceptable salt of the compound and wherein the free base or pharmaceutically acceptable salt is in anhydrous or hydrate form, and one or more pharmaceutically acceptable excipients, wherein the one or more pharmaceutically acceptable excipients comprise:

(b) about 20% by weight to about 97% by weight of one or more fillers, based on the total weight of the oral dosage form;

(c) about 1% by weight to about 20% by weight of one or more disintegrants, based on the total weight of the oral dosage form; and (d) about 0.1% by weight to about 10% by weight of one or more lubricants, based on the total weight of the oral dosage form the process comprising:

(i) blending the compound represented by Formula (I) with the one or more fillers and one or more disintegrants to produce a first blend; and (ii) blending the first blend with the one or more lubricants, thereby preparing the oral dosage form.

Also provided herein is a process of preparing an oral dosage form, the oral dosage form comprising:

(a) about 1% by weight to about 70% by weight, based on the total weight of the oral dosage form, of a compound of Formula (I):

Formula (I)

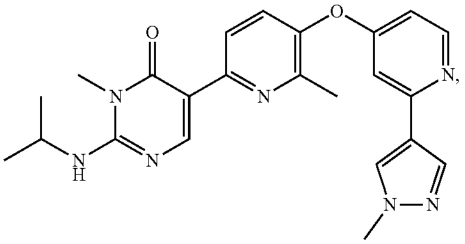

wherein the compound is present in the oral dosage form as a free base, a pharmaceutically acceptable salt of the compound and wherein the free base or pharmaceutically acceptable salt is in anhydrous or hydrate form, and one or more pharmaceutically acceptable excipients, wherein the one or more pharmaceutically acceptable excipients comprise:

(b) about 20% by weight to about 97% by weight of one or more fillers, based on the total weight of the oral dosage form;

(c) about 1% by weight to about 20% by weight of one or more disintegrants, based on the total weight of the oral dosage form; and (d) about 0.1% by weight to about 10% by weight of one or more lubricants, based on the total weight of the oral dosage form the process comprising:

(i) blending the compound represented by Formula (I) with the one or more fillers to produce a first blend;

(ii) blending the first blend with one or more disintegrants to produce a second blend; and (iii) blending the second blend with the one or more lubricants, thereby preparing the oral dosage form.

Also provided herein is a process of preparing an oral dosage form, the oral dosage form consisting essentially of:

(a) about 1% by weight to about 70% by weight, based on the total weight of the oral dosage form, of a compound of Formula (I):

Formula (I)

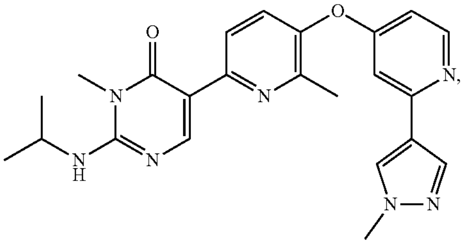

wherein the compound is present in the oral dosage form as a free base, a pharmaceutically acceptable salt of the compound and wherein the free base or pharmaceutically acceptable salt is in anhydrous or hydrate form, and one or more pharmaceutically acceptable excipients, wherein the one or more pharmaceutically acceptable excipients comprise:

(b) about 20% by weight to about 97% by weight of one or more fillers, based on the total weight of the oral dosage form;

(c) about 1% by weight to about 20% by weight of one or more disintegrants, based on the total weight of the oral dosage form; and (d) about 0.1% by weight to about 10% by weight of one or more lubricants, based on the total weight of the oral dosage form the process comprising:

(i) blending the compound represented by Formula (I) with the one or more fillers to produce a first blend;

(ii) blending the first blend with one or more disintegrants to produce a second blend; and (iii) blending the second blend with the one or more lubricants, thereby preparing the oral dosage form.

Also provided herein is a process of preparing an oral dosage form, the oral dosage form comprising:

(a) about 1% by weight to about 70% by weight, based on the total weight of the oral dosage form of a compound of Formula (I):

Formula (I)

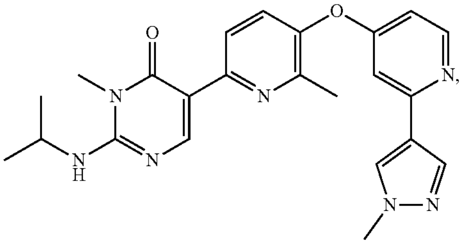

wherein the compound is present in the oral dosage form as a free base, a pharmaceutically acceptable salt of the compound and wherein the free base or pharmaceutically acceptable salt is in anhydrous or hydrate form, and one or more pharmaceutically acceptable excipients, wherein the one or more pharmaceutically acceptable excipients comprise:

(b) about 20% by weight to about 97% by weight of one or more fillers, based on the total weight of the oral dosage form;

(c) about 1% by weight to about 20% by weight of one or more disintegrants, based on the total weight of the oral dosage form; and (d) about 0.1% by weight to about 10% by weight of one or more lubricants, based on the total weight of the oral dosage form the process comprising:

(i) blending the compound represented by Formula (I) with the one or more fillers to produce a first blend;

(ii) blending the first blend with a second blend comprising one or more disintegrants and one or more fillers and optionally a third blend comprising one or more fillers to produce a fourth blend; and (iii) blending the fourth blend with the one or more lubricants, thereby preparing the oral dosage form.

Also provided herein is a process of preparing an oral dosage form, the oral dosage form consisting essentially of:

(a) about 1% by weight to about 70% by weight, based on the total weight of the oral dosage form of a compound of Formula (I):

Formula (I)

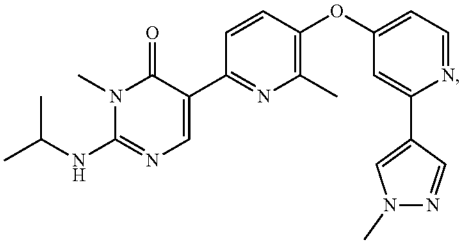

wherein the compound is present in the oral dosage form as a free base, a pharmaceutically acceptable salt of the compound and wherein the free base or pharmaceutically acceptable salt is in anhydrous or hydrate form, and one or more pharmaceutically acceptable excipients, wherein the one or more pharmaceutically acceptable excipients comprise:

(b) about 20% by weight to about 97% by weight of one or more fillers, based on the total weight of the oral dosage form;

(c) about 1% by weight to about 20% by weight of one or more disintegrants, based on the total weight of the oral dosage form; and (d) about 0.1% by weight to about 10% by weight of one or more lubricants, based on the total weight of the oral dosage form the process comprising:

(i) blending the compound represented by Formula (I) with the one or more fillers to produce a first blend;

(ii) blending the first blend with a second blend comprising one or more disintegrants and one or more fillers and optionally a third blend comprising one or more fillers to produce a fourth blend; and (iii) blending the fourth blend with the one or more lubricants, thereby preparing the oral dosage form.

In some embodiments, the oral dosage form comprises about 1% by weight to about 60% by weight, based on the total weight of the oral dosage form, of a compound of Formula (I), wherein the compound is present in the oral dosage form as a free base, or a pharmaceutically acceptable salt of the compound and wherein the free base or pharmaceutically acceptable salt is in anhydrous or hydrate form. In some embodiments, the oral dosage form comprises about 1% by weight to about 50% by weight, based on the total weight of the oral dosage form, of a compound of Formula (I), wherein the compound is present in the oral dosage form as a free base, or a pharmaceutically acceptable salt of the compound and wherein the free base or pharmaceutically acceptable salt is in anhydrous or hydrate form. In some embodiments, the oral dosage form comprises about 1% by weight to about 40% by weight, based on the total weight of the oral dosage form, of a compound of Formula (I), wherein the compound is present in the oral dosage form as a free base, or a pharmaceutically acceptable salt of the compound and wherein the free base or pharmaceutically acceptable salt is in anhydrous or hydrate form. In some embodiments, the oral dosage form comprises about 1% by weight to about 30% by weight, based on the total weight of the oral dosage form, of a compound of Formula (I), wherein the compound is present in the oral dosage form as a free base, or a pharmaceutically acceptable salt of the compound and wherein the free base or pharmaceutically acceptable salt is in anhydrous or hydrate form. In some embodiments, the oral dosage form comprises about 1% by weight to about 20% by weight, based on the total weight of the oral dosage form, of a compound of Formula (I), wherein the compound is present in the oral dosage form as a free base, or a pharmaceutically acceptable salt of the compound and wherein the free base or pharmaceutically acceptable salt is in anhydrous or hydrate form.

In some embodiments, the oral dosage form consists essentially of about 1% by weight to about 60% by weight, based on the total weight of the oral dosage form, of a compound of Formula (I), wherein the compound is present in the oral dosage form as a free base, or a pharmaceutically acceptable salt of the compound and wherein the free base or pharmaceutically acceptable salt is in anhydrous or hydrate form. In some embodiments, the oral dosage form consists essentially of about 1% by weight to about 50% by weight, based on the total weight of the oral dosage form, of a compound of Formula (I), wherein the compound is present in the oral dosage form as a free base, or a pharmaceutically acceptable salt of the compound and wherein the free base or pharmaceutically acceptable salt is in anhydrous or hydrate form. In some embodiments, the oral dosage form consists essentially of about 1% by weight to about 40% by weight, based on the total weight of the oral dosage form, of a compound of Formula (I), wherein the compound is present in the oral dosage form as a free base, or a pharmaceutically acceptable salt of the compound and wherein the free base or pharmaceutically acceptable salt is in anhydrous or hydrate form. In some embodiments, the oral dosage form consists essentially of about 1% by weight to about 30% by weight, based on the total weight of the oral dosage form, of a compound of Formula (I), wherein the compound is present in the oral dosage form as a free base, or a pharmaceutically acceptable salt of the compound and wherein the free base or pharmaceutically acceptable salt is in anhydrous or hydrate form. In some embodiments, the oral dosage form consists essentially of about 1% by weight to about 20% by weight, based on the total weight of the oral dosage form, of a compound of Formula (I), wherein the compound is present in the oral dosage form as a free base, or a pharmaceutically acceptable salt of the compound and wherein the free base or pharmaceutically acceptable salt is in anhydrous or hydrate form.

In some embodiments, the oral dosage form comprises about 1% by weight to about 70% by weight of the compound of Formula (I) based on the total weight of the oral dosage form. In some embodiments, the oral dosage form comprises about 1% by weight to about 65% by weight of the compound of Formula (I) based on the total weight of the oral dosage form. In some embodiments, the oral dosage form comprises about 1% by weight to about 60% by weight of the compound of Formula (I) based on the total weight of the oral dosage form. In some embodiments, the oral dosage form comprises about 1% by weight to about 55% by weight of the compound of Formula (I) based on the total weight of the oral dosage form. In some embodiments, the oral dosage form comprises about 1% by weight to about 50% by weight of the compound of Formula (I) based on the total weight of the oral dosage form. In some embodiments, the oral dosage form comprises about 1% by weight to about 45% by weight of the compound of Formula (I) based on the total weight of the oral dosage form. In some embodiments, the oral dosage form comprises about 1% by weight to about 40% by weight of the compound of Formula (I) based on the total weight of the oral dosage form. In some embodiments, the oral dosage form comprises about 1% by weight to about 35% by weight of the compound of Formula (I) based on the total weight of the oral dosage form. In some embodiments, the oral dosage form comprises about 1% by weight to about 30% by weight of the compound of Formula (I) based on the total weight of the oral dosage form. In some embodiments, the oral dosage form comprises about 1% by weight to about 25% by weight of the compound of Formula (I) based on the total weight of the oral dosage form. In some embodiments, the oral dosage form comprises about 1% by weight to about 20% by weight of the compound of Formula (I) based on the total weight of the oral dosage form. In some embodiments, the oral dosage form comprises about 1% by weight to about 15% by weight of the compound of Formula (I) based on the total weight of the oral dosage form. In some embodiments, the oral dosage form comprises about 1% by weight to about 10% by weight of the compound of Formula (I) based on the total weight of the oral dosage form.

In some embodiments, the oral dosage form consists essentially of about 1% by weight to about 70% by weight of the compound of Formula (I) based on the total weight of the oral dosage form. In some embodiments, the oral dosage form consists essentially of about 1% by weight to about 65% by weight of the compound of Formula (I) based on the total weight of the oral dosage form. In some embodiments, the oral dosage form consists essentially of about 1% by weight to about 60% by weight of the compound of Formula (I) based on the total weight of the oral dosage form. In some embodiments, the oral dosage form consists essentially of about 1% by weight to about 55% by weight of the compound of Formula (I) based on the total weight of the oral dosage form. In some embodiments, the oral dosage form consists essentially of about 1% by weight to about 50% by weight of the compound of Formula (I) based on the total weight of the oral dosage form. In some embodiments, the oral dosage form consists essentially of about 1% by weight to about 45% by weight of the compound of Formula (I) based on the total weight of the oral dosage form. In some embodiments, the oral dosage form consists essentially of about 1% by weight to about 40% by weight of the compound of Formula (I) based on the total weight of the oral dosage form. In some embodiments, the oral dosage form consists essentially of about 1% by weight to about 35% by weight of the compound of Formula (I) based on the total weight of the oral dosage form. In some embodiments, the oral dosage form consists essentially of about 1% by weight to about 30% by weight of the compound of Formula (I) based on the total weight of the oral dosage form. In some embodiments, the oral dosage form consists essentially of about 1% by weight to about 25% by weight of the compound of Formula (I) based on the total weight of the oral dosage form. In some embodiments, the oral dosage form consists essentially of about 1% by weight to about 20% by weight of the compound of Formula (I) based on the total weight of the oral dosage form. In some embodiments, the oral dosage form consists essentially of about 1% by weight to about 15% by weight of the compound of Formula (I) based on the total weight of the oral dosage form. In some embodiments, the oral dosage form consists essentially of about 1% by weight to about 10% by weight of the compound of Formula (I) based on the total weight of the oral dosage form.

In some embodiments, the oral dosage form comprises about 5% by weight to about 30% by weight of the compound of Formula (I) based on the total weight of the oral dosage form. In some embodiments, the oral dosage form comprises about 5% by weight to about 25% by weight of the compound of Formula (I) based on the total weight of the oral dosage form. In some embodiments, the oral dosage form comprises about 5% by weight to about 20% by weight of the compound of Formula (I) based on the total weight of the oral dosage form. In some embodiments, the oral dosage form comprises about 5% by weight to about 15% by weight of the compound of Formula (I) based on the total weight of the oral dosage form. In some embodiments, the oral dosage form comprises about 5% by weight to about 10% by weight of the compound of Formula (I) based on the total weight of the oral dosage form.

In some embodiments, the oral dosage form consists essentially of about 5% by weight to about 30% by weight of the compound of Formula (I) based on the total weight of the oral dosage form. In some embodiments, the oral dosage form consists essentially of about 5% by weight to about 25% by weight of the compound of Formula (I) based on the total weight of the oral dosage form. In some embodiments, the oral dosage form consists essentially of about 5% by weight to about 20% by weight of the compound of Formula (I) based on the total weight of the oral dosage form. In some embodiments, the oral dosage form consists essentially of about 5% by weight to about 15% by weight of the compound of Formula (I) based on the total weight of the oral dosage form. In some embodiments, the oral dosage form consists essentially of about 5% by weight to about 10% by weight of the compound of Formula (I) based on the total weight of the oral dosage form.

In some embodiments, the oral dosage form comprises about 10% to about 30% of the compound of Formula (I) based on the total weight of the oral dosage form. In some embodiments, the oral dosage form comprises about 10% to about 25% of the compound of Formula (I) based on the total weight of the oral dosage form. In some embodiments, the oral dosage form comprises about 10% to about 20% of the compound of Formula (I) based on the total weight of the oral dosage form. In some embodiments, the oral dosage form comprises about 10% by weight to about 15% by weight of the compound of Formula (I) based on the total weight of the oral dosage form.

In some embodiments, the oral dosage form consists essentially of about 10% to about 30% of the compound of Formula (I) based on the total weight of the oral dosage form. In some embodiments, the oral dosage form consists essentially of about 10% to about 25% of the compound of Formula (I) based on the total weight of the oral dosage form. In some embodiments, the oral dosage form consists essentially of about 10% to about 20% of the compound of Formula (I) based on the total weight of the oral dosage form. In some embodiments, the oral dosage form consists essentially of about 10% by weight to about 15% by weight of the compound of Formula (I) based on the total weight of the oral dosage form.

In some embodiments, the oral dosage form comprises about 1% by weight to about 30% by weight of the compound of Formula (I) based on the total weight of the oral dosage form. In some embodiments, the oral dosage form comprises about 1% by weight to about 10% by weight of the compound of Formula (I) based on the total weight of the oral dosage form. In some embodiments, the oral dosage form comprises about 10% to about 20% of the compound of Formula (I) based on the total weight of the oral dosage form. In some embodiments, the oral dosage form comprises about 10% by weight to about 15% by weight of the compound of Formula (I) based on the total weight of the oral dosage form.

In some embodiments, the oral dosage form consists essentially of about 1% by weight to about 30% by weight of the compound of Formula (I) based on the total weight of the oral dosage form. In some embodiments, the oral dosage form consists essentially of about 1% by weight to about 10% by weight of the compound of Formula (I) based on the total weight of the oral dosage form. In some embodiments, the oral dosage form consists essentially of about 10% to about 20% of the compound of Formula (I) based on the total weight of the oral dosage form. In some embodiments, the oral dosage form consists essentially of about 10% by weight to about 15% by weight of the compound of Formula (I) based on the total weight of the oral dosage form.

In some embodiments, the one or more pharmaceutically acceptable excipients comprise about 20% by weight to about 90% by weight of one or more fillers based on the total weight of the oral dosage form. In some embodiments, the one or more pharmaceutically acceptable excipients comprise about 20% by weight to about 85% by weight of one or more fillers based on the total weight of the oral dosage form. In some embodiments, the one or more pharmaceutically acceptable excipients comprise about 20% by weight to about 80% by weight of one or more fillers based on the total weight of the oral dosage form. In some embodiments, the one or more pharmaceutically acceptable excipients comprise about 20% by weight to about 75% by weight of one or more fillers based on the total weight of the oral dosage form. In some embodiments, the one or more pharmaceutically acceptable excipients comprise about 20% by weight to about 70% by weight of one or more fillers based on the total weight of the oral dosage form. In some embodiments, the one or more pharmaceutically acceptable excipients comprise about 20% by weight to about 65% by weight of one or more fillers based on the total weight of the oral dosage form. In some embodiments, the one or more pharmaceutically acceptable excipients comprise about 20% by weight to about 60% by weight of one or more fillers based on the total weight of the oral dosage form. In some embodiments, the one or more pharmaceutically acceptable excipients comprise about 20% by weight to about 55% by weight of one or more fillers based on the total weight of the oral dosage form. In some embodiments, the one or more pharmaceutically acceptable excipients comprise about 20% by weight to about 50% by weight of one or more fillers based on the total weight of the oral dosage form. In some embodiments, the one or more pharmaceutically acceptable excipients comprise about 20% by weight to about 45% by weight of one or more fillers based on the total weight of the oral dosage form. In some embodiments, the one or more pharmaceutically acceptable excipients comprise about 20% by weight to about 40% by weight of one or more fillers based on the total weight of the oral dosage form. In some embodiments, the one or more pharmaceutically acceptable excipients comprise about 20% by weight to about 35% by weight of one or more fillers based on the total weight of the oral dosage form. In some embodiments, the one or more pharmaceutically acceptable excipients comprise about 20% by weight to about 30% by weight of one or more fillers based on the total weight of the oral dosage form. In some embodiments, the one or more pharmaceutically acceptable excipients comprise about 20% by weight to about 25% by weight of one or more fillers based on the total weight of the oral dosage form.

In some embodiments, the one or more pharmaceutically acceptable excipients comprise about 30% by weight to about 90% by weight of one or more fillers based on the total weight of the oral dosage form. In some embodiments, the one or more pharmaceutically acceptable excipients comprise about 30% by weight to about 80% by weight of one or more fillers based on the total weight of the oral dosage form. In some embodiments, the one or more pharmaceutically acceptable excipients comprise about 30% by weight to about 70% by weight of one or more fillers based on the total weight of the oral dosage form. In some embodiments, the one or more pharmaceutically acceptable excipients comprise about 30% by weight to about 60% by weight of one or more fillers based on the total weight of the oral dosage form. In some embodiments, the one or more pharmaceutically acceptable excipients comprise about 30% by weight to about 50% by weight of one or more fillers based on the total weight of the oral dosage form. In some embodiments, the one or more pharmaceutically acceptable excipients comprise about 30% by weight to about 40% by weight of one or more fillers based on the total weight of the oral dosage form.

In some embodiments, the one or more pharmaceutically acceptable excipients comprise about 40% by weight to about 90% by weight of one or more fillers based on the total weight of the oral dosage form. In some embodiments, the one or more pharmaceutically acceptable excipients comprise about 40% by weight to about 80% by weight of one or more fillers based on the total weight of the oral dosage form. In some embodiments, the one or more pharmaceutically acceptable excipients comprise about 40% by weight to about 70% by weight of one or more fillers based on the total weight of the oral dosage form. In some embodiments, the one or more pharmaceutically acceptable excipients comprise about 40% by weight to about 60% by weight of one or more fillers based on the total weight of the oral dosage form. In some embodiments, the one or more pharmaceutically acceptable excipients comprise about 40% by weight to about 50% by weight of one or more fillers based on the total weight of the oral dosage form.

In some embodiments, the one or more pharmaceutically acceptable excipients comprise about 50% by weight to about 90% by weight of one or more fillers based on the total weight of the oral dosage form. In some embodiments, the one or more pharmaceutically acceptable excipients comprise about 50% by weight to about 80% by weight of one or more fillers based on the total weight of the oral dosage form. In some embodiments, the one or more pharmaceutically acceptable excipients comprise about 50% by weight to about 70% by weight of one or more fillers based on the total weight of the oral dosage form. In some embodiments, the one or more pharmaceutically acceptable excipients comprise about 50% by weight to about 60% by weight of one or more fillers based on the total weight of the oral dosage form.

In some embodiments, the one or more pharmaceutically acceptable excipients comprise about 60% by weight to about 90% by weight of one or more fillers based on the total weight of the oral dosage form. In some embodiments, the one or more pharmaceutically acceptable excipients comprise about 60% by weight to about 80% by weight of one or more fillers based on the total weight of the oral dosage form. In some embodiments, the one or more pharmaceutically acceptable excipients comprise about 60% by weight to about 70% by weight of one or more fillers based on the total weight of the oral dosage form.

In some embodiments, the one or more pharmaceutically acceptable excipients comprise about 70% by weight to about 90% by weight of one or more fillers based on the total weight of the oral dosage form. In some embodiments, the one or more pharmaceutically acceptable excipients comprise about 70% by weight to about 80% by weight of one or more fillers based on the total weight of the oral dosage form.

In some embodiments, the one or more pharmaceutically acceptable excipients comprise about 80% by weight to about 90% by weight of one or more fillers based on the total weight of the oral dosage form.

In some embodiments, the one or more pharmaceutically acceptable excipients comprise about 1% by weight to about 20% by weight of one or more disintegrants based on the total weight of the oral dosage form. In some embodiments, the one or more pharmaceutically acceptable excipients comprise about 1% by weight to about 15% by weight of one or more disintegrants based on the total weight of the oral dosage form. In some embodiments, the one or more pharmaceutically acceptable excipients comprise about 1% by weight to about 14% by weight of one or more disintegrants based on the total weight of the oral dosage form. In some embodiments, the one or more pharmaceutically acceptable excipients comprise about 1% by weight to about 13% by weight of one or more disintegrants based on the total weight of the oral dosage form. In some embodiments, the one or more pharmaceutically acceptable excipients comprise about 1% by weight to about 12% by weight of one or more disintegrants based on the total weight of the oral dosage form. In some embodiments, the one or more pharmaceutically acceptable excipients comprise about 1% by weight to about 11% by weight of one or more disintegrants based on the total weight of the oral dosage form. In some embodiments, the one or more pharmaceutically acceptable excipients comprise about 1% by weight to about 10% by weight of one or more disintegrants based on the total weight of the oral dosage form. In some embodiments, the one or more pharmaceutically acceptable excipients comprise about 1% by weight to about 9% by weight of one or more disintegrants based on the total weight of the oral dosage form. In some embodiments, the one or more pharmaceutically acceptable excipients comprise about 1% by weight to about 8% by weight of one or more disintegrants based on the total weight of the oral dosage form. In some embodiments, the one or more pharmaceutically acceptable excipients comprise about 1% by weight to about 7% by weight of one or more disintegrants based on the total weight of the oral dosage form. In some embodiments, the one or more pharmaceutically acceptable excipients comprise about 1% by weight to about 6% by weight of one or more disintegrants based on the total weight of the oral dosage form. In some embodiments, the one or more pharmaceutically acceptable excipients comprise about 1% by weight to about 5% by weight of one or more disintegrants based on the total weight of the oral dosage form. In some embodiments, the one or more pharmaceutically acceptable excipients comprise about 1% by weight to about 4% by weight of one or more disintegrants based on the total weight of the oral dosage form. In some embodiments, the one or more pharmaceutically acceptable excipients comprise about 1% by weight to about 3% by weight of one or more disintegrants based on the total weight of the oral dosage form.

In some embodiments, the one or more pharmaceutically acceptable excipients comprise about 1% by weight of one or more disintegrants based on the total weight of the oral dosage form. In some embodiments, the one or more pharmaceutically acceptable excipients comprise about 2% by weight of one or more disintegrants based on the total weight of the oral dosage form. In some embodiments, the one or more pharmaceutically acceptable excipients comprise about 3% by weight of one or more disintegrants based on the total weight of the oral dosage form. In some embodiments, the one or more pharmaceutically acceptable excipients comprise about 4% by weight of one or more disintegrants based on the total weight of the oral dosage form. In some embodiments, the one or more pharmaceutically acceptable excipients comprise about 5% by weight of one or more disintegrants based on the total weight of the oral dosage form. In some embodiments, the one or more pharmaceutically acceptable excipients comprise about 6% by weight of one or more disintegrants based on the total weight of the oral dosage form. In some embodiments, the one or more pharmaceutically acceptable excipients comprise about 7% by weight of one or more disintegrants based on the total weight of the oral dosage form. In some embodiments, the one or more pharmaceutically acceptable excipients comprise about 8% by weight of one or more disintegrants based on the total weight of the oral dosage form. In some embodiments, the one or more pharmaceutically acceptable excipients comprise about 9% by weight of one or more disintegrants based on the total weight of the oral dosage form. In some embodiments, the one or more pharmaceutically acceptable excipients comprise about 10% by weight of one or more disintegrants based on the total weight of the oral dosage form. In some embodiments, the one or more pharmaceutically acceptable excipients comprise about 11% by weight of one or more disintegrants based on the total weight of the oral dosage form. In some embodiments, the one or more pharmaceutically acceptable excipients comprise about 12% by weight of one or more disintegrants based on the total weight of the oral dosage form. In some embodiments, the one or more pharmaceutically acceptable excipients comprise about 13% by weight of one or more disintegrants based on the total weight of the oral dosage form. In some embodiments, the one or more pharmaceutically acceptable excipients comprise about 14% by weight of one or more disintegrants based on the total weight of the oral dosage form. In some embodiments, the one or more pharmaceutically acceptable excipients comprise about 15% by weight of one or more disintegrants based on the total weight of the oral dosage form.

In some embodiments, the one or more pharmaceutically acceptable excipients comprise about 0.1% by weight to about 10% by weight of one or more lubricants based on the total weight of the oral dosage form. In some embodiments, the one or more pharmaceutically acceptable excipients comprise about 0.1% by weight to about 9% by weight of one or more lubricants based on the total weight of the oral dosage form. In some embodiments, the one or more pharmaceutically acceptable excipients comprise about 0.1% by weight to about 8% by weight of one or more lubricants based on the total weight of the oral dosage form. In some embodiments, the one or more pharmaceutically acceptable excipients comprise about 0.1% by weight to about 7% by weight of one or more lubricants based on the total weight of the oral dosage form. In some embodiments, the one or more pharmaceutically acceptable excipients comprise about 0.1% by weight to about 6% by weight of one or more lubricants based on the total weight of the oral dosage form. In some embodiments, the one or more pharmaceutically acceptable excipients comprise about 0.1% by weight to about 5% by weight of one or more lubricants based on the total weight of the oral dosage form. In some embodiments, the one or more pharmaceutically acceptable excipients comprise about 0.1% by weight to about 4% by weight of one or more lubricants based on the total weight of the oral dosage form. In some embodiments, the one or more pharmaceutically acceptable excipients comprise about 0.1% by weight to about 3% by weight of one or more lubricants based on the total weight of the oral dosage form. In some embodiments, the one or more pharmaceutically acceptable excipients comprise about 0.1% by weight to about 2% by weight of one or more lubricants based on the total weight of the oral dosage form.

In some embodiments, the one or more pharmaceutically acceptable excipients comprise about 0.1% by weight to about 1.9% by weight of one or more lubricants based on the total weight of the oral dosage form. In some embodiments, the one or more pharmaceutically acceptable excipients comprise about 0.1% by weight to about 1.8% by weight of one or more lubricants based on the total weight of the oral dosage form. In some embodiments, the one or more pharmaceutically acceptable excipients comprise about 0.1% by weight to about 1.7% by weight of one or more lubricants based on the total weight of the oral dosage form. In some embodiments, the one or more pharmaceutically acceptable excipients comprise about 0.1% by weight to about 1.6% by weight of one or more lubricants based on the total weight of the oral dosage form. In some embodiments, the one or more pharmaceutically acceptable excipients comprise about 0.1% by weight to about 1.5% by weight of one or more lubricants based on the total weight of the oral dosage form. In some embodiments, the one or more pharmaceutically acceptable excipients comprise about 0.1% by weight to about 1.4% by weight of one or more lubricants based on the total weight of the oral dosage form. In some embodiments, the one or more pharmaceutically acceptable excipients comprise about 0.1% by weight to about 1.3% by weight of one or more lubricants based on the total weight of the oral dosage form. In some embodiments, the one or more pharmaceutically acceptable excipients comprise about 0.1% by weight to about 1.2% by weight of one or more lubricants based on the total weight of the oral dosage form. In some embodiments, the one or more pharmaceutically acceptable excipients comprise about 0.1% by weight to about 1.1% by weight of one or more lubricants based on the total weight of the oral dosage form. In some embodiments, the one or more pharmaceutically acceptable excipients comprise about 0.1% by weight to about 1.0% by weight of one or more lubricants based on the total weight of the oral dosage form. In some embodiments, the one or more pharmaceutically acceptable excipients comprise about 0.1% by weight to about 0.9% by weight of one or more lubricants based on the total weight of the oral dosage form. In some embodiments, the one or more pharmaceutically acceptable excipients comprise about 0.1% by weight to about 0.8% by weight of one or more lubricants based on the total weight of the oral dosage form. In some embodiments, the one or more pharmaceutically acceptable excipients comprise about 0.1% by weight to about 0.7% by weight of one or more lubricants based on the total weight of the oral dosage form. In some embodiments, the one or more pharmaceutically acceptable excipients comprise about 0.1% by weight to about 0.6% by weight of one or more lubricants based on the total weight of the oral dosage form. In some embodiments, the one or more pharmaceutically acceptable excipients comprise about 0.1% by weight to about 0.5% by weight of one or more lubricants based on the total weight of the oral dosage form. In some embodiments, the one or more pharmaceutically acceptable excipients comprise about 0.1% by weight to about 0.4% by weight of one or more lubricants based on the total weight of the oral dosage form. In some embodiments, the one or more pharmaceutically acceptable excipients comprise about 0.1% by weight to about 0.3% by weight of one or more lubricants based on the total weight of the oral dosage form. In some embodiments, the one or more pharmaceutically acceptable excipients comprise about 0.1% by weight to about 0.2% by weight of one or more lubricants based on the total weight of the oral dosage form.

In some embodiments, the oral dosage form comprises: (a) about 1% by weight to about 30% by weight of the compound of Formula (I) based on the total weight of the oral dosage form; (b) about 20% by weight to about 90% by weight of one or more fillers based on the total weight of the oral dosage form; (c) about 1% by weight to about 20% by weight of one or more disintegrants based on the total weight of the oral dosage form; and (d) about 0.1% by weight to about 10% by weight of one or more lubricants based on the total weight of the oral dosage form.

In some embodiments, the oral dosage form consists essentially of: (a) about 1% by weight to about 30% by weight of the compound of Formula (I) based on the total weight of the oral dosage form; (b) about 20% by weight to about 90% by weight of one or more fillers based on the total weight of the oral dosage form; (c) about 1% by weight to about 20% by weight of one or more disintegrants based on the total weight of the oral dosage form; and (d) about 0.1% by weight to about 10% by weight of one or more lubricants based on the total weight of the oral dosage form.

In some embodiments, the oral dosage form comprises (a) about 5% by weight to about 25% by weight of the compound of Formula (I) based on the total weight of the oral dosage form; (b) about 60% by weight to about 90% by weight of one or more fillers based on the total weight of the oral dosage form; (c) about 1% by weight to about 15% by weight of one or more disintegrants based on the total weight of the oral dosage form; and (d) about 0.1% by weight to about 4% by weight of one or more lubricants based on the total weight of the oral dosage form.

In some embodiments, the oral dosage form consists essentially of: (a) about 5% by weight to about 25% by weight of the compound of Formula (I) based on the total weight of the oral dosage form; (b) about 60% by weight to about 90% by weight of one or more fillers based on the total weight of the oral dosage form; (c) about 1% by weight to about 15% by weight of one or more disintegrants based on the total weight of the oral dosage form; and (d) about 0.1% by weight to about 4% by weight of one or more lubricants based on the total weight of the oral dosage form.

In some embodiments, the oral dosage form comprises: (a) about 10% by weight to about 30% by weight of the compound of Formula (I) based on the total weight of the oral dosage form; (b) about 70% by weight to about 90% by weight of one or more fillers based on the total weight of the oral dosage form; (c) about 1% by weight to about 10% by weight of one or more disintegrants based on the total weight of the oral dosage form; and (d) about 0.1% by weight to about 3% by weight of one or more lubricants based on the total weight of the oral dosage form.

In some embodiments, the oral dosage form consists essentially of: (a) about 10% by weight to about 30% by weight of the compound of Formula (I) based on the total weight of the oral dosage form; (b) about 70% by weight to about 90% by weight of one or more fillers based on the total weight of the oral dosage form; (c) about 1% by weight to about 10% by weight of one or more disintegrants based on the total weight of the oral dosage form; and (d) about 0.1% by weight to about 3% by weight of one or more lubricants based on the total weight of the oral dosage form.

In some embodiments, the one or more pharmaceutically acceptable excipients is one or more fillers selected from the group consisting of calcium phosphate, dicalcium phosphate, dicalcium phosphate dihydrate, calcium sulfate, calcium sulfate dihydrate, starch, calcium carbonate, magnesium carbonate, magnesium oxide, kaolin (natural hydrated aluminum silicate), sodium chloride, partially gelatinized starch, anhydrous lactose, lactose monohydrate, lactose dihydrate, trehalose dihydrate, spray dried lactose, sucrose, dextrose, dextrates, dextrin, cellulose, microcrystalline cellulose, silicified microcrystalline cellulose, powdered cellulose, partially depolymerized cellulose, mannitol, granulated mannitol, spray dried mannitol, maltodextrin, maltitol, confectioner's sugar, compressible sugar, sorbitol, starch and talc. In some embodiments, the one or more fillers is lactose monohydrate.

In some embodiments, the one or more disintegrants is one or more disintegrants selected from the group consisting of sodium starch glycolate, pregelatinized starch, clay, cellulose, alginic acid, alginate gum, polyvinylpyrrolidone, cross-linked polyvinylpyrrolidone, cross-linked calcium carboxymethylcellulose, cross-linked sodium carboxymethylcellulose, sodium croscarmellose, sodium carmellose, low substituted hydroxypropyl cellulose, low substituted hydroxypropyl cellulose sodium, guar gum, magnesium aluminum silicate, polacrilin potassium, powdered cellulose, sodium alginate and soy polysaccharides. In some embodiments, the one or more disintegrants is cross-linked polyvinylpyrrolidone (also referred to as crospovidone).

In some embodiments, the one or more lubricants is one or more lubricants selected from the group consisting of colloidal silica, magnesium trisilicate, talc, magnesium carbonate, magnesium oxide, glyceryl behaptate, mono, di and tri glyceryl behenate, bees wax, behenoyl polyoxyl-8 glycerides, hydrogenated vegetable oil, polyethylene glycol, ethylene oxide polymer, copolymer comprising poly(ethylene oxide) and poly(propylene oxide) (such as poloxomer 188), copolymer comprising polypropylene glycol and polyethylene glycol (such as poloxomer 407), sodium lauryl sulfate, magnesium stearate, aluminum stearate, calcium stearate, sodium stearyl fumarate, stearic acid, magnesium lauryl stearate, mixtures of magnesium stearate with sodium lauryl sulfate. In some embodiments, the one or more lubricants is magnesium stearate.

In some embodiments, the oral dosage form further comprises cross-linked polyvinylpyrrolidone and magnesium stearate. In some embodiments, the one or more pharmaceutically acceptable excipients is lactose monohydrate and the oral dosage form further comprises cross-linked polyvinylpyrrolidone and magnesium stearate.

In some embodiments, the oral dosage form is a tablet or a capsule. In some embodiments, the oral dosage form is a tablet. In some embodiments, the oral dosage form is a capsule. In some embodiments, the oral dosage form is a sachet. In some embodiments, the oral dosage form is a powder in a packet.

In some embodiments, the oral dosage form comprises about 1 mg to about 40 mg of the compound of Formula (I). In some embodiments, the oral dosage form comprises about 1 mg to about 30 mg of the compound of Formula (I). In some embodiments, the oral dosage form comprises about 1 mg to about 20 mg of the compound of Formula (I). In some embodiments, the oral dosage form comprises about 1 mg to about 15 mg of the compound of Formula (I). In some embodiments, the oral dosage form comprises about 5 mg to about 40 mg of the compound of Formula (I). In some embodiments, the oral dosage form comprises about 5 mg to about 30 mg of the compound of Formula (I). In some embodiments, the oral dosage form comprises about 5 mg to about 20 mg of the compound of Formula (I). In some embodiments, the oral dosage form comprises about 5 mg to about 15 mg of the compound of Formula (I). In some embodiments, the oral dosage form comprises about 10 mg to about 40 mg of the compound of Formula (I). In some embodiments, the oral dosage form comprises about 10 mg to about 30 mg of the compound of Formula (I). In some embodiments, the oral dosage form comprises about 10 mg to about 20 mg of the compound of Formula (I). In some embodiments, the oral dosage form comprises about 10 mg to about 15 mg of the compound of Formula (I).

In some embodiments, the oral dosage form consists essentially of about 1 mg to about 40 mg of the compound of Formula (I). In some embodiments, the oral dosage form consists essentially of about 1 mg to about 30 mg of the compound of Formula (I). In some embodiments, the oral dosage form consists essentially of about 1 mg to about 20 mg of the compound of Formula (I). In some embodiments, the oral dosage form consists essentially of about 1 mg to about 15 mg of the compound of Formula (I). In some embodiments, the oral dosage form consists essentially of about 5 mg to about 40 mg of the compound of Formula (I). In some embodiments, the oral dosage form consists essentially of about 5 mg to about 30 mg of the compound of Formula (I). In some embodiments, the oral dosage form consists essentially of about 5 mg to about 20 mg of the compound of Formula (I). In some embodiments, the oral dosage form consists essentially of about 5 mg to about 15 mg of the compound of Formula (I). In some embodiments, the oral dosage form consists essentially of about 10 mg to about 40 mg of the compound of Formula (I). In some embodiments, the oral dosage form consists essentially of about 10 mg to about 30 mg of the compound of Formula (I). In some embodiments, the oral dosage form consists essentially of about 10 mg to about 20 mg of the compound of Formula (I). In some embodiments, the oral dosage form consists essentially of about 10 mg to about 15 mg of the compound of Formula (I).

In some embodiments, compound of Formula (I) is present in the oral dosage form as a cocrystal. In some embodiments, compound of Formula (I) is present in the oral dosage form as a channel crystal. In some embodiments, compound of Formula (I) is present in the oral dosage form as a crystalline dihydrate form. In some embodiments, the compound of Formula (I) is present in the oral dosage form as a crystalline anhydrous form. In some embodiments, compound of Formula (I) is present in the oral dosage form as a solvate.

In some embodiments, the oral dosage form comprises about 0.5 mg to about 5 mg, about 6 mg to about 14 mg, about 11 mg to about 19 mg, about 17 mg to about 25 mg, or about 28 mg to about 36 mg of the compound of Formula (I) as a crystalline dihydrate form. In some embodiments, the oral dosage form comprises about 1 mg to about 4 mg, about 8 mg to about 12 mg, about 13 mg to about 17 mg, about 19 mg to about 23 mg, or about 30 mg to about 34 mg of the compound of Formula (I) as a crystalline dihydrate form. In some embodiments, the oral dosage form comprises about 2.2 mg, about 10.8 mg, about 15.2 mg, about 21.7 mg, or about 32.5 mg of the compound of Formula (I) as a crystalline dihydrate form.

In some embodiments, the oral dosage form consists essentially of about 0.5 mg to about 5 mg, about 6 mg to about 14 mg, about 11 mg to about 19 mg, about 17 mg to about 25 mg, or about 28 mg to about 36 mg of the compound of Formula (I) as a crystalline dihydrate form. In some embodiments, the oral dosage form consists essentially of about 1 mg to about 4 mg, about 8 mg to about 12 mg, about 13 mg to about 17 mg, about 19 mg to about 23 mg, or about 30 mg to about 34 mg of the compound of Formula (I) as a crystalline dihydrate form. In some embodiments, the oral dosage form consists essentially of about 2.2 mg, about 10.8 mg, about 15.2 mg, about 21.7 mg, or about 32.5 mg of the compound of Formula (I) as a crystalline dihydrate form.

Also provided herein is a process of preparing an oral dosage form, the oral dosage form comprising:

(a) about 1% by weight to about 70% by weight, based on the total weight of the oral dosage form, of a crystalline dihydrate form of a compound of Formula (I):

Formula (I)

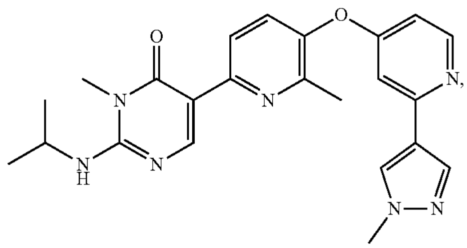

, and one or more pharmaceutically acceptable excipients, wherein the one or more pharmaceutically acceptable excipients comprise:

(b) about 20% by weight to about 97% by weight of one or more fillers, based on the total weight of the oral dosage form;

(c) about 1% by weight to about 20% by weight of one or more disintegrants, based on the total weight of the oral dosage form; and (d) about 0.1% by weight to about 10% by weight of one or more lubricants, based on the total weight of the oral dosage form the process comprising:

(i) blending the crystalline dihydrate form of a compound represented by Formula (I) with the one or more fillers and one or more disintegrants to produce a first blend; and (ii) blending the first blend with the one or more lubricants, thereby preparing the oral dosage form.

Also provided herein is a process of preparing an oral dosage form, the oral dosage form consisting essentially of:

(a) about 1% by weight to about 70% by weight, based on the total weight of the oral dosage form, of a crystalline dihydrate form of a compound of Formula (I):

Formula (I)

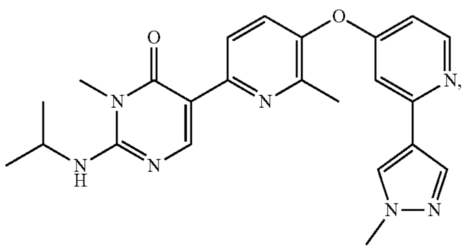

and one or more pharmaceutically acceptable excipients, wherein the one or more pharmaceutically acceptable excipients comprise:

(b) about 20% by weight to about 97% by weight of one or more fillers, based on the total weight of the oral dosage form;

(c) about 1% by weight to about 20% by weight of one or more disintegrants, based on the total weight of the oral dosage form; and (d) about 0.1% by weight to about 10% by weight of one or more lubricants, based on the total weight of the oral dosage form the process comprising:

(i) blending the crystalline dihydrate form of a compound represented by Formula (I) with the one or more fillers and one or more disintegrants to produce a first blend; and (ii) blending the first blend with the one or more lubricants, thereby preparing the oral dosage form.

Also provided herein is a process of preparing an oral dosage form, the oral dosage form comprising:

(a) about 1% by weight to about 70% by weight, based on the total weight of the oral dosage form of a crystalline dihydrate form of a compound of Formula (I):

Formula (I)

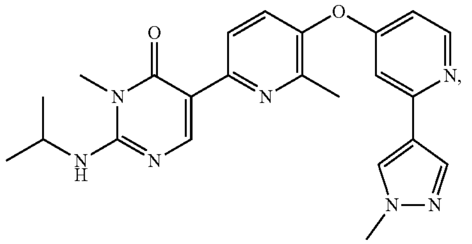

and one or more pharmaceutically acceptable excipients, wherein the one or more pharmaceutically acceptable excipients comprise:

(b) about 20% by weight to about 97% by weight of one or more fillers, based on the total weight of the oral dosage form;

(c) about 1% by weight to about 20% by weight of one or more disintegrants, based on the total weight of the oral dosage form; and (d) about 0.1% by weight to about 10% by weight of one or more lubricants, based on the total weight of the oral dosage form the process comprising:

(i) blending the crystalline dihydrate form of a compound represented by Formula (I) with the one or more fillers to produce a first blend;

(ii) blending the first blend with one or more disintegrants to produce a second blend; and (iii) blending the second blend with the one or more lubricants, thereby preparing the oral dosage form.

Also provided herein is a process of preparing an oral dosage form, the oral dosage form consisting essentially of:

(a) about 1% by weight to about 70% by weight, based on the total weight of the oral dosage form of a crystalline dihydrate form of a compound of Formula (I):

Formula (I)

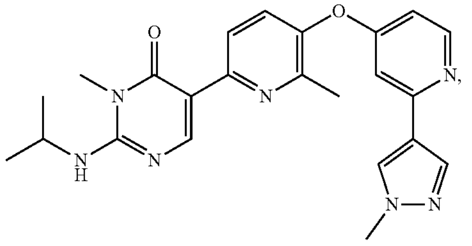

and one or more pharmaceutically acceptable excipients, wherein the one or more pharmaceutically acceptable excipients comprise:

(b) about 20% by weight to about 97% by weight of one or more fillers, based on the total weight of the oral dosage form;

(c) about 1% by weight to about 20% by weight of one or more disintegrants, based on the total weight of the oral dosage form; and (d) about 0.1% by weight to about 10% by weight of one or more lubricants, based on the total weight of the oral dosage form the process comprising:

(i) blending the crystalline dihydrate form of a compound represented by Formula (I) with the one or more fillers to produce a first blend;

(ii) blending the first blend with one or more disintegrants to produce a second blend; and (iii) blending the second blend with the one or more lubricants, thereby preparing the oral dosage form.

Also provided herein is a process of preparing an oral dosage form, the oral dosage form comprising:

(a) about 1% by weight to about 70% by weight, based on the total weight of the oral dosage form of a crystalline dihydrate form of a compound of Formula (I):

Formula (I)

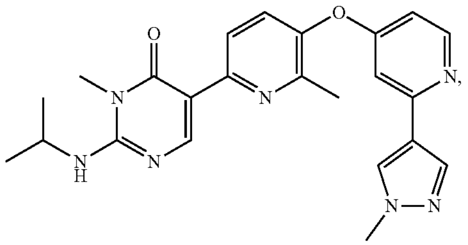

and one or more pharmaceutically acceptable excipients, wherein the one or more pharmaceutically acceptable excipients comprise:

(b) about 20% by weight to about 97% by weight of one or more fillers, based on the total weight of the oral dosage form;

(c) about 1% by weight to about 20% by weight of one or more disintegrants, based on the total weight of the oral dosage form; and (d) about 0.1% by weight to about 10% by weight of one or more lubricants, based on the total weight of the oral dosage form the process comprising:

(i) blending the crystalline dihydrate form of a compound represented by Formula (I) with the one or more fillers to produce a first blend;

(ii) blending the first blend with a second blend comprising one or more disintegrants and one or more fillers and optionally a third blend comprising one or more fillers to produce a fourth blend; and (iii) blending the fourth blend with the one or more lubricants, thereby preparing the oral dosage form.

Also provided herein is a process of preparing an oral dosage form, the oral dosage form consisting essentially of:

(a) about 1% by weight to about 70% by weight, based on the total weight of the oral dosage form of a crystalline dihydrate form of a compound of Formula (I):

Formula (I)

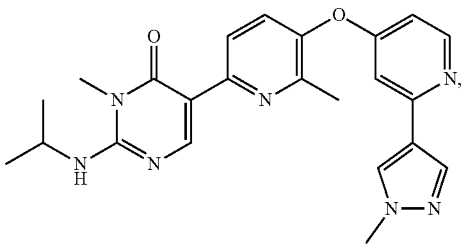

and one or more pharmaceutically acceptable excipients, wherein the one or more pharmaceutically acceptable excipients comprise:

(b) about 20% by weight to about 97% by weight of one or more fillers, based on the total weight of the oral dosage form;

(c) about 1% by weight to about 20% by weight of one or more disintegrants, based on the total weight of the oral dosage form; and (d) about 0.1% by weight to about 10% by weight of one or more lubricants, based on the total weight of the oral dosage form the process comprising:

(i) blending the crystalline dihydrate form of a compound represented by Formula (I) with the one or more fillers to produce a first blend;

(ii) blending the first blend with a second blend comprising one or more disintegrants and one or more fillers and optionally a third blend comprising one or more fillers to produce a fourth blend; and (iii) blending the fourth blend with the one or more lubricants, thereby preparing the oral dosage form.

In some embodiments, the oral dosage form comprising the crystalline dihydrate form of the compound represented by Formula (I), has no more than about 10 mol %, no more than about 5 mol %, no more than about 3 mol %, or no more than about 1 mol % of other solid-state forms of the compound represented by Formula (I). In some embodiments, the oral dosage form comprising the crystalline dihydrate forms of the compound represented by Formula (I), has no more than about 10 mol % of other solid-state forms of the compound represented by Formula (I). In some embodiments, the oral dosage form comprising the crystalline dihydrate forms of the compound represented by Formula (I), has no more than about 9 mol % of other solid-state forms of the compound represented by Formula (I). In some embodiments, the oral dosage form comprising the crystalline dihydrate forms of the compound represented by Formula (I), has no more than about 8 mol % of other solid-state forms of the compound represented by Formula (I). In some embodiments, the oral dosage form comprising the crystalline dihydrate forms of the compound represented by Formula (I), has no more than about 7 mol % of other solid-state forms of the compound represented by Formula (I). In some embodiments, the oral dosage form comprising the crystalline dihydrate forms of the compound represented by Formula (I), has no more than about 6 mol % of other solid-state forms of the compound represented by Formula (I). In some embodiments, the oral dosage form comprising the crystalline dihydrate forms of the compound represented by Formula (I), has no more than about 5 mol % of other solid-state forms of the compound represented by Formula (I). In some embodiments, the oral dosage form comprising the crystalline dihydrate forms of the compound represented by Formula (I), has no more than about 4 mol % of other solid-state forms of the compound represented by Formula (I). In some embodiments, the oral dosage form comprising the crystalline dihydrate forms of the compound represented by Formula (I), has no more than about 3 mol % of other solid-state forms of the compound represented by Formula (I). In some embodiments, the oral dosage form comprising the crystalline dihydrate forms of the compound represented by Formula (I), has no more than about 2 mol % of other solid-state forms of the compound represented by Formula (I). In some embodiments, the oral dosage form comprising the crystalline dihydrate forms of the compound represented by Formula (I), has no more than about 1 mol % of other solid-state forms of the compound represented by Formula (I).

In some embodiments, the oral dosage form comprises about 1% by weight to about 60% by weight, based on the total weight of the oral dosage form, of a crystalline dihydrate form of a compound of Formula (I). In some embodiments, the oral dosage form comprises about 1% by weight to about 50% by weight, based on the total weight of the oral dosage form, of a crystalline dihydrate form of a compound of Formula (I). In some embodiments, the oral dosage form comprises about 1% by weight to about 40% by weight, based on the total weight of the oral dosage form, of a crystalline dihydrate form of a compound of Formula (I). In some embodiments, the oral dosage form comprises about 1% by weight to about 30% by weight, based on the total weight of the oral dosage form, of a crystalline dihydrate form of a compound of Formula (I). In some embodiments, the oral dosage form comprises about 1% by weight to about 20% by weight, based on the total weight of the oral dosage form, of a crystalline dihydrate form of a compound of Formula (I).

In some embodiments, the oral dosage form consists essentially of about 1% by weight to about 60% by weight, based on the total weight of the oral dosage form, of a crystalline dihydrate form of a compound of Formula (I). In some embodiments, the oral dosage form consists essentially of about 1% by weight to about 50% by weight, based on the total weight of the oral dosage form, of a crystalline dihydrate form of a compound of Formula (I). In some embodiments, the oral dosage form consists essentially of about 1% by weight to about 40% by weight, based on the total weight of the oral dosage form, of a crystalline dihydrate form of a compound of Formula (I). In some embodiments, the oral dosage form consists essentially of about 1% by weight to about 30% by weight, based on the total weight of the oral dosage form, of a crystalline dihydrate form of a compound of Formula (I). In some embodiments, the oral dosage form consists essentially of about 1% by weight to about 20% by weight, based on the total weight of the oral dosage form, of a crystalline dihydrate form of a compound of Formula (I).

In some embodiments, the oral dosage form comprises about 1% by weight to about 70% by weight of the crystalline dihydrate form of the compound of Formula (I) based on the total weight of the oral dosage form. In some embodiments, the oral dosage form comprises about 1% by weight to about 65% by weight of the crystalline dihydrate form of the compound of Formula (I) based on the total weight of the oral dosage form. In some embodiments, the oral dosage form comprises about 1% by weight to about 60% by weight of the crystalline dihydrate form of the compound of Formula (I) based on the total weight of the oral dosage form. In some embodiments, the oral dosage form comprises about 1% by weight to about 55% by weight of the crystalline dihydrate form of the compound of Formula (I) based on the total weight of the oral dosage form. In some embodiments, the oral dosage form comprises about 1% by weight to about 50% by weight of the crystalline dihydrate form of the compound of Formula (I) based on the total weight of the oral dosage form. In some embodiments, the oral dosage form comprises about 1% by weight to about 45% by weight of the crystalline dihydrate form of the compound of Formula (I) based on the total weight of the oral dosage form. In some embodiments, the oral dosage form comprises about 1% by weight to about 40% by weight of the crystalline dihydrate form of the compound of Formula (I) based on the total weight of the oral dosage form. In some embodiments, the oral dosage form comprises about 1% by weight to about 35% by weight of the crystalline dihydrate form of the compound of Formula (I) based on the total weight of the oral dosage form. In some embodiments, the oral dosage form comprises about 1% by weight to about 30% by weight of the crystalline dihydrate form of the compound of Formula (I) based on the total weight of the oral dosage form. In some embodiments, the oral dosage form comprises about 1% by weight to about 25% by weight of the crystalline dihydrate form of the compound of Formula (I) based on the total weight of the oral dosage form. In some embodiments, the oral dosage form comprises about 1% by weight to about 20% by weight of the crystalline dihydrate form of the compound of Formula (I) based on the total weight of the oral dosage form. In some embodiments, the oral dosage form comprises about 1% by weight to about 15% by weight of the crystalline dihydrate form of the compound of Formula (I) based on the total weight of the oral dosage form. In some embodiments, the oral dosage form comprises about 1% by weight to about 10% by weight of the crystalline dihydrate form of the compound of Formula (I) based on the total weight of the oral dosage form.

In some embodiments, the oral dosage form consists essentially of about 1% by weight to about 70% by weight of the crystalline dihydrate form of the compound of Formula (I) based on the total weight of the oral dosage form. In some embodiments, the oral dosage form consists essentially of about 1% by weight to about 65% by weight of the crystalline dihydrate form of the compound of Formula (I) based on the total weight of the oral dosage form. In some embodiments, the oral dosage form consists essentially of about 1% by weight to about 60% by weight of the crystalline dihydrate form of the compound of Formula (I) based on the total weight of the oral dosage form. In some embodiments, the oral dosage form consists essentially of about 1% by weight to about 55% by weight of the crystalline dihydrate form of the compound of Formula (I) based on the total weight of the oral dosage form. In some embodiments, the oral dosage form consists essentially of about 1% by weight to about 50% by weight of the crystalline dihydrate form of the compound of Formula (I) based on the total weight of the oral dosage form. In some embodiments, the oral dosage form consists essentially of about 1% by weight to about 45% by weight of the crystalline dihydrate form of the compound of Formula (I) based on the total weight of the oral dosage form. In some embodiments, the oral dosage form consists essentially of about 1% by weight to about 40% by weight of the crystalline dihydrate form of the compound of Formula (I) based on the total weight of the oral dosage form. In some embodiments, the oral dosage form consists essentially of about 1% by weight to about 35% by weight of the crystalline dihydrate form of the compound of Formula (I) based on the total weight of the oral dosage form. In some embodiments, the oral dosage form consists essentially of about 1% by weight to about 30% by weight of the crystalline dihydrate form of the compound of Formula (I) based on the total weight of the oral dosage form. In some embodiments, the oral dosage form consists essentially of about 1% by weight to about 25% by weight of the crystalline dihydrate form of the compound of Formula (I) based on the total weight of the oral dosage form. In some embodiments, the oral dosage form consists essentially of about 1% by weight to about 20% by weight of the crystalline dihydrate form of the compound of Formula (I) based on the total weight of the oral dosage form. In some embodiments, the oral dosage form consists essentially of about 1% by weight to about 15% by weight of the crystalline dihydrate form of the compound of Formula (I) based on the total weight of the oral dosage form. In some embodiments, the oral dosage form consists essentially of about 1% by weight to about 10% by weight of the crystalline dihydrate form of the compound of Formula (I) based on the total weight of the oral dosage form.

In some embodiments, the oral dosage form comprises about 5% by weight to about 30% by weight of the crystalline dihydrate form of the compound of Formula (I) based on the total weight of the oral dosage form. In some embodiments, the oral dosage form comprises about 5% by weight to about 25% by weight of the crystalline dihydrate form of the compound of Formula (I) based on the total weight of the oral dosage form. In some embodiments, the oral dosage form comprises about 5% by weight to about 20% by weight of the crystalline dihydrate form of the compound of Formula (I) based on the total weight of the oral dosage form. In some embodiments, the oral dosage form comprises about 5% by weight to about 15% by weight of the crystalline dihydrate form of the compound of Formula (I) based on the total weight of the oral dosage form. In some embodiments, the oral dosage form comprises about 5% by weight to about 10% by weight of the crystalline dihydrate form of the compound of Formula (I) based on the total weight of the oral dosage form.

In some embodiments, the oral dosage form consists essentially of about 5% by weight to about 30% by weight of the crystalline dihydrate form of the compound of Formula (I) based on the total weight of the oral dosage form. In some embodiments, the oral dosage form consists essentially of about 5% by weight to about 25% by weight of the crystalline dihydrate form of the compound of Formula (I) based on the total weight of the oral dosage form. In some embodiments, the oral dosage form consists essentially of about 5% by weight to about 20% by weight of the crystalline dihydrate form of the compound of Formula (I) based on the total weight of the oral dosage form. In some embodiments, the oral dosage form consists essentially of about 5% by weight to about 15% by weight of the crystalline dihydrate form of the compound of Formula (I) based on the total weight of the oral dosage form. In some embodiments, the oral dosage form consists essentially of about 5% by weight to about 10% by weight of the crystalline dihydrate form of the compound of Formula (I) based on the total weight of the oral dosage form.

In some embodiments, the oral dosage form comprises about 10% to about 30% of the compound of Formula (I) based on the total weight of the oral dosage form. In some embodiments, the oral dosage form comprises about 10% to about 25% of the compound of Formula (I) based on the total weight of the oral dosage form. In some embodiments, the oral dosage form comprises about 10% to about 20% of the compound of Formula (I) based on the total weight of the oral dosage form. In some embodiments, the oral dosage form comprises about 10% by weight to about 15% by weight of the crystalline dihydrate form of the compound of Formula (I) based on the total weight of the oral dosage form.

In some embodiments, the oral dosage form consists essentially of about 10% to about 30% of the crystalline dihydrate form of the compound of Formula (I) based on the total weight of the oral dosage form. In some embodiments, the oral dosage form consists essentially of about 10% to about 25% of the crystalline dihydrate form of the compound of Formula (I) based on the total weight of the oral dosage form. In some embodiments, the oral dosage form consists essentially of about 10% to about 20% of the crystalline dihydrate form of the compound of Formula (I) based on the total weight of the oral dosage form. In some embodiments, the oral dosage form consists essentially of about 10% by weight to about 15% by weight of the crystalline dihydrate form of the compound of Formula (I) based on the total weight of the oral dosage form.

In some embodiments, the oral dosage form comprises about 1% by weight to about 30% by weight of the crystalline dihydrate form of the compound of Formula (I) based on the total weight of the oral dosage form. In some embodiments, the oral dosage form comprises about 1% by weight to about 10% by weight of the crystalline dihydrate form of the compound of Formula (I) based on the total weight of the oral dosage form. In some embodiments, the oral dosage form comprises about 10% to about 20% of the compound of Formula (I) based on the total weight of the oral dosage form. In some embodiments, the oral dosage form comprises about 10% by weight to about 15% by weight of the crystalline dihydrate form of the compound of Formula (I) based on the total weight of the oral dosage form.

In some embodiments, the oral dosage form consists essentially of about 1% by weight to about 30% by weight of the crystalline dihydrate form of the compound of Formula (I) based on the total weight of the oral dosage form. In some embodiments, the oral dosage form consists essentially of about 1% by weight to about 10% by weight of the crystalline dihydrate form of the compound of Formula (I) based on the total weight of the oral dosage form. In some embodiments, the oral dosage form consists essentially of about 10% to about 20% of the crystalline dihydrate form of the compound of Formula (I) based on the total weight of the oral dosage form. In some embodiments, the oral dosage form consists essentially of about 10% by weight to about 15% by weight of the crystalline dihydrate form of the compound of Formula (I) based on the total weight of the oral dosage form.

In some embodiments, the one or more pharmaceutically acceptable excipients comprise about 20% by weight to about 90% by weight of one or more fillers based on the total weight of the oral dosage form. In some embodiments, the one or more pharmaceutically acceptable excipients comprise about 20% by weight to about 85% by weight of one or more fillers based on the total weight of the oral dosage form. In some embodiments, the one or more pharmaceutically acceptable excipients comprise about 20% by weight to about 80% by weight of one or more fillers based on the total weight of the oral dosage form. In some embodiments, the one or more pharmaceutically acceptable excipients comprise about 20% by weight to about 75% by weight of one or more fillers based on the total weight of the oral dosage form. In some embodiments, the one or more pharmaceutically acceptable excipients comprise about 20% by weight to about 70% by weight of one or more fillers based on the total weight of the oral dosage form. In some embodiments, the one or more pharmaceutically acceptable excipients comprise about 20% by weight to about 65% by weight of one or more fillers based on the total weight of the oral dosage form. In some embodiments, the one or more pharmaceutically acceptable excipients comprise about 20% by weight to about 60% by weight of one or more fillers based on the total weight of the oral dosage form. In some embodiments, the one or more pharmaceutically acceptable excipients comprise about 20% by weight to about 55% by weight of one or more fillers based on the total weight of the oral dosage form. In some embodiments, the one or more pharmaceutically acceptable excipients comprise about 20% by weight to about 50% by weight of one or more fillers based on the total weight of the oral dosage form. In some embodiments, the one or more pharmaceutically acceptable excipients comprise about 20% by weight to about 45% by weight of one or more fillers based on the total weight of the oral dosage form. In some embodiments, the one or more pharmaceutically acceptable excipients comprise about 20% by weight to about 40% by weight of one or more fillers based on the total weight of the oral dosage form. In some embodiments, the one or more pharmaceutically acceptable excipients comprise about 20% by weight to about 35% by weight of one or more fillers based on the total weight of the oral dosage form. In some embodiments, the one or more pharmaceutically acceptable excipients comprise about 20% by weight to about 30% by weight of one or more fillers based on the total weight of the oral dosage form. In some embodiments, the one or more pharmaceutically acceptable excipients comprise about 20% by weight to about 25% by weight of one or more fillers based on the total weight of the oral dosage form.

In some embodiments, the one or more pharmaceutically acceptable excipients comprise about 30% by weight to about 90% by weight of one or more fillers based on the total weight of the oral dosage form. In some embodiments, the one or more pharmaceutically acceptable excipients comprise about 30% by weight to about 80% by weight of one or more fillers based on the total weight of the oral dosage form. In some embodiments, the one or more pharmaceutically acceptable excipients comprise about 30% by weight to about 70% by weight of one or more fillers based on the total weight of the oral dosage form. In some embodiments, the one or more pharmaceutically acceptable excipients comprise about 30% by weight to about 60% by weight of one or more fillers based on the total weight of the oral dosage form. In some embodiments, the one or more pharmaceutically acceptable excipients comprise about 30% by weight to about 50% by weight of one or more fillers based on the total weight of the oral dosage form. In some embodiments, the one or more pharmaceutically acceptable excipients comprise about 30% by weight to about 40% by weight of one or more fillers based on the total weight of the oral dosage form.

In some embodiments, the one or more pharmaceutically acceptable excipients comprise about 40% by weight to about 90% by weight of one or more fillers based on the total weight of the oral dosage form. In some embodiments, the one or more pharmaceutically acceptable excipients comprise about 40% by weight to about 80% by weight of one or more fillers based on the total weight of the oral dosage form. In some embodiments, the one or more pharmaceutically acceptable excipients comprise about 40% by weight to about 70% by weight of one or more fillers based on the total weight of the oral dosage form. In some embodiments, the one or more pharmaceutically acceptable excipients comprise about 40% by weight to about 60% by weight of one or more fillers based on the total weight of the oral dosage form. In some embodiments, the one or more pharmaceutically acceptable excipients comprise about 40% by weight to about 50% by weight of one or more fillers based on the total weight of the oral dosage form.

In some embodiments, the one or more pharmaceutically acceptable excipients comprise about 50% by weight to about 90% by weight of one or more fillers based on the total weight of the oral dosage form. In some embodiments, the one or more pharmaceutically acceptable excipients comprise about 50% by weight to about 80% by weight of one or more fillers based on the total weight of the oral dosage form. In some embodiments, the one or more pharmaceutically acceptable excipients comprise about 50% by weight to about 70% by weight of one or more fillers based on the total weight of the oral dosage form. In some embodiments, the one or more pharmaceutically acceptable excipients comprise about 50% by weight to about 60% by weight of one or more fillers based on the total weight of the oral dosage form.

In some embodiments, the one or more pharmaceutically acceptable excipients comprise about 60% by weight to about 90% by weight of one or more fillers based on the total weight of the oral dosage form. In some embodiments, the one or more pharmaceutically acceptable excipients comprise about 60% by weight to about 80% by weight of one or more fillers based on the total weight of the oral dosage form. In some embodiments, the one or more pharmaceutically acceptable excipients comprise about 60% by weight to about 70% by weight of one or more fillers based on the total weight of the oral dosage form.

In some embodiments, the one or more pharmaceutically acceptable excipients comprise about 70% by weight to about 90% by weight of one or more fillers based on the total weight of the oral dosage form. In some embodiments, the one or more pharmaceutically acceptable excipients comprise about 70% by weight to about 80% by weight of one or more fillers based on the total weight of the oral dosage form.

In some embodiments, the one or more pharmaceutically acceptable excipients comprise about 80% by weight to about 90% by weight of one or more fillers based on the total weight of the oral dosage form.

In some embodiments, the one or more pharmaceutically acceptable excipients comprise about 1% by weight to about 20% by weight of one or more disintegrants based on the total weight of the oral dosage form. In some embodiments, the one or more pharmaceutically acceptable excipients comprise about 1% by weight to about 15% by weight of one or more disintegrants based on the total weight of the oral dosage form. In some embodiments, the one or more pharmaceutically acceptable excipients comprise about 1% by weight to about 14% by weight of one or more disintegrants based on the total weight of the oral dosage form. In some embodiments, the one or more pharmaceutically acceptable excipients comprise about 1% by weight to about 13% by weight of one or more disintegrants based on the total weight of the oral dosage form. In some embodiments, the one or more pharmaceutically acceptable excipients comprise about 1% by weight to about 12% by weight of one or more disintegrants based on the total weight of the oral dosage form. In some embodiments, the one or more pharmaceutically acceptable excipients comprise about 1% by weight to about 11% by weight of one or more disintegrants based on the total weight of the oral dosage form. In some embodiments, the one or more pharmaceutically acceptable excipients comprise about 1% by weight to about 10% by weight of one or more disintegrants based on the total weight of the oral dosage form. In some embodiments, the one or more pharmaceutically acceptable excipients comprise about 1% by weight to about 9% by weight of one or more disintegrants based on the total weight of the oral dosage form. In some embodiments, the one or more pharmaceutically acceptable excipients comprise about 1% by weight to about 8% by weight of one or more disintegrants based on the total weight of the oral dosage form. In some embodiments, the one or more pharmaceutically acceptable excipients comprise about 1% by weight to about 7% by weight of one or more disintegrants based on the total weight of the oral dosage form. In some embodiments, the one or more pharmaceutically acceptable excipients comprise about 1% by weight to about 6% by weight of one or more disintegrants based on the total weight of the oral dosage form. In some embodiments, the one or more pharmaceutically acceptable excipients comprise about 1% by weight to about 5% by weight of one or more disintegrants based on the total weight of the oral dosage form. In some embodiments, the one or more pharmaceutically acceptable excipients comprise about 1% by weight to about 4% by weight of one or more disintegrants based on the total weight of the oral dosage form. In some embodiments, the one or more pharmaceutically acceptable excipients comprise about 1% by weight to about 3% by weight of one or more disintegrants based on the total weight of the oral dosage form.

In some embodiments, the one or more pharmaceutically acceptable excipients comprise about 1% by weight of one or more disintegrants based on the total weight of the oral dosage form. In some embodiments, the one or more pharmaceutically acceptable excipients comprise about 2% by weight of one or more disintegrants based on the total weight of the oral dosage form. In some embodiments, the one or more pharmaceutically acceptable excipients comprise about 3% by weight of one or more disintegrants based on the total weight of the oral dosage form. In some embodiments, the one or more pharmaceutically acceptable excipients comprise about 4% by weight of one or more disintegrants based on the total weight of the oral dosage form. In some embodiments, the one or more pharmaceutically acceptable excipients comprise about 5% by weight of one or more disintegrants based on the total weight of the oral dosage form. In some embodiments, the one or more pharmaceutically acceptable excipients comprise about 6% by weight of one or more disintegrants based on the total weight of the oral dosage form. In some embodiments, the one or more pharmaceutically acceptable excipients comprise about 7% by weight of one or more disintegrants based on the total weight of the oral dosage form. In some embodiments, the one or more pharmaceutically acceptable excipients comprise about 8% by weight of one or more disintegrants based on the total weight of the oral dosage form. In some embodiments, the one or more pharmaceutically acceptable excipients comprise about 9% by weight of one or more disintegrants based on the total weight of the oral dosage form. In some embodiments, the one or more pharmaceutically acceptable excipients comprise about 10% by weight of one or more disintegrants based on the total weight of the oral dosage form. In some embodiments, the one or more pharmaceutically acceptable excipients comprise about 11% by weight of one or more disintegrants based on the total weight of the oral dosage form. In some embodiments, the one or more pharmaceutically acceptable excipients comprise about 12% by weight of one or more disintegrants based on the total weight of the oral dosage form. In some embodiments, the one or more pharmaceutically acceptable excipients comprise about 13% by weight of one or more disintegrants based on the total weight of the oral dosage form. In some embodiments, the one or more pharmaceutically acceptable excipients comprise about 14% by weight of one or more disintegrants based on the total weight of the oral dosage form. In some embodiments, the one or more pharmaceutically acceptable excipients comprise about 15% by weight of one or more disintegrants based on the total weight of the oral dosage form.

In some embodiments, the one or more pharmaceutically acceptable excipients comprise about 0.1% by weight to about 10% by weight of one or more lubricants based on the total weight of the oral dosage form. In some embodiments, the one or more pharmaceutically acceptable excipients comprise about 0.1% by weight to about 9% by weight of one or more lubricants based on the total weight of the oral dosage form. In some embodiments, the one or more pharmaceutically acceptable excipients comprise about 0.1% by weight to about 8% by weight of one or more lubricants based on the total weight of the oral dosage form. In some embodiments, the one or more pharmaceutically acceptable excipients comprise about 0.1% by weight to about 7% by weight of one or more lubricants based on the total weight of the oral dosage form. In some embodiments, the one or more pharmaceutically acceptable excipients comprise about 0.1% by weight to about 6% by weight of one or more lubricants based on the total weight of the oral dosage form. In some embodiments, the one or more pharmaceutically acceptable excipients comprise about 0.1% by weight to about 5% by weight of one or more lubricants based on the total weight of the oral dosage form. In some embodiments, the one or more pharmaceutically acceptable excipients comprise about 0.1% by weight to about 4% by weight of one or more lubricants based on the total weight of the oral dosage form. In some embodiments, the one or more pharmaceutically acceptable excipients comprise about 0.1% by weight to about 3% by weight of one or more lubricants based on the total weight of the oral dosage form. In some embodiments, the one or more pharmaceutically acceptable excipients comprise about 0.1% by weight to about 2% by weight of one or more lubricants based on the total weight of the oral dosage form.

In some embodiments, the one or more pharmaceutically acceptable excipients comprise about 0.1% by weight to about 1.9% by weight of one or more lubricants based on the total weight of the oral dosage form. In some embodiments, the one or more pharmaceutically acceptable excipients comprise about 0.1% by weight to about 1.8% by weight of one or more lubricants based on the total weight of the oral dosage form. In some embodiments, the one or more pharmaceutically acceptable excipients comprise about 0.1% by weight to about 1.7% by weight of one or more lubricants based on the total weight of the oral dosage form. In some embodiments, the one or more pharmaceutically acceptable excipients comprise about 0.1% by weight to about 1.6% by weight of one or more lubricants based on the total weight of the oral dosage form. In some embodiments, the one or more pharmaceutically acceptable excipients comprise about 0.1% by weight to about 1.5% by weight of one or more lubricants based on the total weight of the oral dosage form. In some embodiments, the one or more pharmaceutically acceptable excipients comprise about 0.1% by weight to about 1.4% by weight of one or more lubricants based on the total weight of the oral dosage form. In some embodiments, the one or more pharmaceutically acceptable excipients comprise about 0.1% by weight to about 1.3% by weight of one or more lubricants based on the total weight of the oral dosage form. In some embodiments, the one or more pharmaceutically acceptable excipients comprise about 0.1% by weight to about 1.2% by weight of one or more lubricants based on the total weight of the oral dosage form. In some embodiments, the one or more pharmaceutically acceptable excipients comprise about 0.1% by weight to about 1.1% by weight of one or more lubricants based on the total weight of the oral dosage form. In some embodiments, the one or more pharmaceutically acceptable excipients comprise about 0.1% by weight to about 1.0% by weight of one or more lubricants based on the total weight of the oral dosage form. In some embodiments, the one or more pharmaceutically acceptable excipients comprise about 0.1% by weight to about 0.9% by weight of one or more lubricants based on the total weight of the oral dosage form. In some embodiments, the one or more pharmaceutically acceptable excipients comprise about 0.1% by weight to about 0.8% by weight of one or more lubricants based on the total weight of the oral dosage form. In some embodiments, the one or more pharmaceutically acceptable excipients comprise about 0.1% by weight to about 0.7% by weight of one or more lubricants based on the total weight of the oral dosage form. In some embodiments, the one or more pharmaceutically acceptable excipients comprise about 0.1% by weight to about 0.6% by weight of one or more lubricants based on the total weight of the oral dosage form. In some embodiments, the one or more pharmaceutically acceptable excipients comprise about 0.1% by weight to about 0.5% by weight of one or more lubricants based on the total weight of the oral dosage form. In some embodiments, the one or more pharmaceutically acceptable excipients comprise about 0.1% by weight to about 0.4% by weight of one or more lubricants based on the total weight of the oral dosage form. In some embodiments, the one or more pharmaceutically acceptable excipients comprise about 0.1% by weight to about 0.3% by weight of one or more lubricants based on the total weight of the oral dosage form. In some embodiments, the one or more pharmaceutically acceptable excipients comprise about 0.1% by weight to about 0.2% by weight of one or more lubricants based on the total weight of the oral dosage form.

In some embodiments, the one or more pharmaceutically acceptable excipients comprise about 0.1% by weight of one or more lubricants based on the total weight of the oral dosage form. In some embodiments, the one or more pharmaceutically acceptable excipients comprise about 0.2% by weight of one or more lubricants based on the total weight of the oral dosage form. In some embodiments, the one or more pharmaceutically acceptable excipients comprise about 0.3% by weight of one or more lubricants based on the total weight of the oral dosage form. In some embodiments, the one or more pharmaceutically acceptable excipients comprise about 0.4% by weight of one or more lubricants based on the total weight of the oral dosage form. In some embodiments, the one or more pharmaceutically acceptable excipients comprise about 0.5% by weight of one or more lubricants based on the total weight of the oral dosage form. In some embodiments, the one or more pharmaceutically acceptable excipients comprise about 0.6% by weight of one or more lubricants based on the total weight of the oral dosage form. In some embodiments, the one or more pharmaceutically acceptable excipients comprise about 0.7% by weight of one or more lubricants based on the total weight of the oral dosage form. In some embodiments, the one or more pharmaceutically acceptable excipients comprise about 0.8% by weight of one or more lubricants based on the total weight of the oral dosage form. In some embodiments, the one or more pharmaceutically acceptable excipients comprise about 0.9% by weight of one or more lubricants based on the total weight of the oral dosage form. In some embodiments, the one or more pharmaceutically acceptable excipients comprise about 1.0% by weight of one or more lubricants based on the total weight of the oral dosage form.

In some embodiments, the oral dosage form comprises: (a) about 1% by weight to about 30% by weight of the compound of Formula (I) based on the total weight of the oral dosage form; (b) about 20% by weight to about 90% by weight of one or more fillers based on the total weight of the oral dosage form; (c) about 1% by weight to about 20% by weight of one or more disintegrants based on the total weight of the oral dosage form; and (d) about 0.1% by weight to about 10% by weight of one or more lubricants based on the total weight of the oral dosage form.

In some embodiments, the oral dosage form consists essentially of: (a) about 1% by weight to about 30% by weight of the compound of Formula (I) based on the total weight of the oral dosage form; (b) about 20% by weight to about 90% by weight of one or more fillers based on the total weight of the oral dosage form; (c) about 1% by weight to about 20% by weight of one or more disintegrants based on the total weight of the oral dosage form; and (d) about 0.1% by weight to about 10% by weight of one or more lubricants based on the total weight of the oral dosage form.

In some embodiments, the oral dosage form comprises (a) about 5% by weight to about 25% by weight of the crystalline dihydrate form of the compound of Formula (I) based on the total weight of the oral dosage form; (b) about 60% by weight to about 90% by weight of one or more fillers based on the total weight of the oral dosage form; (c) about 1% by weight to about 15% by weight of one or more disintegrants based on the total weight of the oral dosage form; and (d) about 0.1% by weight to about 4% by weight of one or more lubricants based on the total weight of the oral dosage form.

In some embodiments, the oral dosage form consists essentially of: (a) about 5% by weight to about 25% by weight of the crystalline dihydrate form of the compound of Formula (I) based on the total weight of the oral dosage form; (b) about 60% by weight to about 90% by weight of one or more fillers based on the total weight of the oral dosage form; (c) about 1% by weight to about 15% by weight of one or more disintegrants based on the total weight of the oral dosage form; and (d) about 0.1% by weight to about 4% by weight of one or more lubricants based on the total weight of the oral dosage form.

In some embodiments, the oral dosage form comprises (a) about 10% by weight to about 30% by weight of the crystalline dihydrate form of the compound of Formula (I) based on the total weight of the oral dosage form; (b) about 70% by weight to about 90% by weight of one or more fillers based on the total weight of the oral dosage form; (c) about 1% by weight to about 10% by weight of one or more disintegrants based on the total weight of the oral dosage form; and (d) about 0.1% by weight to about 3% by weight of one or more lubricants based on the total weight of the oral dosage form.

In some embodiments, the oral dosage form consists essentially of: (a) about 10% by weight to about 30% by weight of the crystalline dihydrate form of the compound of Formula (I) based on the total weight of the oral dosage form; (b) about 70% by weight to about 90% by weight of one or more fillers based on the total weight of the oral dosage form; (c) about 1% by weight to about 10% by weight of one or more disintegrants based on the total weight of the oral dosage form; and (d) about 0.1% by weight to about 3% by weight of one or more lubricants based on the total weight of the oral dosage form.

In some embodiments, the one or more pharmaceutically acceptable excipients is one or more fillers selected from the group consisting of calcium phosphate, dicalcium phosphate, dicalcium phosphate dihydrate, calcium sulfate, calcium sulfate dihydrate, starch, calcium carbonate, magnesium carbonate, magnesium oxide, kaolin (natural hydrated aluminum silicate), sodium chloride, partially gelatinized starch, anhydrous lactose, lactose monohydrate, lactose dihydrate, trehalose dihydrate, spray dried lactose, sucrose, dextrose, dextrates, dextrin, cellulose, microcrystalline cellulose, silicified microcrystalline cellulose, powdered cellulose, partially depolymerized cellulose, mannitol, granulated mannitol, spray dried mannitol, maltodextrin, maltitol, confectioner's sugar, compressible sugar, sorbitol, starch and talc. In some embodiments, the one or more fillers is lactose monohydrate.

In some embodiments, the one or more disintegrants is one or more disintegrants selected from the group consisting of sodium starch glycolate, pregelatinized starch, clay, cellulose, alginic acid, alginate gum, polyvinylpyrrolidone, cross-linked polyvinylpyrrolidone, cross-linked calcium carboxymethylcellulose, cross-linked sodium carboxymethylcellulose, sodium croscarmellose, sodium carmellose, low substituted hydroxypropyl cellulose, low substituted hydroxypropyl cellulose sodium, guar gum, magnesium aluminum silicate, polacrilin potassium, powdered cellulose, sodium alginate and soy polysaccharides. In some embodiments, the one or more disintegrants is cross-linked polyvinylpyrrolidone (also referred to as crospovidone).

In some embodiments, the one or more lubricants is one or more lubricants selected from the group consisting of colloidal silica, magnesium trisilicate, talc, magnesium carbonate, magnesium oxide, glyceryl behaptate, mono, di and tri glyceryl behenate, bees wax, behenoyl polyoxyl-8 glycerides, hydrogenated vegetable oil, polyethylene glycol, ethylene oxide polymer, copolymer comprising poly(ethylene oxide) and poly(propylene oxide) (such as poloxomer 188), copolymer comprising polypropylene glycol and polyethylene glycol (such as poloxomer 407), sodium lauryl sulfate, magnesium stearate, aluminum stearate, calcium stearate, sodium stearyl fumarate, stearic acid, magnesium lauryl stearate, mixtures of magnesium stearate with sodium lauryl sulfate. In some embodiments, the one or more lubricants is magnesium stearate.

In some embodiments, the one or more disintegrants is selected from the group consisting of cross-linked polyvinylpyrrolidone, croscarmellose sodium, and sodium starch glycolate; and the one or more lubricants is selected from the group consisting of sodium stearyl fumarate, stearic acid, talc, calcium stearate, magnesium stearate, solid polyethylene glycols, and sodium lauryl sulfate. In some embodiments, the oral dosage form comprises cross-linked polyvinylpyrrolidone and magnesium stearate. In some embodiments, the one or more pharmaceutically acceptable excipients is lactose monohydrate and the oral dosage form further comprises cross-linked polyvinylpyrrolidone and magnesium stearate.

In some embodiments, the oral dosage form is a tablet or capsule. In some embodiments, the oral dosage form is a tablet. In some embodiments, the oral dosage form is a capsule. In some embodiments, the oral dosage form is a sachet. In some embodiments, the oral dosage form is a powder in a packet.

In some embodiments, the oral dosage form comprises about 1 mg to about 40 mg of the crystalline dihydrate form of the compound of Formula (I). In some embodiments, the oral dosage form comprises about 5 mg to about 35 mg of the crystalline dihydrate form of the compound of Formula (I). In some embodiments, the oral dosage form comprises about 10 mg to about 35 mg of the crystalline dihydrate form of the compound of Formula (I). In some embodiments, the oral dosage form comprises about 0.5 mg to about 5 mg, about 6 mg to about 14 mg, about 11 mg to about 19 mg, about 17 mg to about 25 mg, or about 28 mg to about 36 mg of the crystalline dihydrate form of the compound of Formula (I). In some embodiments, the oral dosage form comprises about 1 mg to about 4 mg, about 8 mg to about 12 mg, about 13 mg to about 17 mg, about 19 mg to about 23 mg, or about 30 mg to about 34 mg of the crystalline dihydrate form of the compound of Formula (I). In some embodiments, the oral dosage form comprises about 2.2 mg, about 10.8 mg, about 15.2 mg, about 21.7 mg, or about 32.5 mg of the crystalline dihydrate form of the compound of Formula (I). In some embodiments, the crystalline dihydrate form of the compound of Formula (I) is present in an amount of about 2.2 mg. In some embodiments, the crystalline dihydrate form of the compound of Formula (I) is present in an amount of about 10.8 mg. In some embodiments, the crystalline dihydrate form of the compound of Formula (I) is present in an amount of about 15.2 mg. In some embodiments, the crystalline dihydrate form of the compound of Formula (I) is present in an amount of about 21.7 mg. In some embodiments, the crystalline dihydrate form of the compound of Formula (I) is present in an amount of about 32.5 mg.

In some embodiments, the oral dosage form consists essentially of about 1 mg to about 40 mg of the crystalline dihydrate form of the compound of Formula (I). In some embodiments, the oral dosage form consists essentially of about 5 mg to about 35 mg of the crystalline dihydrate form of the compound of Formula (I). In some embodiments, the oral dosage form consists essentially of about 10 mg to about 35 mg of the crystalline dihydrate form of the compound of Formula (I). In some embodiments, the oral dosage form consists essentially of about 0.5 mg to about 5 mg, about 6 mg to about 14 mg, about 11 mg to about 19 mg, about 17 mg to about 25 mg, or about 28 mg to about 36 mg of the crystalline dihydrate form of the compound of Formula (I). In some embodiments, the oral dosage form consists essentially of about 1 mg to about 4 mg, about 8 mg to about 12 mg, about 13 mg to about 17 mg, about 19 mg to about 23 mg, or about 30 mg to about 34 mg of the crystalline dihydrate form of the compound of Formula (I). In some embodiments, the oral dosage form consists essentially of about 2.2 mg, about 10.8 mg, about 15.2 mg, about 21.7 mg, or about 32.5 mg of the crystalline dihydrate form of the compound of Formula (I). In some embodiments, the crystalline dihydrate form of the compound of Formula (I) is present in an amount of about 2.2 mg. In some embodiments, the crystalline dihydrate form of the compound of Formula (I) is present in an amount of about 10.8 mg. In some embodiments, the crystalline dihydrate form of the compound of Formula (I) is present in an amount of about 15.2 mg. In some embodiments, the crystalline dihydrate form of the compound of Formula (I) is present in an amount of about 21.7 mg. In some embodiments, the crystalline dihydrate form of the compound of Formula (I) is present in an amount of about 32.5 mg.

Also provided herein, in some embodiments, is a process of preparing a pharmaceutically acceptable capsule, the pharmaceutically acceptable capsule comprising:

(a) about 1% to about 70%, based on the total weight of the pharmaceutically acceptable capsule, of a compound of Formula (I):

Formula (I)

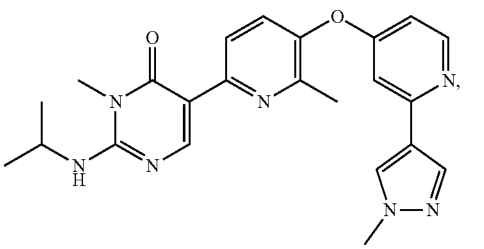

wherein the compound is present in the pharmaceutically acceptable capsule as a free base, or a pharmaceutically acceptable salt of the compound and wherein the free base or pharmaceutically acceptable salt is in anhydrous or hydrate form, and one or more pharmaceutically acceptable excipients, wherein the one or more pharmaceutically acceptable excipients comprise:

(b) about 20% by weight to about 97% by weight of one or more fillers, based on the total weight of the pharmaceutically acceptable capsule;

(c) about 1% by weight to about 20% by weight of one or more disintegrants, based on the total weight of the pharmaceutically acceptable capsule; and (d) about 0.1% by weight to about 10% by weight of one or more lubricants, based on the total weight of the pharmaceutically acceptable capsule;

the process comprising:

(i) blending the compound represented by Formula (I) with the one or more fillers and one or more disintegrants to produce a first blend;

(ii) blending the first blend with the one or more lubricants to form a second blend; and (iii) dispensing the second blend into an empty pharmaceutically acceptable capsule, thereby forming the pharmaceutically acceptable capsule.

Also provided herein, in some embodiments, is a process of preparing a pharmaceutically acceptable capsule, the pharmaceutically acceptable capsule consisting essentially of:

(a) about 1% to about 70%, based on the total weight of the pharmaceutically acceptable capsule, of a compound of Formula (I):

Formula (I)

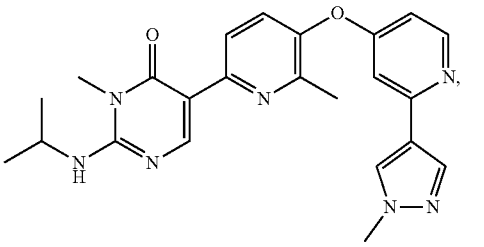

and one or more pharmaceutically acceptable excipients, wherein the one or more pharmaceutically acceptable excipients comprise:

(b) about 20% by weight to about 97% by weight of one or more fillers, based on the total weight of the pharmaceutically acceptable capsule;

(c) about 1% by weight to about 20% by weight of one or more disintegrants, based on the total weight of the pharmaceutically acceptable capsule; and (d) about 0.1% by weight to about 10% by weight of one or more lubricants, based on the total weight of the pharmaceutically acceptable capsule;

the process comprising:

(i) blending the compound represented by Formula (I) with the one or more fillers and one or more disintegrants to produce a first blend;

(ii) blending the first blend with the one or more lubricants to form a second blend; and (iii) dispensing the second blend into an empty pharmaceutically acceptable capsule, thereby forming the pharmaceutically acceptable capsule.

Also provided herein, in some embodiments, is a process of preparing a pharmaceutically acceptable capsule, the pharmaceutically acceptable capsule comprising:

(a) about 1% to about 70%, based on the total weight of the pharmaceutically acceptable capsule, of a compound of Formula (I):

Formula (I)

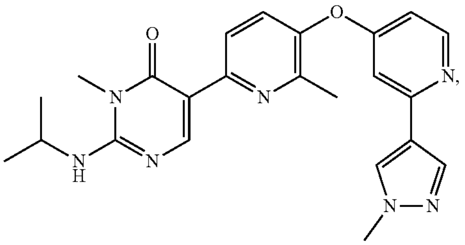

and one or more pharmaceutically acceptable excipients, wherein the one or more pharmaceutically acceptable excipients comprise:

(b) about 20% by weight to about 97% by weight of one or more fillers, based on the total weight of the pharmaceutically acceptable capsule;

(c) about 1% by weight to about 20% by weight of one or more disintegrants, based on the total weight of the pharmaceutically acceptable capsule; and (d) about 0.1% by weight to about 10% by weight of one or more lubricants, based on the total weight of the pharmaceutically acceptable capsule;

the process comprising:

(i) blending the compound represented by Formula (I) with the one or more fillers to produce a first blend;

(ii) blending the first blend with the one or more disintegrants to form a second blend;

(iii) blending the second blend with the one or more lubricants to form a third blend; and (iv) dispensing the third blend into an empty pharmaceutically acceptable capsule, thereby forming the pharmaceutically acceptable capsule.

Also provided herein, in some embodiments, is a process of preparing a pharmaceutically acceptable capsule, the pharmaceutically acceptable capsule consisting essentially of:

(a) about 1% to about 70%, based on the total weight of the pharmaceutically acceptable capsule, of a compound of Formula (I):

Formula (I)

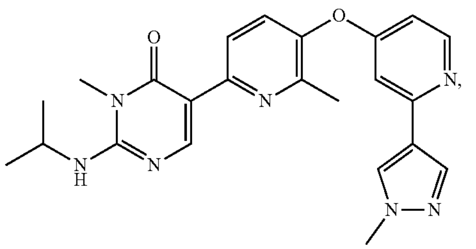

and one or more pharmaceutically acceptable excipients, wherein the one or more pharmaceutically acceptable excipients comprise:

(b) about 20% by weight to about 97% by weight of one or more fillers, based on the total weight of the pharmaceutically acceptable capsule;

(c) about 1% by weight to about 20% by weight of one or more disintegrants, based on the total weight of the pharmaceutically acceptable capsule; and (d) about 0.1% by weight to about 10% by weight of one or more lubricants, based on the total weight of the pharmaceutically acceptable capsule;

the process comprising:

(i) blending the compound represented by Formula (I) with the one or more fillers to produce a first blend;

(ii) blending the first blend with the one or more disintegrants to form a second blend;

(iii) blending the second blend with the one or more lubricants to form a third blend; and (iv) dispensing the third blend into an empty pharmaceutically acceptable capsule, thereby forming the pharmaceutically acceptable capsule.

Also provided herein, in some embodiments, is a process of preparing a pharmaceutically acceptable capsule, the pharmaceutically acceptable capsule comprising:

(a) about 1% to about 70%, based on the total weight of the pharmaceutically acceptable capsule, of a compound of Formula (I):

Formula (I)

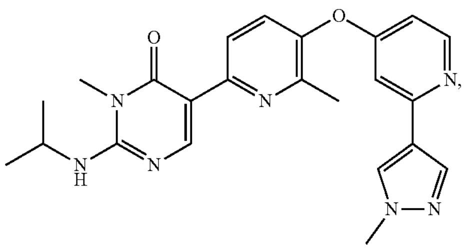

and one or more pharmaceutically acceptable excipients, wherein the one or more pharmaceutically acceptable excipients comprise:

(b) about 20% by weight to about 97% by weight of one or more fillers, based on the total weight of the pharmaceutically acceptable capsule;

(c) about 1% by weight to about 20% by weight of one or more disintegrants, based on the total weight of the pharmaceutically acceptable capsule; and (d) about 0.1% by weight to about 10% by weight of one or more lubricants, based on the total weight of the pharmaceutically acceptable capsule;

the process comprising:

(i) blending the compound represented by Formula (I) with the one or more fillers to produce a first blend;

(ii) blending the first blend with a second blend comprising one or more disintegrants and one or more fillers and optionally a third blend comprising one or more fillers to form a fourth blend;

(iii) blending the fourth blend with the one or more lubricants to form a fifth blend; and (iv) dispensing the fifth blend into an empty pharmaceutically acceptable capsule, thereby forming the pharmaceutically acceptable capsule.

Also provided herein, in some embodiments, is a process of preparing a pharmaceutically acceptable capsule, the pharmaceutically acceptable capsule consisting essentially of:

(a) about 1% to about 70%, based on the total weight of the pharmaceutically acceptable capsule, of a compound of Formula (I):

Formula (I)

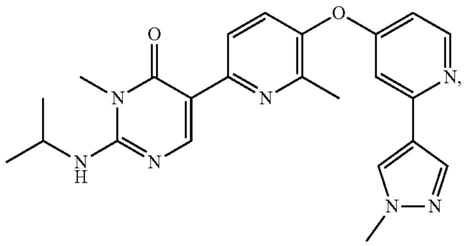

and one or more pharmaceutically acceptable excipients, wherein the one or more pharmaceutically acceptable excipients comprise:

(b) about 20% by weight to about 97% by weight of one or more fillers, based on the total weight of the pharmaceutically acceptable capsule;

(c) about 1% by weight to about 20% by weight of one or more disintegrants, based on the total weight of the pharmaceutically acceptable capsule; and (d) about 0.1% by weight to about 10% by weight of one or more lubricants, based on the total weight of the pharmaceutically acceptable capsule;

the process comprising:

(i) blending the compound represented by Formula (I) with the one or more fillers to produce a first blend;

(ii) blending the first blend with a second blend comprising one or more disintegrants and one or more fillers and optionally a third blend comprising one or more fillers to form a fourth blend;

(iii) blending the fourth blend with the one or more lubricants to form a fifth blend; and (iv) dispensing the fifth blend into an empty pharmaceutically acceptable capsule, thereby forming the pharmaceutically acceptable capsule.

In some embodiments, the pharmaceutically acceptable capsule comprises about 1% by weight to about 60% by weight, based on the total weight of the pharmaceutically acceptable capsule, of a compound of Formula (I). In some embodiments, the pharmaceutically acceptable capsule comprises about 1% by weight to about 50% by weight, based on the total weight of the pharmaceutically acceptable capsule, of a compound of Formula (I). In some embodiments, the pharmaceutically acceptable capsule comprises about 1% by weight to about 40% by weight, based on the total weight of the pharmaceutically acceptable capsule, of a compound of Formula (I). In some embodiments, the pharmaceutically acceptable capsule comprises about 1% by weight to about 30% by weight, based on the total weight of the pharmaceutically acceptable capsule, of a compound of Formula (I). In some embodiments, the pharmaceutically acceptable capsule comprises about 1% by weight to about 20% by weight, based on the total weight of the pharmaceutically acceptable capsule, of a compound of Formula (I).

In some embodiments, the pharmaceutically acceptable capsule consists essentially of about 1% by weight to about 60% by weight, based on the total weight of the pharmaceutically acceptable capsule, of a compound of Formula (I). In some embodiments, the pharmaceutically acceptable capsule consists essentially of about 1% by weight to about 50% by weight, based on the total weight of the pharmaceutically acceptable capsule, of a compound of Formula (I). In some embodiments, the pharmaceutically acceptable capsule consists essentially of about 1% by weight to about 40% by weight, based on the total weight of the pharmaceutically acceptable capsule, of a compound of Formula (I). In some embodiments, the pharmaceutically acceptable capsule consists essentially of about 1% by weight to about 30% by weight, based on the total weight of the pharmaceutically acceptable capsule, of a compound of Formula (I). In some embodiments, the pharmaceutically acceptable capsule consists essentially of about 1% by weight to about 20% by weight, based on the total weight of the pharmaceutically acceptable capsule, of a compound of Formula (I).

In some embodiments, the pharmaceutically acceptable capsule comprises about 1% by weight to about 70% by weight of the compound of Formula (I) based on the total weight of the pharmaceutically acceptable capsule. In some embodiments, the pharmaceutically acceptable capsule comprises about 1% by weight to about 65% by weight of the compound of Formula (I) based on the total weight of the pharmaceutically acceptable capsule. In some embodiments, the pharmaceutically acceptable capsule comprises about 1% by weight to about 60% by weight of the compound of Formula (I) based on the total weight of the pharmaceutically acceptable capsule. In some embodiments, the pharmaceutically acceptable capsule comprises about 1% by weight to about 55% by weight of the compound of Formula (I) based on the total weight of the pharmaceutically acceptable capsule. In some embodiments, the pharmaceutically acceptable capsule comprises about 1% by weight to about 50% by weight of the compound of Formula (I) based on the total weight of the pharmaceutically acceptable capsule. In some embodiments, the pharmaceutically acceptable capsule comprises about 1% by weight to about 45% by weight of the compound of Formula (I) based on the total weight of the pharmaceutically acceptable capsule. In some embodiments, the pharmaceutically acceptable capsule comprises about 1% by weight to about 40% by weight of the compound of Formula (I) based on the total weight of the pharmaceutically acceptable capsule. In some embodiments, the pharmaceutically acceptable capsule comprises about 1% by weight to about 35% by weight of the compound of Formula (I) based on the total weight of the pharmaceutically acceptable capsule. In some embodiments, the pharmaceutically acceptable capsule comprises about 1% by weight to about 30% by weight of the compound of Formula (I) based on the total weight of the pharmaceutically acceptable capsule. In some embodiments, the pharmaceutically acceptable capsule comprises about 1% by weight to about 25% by weight of the compound of Formula (I) based on the total weight of the pharmaceutically acceptable capsule. In some embodiments, the pharmaceutically acceptable capsule comprises about 1% by weight to about 20% by weight of the compound of Formula (I) based on the total weight of the pharmaceutically acceptable capsule. In some embodiments, the pharmaceutically acceptable capsule comprises about 1% by weight to about 15% by weight of the compound of Formula (I) based on the total weight of the pharmaceutically acceptable capsule. In some embodiments, the pharmaceutically acceptable capsule comprises about 1% by weight to about 10% by weight of the compound of Formula (I) based on the total weight of the pharmaceutically acceptable capsule.

In some embodiments, the pharmaceutically acceptable capsule consists essentially of about 1% by weight to about 70% by weight of the compound of Formula (I) based on the total weight of the pharmaceutically acceptable capsule. In some embodiments, the pharmaceutically acceptable capsule consists essentially of about 1% by weight to about 65% by weight of the compound of Formula (I) based on the total weight of the pharmaceutically acceptable capsule. In some embodiments, the pharmaceutically acceptable capsule consists essentially of about 1% by weight to about 60% by weight of the compound of Formula (I) based on the total weight of the pharmaceutically acceptable capsule. In some embodiments, the pharmaceutically acceptable capsule consists essentially of about 1% by weight to about 55% by weight of the compound of Formula (I) based on the total weight of the pharmaceutically acceptable capsule. In some embodiments, the pharmaceutically acceptable capsule consists essentially of about 1% by weight to about 50% by weight of the compound of Formula (I) based on the total weight of the pharmaceutically acceptable capsule. In some embodiments, the pharmaceutically acceptable capsule consists essentially of about 1% by weight to about 45% by weight of the compound of Formula (I) based on the total weight of the pharmaceutically acceptable capsule. In some embodiments, the pharmaceutically acceptable capsule consists essentially of about 1% by weight to about 40% by weight of the compound of Formula (I) based on the total weight of the pharmaceutically acceptable capsule. In some embodiments, the pharmaceutically acceptable capsule consists essentially of about 1% by weight to about 35% by weight of the compound of Formula (I) based on the total weight of the pharmaceutically acceptable capsule. In some embodiments, the pharmaceutically acceptable capsule consists essentially of about 1% by weight to about 30% by weight of the compound of Formula (I) based on the total weight of the pharmaceutically acceptable capsule. In some embodiments, the pharmaceutically acceptable capsule consists essentially of about 1% by weight to about 25% by weight of the compound of Formula (I) based on the total weight of the pharmaceutically acceptable capsule. In some embodiments, the pharmaceutically acceptable capsule consists essentially of about 1% by weight to about 20% by weight of the compound of Formula (I) based on the total weight of the pharmaceutically acceptable capsule. In some embodiments, the pharmaceutically acceptable capsule consists essentially of about 1% by weight to about 15% by weight of the compound of Formula (I) based on the total weight of the pharmaceutically acceptable capsule. In some embodiments, the pharmaceutically acceptable capsule consists essentially of about 1% by weight to about 10% by weight of the compound of Formula (I) based on the total weight of the pharmaceutically acceptable capsule.

In some embodiments, the pharmaceutically acceptable capsule comprises about 5% by weight to about 30% by weight of the compound of Formula (I) based on the total weight of the pharmaceutically acceptable capsule. In some embodiments, the pharmaceutically acceptable capsule comprises about 5% by weight to about 25% by weight of the compound of Formula (I) based on the total weight of the pharmaceutically acceptable capsule. In some embodiments, the pharmaceutically acceptable capsule comprises about 5% by weight to about 20% by weight of the compound of Formula (I) based on the total weight of the pharmaceutically acceptable capsule. In some embodiments, the pharmaceutically acceptable capsule comprises about 5% by weight to about 15% by weight of the compound of Formula (I) based on the total weight of the pharmaceutically acceptable capsule. In some embodiments, the pharmaceutically acceptable capsule comprises about 5% by weight to about 10% by weight of the compound of Formula (I) based on the total weight of the pharmaceutically acceptable capsule.

In some embodiments, the pharmaceutically acceptable capsule consists essentially of about 5% by weight to about 30% by weight of the compound of Formula (I) based on the total weight of the pharmaceutically acceptable capsule. In some embodiments, the pharmaceutically acceptable capsule consists essentially of about 5% by weight to about 25% by weight of the compound of Formula (I) based on the total weight of the pharmaceutically acceptable capsule. In some embodiments, the pharmaceutically acceptable capsule consists essentially of about 5% by weight to about 20% by weight of the compound of Formula (I) based on the total weight of the pharmaceutically acceptable capsule. In some embodiments, the pharmaceutically acceptable capsule consists essentially of about 5% by weight to about 15% by weight of the compound of Formula (I) based on the total weight of the pharmaceutically acceptable capsule. In some embodiments, the pharmaceutically acceptable capsule consists essentially of about 5% by weight to about 10% by weight of the compound of Formula (I) based on the total weight of the pharmaceutically acceptable capsule.

In some embodiments, the pharmaceutically acceptable capsule comprises about 10% to about 30% of the compound of Formula (I) based on the total weight of the pharmaceutically acceptable capsule. In some embodiments, the pharmaceutically acceptable capsule comprises about 10% to about 25% of the compound of Formula (I) based on the total weight of the pharmaceutically acceptable capsule. In some embodiments, the pharmaceutically acceptable capsule comprises about 10% to about 20% of the compound of Formula (I) based on the total weight of the pharmaceutically acceptable capsule. In some embodiments, the pharmaceutically acceptable capsule comprises about 10% by weight to about 15% by weight of the compound of Formula (I) based on the total weight of the pharmaceutically acceptable capsule.

In some embodiments, the pharmaceutically acceptable capsule consists essentially of about 10% to about 30% of the compound of Formula (I) based on the total weight of the pharmaceutically acceptable capsule. In some embodiments, the pharmaceutically acceptable capsule consists essentially of about 10% to about 25% of the compound of Formula (I) based on the total weight of the pharmaceutically acceptable capsule. In some embodiments, the pharmaceutically acceptable capsule consists essentially of about 10% to about 20% of the compound of Formula (I) based on the total weight of the pharmaceutically acceptable capsule. In some embodiments, the pharmaceutically acceptable capsule consists essentially of about 10% by weight to about 15% by weight of the compound of Formula (I) based on the total weight of the pharmaceutically acceptable capsule.

In some embodiments, the pharmaceutically acceptable capsule comprises about 1% by weight to about 30% by weight of the compound of Formula (I) based on the total weight of the pharmaceutically acceptable capsule. In some embodiments, the pharmaceutically acceptable capsule comprises about 1% by weight to about 10% by weight of the compound of Formula (I) based on the total weight of the pharmaceutically acceptable capsule. In some embodiments, the pharmaceutically acceptable capsule comprises about 10% to about 20% of the compound of Formula (I) based on the total weight of the pharmaceutically acceptable capsule. In some embodiments, the pharmaceutically acceptable capsule comprises about 10% by weight to about 15% by weight of the compound of Formula (I) based on the total weight of the pharmaceutically acceptable capsule.

In some embodiments, the pharmaceutically acceptable capsule consists essentially of about 1% by weight to about 30% by weight of the compound of Formula (I) based on the total weight of the pharmaceutically acceptable capsule. In some embodiments, the pharmaceutically acceptable capsule consists essentially of about 1% by weight to about 10% by weight of the compound of Formula (I) based on the total weight of the pharmaceutically acceptable capsule. In some embodiments, the pharmaceutically acceptable capsule consists essentially of about 10% to about 20% of the compound of Formula (I) based on the total weight of the pharmaceutically acceptable capsule. In some embodiments, the pharmaceutically acceptable capsule consists essentially of about 10% by weight to about 15% by weight of the compound of Formula (I) based on the total weight of the pharmaceutically acceptable capsule.

In some embodiments, the one or more pharmaceutically acceptable excipients comprise about 20% by weight to about 90% by weight of one or more fillers based on the total weight of the pharmaceutically acceptable capsule. In some embodiments, the one or more pharmaceutically acceptable excipients comprise about 20% by weight to about 85% by weight of one or more fillers based on the total weight of the pharmaceutically acceptable capsule. In some embodiments, the one or more pharmaceutically acceptable excipients comprise about 20% by weight to about 80% by weight of one or more fillers based on the total weight of the pharmaceutically acceptable capsule. In some embodiments, the one or more pharmaceutically acceptable excipients comprise about 20% by weight to about 75% by weight of one or more fillers based on the total weight of the pharmaceutically acceptable capsule. In some embodiments, the one or more pharmaceutically acceptable excipients comprise about 20% by weight to about 70% by weight of one or more fillers based on the total weight of the pharmaceutically acceptable capsule. In some embodiments, the one or more pharmaceutically acceptable excipients comprise about 20% by weight to about 65% by weight of one or more fillers based on the total weight of the pharmaceutically acceptable capsule. In some embodiments, the one or more pharmaceutically acceptable excipients comprise about 20% by weight to about 60% by weight of one or more fillers based on the total weight of the pharmaceutically acceptable capsule. In some embodiments, the one or more pharmaceutically acceptable excipients comprise about 20% by weight to about 55% by weight of one or more fillers based on the total weight of the pharmaceutically acceptable capsule. In some embodiments, the one or more pharmaceutically acceptable excipients comprise about 20% by weight to about 50% by weight of one or more fillers based on the total weight of the pharmaceutically acceptable capsule. In some embodiments, the one or more pharmaceutically acceptable excipients comprise about 20% by weight to about 45% by weight of one or more fillers based on the total weight of the pharmaceutically acceptable capsule. In some embodiments, the one or more pharmaceutically acceptable excipients comprise about 20% by weight to about 40% by weight of one or more fillers based on the total weight of the pharmaceutically acceptable capsule. In some embodiments, the one or more pharmaceutically acceptable excipients comprise about 20% by weight to about 35% by weight of one or more fillers based on the total weight of the pharmaceutically acceptable capsule. In some embodiments, the one or more pharmaceutically acceptable excipients comprise about 20% by weight to about 30% by weight of one or more fillers based on the total weight of the pharmaceutically acceptable capsule. In some embodiments, the one or more pharmaceutically acceptable excipients comprise about 20% by weight to about 25% by weight of one or more fillers based on the total weight of the pharmaceutically acceptable capsule.

In some embodiments, the one or more pharmaceutically acceptable excipients comprise about 30% by weight to about 90% by weight of one or more fillers based on the total weight of the pharmaceutically acceptable capsule. In some embodiments, the one or more pharmaceutically acceptable excipients comprise about 30% by weight to about 80% by weight of one or more fillers based on the total weight of the pharmaceutically acceptable capsule. In some embodiments, the one or more pharmaceutically acceptable excipients comprise about 30% by weight to about 70% by weight of one or more fillers based on the total weight of the pharmaceutically acceptable capsule. In some embodiments, the one or more pharmaceutically acceptable excipients comprise about 30% by weight to about 60% by weight of one or more fillers based on the total weight of the pharmaceutically acceptable capsule. In some embodiments, the one or more pharmaceutically acceptable excipients comprise about 30% by weight to about 50% by weight of one or more fillers based on the total weight of the pharmaceutically acceptable capsule. In some embodiments, the one or more pharmaceutically acceptable excipients comprise about 30% by weight to about 40% by weight of one or more fillers based on the total weight of the pharmaceutically acceptable capsule.

In some embodiments, the one or more pharmaceutically acceptable excipients comprise about 40% by weight to about 90% by weight of one or more fillers based on the total weight of the pharmaceutically acceptable capsule. In some embodiments, the one or more pharmaceutically acceptable excipients comprise about 40% by weight to about 80% by weight of one or more fillers based on the total weight of the pharmaceutically acceptable capsule. In some embodiments, the one or more pharmaceutically acceptable excipients comprise about 40% by weight to about 70% by weight of one or more fillers based on the total weight of the pharmaceutically acceptable capsule. In some embodiments, the one or more pharmaceutically acceptable excipients comprise about 40% by weight to about 60% by weight of one or more fillers based on the total weight of the pharmaceutically acceptable capsule. In some embodiments, the one or more pharmaceutically acceptable excipients comprise about 40% by weight to about 50% by weight of one or more fillers based on the total weight of the pharmaceutically acceptable capsule.

In some embodiments, the one or more pharmaceutically acceptable excipients comprise about 50% by weight to about 90% by weight of one or more fillers based on the total weight of the pharmaceutically acceptable capsule. In some embodiments, the one or more pharmaceutically acceptable excipients comprise about 50% by weight to about 80% by weight of one or more fillers based on the total weight of the pharmaceutically acceptable capsule. In some embodiments, the one or more pharmaceutically acceptable excipients comprise about 50% by weight to about 70% by weight of one or more fillers based on the total weight of the pharmaceutically acceptable capsule. In some embodiments, the one or more pharmaceutically acceptable excipients comprise about 50% by weight to about 60% by weight of one or more fillers based on the total weight of the pharmaceutically acceptable capsule.

In some embodiments, the one or more pharmaceutically acceptable excipients comprise about 60% by weight to about 90% by weight of one or more fillers based on the total weight of the pharmaceutically acceptable capsule. In some embodiments, the one or more pharmaceutically acceptable excipients comprise about 60% by weight to about 80% by weight of one or more fillers based on the total weight of the pharmaceutically acceptable capsule. In some embodiments, the one or more pharmaceutically acceptable excipients comprise about 60% by weight to about 70% by weight of one or more fillers based on the total weight of the pharmaceutically acceptable capsule.

In some embodiments, the one or more pharmaceutically acceptable excipients comprise about 70% by weight to about 90% by weight of one or more fillers based on the total weight of the pharmaceutically acceptable capsule. In some embodiments, the one or more pharmaceutically acceptable excipients comprise about 70% by weight to about 80% by weight of one or more fillers based on the total weight of the pharmaceutically acceptable capsule.

In some embodiments, the one or more pharmaceutically acceptable excipients comprise about 80% by weight to about 90% by weight of one or more fillers based on the total weight of the pharmaceutically acceptable capsule.

In some embodiments, the one or more pharmaceutically acceptable excipients comprise about 1% by weight to about 20% by weight of one or more disintegrants based on the total weight of the pharmaceutically acceptable capsule. In some embodiments, the one or more pharmaceutically acceptable excipients comprise about 1% by weight to about 15% by weight of one or more disintegrants based on the total weight of the pharmaceutically acceptable capsule. In some embodiments, the one or more pharmaceutically acceptable excipients comprise about 1% by weight to about 14% by weight of one or more disintegrants based on the total weight of the pharmaceutically acceptable capsule. In some embodiments, the one or more pharmaceutically acceptable excipients comprise about 1% by weight to about 13% by weight of one or more disintegrants based on the total weight of the pharmaceutically acceptable capsule. In some embodiments, the one or more pharmaceutically acceptable excipients comprise about 1% by weight to about 12% by weight of one or more disintegrants based on the total weight of the pharmaceutically acceptable capsule. In some embodiments, the one or more pharmaceutically acceptable excipients comprise about 1% by weight to about 11% by weight of one or more disintegrants based on the total weight of the pharmaceutically acceptable capsule. In some embodiments, the one or more pharmaceutically acceptable excipients comprise about 1% by weight to about 10% by weight of one or more disintegrants based on the total weight of the pharmaceutically acceptable capsule. In some embodiments, the one or more pharmaceutically acceptable excipients comprise about 1% by weight to about 9% by weight of one or more disintegrants based on the total weight of the pharmaceutically acceptable capsule. In some embodiments, the one or more pharmaceutically acceptable excipients comprise about 1% by weight to about 8% by weight of one or more disintegrants based on the total weight of the pharmaceutically acceptable capsule. In some embodiments, the one or more pharmaceutically acceptable excipients comprise about 1% by weight to about 7% by weight of one or more disintegrants based on the total weight of the pharmaceutically acceptable capsule. In some embodiments, the one or more pharmaceutically acceptable excipients comprise about 1% by weight to about 6% by weight of one or more disintegrants based on the total weight of the pharmaceutically acceptable capsule. In some embodiments, the one or more pharmaceutically acceptable excipients comprise about 1% by weight to about 5% by weight of one or more disintegrants based on the total weight of the pharmaceutically acceptable capsule. In some embodiments, the one or more pharmaceutically acceptable excipients comprise about 1% by weight to about 4% by weight of one or more disintegrants based on the total weight of the pharmaceutically acceptable capsule. In some embodiments, the one or more pharmaceutically acceptable excipients comprise about 1% by weight to about 3% by weight of one or more disintegrants based on the total weight of the pharmaceutically acceptable capsule.

In some embodiments, the one or more pharmaceutically acceptable excipients comprise about 1% by weight of one or more disintegrants based on the total weight of the pharmaceutically acceptable capsule. In some embodiments, the one or more pharmaceutically acceptable excipients comprise about 2% by weight of one or more disintegrants based on the total weight of the pharmaceutically acceptable capsule. In some embodiments, the one or more pharmaceutically acceptable excipients comprise about 3% by weight of one or more disintegrants based on the total weight of the pharmaceutically acceptable capsule. In some embodiments, the one or more pharmaceutically acceptable excipients comprise about 4% by weight of one or more disintegrants based on the total weight of the pharmaceutically acceptable capsule. In some embodiments, the one or more pharmaceutically acceptable excipients comprise about 5% by weight of one or more disintegrants based on the total weight of the pharmaceutically acceptable capsule. In some embodiments, the one or more pharmaceutically acceptable excipients comprise about 6% by weight of one or more disintegrants based on the total weight of the pharmaceutically acceptable capsule. In some embodiments, the one or more pharmaceutically acceptable excipients comprise about 7% by weight of one or more disintegrants based on the total weight of the pharmaceutically acceptable capsule. In some embodiments, the one or more pharmaceutically acceptable excipients comprise about 8% by weight of one or more disintegrants based on the total weight of the pharmaceutically acceptable capsule. In some embodiments, the one or more pharmaceutically acceptable excipients comprise about 9% by weight of one or more disintegrants based on the total weight of the pharmaceutically acceptable capsule. In some embodiments, the one or more pharmaceutically acceptable excipients comprise about 10% by weight of one or more disintegrants based on the total weight of the pharmaceutically acceptable capsule. In some embodiments, the one or more pharmaceutically acceptable excipients comprise about 11% by weight of one or more disintegrants based on the total weight of the pharmaceutically acceptable capsule. In some embodiments, the one or more pharmaceutically acceptable excipients comprise about 12% by weight of one or more disintegrants based on the total weight of the pharmaceutically acceptable capsule. In some embodiments, the one or more pharmaceutically acceptable excipients comprise about 13% by weight of one or more disintegrants based on the total weight of the pharmaceutically acceptable capsule. In some embodiments, the one or more pharmaceutically acceptable excipients comprise about 14% by weight of one or more disintegrants based on the total weight of the pharmaceutically acceptable capsule. In some embodiments, the one or more pharmaceutically acceptable excipients comprise about 15% by weight of one or more disintegrants based on the total weight of the pharmaceutically acceptable capsule.

In some embodiments, the one or more pharmaceutically acceptable excipients comprise about 0.1% by weight to about 10% by weight of one or more lubricants based on the total weight of the pharmaceutically acceptable capsule. In some embodiments, the one or more pharmaceutically acceptable excipients comprise about 0.1% by weight to about 9% by weight of one or more lubricants based on the total weight of the pharmaceutically acceptable capsule. In some embodiments, the one or more pharmaceutically acceptable excipients comprise about 0.1% by weight to about 8% by weight of one or more lubricants based on the total weight of the pharmaceutically acceptable capsule. In some embodiments, the one or more pharmaceutically acceptable excipients comprise about 0.1% by weight to about 7% by weight of one or more lubricants based on the total weight of the pharmaceutically acceptable capsule. In some embodiments, the one or more pharmaceutically acceptable excipients comprise about 0.1% by weight to about 6% by weight of one or more lubricants based on the total weight of the pharmaceutically acceptable capsule. In some embodiments, the one or more pharmaceutically acceptable excipients comprise about 0.1% by weight to about 5% by weight of one or more lubricants based on the total weight of the pharmaceutically acceptable capsule. In some embodiments, the one or more pharmaceutically acceptable excipients comprise about 0.1% by weight to about 4% by weight of one or more lubricants based on the total weight of the pharmaceutically acceptable capsule. In some embodiments, the one or more pharmaceutically acceptable excipients comprise about 0.1% by weight to about 3% by weight of one or more lubricants based on the total weight of the pharmaceutically acceptable capsule. In some embodiments, the one or more pharmaceutically acceptable excipients comprise about 0.1% by weight to about 2% by weight of one or more lubricants based on the total weight of the pharmaceutically acceptable capsule.

In some embodiments, the one or more pharmaceutically acceptable excipients comprise about 0.1% by weight to about 1.9% by weight of one or more lubricants based on the total weight of the pharmaceutically acceptable capsule. In some embodiments, the one or more pharmaceutically acceptable excipients comprise about 0.1% by weight to about 1.8% by weight of one or more lubricants based on the total weight of the pharmaceutically acceptable capsule. In some embodiments, the one or more pharmaceutically acceptable excipients comprise about 0.1% by weight to about 1.7% by weight of one or more lubricants based on the total weight of the pharmaceutically acceptable capsule. In some embodiments, the one or more pharmaceutically acceptable excipients comprise about 0.1% by weight to about 1.6% by weight of one or more lubricants based on the total weight of the pharmaceutically acceptable capsule. In some embodiments, the one or more pharmaceutically acceptable excipients comprise about 0.1% by weight to about 1.5% by weight of one or more lubricants based on the total weight of the pharmaceutically acceptable capsule. In some embodiments, the one or more pharmaceutically acceptable excipients comprise about 0.1% by weight to about 1.4% by weight of one or more lubricants based on the total weight of the pharmaceutically acceptable capsule. In some embodiments, the one or more pharmaceutically acceptable excipients comprise about 0.1% by weight to about 1.3% by weight of one or more lubricants based on the total weight of the pharmaceutically acceptable capsule. In some embodiments, the one or more pharmaceutically acceptable excipients comprise about 0.1% by weight to about 1.2% by weight of one or more lubricants based on the total weight of the pharmaceutically acceptable capsule. In some embodiments, the one or more pharmaceutically acceptable excipients comprise about 0.1% by weight to about 1.1% by weight of one or more lubricants based on the total weight of the pharmaceutically acceptable capsule. In some embodiments, the one or more pharmaceutically acceptable excipients comprise about 0.1% by weight to about 1.0% by weight of one or more lubricants based on the total weight of the pharmaceutically acceptable capsule. In some embodiments, the one or more pharmaceutically acceptable excipients comprise about 0.1% by weight to about 0.9% by weight of one or more lubricants based on the total weight of the pharmaceutically acceptable capsule. In some embodiments, the one or more pharmaceutically acceptable excipients comprise about 0.1% by weight to about 0.8% by weight of one or more lubricants based on the total weight of the pharmaceutically acceptable capsule. In some embodiments, the one or more pharmaceutically acceptable excipients comprise about 0.1% by weight to about 0.7% by weight of one or more lubricants based on the total weight of the pharmaceutically acceptable capsule. In some embodiments, the one or more pharmaceutically acceptable excipients comprise about 0.1% by weight to about 0.6% by weight of one or more lubricants based on the total weight of the pharmaceutically acceptable capsule. In some embodiments, the one or more pharmaceutically acceptable excipients comprise about 0.1% by weight to about 0.5% by weight of one or more lubricants based on the total weight of the pharmaceutically acceptable capsule. In some embodiments, the one or more pharmaceutically acceptable excipients comprise about 0.1% by weight to about 0.4% by weight of one or more lubricants based on the total weight of the pharmaceutically acceptable capsule. In some embodiments, the one or more pharmaceutically acceptable excipients comprise about 0.1% by weight to about 0.3% by weight of one or more lubricants based on the total weight of the pharmaceutically acceptable capsule. In some embodiments, the one or more pharmaceutically acceptable excipients comprise about 0.1% by weight to about 0.2% by weight of one or more lubricants based on the total weight of the pharmaceutically acceptable capsule.

In some embodiments, the one or more pharmaceutically acceptable excipients comprise about 0.1% by weight of one or more lubricants based on the total weight of the pharmaceutically acceptable capsule. In some embodiments, the one or more pharmaceutically acceptable excipients comprise about 0.2% by weight of one or more lubricants based on the total weight of the pharmaceutically acceptable capsule. In some embodiments, the one or more pharmaceutically acceptable excipients comprise about 0.3% by weight of one or more lubricants based on the total weight of the pharmaceutically acceptable capsule. In some embodiments, the one or more pharmaceutically acceptable excipients comprise about 0.4% by weight of one or more lubricants based on the total weight of the pharmaceutically acceptable capsule. In some embodiments, the one or more pharmaceutically acceptable excipients comprise about 0.5% by weight of one or more lubricants based on the total weight of the pharmaceutically acceptable capsule. In some embodiments, the one or more pharmaceutically acceptable excipients comprise about 0.6% by weight of one or more lubricants based on the total weight of the pharmaceutically acceptable capsule. In some embodiments, the one or more pharmaceutically acceptable excipients comprise about 0.7% by weight of one or more lubricants based on the total weight of the pharmaceutically acceptable capsule. In some embodiments, the one or more pharmaceutically acceptable excipients comprise about 0.8% by weight of one or more lubricants based on the total weight of the pharmaceutically acceptable capsule. In some embodiments, the one or more pharmaceutically acceptable excipients comprise about 0.9% by weight of one or more lubricants based on the total weight of the pharmaceutically acceptable capsule. In some embodiments, the one or more pharmaceutically acceptable excipients comprise about 1.0% by weight of one or more lubricants based on the total weight of the pharmaceutically acceptable capsule.

In some embodiments, the pharmaceutically acceptable capsule comprises (a) about 1% by weight to about 30% by weight of the compound of Formula (I) based on the total weight of the pharmaceutically acceptable capsule; (b) about 20% by weight to about 90% by weight of one or more fillers based on the total weight of the pharmaceutically acceptable capsule; (c) about 1% by weight to about 20% by weight of one or more disintegrants based on the total weight of the pharmaceutically acceptable capsule; and (d) about 0.1% by weight to about 10% by weight of one or more lubricants based on the total weight of the pharmaceutically acceptable capsule.

In some embodiments, the pharmaceutically acceptable capsule consists essentially of: (a) about 1% by weight to about 30% by weight of the compound of Formula (I) based on the total weight of the pharmaceutically acceptable capsule; (b) about 20% by weight to about 90% by weight of one or more fillers based on the total weight of the pharmaceutically acceptable capsule; (c) about 1% by weight to about 20% by weight of one or more disintegrants based on the total weight of the pharmaceutically acceptable capsule; and (d) about 0.1% by weight to about 10% by weight of one or more lubricants based on the total weight of the pharmaceutically acceptable capsule.

In some embodiments, the pharmaceutically acceptable capsule comprises (a) about 5% by weight to about 25% by weight of the compound of Formula (I) based on the total weight of the pharmaceutically acceptable capsule; (b) about 60% by weight to about 90% by weight of one or more fillers based on the total weight of the pharmaceutically acceptable capsule; (c) about 1% by weight to about 15% by weight of one or more disintegrants based on the total weight of the pharmaceutically acceptable capsule; and (d) about 0.1% by weight to about 4% by weight of one or more lubricants based on the total weight of the pharmaceutically acceptable capsule.

In some embodiments, the pharmaceutically acceptable capsule consists essentially of (a) about 5% by weight to about 25% by weight of the compound of Formula (I) based on the total weight of the pharmaceutically acceptable capsule; (b) about 60% by weight to about 90% by weight of one or more fillers based on the total weight of the pharmaceutically acceptable capsule; (c) about 1% by weight to about 15% by weight of one or more disintegrants based on the total weight of the pharmaceutically acceptable capsule; and (d) about 0.1% by weight to about 4% by weight of one or more lubricants based on the total weight of the pharmaceutically acceptable capsule.

In some embodiments, the pharmaceutically acceptable capsule comprises (a) about 10% by weight to about 30% by weight of the compound of Formula (I) based on the total weight of the pharmaceutically acceptable capsule; (b) about 70% by weight to about 90% by weight of one or more fillers based on the total weight of the pharmaceutically acceptable capsule; (c) about 1% by weight to about 10% by weight of one or more disintegrants based on the total weight of the pharmaceutically acceptable capsule; and (d) about 0.1% by weight to about 3% by weight of one or more lubricants based on the total weight of the pharmaceutically acceptable capsule.

In some embodiments, the pharmaceutically acceptable capsule consists essentially of (a) about 10% by weight to about 30% by weight of the compound of Formula (I) based on the total weight of the pharmaceutically acceptable capsule; (b) about 70% by weight to about 90% by weight of one or more fillers based on the total weight of the pharmaceutically acceptable capsule; (c) about 1% by weight to about 10% by weight of one or more disintegrants based on the total weight of the pharmaceutically acceptable capsule; and (d) about 0.1% by weight to about 3% by weight of one or more lubricants based on the total weight of the pharmaceutically acceptable capsule.

In some embodiments, the one or more pharmaceutically acceptable excipients is one or more fillers selected from the group consisting of calcium phosphate, dicalcium phosphate, dicalcium phosphate dihydrate, calcium sulfate, calcium sulfate dihydrate, starch, calcium carbonate, magnesium carbonate, magnesium oxide, kaolin (natural hydrated aluminum silicate), sodium chloride, partially gelatinized starch, anhydrous lactose, lactose monohydrate, lactose dihydrate, trehalose dihydrate, spray dried lactose, sucrose, dextrose, dextrates, dextrin, cellulose, microcrystalline cellulose, silicified microcrystalline cellulose, powdered cellulose, partially depolymerized cellulose, mannitol, granulated mannitol, spray dried mannitol, maltodextrin, maltitol, confectioner's sugar, compressible sugar, sorbitol, starch and talc. In some embodiments, the one or more fillers is lactose monohydrate.

In some embodiments, the one or more disintegrants is one or more disintegrants selected from the group consisting of sodium starch glycolate, pregelatinized starch, clay, cellulose, alginic acid, alginate gum, polyvinylpyrrolidone, cross-linked polyvinylpyrrolidone, cross-linked calcium carboxymethylcellulose, cross-linked sodium carboxymethylcellulose, sodium croscarmellose, sodium carmellose, low substituted hydroxypropyl cellulose, low substituted hydroxypropyl cellulose sodium, guar gum, magnesium aluminum silicate, polacrilin potassium, powdered cellulose, sodium alginate and soy polysaccharides. In some embodiments, the one or more disintegrants is cross-linked polyvinylpyrrolidone (also referred to as crospovidone).

In some embodiments, the one or more lubricants is one or more lubricants selected from the group consisting of colloidal silica, magnesium trisilicate, talc, magnesium carbonate, magnesium oxide, glyceryl behaptate, mono, di and tri glyceryl behenate, bees wax, behenoyl polyoxyl-8 glycerides, hydrogenated vegetable oil, polyethylene glycol, ethylene oxide polymer, copolymer comprising poly(ethylene oxide) and poly(propylene oxide) (such as poloxomer 188), copolymer comprising polypropylene glycol and polyethylene glycol (such as poloxomer 407), sodium lauryl sulfate, magnesium stearate, aluminum stearate, calcium stearate, sodium stearyl fumarate, stearic acid, magnesium lauryl stearate, mixtures of magnesium stearate with sodium lauryl sulfate. In some embodiments, the one or more lubricants is magnesium stearate.

In some embodiments, the pharmaceutically acceptable capsule further comprises cross-linked polyvinylpyrrolidone and magnesium stearate. In some embodiments, the one or more pharmaceutically acceptable excipients is lactose monohydrate and the pharmaceutically acceptable capsule further comprises cross-linked polyvinylpyrrolidone and magnesium stearate.

In some embodiments, the pharmaceutically acceptable capsule is for oral administration.

In some embodiments, the pharmaceutically acceptable capsule is a solid dosage form.

In some embodiments, the pharmaceutically acceptable capsule comprises about 1 mg to about 40 mg of the compound of Formula (I). In some embodiments, the pharmaceutically acceptable capsule comprises about 1 mg to about 30 mg of the compound of Formula (I). In some embodiments, the pharmaceutically acceptable capsule comprises about 1 mg to about 20 mg of the compound of Formula (I). In some embodiments, the pharmaceutically acceptable capsule comprises about 1 mg to about 15 mg of the compound of Formula (I). In some embodiments, the pharmaceutically acceptable capsule comprises about 5 mg to about 40 mg of the compound of Formula (I). In some embodiments, the pharmaceutically acceptable capsule comprises about 5 mg to about 30 mg of the compound of Formula (I). In some embodiments, the pharmaceutically acceptable capsule comprises about 5 mg to about 20 mg of the compound of Formula (I). In some embodiments, the pharmaceutically acceptable capsule comprises about 5 mg to about 15 mg of the compound of Formula (I). In some embodiments, the pharmaceutically acceptable capsule comprises about 10 mg to about 40 mg of the compound of Formula (I). In some embodiments, the pharmaceutically acceptable capsule comprises about 10 mg to about 30 mg of the compound of Formula (I). In some embodiments, the pharmaceutically acceptable capsule comprises about 10 mg to about 20 mg of the compound of Formula (I). In some embodiments, the pharmaceutically acceptable capsule comprises about 10 mg to about 15 mg of the compound of Formula (I).

In some embodiments, the pharmaceutically acceptable capsule consists essentially of about 1 mg to about 40 mg of the compound of Formula (I). In some embodiments, the pharmaceutically acceptable capsule consists essentially of about 1 mg to about 30 mg of the compound of Formula (I). In some embodiments, the pharmaceutically acceptable capsule consists essentially of about 1 mg to about 20 mg of the compound of Formula (I). In some embodiments, the pharmaceutically acceptable capsule consists essentially of about 1 mg to about 15 mg of the compound of Formula (I). In some embodiments, the pharmaceutically acceptable capsule consists essentially of about 5 mg to about 40 mg of the compound of Formula (I). In some embodiments, the pharmaceutically acceptable capsule consists essentially of about 5 mg to about 30 mg of the compound of Formula (I). In some embodiments, the pharmaceutically acceptable capsule consists essentially of about 5 mg to about 20 mg of the compound of Formula (I). In some embodiments, the pharmaceutically acceptable capsule consists essentially of about 5 mg to about 15 mg of the compound of Formula (I). In some embodiments, the pharmaceutically acceptable capsule consists essentially of about 10 mg to about 40 mg of the compound of Formula (I). In some embodiments, the pharmaceutically acceptable capsule consists essentially of about 10 mg to about 30 mg of the compound of Formula (I). In some embodiments, the pharmaceutically acceptable capsule consists essentially of about 10 mg to about 20 mg of the compound of Formula (I). In some embodiments, the pharmaceutically acceptable capsule consists essentially of about 10 mg to about 15 mg of the compound of Formula (I).

In some embodiments, compound of Formula (I) is present in the pharmaceutically acceptable capsule as a cocrystal. In some embodiments, compound of Formula (I) is present in the pharmaceutically acceptable capsule as a channel crystal. In some embodiments, compound of Formula (I) is present in the pharmaceutically acceptable capsule as a crystalline dihydrate form. In some embodiments, the compound of Formula (I) is present in the pharmaceutically acceptable capsule as a crystalline anhydrous form. In some embodiments, compound of Formula (I) is present in the pharmaceutically acceptable capsule as a solvate.

In some embodiments, the pharmaceutically acceptable capsule comprises about 0.5 mg to about 5 mg, about 6 mg to about 14 mg, about 11 mg to about 19 mg, about 17 mg to about 25 mg, or about 28 mg to about 36 mg of the compound of Formula (I) as a crystalline dihydrate form. In some embodiments, the pharmaceutically acceptable capsule comprises about 1 mg to about 4 mg, about 8 mg to about 12 mg, about 13 mg to about 17 mg, about 19 mg to about 23 mg, or about 30 mg to about 34 mg of the compound of Formula (I) as a crystalline dihydrate form. In some embodiments, the pharmaceutically acceptable capsule comprises about 2.2 mg, about 10.8 mg, about 15.2 mg, about 21.7 mg, or about 32.5 mg of the compound of Formula (I) as a crystalline dihydrate form.

In some embodiments, the pharmaceutically acceptable capsule consists essentially of about 0.5 mg to about 5 mg, about 6 mg to about 14 mg, about 11 mg to about 19 mg, about 17 mg to about 25 mg, or about 28 mg to about 36 mg of the compound of Formula (I) as a crystalline dihydrate form. In some embodiments, the pharmaceutically acceptable capsule consists essentially of about 1 mg to about 4 mg, about 8 mg to about 12 mg, about 13 mg to about 17 mg, about 19 mg to about 23 mg, or about 30 mg to about 34 mg of the compound of Formula (I) as a crystalline dihydrate form. In some embodiments, the pharmaceutically acceptable capsule consists essentially of about 2.2 mg, about 10.8 mg, about 15.2 mg, about 21.7 mg, or about 32.5 mg of the compound of Formula (I) as a crystalline dihydrate form.

Also provided herein, in some embodiments, is a process of preparing a pharmaceutically acceptable capsule, the pharmaceutically acceptable capsule comprising:

(a) about 1% to about 70%, based on the total weight of the pharmaceutically acceptable capsule, of a crystalline dihydrate form of a compound of Formula (I):

Formula (I)

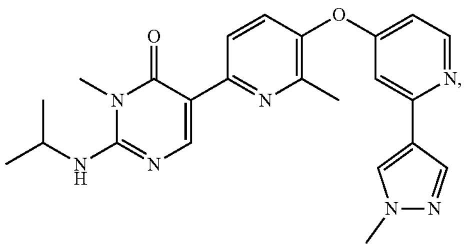

and one or more pharmaceutically acceptable excipients, wherein the one or more pharmaceutically acceptable excipients comprise:

(b) about 20% by weight to about 97% by weight of one or more fillers, based on the total weight of the pharmaceutically acceptable capsule;

(c) about 1% by weight to about 20% by weight of one or more disintegrants, based on the total weight of the pharmaceutically acceptable capsule; and (d) about 0.1% by weight to about 10% by weight of one or more lubricants, based on the total weight of the pharmaceutically acceptable capsule;

the process comprising:

(i) blending the crystalline dihydrate form of a compound represented by Formula (I) with the one or more fillers and one or more disintegrants to produce a first blend;

(ii) blending the first blend with the one or more lubricants to form a second blend; and (iii) dispensing the second blend into an empty pharmaceutically acceptable capsule, thereby forming the pharmaceutically acceptable capsule.

Also provided herein, in some embodiments, is a process of preparing a pharmaceutically acceptable capsule, the pharmaceutically acceptable capsule consisting essentially of:

(a) about 1% to about 70%, based on the total weight of the pharmaceutically acceptable capsule, of a crystalline dihydrate form of a compound of Formula (I):

Formula (I)

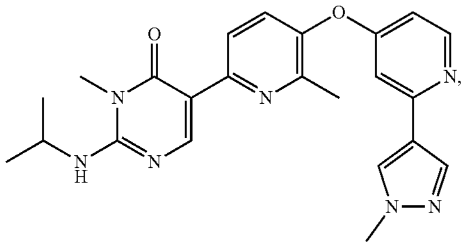

and one or more pharmaceutically acceptable excipients, wherein the one or more pharmaceutically acceptable excipients comprise:

(b) about 20% by weight to about 97% by weight of one or more fillers, based on the total weight of the pharmaceutically acceptable capsule;

(c) about 1% by weight to about 20% by weight of one or more disintegrants, based on the total weight of the pharmaceutically acceptable capsule; and (d) about 0.1% by weight to about 10% by weight of one or more lubricants, based on the total weight of the pharmaceutically acceptable capsule;

the process comprising:

(i) blending the crystalline dihydrate form of a compound represented by Formula (I) with the one or more fillers and one or more disintegrants to produce a first blend;

(ii) blending the first blend with the one or more lubricants to form a second blend; and (iii) dispensing the second blend into an empty pharmaceutically acceptable capsule, thereby forming the pharmaceutically acceptable capsule.

Also provided herein, in some embodiments, is a process of preparing a pharmaceutically acceptable capsule, the pharmaceutically acceptable capsule comprising:

(a) about 1% to about 70%, based on the total weight of the pharmaceutically acceptable capsule, of a crystalline dihydrate form of a compound of Formula (I):

Formula (I)

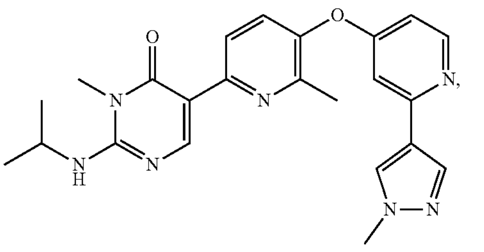

and one or more pharmaceutically acceptable excipients, wherein the one or more pharmaceutically acceptable excipients comprise:

(b) about 20% by weight to about 97% by weight of one or more fillers, based on the total weight of the pharmaceutically acceptable capsule;

(c) about 1% by weight to about 20% by weight of one or more disintegrants, based on the total weight of the pharmaceutically acceptable capsule; and (d) about 0.1% by weight to about 10% by weight of one or more lubricants, based on the total weight of the pharmaceutically acceptable capsule;

the process comprising:

(i) blending the crystalline dihydrate form of a compound represented by Formula (I) with the one or more fillers to produce a first blend;

(ii) blending the first blend with the one or more disintegrants to form a second blend;

(iii) blending the second blend with the one or more lubricants to form a third blend; and (iv) dispensing the third blend into an empty pharmaceutically acceptable capsule, thereby forming the pharmaceutically acceptable capsule.

Also provided herein, in some embodiments, is a process of preparing a pharmaceutically acceptable capsule, the pharmaceutically acceptable capsule consisting essentially of:

(a) about 1% to about 70%, based on the total weight of the pharmaceutically acceptable capsule, of a crystalline dihydrate form of a compound of Formula (I):

Formula (I)

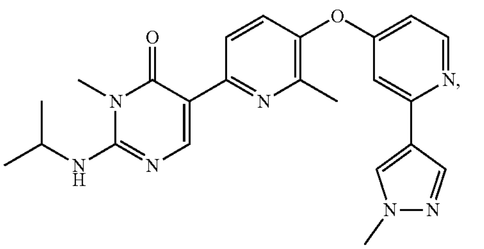

and one or more pharmaceutically acceptable excipients, wherein the one or more pharmaceutically acceptable excipients comprise:

(b) about 20% by weight to about 97% by weight of one or more fillers, based on the total weight of the pharmaceutically acceptable capsule;

(c) about 1% by weight to about 20% by weight of one or more disintegrants, based on the total weight of the pharmaceutically acceptable capsule; and (d) about 0.1% by weight to about 10% by weight of one or more lubricants, based on the total weight of the pharmaceutically acceptable capsule;

the process comprising:

(i) blending the crystalline dihydrate form of a compound represented by Formula (I) with the one or more fillers to produce a first blend;

(ii) blending the first blend with the one or more disintegrants to form a second blend;

(iii) blending the second blend with the one or more lubricants to form a third blend; and (iv) dispensing the third blend into an empty pharmaceutically acceptable capsule, thereby forming the pharmaceutically acceptable capsule.

Also provided herein, in some embodiments, is a process of preparing a pharmaceutically acceptable capsule, the pharmaceutically acceptable capsule comprising:

(a) about 1% to about 70%, based on the total weight of the pharmaceutically acceptable capsule, of a crystalline dihydrate form of a compound of Formula (I):

Formula (I)

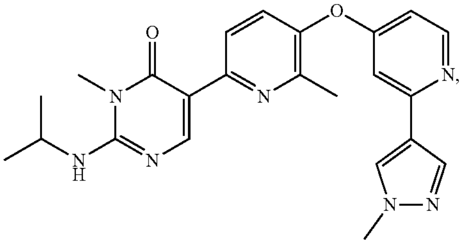

and one or more pharmaceutically acceptable excipients, wherein the one or more pharmaceutically acceptable excipients comprise:

(b) about 20% by weight to about 97% by weight of one or more fillers, based on the total weight of the pharmaceutically acceptable capsule;

(c) about 1% by weight to about 20% by weight of one or more disintegrants, based on the total weight of the pharmaceutically acceptable capsule; and (d) about 0.1% by weight to about 10% by weight of one or more lubricants, based on the total weight of the pharmaceutically acceptable capsule;

the process comprising:

(i) blending the crystalline dihydrate form of a compound represented by Formula (I) with the one or more fillers to produce a first blend;

(ii) blending the first blend with a second blend comprising one or more disintegrants and one or more fillers and optionally a third blend comprising one or more fillers to form a fourth blend;

(iii) blending the fourth blend with the one or more lubricants to form a fifth blend; and (iv) dispensing the fifth blend into an empty pharmaceutically acceptable capsule, thereby forming the pharmaceutically acceptable capsule.

Also provided herein, in some embodiments, is a process of preparing a pharmaceutically acceptable capsule, the pharmaceutically acceptable capsule consisting essentially of:

(a) about 1% to about 70%, based on the total weight of the pharmaceutically acceptable capsule, of a crystalline dihydrate form of a compound of Formula (I):

Formula (I)

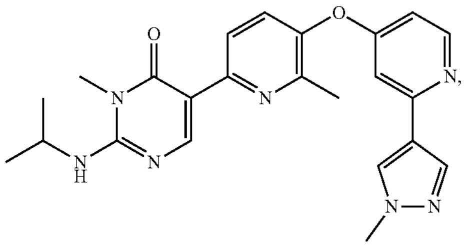

and one or more pharmaceutically acceptable excipients, wherein the one or more pharmaceutically acceptable excipients comprise:

(b) about 20% by weight to about 97% by weight of one or more fillers, based on the total weight of the pharmaceutically acceptable capsule;

(c) about 1% by weight to about 20% by weight of one or more disintegrants, based on the total weight of the pharmaceutically acceptable capsule; and (d) about 0.1% by weight to about 10% by weight of one or more lubricants, based on the total weight of the pharmaceutically acceptable capsule;

the process comprising:

(i) blending the crystalline dihydrate form of a compound represented by Formula (I) with the one or more fillers to produce a first blend;

(ii) blending the first blend with a second blend comprising one or more disintegrants and one or more fillers and optionally a third blend comprising one or more fillers to form a fourth blend;

(iii) blending the fourth blend with the one or more lubricants to form a fifth blend; and (iv) dispensing the fifth blend into an empty pharmaceutically acceptable capsule, thereby forming the pharmaceutically acceptable capsule.

In some embodiments, the pharmaceutically acceptable capsule comprising the crystalline dihydrate form of the compound represented by Formula (I), has no more than about 10 mol %, no more than about 5 mol %, no more than about 3 mol %, or no more than about 1 mol % of other solid-state forms of the compound represented by Formula (I). In some embodiments, the pharmaceutically acceptable capsule comprising the crystalline dihydrate forms of the compound represented by Formula (I), has no more than about 10 mol % of other solid-state forms of the compound represented by Formula (I). In some embodiments, the pharmaceutically acceptable capsule comprising the crystalline dihydrate forms of the compound represented by Formula (I), has no more than about 9 mol % of other solid-state forms of the compound represented by Formula (I). In some embodiments, the pharmaceutically acceptable capsule comprising the crystalline dihydrate forms of the compound represented by Formula (I), has no more than about 8 mol % of other solid-state forms of the compound represented by Formula (I). In some embodiments, the pharmaceutically acceptable capsule comprising the crystalline dihydrate forms of the compound represented by Formula (I), has no more than about 7 mol % of other solid-state forms of the compound represented by Formula (I). In some embodiments, the pharmaceutically acceptable capsule comprising the crystalline dihydrate forms of the compound represented by Formula (I), has no more than about 6 mol % of other solid-state forms of the compound represented by Formula (I). In some embodiments, the pharmaceutically acceptable capsule comprising the crystalline dihydrate forms of the compound represented by Formula (I), has no more than about 5 mol % of other solid-state forms of the compound represented by Formula (I). In some embodiments, the pharmaceutically acceptable capsule comprising the crystalline dihydrate forms of the compound represented by Formula (I), has no more than about 4 mol % of other solid-state forms of the compound represented by Formula (I). In some embodiments, the pharmaceutically acceptable capsule comprising the crystalline dihydrate forms of the compound represented by Formula (I), has no more than about 3 mol % of other solid-state forms of the compound represented by Formula (I). In some embodiments, the pharmaceutically acceptable capsule comprising the crystalline dihydrate forms of the compound represented by Formula (I), has no more than about 2 mol % of other solid-state forms of the compound represented by Formula (I). In some embodiments, the pharmaceutically acceptable capsule comprising the crystalline dihydrate forms of the compound represented by Formula (I), has no more than about 1 mol % of other solid-state forms of the compound represented by Formula (I).

In some embodiments, the pharmaceutically acceptable capsule comprises about 1% by weight to about 60% by weight, based on the total weight of the pharmaceutically acceptable capsule, of a crystalline dihydrate form of a compound of Formula (I). In some embodiments, the pharmaceutically acceptable capsule comprises about 1% by weight to about 50% by weight, based on the total weight of the pharmaceutically acceptable capsule, of a crystalline dihydrate form of a compound of Formula (I). In some embodiments, the pharmaceutically acceptable capsule comprises about 1% by weight to about 40% by weight, based on the total weight of the pharmaceutically acceptable capsule, of a crystalline dihydrate form of a compound of Formula (I). In some embodiments, the pharmaceutically acceptable capsule comprises about 1% by weight to about 30% by weight, based on the total weight of the pharmaceutically acceptable capsule, of a crystalline dihydrate form of a compound of Formula (I). In some embodiments, the pharmaceutically acceptable capsule comprises about 1% by weight to about 20% by weight, based on the total weight of the pharmaceutically acceptable capsule, of a crystalline dihydrate form of a compound of Formula (I).

In some embodiments, the pharmaceutically acceptable capsule consists essentially of about 1% by weight to about 60% by weight, based on the total weight of the pharmaceutically acceptable capsule, of a crystalline dihydrate form of a compound of Formula (I). In some embodiments, the pharmaceutically acceptable capsule consists essentially of about 1% by weight to about 50% by weight, based on the total weight of the pharmaceutically acceptable capsule, of a crystalline dihydrate form of a compound of Formula (I). In some embodiments, the pharmaceutically acceptable capsule consists essentially of about 1% by weight to about 40% by weight, based on the total weight of the pharmaceutically acceptable capsule, of a crystalline dihydrate form of a compound of Formula (I). In some embodiments, the pharmaceutically acceptable capsule consists essentially of about 1% by weight to about 30% by weight, based on the total weight of the pharmaceutically acceptable capsule, of a crystalline dihydrate form of a compound of Formula (I). In some embodiments, the pharmaceutically acceptable capsule consists essentially of about 1% by weight to about 20% by weight, based on the total weight of the pharmaceutically acceptable capsule, of a crystalline dihydrate form of a compound of Formula (I).

In some embodiments, the pharmaceutically acceptable capsule comprises about 1% by weight to about 70% by weight of the compound of Formula (I) based on the total weight of the pharmaceutically acceptable capsule. In some embodiments, the pharmaceutically acceptable capsule comprises about 1% by weight to about 65% by weight of the compound of Formula (I) based on the total weight of the pharmaceutically acceptable capsule. In some embodiments, the pharmaceutically acceptable capsule comprises about 1% by weight to about 60% by weight of the compound of Formula (I) based on the total weight of the pharmaceutically acceptable capsule. In some embodiments, the pharmaceutically acceptable capsule comprises about 1% by weight to about 55% by weight of the compound of Formula (I) based on the total weight of the pharmaceutically acceptable capsule. In some embodiments, the pharmaceutically acceptable capsule comprises about 1% by weight to about 50% by weight of the compound of Formula (I) based on the total weight of the pharmaceutically acceptable capsule. In some embodiments, the pharmaceutically acceptable capsule comprises about 1% by weight to about 45% by weight of the compound of Formula (I) based on the total weight of the pharmaceutically acceptable capsule. In some embodiments, the pharmaceutically acceptable capsule comprises about 1% by weight to about 40% by weight of the compound of Formula (I) based on the total weight of the pharmaceutically acceptable capsule. In some embodiments, the pharmaceutically acceptable capsule comprises about 1% by weight to about 35% by weight of the compound of Formula (I) based on the total weight of the pharmaceutically acceptable capsule. In some embodiments, the pharmaceutically acceptable capsule comprises about 1% by weight to about 30% by weight of the compound of Formula (I) based on the total weight of the pharmaceutically acceptable capsule. In some embodiments, the pharmaceutically acceptable capsule comprises about 1% by weight to about 25% by weight of the compound of Formula (I) based on the total weight of the pharmaceutically acceptable capsule. In some embodiments, the pharmaceutically acceptable capsule comprises about 1% by weight to about 20% by weight of the compound of Formula (I) based on the total weight of the pharmaceutically acceptable capsule. In some embodiments, the pharmaceutically acceptable capsule comprises about 1% by weight to about 15% by weight of the compound of Formula (I) based on the total weight of the pharmaceutically acceptable capsule. In some embodiments, the pharmaceutically acceptable capsule comprises about 1% by weight to about 10% by weight of the compound of Formula (I) based on the total weight of the pharmaceutically acceptable capsule.

In some embodiments, the pharmaceutically acceptable capsule consists essentially of about 1% by weight to about 70% by weight of the compound of Formula (I) based on the total weight of the pharmaceutically acceptable capsule. In some embodiments, the pharmaceutically acceptable capsule consists essentially of about 1% by weight to about 65% by weight of the compound of Formula (I) based on the total weight of the pharmaceutically acceptable capsule. In some embodiments, the pharmaceutically acceptable capsule consists essentially of about 1% by weight to about 60% by weight of the compound of Formula (I) based on the total weight of the pharmaceutically acceptable capsule. In some embodiments, the pharmaceutically acceptable capsule consists essentially of about 1% by weight to about 55% by weight of the compound of Formula (I) based on the total weight of the pharmaceutically acceptable capsule. In some embodiments, the pharmaceutically acceptable capsule consists essentially of about 1% by weight to about 50% by weight of the compound of Formula (I) based on the total weight of the pharmaceutically acceptable capsule. In some embodiments, the pharmaceutically acceptable capsule consists essentially of about 1% by weight to about 45% by weight of the compound of Formula (I) based on the total weight of the pharmaceutically acceptable capsule. In some embodiments, the pharmaceutically acceptable capsule consists essentially of about 1% by weight to about 40% by weight of the compound of Formula (I) based on the total weight of the pharmaceutically acceptable capsule. In some embodiments, the pharmaceutically acceptable capsule consists essentially of about 1% by weight to about 35% by weight of the compound of Formula (I) based on the total weight of the pharmaceutically acceptable capsule. In some embodiments, the pharmaceutically acceptable capsule consists essentially of about 1% by weight to about 30% by weight of the compound of Formula (I) based on the total weight of the pharmaceutically acceptable capsule. In some embodiments, the pharmaceutically acceptable capsule consists essentially of about 1% by weight to about 25% by weight of the compound of Formula (I) based on the total weight of the pharmaceutically acceptable capsule. In some embodiments, the pharmaceutically acceptable capsule consists essentially of about 1% by weight to about 20% by weight of the compound of Formula (I) based on the total weight of the pharmaceutically acceptable capsule. In some embodiments, the pharmaceutically acceptable capsule consists essentially of about 1% by weight to about 15% by weight of the compound of Formula (I) based on the total weight of the pharmaceutically acceptable capsule. In some embodiments, the pharmaceutically acceptable capsule consists essentially of about 1% by weight to about 10% by weight of the compound of Formula (I) based on the total weight of the pharmaceutically acceptable capsule.

In some embodiments, the pharmaceutically acceptable capsule comprises about 5% by weight to about 30% by weight of the compound of Formula (I) based on the total weight of the pharmaceutically acceptable capsule. In some embodiments, the pharmaceutically acceptable capsule comprises about 5% by weight to about 25% by weight of the compound of Formula (I) based on the total weight of the pharmaceutically acceptable capsule. In some embodiments, the pharmaceutically acceptable capsule comprises about 5% by weight to about 20% by weight of the compound of Formula (I) based on the total weight of the pharmaceutically acceptable capsule. In some embodiments, the pharmaceutically acceptable capsule comprises about 5% by weight to about 15% by weight of the compound of Formula (I) based on the total weight of the pharmaceutically acceptable capsule. In some embodiments, the pharmaceutically acceptable capsule comprises about 5% by weight to about 10% by weight of the compound of Formula (I) based on the total weight of the pharmaceutically acceptable capsule.

In some embodiments, the pharmaceutically acceptable capsule consists essentially of about 5% by weight to about 30% by weight of the compound of Formula (I) based on the total weight of the pharmaceutically acceptable capsule. In some embodiments, the pharmaceutically acceptable capsule consists essentially of about 5% by weight to about 25% by weight of the compound of Formula (I) based on the total weight of the pharmaceutically acceptable capsule. In some embodiments, the pharmaceutically acceptable capsule consists essentially of about 5% by weight to about 20% by weight of the compound of Formula (I) based on the total weight of the pharmaceutically acceptable capsule. In some embodiments, the pharmaceutically acceptable capsule consists essentially of about 5% by weight to about 15% by weight of the compound of Formula (I) based on the total weight of the pharmaceutically acceptable capsule. In some embodiments, the pharmaceutically acceptable capsule consists essentially of about 5% by weight to about 10% by weight of the compound of Formula (I) based on the total weight of the pharmaceutically acceptable capsule.

In some embodiments, the pharmaceutically acceptable capsule comprises about 10% to about 30% of the compound of Formula (I) based on the total weight of the pharmaceutically acceptable capsule. In some embodiments, the pharmaceutically acceptable capsule comprises about 10% to about 25% of the compound of Formula (I) based on the total weight of the pharmaceutically acceptable capsule. In some embodiments, the pharmaceutically acceptable capsule comprises about 10% to about 20% of the compound of Formula (I) based on the total weight of the pharmaceutically acceptable capsule. In some embodiments, the pharmaceutically acceptable capsule comprises about 10% by weight to about 15% by weight of the compound of Formula (I) based on the total weight of the pharmaceutically acceptable capsule.

In some embodiments, the pharmaceutically acceptable capsule consists essentially of about 10% to about 30% of the compound of Formula (I) based on the total weight of the pharmaceutically acceptable capsule. In some embodiments, the pharmaceutically acceptable capsule consists essentially of about 10% to about 25% of the compound of Formula (I) based on the total weight of the pharmaceutically acceptable capsule. In some embodiments, the pharmaceutically acceptable capsule consists essentially of about 10% to about 20% of the compound of Formula (I) based on the total weight of the pharmaceutically acceptable capsule. In some embodiments, the pharmaceutically acceptable capsule consists essentially of about 10% by weight to about 15% by weight of the compound of Formula (I) based on the total weight of the pharmaceutically acceptable capsule.

In some embodiments, the pharmaceutically acceptable capsule comprises about 1% by weight to about 30% by weight of the compound of Formula (I) based on the total weight of the pharmaceutically acceptable capsule. In some embodiments, the pharmaceutically acceptable capsule comprises about 1% by weight to about 10% by weight of the compound of Formula (I) based on the total weight of the pharmaceutically acceptable capsule. In some embodiments, the pharmaceutically acceptable capsule comprises about 10% to about 20% of the compound of Formula (I) based on the total weight of the pharmaceutically acceptable capsule. In some embodiments, the pharmaceutically acceptable capsule comprises about 10% by weight to about 15% by weight of the compound of Formula (I) based on the total weight of the pharmaceutically acceptable capsule.

In some embodiments, the pharmaceutically acceptable capsule consists essentially of about 1% by weight to about 30% by weight of the compound of Formula (I) based on the total weight of the pharmaceutically acceptable capsule. In some embodiments, the pharmaceutically acceptable capsule consists essentially of about 1% by weight to about 10% by weight of the compound of Formula (I) based on the total weight of the pharmaceutically acceptable capsule. In some embodiments, the pharmaceutically acceptable capsule consists essentially of about 10% to about 20% of the compound of Formula (I) based on the total weight of the pharmaceutically acceptable capsule. In some embodiments, the pharmaceutically acceptable capsule consists essentially of about 10% by weight to about 15% by weight of the compound of Formula (I) based on the total weight of the pharmaceutically acceptable capsule.

In some embodiments, the one or more pharmaceutically acceptable excipients comprise about 20% by weight to about 90% by weight of one or more fillers based on the total weight of the pharmaceutically acceptable capsule. In some embodiments, the one or more pharmaceutically acceptable excipients comprise about 20% by weight to about 85% by weight of one or more fillers based on the total weight of the pharmaceutically acceptable capsule. In some embodiments, the one or more pharmaceutically acceptable excipients comprise about 20% by weight to about 80% by weight of one or more fillers based on the total weight of the pharmaceutically acceptable capsule. In some embodiments, the one or more pharmaceutically acceptable excipients comprise about 20% by weight to about 75% by weight of one or more fillers based on the total weight of the pharmaceutically acceptable capsule. In some embodiments, the one or more pharmaceutically acceptable excipients comprise about 20% by weight to about 70% by weight of one or more fillers based on the total weight of the pharmaceutically acceptable capsule. In some embodiments, the one or more pharmaceutically acceptable excipients comprise about 20% by weight to about 65% by weight of one or more fillers based on the total weight of the pharmaceutically acceptable capsule. In some embodiments, the one or more pharmaceutically acceptable excipients comprise about 20% by weight to about 60% by weight of one or more fillers based on the total weight of the pharmaceutically acceptable capsule. In some embodiments, the one or more pharmaceutically acceptable excipients comprise about 20% by weight to about 55% by weight of one or more fillers based on the total weight of the pharmaceutically acceptable capsule. In some embodiments, the one or more pharmaceutically acceptable excipients comprise about 20% by weight to about 50% by weight of one or more fillers based on the total weight of the pharmaceutically acceptable capsule. In some embodiments, the one or more pharmaceutically acceptable excipients comprise about 20% by weight to about 45% by weight of one or more fillers based on the total weight of the pharmaceutically acceptable capsule. In some embodiments, the one or more pharmaceutically acceptable excipients comprise about 20% by weight to about 40% by weight of one or more fillers based on the total weight of the pharmaceutically acceptable capsule. In some embodiments, the one or more pharmaceutically acceptable excipients comprise about 20% by weight to about 35% by weight of one or more fillers based on the total weight of the pharmaceutically acceptable capsule. In some embodiments, the one or more pharmaceutically acceptable excipients comprise about 20% by weight to about 30% by weight of one or more fillers based on the total weight of the pharmaceutically acceptable capsule. In some embodiments, the one or more pharmaceutically acceptable excipients comprise about 20% by weight to about 25% by weight of one or more fillers based on the total weight of the pharmaceutically acceptable capsule.

In some embodiments, the one or more pharmaceutically acceptable excipients comprise about 30% by weight to about 90% by weight of one or more fillers based on the total weight of the pharmaceutically acceptable capsule. In some embodiments, the one or more pharmaceutically acceptable excipients comprise about 30% by weight to about 80% by weight of one or more fillers based on the total weight of the pharmaceutically acceptable capsule. In some embodiments, the one or more pharmaceutically acceptable excipients comprise about 30% by weight to about 70% by weight of one or more fillers based on the total weight of the pharmaceutically acceptable capsule. In some embodiments, the one or more pharmaceutically acceptable excipients comprise about 30% by weight to about 60% by weight of one or more fillers based on the total weight of the pharmaceutically acceptable capsule. In some embodiments, the one or more pharmaceutically acceptable excipients comprise about 30% by weight to about 50% by weight of one or more fillers based on the total weight of the pharmaceutically acceptable capsule. In some embodiments, the one or more pharmaceutically acceptable excipients comprise about 30% by weight to about 40% by weight of one or more fillers based on the total weight of the pharmaceutically acceptable capsule.

In some embodiments, the one or more pharmaceutically acceptable excipients comprise about 40% by weight to about 90% by weight of one or more fillers based on the total weight of the pharmaceutically acceptable capsule. In some embodiments, the one or more pharmaceutically acceptable excipients comprise about 40% by weight to about 80% by weight of one or more fillers based on the total weight of the pharmaceutically acceptable capsule. In some embodiments, the one or more pharmaceutically acceptable excipients comprise about 40% by weight to about 70% by weight of one or more fillers based on the total weight of the pharmaceutically acceptable capsule. In some embodiments, the one or more pharmaceutically acceptable excipients comprise about 40% by weight to about 60% by weight of one or more fillers based on the total weight of the pharmaceutically acceptable capsule. In some embodiments, the one or more pharmaceutically acceptable excipients comprise about 40% by weight to about 50% by weight of one or more fillers based on the total weight of the pharmaceutically acceptable capsule.

In some embodiments, the one or more pharmaceutically acceptable excipients comprise about 50% by weight to about 90% by weight of one or more fillers based on the total weight of the pharmaceutically acceptable capsule. In some embodiments, the one or more pharmaceutically acceptable excipients comprise about 50% by weight to about 80% by weight of one or more fillers based on the total weight of the pharmaceutically acceptable capsule. In some embodiments, the one or more pharmaceutically acceptable excipients comprise about 50% by weight to about 70% by weight of one or more fillers based on the total weight of the pharmaceutically acceptable capsule. In some embodiments, the one or more pharmaceutically acceptable excipients comprise about 50% by weight to about 60% by weight of one or more fillers based on the total weight of the pharmaceutically acceptable capsule.

In some embodiments, the one or more pharmaceutically acceptable excipients comprise about 60% by weight to about 90% by weight of one or more fillers based on the total weight of the pharmaceutically acceptable capsule. In some embodiments, the one or more pharmaceutically acceptable excipients comprise about 60% by weight to about 80% by weight of one or more fillers based on the total weight of the pharmaceutically acceptable capsule. In some embodiments, the one or more pharmaceutically acceptable excipients comprise about 60% by weight to about 70% by weight of one or more fillers based on the total weight of the pharmaceutically acceptable capsule.

In some embodiments, the one or more pharmaceutically acceptable excipients comprise about 70% by weight to about 90% by weight of one or more fillers based on the total weight of the pharmaceutically acceptable capsule. In some embodiments, the one or more pharmaceutically acceptable excipients comprise about 70% by weight to about 80% by weight of one or more fillers based on the total weight of the pharmaceutically acceptable capsule.

In some embodiments, the one or more pharmaceutically acceptable excipients comprise about 80% by weight to about 90% by weight of one or more fillers based on the total weight of the pharmaceutically acceptable capsule.

In some embodiments, the one or more pharmaceutically acceptable excipients comprise about 1% by weight to about 20% by weight of one or more disintegrants based on the total weight of the pharmaceutically acceptable capsule. In some embodiments, the one or more pharmaceutically acceptable excipients comprise about 1% by weight to about 15% by weight of one or more disintegrants based on the total weight of the pharmaceutically acceptable capsule. In some embodiments, the one or more pharmaceutically acceptable excipients comprise about 1% by weight to about 14% by weight of one or more disintegrants based on the total weight of the pharmaceutically acceptable capsule. In some embodiments, the one or more pharmaceutically acceptable excipients comprise about 1% by weight to about 13% by weight of one or more disintegrants based on the total weight of the pharmaceutically acceptable capsule. In some embodiments, the one or more pharmaceutically acceptable excipients comprise about 1% by weight to about 12% by weight of one or more disintegrants based on the total weight of the pharmaceutically acceptable capsule. In some embodiments, the one or more pharmaceutically acceptable excipients comprise about 1% by weight to about 11% by weight of one or more disintegrants based on the total weight of the pharmaceutically acceptable capsule. In some embodiments, the one or more pharmaceutically acceptable excipients comprise about 1% by weight to about 10% by weight of one or more disintegrants based on the total weight of the pharmaceutically acceptable capsule. In some embodiments, the one or more pharmaceutically acceptable excipients comprise about 1% by weight to about 9% by weight of one or more disintegrants based on the total weight of the pharmaceutically acceptable capsule. In some embodiments, the one or more pharmaceutically acceptable excipients comprise about 1% by weight to about 8% by weight of one or more disintegrants based on the total weight of the pharmaceutically acceptable capsule. In some embodiments, the one or more pharmaceutically acceptable excipients comprise about 1% by weight to about 7% by weight of one or more disintegrants based on the total weight of the pharmaceutically acceptable capsule. In some embodiments, the one or more pharmaceutically acceptable excipients comprise about 1% by weight to about 6% by weight of one or more disintegrants based on the total weight of the pharmaceutically acceptable capsule. In some embodiments, the one or more pharmaceutically acceptable excipients comprise about 1% by weight to about 5% by weight of one or more disintegrants based on the total weight of the pharmaceutically acceptable capsule. In some embodiments, the one or more pharmaceutically acceptable excipients comprise about 1% by weight to about 4% by weight of one or more disintegrants based on the total weight of the pharmaceutically acceptable capsule. In some embodiments, the one or more pharmaceutically acceptable excipients comprise about 1% by weight to about 3% by weight of one or more disintegrants based on the total weight of the pharmaceutically acceptable capsule.

In some embodiments, the one or more pharmaceutically acceptable excipients comprise about 1% by weight of one or more disintegrants based on the total weight of the pharmaceutically acceptable capsule. In some embodiments, the one or more pharmaceutically acceptable excipients comprise about 2% by weight of one or more disintegrants based on the total weight of the pharmaceutically acceptable capsule. In some embodiments, the one or more pharmaceutically acceptable excipients comprise about 3% by weight of one or more disintegrants based on the total weight of the pharmaceutically acceptable capsule. In some embodiments, the one or more pharmaceutically acceptable excipients comprise about 4% by weight of one or more disintegrants based on the total weight of the pharmaceutically acceptable capsule. In some embodiments, the one or more pharmaceutically acceptable excipients comprise about 5% by weight of one or more disintegrants based on the total weight of the pharmaceutically acceptable capsule. In some embodiments, the one or more pharmaceutically acceptable excipients comprise about 6% by weight of one or more disintegrants based on the total weight of the pharmaceutically acceptable capsule. In some embodiments, the one or more pharmaceutically acceptable excipients comprise about 7% by weight of one or more disintegrants based on the total weight of the pharmaceutically acceptable capsule. In some embodiments, the one or more pharmaceutically acceptable excipients comprise about 8% by weight of one or more disintegrants based on the total weight of the pharmaceutically acceptable capsule. In some embodiments, the one or more pharmaceutically acceptable excipients comprise about 9% by weight of one or more disintegrants based on the total weight of the pharmaceutically acceptable capsule. In some embodiments, the one or more pharmaceutically acceptable excipients comprise about 10% by weight of one or more disintegrants based on the total weight of the pharmaceutically acceptable capsule. In some embodiments, the one or more pharmaceutically acceptable excipients comprise about 11% by weight of one or more disintegrants based on the total weight of the pharmaceutically acceptable capsule. In some embodiments, the one or more pharmaceutically acceptable excipients comprise about 12% by weight of one or more disintegrants based on the total weight of the pharmaceutically acceptable capsule. In some embodiments, the one or more pharmaceutically acceptable excipients comprise about 13% by weight of one or more disintegrants based on the total weight of the pharmaceutically acceptable capsule. In some embodiments, the one or more pharmaceutically acceptable excipients comprise about 14% by weight of one or more disintegrants based on the total weight of the pharmaceutically acceptable capsule. In some embodiments, the one or more pharmaceutically acceptable excipients comprise about 15% by weight of one or more disintegrants based on the total weight of the pharmaceutically acceptable capsule.

In some embodiments, the one or more pharmaceutically acceptable excipients comprise about 0.1% by weight to about 10% by weight of one or more lubricants based on the total weight of the pharmaceutically acceptable capsule. In some embodiments, the one or more pharmaceutically acceptable excipients comprise about 0.1% by weight to about 9% by weight of one or more lubricants based on the total weight of the pharmaceutically acceptable capsule. In some embodiments, the one or more pharmaceutically acceptable excipients comprise about 0.1% by weight to about 8% by weight of one or more lubricants based on the total weight of the pharmaceutically acceptable capsule. In some embodiments, the one or more pharmaceutically acceptable excipients comprise about 0.1% by weight to about 7% by weight of one or more lubricants based on the total weight of the pharmaceutically acceptable capsule. In some embodiments, the one or more pharmaceutically acceptable excipients comprise about 0.1% by weight to about 6% by weight of one or more lubricants based on the total weight of the pharmaceutically acceptable capsule. In some embodiments, the one or more pharmaceutically acceptable excipients comprise about 0.1% by weight to about 5% by weight of one or more lubricants based on the total weight of the pharmaceutically acceptable capsule. In some embodiments, the one or more pharmaceutically acceptable excipients comprise about 0.1% by weight to about 4% by weight of one or more lubricants based on the total weight of the pharmaceutically acceptable capsule. In some embodiments, the one or more pharmaceutically acceptable excipients comprise about 0.1% by weight to about 3% by weight of one or more lubricants based on the total weight of the pharmaceutically acceptable capsule. In some embodiments, the one or more pharmaceutically acceptable excipients comprise about 0.1% by weight to about 2% by weight of one or more lubricants based on the total weight of the pharmaceutically acceptable capsule.

In some embodiments, the one or more pharmaceutically acceptable excipients comprise about 0.1% by weight to about 1.9% by weight of one or more lubricants based on the total weight of the pharmaceutically acceptable capsule. In some embodiments, the one or more pharmaceutically acceptable excipients comprise about 0.1% by weight to about 1.8% by weight of one or more lubricants based on the total weight of the pharmaceutically acceptable capsule. In some embodiments, the one or more pharmaceutically acceptable excipients comprise about 0.1% by weight to about 1.7% by weight of one or more lubricants based on the total weight of the pharmaceutically acceptable capsule. In some embodiments, the one or more pharmaceutically acceptable excipients comprise about 0.1% by weight to about 1.6% by weight of one or more lubricants based on the total weight of the pharmaceutically acceptable capsule. In some embodiments, the one or more pharmaceutically acceptable excipients comprise about 0.1% by weight to about 1.5% by weight of one or more lubricants based on the total weight of the pharmaceutically acceptable capsule. In some embodiments, the one or more pharmaceutically acceptable excipients comprise about 0.1% by weight to about 1.4% by weight of one or more lubricants based on the total weight of the pharmaceutically acceptable capsule. In some embodiments, the one or more pharmaceutically acceptable excipients comprise about 0.1% by weight to about 1.3% by weight of one or more lubricants based on the total weight of the pharmaceutically acceptable capsule. In some embodiments, the one or more pharmaceutically acceptable excipients comprise about 0.1% by weight to about 1.2% by weight of one or more lubricants based on the total weight of the pharmaceutically acceptable capsule. In some embodiments, the one or more pharmaceutically acceptable excipients comprise about 0.1% by weight to about 1.1% by weight of one or more lubricants based on the total weight of the pharmaceutically acceptable capsule. In some embodiments, the one or more pharmaceutically acceptable excipients comprise about 0.1% by weight to about 1.0% by weight of one or more lubricants based on the total weight of the pharmaceutically acceptable capsule. In some embodiments, the one or more pharmaceutically acceptable excipients comprise about 0.1% by weight to about 0.9% by weight of one or more lubricants based on the total weight of the pharmaceutically acceptable capsule. In some embodiments, the one or more pharmaceutically acceptable excipients comprise about 0.1% by weight to about 0.8% by weight of one or more lubricants based on the total weight of the pharmaceutically acceptable capsule. In some embodiments, the one or more pharmaceutically acceptable excipients comprise about 0.1% by weight to about 0.7% by weight of one or more lubricants based on the total weight of the pharmaceutically acceptable capsule. In some embodiments, the one or more pharmaceutically acceptable excipients comprise about 0.1% by weight to about 0.6% by weight of one or more lubricants based on the total weight of the pharmaceutically acceptable capsule. In some embodiments, the one or more pharmaceutically acceptable excipients comprise about 0.1% by weight to about 0.5% by weight of one or more lubricants based on the total weight of the pharmaceutically acceptable capsule. In some embodiments, the one or more pharmaceutically acceptable excipients comprise about 0.1% by weight to about 0.4% by weight of one or more lubricants based on the total weight of the pharmaceutically acceptable capsule. In some embodiments, the one or more pharmaceutically acceptable excipients comprise about 0.1% by weight to about 0.3% by weight of one or more lubricants based on the total weight of the pharmaceutically acceptable capsule. In some embodiments, the one or more pharmaceutically acceptable excipients comprise about 0.1% by weight to about 0.2% by weight of one or more lubricants based on the total weight of the pharmaceutically acceptable capsule.

In some embodiments, the one or more pharmaceutically acceptable excipients comprise about 0.1% by weight of one or more lubricants based on the total weight of the pharmaceutically acceptable capsule. In some embodiments, the one or more pharmaceutically acceptable excipients comprise about 0.2% by weight of one or more lubricants based on the total weight of the pharmaceutically acceptable capsule. In some embodiments, the one or more pharmaceutically acceptable excipients comprise about 0.3% by weight of one or more lubricants based on the total weight of the pharmaceutically acceptable capsule. In some embodiments, the one or more pharmaceutically acceptable excipients comprise about 0.4% by weight of one or more lubricants based on the total weight of the pharmaceutically acceptable capsule. In some embodiments, the one or more pharmaceutically acceptable excipients comprise about 0.5% by weight of one or more lubricants based on the total weight of the pharmaceutically acceptable capsule. In some embodiments, the one or more pharmaceutically acceptable excipients comprise about 0.6% by weight of one or more lubricants based on the total weight of the pharmaceutically acceptable capsule. In some embodiments, the one or more pharmaceutically acceptable excipients comprise about 0.7% by weight of one or more lubricants based on the total weight of the pharmaceutically acceptable capsule. In some embodiments, the one or more pharmaceutically acceptable excipients comprise about 0.8% by weight of one or more lubricants based on the total weight of the pharmaceutically acceptable capsule. In some embodiments, the one or more pharmaceutically acceptable excipients comprise about 0.9% by weight of one or more lubricants based on the total weight of the pharmaceutically acceptable capsule. In some embodiments, the one or more pharmaceutically acceptable excipients comprise about 1.0% by weight of one or more lubricants based on the total weight of the pharmaceutically acceptable capsule.

In some embodiments, the pharmaceutically acceptable capsule comprises (a) about 1% by weight to about 30% by weight of the compound of Formula (I) based on the total weight of the pharmaceutically acceptable capsule; (b) about 20% by weight to about 90% by weight of one or more fillers based on the total weight of the pharmaceutically acceptable capsule; (c) about 1% by weight to about 20% by weight of one or more disintegrants based on the total weight of the pharmaceutically acceptable capsule; and (d) about 0.1% by weight to about 10% by weight of one or more lubricants based on the total weight of the pharmaceutically acceptable capsule.

In some embodiments, the pharmaceutically acceptable capsule consists essentially of: (a) about 1% by weight to about 30% by weight of the compound of Formula (I) based on the total weight of the pharmaceutically acceptable capsule; (b) about 20% by weight to about 90% by weight of one or more fillers based on the total weight of the pharmaceutically acceptable capsule; (c) about 1% by weight to about 20% by weight of one or more disintegrants based on the total weight of the pharmaceutically acceptable capsule; and (d) about 0.1% by weight to about 10% by weight of one or more lubricants based on the total weight of the pharmaceutically acceptable capsule.

In some embodiments, the pharmaceutically acceptable capsule comprises (a) about 5% by weight to about 25% by weight of the compound of Formula (I) based on the total weight of the pharmaceutically acceptable capsule; (b) about 60% by weight to about 90% by weight of one or more fillers based on the total weight of the pharmaceutically acceptable capsule; (c) about 1% by weight to about 15% by weight of one or more disintegrants based on the total weight of the pharmaceutically acceptable capsule; and (d) about 0.1% by weight to about 4% by weight of one or more lubricants based on the total weight of the pharmaceutically acceptable capsule.

In some embodiments, the pharmaceutically acceptable capsule consists essentially of (a) about 5% by weight to about 25% by weight of the compound of Formula (I) based on the total weight of the pharmaceutically acceptable capsule; (b) about 60% by weight to about 90% by weight of one or more fillers based on the total weight of the pharmaceutically acceptable capsule; (c) about 1% by weight to about 15% by weight of one or more disintegrants based on the total weight of the pharmaceutically acceptable capsule; and (d) about 0.1% by weight to about 4% by weight of one or more lubricants based on the total weight of the pharmaceutically acceptable capsule.

In some embodiments, the pharmaceutically acceptable capsule comprises (a) about 10% by weight to about 30% by weight of the compound of Formula (I) based on the total weight of the pharmaceutically acceptable capsule; (b) about 70% by weight to about 90% by weight of one or more fillers based on the total weight of the pharmaceutically acceptable capsule; (c) about 1% by weight to about 10% by weight of one or more disintegrants based on the total weight of the pharmaceutically acceptable capsule; and (d) about 0.1% by weight to about 3% by weight of one or more lubricants based on the total weight of the pharmaceutically acceptable capsule.

In some embodiments, the pharmaceutically acceptable capsule consists essentially of (a) about 10% by weight to about 30% by weight of the compound of Formula (I) based on the total weight of the pharmaceutically acceptable capsule; (b) about 70% by weight to about 90% by weight of one or more fillers based on the total weight of the pharmaceutically acceptable capsule; (c) about 1% by weight to about 10% by weight of one or more disintegrants based on the total weight of the pharmaceutically acceptable capsule; and (d) about 0.1% by weight to about 3% by weight of one or more lubricants based on the total weight of the pharmaceutically acceptable capsule.

In some embodiments, the one or more pharmaceutically acceptable excipients is one or more fillers selected from the group consisting of calcium phosphate, dicalcium phosphate, dicalcium phosphate dihydrate, calcium sulfate, calcium sulfate dihydrate, starch, calcium carbonate, magnesium carbonate, magnesium oxide, kaolin (natural hydrated aluminum silicate), sodium chloride, partially gelatinized starch, anhydrous lactose, lactose monohydrate, lactose dihydrate, trehalose dihydrate, spray dried lactose, sucrose, dextrose, dextrates, dextrin, cellulose, microcrystalline cellulose, silicified microcrystalline cellulose, powdered cellulose, partially depolymerized cellulose, mannitol, granulated mannitol, spray dried mannitol, maltodextrin, maltitol, confectioner's sugar, compressible sugar, sorbitol, starch and talc. In some embodiments, the one or more fillers is lactose monohydrate.

In some embodiments, the one or more disintegrants is one or more disintegrants selected from the group consisting of sodium starch glycolate, pregelatinized starch, clay, cellulose, alginic acid, alginate gum, polyvinylpyrrolidone, cross-linked polyvinylpyrrolidone, cross-linked calcium carboxymethylcellulose, cross-linked sodium carboxymethylcellulose, sodium croscarmellose, sodium carmellose, low substituted hydroxypropyl cellulose, low substituted hydroxypropyl cellulose sodium, guar gum, magnesium aluminum silicate, polacrilin potassium, powdered cellulose, sodium alginate and soy polysaccharides. In some embodiments, the one or more disintegrants is cross-linked polyvinylpyrrolidone (also referred to as crospovidone).

In some embodiments, the one or more lubricants is one or more lubricants selected from the group consisting of colloidal silica, magnesium trisilicate, talc, magnesium carbonate, magnesium oxide, glyceryl behaptate, mono, di and tri glyceryl behenate, bees wax, behenoyl polyoxyl-8 glycerides, hydrogenated vegetable oil, polyethylene glycol, ethylene oxide polymer, copolymer comprising poly(ethylene oxide) and poly(propylene oxide) (such as poloxomer 188), copolymer comprising polypropylene glycol and polyethylene glycol (such as poloxomer 407), sodium lauryl sulfate, magnesium stearate, aluminum stearate, calcium stearate, sodium stearyl fumarate, stearic acid, magnesium lauryl stearate, mixtures of magnesium stearate with sodium lauryl sulfate. In some embodiments, the one or more lubricants is magnesium stearate.

In some embodiments, the pharmaceutically acceptable capsule further comprises cross-linked polyvinylpyrrolidone and magnesium stearate. In some embodiments, the one or more pharmaceutically acceptable excipients is lactose monohydrate and the pharmaceutically acceptable capsule further comprises cross-linked polyvinylpyrrolidone and magnesium stearate.

In some embodiments, the pharmaceutically acceptable capsule is for oral administration.

In some embodiments, the pharmaceutically acceptable capsule is a solid dosage form.

In some embodiments, the pharmaceutically acceptable capsule comprises about 0.5 mg to about 5 mg, about 6 mg to about 14 mg, about 11 mg to about 19 mg, about 17 mg to about 25 mg, or about 28 mg to about 36 mg of the compound of Formula (I) as a crystalline dihydrate form. In some embodiments, the pharmaceutically acceptable capsule comprises about 1 mg to about 4 mg, about 8 mg to about 12 mg, about 13 mg to about 17 mg, about 19 mg to about 23 mg, or about 30 mg to about 34 mg of the compound of Formula (I) as a crystalline dihydrate form. In some embodiments, the pharmaceutically acceptable capsule comprises about 2.2 mg, about 10.8 mg, about 15.2 mg, about 21.7 mg, or about 32.5 mg of the compound of Formula (I) as a crystalline dihydrate form.

In some embodiments, the pharmaceutically acceptable capsule consists essentially of about 0.5 mg to about 5 mg, about 6 mg to about 14 mg, about 11 mg to about 19 mg, about 17 mg to about 25 mg, or about 28 mg to about 36 mg of the compound of Formula (I) as a crystalline dihydrate form. In some embodiments, the pharmaceutically acceptable capsule consists essentially of about 1 mg to about 4 mg, about 8 mg to about 12 mg, about 13 mg to about 17 mg, about 19 mg to about 23 mg, or about 30 mg to about 34 mg of the compound of Formula (I) as a crystalline dihydrate form. In some embodiments, the pharmaceutically acceptable capsule consists essentially of about 2.2 mg, about 10.8 mg, about 15.2 mg, about 21.7 mg, or about 32.5 mg of the compound of Formula (I) as a crystalline dihydrate form.

Also provided herein is a process of preparing a pharmaceutically acceptable unit formulation, the pharmaceutically acceptable unit formulation comprising:

(a) about 1% by weight to about 70% by weight, based on the weight of the pharmaceutically acceptable unit formulation, of a crystalline anhydrous form of a compound of Formula (I):

Formula (I)

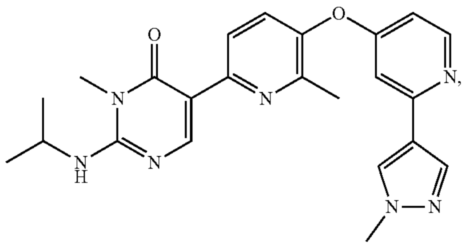

and one or more pharmaceutically acceptable excipients, wherein the one or more pharmaceutically acceptable excipients comprise:

(b) about 20% by weight to about 97% by weight of one or more fillers, based on the weight of the pharmaceutically acceptable unit formulation;

(c) about 1% by weight to about 20% by weight of one or more disintegrants, based on the weight of the pharmaceutically acceptable unit formulation; and (d) about 0.1% by weight to about 10% by weight of one or more lubricants, based on the weight of the pharmaceutically acceptable unit formulation the process comprising:

(i) blending the crystalline anhydrous form of a compound represented by Formula (I) with the one or more fillers and one or more disintegrants to produce a first blend; and (ii) blending the first blend with the one or more lubricants, thereby preparing the pharmaceutically acceptable unit formulation.

Also provided herein is a process of preparing a pharmaceutically acceptable unit formulation, the pharmaceutically acceptable unit formulation consisting essentially of:

(a) about 1% by weight to about 70% by weight, based on the weight of the pharmaceutically acceptable unit formulation, of a crystalline anhydrous form of a compound of Formula (I):

Formula (I)

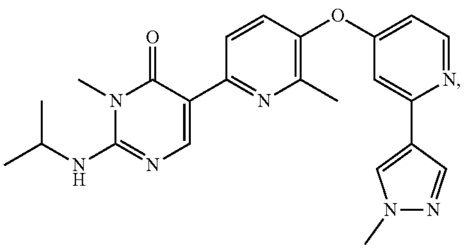

and one or more pharmaceutically acceptable excipients, wherein the one or more pharmaceutically acceptable excipients comprise:

(b) about 20% by weight to about 97% by weight of one or more fillers, based on the weight of the pharmaceutically acceptable unit formulation;

(c) about 1% by weight to about 20% by weight of one or more disintegrants, based on the weight of the pharmaceutically acceptable unit formulation; and (d) about 0.1% by weight to about 10% by weight of one or more lubricants, based on the weight of the pharmaceutically acceptable unit formulation the process comprising:

(i) blending the crystalline anhydrous form of a compound represented by Formula (I) with the one or more fillers and one or more disintegrants to produce a first blend; and (ii) blending the first blend with the one or more lubricants, thereby preparing the pharmaceutically acceptable unit formulation.

Also provided herein is a process of preparing a pharmaceutically acceptable unit formulation, the pharmaceutically acceptable unit formulation comprising:

(a) about 1% by weight to about 70% by weight, based on the weight of the pharmaceutically acceptable unit formulation of a crystalline anhydrous form of a compound of Formula (I):

Formula (I)

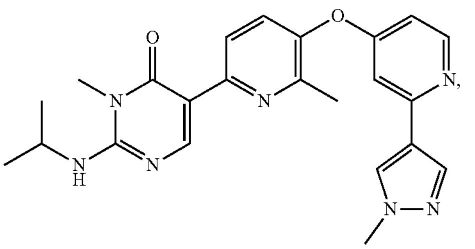

and one or more pharmaceutically acceptable excipients, wherein the one or more pharmaceutically acceptable excipients comprise:

(b) about 20% by weight to about 97% by weight of one or more fillers, based on the weight of the pharmaceutically acceptable unit formulation;

(c) about 1% by weight to about 20% by weight of one or more disintegrants, based on the weight of the pharmaceutically acceptable unit formulation; and (d) about 0.1% by weight to about 10% by weight of one or more lubricants, based on the weight of the pharmaceutically acceptable unit formulation the process comprising:

(i) blending the crystalline anhydrous form of a compound represented by Formula (I) with the one or more fillers to produce a first blend;

(ii) blending the first blend with one or more disintegrants to produce a second blend; and (iii) blending the second blend with the one or more lubricants, thereby preparing the pharmaceutically acceptable unit formulation.

Also provided herein is a process of preparing a pharmaceutically acceptable unit formulation, the pharmaceutically acceptable unit formulation consisting essentially of:

(a) about 1% by weight to about 70% by weight, based on the weight of the pharmaceutically acceptable unit formulation of a crystalline anhydrous form of a compound of Formula (I):

Formula (I)

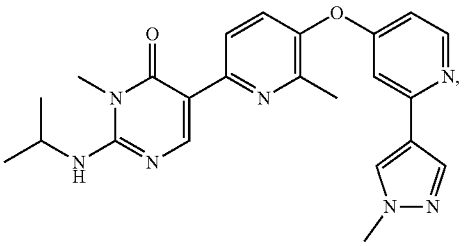

and one or more pharmaceutically acceptable excipients, wherein the one or more pharmaceutically acceptable excipients comprise:

(b) about 20% by weight to about 97% by weight of one or more fillers, based on the weight of the pharmaceutically acceptable unit formulation;

(c) about 1% by weight to about 20% by weight of one or more disintegrants, based on the weight of the pharmaceutically acceptable unit formulation; and (d) about 0.1% by weight to about 10% by weight of one or more lubricants, based on the weight of the pharmaceutically acceptable unit formulation the process comprising:

(i) blending the crystalline anhydrous form of a compound represented by Formula (I) with the one or more fillers to produce a first blend;

(ii) blending the first blend with one or more disintegrants to produce a second blend; and (iii) blending the second blend with the one or more lubricants, thereby preparing the pharmaceutically acceptable unit formulation.

Also provided herein is a process of preparing a pharmaceutically acceptable unit formulation, the pharmaceutically acceptable unit formulation comprising:

(a) about 1% by weight to about 70% by weight, based on the weight of the pharmaceutically acceptable unit formulation of a crystalline anhydrous form of a compound of Formula (I):

Formula (I)

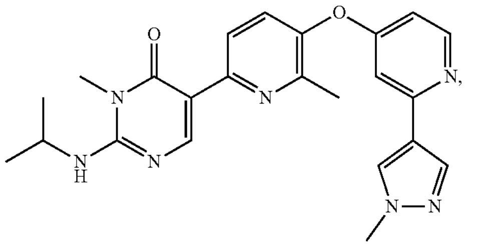

and one or more pharmaceutically acceptable excipients, wherein the one or more pharmaceutically acceptable excipients comprise:

(b) about 20% by weight to about 97% by weight of one or more fillers, based on the weight of the pharmaceutically acceptable unit formulation;

(c) about 1% by weight to about 20% by weight of one or more disintegrants, based on the weight of the pharmaceutically acceptable unit formulation; and (d) about 0.1% by weight to about 10% by weight of one or more lubricants, based on the weight of the pharmaceutically acceptable unit formulation the process comprising:

(i) blending the crystalline anhydrous form of a compound represented by Formula (I) with the one or more fillers to produce a first blend;

(ii) blending the first blend with a second blend comprising one or more disintegrants and one or more fillers and optionally a third blend comprising one or more fillers to produce a fourth blend; and (iii) blending the fourth blend with the one or more lubricants, thereby preparing the pharmaceutically acceptable unit formulation.

Also provided herein is a process of preparing a pharmaceutically acceptable unit formulation, the pharmaceutically acceptable unit formulation consisting essentially of:

(a) about 1% by weight to about 70% by weight, based on the weight of the pharmaceutically acceptable unit formulation of a crystalline anhydrous form of a compound of Formula (I):

Formula (I)

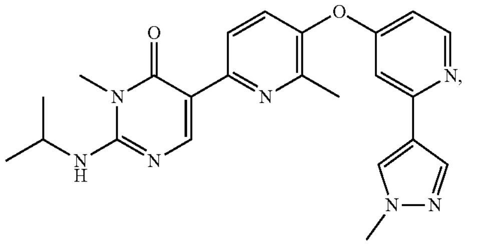

and one or more pharmaceutically acceptable excipients, wherein the one or more pharmaceutically acceptable excipients comprise:

(b) about 20% by weight to about 97% by weight of one or more fillers, based on the weight of the pharmaceutically acceptable unit formulation;

(c) about 1% by weight to about 20% by weight of one or more disintegrants, based on the weight of the pharmaceutically acceptable unit formulation; and (d) about 0.1% by weight to about 10% by weight of one or more lubricants, based on the weight of the pharmaceutically acceptable unit formulation the process comprising:

(i) blending the crystalline anhydrous form of a compound represented by Formula (I) with the one or more fillers to produce a first blend;

(ii) blending the first blend with a second blend comprising one or more disintegrants and one or more fillers and optionally a third blend comprising one or more fillers to produce a fourth blend; and (iii) blending the fourth blend with the one or more lubricants, thereby preparing the pharmaceutically acceptable unit formulation.

In some embodiments, the pharmaceutically acceptable unit formulation comprises about 1% by weight to about 60% by weight, based on the weight of the pharmaceutically acceptable unit formulation, of a crystalline anhydrous form of a compound of Formula (I). In some embodiments, the pharmaceutically acceptable unit formulation comprises about 1% by weight to about 50% by weight, based on the weight of the pharmaceutically acceptable unit formulation, of a crystalline anhydrous form of a compound of Formula (I). In some embodiments, the pharmaceutically acceptable unit formulation comprises about 1% by weight to about 40% by weight, based on the weight of the pharmaceutically acceptable unit formulation, of a crystalline anhydrous form of a compound of Formula (I). In some embodiments, the pharmaceutically acceptable unit formulation comprises about 1% by weight to about 30% by weight, based on the weight of the pharmaceutically acceptable unit formulation, of a crystalline anhydrous form of a compound of Formula (I). In some embodiments, the pharmaceutically acceptable unit formulation comprises about 1% by weight to about 20% by weight, based on the weight of the pharmaceutically acceptable unit formulation, of a crystalline anhydrous form of a compound of Formula (I).

In some embodiments, the pharmaceutically acceptable unit formulation consists essentially of about 1% by weight to about 60% by weight, based on the weight of the pharmaceutically acceptable unit formulation, of a crystalline anhydrous form of a compound of Formula (I). In some embodiments, the pharmaceutically acceptable unit formulation consists essentially of about 1% by weight to about 50% by weight, based on the weight of the pharmaceutically acceptable unit formulation, of a crystalline anhydrous form of a compound of Formula (I). In some embodiments, the pharmaceutically acceptable unit formulation consists essentially of about 1% by weight to about 40% by weight, based on the weight of the pharmaceutically acceptable unit formulation, of a crystalline anhydrous form of a compound of Formula (I). In some embodiments, the pharmaceutically acceptable unit formulation consists essentially of about 1% by weight to about 30% by weight, based on the weight of the pharmaceutically acceptable unit formulation, of a crystalline anhydrous form of a compound of Formula (I). In some embodiments, the pharmaceutically acceptable unit formulation consists essentially of about 1% by weight to about 20% by weight, based on the weight of the pharmaceutically acceptable unit formulation, of a crystalline anhydrous form of a compound of Formula (I).

In some embodiments, the pharmaceutically acceptable unit formulation comprises about 1% by weight to about 70% by weight of the crystalline anhydrous form of the compound of Formula (I) based on the weight of the pharmaceutically acceptable unit formulation. In some embodiments, the pharmaceutically acceptable unit formulation comprises about 1% by weight to about 65% by weight of the crystalline anhydrous form of the compound of Formula (I) based on the weight of the pharmaceutically acceptable unit formulation. In some embodiments, the pharmaceutically acceptable unit formulation comprises about 1% by weight to about 60% by weight of the crystalline anhydrous form of the compound of Formula (I) based on the weight of the pharmaceutically acceptable unit formulation. In some embodiments, the pharmaceutically acceptable unit formulation comprises about 1% by weight to about 55% by weight of the crystalline anhydrous form of the compound of Formula (I) based on the weight of the pharmaceutically acceptable unit formulation. In some embodiments, the pharmaceutically acceptable unit formulation comprises about 1% by weight to about 50% by weight of the crystalline anhydrous form of the compound of Formula (I) based on the weight of the pharmaceutically acceptable unit formulation. In some embodiments, the pharmaceutically acceptable unit formulation comprises about 1% by weight to about 45% by weight of the crystalline anhydrous form of the compound of Formula (I) based on the weight of the pharmaceutically acceptable unit formulation. In some embodiments, the pharmaceutically acceptable unit formulation comprises about 1% by weight to about 40% by weight of the crystalline anhydrous form of the compound of Formula (I) based on the weight of the pharmaceutically acceptable unit formulation. In some embodiments, the pharmaceutically acceptable unit formulation comprises about 1% by weight to about 35% by weight of the crystalline anhydrous form of the compound of Formula (I) based on the weight of the pharmaceutically acceptable unit formulation. In some embodiments, the pharmaceutically acceptable unit formulation comprises about 1% by weight to about 30% by weight of the crystalline anhydrous form of the compound of Formula (I) based on the weight of the pharmaceutically acceptable unit formulation. In some embodiments, the pharmaceutically acceptable unit formulation comprises about 1% by weight to about 25% by weight of the crystalline anhydrous form of the compound of Formula (I) based on the weight of the pharmaceutically acceptable unit formulation. In some embodiments, the pharmaceutically acceptable unit formulation comprises about 1% by weight to about 20% by weight of the crystalline anhydrous form of the compound of Formula (I) based on the weight of the pharmaceutically acceptable unit formulation. In some embodiments, the pharmaceutically acceptable unit formulation comprises about 1% by weight to about 15% by weight of the crystalline anhydrous form of the compound of Formula (I) based on the weight of the pharmaceutically acceptable unit formulation. In some embodiments, the pharmaceutically acceptable unit formulation comprises about 1% by weight to about 10% by weight of the crystalline anhydrous form of the compound of Formula (I) based on the weight of the pharmaceutically acceptable unit formulation.

In some embodiments, the pharmaceutically acceptable unit formulation consists essentially of about 1% by weight to about 70% by weight of the crystalline anhydrous form of the compound of Formula (I) based on the weight of the pharmaceutically acceptable unit formulation. In some embodiments, the pharmaceutically acceptable unit formulation consists essentially of about 1% by weight to about 65% by weight of the crystalline anhydrous form of the compound of Formula (I) based on the weight of the pharmaceutically acceptable unit formulation. In some embodiments, the pharmaceutically acceptable unit formulation consists essentially of about 1% by weight to about 60% by weight of the crystalline anhydrous form of the compound of Formula (I) based on the weight of the pharmaceutically acceptable unit formulation. In some embodiments, the pharmaceutically acceptable unit formulation consists essentially of about 1% by weight to about 55% by weight of the crystalline anhydrous form of the compound of Formula (I) based on the weight of the pharmaceutically acceptable unit formulation. In some embodiments, the pharmaceutically acceptable unit formulation consists essentially of about 1% by weight to about 50% by weight of the crystalline anhydrous form of the compound of Formula (I) based on the weight of the pharmaceutically acceptable unit formulation. In some embodiments, the pharmaceutically acceptable unit formulation consists essentially of about 1% by weight to about 45% by weight of the crystalline anhydrous form of the compound of Formula (I) based on the weight of the pharmaceutically acceptable unit formulation. In some embodiments, the pharmaceutically acceptable unit formulation consists essentially of about 1% by weight to about 40% by weight of the crystalline anhydrous form of the compound of Formula (I) based on the weight of the pharmaceutically acceptable unit formulation. In some embodiments, the pharmaceutically acceptable unit formulation consists essentially of about 1% by weight to about 35% by weight of the crystalline anhydrous form of the compound of Formula (I) based on the weight of the pharmaceutically acceptable unit formulation. In some embodiments, the pharmaceutically acceptable unit formulation consists essentially of about 1% by weight to about 30% by weight of the crystalline anhydrous form of the compound of Formula (I) based on the weight of the pharmaceutically acceptable unit formulation. In some embodiments, the pharmaceutically acceptable unit formulation consists essentially of about 1% by weight to about 25% by weight of the crystalline anhydrous form of the compound of Formula (I) based on the weight of the pharmaceutically acceptable unit formulation. In some embodiments, the pharmaceutically acceptable unit formulation consists essentially of about 1% by weight to about 20% by weight of the crystalline anhydrous form of the compound of Formula (I) based on the weight of the pharmaceutically acceptable unit formulation. In some embodiments, the pharmaceutically acceptable unit formulation consists essentially of about 1% by weight to about 15% by weight of the crystalline anhydrous form of the compound of Formula (I) based on the weight of the pharmaceutically acceptable unit formulation. In some embodiments, the pharmaceutically acceptable unit formulation consists essentially of about 1% by weight to about 10% by weight of the crystalline anhydrous form of the compound of Formula (I) based on the weight of the pharmaceutically acceptable unit formulation.

In some embodiments, the pharmaceutically acceptable unit formulation comprises about 5% by weight to about 30% by weight of the crystalline anhydrous form of the compound of Formula (I) based on the weight of the pharmaceutically acceptable unit formulation. In some embodiments, the pharmaceutically acceptable unit formulation comprises about 5% by weight to about 25% by weight of the crystalline anhydrous form of the compound of Formula (I) based on the weight of the pharmaceutically acceptable unit formulation. In some embodiments, the pharmaceutically acceptable unit formulation comprises about 5% by weight to about 20% by weight of the crystalline anhydrous form of the compound of Formula (I) based on the weight of the pharmaceutically acceptable unit formulation. In some embodiments, the pharmaceutically acceptable unit formulation comprises about 5% by weight to about 15% by weight of the crystalline anhydrous form of the compound of Formula (I) based on the weight of the pharmaceutically acceptable unit formulation. In some embodiments, the pharmaceutically acceptable unit formulation comprises about 5% by weight to about 10% by weight of the crystalline anhydrous form of the compound of Formula (I) based on the weight of the pharmaceutically acceptable unit formulation.

In some embodiments, the pharmaceutically acceptable unit formulation consists essentially of about 5% by weight to about 30% by weight of the crystalline anhydrous form of the compound of Formula (I) based on the weight of the pharmaceutically acceptable unit formulation. In some embodiments, the pharmaceutically acceptable unit formulation consists essentially of about 5% by weight to about 25% by weight of the crystalline anhydrous form of the compound of Formula (I) based on the weight of the pharmaceutically acceptable unit formulation. In some embodiments, the pharmaceutically acceptable unit formulation consists essentially of about 5% by weight to about 20% by weight of the crystalline anhydrous form of the compound of Formula (I) based on the weight of the pharmaceutically acceptable unit formulation. In some embodiments, the pharmaceutically acceptable unit formulation consists essentially of about 5% by weight to about 15% by weight of the crystalline anhydrous form of the compound of Formula (I) based on the weight of the pharmaceutically acceptable unit formulation. In some embodiments, the pharmaceutically acceptable unit formulation consists essentially of about 5% by weight to about 10% by weight of the crystalline anhydrous form of the compound of Formula (I) based on the weight of the pharmaceutically acceptable unit formulation.

In some embodiments, the pharmaceutically acceptable unit formulation comprises about 10% to about 30% of the compound of Formula (I) based on the weight of the pharmaceutically acceptable unit formulation. In some embodiments, the pharmaceutically acceptable unit formulation comprises about 10% to about 25% of the compound of Formula (I) based on the weight of the pharmaceutically acceptable unit formulation. In some embodiments, the pharmaceutically acceptable unit formulation comprises about 10% to about 20% of the compound of Formula (I) based on the weight of the pharmaceutically acceptable unit formulation. In some embodiments, the pharmaceutically acceptable unit formulation comprises about 10% by weight to about 15% by weight of the crystalline anhydrous form of the compound of Formula (I) based on the weight of the pharmaceutically acceptable unit formulation.

In some embodiments, the pharmaceutically acceptable unit formulation consists essentially of about 10% to about 30% of the crystalline anhydrous form of the compound of Formula (I) based on the weight of the pharmaceutically acceptable unit formulation. In some embodiments, the pharmaceutically acceptable unit formulation consists essentially of about 10% to about 25% of the crystalline anhydrous form of the compound of Formula (I) based on the weight of the pharmaceutically acceptable unit formulation. In some embodiments, the pharmaceutically acceptable unit formulation consists essentially of about 10% to about 20% of the crystalline anhydrous form of the compound of Formula (I) based on the weight of the pharmaceutically acceptable unit formulation. In some embodiments, the pharmaceutically acceptable unit formulation consists essentially of about 10% by weight to about 15% by weight of the crystalline anhydrous form of the compound of Formula (I) based on the weight of the pharmaceutically acceptable unit formulation.

In some embodiments, the pharmaceutically acceptable unit formulation comprises about 1% by weight to about 30% by weight of the crystalline anhydrous form of the compound of Formula (I) based on the weight of the pharmaceutically acceptable unit formulation. In some embodiments, the pharmaceutically acceptable unit formulation comprises about 1% by weight to about 10% by weight of the crystalline anhydrous form of the compound of Formula (I) based on the weight of the pharmaceutically acceptable unit formulation. In some embodiments, the pharmaceutically acceptable unit formulation comprises about 10% to about 20% of the compound of Formula (I) based on the weight of the pharmaceutically acceptable unit formulation. In some embodiments, the pharmaceutically acceptable unit formulation comprises about 10% by weight to about 15% by weight of the crystalline anhydrous form of the compound of Formula (I) based on the weight of the pharmaceutically acceptable unit formulation.

In some embodiments, the pharmaceutically acceptable unit formulation consists essentially of about 1% by weight to about 30% by weight of the crystalline anhydrous form of the compound of Formula (I) based on the weight of the pharmaceutically acceptable unit formulation. In some embodiments, the pharmaceutically acceptable unit formulation consists essentially of about 1% by weight to about 10% by weight of the crystalline anhydrous form of the compound of Formula (I) based on the weight of the pharmaceutically acceptable unit formulation. In some embodiments, the pharmaceutically acceptable unit formulation consists essentially of about 10% to about 20% of the crystalline anhydrous form of the compound of Formula (I) based on the weight of the pharmaceutically acceptable unit formulation. In some embodiments, the pharmaceutically acceptable unit formulation consists essentially of about 10% by weight to about 15% by weight of the crystalline anhydrous form of the compound of Formula (I) based on the weight of the pharmaceutically acceptable unit formulation.

In some embodiments, the one or more pharmaceutically acceptable excipients comprise about 20% by weight to about 90% by weight of one or more fillers based on the weight of the pharmaceutically acceptable unit formulation. In some embodiments, the one or more pharmaceutically acceptable excipients comprise about 20% by weight to about 85% by weight of one or more fillers based on the weight of the pharmaceutically acceptable unit formulation. In some embodiments, the one or more pharmaceutically acceptable excipients comprise about 20% by weight to about 80% by weight of one or more fillers based on the weight of the pharmaceutically acceptable unit formulation. In some embodiments, the one or more pharmaceutically acceptable excipients comprise about 20% by weight to about 75% by weight of one or more fillers based on the weight of the pharmaceutically acceptable unit formulation. In some embodiments, the one or more pharmaceutically acceptable excipients comprise about 20% by weight to about 70% by weight of one or more fillers based on the weight of the pharmaceutically acceptable unit formulation. In some embodiments, the one or more pharmaceutically acceptable excipients comprise about 20% by weight to about 65% by weight of one or more fillers based on the weight of the pharmaceutically acceptable unit formulation. In some embodiments, the one or more pharmaceutically acceptable excipients comprise about 20% by weight to about 60% by weight of one or more fillers based on the weight of the pharmaceutically acceptable unit formulation. In some embodiments, the one or more pharmaceutically acceptable excipients comprise about 20% by weight to about 55% by weight of one or more fillers based on the weight of the pharmaceutically acceptable unit formulation. In some embodiments, the one or more pharmaceutically acceptable excipients comprise about 20% by weight to about 50% by weight of one or more fillers based on the weight of the pharmaceutically acceptable unit formulation. In some embodiments, the one or more pharmaceutically acceptable excipients comprise about 20% by weight to about 45% by weight of one or more fillers based on the weight of the pharmaceutically acceptable unit formulation. In some embodiments, the one or more pharmaceutically acceptable excipients comprise about 20% by weight to about 40% by weight of one or more fillers based on the weight of the pharmaceutically acceptable unit formulation. In some embodiments, the one or more pharmaceutically acceptable excipients comprise about 20% by weight to about 35% by weight of one or more fillers based on the weight of the pharmaceutically acceptable unit formulation. In some embodiments, the one or more pharmaceutically acceptable excipients comprise about 20% by weight to about 30% by weight of one or more fillers based on the weight of the pharmaceutically acceptable unit formulation. In some embodiments, the one or more pharmaceutically acceptable excipients comprise about 20% by weight to about 25% by weight of one or more fillers based on the weight of the pharmaceutically acceptable unit formulation.

In some embodiments, the one or more pharmaceutically acceptable excipients comprise about 30% by weight to about 90% by weight of one or more fillers based on the weight of the pharmaceutically acceptable unit formulation. In some embodiments, the one or more pharmaceutically acceptable excipients comprise about 30% by weight to about 80% by weight of one or more fillers based on the weight of the pharmaceutically acceptable unit formulation. In some embodiments, the one or more pharmaceutically acceptable excipients comprise about 30% by weight to about 70% by weight of one or more fillers based on the weight of the pharmaceutically acceptable unit formulation. In some embodiments, the one or more pharmaceutically acceptable excipients comprise about 30% by weight to about 60% by weight of one or more fillers based on the weight of the pharmaceutically acceptable unit formulation. In some embodiments, the one or more pharmaceutically acceptable excipients comprise about 30% by weight to about 50% by weight of one or more fillers based on the weight of the pharmaceutically acceptable unit formulation. In some embodiments, the one or more pharmaceutically acceptable excipients comprise about 30% by weight to about 40% by weight of one or more fillers based on the weight of the pharmaceutically acceptable unit formulation.

In some embodiments, the one or more pharmaceutically acceptable excipients comprise about 40% by weight to about 90% by weight of one or more fillers based on the weight of the pharmaceutically acceptable unit formulation. In some embodiments, the one or more pharmaceutically acceptable excipients comprise about 40% by weight to about 80% by weight of one or more fillers based on the weight of the pharmaceutically acceptable unit formulation. In some embodiments, the one or more pharmaceutically acceptable excipients comprise about 40% by weight to about 70% by weight of one or more fillers based on the weight of the pharmaceutically acceptable unit formulation. In some embodiments, the one or more pharmaceutically acceptable excipients comprise about 40% by weight to about 60% by weight of one or more fillers based on the weight of the pharmaceutically acceptable unit formulation. In some embodiments, the one or more pharmaceutically acceptable excipients comprise about 40% by weight to about 50% by weight of one or more fillers based on the weight of the pharmaceutically acceptable unit formulation.

In some embodiments, the one or more pharmaceutically acceptable excipients comprise about 50% by weight to about 90% by weight of one or more fillers based on the weight of the pharmaceutically acceptable unit formulation. In some embodiments, the one or more pharmaceutically acceptable excipients comprise about 50% by weight to about 80% by weight of one or more fillers based on the weight of the pharmaceutically acceptable unit formulation. In some embodiments, the one or more pharmaceutically acceptable excipients comprise about 50% by weight to about 70% by weight of one or more fillers based on the weight of the pharmaceutically acceptable unit formulation. In some embodiments, the one or more pharmaceutically acceptable excipients comprise about 50% by weight to about 60% by weight of one or more fillers based on the weight of the pharmaceutically acceptable unit formulation.

In some embodiments, the one or more pharmaceutically acceptable excipients comprise about 60% by weight to about 90% by weight of one or more fillers based on the weight of the pharmaceutically acceptable unit formulation. In some embodiments, the one or more pharmaceutically acceptable excipients comprise about 60% by weight to about 80% by weight of one or more fillers based on the weight of the pharmaceutically acceptable unit formulation. In some embodiments, the one or more pharmaceutically acceptable excipients comprise about 60% by weight to about 70% by weight of one or more fillers based on the weight of the pharmaceutically acceptable unit formulation.

In some embodiments, the one or more pharmaceutically acceptable excipients comprise about 70% by weight to about 90% by weight of one or more fillers based on the weight of the pharmaceutically acceptable unit formulation. In some embodiments, the one or more pharmaceutically acceptable excipients comprise about 70% by weight to about 80% by weight of one or more fillers based on the weight of the pharmaceutically acceptable unit formulation.

In some embodiments, the one or more pharmaceutically acceptable excipients comprise about 80% by weight to about 90% by weight of one or more fillers based on the weight of the pharmaceutically acceptable unit formulation.

In some embodiments, the one or more pharmaceutically acceptable excipients comprise about 1% by weight to about 20% by weight of one or more disintegrants based on the weight of the pharmaceutically acceptable unit formulation. In some embodiments, the one or more pharmaceutically acceptable excipients comprise about 1% by weight to about 15% by weight of one or more disintegrants based on the weight of the pharmaceutically acceptable unit formulation. In some embodiments, the one or more pharmaceutically acceptable excipients comprise about 1% by weight to about 14% by weight of one or more disintegrants based on the weight of the pharmaceutically acceptable unit formulation. In some embodiments, the one or more pharmaceutically acceptable excipients comprise about 1% by weight to about 13% by weight of one or more disintegrants based on the weight of the pharmaceutically acceptable unit formulation. In some embodiments, the one or more pharmaceutically acceptable excipients comprise about 1% by weight to about 12% by weight of one or more disintegrants based on the weight of the pharmaceutically acceptable unit formulation.

In some embodiments, the one or more pharmaceutically acceptable excipients comprise about 1% by weight to about 11% by weight of one or more disintegrants based on the weight of the pharmaceutically acceptable unit formulation. In some embodiments, the one or more pharmaceutically acceptable excipients comprise about 1% by weight to about 10% by weight of one or more disintegrants based on the weight of the pharmaceutically acceptable unit formulation. In some embodiments, the one or more pharmaceutically acceptable excipients comprise about 1% by weight to about 9% by weight of one or more disintegrants based on the weight of the pharmaceutically acceptable unit formulation. In some embodiments, the one or more pharmaceutically acceptable excipients comprise about 1% by weight to about 8% by weight of one or more disintegrants based on the weight of the pharmaceutically acceptable unit formulation. In some embodiments, the one or more pharmaceutically acceptable excipients comprise about 1% by weight to about 7% by weight of one or more disintegrants based on the weight of the pharmaceutically acceptable unit formulation. In some embodiments, the one or more pharmaceutically acceptable excipients comprise about 1% by weight to about 6% by weight of one or more disintegrants based on the weight of the pharmaceutically acceptable unit formulation. In some embodiments, the one or more pharmaceutically acceptable excipients comprise about 1% by weight to about 5% by weight of one or more disintegrants based on the weight of the pharmaceutically acceptable unit formulation. In some embodiments, the one or more pharmaceutically acceptable excipients comprise about 1% by weight to about 4% by weight of one or more disintegrants based on the weight of the pharmaceutically acceptable unit formulation. In some embodiments, the one or more pharmaceutically acceptable excipients comprise about 1% by weight to about 3% by weight of one or more disintegrants based on the weight of the pharmaceutically acceptable unit formulation.

In some embodiments, the one or more pharmaceutically acceptable excipients comprise about 1% by weight of one or more disintegrants based on the weight of the pharmaceutically acceptable unit formulation. In some embodiments, the one or more pharmaceutically acceptable excipients comprise about 2% by weight of one or more disintegrants based on the weight of the pharmaceutically acceptable unit formulation. In some embodiments, the one or more pharmaceutically acceptable excipients comprise about 3% by weight of one or more disintegrants based on the weight of the pharmaceutically acceptable unit formulation. In some embodiments, the one or more pharmaceutically acceptable excipients comprise about 4% by weight of one or more disintegrants based on the weight of the pharmaceutically acceptable unit formulation. In some embodiments, the one or more pharmaceutically acceptable excipients comprise about 5% by weight of one or more disintegrants based on the weight of the pharmaceutically acceptable unit formulation. In some embodiments, the one or more pharmaceutically acceptable excipients comprise about 6% by weight of one or more disintegrants based on the weight of the pharmaceutically acceptable unit formulation. In some embodiments, the one or more pharmaceutically acceptable excipients comprise about 7% by weight of one or more disintegrants based on the weight of the pharmaceutically acceptable unit formulation. In some embodiments, the one or more pharmaceutically acceptable excipients comprise about 8% by weight of one or more disintegrants based on the weight of the pharmaceutically acceptable unit formulation. In some embodiments, the one or more pharmaceutically acceptable excipients comprise about 9% by weight of one or more disintegrants based on the weight of the pharmaceutically acceptable unit formulation. In some embodiments, the one or more pharmaceutically acceptable excipients comprise about 10% by weight of one or more disintegrants based on the weight of the pharmaceutically acceptable unit formulation. In some embodiments, the one or more pharmaceutically acceptable excipients comprise about 11% by weight of one or more disintegrants based on the weight of the pharmaceutically acceptable unit formulation. In some embodiments, the one or more pharmaceutically acceptable excipients comprise about 12% by weight of one or more disintegrants based on the weight of the pharmaceutically acceptable unit formulation. In some embodiments, the one or more pharmaceutically acceptable excipients comprise about 13% by weight of one or more disintegrants based on the weight of the pharmaceutically acceptable unit formulation. In some embodiments, the one or more pharmaceutically acceptable excipients comprise about 14% by weight of one or more disintegrants based on the weight of the pharmaceutically acceptable unit formulation. In some embodiments, the one or more pharmaceutically acceptable excipients comprise about 15% by weight of one or more disintegrants based on the weight of the pharmaceutically acceptable unit formulation.

In some embodiments, the one or more pharmaceutically acceptable excipients comprise about 0.1% by weight to about 10% by weight of one or more lubricants based on the weight of the pharmaceutically acceptable unit formulation. In some embodiments, the one or more pharmaceutically acceptable excipients comprise about 0.1% by weight to about 9% by weight of one or more lubricants based on the weight of the pharmaceutically acceptable unit formulation. In some embodiments, the one or more pharmaceutically acceptable excipients comprise about 0.1% by weight to about 8% by weight of one or more lubricants based on the weight of the pharmaceutically acceptable unit formulation. In some embodiments, the one or more pharmaceutically acceptable excipients comprise about 0.1% by weight to about 7% by weight of one or more lubricants based on the weight of the pharmaceutically acceptable unit formulation. In some embodiments, the one or more pharmaceutically acceptable excipients comprise about 0.1% by weight to about 6% by weight of one or more lubricants based on the weight of the pharmaceutically acceptable unit formulation. In some embodiments, the one or more pharmaceutically acceptable excipients comprise about 0.1% by weight to about 5% by weight of one or more lubricants based on the weight of the pharmaceutically acceptable unit formulation. In some embodiments, the one or more pharmaceutically acceptable excipients comprise about 0.1% by weight to about 4% by weight of one or more lubricants based on the weight of the pharmaceutically acceptable unit formulation. In some embodiments, the one or more pharmaceutically acceptable excipients comprise about 0.1% by weight to about 3% by weight of one or more lubricants based on the weight of the pharmaceutically acceptable unit formulation. In some embodiments, the one or more pharmaceutically acceptable excipients comprise about 0.1% by weight to about 2% by weight of one or more lubricants based on the weight of the pharmaceutically acceptable unit formulation.

In some embodiments, the one or more pharmaceutically acceptable excipients comprise about 0.1% by weight to about 1.9% by weight of one or more lubricants based on the weight of the pharmaceutically acceptable unit formulation. In some embodiments, the one or more pharmaceutically acceptable excipients comprise about 0.1% by weight to about 1.8% by weight of one or more lubricants based on the weight of the pharmaceutically acceptable unit formulation. In some embodiments, the one or more pharmaceutically acceptable excipients comprise about 0.1% by weight to about 1.7% by weight of one or more lubricants based on the weight of the pharmaceutically acceptable unit formulation. In some embodiments, the one or more pharmaceutically acceptable excipients comprise about 0.1% by weight to about 1.6% by weight of one or more lubricants based on the weight of the pharmaceutically acceptable unit formulation. In some embodiments, the one or more pharmaceutically acceptable excipients comprise about 0.1% by weight to about 1.5% by weight of one or more lubricants based on the weight of the pharmaceutically acceptable unit formulation. In some embodiments, the one or more pharmaceutically acceptable excipients comprise about 0.1% by weight to about 1.4% by weight of one or more lubricants based on the weight of the pharmaceutically acceptable unit formulation. In some embodiments, the one or more pharmaceutically acceptable excipients comprise about 0.1% by weight to about 1.3% by weight of one or more lubricants based on the weight of the pharmaceutically acceptable unit formulation. In some embodiments, the one or more pharmaceutically acceptable excipients comprise about 0.1% by weight to about 1.2% by weight of one or more lubricants based on the weight of the pharmaceutically acceptable unit formulation. In some embodiments, the one or more pharmaceutically acceptable excipients comprise about 0.1% by weight to about 1.1% by weight of one or more lubricants based on the weight of the pharmaceutically acceptable unit formulation. In some embodiments, the one or more pharmaceutically acceptable excipients comprise about 0.1% by weight to about 1.0% by weight of one or more lubricants based on the weight of the pharmaceutically acceptable unit formulation. In some embodiments, the one or more pharmaceutically acceptable excipients comprise about 0.1% by weight to about 0.9% by weight of one or more lubricants based on the weight of the pharmaceutically acceptable unit formulation. In some embodiments, the one or more pharmaceutically acceptable excipients comprise about 0.1% by weight to about 0.8% by weight of one or more lubricants based on the weight of the pharmaceutically acceptable unit formulation. In some embodiments, the one or more pharmaceutically acceptable excipients comprise about 0.1% by weight to about 0.7% by weight of one or more lubricants based on the weight of the pharmaceutically acceptable unit formulation. In some embodiments, the one or more pharmaceutically acceptable excipients comprise about 0.1% by weight to about 0.6% by weight of one or more lubricants based on the weight of the pharmaceutically acceptable unit formulation. In some embodiments, the one or more pharmaceutically acceptable excipients comprise about 0.1% by weight to about 0.5% by weight of one or more lubricants based on the weight of the pharmaceutically acceptable unit formulation. In some embodiments, the one or more pharmaceutically acceptable excipients comprise about 0.1% by weight to about 0.4% by weight of one or more lubricants based on the weight of the pharmaceutically acceptable unit formulation. In some embodiments, the one or more pharmaceutically acceptable excipients comprise about 0.1% by weight to about 0.3% by weight of one or more lubricants based on the weight of the pharmaceutically acceptable unit formulation. In some embodiments, the one or more pharmaceutically acceptable excipients comprise about 0.1% by weight to about 0.2% by weight of one or more lubricants based on the weight of the pharmaceutically acceptable unit formulation.

In some embodiments, the one or more pharmaceutically acceptable excipients comprise about 0.1% by weight of one or more lubricants based on the weight of the pharmaceutically acceptable unit formulation. In some embodiments, the one or more pharmaceutically acceptable excipients comprise about 0.2% by weight of one or more lubricants based on the weight of the pharmaceutically acceptable unit formulation. In some embodiments, the one or more pharmaceutically acceptable excipients comprise about 0.3% by weight of one or more lubricants based on the weight of the pharmaceutically acceptable unit formulation. In some embodiments, the one or more pharmaceutically acceptable excipients comprise about 0.4% by weight of one or more lubricants based on the weight of the pharmaceutically acceptable unit formulation. In some embodiments, the one or more pharmaceutically acceptable excipients comprise about 0.5% by weight of one or more lubricants based on the weight of the pharmaceutically acceptable unit formulation. In some embodiments, the one or more pharmaceutically acceptable excipients comprise about 0.6% by weight of one or more lubricants based on the weight of the pharmaceutically acceptable unit formulation. In some embodiments, the one or more pharmaceutically acceptable excipients comprise about 0.7% by weight of one or more lubricants based on the weight of the pharmaceutically acceptable unit formulation. In some embodiments, the one or more pharmaceutically acceptable excipients comprise about 0.8% by weight of one or more lubricants based on the weight of the pharmaceutically acceptable unit formulation. In some embodiments, the one or more pharmaceutically acceptable excipients comprise about 0.9% by weight of one or more lubricants based on the weight of the pharmaceutically acceptable unit formulation. In some embodiments, the one or more pharmaceutically acceptable excipients comprise about 1.0% by weight of one or more lubricants based on the weight of the pharmaceutically acceptable unit formulation.

In some embodiments, the pharmaceutically acceptable unit formulation comprises: (a) about 1% by weight to about 30% by weight of the compound of Formula (I) based on the weight of the pharmaceutically acceptable unit formulation; (b) about 20% by weight to about 90% by weight of one or more fillers based on the weight of the pharmaceutically acceptable unit formulation; (c) about 1% by weight to about 20% by weight of one or more disintegrants based on the weight of the pharmaceutically acceptable unit formulation; and (d) about 0.1% by weight to about 10% by weight of one or more lubricants based on the weight of the pharmaceutically acceptable unit formulation.

In some embodiments, the pharmaceutically acceptable unit formulation consists essentially of: (a) about 1% by weight to about 30% by weight of the compound of Formula (I) based on the weight of the pharmaceutically acceptable unit formulation; (b) about 20% by weight to about 90% by weight of one or more fillers based on the weight of the pharmaceutically acceptable unit formulation; (c) about 1% by weight to about 20% by weight of one or more disintegrants based on the weight of the pharmaceutically acceptable unit formulation; and (d) about 0.1% by weight to about 10% by weight of one or more lubricants based on the weight of the pharmaceutically acceptable unit formulation.

In some embodiments, the pharmaceutically acceptable unit formulation comprises (a) about 5% by weight to about 25% by weight of the crystalline anhydrous form of the compound of Formula (I) based on the weight of the pharmaceutically acceptable unit formulation; (b) about 60% by weight to about 90% by weight of one or more fillers based on the weight of the pharmaceutically acceptable unit formulation; (c) about 1% by weight to about 15% by weight of one or more disintegrants based on the weight of the pharmaceutically acceptable unit formulation; and (d) about 0.1% by weight to about 4% by weight of one or more lubricants based on the weight of the pharmaceutically acceptable unit formulation.

In some embodiments, the pharmaceutically acceptable unit formulation consists essentially of: (a) about 5% by weight to about 25% by weight of the crystalline anhydrous form of the compound of Formula (I) based on the weight of the pharmaceutically acceptable unit formulation; (b) about 60% by weight to about 90% by weight of one or more fillers based on the weight of the pharmaceutically acceptable unit formulation; (c) about 1% by weight to about 15% by weight of one or more disintegrants based on the weight of the pharmaceutically acceptable unit formulation; and (d) about 0.1% by weight to about 4% by weight of one or more lubricants based on the weight of the pharmaceutically acceptable unit formulation.

In some embodiments, the pharmaceutically acceptable unit formulation comprises (a) about 10% by weight to about 30% by weight of the crystalline anhydrous form of the compound of Formula (I) based on the weight of the pharmaceutically acceptable unit formulation; (b) about 70% by weight to about 90% by weight of one or more fillers based on the weight of the pharmaceutically acceptable unit formulation; (c) about 1% by weight to about 10% by weight of one or more disintegrants based on the weight of the pharmaceutically acceptable unit formulation; and (d) about 0.1% by weight to about 3% by weight of one or more lubricants based on the weight of the pharmaceutically acceptable unit formulation.

In some embodiments, the pharmaceutically acceptable unit formulation consists essentially of: (a) about 10% by weight to about 30% by weight of the crystalline anhydrous form of the compound of Formula (I) based on the weight of the pharmaceutically acceptable unit formulation; (b) about 70% by weight to about 90% by weight of one or more fillers based on the weight of the pharmaceutically acceptable unit formulation; (c) about 1% by weight to about 10% by weight of one or more disintegrants based on the weight of the pharmaceutically acceptable unit formulation; and (d) about 0.1% by weight to about 3% by weight of one or more lubricants based on the weight of the pharmaceutically acceptable unit formulation.

In some embodiments, the one or more pharmaceutically acceptable excipients is one or more fillers selected from the group consisting of calcium phosphate, dicalcium phosphate, dicalcium phosphate dihydrate, calcium sulfate, calcium sulfate dihydrate, starch, calcium carbonate, magnesium carbonate, magnesium oxide, kaolin (natural hydrated aluminum silicate), sodium chloride, partially gelatinized starch, anhydrous lactose, lactose monohydrate, lactose dihydrate, trehalose dihydrate, spray dried lactose, sucrose, dextrose, dextrates, dextrin, cellulose, microcrystalline cellulose, silicified microcrystalline cellulose, powdered cellulose, partially depolymerized cellulose, mannitol, granulated mannitol, spray dried mannitol, maltodextrin, maltitol, confectioner's sugar, compressible sugar, sorbitol, starch and talc. In some embodiments, the one or more fillers is lactose monohydrate.

In some embodiments, the one or more disintegrants is one or more disintegrants selected from the group consisting of sodium starch glycolate, pregelatinized starch, clay, cellulose, alginic acid, alginate gum, polyvinylpyrrolidone, cross-linked polyvinylpyrrolidone, cross-linked calcium carboxymethylcellulose, cross-linked sodium carboxymethylcellulose, sodium croscarmellose, sodium carmellose, low substituted hydroxypropyl cellulose, low substituted hydroxypropyl cellulose sodium, guar gum, magnesium aluminum silicate, polacrilin potassium, powdered cellulose, sodium alginate and soy polysaccharides. In some embodiments, the one or more disintegrants is cross-linked polyvinylpyrrolidone (also referred to as crospovidone).

In some embodiments, the one or more lubricants is one or more lubricants selected from the group consisting of colloidal silica, magnesium trisilicate, talc, magnesium carbonate, magnesium oxide, glyceryl behaptate, mono, di and tri glyceryl behenate, bees wax, behenoyl polyoxyl-8 glycerides, hydrogenated vegetable oil, polyethylene glycol, ethylene oxide polymer, copolymer comprising poly(ethylene oxide) and poly(propylene oxide) (such as poloxomer 188), copolymer comprising polypropylene glycol and polyethylene glycol (such as poloxomer 407), sodium lauryl sulfate, magnesium stearate, aluminum stearate, calcium stearate, sodium stearyl fumarate, stearic acid, magnesium lauryl stearate, mixtures of magnesium stearate with sodium lauryl sulfate. In some embodiments, the one or more lubricants is magnesium stearate.

In some embodiments, the one or more disintegrants is selected from the group consisting of cross-linked polyvinylpyrrolidone, croscarmellose sodium, and sodium starch glycolate; and the one or more lubricants is selected from the group consisting of sodium stearyl fumarate, stearic acid, talc, calcium stearate, magnesium stearate, solid polyethylene glycols, and sodium lauryl sulfate. In some embodiments, the pharmaceutically acceptable unit formulation comprises cross-linked polyvinylpyrrolidone and magnesium stearate. In some embodiments, the one or more pharmaceutically acceptable excipients is lactose monohydrate and the pharmaceutically acceptable unit formulation further comprises cross-linked polyvinylpyrrolidone and magnesium stearate.

In some embodiments, the pharmaceutically acceptable unit formulation is a tablet or capsule. In some embodiments, the pharmaceutically acceptable unit formulation is a tablet. In some embodiments, the pharmaceutically acceptable unit formulation is a capsule. In some embodiments, the pharmaceutically acceptable unit formulation is a sachet. In some embodiments, the pharmaceutically acceptable unit formulation is a powder in a packet.

In some embodiments, the pharmaceutically acceptable unit formulation comprises about 1 mg to about 40 mg of the crystalline anhydrous form of the compound of Formula (I). In some embodiments, the pharmaceutically acceptable unit formulation comprises about 5 mg to about 35 mg of the crystalline anhydrous form of the compound of Formula (I). In some embodiments, the pharmaceutically acceptable unit formulation comprises about 10 mg to about 35 mg of the crystalline anhydrous form of the compound of Formula (I). In some embodiments, the pharmaceutically acceptable unit formulation comprises about 0.5 mg to about 5 mg, about 6 mg to about 14 mg, about 10 mg to about 18 mg, about 16 mg to about 24 mg, or about 26 mg to about 34 mg of the crystalline anhydrous form of the compound of Formula (I). In some embodiments, the pharmaceutically acceptable unit formulation comprises about 1 mg to about 3 mg, about 8 mg to about 12 mg, about 12 mg to about 16 mg, about 18 mg to about 22 mg, or about 28 mg to about 32 mg of the crystalline anhydrous form of the compound of Formula (I). In some embodiments, the pharmaceutically acceptable unit formulation comprises about 2 mg, about 10 mg, about 14 mg, about 20 mg, or about 30 mg of the crystalline anhydrous form of the compound of Formula (I). In some embodiments, the crystalline anhydrous form of the compound of Formula (I) is present in an amount of about 2 mg. In some embodiments, the crystalline anhydrous form of the compound of Formula (I) is present in an amount of about 10 mg. In some embodiments, the crystalline anhydrous form of the compound of Formula (I) is present in an amount of about 14 mg. In some embodiments, the crystalline anhydrous form of the compound of Formula (I) is present in an amount of about 20 mg. In some embodiments, the crystalline anhydrous form of the compound of Formula (I) is present in an amount of about 30 mg.

In some embodiments, the pharmaceutically acceptable unit formulation consists essentially of about 1 mg to about 40 mg of the crystalline anhydrous form of the compound of Formula (I). In some embodiments, the pharmaceutically acceptable unit formulation consists essentially of about 5 mg to about 35 mg of the crystalline anhydrous form of the compound of Formula (I). In some embodiments, the pharmaceutically acceptable unit formulation consists essentially of about 10 mg to about 35 mg of the crystalline anhydrous form of the compound of Formula (I). In some embodiments, the pharmaceutically acceptable unit formulation consists essentially of about 0.5 mg to about 5 mg, about 6 mg to about 14 mg, about 10 mg to about 18 mg, about 16 mg to about 24 mg, or about 26 mg to about 34 mg of the crystalline anhydrous form of the compound of Formula (I). In some embodiments, the pharmaceutically acceptable unit formulation consists essentially of about 1 mg to about 3 mg, about 8 mg to about 12 mg, about 12 mg to about 16 mg, about 18 mg to about 22 mg, or about 28 mg to about 32 mg of the crystalline anhydrous form of the compound of Formula (I). In some embodiments, the pharmaceutically acceptable unit formulation consists essentially of about 2 mg, about 10 mg, about 14 mg, about 20 mg, or about 30 mg of the crystalline anhydrous form of the compound of Formula (I). In some embodiments, the crystalline anhydrous form of the compound of Formula (I) is present in an amount of about 2 mg. In some embodiments, the crystalline anhydrous form of the compound of Formula (I) is present in an amount of about 10 mg. In some embodiments, the crystalline anhydrous form of the compound of Formula (I) is present in an amount of about 14 mg. In some embodiments, the crystalline anhydrous form of the compound of Formula (I) is present in an amount of about 20 mg. In some embodiments, the crystalline anhydrous form of the compound of Formula (I) is present in an amount of about 30 mg.

In some embodiments, the pharmaceutically acceptable unit formulation has an acceptance value of less than about 15 as determined by USP Uniformity of Dosage Unit <905>. In some embodiments, the pharmaceutically acceptable unit formulation has a maximum acceptance value of equal to or less than about 15 as determined by USP Uniformity of Dosage Unit <905>.

In some embodiments, the uniformity of the pharmaceutically acceptable formulation represents the degree of uniformity in the amount of the compound of Formula (I) in the pharmaceutically acceptable formulation.

In some embodiments, the uniformity of the oral dosage form represents the degree of uniformity in the amount of the compound of Formula (I) in the oral dosage form.

In some embodiments, the uniformity of the pharmaceutically acceptable capsule represents the degree of uniformity in the amount of the compound of Formula (I) in the pharmaceutically acceptable capsule.

Also provided herein is a process of preparing an oral dosage form, the oral dosage form comprising:

(a) about 1% by weight to about 70% by weight, based on the total weight of the oral dosage form, of a crystalline anhydrous form of a compound of Formula (I):

Formula (I)

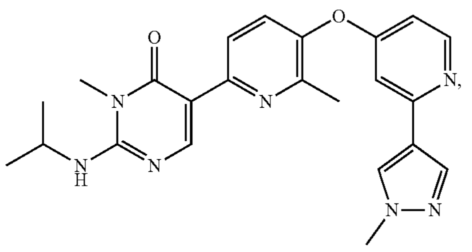

and one or more pharmaceutically acceptable excipients, wherein the one or more pharmaceutically acceptable excipients comprise:

(b) about 20% by weight to about 97% by weight of one or more fillers, based on the total weight of the oral dosage form;

(c) about 1% by weight to about 20% by weight of one or more disintegrants, based on the total weight of the oral dosage form; and (d) about 0.1% by weight to about 10% by weight of one or more lubricants, based on the total weight of the oral dosage form the process comprising:

(i) blending the crystalline anhydrous form of a compound represented by Formula (I) with the one or more fillers and one or more disintegrants to produce a first blend; and (ii) blending the first blend with the one or more lubricants, thereby preparing the oral dosage form.

Also provided herein is a process of preparing an oral dosage form, the oral dosage form consisting essentially of:

(a) about 1% by weight to about 70% by weight, based on the total weight of the oral dosage form, of a crystalline anhydrous form of a compound of Formula (I):

Formula (I)

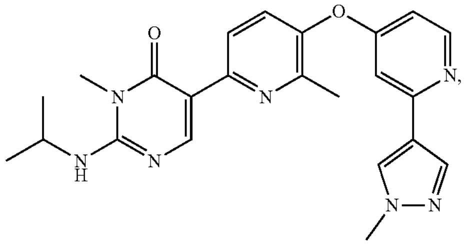

and one or more pharmaceutically acceptable excipients, wherein the one or more pharmaceutically acceptable excipients comprise:

(b) about 20% by weight to about 97% by weight of one or more fillers, based on the total weight of the oral dosage form;

(c) about 1% by weight to about 20% by weight of one or more disintegrants, based on the total weight of the oral dosage form; and (d) about 0.1% by weight to about 10% by weight of one or more lubricants, based on the total weight of the oral dosage form the process comprising:

(i) blending the crystalline anhydrous form of a compound represented by Formula (I) with the one or more fillers and one or more disintegrants to produce a first blend; and (ii) blending the first blend with the one or more lubricants, thereby preparing the oral dosage form.

Also provided herein is a process of preparing an oral dosage form, the oral dosage form comprising:

(a) about 1% by weight to about 70% by weight, based on the total weight of the oral dosage form of a crystalline anhydrous form of a compound of Formula (I):

Formula (I)

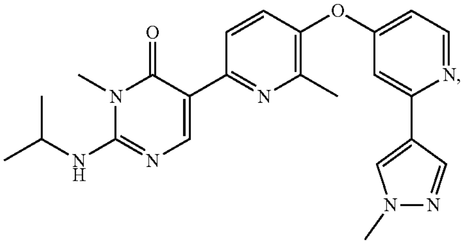

and one or more pharmaceutically acceptable excipients, wherein the one or more pharmaceutically acceptable excipients comprise:

(b) about 20% by weight to about 97% by weight of one or more fillers, based on the total weight of the oral dosage form;

(c) about 1% by weight to about 20% by weight of one or more disintegrants, based on the total weight of the oral dosage form; and (d) about 0.1% by weight to about 10% by weight of one or more lubricants, based on the total weight of the oral dosage form the process comprising:

(i) blending the crystalline anhydrous form of a compound represented by Formula (I) with the one or more fillers to produce a first blend;

(ii) blending the first blend with one or more disintegrants to produce a second blend; and (iii) blending the second blend with the one or more lubricants, thereby preparing the oral dosage form.

Also provided herein is a process of preparing an oral dosage form, the oral dosage form consisting essentially of:

(a) about 1% by weight to about 70% by weight, based on the total weight of the oral dosage form of a crystalline anhydrous form of a compound of Formula (I):

Formula (I)

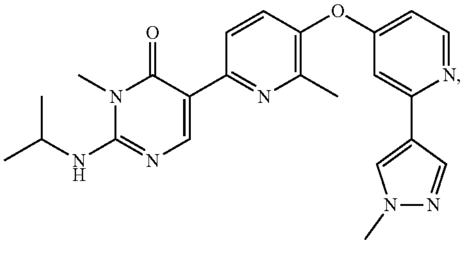

and one or more pharmaceutically acceptable excipients, wherein the one or more pharmaceutically acceptable excipients comprise:

(b) about 20% by weight to about 97% by weight of one or more fillers, based on the total weight of the oral dosage form;

(c) about 1% by weight to about 20% by weight of one or more disintegrants, based on the total weight of the oral dosage form; and (d) about 0.1% by weight to about 10% by weight of one or more lubricants, based on the total weight of the oral dosage form the process comprising:

(i) blending the crystalline anhydrous form of a compound represented by Formula (I) with the one or more fillers to produce a first blend;

(ii) blending the first blend with one or more disintegrants to produce a second blend; and (iii) blending the second blend with the one or more lubricants, thereby preparing the oral dosage form.

Also provided herein is a process of preparing an oral dosage form, the oral dosage form comprising:

(a) about 1% by weight to about 70% by weight, based on the total weight of the oral dosage form of a crystalline anhydrous form of a compound of Formula (I):

Formula (I)

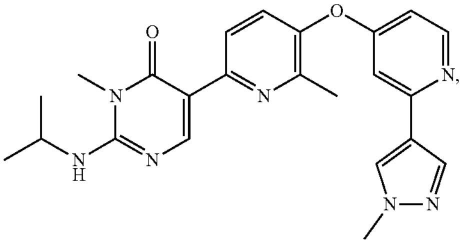

and one or more pharmaceutically acceptable excipients, wherein the one or more pharmaceutically acceptable excipients comprise:

(b) about 20% by weight to about 97% by weight of one or more fillers, based on the total weight of the oral dosage form;

(c) about 1% by weight to about 20% by weight of one or more disintegrants, based on the total weight of the oral dosage form; and (d) about 0.1% by weight to about 10% by weight of one or more lubricants, based on the total weight of the oral dosage form the process comprising:

(i) blending the crystalline anhydrous form of a compound represented by Formula (I) with the one or more fillers to produce a first blend;

(ii) blending the first blend with a second blend comprising one or more disintegrants and one or more fillers and optionally a third blend comprising one or more fillers to produce a fourth blend; and (iii) blending the fourth blend with the one or more lubricants, thereby preparing the oral dosage form.

Also provided herein is a process of preparing an oral dosage form, the oral dosage form consisting essentially of:

(a) about 1% by weight to about 70% by weight, based on the total weight of the oral dosage form of a crystalline anhydrous form of a compound of Formula (I):

Formula (I)

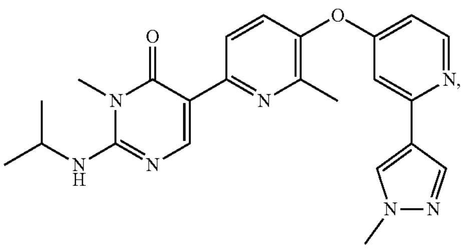

and one or more pharmaceutically acceptable excipients, wherein the one or more pharmaceutically acceptable excipients comprise:

(b) about 20% by weight to about 97% by weight of one or more fillers, based on the total weight of the oral dosage form;

(c) about 1% by weight to about 20% by weight of one or more disintegrants, based on the total weight of the oral dosage form; and (d) about 0.1% by weight to about 10% by weight of one or more lubricants, based on the total weight of the oral dosage form the process comprising:

(i) blending the crystalline anhydrous form of a compound represented by Formula (I) with the one or more fillers to produce a first blend;

(ii) blending the first blend with a second blend comprising one or more disintegrants and one or more fillers and optionally a third blend comprising one or more fillers to produce a fourth blend; and (iii) blending the fourth blend with the one or more lubricants, thereby preparing the oral dosage form.

In some embodiments, the oral dosage form comprises about 1% by weight to about 60% by weight, based on the total weight of the oral dosage form, of a crystalline anhydrous form of a compound of Formula (I). In some embodiments, the oral dosage form comprises about 1% by weight to about 50% by weight, based on the total weight of the oral dosage form, of a crystalline anhydrous form of a compound of Formula (I). In some embodiments, the oral dosage form comprises about 1% by weight to about 40% by weight, based on the total weight of the oral dosage form, of a crystalline anhydrous form of a compound of Formula (I). In some embodiments, the oral dosage form comprises about 1% by weight to about 30% by weight, based on the total weight of the oral dosage form, of a crystalline anhydrous form of a compound of Formula (I). In some embodiments, the oral dosage form comprises about 1% by weight to about 20% by weight, based on the total weight of the oral dosage form, of a crystalline anhydrous form of a compound of Formula (I).

In some embodiments, the oral dosage form consists essentially of about 1% by weight to about 60% by weight, based on the total weight of the oral dosage form, of a crystalline anhydrous form of a compound of Formula (I). In some embodiments, the oral dosage form consists essentially of about 1% by weight to about 50% by weight, based on the total weight of the oral dosage form, of a crystalline anhydrous form of a compound of Formula (I). In some embodiments, the oral dosage form consists essentially of about 1% by weight to about 40% by weight, based on the total weight of the oral dosage form, of a crystalline anhydrous form of a compound of Formula (I). In some embodiments, the oral dosage form consists essentially of about 1% by weight to about 30% by weight, based on the total weight of the oral dosage form, of a crystalline anhydrous form of a compound of Formula (I). In some embodiments, the oral dosage form consists essentially of about 1% by weight to about 20% by weight, based on the total weight of the oral dosage form, of a crystalline anhydrous form of a compound of Formula (I).

In some embodiments, the oral dosage form comprises about 1% by weight to about 70% by weight of the crystalline anhydrous form of the compound of Formula (I) based on the total weight of the oral dosage form. In some embodiments, the oral dosage form comprises about 1% by weight to about 65% by weight of the crystalline anhydrous form of the compound of Formula (I) based on the total weight of the oral dosage form. In some embodiments, the oral dosage form comprises about 1% by weight to about 60% by weight of the crystalline anhydrous form of the compound of Formula (I) based on the total weight of the oral dosage form. In some embodiments, the oral dosage form comprises about 1% by weight to about 55% by weight of the crystalline anhydrous form of the compound of Formula (I) based on the total weight of the oral dosage form. In some embodiments, the oral dosage form comprises about 1% by weight to about 50% by weight of the crystalline anhydrous form of the compound of Formula (I) based on the total weight of the oral dosage form. In some embodiments, the oral dosage form comprises about 1% by weight to about 45% by weight of the crystalline anhydrous form of the compound of Formula (I) based on the total weight of the oral dosage form. In some embodiments, the oral dosage form comprises about 1% by weight to about 40% by weight of the crystalline anhydrous form of the compound of Formula (I) based on the total weight of the oral dosage form. In some embodiments, the oral dosage form comprises about 1% by weight to about 35% by weight of the crystalline anhydrous form of the compound of Formula (I) based on the total weight of the oral dosage form. In some embodiments, the oral dosage form comprises about 1% by weight to about 30% by weight of the crystalline anhydrous form of the compound of Formula (I) based on the total weight of the oral dosage form. In some embodiments, the oral dosage form comprises about 1% by weight to about 25% by weight of the crystalline anhydrous form of the compound of Formula (I) based on the total weight of the oral dosage form. In some embodiments, the oral dosage form comprises about 1% by weight to about 20% by weight of the crystalline anhydrous form of the compound of Formula (I) based on the total weight of the oral dosage form. In some embodiments, the oral dosage form comprises about 1% by weight to about 15% by weight of the crystalline anhydrous form of the compound of Formula (I) based on the total weight of the oral dosage form. In some embodiments, the oral dosage form comprises about 1% by weight to about 10% by weight of the crystalline anhydrous form of the compound of Formula (I) based on the total weight of the oral dosage form.

In some embodiments, the oral dosage form consists essentially of about 1% by weight to about 70% by weight of the crystalline anhydrous form of the compound of Formula (I) based on the total weight of the oral dosage form. In some embodiments, the oral dosage form consists essentially of about 1% by weight to about 65% by weight of the crystalline anhydrous form of the compound of Formula (I) based on the total weight of the oral dosage form. In some embodiments, the oral dosage form consists essentially of about 1% by weight to about 60% by weight of the crystalline anhydrous form of the compound of Formula (I) based on the total weight of the oral dosage form. In some embodiments, the oral dosage form consists essentially of about 1% by weight to about 55% by weight of the crystalline anhydrous form of the compound of Formula (I) based on the total weight of the oral dosage form. In some embodiments, the oral dosage form consists essentially of about 1% by weight to about 50% by weight of the crystalline anhydrous form of the compound of Formula (I) based on the total weight of the oral dosage form. In some embodiments, the oral dosage form consists essentially of about 1% by weight to about 45% by weight of the crystalline anhydrous form of the compound of Formula (I) based on the total weight of the oral dosage form. In some embodiments, the oral dosage form consists essentially of about 1% by weight to about 40% by weight of the crystalline anhydrous form of the compound of Formula (I) based on the total weight of the oral dosage form. In some embodiments, the oral dosage form consists essentially of about 1% by weight to about 35% by weight of the crystalline anhydrous form of the compound of Formula (I) based on the total weight of the oral dosage form. In some embodiments, the oral dosage form consists essentially of about 1% by weight to about 30% by weight of the crystalline anhydrous form of the compound of Formula (I) based on the total weight of the oral dosage form. In some embodiments, the oral dosage form consists essentially of about 1% by weight to about 25% by weight of the crystalline anhydrous form of the compound of Formula (I) based on the total weight of the oral dosage form. In some embodiments, the oral dosage form consists essentially of about 1% by weight to about 20% by weight of the crystalline anhydrous form of the compound of Formula (I) based on the total weight of the oral dosage form. In some embodiments, the oral dosage form consists essentially of about 1% by weight to about 15% by weight of the crystalline anhydrous form of the compound of Formula (I) based on the total weight of the oral dosage form. In some embodiments, the oral dosage form consists essentially of about 1% by weight to about 10% by weight of the crystalline anhydrous form of the compound of Formula (I) based on the total weight of the oral dosage form.

In some embodiments, the oral dosage form comprises about 5% by weight to about 30% by weight of the crystalline anhydrous form of the compound of Formula (I) based on the total weight of the oral dosage form. In some embodiments, the oral dosage form comprises about 5% by weight to about 25% by weight of the crystalline anhydrous form of the compound of Formula (I) based on the total weight of the oral dosage form. In some embodiments, the oral dosage form comprises about 5% by weight to about 20% by weight of the crystalline anhydrous form of the compound of Formula (I) based on the total weight of the oral dosage form. In some embodiments, the oral dosage form comprises about 5% by weight to about 15% by weight of the crystalline anhydrous form of the compound of Formula (I) based on the total weight of the oral dosage form. In some embodiments, the oral dosage form comprises about 5% by weight to about 10% by weight of the crystalline anhydrous form of the compound of Formula (I) based on the total weight of the oral dosage form.

In some embodiments, the oral dosage form consists essentially of about 5% by weight to about 30% by weight of the crystalline anhydrous form of the compound of Formula (I) based on the total weight of the oral dosage form. In some embodiments, the oral dosage form consists essentially of about 5% by weight to about 25% by weight of the crystalline anhydrous form of the compound of Formula (I) based on the total weight of the oral dosage form. In some embodiments, the oral dosage form consists essentially of about 5% by weight to about 20% by weight of the crystalline anhydrous form of the compound of Formula (I) based on the total weight of the oral dosage form. In some embodiments, the oral dosage form consists essentially of about 5% by weight to about 15% by weight of the crystalline anhydrous form of the compound of Formula (I) based on the total weight of the oral dosage form. In some embodiments, the oral dosage form consists essentially of about 5% by weight to about 10% by weight of the crystalline anhydrous form of the compound of Formula (I) based on the total weight of the oral dosage form.

In some embodiments, the oral dosage form comprises about 10% to about 30% of the compound of Formula (I) based on the total weight of the oral dosage form. In some embodiments, the oral dosage form comprises about 10% to about 25% of the compound of Formula (I) based on the total weight of the oral dosage form. In some embodiments, the oral dosage form comprises about 10% to about 20% of the compound of Formula (I) based on the total weight of the oral dosage form. In some embodiments, the oral dosage form comprises about 10% by weight to about 15% by weight of the crystalline anhydrous form of the compound of Formula (I) based on the total weight of the oral dosage form.

In some embodiments, the oral dosage form consists essentially of about 10% to about 30% of the crystalline anhydrous form of the compound of Formula (I) based on the total weight of the oral dosage form. In some embodiments, the oral dosage form consists essentially of about 10% to about 25% of the crystalline anhydrous form of the compound of Formula (I) based on the total weight of the oral dosage form. In some embodiments, the oral dosage form consists essentially of about 10% to about 20% of the crystalline anhydrous form of the compound of Formula (I) based on the total weight of the oral dosage form. In some embodiments, the oral dosage form consists essentially of about 10% by weight to about 15% by weight of the crystalline anhydrous form of the compound of Formula (I) based on the total weight of the oral dosage form.

In some embodiments, the oral dosage form comprises about 1% by weight to about 30% by weight of the crystalline anhydrous form of the compound of Formula (I) based on the total weight of the oral dosage form. In some embodiments, the oral dosage form comprises about 1% by weight to about 10% by weight of the crystalline anhydrous form of the compound of Formula (I) based on the total weight of the oral dosage form. In some embodiments, the oral dosage form comprises about 10% to about 20% of the compound of Formula (I) based on the total weight of the oral dosage form. In some embodiments, the oral dosage form comprises about 10% by weight to about 15% by weight of the crystalline anhydrous form of the compound of Formula (I) based on the total weight of the oral dosage form.

In some embodiments, the oral dosage form consists essentially of about 1% by weight to about 30% by weight of the crystalline anhydrous form of the compound of Formula (I) based on the total weight of the oral dosage form. In some embodiments, the oral dosage form consists essentially of about 1% by weight to about 10% by weight of the crystalline anhydrous form of the compound of Formula (I) based on the total weight of the oral dosage form. In some embodiments, the oral dosage form consists essentially of about 10% to about 20% of the crystalline anhydrous form of the compound of Formula (I) based on the total weight of the oral dosage form. In some embodiments, the oral dosage form consists essentially of about 10% by weight to about 15% by weight of the crystalline anhydrous form of the compound of Formula (I) based on the total weight of the oral dosage form.

In some embodiments, the one or more pharmaceutically acceptable excipients comprise about 20% by weight to about 90% by weight of one or more fillers based on the total weight of the oral dosage form. In some embodiments, the one or more pharmaceutically acceptable excipients comprise about 20% by weight to about 85% by weight of one or more fillers based on the total weight of the oral dosage form. In some embodiments, the one or more pharmaceutically acceptable excipients comprise about 20% by weight to about 80% by weight of one or more fillers based on the total weight of the oral dosage form. In some embodiments, the one or more pharmaceutically acceptable excipients comprise about 20% by weight to about 75% by weight of one or more fillers based on the total weight of the oral dosage form. In some embodiments, the one or more pharmaceutically acceptable excipients comprise about 20% by weight to about 70% by weight of one or more fillers based on the total weight of the oral dosage form. In some embodiments, the one or more pharmaceutically acceptable excipients comprise about 20% by weight to about 65% by weight of one or more fillers based on the total weight of the oral dosage form. In some embodiments, the one or more pharmaceutically acceptable excipients comprise about 20% by weight to about 60% by weight of one or more fillers based on the total weight of the oral dosage form. In some embodiments, the one or more pharmaceutically acceptable excipients comprise about 20% by weight to about 55% by weight of one or more fillers based on the total weight of the oral dosage form. In some embodiments, the one or more pharmaceutically acceptable excipients comprise about 20% by weight to about 50% by weight of one or more fillers based on the total weight of the oral dosage form. In some embodiments, the one or more pharmaceutically acceptable excipients comprise about 20% by weight to about 45% by weight of one or more fillers based on the total weight of the oral dosage form. In some embodiments, the one or more pharmaceutically acceptable excipients comprise about 20% by weight to about 40% by weight of one or more fillers based on the total weight of the oral dosage form. In some embodiments, the one or more pharmaceutically acceptable excipients comprise about 20% by weight to about 35% by weight of one or more fillers based on the total weight of the oral dosage form. In some embodiments, the one or more pharmaceutically acceptable excipients comprise about 20% by weight to about 30% by weight of one or more fillers based on the total weight of the oral dosage form. In some embodiments, the one or more pharmaceutically acceptable excipients comprise about 20% by weight to about 25% by weight of one or more fillers based on the total weight of the oral dosage form.

In some embodiments, the one or more pharmaceutically acceptable excipients comprise about 30% by weight to about 90% by weight of one or more fillers based on the total weight of the oral dosage form. In some embodiments, the one or more pharmaceutically acceptable excipients comprise about 30% by weight to about 80% by weight of one or more fillers based on the total weight of the oral dosage form. In some embodiments, the one or more pharmaceutically acceptable excipients comprise about 30% by weight to about 70% by weight of one or more fillers based on the total weight of the oral dosage form. In some embodiments, the one or more pharmaceutically acceptable excipients comprise about 30% by weight to about 60% by weight of one or more fillers based on the total weight of the oral dosage form. In some embodiments, the one or more pharmaceutically acceptable excipients comprise about 30% by weight to about 50% by weight of one or more fillers based on the total weight of the oral dosage form. In some embodiments, the one or more pharmaceutically acceptable excipients comprise about 30% by weight to about 40% by weight of one or more fillers based on the total weight of the oral dosage form.

In some embodiments, the one or more pharmaceutically acceptable excipients comprise about 40% by weight to about 90% by weight of one or more fillers based on the total weight of the oral dosage form. In some embodiments, the one or more pharmaceutically acceptable excipients comprise about 40% by weight to about 80% by weight of one or more fillers based on the total weight of the oral dosage form. In some embodiments, the one or more pharmaceutically acceptable excipients comprise about 40% by weight to about 70% by weight of one or more fillers based on the total weight of the oral dosage form. In some embodiments, the one or more pharmaceutically acceptable excipients comprise about 40% by weight to about 60% by weight of one or more fillers based on the total weight of the oral dosage form. In some embodiments, the one or more pharmaceutically acceptable excipients comprise about 40% by weight to about 50% by weight of one or more fillers based on the total weight of the oral dosage form.

In some embodiments, the one or more pharmaceutically acceptable excipients comprise about 50% by weight to about 90% by weight of one or more fillers based on the total weight of the oral dosage form. In some embodiments, the one or more pharmaceutically acceptable excipients comprise about 50% by weight to about 80% by weight of one or more fillers based on the total weight of the oral dosage form. In some embodiments, the one or more pharmaceutically acceptable excipients comprise about 50% by weight to about 70% by weight of one or more fillers based on the total weight of the oral dosage form. In some embodiments, the one or more pharmaceutically acceptable excipients comprise about 50% by weight to about 60% by weight of one or more fillers based on the total weight of the oral dosage form.

In some embodiments, the one or more pharmaceutically acceptable excipients comprise about 60% by weight to about 90% by weight of one or more fillers based on the total weight of the oral dosage form. In some embodiments, the one or more pharmaceutically acceptable excipients comprise about 60% by weight to about 80% by weight of one or more fillers based on the total weight of the oral dosage form. In some embodiments, the one or more pharmaceutically acceptable excipients comprise about 60% by weight to about 70% by weight of one or more fillers based on the total weight of the oral dosage form.

In some embodiments, the one or more pharmaceutically acceptable excipients comprise about 70% by weight to about 90% by weight of one or more fillers based on the total weight of the oral dosage form. In some embodiments, the one or more pharmaceutically acceptable excipients comprise about 70% by weight to about 80% by weight of one or more fillers based on the total weight of the oral dosage form.

In some embodiments, the one or more pharmaceutically acceptable excipients comprise about 80% by weight to about 90% by weight of one or more fillers based on the total weight of the oral dosage form.

In some embodiments, the one or more pharmaceutically acceptable excipients comprise about 1% by weight to about 20% by weight of one or more disintegrants based on the total weight of the oral dosage form. In some embodiments, the one or more pharmaceutically acceptable excipients comprise about 1% by weight to about 15% by weight of one or more disintegrants based on the total weight of the oral dosage form. In some embodiments, the one or more pharmaceutically acceptable excipients comprise about 1% by weight to about 14% by weight of one or more disintegrants based on the total weight of the oral dosage form. In some embodiments, the one or more pharmaceutically acceptable excipients comprise about 1% by weight to about 13% by weight of one or more disintegrants based on the total weight of the oral dosage form. In some embodiments, the one or more pharmaceutically acceptable excipients comprise about 1% by weight to about 12% by weight of one or more disintegrants based on the total weight of the oral dosage form. In some embodiments, the one or more pharmaceutically acceptable excipients comprise about 1% by weight to about 11% by weight of one or more disintegrants based on the total weight of the oral dosage form. In some embodiments, the one or more pharmaceutically acceptable excipients comprise about 1% by weight to about 10% by weight of one or more disintegrants based on the total weight of the oral dosage form. In some embodiments, the one or more pharmaceutically acceptable excipients comprise about 1% by weight to about 9% by weight of one or more disintegrants based on the total weight of the oral dosage form. In some embodiments, the one or more pharmaceutically acceptable excipients comprise about 1% by weight to about 8% by weight of one or more disintegrants based on the total weight of the oral dosage form. In some embodiments, the one or more pharmaceutically acceptable excipients comprise about 1% by weight to about 7% by weight of one or more disintegrants based on the total weight of the oral dosage form. In some embodiments, the one or more pharmaceutically acceptable excipients comprise about 1% by weight to about 6% by weight of one or more disintegrants based on the total weight of the oral dosage form. In some embodiments, the one or more pharmaceutically acceptable excipients comprise about 1% by weight to about 5% by weight of one or more disintegrants based on the total weight of the oral dosage form. In some embodiments, the one or more pharmaceutically acceptable excipients comprise about 1% by weight to about 4% by weight of one or more disintegrants based on the total weight of the oral dosage form. In some embodiments, the one or more pharmaceutically acceptable excipients comprise about 1% by weight to about 3% by weight of one or more disintegrants based on the total weight of the oral dosage form.

In some embodiments, the one or more pharmaceutically acceptable excipients comprise about 1% by weight of one or more disintegrants based on the total weight of the oral dosage form. In some embodiments, the one or more pharmaceutically acceptable excipients comprise about 2% by weight of one or more disintegrants based on the total weight of the oral dosage form. In some embodiments, the one or more pharmaceutically acceptable excipients comprise about 3% by weight of one or more disintegrants based on the total weight of the oral dosage form. In some embodiments, the one or more pharmaceutically acceptable excipients comprise about 4% by weight of one or more disintegrants based on the total weight of the oral dosage form. In some embodiments, the one or more pharmaceutically acceptable excipients comprise about 5% by weight of one or more disintegrants based on the total weight of the oral dosage form. In some embodiments, the one or more pharmaceutically acceptable excipients comprise about 6% by weight of one or more disintegrants based on the total weight of the oral dosage form. In some embodiments, the one or more pharmaceutically acceptable excipients comprise about 7% by weight of one or more disintegrants based on the total weight of the oral dosage form. In some embodiments, the one or more pharmaceutically acceptable excipients comprise about 8% by weight of one or more disintegrants based on the total weight of the oral dosage form. In some embodiments, the one or more pharmaceutically acceptable excipients comprise about 9% by weight of one or more disintegrants based on the total weight of the oral dosage form. In some embodiments, the one or more pharmaceutically acceptable excipients comprise about 10% by weight of one or more disintegrants based on the total weight of the oral dosage form. In some embodiments, the one or more pharmaceutically acceptable excipients comprise about 11% by weight of one or more disintegrants based on the total weight of the oral dosage form. In some embodiments, the one or more pharmaceutically acceptable excipients comprise about 12% by weight of one or more disintegrants based on the total weight of the oral dosage form. In some embodiments, the one or more pharmaceutically acceptable excipients comprise about 13% by weight of one or more disintegrants based on the total weight of the oral dosage form. In some embodiments, the one or more pharmaceutically acceptable excipients comprise about 14% by weight of one or more disintegrants based on the total weight of the oral dosage form. In some embodiments, the one or more pharmaceutically acceptable excipients comprise about 15% by weight of one or more disintegrants based on the total weight of the oral dosage form.

In some embodiments, the one or more pharmaceutically acceptable excipients comprise about 0.1% by weight to about 10% by weight of one or more lubricants based on the total weight of the oral dosage form. In some embodiments, the one or more pharmaceutically acceptable excipients comprise about 0.1% by weight to about 9% by weight of one or more lubricants based on the total weight of the oral dosage form. In some embodiments, the one or more pharmaceutically acceptable excipients comprise about 0.1% by weight to about 8% by weight of one or more lubricants based on the total weight of the oral dosage form. In some embodiments, the one or more pharmaceutically acceptable excipients comprise about 0.1% by weight to about 7% by weight of one or more lubricants based on the total weight of the oral dosage form. In some embodiments, the one or more pharmaceutically acceptable excipients comprise about 0.1% by weight to about 6% by weight of one or more lubricants based on the total weight of the oral dosage form. In some embodiments, the one or more pharmaceutically acceptable excipients comprise about 0.1% by weight to about 5% by weight of one or more lubricants based on the total weight of the oral dosage form. In some embodiments, the one or more pharmaceutically acceptable excipients comprise about 0.1% by weight to about 4% by weight of one or more lubricants based on the total weight of the oral dosage form. In some embodiments, the one or more pharmaceutically acceptable excipients comprise about 0.1% by weight to about 3% by weight of one or more lubricants based on the total weight of the oral dosage form. In some embodiments, the one or more pharmaceutically acceptable excipients comprise about 0.1% by weight to about 2% by weight of one or more lubricants based on the total weight of the oral dosage form.

In some embodiments, the one or more pharmaceutically acceptable excipients comprise about 0.1% by weight to about 1.9% by weight of one or more lubricants based on the total weight of the oral dosage form. In some embodiments, the one or more pharmaceutically acceptable excipients comprise about 0.1% by weight to about 1.8% by weight of one or more lubricants based on the total weight of the oral dosage form. In some embodiments, the one or more pharmaceutically acceptable excipients comprise about 0.1% by weight to about 1.7% by weight of one or more lubricants based on the total weight of the oral dosage form. In some embodiments, the one or more pharmaceutically acceptable excipients comprise about 0.1% by weight to about 1.6% by weight of one or more lubricants based on the total weight of the oral dosage form. In some embodiments, the one or more pharmaceutically acceptable excipients comprise about 0.1% by weight to about 1.5% by weight of one or more lubricants based on the total weight of the oral dosage form. In some embodiments, the one or more pharmaceutically acceptable excipients comprise about 0.1% by weight to about 1.4% by weight of one or more lubricants based on the total weight of the oral dosage form. In some embodiments, the one or more pharmaceutically acceptable excipients comprise about 0.1% by weight to about 1.3% by weight of one or more lubricants based on the total weight of the oral dosage form. In some embodiments, the one or more pharmaceutically acceptable excipients comprise about 0.1% by weight to about 1.2% by weight of one or more lubricants based on the total weight of the oral dosage form. In some embodiments, the one or more pharmaceutically acceptable excipients comprise about 0.1% by weight to about 1.1% by weight of one or more lubricants based on the total weight of the oral dosage form. In some embodiments, the one or more pharmaceutically acceptable excipients comprise about 0.1% by weight to about 1.0% by weight of one or more lubricants based on the total weight of the oral dosage form. In some embodiments, the one or more pharmaceutically acceptable excipients comprise about 0.1% by weight to about 0.9% by weight of one or more lubricants based on the total weight of the oral dosage form. In some embodiments, the one or more pharmaceutically acceptable excipients comprise about 0.1% by weight to about 0.8% by weight of one or more lubricants based on the total weight of the oral dosage form. In some embodiments, the one or more pharmaceutically acceptable excipients comprise about 0.1% by weight to about 0.7% by weight of one or more lubricants based on the total weight of the oral dosage form. In some embodiments, the one or more pharmaceutically acceptable excipients comprise about 0.1% by weight to about 0.6% by weight of one or more lubricants based on the total weight of the oral dosage form. In some embodiments, the one or more pharmaceutically acceptable excipients comprise about 0.1% by weight to about 0.5% by weight of one or more lubricants based on the total weight of the oral dosage form. In some embodiments, the one or more pharmaceutically acceptable excipients comprise about 0.1% by weight to about 0.4% by weight of one or more lubricants based on the total weight of the oral dosage form. In some embodiments, the one or more pharmaceutically acceptable excipients comprise about 0.1% by weight to about 0.3% by weight of one or more lubricants based on the total weight of the oral dosage form. In some embodiments, the one or more pharmaceutically acceptable excipients comprise about 0.1% by weight to about 0.2% by weight of one or more lubricants based on the total weight of the oral dosage form.

In some embodiments, the one or more pharmaceutically acceptable excipients comprise about 0.1% by weight of one or more lubricants based on the total weight of the oral dosage form. In some embodiments, the one or more pharmaceutically acceptable excipients comprise about 0.2% by weight of one or more lubricants based on the total weight of the oral dosage form. In some embodiments, the one or more pharmaceutically acceptable excipients comprise about 0.3% by weight of one or more lubricants based on the total weight of the oral dosage form. In some embodiments, the one or more pharmaceutically acceptable excipients comprise about 0.4% by weight of one or more lubricants based on the total weight of the oral dosage form. In some embodiments, the one or more pharmaceutically acceptable excipients comprise about 0.5% by weight of one or more lubricants based on the total weight of the oral dosage form. In some embodiments, the one or more pharmaceutically acceptable excipients comprise about 0.6% by weight of one or more lubricants based on the total weight of the oral dosage form. In some embodiments, the one or more pharmaceutically acceptable excipients comprise about 0.7% by weight of one or more lubricants based on the total weight of the oral dosage form. In some embodiments, the one or more pharmaceutically acceptable excipients comprise about 0.8% by weight of one or more lubricants based on the total weight of the oral dosage form. In some embodiments, the one or more pharmaceutically acceptable excipients comprise about 0.9% by weight of one or more lubricants based on the total weight of the oral dosage form. In some embodiments, the one or more pharmaceutically acceptable excipients comprise about 1.0% by weight of one or more lubricants based on the total weight of the oral dosage form.

In some embodiments, the oral dosage form comprises: (a) about 1% by weight to about 30% by weight of the compound of Formula (I) based on the total weight of the oral dosage form; (b) about 20% by weight to about 90% by weight of one or more fillers based on the total weight of the oral dosage form; (c) about 1% by weight to about 20% by weight of one or more disintegrants based on the total weight of the oral dosage form; and (d) about 0.1% by weight to about 10% by weight of one or more lubricants based on the total weight of the oral dosage form.

In some embodiments, the oral dosage form consists essentially of: (a) about 1% by weight to about 30% by weight of the compound of Formula (I) based on the total weight of the oral dosage form; (b) about 20% by weight to about 90% by weight of one or more fillers based on the total weight of the oral dosage form; (c) about 1% by weight to about 20% by weight of one or more disintegrants based on the total weight of the oral dosage form; and (d) about 0.1% by weight to about 10% by weight of one or more lubricants based on the total weight of the oral dosage form.

In some embodiments, the oral dosage form comprises (a) about 5% by weight to about 25% by weight of the crystalline anhydrous form of the compound of Formula (I) based on the total weight of the oral dosage form; (b) about 60% by weight to about 90% by weight of one or more fillers based on the total weight of the oral dosage form; (c) about 1% by weight to about 15% by weight of one or more disintegrants based on the total weight of the oral dosage form; and (d) about 0.1% by weight to about 4% by weight of one or more lubricants based on the total weight of the oral dosage form.

In some embodiments, the oral dosage form consists essentially of: (a) about 5% by weight to about 25% by weight of the crystalline anhydrous form of the compound of Formula (I) based on the total weight of the oral dosage form; (b) about 60% by weight to about 90% by weight of one or more fillers based on the total weight of the oral dosage form; (c) about 1% by weight to about 15% by weight of one or more disintegrants based on the total weight of the oral dosage form; and (d) about 0.1% by weight to about 4% by weight of one or more lubricants based on the total weight of the oral dosage form.

In some embodiments, the oral dosage form comprises (a) about 10% by weight to about 30% by weight of the crystalline anhydrous form of the compound of Formula (I) based on the total weight of the oral dosage form; (b) about 70% by weight to about 90% by weight of one or more fillers based on the total weight of the oral dosage form; (c) about 1% by weight to about 10% by weight of one or more disintegrants based on the total weight of the oral dosage form; and (d) about 0.1% by weight to about 3% by weight of one or more lubricants based on the total weight of the oral dosage form.

In some embodiments, the oral dosage form consists essentially of: (a) about 10% by weight to about 30% by weight of the crystalline anhydrous form of the compound of Formula (I) based on the total weight of the oral dosage form; (b) about 70% by weight to about 90% by weight of one or more fillers based on the total weight of the oral dosage form; (c) about 1% by weight to about 10% by weight of one or more disintegrants based on the total weight of the oral dosage form; and (d) about 0.1% by weight to about 3% by weight of one or more lubricants based on the total weight of the oral dosage form.

In some embodiments, the one or more pharmaceutically acceptable excipients is one or more fillers selected from the group consisting of calcium phosphate, dicalcium phosphate, dicalcium phosphate dihydrate, calcium sulfate, calcium sulfate dihydrate, starch, calcium carbonate, magnesium carbonate, magnesium oxide, kaolin (natural hydrated aluminum silicate), sodium chloride, partially gelatinized starch, anhydrous lactose, lactose monohydrate, lactose dihydrate, trehalose dihydrate, spray dried lactose, sucrose, dextrose, dextrates, dextrin, cellulose, microcrystalline cellulose, silicified microcrystalline cellulose, powdered cellulose, partially depolymerized cellulose, mannitol, granulated mannitol, spray dried mannitol, maltodextrin, maltitol, confectioner's sugar, compressible sugar, sorbitol, starch and talc. In some embodiments, the one or more fillers is lactose monohydrate.

In some embodiments, the one or more disintegrants is one or more disintegrants selected from the group consisting of sodium starch glycolate, pregelatinized starch, clay, cellulose, alginic acid, alginate gum, polyvinylpyrrolidone, cross-linked polyvinylpyrrolidone, cross-linked calcium carboxymethylcellulose, cross-linked sodium carboxymethylcellulose, sodium croscarmellose, sodium carmellose, low substituted hydroxypropyl cellulose, low substituted hydroxypropyl cellulose sodium, guar gum, magnesium aluminum silicate, polacrilin potassium, powdered cellulose, sodium alginate and soy polysaccharides. In some embodiments, the one or more disintegrants is cross-linked polyvinylpyrrolidone (also referred to as crospovidone).

In some embodiments, the one or more lubricants is one or more lubricants selected from the group consisting of colloidal silica, magnesium trisilicate, talc, magnesium carbonate, magnesium oxide, glyceryl behaptate, mono, di and tri glyceryl behenate, bees wax, behenoyl polyoxyl-8 glycerides, hydrogenated vegetable oil, polyethylene glycol, ethylene oxide polymer, copolymer comprising poly(ethylene oxide) and poly(propylene oxide) (such as poloxomer 188), copolymer comprising polypropylene glycol and polyethylene glycol (such as poloxomer 407), sodium lauryl sulfate, magnesium stearate, aluminum stearate, calcium stearate, sodium stearyl fumarate, stearic acid, magnesium lauryl stearate, mixtures of magnesium stearate with sodium lauryl sulfate. In some embodiments, the one or more lubricants is magnesium stearate.

In some embodiments, the one or more disintegrants is selected from the group consisting of cross-linked polyvinylpyrrolidone, croscarmellose sodium, and sodium starch glycolate; and the one or more lubricants is selected from the group consisting of sodium stearyl fumarate, stearic acid, talc, calcium stearate, magnesium stearate, solid polyethylene glycols, and sodium lauryl sulfate. In some embodiments, the oral dosage form comprises cross-linked polyvinylpyrrolidone and magnesium stearate. In some embodiments, the one or more pharmaceutically acceptable excipients is lactose monohydrate and the oral dosage form further comprises cross-linked polyvinylpyrrolidone and magnesium stearate.

In some embodiments, the oral dosage form is a tablet or capsule. In some embodiments, the oral dosage form is a tablet. In some embodiments, the oral dosage form is a capsule. In some embodiments, the oral dosage form is a sachet. In some embodiments, the oral dosage form is a powder in a packet.

In some embodiments, the oral dosage form comprises about 1 mg to about 40 mg of the crystalline anhydrous form of the compound of Formula (I). In some embodiments, the oral dosage form comprises about 5 mg to about 35 mg of the crystalline anhydrous form of the compound of Formula (I). In some embodiments, the oral dosage form comprises about 10 mg to about 35 mg of the crystalline anhydrous form of the compound of Formula (I). In some embodiments, the oral dosage form comprises about 0.5 mg to about 5 mg, about 6 mg to about 14 mg, about 10 mg to about 18 mg, about 16 mg to about 24 mg, or about 26 mg to about 34 mg of the crystalline anhydrous form of the compound of Formula (I). In some embodiments, the oral dosage form comprises about 1 mg to about 3 mg, about 8 mg to about 12 mg, about 12 mg to about 16 mg, about 18 mg to about 22 mg, or about 28 mg to about 32 mg of the crystalline anhydrous form of the compound of Formula (I). In some embodiments, the oral dosage form comprises about 2 mg, about 10 mg, about 14 mg, about 20 mg, or about 30 mg of the crystalline anhydrous form of the compound of Formula (I). In some embodiments, the crystalline anhydrous form of the compound of Formula (I) is present in an amount of about 2 mg. In some embodiments, the crystalline anhydrous form of the compound of Formula (I) is present in an amount of about 10 mg. In some embodiments, the crystalline anhydrous form of the compound of Formula (I) is present in an amount of about 14 mg. In some embodiments, the crystalline anhydrous form of the compound of Formula (I) is present in an amount of about 20 mg. In some embodiments, the crystalline anhydrous form of the compound of Formula (I) is present in an amount of about 30 mg.

In some embodiments, the oral dosage form consists essentially of about 1 mg to about 40 mg of the crystalline anhydrous form of the compound of Formula (I). In some embodiments, the oral dosage form consists essentially of about 5 mg to about 35 mg of the crystalline anhydrous form of the compound of Formula (I). In some embodiments, the oral dosage form consists essentially of about 10 mg to about 35 mg of the crystalline anhydrous form of the compound of Formula (I). In some embodiments, the oral dosage form consists essentially of about 0.5 mg to about 5 mg, about 6 mg to about 14 mg, about 10 mg to about 18 mg, about 16 mg to about 24 mg, or about 26 mg to about 34 mg of the crystalline anhydrous form of the compound of Formula (I). In some embodiments, the oral dosage form consists essentially of about 1 mg to about 3 mg, about 8 mg to about 12 mg, about 12 mg to about 16 mg, about 18 mg to about 22 mg, or about 28 mg to about 32 mg of the crystalline anhydrous form of the compound of Formula (I). In some embodiments, the oral dosage form consists essentially of about 2 mg, about 10 mg, about 14 mg, about 20 mg, or about 30 mg of the crystalline anhydrous form of the compound of Formula (I). In some embodiments, the crystalline anhydrous form of the compound of Formula (I) is present in an amount of about 2 mg. In some embodiments, the crystalline anhydrous form of the compound of Formula (I) is present in an amount of about 10 mg. In some embodiments, the crystalline anhydrous form of the compound of Formula (I) is present in an amount of about 14 mg. In some embodiments, the crystalline anhydrous form of the compound of Formula (I) is present in an amount of about 20 mg. In some embodiments, the crystalline anhydrous form of the compound of Formula (I) is present in an amount of about 30 mg.

Also provided herein, in some embodiments, is a process of preparing a pharmaceutically acceptable capsule, the pharmaceutically acceptable capsule comprising:

(a) about 1% to about 70%, based on the total weight of the pharmaceutically acceptable capsule, of a crystalline anhydrous form of a compound of Formula (I):

Formula (I)

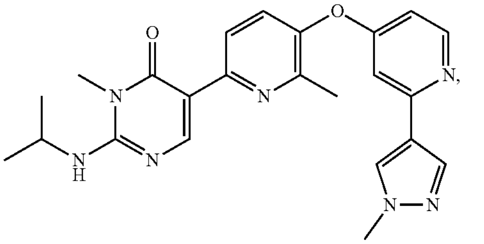

and one or more pharmaceutically acceptable excipients, wherein the one or more pharmaceutically acceptable excipients comprise:

(b) about 20% by weight to about 97% by weight of one or more fillers, based on the total weight of the pharmaceutically acceptable capsule;
(c) about 1% by weight to about 20% by weight of one or more disintegrants, based on the total weight of the pharmaceutically acceptable capsule; and
(d) about 0.1% by weight to about 10% by weight of one or more lubricants, based on the total weight of the pharmaceutically acceptable capsule;

the process comprising:

(i) blending the crystalline anhydrous form of a compound represented by Formula (I) with the one or more fillers and one or more disintegrants to produce a first blend;
(ii) blending the first blend with the one or more lubricants to form a second blend; and
(iii) dispensing the second blend into an empty pharmaceutically acceptable capsule, thereby forming the pharmaceutically acceptable capsule.

Also provided herein, in some embodiments, is a process of preparing a pharmaceutically acceptable capsule, the pharmaceutically acceptable capsule consisting essentially of:

(a) about 1% to about 70%, based on the total weight of the pharmaceutically acceptable capsule, of a crystalline anhydrous form of a compound of Formula (I):

Formula (I)

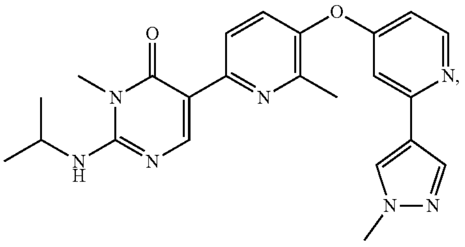

and one or more pharmaceutically acceptable excipients, wherein the one or more pharmaceutically acceptable excipients comprise:

(b) about 20% by weight to about 97% by weight of one or more fillers, based on the total weight of the pharmaceutically acceptable capsule;
(c) about 1% by weight to about 20% by weight of one or more disintegrants, based on the total weight of the pharmaceutically acceptable capsule; and
(d) about 0.1% by weight to about 10% by weight of one or more lubricants, based on the total weight of the pharmaceutically acceptable capsule;

the process comprising:

(i) blending the crystalline anhydrous form of a compound represented by Formula (I) with the one or more fillers and one or more disintegrants to produce a first blend;
(ii) blending the first blend with the one or more lubricants to form a second blend; and
(iii) dispensing the second blend into an empty pharmaceutically acceptable capsule, thereby forming the pharmaceutically acceptable capsule.

Also provided herein, in some embodiments, is a process of preparing a pharmaceutically acceptable capsule, the pharmaceutically acceptable capsule comprising:

(a) about 1% to about 70%, based on the total weight of the pharmaceutically acceptable capsule, of a crystalline anhydrous form of a compound of Formula (I):

Formula (I)

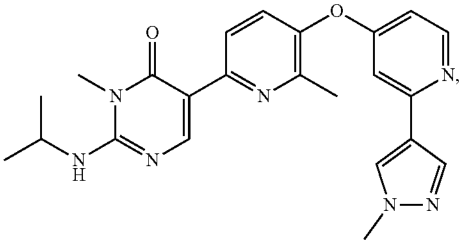

and one or more pharmaceutically acceptable excipients, wherein the one or more pharmaceutically acceptable excipients comprise:

(b) about 20% by weight to about 97% by weight of one or more fillers, based on the total weight of the pharmaceutically acceptable capsule;

(c) about 1% by weight to about 20% by weight of one or more disintegrants, based on the total weight of the pharmaceutically acceptable capsule; and (d) about 0.1% by weight to about 10% by weight of one or more lubricants, based on the total weight of the pharmaceutically acceptable capsule;

the process comprising:

(i) blending the crystalline anhydrous form of a compound represented by Formula (I) with the one or more fillers to produce a first blend;

(ii) blending the first blend with the one or more disintegrants to form a second blend;

(iii) blending the second blend with the one or more lubricants to form a third blend; and (iv) dispensing the third blend into an empty pharmaceutically acceptable capsule, thereby forming the pharmaceutically acceptable capsule.

Also provided herein, in some embodiments, is a process of preparing a pharmaceutically acceptable capsule, the pharmaceutically acceptable capsule consisting essentially of:

(a) about 1% to about 70%, based on the total weight of the pharmaceutically acceptable capsule, of a crystalline anhydrous form of a compound of Formula (I):

Formula (I)

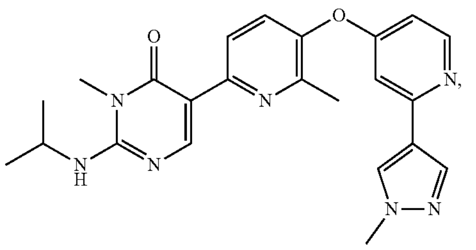

and one or more pharmaceutically acceptable excipients, wherein the one or more pharmaceutically acceptable excipients comprise:

(b) about 20% by weight to about 97% by weight of one or more fillers, based on the total weight of the pharmaceutically acceptable capsule;

(c) about 1% by weight to about 20% by weight of one or more disintegrants, based on the total weight of the pharmaceutically acceptable capsule; and (d) about 0.1% by weight to about 10% by weight of one or more lubricants, based on the total weight of the pharmaceutically acceptable capsule;

the process comprising:

(i) blending the crystalline anhydrous form of a compound represented by Formula (I) with the one or more fillers to produce a first blend;

(ii) blending the first blend with the one or more disintegrants to form a second blend;

(iii) blending the second blend with the one or more lubricants to form a third blend; and (iv) dispensing the third blend into an empty pharmaceutically acceptable capsule, thereby forming the pharmaceutically acceptable capsule.

Also provided herein, in some embodiments, is a process of preparing a pharmaceutically acceptable capsule, the pharmaceutically acceptable capsule comprising:

(a) about 1% to about 70%, based on the total weight of the pharmaceutically acceptable capsule, of a crystalline anhydrous form of a compound of Formula (I):

Formula (I)

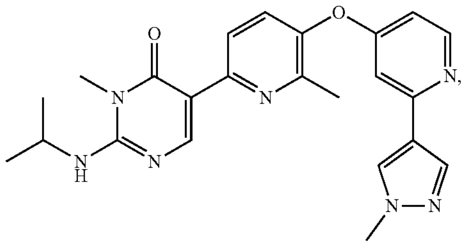

and one or more pharmaceutically acceptable excipients, wherein the one or more pharmaceutically acceptable excipients comprise:

(b) about 20% by weight to about 97% by weight of one or more fillers, based on the total weight of the pharmaceutically acceptable capsule;

(c) about 1% by weight to about 20% by weight of one or more disintegrants, based on the total weight of the pharmaceutically acceptable capsule; and (d) about 0.1% by weight to about 10% by weight of one or more lubricants, based on the total weight of the pharmaceutically acceptable capsule;

the process comprising:

(i) blending the crystalline anhydrous form of a compound represented by Formula (I) with the one or more fillers to produce a first blend;

(ii) blending the first blend with a second blend comprising one or more disintegrants and one or more fillers and optionally a third blend comprising one or more fillers to form a fourth blend;

(iii) blending the fourth blend with the one or more lubricants to form a fifth blend; and (iv) dispensing the fifth blend into an empty pharmaceutically acceptable capsule, thereby forming the pharmaceutically acceptable capsule.

Also provided herein, in some embodiments, is a process of preparing a pharmaceutically acceptable capsule, the pharmaceutically acceptable capsule consisting essentially of:

(a) about 1% to about 70%, based on the total weight of the pharmaceutically acceptable capsule, of a crystalline anhydrous form of a compound of Formula (I):

Formula (I)

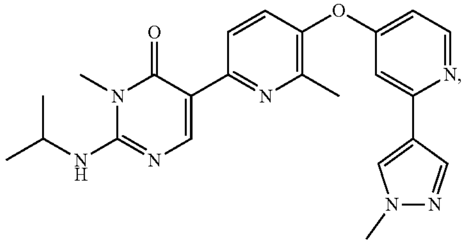

and one or more pharmaceutically acceptable excipients, wherein the one or more pharmaceutically acceptable excipients comprise:

(b) about 20% by weight to about 97% by weight of one or more fillers, based on the total weight of the pharmaceutically acceptable capsule;

(c) about 1% by weight to about 20% by weight of one or more disintegrants, based on the total weight of the pharmaceutically acceptable capsule; and (d) about 0.1% by weight to about 10% by weight of one or more lubricants, based on the total weight of the pharmaceutically acceptable capsule;

the process comprising:

(i) blending the crystalline anhydrous form of a compound represented by Formula (I) with the one or more fillers to produce a first blend;

(ii) blending the first blend with a second blend comprising one or more disintegrants and one or more fillers and optionally a third blend comprising one or more fillers to form a fourth blend;

(iii) blending the fourth blend with the one or more lubricants to form a fifth blend; and (iv) dispensing the fifth blend into an empty pharmaceutically acceptable capsule, thereby forming the pharmaceutically acceptable capsule.

In some embodiments, the pharmaceutically acceptable capsule comprises about 1% by weight to about 60% by weight, based on the total weight of the pharmaceutically acceptable capsule, of a crystalline anhydrous form of a compound of Formula (I). In some embodiments, the pharmaceutically acceptable capsule comprises about 1% by weight to about 50% by weight, based on the total weight of the pharmaceutically acceptable capsule, of a crystalline anhydrous form of a compound of Formula (I). In some embodiments, the pharmaceutically acceptable capsule comprises about 1% by weight to about 40% by weight, based on the total weight of the pharmaceutically acceptable capsule, of a crystalline anhydrous form of a compound of Formula (I). In some embodiments, the pharmaceutically acceptable capsule comprises about 1% by weight to about 30% by weight, based on the total weight of the pharmaceutically acceptable capsule, of a crystalline anhydrous form of a compound of Formula (I). In some embodiments, the pharmaceutically acceptable capsule comprises about 1% by weight to about 20% by weight, based on the total weight of the pharmaceutically acceptable capsule, of a crystalline anhydrous form of a compound of Formula (I).

In some embodiments, the pharmaceutically acceptable capsule consists essentially of about 1% by weight to about 60% by weight, based on the total weight of the pharmaceutically acceptable capsule, of a crystalline anhydrous form of a compound of Formula (I). In some embodiments, the pharmaceutically acceptable capsule consists essentially of about 1% by weight to about 50% by weight, based on the total weight of the pharmaceutically acceptable capsule, of a crystalline anhydrous form of a compound of Formula (I). In some embodiments, the pharmaceutically acceptable capsule consists essentially of about 1% by weight to about 40% by weight, based on the total weight of the pharmaceutically acceptable capsule, of a crystalline anhydrous form of a compound of Formula (I). In some embodiments, the pharmaceutically acceptable capsule consists essentially of about 1% by weight to about 30% by weight, based on the total weight of the pharmaceutically acceptable capsule, of a crystalline anhydrous form of a compound of Formula (I). In some embodiments, the pharmaceutically acceptable capsule consists essentially of about 1% by weight to about 20% by weight, based on the total weight of the pharmaceutically acceptable capsule, of a crystalline anhydrous form of a compound of Formula (I).

In some embodiments, the pharmaceutically acceptable capsule comprises about 1% by weight to about 70% by weight of the compound of Formula (I) based on the total weight of the pharmaceutically acceptable capsule. In some embodiments, the pharmaceutically acceptable capsule comprises about 1% by weight to about 65% by weight of the compound of Formula (I) based on the total weight of the pharmaceutically acceptable capsule. In some embodiments, the pharmaceutically acceptable capsule comprises about 1% by weight to about 60% by weight of the compound of Formula (I) based on the total weight of the pharmaceutically acceptable capsule. In some embodiments, the pharmaceutically acceptable capsule comprises about 1% by weight to about 55% by weight of the compound of Formula (I) based on the total weight of the pharmaceutically acceptable capsule. In some embodiments, the pharmaceutically acceptable capsule comprises about 1% by weight to about 50% by weight of the compound of Formula (I) based on the total weight of the pharmaceutically acceptable capsule. In some embodiments, the pharmaceutically acceptable capsule comprises about 1% by weight to about 45% by weight of the compound of Formula (I) based on the total weight of the pharmaceutically acceptable capsule. In some embodiments, the pharmaceutically acceptable capsule comprises about 1% by weight to about 40% by weight of the compound of Formula (I) based on the total weight of the pharmaceutically acceptable capsule. In some embodiments, the pharmaceutically acceptable capsule comprises about 1% by weight to about 35% by weight of the compound of Formula (I) based on the total weight of the pharmaceutically acceptable capsule. In some embodiments, the pharmaceutically acceptable capsule comprises about 1% by weight to about 30% by weight of the compound of Formula (I) based on the total weight of the pharmaceutically acceptable capsule. In some embodiments, the pharmaceutically acceptable capsule comprises about 1% by weight to about 25% by weight of the compound of Formula (I) based on the total weight of the pharmaceutically acceptable capsule. In some embodiments, the pharmaceutically acceptable capsule comprises about 1% by weight to about 20% by weight of the compound of Formula (I) based on the total weight of the pharmaceutically acceptable capsule. In some embodiments, the pharmaceutically acceptable capsule comprises about 1% by weight to about 15% by weight of the compound of Formula (I) based on the total weight of the pharmaceutically acceptable capsule. In some embodiments, the pharmaceutically acceptable capsule comprises about 1% by weight to about 10% by weight of the compound of Formula (I) based on the total weight of the pharmaceutically acceptable capsule.

In some embodiments, the pharmaceutically acceptable capsule consists essentially of about 1% by weight to about 70% by weight of the compound of Formula (I) based on the total weight of the pharmaceutically acceptable capsule. In some embodiments, the pharmaceutically acceptable capsule consists essentially of about 1% by weight to about 65% by weight of the compound of Formula (I) based on the total weight of the pharmaceutically acceptable capsule. In some embodiments, the pharmaceutically acceptable capsule consists essentially of about 1% by weight to about 60% by weight of the compound of Formula (I) based on the total weight of the pharmaceutically acceptable capsule. In some embodiments, the pharmaceutically acceptable capsule consists essentially of about 1% by weight to about 55% by weight of the compound of Formula (I) based on the total weight of the pharmaceutically acceptable capsule. In some embodiments, the pharmaceutically acceptable capsule consists essentially of about 1% by weight to about 50% by weight of the compound of Formula (I) based on the total weight of the pharmaceutically acceptable capsule. In some embodiments, the pharmaceutically acceptable capsule consists essentially of about 1% by weight to about 45% by weight of the compound of Formula (I) based on the total weight of the pharmaceutically acceptable capsule. In some embodiments, the pharmaceutically acceptable capsule consists essentially of about 1% by weight to about 40% by weight of the compound of Formula (I) based on the total weight of the pharmaceutically acceptable capsule. In some embodiments, the pharmaceutically acceptable capsule consists essentially of about 1% by weight to about 35% by weight of the compound of Formula (I) based on the total weight of the pharmaceutically acceptable capsule. In some embodiments, the pharmaceutically acceptable capsule consists essentially of about 1% by weight to about 30% by weight of the compound of Formula (I) based on the total weight of the pharmaceutically acceptable capsule. In some embodiments, the pharmaceutically acceptable capsule consists essentially of about 1% by weight to about 25% by weight of the compound of Formula (I) based on the total weight of the pharmaceutically acceptable capsule. In some embodiments, the pharmaceutically acceptable capsule consists essentially of about 1% by weight to about 20% by weight of the compound of Formula (I) based on the total weight of the pharmaceutically acceptable capsule. In some embodiments, the pharmaceutically acceptable capsule consists essentially of about 1% by weight to about 15% by weight of the compound of Formula (I) based on the total weight of the pharmaceutically acceptable capsule. In some embodiments, the pharmaceutically acceptable capsule consists essentially of about 1% by weight to about 10% by weight of the compound of Formula (I) based on the total weight of the pharmaceutically acceptable capsule.

In some embodiments, the pharmaceutically acceptable capsule comprises about 5% by weight to about 30% by weight of the compound of Formula (I) based on the total weight of the pharmaceutically acceptable capsule. In some embodiments, the pharmaceutically acceptable capsule comprises about 5% by weight to about 25% by weight of the compound of Formula (I) based on the total weight of the pharmaceutically acceptable capsule. In some embodiments, the pharmaceutically acceptable capsule comprises about 5% by weight to about 20% by weight of the compound of Formula (I) based on the total weight of the pharmaceutically acceptable capsule. In some embodiments, the pharmaceutically acceptable capsule comprises about 5% by weight to about 15% by weight of the compound of Formula (I) based on the total weight of the pharmaceutically acceptable capsule. In some embodiments, the pharmaceutically acceptable capsule comprises about 5% by weight to about 10% by weight of the compound of Formula (I) based on the total weight of the pharmaceutically acceptable capsule.

In some embodiments, the pharmaceutically acceptable capsule consists essentially of about 5% by weight to about 30% by weight of the compound of Formula (I) based on the total weight of the pharmaceutically acceptable capsule. In some embodiments, the pharmaceutically acceptable capsule consists essentially of about 5% by weight to about 25% by weight of the compound of Formula (I) based on the total weight of the pharmaceutically acceptable capsule. In some embodiments, the pharmaceutically acceptable capsule consists essentially of about 5% by weight to about 20% by weight of the compound of Formula (I) based on the total weight of the pharmaceutically acceptable capsule. In some embodiments, the pharmaceutically acceptable capsule consists essentially of about 5% by weight to about 15% by weight of the compound of Formula (I) based on the total weight of the pharmaceutically acceptable capsule. In some embodiments, the pharmaceutically acceptable capsule consists essentially of about 5% by weight to about 10% by weight of the compound of Formula (I) based on the total weight of the pharmaceutically acceptable capsule.

In some embodiments, the pharmaceutically acceptable capsule comprises about 10% to about 30% of the compound of Formula (I) based on the total weight of the pharmaceutically acceptable capsule. In some embodiments, the pharmaceutically acceptable capsule comprises about 10% to about 25% of the compound of Formula (I) based on the total weight of the pharmaceutically acceptable capsule. In some embodiments, the pharmaceutically acceptable capsule comprises about 10% to about 20% of the compound of Formula (I) based on the total weight of the pharmaceutically acceptable capsule. In some embodiments, the pharmaceutically acceptable capsule comprises about 10% by weight to about 15% by weight of the compound of Formula (I) based on the total weight of the pharmaceutically acceptable capsule.

In some embodiments, the pharmaceutically acceptable capsule consists essentially of about 10% to about 30% of the compound of Formula (I) based on the total weight of the pharmaceutically acceptable capsule. In some embodiments, the pharmaceutically acceptable capsule consists essentially of about 10% to about 25% of the compound of Formula (I) based on the total weight of the pharmaceutically acceptable capsule. In some embodiments, the pharmaceutically acceptable capsule consists essentially of about 10% to about 20% of the compound of Formula (I) based on the total weight of the pharmaceutically acceptable capsule. In some embodiments, the pharmaceutically acceptable capsule consists essentially of about 10% by weight to about 15% by weight of the compound of Formula (I) based on the total weight of the pharmaceutically acceptable capsule.

In some embodiments, the pharmaceutically acceptable capsule comprises about 1% by weight to about 30% by weight of the compound of Formula (I) based on the total weight of the pharmaceutically acceptable capsule. In some embodiments, the pharmaceutically acceptable capsule comprises about 1% by weight to about 10% by weight of the compound of Formula (I) based on the total weight of the pharmaceutically acceptable capsule. In some embodiments, the pharmaceutically acceptable capsule comprises about 10% to about 20% of the compound of Formula (I) based on the total weight of the pharmaceutically acceptable capsule. In some embodiments, the pharmaceutically acceptable capsule comprises about 10% by weight to about 15% by weight of the compound of Formula (I) based on the total weight of the pharmaceutically acceptable capsule.

In some embodiments, the pharmaceutically acceptable capsule consists essentially of about 1% by weight to about 30% by weight of the compound of Formula (I) based on the total weight of the pharmaceutically acceptable capsule. In some embodiments, the pharmaceutically acceptable capsule consists essentially of about 1% by weight to about 10% by weight of the compound of Formula (I) based on the total weight of the pharmaceutically acceptable capsule. In some embodiments, the pharmaceutically acceptable capsule consists essentially of about 10% to about 20% of the compound of Formula (I) based on the total weight of the pharmaceutically acceptable capsule. In some embodiments, the pharmaceutically acceptable capsule consists essentially of about 10% by weight to about 15% by weight of the compound of Formula (I) based on the total weight of the pharmaceutically acceptable capsule.

In some embodiments, the one or more pharmaceutically acceptable excipients comprise about 20% by weight to about 90% by weight of one or more fillers based on the total weight of the pharmaceutically acceptable capsule. In some embodiments, the one or more pharmaceutically acceptable excipients comprise about 20% by weight to about 85% by weight of one or more fillers based on the total weight of the pharmaceutically acceptable capsule. In some embodiments, the one or more pharmaceutically acceptable excipients comprise about 20% by weight to about 80% by weight of one or more fillers based on the total weight of the pharmaceutically acceptable capsule. In some embodiments, the one or more pharmaceutically acceptable excipients comprise about 20% by weight to about 75% by weight of one or more fillers based on the total weight of the pharmaceutically acceptable capsule. In some embodiments, the one or more pharmaceutically acceptable excipients comprise about 20% by weight to about 70% by weight of one or more fillers based on the total weight of the pharmaceutically acceptable capsule. In some embodiments, the one or more pharmaceutically acceptable excipients comprise about 20% by weight to about 65% by weight of one or more fillers based on the total weight of the pharmaceutically acceptable capsule. In some embodiments, the one or more pharmaceutically acceptable excipients comprise about 20% by weight to about 60% by weight of one or more fillers based on the total weight of the pharmaceutically acceptable capsule. In some embodiments, the one or more pharmaceutically acceptable excipients comprise about 20% by weight to about 55% by weight of one or more fillers based on the total weight of the pharmaceutically acceptable capsule. In some embodiments, the one or more pharmaceutically acceptable excipients comprise about 20% by weight to about 50% by weight of one or more fillers based on the total weight of the pharmaceutically acceptable capsule. In some embodiments, the one or more pharmaceutically acceptable excipients comprise about 20% by weight to about 45% by weight of one or more fillers based on the total weight of the pharmaceutically acceptable capsule. In some embodiments, the one or more pharmaceutically acceptable excipients comprise about 20% by weight to about 40% by weight of one or more fillers based on the total weight of the pharmaceutically acceptable capsule. In some embodiments, the one or more pharmaceutically acceptable excipients comprise about 20% by weight to about 35% by weight of one or more fillers based on the total weight of the pharmaceutically acceptable capsule. In some embodiments, the one or more pharmaceutically acceptable excipients comprise about 20% by weight to about 30% by weight of one or more fillers based on the total weight of the pharmaceutically acceptable capsule. In some embodiments, the one or more pharmaceutically acceptable excipients comprise about 20% by weight to about 25% by weight of one or more fillers based on the total weight of the pharmaceutically acceptable capsule.

In some embodiments, the one or more pharmaceutically acceptable excipients comprise about 30% by weight to about 90% by weight of one or more fillers based on the total weight of the pharmaceutically acceptable capsule. In some embodiments, the one or more pharmaceutically acceptable excipients comprise about 30% by weight to about 80% by weight of one or more fillers based on the total weight of the pharmaceutically acceptable capsule. In some embodiments, the one or more pharmaceutically acceptable excipients comprise about 30% by weight to about 70% by weight of one or more fillers based on the total weight of the pharmaceutically acceptable capsule. In some embodiments, the one or more pharmaceutically acceptable excipients comprise about 30% by weight to about 60% by weight of one or more fillers based on the total weight of the pharmaceutically acceptable capsule. In some embodiments, the one or more pharmaceutically acceptable excipients comprise about 30% by weight to about 50% by weight of one or more fillers based on the total weight of the pharmaceutically acceptable capsule. In some embodiments, the one or more pharmaceutically acceptable excipients comprise about 30% by weight to about 40% by weight of one or more fillers based on the total weight of the pharmaceutically acceptable capsule.

In some embodiments, the one or more pharmaceutically acceptable excipients comprise about 40% by weight to about 90% by weight of one or more fillers based on the total weight of the pharmaceutically acceptable capsule. In some embodiments, the one or more pharmaceutically acceptable excipients comprise about 40% by weight to about 80% by weight of one or more fillers based on the total weight of the pharmaceutically acceptable capsule. In some embodiments, the one or more pharmaceutically acceptable excipients comprise about 40% by weight to about 70% by weight of one or more fillers based on the total weight of the pharmaceutically acceptable capsule. In some embodiments, the one or more pharmaceutically acceptable excipients comprise about 40% by weight to about 60% by weight of one or more fillers based on the total weight of the pharmaceutically acceptable capsule. In some embodiments, the one or more pharmaceutically acceptable excipients comprise about 40% by weight to about 50% by weight of one or more fillers based on the total weight of the pharmaceutically acceptable capsule.

In some embodiments, the one or more pharmaceutically acceptable excipients comprise about 50% by weight to about 90% by weight of one or more fillers based on the total weight of the pharmaceutically acceptable capsule. In some embodiments, the one or more pharmaceutically acceptable excipients comprise about 50% by weight to about 80% by weight of one or more fillers based on the total weight of the pharmaceutically acceptable capsule. In some embodiments, the one or more pharmaceutically acceptable excipients comprise about 50% by weight to about 70% by weight of one or more fillers based on the total weight of the pharmaceutically acceptable capsule. In some embodiments, the one or more pharmaceutically acceptable excipients comprise about 50% by weight to about 60% by weight of one or more fillers based on the total weight of the pharmaceutically acceptable capsule.

In some embodiments, the one or more pharmaceutically acceptable excipients comprise about 60% by weight to about 90% by weight of one or more fillers based on the total weight of the pharmaceutically acceptable capsule. In some embodiments, the one or more pharmaceutically acceptable excipients comprise about 60% by weight to about 80% by weight of one or more fillers based on the total weight of the pharmaceutically acceptable capsule. In some embodiments, the one or more pharmaceutically acceptable excipients comprise about 60% by weight to about 70% by weight of one or more fillers based on the total weight of the pharmaceutically acceptable capsule.

In some embodiments, the one or more pharmaceutically acceptable excipients comprise about 70% by weight to about 90% by weight of one or more fillers based on the total weight of the pharmaceutically acceptable capsule. In some embodiments, the one or more pharmaceutically acceptable excipients comprise about 70% by weight to about 80% by weight of one or more fillers based on the total weight of the pharmaceutically acceptable capsule.

In some embodiments, the one or more pharmaceutically acceptable excipients comprise about 80% by weight to about 90% by weight of one or more fillers based on the total weight of the pharmaceutically acceptable capsule.

In some embodiments, the one or more pharmaceutically acceptable excipients comprise about 1% by weight to about 20% by weight of one or more disintegrants based on the total weight of the pharmaceutically acceptable capsule. In some embodiments, the one or more pharmaceutically acceptable excipients comprise about 1% by weight to about 15% by weight of one or more disintegrants based on the total weight of the pharmaceutically acceptable capsule. In some embodiments, the one or more pharmaceutically acceptable excipients comprise about 1% by weight to about 14% by weight of one or more disintegrants based on the total weight of the pharmaceutically acceptable capsule. In some embodiments, the one or more pharmaceutically acceptable excipients comprise about 1% by weight to about 13% by weight of one or more disintegrants based on the total weight of the pharmaceutically acceptable capsule. In some embodiments, the one or more pharmaceutically acceptable excipients comprise about 1% by weight to about 12% by weight of one or more disintegrants based on the total weight of the pharmaceutically acceptable capsule. In some embodiments, the one or more pharmaceutically acceptable excipients comprise about 1% by weight to about 11% by weight of one or more disintegrants based on the total weight of the pharmaceutically acceptable capsule. In some embodiments, the one or more pharmaceutically acceptable excipients comprise about 1% by weight to about 10% by weight of one or more disintegrants based on the total weight of the pharmaceutically acceptable capsule. In some embodiments, the one or more pharmaceutically acceptable excipients comprise about 1% by weight to about 9% by weight of one or more disintegrants based on the total weight of the pharmaceutically acceptable capsule. In some embodiments, the one or more pharmaceutically acceptable excipients comprise about 1% by weight to about 8% by weight of one or more disintegrants based on the total weight of the pharmaceutically acceptable capsule. In some embodiments, the one or more pharmaceutically acceptable excipients comprise about 1% by weight to about 7% by weight of one or more disintegrants based on the total weight of the pharmaceutically acceptable capsule. In some embodiments, the one or more pharmaceutically acceptable excipients comprise about 1% by weight to about 6% by weight of one or more disintegrants based on the total weight of the pharmaceutically acceptable capsule. In some embodiments, the one or more pharmaceutically acceptable excipients comprise about 1% by weight to about 5% by weight of one or more disintegrants based on the total weight of the pharmaceutically acceptable capsule. In some embodiments, the one or more pharmaceutically acceptable excipients comprise about 1% by weight to about 4% by weight of one or more disintegrants based on the total weight of the pharmaceutically acceptable capsule. In some embodiments, the one or more pharmaceutically acceptable excipients comprise about 1% by weight to about 3% by weight of one or more disintegrants based on the total weight of the pharmaceutically acceptable capsule.

In some embodiments, the one or more pharmaceutically acceptable excipients comprise about 1% by weight of one or more disintegrants based on the total weight of the pharmaceutically acceptable capsule. In some embodiments, the one or more pharmaceutically acceptable excipients comprise about 2% by weight of one or more disintegrants based on the total weight of the pharmaceutically acceptable capsule. In some embodiments, the one or more pharmaceutically acceptable excipients comprise about 3% by weight of one or more disintegrants based on the total weight of the pharmaceutically acceptable capsule. In some embodiments, the one or more pharmaceutically acceptable excipients comprise about 4% by weight of one or more disintegrants based on the total weight of the pharmaceutically acceptable capsule. In some embodiments, the one or more pharmaceutically acceptable excipients comprise about 5% by weight of one or more disintegrants based on the total weight of the pharmaceutically acceptable capsule. In some embodiments, the one or more pharmaceutically acceptable excipients comprise about 6% by weight of one or more disintegrants based on the total weight of the pharmaceutically acceptable capsule. In some embodiments, the one or more pharmaceutically acceptable excipients comprise about 7% by weight of one or more disintegrants based on the total weight of the pharmaceutically acceptable capsule. In some embodiments, the one or more pharmaceutically acceptable excipients comprise about 8% by weight of one or more disintegrants based on the total weight of the pharmaceutically acceptable capsule. In some embodiments, the one or more pharmaceutically acceptable excipients comprise about 9% by weight of one or more disintegrants based on the total weight of the pharmaceutically acceptable capsule. In some embodiments, the one or more pharmaceutically acceptable excipients comprise about 10% by weight of one or more disintegrants based on the total weight of the pharmaceutically acceptable capsule. In some embodiments, the one or more pharmaceutically acceptable excipients comprise about 11% by weight of one or more disintegrants based on the total weight of the pharmaceutically acceptable capsule. In some embodiments, the one or more pharmaceutically acceptable excipients comprise about 12% by weight of one or more disintegrants based on the total weight of the pharmaceutically acceptable capsule. In some embodiments, the one or more pharmaceutically acceptable excipients comprise about 13% by weight of one or more disintegrants based on the total weight of the pharmaceutically acceptable capsule. In some embodiments, the one or more pharmaceutically acceptable excipients comprise about 14% by weight of one or more disintegrants based on the total weight of the pharmaceutically acceptable capsule. In some embodiments, the one or more pharmaceutically acceptable excipients comprise about 15% by weight of one or more disintegrants based on the total weight of the pharmaceutically acceptable capsule.

In some embodiments, the one or more pharmaceutically acceptable excipients comprise about 0.1% by weight to about 10% by weight of one or more lubricants based on the total weight of the pharmaceutically acceptable capsule. In some embodiments, the one or more pharmaceutically acceptable excipients comprise about 0.1% by weight to about 9% by weight of one or more lubricants based on the total weight of the pharmaceutically acceptable capsule. In some embodiments, the one or more pharmaceutically acceptable excipients comprise about 0.1% by weight to about 8% by weight of one or more lubricants based on the total weight of the pharmaceutically acceptable capsule. In some embodiments, the one or more pharmaceutically acceptable excipients comprise about 0.1% by weight to about 7% by weight of one or more lubricants based on the total weight of the pharmaceutically acceptable capsule. In some embodiments, the one or more pharmaceutically acceptable excipients comprise about 0.1% by weight to about 6% by weight of one or more lubricants based on the total weight of the pharmaceutically acceptable capsule. In some embodiments, the one or more pharmaceutically acceptable excipients comprise about 0.1% by weight to about 5% by weight of one or more lubricants based on the total weight of the pharmaceutically acceptable capsule. In some embodiments, the one or more pharmaceutically acceptable excipients comprise about 0.1% by weight to about 4% by weight of one or more lubricants based on the total weight of the pharmaceutically acceptable capsule. In some embodiments, the one or more pharmaceutically acceptable excipients comprise about 0.1% by weight to about 3% by weight of one or more lubricants based on the total weight of the pharmaceutically acceptable capsule. In some embodiments, the one or more pharmaceutically acceptable excipients comprise about 0.1% by weight to about 2% by weight of one or more lubricants based on the total weight of the pharmaceutically acceptable capsule.

In some embodiments, the one or more pharmaceutically acceptable excipients comprise about 0.1% by weight to about 1.9% by weight of one or more lubricants based on the total weight of the pharmaceutically acceptable capsule. In some embodiments, the one or more pharmaceutically acceptable excipients comprise about 0.1% by weight to about 1.8% by weight of one or more lubricants based on the total weight of the pharmaceutically acceptable capsule. In some embodiments, the one or more pharmaceutically acceptable excipients comprise about 0.1% by weight to about 1.7% by weight of one or more lubricants based on the total weight of the pharmaceutically acceptable capsule. In some embodiments, the one or more pharmaceutically acceptable excipients comprise about 0.1% by weight to about 1.6% by weight of one or more lubricants based on the total weight of the pharmaceutically acceptable capsule. In some embodiments, the one or more pharmaceutically acceptable excipients comprise about 0.1% by weight to about 1.5% by weight of one or more lubricants based on the total weight of the pharmaceutically acceptable capsule. In some embodiments, the one or more pharmaceutically acceptable excipients comprise about 0.1% by weight to about 1.4% by weight of one or more lubricants based on the total weight of the pharmaceutically acceptable capsule. In some embodiments, the one or more pharmaceutically acceptable excipients comprise about 0.1% by weight to about 1.3% by weight of one or more lubricants based on the total weight of the pharmaceutically acceptable capsule. In some embodiments, the one or more pharmaceutically acceptable excipients comprise about 0.1% by weight to about 1.2% by weight of one or more lubricants based on the total weight of the pharmaceutically acceptable capsule. In some embodiments, the one or more pharmaceutically acceptable excipients comprise about 0.1% by weight to about 1.1% by weight of one or more lubricants based on the total weight of the pharmaceutically acceptable capsule. In some embodiments, the one or more pharmaceutically acceptable excipients comprise about 0.1% by weight to about 1.0% by weight of one or more lubricants based on the total weight of the pharmaceutically acceptable capsule. In some embodiments, the one or more pharmaceutically acceptable excipients comprise about 0.1% by weight to about 0.9% by weight of one or more lubricants based on the total weight of the pharmaceutically acceptable capsule. In some embodiments, the one or more pharmaceutically acceptable excipients comprise about 0.1% by weight to about 0.8% by weight of one or more lubricants based on the total weight of the pharmaceutically acceptable capsule. In some embodiments, the one or more pharmaceutically acceptable excipients comprise about 0.1% by weight to about 0.7% by weight of one or more lubricants based on the total weight of the pharmaceutically acceptable capsule. In some embodiments, the one or more pharmaceutically acceptable excipients comprise about 0.1% by weight to about 0.6% by weight of one or more lubricants based on the total weight of the pharmaceutically acceptable capsule. In some embodiments, the one or more pharmaceutically acceptable excipients comprise about 0.1% by weight to about 0.5% by weight of one or more lubricants based on the total weight of the pharmaceutically acceptable capsule. In some embodiments, the one or more pharmaceutically acceptable excipients comprise about 0.1% by weight to about 0.4% by weight of one or more lubricants based on the total weight of the pharmaceutically acceptable capsule. In some embodiments, the one or more pharmaceutically acceptable excipients comprise about 0.1% by weight to about 0.3% by weight of one or more lubricants based on the total weight of the pharmaceutically acceptable capsule. In some embodiments, the one or more pharmaceutically acceptable excipients comprise about 0.1% by weight to about 0.2% by weight of one or more lubricants based on the total weight of the pharmaceutically acceptable capsule.

In some embodiments, the one or more pharmaceutically acceptable excipients comprise about 0.1% by weight of one or more lubricants based on the total weight of the pharmaceutically acceptable capsule. In some embodiments, the one or more pharmaceutically acceptable excipients comprise about 0.2% by weight of one or more lubricants based on the total weight of the pharmaceutically acceptable capsule. In some embodiments, the one or more pharmaceutically acceptable excipients comprise about 0.3% by weight of one or more lubricants based on the total weight of the pharmaceutically acceptable capsule. In some embodiments, the one or more pharmaceutically acceptable excipients comprise about 0.4% by weight of one or more lubricants based on the total weight of the pharmaceutically acceptable capsule. In some embodiments, the one or more pharmaceutically acceptable excipients comprise about 0.5% by weight of one or more lubricants based on the total weight of the pharmaceutically acceptable capsule. In some embodiments, the one or more pharmaceutically acceptable excipients comprise about 0.6% by weight of one or more lubricants based on the total weight of the pharmaceutically acceptable capsule. In some embodiments, the one or more pharmaceutically acceptable excipients comprise about 0.7% by weight of one or more lubricants based on the total weight of the pharmaceutically acceptable capsule. In some embodiments, the one or more pharmaceutically acceptable excipients comprise about 0.8% by weight of one or more lubricants based on the total weight of the pharmaceutically acceptable capsule. In some embodiments, the one or more pharmaceutically acceptable excipients comprise about 0.9% by weight of one or more lubricants based on the total weight of the pharmaceutically acceptable capsule. In some embodiments, the one or more pharmaceutically acceptable excipients comprise about 1.0% by weight of one or more lubricants based on the total weight of the pharmaceutically acceptable capsule.

In some embodiments, the pharmaceutically acceptable capsule comprises (a) about 1% by weight to about 30% by weight of the compound of Formula (I) based on the total weight of the pharmaceutically acceptable capsule; (b) about 20% by weight to about 90% by weight of one or more fillers based on the total weight of the pharmaceutically acceptable capsule; (c) about 1% by weight to about 20% by weight of one or more disintegrants based on the total weight of the pharmaceutically acceptable capsule; and (d) about 0.1% by weight to about 10% by weight of one or more lubricants based on the total weight of the pharmaceutically acceptable capsule.

In some embodiments, the pharmaceutically acceptable capsule consists essentially of: (a) about 1% by weight to about 30% by weight of the compound of Formula (I) based on the total weight of the pharmaceutically acceptable capsule; (b) about 20% by weight to about 90% by weight of one or more fillers based on the total weight of the pharmaceutically acceptable capsule; (c) about 1% by weight to about 20% by weight of one or more disintegrants based on the total weight of the pharmaceutically acceptable capsule; and (d) about 0.1% by weight to about 10% by weight of one or more lubricants based on the total weight of the pharmaceutically acceptable capsule.

In some embodiments, the pharmaceutically acceptable capsule comprises (a) about 5% by weight to about 25% by weight of the compound of Formula (I) based on the total weight of the pharmaceutically acceptable capsule; (b) about 60% by weight to about 90% by weight of one or more fillers based on the total weight of the pharmaceutically acceptable capsule; (c) about 1% by weight to about 15% by weight of one or more disintegrants based on the total weight of the pharmaceutically acceptable capsule; and (d) about 0.1% by weight to about 4% by weight of one or more lubricants based on the total weight of the pharmaceutically acceptable capsule.

In some embodiments, the pharmaceutically acceptable capsule consists essentially of (a) about 5% by weight to about 25% by weight of the compound of Formula (I) based on the total weight of the pharmaceutically acceptable capsule; (b) about 60% by weight to about 90% by weight of one or more fillers based on the total weight of the pharmaceutically acceptable capsule; (c) about 1% by weight to about 15% by weight of one or more disintegrants based on the total weight of the pharmaceutically acceptable capsule; and (d) about 0.1% by weight to about 4% by weight of one or more lubricants based on the total weight of the pharmaceutically acceptable capsule.

In some embodiments, the pharmaceutically acceptable capsule comprises (a) about 10% by weight to about 30% by weight of the compound of Formula (I) based on the total weight of the pharmaceutically acceptable capsule; (b) about 70% by weight to about 90% by weight of one or more fillers based on the total weight of the pharmaceutically acceptable capsule; (c) about 1% by weight to about 10% by weight of one or more disintegrants based on the total weight of the pharmaceutically acceptable capsule; and (d) about 0.1% by weight to about 3% by weight of one or more lubricants based on the total weight of the pharmaceutically acceptable capsule.

In some embodiments, the pharmaceutically acceptable capsule consists essentially of (a) about 10% by weight to about 30% by weight of the compound of Formula (I) based on the total weight of the pharmaceutically acceptable capsule; (b) about 70% by weight to about 90% by weight of one or more fillers based on the total weight of the pharmaceutically acceptable capsule; (c) about 1% by weight to about 10% by weight of one or more disintegrants based on the total weight of the pharmaceutically acceptable capsule; and (d) about 0.1% by weight to about 3% by weight of one or more lubricants based on the total weight of the pharmaceutically acceptable capsule.

In some embodiments, the one or more pharmaceutically acceptable excipients is one or more fillers selected from the group consisting of calcium phosphate, dicalcium phosphate, dicalcium phosphate dihydrate, calcium sulfate, calcium sulfate dihydrate, starch, calcium carbonate, magnesium carbonate, magnesium oxide, kaolin (natural hydrated aluminum silicate), sodium chloride, partially gelatinized starch, anhydrous lactose, lactose monohydrate, lactose dihydrate, trehalose dihydrate, spray dried lactose, sucrose, dextrose, dextrates, dextrin, cellulose, microcrystalline cellulose, silicified microcrystalline cellulose, powdered cellulose, partially depolymerized cellulose, mannitol, granulated mannitol, spray dried mannitol, maltodextrin, maltitol, confectioner's sugar, compressible sugar, sorbitol, starch and talc. In some embodiments, the one or more fillers is lactose monohydrate.

In some embodiments, the one or more disintegrants is one or more disintegrants selected from the group consisting of sodium starch glycolate, pregelatinized starch, clay, cellulose, alginic acid, alginate gum, polyvinylpyrrolidone, cross-linked polyvinylpyrrolidone, cross-linked calcium carboxymethylcellulose, cross-linked sodium carboxymethylcellulose, sodium croscarmellose, sodium carmellose, low substituted hydroxypropyl cellulose, low substituted hydroxypropyl cellulose sodium, guar gum, magnesium aluminum silicate, polacrilin potassium, powdered cellulose, sodium alginate and soy polysaccharides. In some embodiments, the one or more disintegrants is cross-linked polyvinylpyrrolidone (also referred to as crospovidone).

In some embodiments, the one or more lubricants is one or more lubricants selected from the group consisting of colloidal silica, magnesium trisilicate, talc, magnesium carbonate, magnesium oxide, glyceryl behaptate, mono, di and tri glyceryl behenate, bees wax, behenoyl polyoxyl-8 glycerides, hydrogenated vegetable oil, polyethylene glycol, ethylene oxide polymer, copolymer comprising poly(ethylene oxide) and poly(propylene oxide) (such as poloxomer 188), copolymer comprising polypropylene glycol and polyethylene glycol (such as poloxomer 407), sodium lauryl sulfate, magnesium stearate, aluminum stearate, calcium stearate, sodium stearyl fumarate, stearic acid, magnesium lauryl stearate, mixtures of magnesium stearate with sodium lauryl sulfate. In some embodiments, the one or more lubricants is magnesium stearate.

In some embodiments, the pharmaceutically acceptable capsule further comprises cross-linked polyvinylpyrrolidone and magnesium stearate. In some embodiments, the one or more pharmaceutically acceptable excipients is lactose monohydrate and the pharmaceutically acceptable capsule further comprises cross-linked polyvinylpyrrolidone and magnesium stearate.

In some embodiments, the pharmaceutically acceptable capsule is for oral administration.

In some embodiments, the pharmaceutically acceptable capsule is a solid dosage form.

In some embodiments, the pharmaceutically acceptable capsule comprises about 1 mg to about 40 mg of the crystalline anhydrous form of the compound of Formula (I). In some embodiments, the pharmaceutically acceptable capsule comprises about 5 mg to about 35 mg of the crystalline anhydrous form of the compound of Formula (I). In some embodiments, the pharmaceutically acceptable capsule comprises about 10 mg to about 35 mg of the crystalline anhydrous form of the compound of Formula (I). In some embodiments, the pharmaceutically acceptable capsule comprises about 0.5 mg to about 5 mg, about 6 mg to about 14 mg, about 10 mg to about 18 mg, about 16 mg to about 24 mg, or about 26 mg to about 34 mg of the crystalline anhydrous form of the compound of Formula (I). In some embodiments, the pharmaceutically acceptable capsule comprises about 1 mg to about 3 mg, about 8 mg to about 12 mg, about 12 mg to about 16 mg, about 18 mg to about 22 mg, or about 28 mg to about 32 mg of the crystalline anhydrous form of the compound of Formula (I). In some embodiments, the pharmaceutically acceptable capsule comprises about 2 mg, about 10 mg, about 14 mg, about 20 mg, or about 30 mg of the crystalline anhydrous form of the compound of Formula (I). In some embodiments, the crystalline anhydrous form of the compound of Formula (I) is present in an amount of about 2 mg. In some embodiments, the crystalline anhydrous form of the compound of Formula (I) is present in an amount of about 10 mg. In some embodiments, the crystalline anhydrous form of the compound of Formula (I) is present in an amount of about 14 mg. In some embodiments, the crystalline anhydrous form of the compound of Formula (I) is present in an amount of about 20 mg. In some embodiments, the crystalline anhydrous form of the compound of Formula (I) is present in an amount of about 30 mg.

In some embodiments, the pharmaceutically acceptable capsule consists essentially of about 1 mg to about 40 mg of the crystalline anhydrous form of the compound of Formula (I). In some embodiments, the pharmaceutically acceptable capsule consists essentially of about 5 mg to about 35 mg of the crystalline anhydrous form of the compound of Formula (I). In some embodiments, the pharmaceutically acceptable capsule consists essentially of about 10 mg to about 35 mg of the crystalline anhydrous form of the compound of Formula (I). In some embodiments, the pharmaceutically acceptable capsule consists essentially of about 0.5 mg to about 5 mg, about 6 mg to about 14 mg, about 10 mg to about 18 mg, about 16 mg to about 24 mg, or about 26 mg to about 34 mg of the crystalline anhydrous form of the compound of Formula (I). In some embodiments, the pharmaceutically acceptable capsule consists essentially of about 1 mg to about 3 mg, about 8 mg to about 12 mg, about 12 mg to about 16 mg, about 18 mg to about 22 mg, or about 28 mg to about 32 mg of the crystalline anhydrous form of the compound of Formula (I). In some embodiments, the pharmaceutically acceptable capsule consists essentially of about 2 mg, about 10 mg, about 14 mg, about 20 mg, or about 30 mg of the crystalline anhydrous form of the compound of Formula (I). In some embodiments, the crystalline anhydrous form of the compound of Formula (I) is present in an amount of about 2 mg. In some embodiments, the crystalline anhydrous form of the compound of Formula (I) is present in an amount of about 10 mg. In some embodiments, the crystalline anhydrous form of the compound of Formula (I) is present in an amount of about 14 mg. In some embodiments, the crystalline anhydrous form of the compound of Formula (I) is present in an amount of about 20 mg. In some embodiments, the crystalline anhydrous form of the compound of Formula (I) is present in an amount of about 30 mg.

In some embodiments, provided herein is a pharmaceutically acceptable formulation comprising:

a solid-state form of a compound represented by Formula (I):

Formula (I)

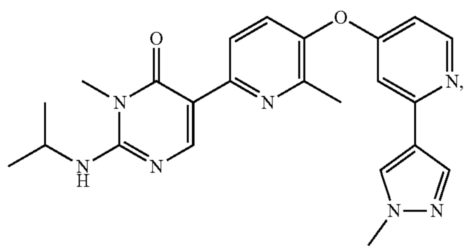

or a pharmaceutically acceptable salt and/or hydrate thereof, wherein the solid-state form of the compound of Formula (I) is present in the formulation in an amount to provide about 2 mg, about 10 mg, about 14 mg, about 20 mg or about 30 mg of the free base of the compound;

a means for obtaining a dissolution profile of the formulation such that in a dissolution test, at least 90% of the compound of Formula (I) is released in under 30 min; and one or more pharmaceutically acceptable excipients.

In some embodiments, provided herein is a pharmaceutically acceptable formulation comprising:

a solid-state form of a compound represented by Formula (I):

Formula (I)

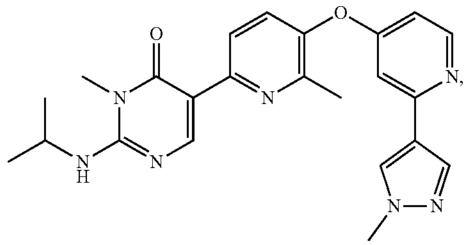

or a pharmaceutically acceptable salt and/or hydrate thereof, wherein the solid-state form of the compound of Formula (I) is present in the formulation in an amount to provide about 2 mg, about 10 mg, about 14 mg, about 20 mg or about 30 mg of the free base of the compound;

a means for making the composition uniform with an acceptance value of less than 15 according to USP <905>; and one or more pharmaceutically acceptable excipients.

In some embodiments, provided herein is a pharmaceutically acceptable formulation comprising:

a solid-state form of a compound represented by Formula (I):

Formula (I)

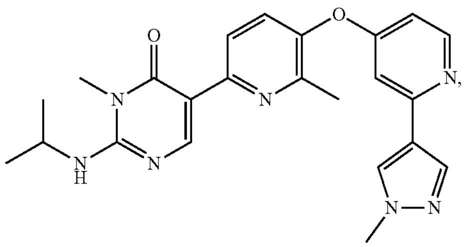

or a pharmaceutically acceptable salt and/or hydrate thereof, wherein the solid-state form of the compound of Formula (I) is present in the formulation in an amount to provide about 2 mg, about 10 mg, about 14 mg, about 20 mg or about 30 mg of the free base of the compound; and one or more pharmaceutically acceptable excipients.

In some embodiments, provided herein is a pharmaceutically acceptable formulation comprising:

a stable crystalline form of a compound represented by Formula (I):

Formula (I)

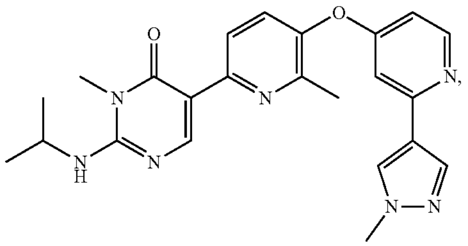

or a pharmaceutically acceptable salt and/or hydrate thereof, wherein the stable crystalline form of the compound of Formula (I) is present in the formulation in an amount to provide about 2 mg, about 10 mg, about 14 mg, about 20 mg or about 30 mg of the free base of the compound;

a means for obtaining a dissolution profile of the formulation such that in a dissolution test, at least 90% of the compound of Formula (I) is released in under 30 min; and one or more pharmaceutically acceptable excipients.

In some embodiments, provided herein is a pharmaceutically acceptable formulation comprising:

a stable crystalline form of a compound represented by Formula (I):

Formula (I)

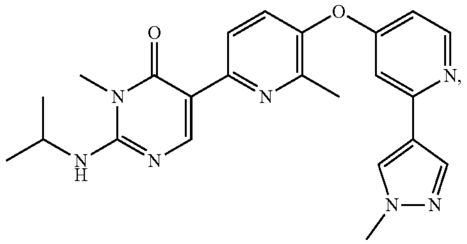

or a pharmaceutically acceptable salt and/or hydrate thereof, wherein the stable crystalline form of the compound of Formula (I) is present in the formulation in an amount to provide about 2 mg, about 10 mg, about 14 mg, about 20 mg or about 30 mg of the free base of the compound;

a means for making the composition uniform with an acceptance value of less than 15 according to USP <905>; and one or more pharmaceutically acceptable excipients.

In some embodiments, provided herein is a pharmaceutically acceptable formulation comprising:

a stable crystalline form of a compound represented by Formula (I):

Formula (I)

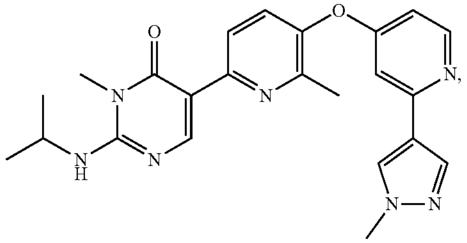

or a pharmaceutically acceptable salt and/or hydrate thereof, wherein the stable crystalline form of the compound of Formula (I) is present in the formulation in an amount to provide about 2 mg, about 10 mg, about 14 mg, about 20 mg or about 30 mg of the free base of the compound; and one or more pharmaceutically acceptable excipients.

In some embodiments, provided herein is a pharmaceutically acceptable formulation comprising:

a crystalline dihydrate form of a compound represented by Formula (I):

Formula (I)

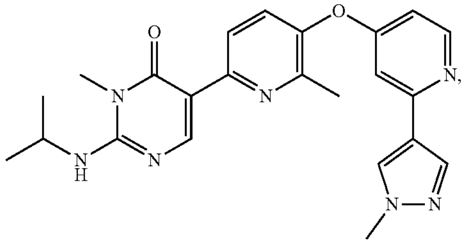

wherein the crystalline dihydrate form of the compound of Formula (I) is present in the formulation in an amount of about 2.2 mg, about 10.8 mg, about 15.2 mg, about 21.7 mg, or about 32.5 mg;

a means for obtaining a dissolution profile of the formulation such that in a dissolution test, at least 90% of the compound of Formula (I) is released in under 30 min; and one or more pharmaceutically acceptable excipients.

In some embodiments, provided herein is a pharmaceutically acceptable formulation comprising:

a crystalline dihydrate form of a compound represented by Formula (I):

Formula (I)

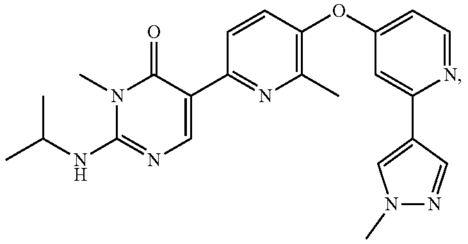

wherein the crystalline dihydrate form of the compound of Formula (I) is present in the formulation in an amount of about 2.2 mg, about 10.8 mg, about 15.2 mg, about 21.7 mg, or about 32.5 mg;

a means for making the composition uniform with an acceptance value of less than 15 according to USP <905>; and one or more pharmaceutically acceptable excipients.

In some embodiments, provided herein is a pharmaceutically acceptable formulation comprising:

a crystalline dihydrate form of a compound represented by Formula (I):

Formula (I)

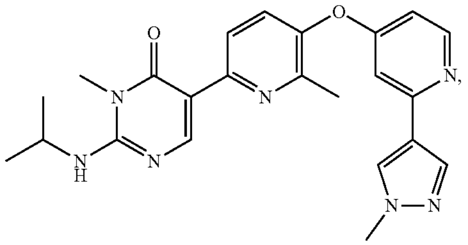

wherein the crystalline dihydrate form of the compound of Formula (I) is present in the formulation in an amount of about 2.2 mg, about 10.8 mg, about 15.2 mg, about 21.7 mg, or about 32.5 mg; and one or more pharmaceutically acceptable excipients.

In some embodiments, provided herein is a pharmaceutically acceptable formulation comprising:

a crystalline anhydrous form of a compound represented by Formula (I):

Formula (I)

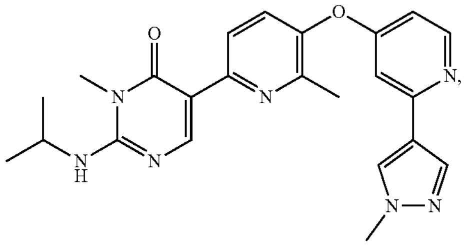

wherein the crystalline anhydrous form of the compound of Formula (I) is present in the formulation in an amount of about 2 mg, about 10 mg, about 14 mg, about 20 mg, or about 30 mg;

a means for obtaining a dissolution profile of the formulation such that in a dissolution test, at least 90% of the compound of Formula (I) is released in under 30 min; and one or more pharmaceutically acceptable excipients.

In some embodiments, provided herein is a pharmaceutically acceptable formulation comprising:

a crystalline anhydrous form of a compound represented by Formula (I):

Formula (I)

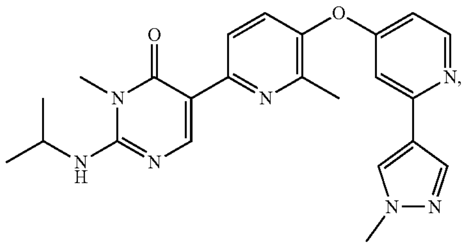

wherein the crystalline anhydrous form of the compound of Formula (I) is present in the formulation in an amount of about 2 mg, about 10 mg, about 14 mg, about 20 mg, or about 30 mg;

a means for making the composition uniform with an acceptance value of less than 15 according to USP <905>; and one or more pharmaceutically acceptable excipients.

In some embodiments, provided herein is a pharmaceutically acceptable formulation comprising:

a crystalline anhydrous form of a compound represented by Formula (I):

Formula (I)

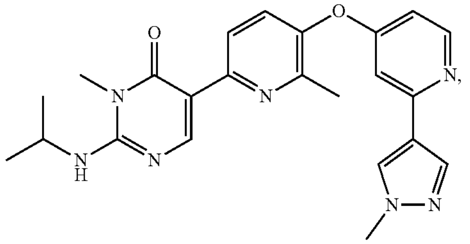

wherein the crystalline anhydrous form of the compound of Formula (I) is present in the formulation in an amount of about 2 mg, about 10 mg, about 14 mg, about 20 mg, or about 30 mg; and one or more pharmaceutically acceptable excipients.

In some embodiments, provided herein is a pharmaceutically acceptable capsule encapsulating a uniform pharmaceutical composition comprising:

a solid-state form of a compound represented by Formula (I):

Formula (I)

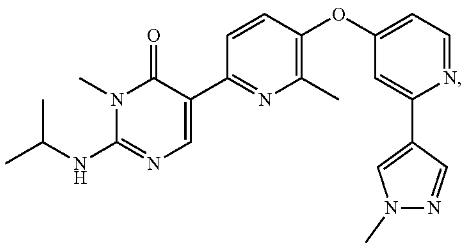

or a pharmaceutically acceptable salt and/or hydrate thereof, wherein the solid-state form of the compound of Formula (I) is present in the capsule in an amount to provide about 2 mg, about 10 mg, about 14 mg, about 20 mg or about 30 mg of the free base of the compound;

a means for obtaining a dissolution profile of the formulation such that in a dissolution test, at least 90% of the compound of Formula (I) is released in under 30 min; and one or more pharmaceutically acceptable excipients.

In some embodiments, provided herein is a pharmaceutically acceptable capsule encapsulating a uniform pharmaceutical composition comprising:

a solid-state form of a compound represented by Formula (I):

Formula (I)

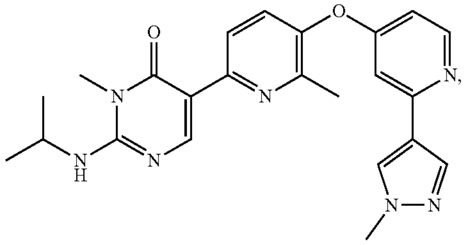

or a pharmaceutically acceptable salt and/or hydrate thereof, wherein the solid-state form of the compound of Formula (I) is present in the capsule in an amount to provide about 2 mg, about 10 mg, about 14 mg, about 20 mg or about 30 mg of the free base of the compound;

a means for making the composition uniform with an acceptance value of less than 15 according to USP <905>; and one or more pharmaceutically acceptable excipients.

In some embodiments, provided herein is a pharmaceutically acceptable capsule encapsulating a uniform pharmaceutical composition comprising:

a solid-state form of a compound represented by Formula (I):

Formula (I)

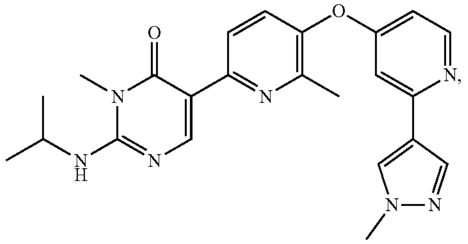

or a pharmaceutically acceptable salt and/or hydrate thereof, wherein the solid-state form of the compound of Formula (I) is present in the capsule in an amount to provide about 2 mg, about 10 mg, about 14 mg, about 20 mg or about 30 mg of the free base of the compound; and one or more pharmaceutically acceptable excipients.

In some embodiments, provided herein is a pharmaceutically acceptable capsule encapsulating a uniform pharmaceutical composition comprising:

a stable crystalline form of a compound represented by Formula (I):

Formula (I)

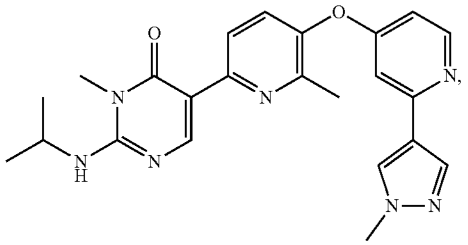

or a pharmaceutically acceptable salt and/or hydrate thereof, wherein the stable crystalline form of the compound of Formula (I) is present in the capsule in an amount to provide about 2 mg, about 10 mg, about 14 mg, about 20 mg or about 30 mg of the free base of the compound;

a means for obtaining a dissolution profile of the formulation such that in a dissolution test, at least 90% of the compound of Formula (I) is released in under 30 min; and one or more pharmaceutically acceptable excipients.

In some embodiments, provided herein is a pharmaceutically acceptable capsule encapsulating a uniform pharmaceutical composition comprising:

a stable crystalline form of a compound represented by Formula (I):

Formula (I)

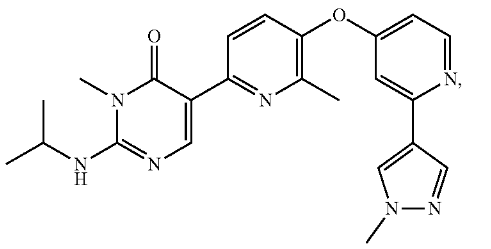

or a pharmaceutically acceptable salt and/or hydrate thereof, wherein the stable crystalline form of the compound of Formula (I) is present in the capsule in an amount to provide about 2 mg, about 10 mg, about 14 mg, about 20 mg or about 30 mg of the free base of the compound;

a means for making the composition uniform with an acceptance value of less than 15 according to USP <905>; and one or more pharmaceutically acceptable excipients.

In some embodiments, provided herein is a pharmaceutically acceptable capsule encapsulating a uniform pharmaceutical composition comprising:

a stable crystalline form of a compound represented by Formula (I):

Formula (I)

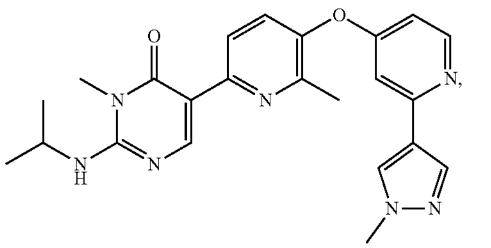

or a pharmaceutically acceptable salt and/or hydrate thereof, wherein the stable crystalline form of the compound of Formula (I) is present in the capsule in an amount to provide about 2 mg, about 10 mg, about 14 mg, about 20 mg or about 30 mg of the free base of the compound; and one or more pharmaceutically acceptable excipients.

In some embodiments, provided herein is a pharmaceutically acceptable capsule encapsulating a uniform pharmaceutical composition comprising:

a crystalline dihydrate form of a compound represented by Formula (I):

Formula (I)

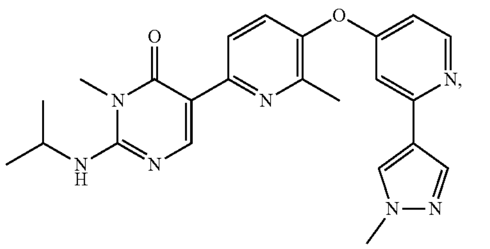

wherein the crystalline dihydrate form of the compound of Formula (I) is present in the formulation in an amount of about 2.2 mg, about 10.8 mg, about 15.2 mg, about 21.7 mg, or about 32.5 mg;

a means for obtaining a dissolution profile of the capsule such that in a dissolution test, at least 90% of the compound of Formula (I) is released in under 30 min; and one or more pharmaceutically acceptable excipients.

In some embodiments, provided herein is a pharmaceutically acceptable capsule encapsulating a uniform pharmaceutical composition comprising:

a crystalline dihydrate form of a compound represented by Formula (I):

Formula (I)

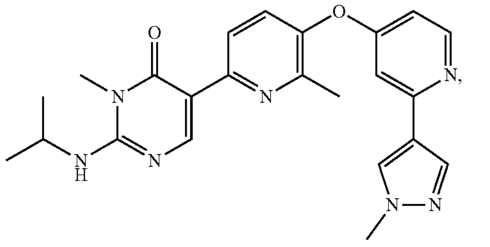

wherein the crystalline dihydrate form of the compound of Formula (I) is present in the capsule in an amount of about 2.2 mg, about 10.8 mg, about 15.2 mg, about 21.7 mg, or about 32.5 mg;

a means for making the composition uniform with an acceptance value of less than 15 according to USP <905>; and one or more pharmaceutically acceptable excipients.

In some embodiments, provided herein is a pharmaceutically acceptable capsule encapsulating a uniform pharmaceutical composition comprising:

a crystalline dihydrate form of a compound represented by Formula (I):

Formula (I)

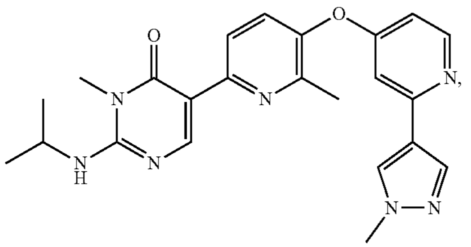

wherein the crystalline dihydrate form of the compound of Formula (I) is present in the capsule in an amount of about 2.2 mg, about 10.8 mg, about 15.2 mg, about 21.7 mg, or about 32.5 mg; and one or more pharmaceutically acceptable excipients.

In some embodiments, provided herein is a pharmaceutically acceptable capsule encapsulating a uniform pharmaceutical composition comprising:

a crystalline anhydrous form of a compound represented by Formula (I):

Formula (I)

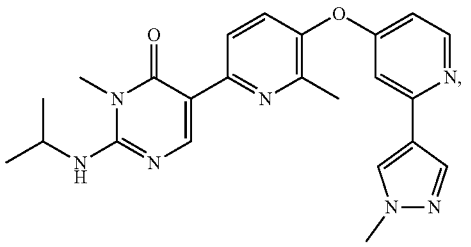

wherein the crystalline anhydrous form of the compound of Formula (I) is present in the formulation in an amount of about 2 mg, about 10 mg, about 14 mg, about 20 mg, or about 30 mg;

a means for obtaining a dissolution profile of the capsule such that in a dissolution test, at least 90% of the compound of Formula (I) is released in under 30 min; and one or more pharmaceutically acceptable excipients.

In some embodiments, provided herein is a pharmaceutically acceptable capsule encapsulating a uniform pharmaceutical composition comprising:

a crystalline anhydrous form of a compound represented by Formula (I):

Formula (I)

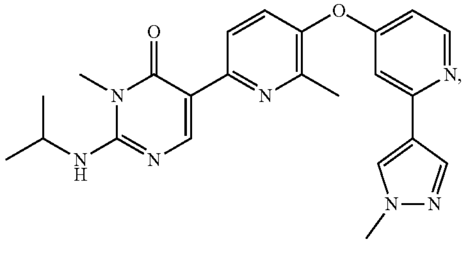

wherein the crystalline anhydrous form of the compound of Formula (I) is present in the capsule in an amount of about 2 mg, about 10 mg, about 14 mg, about 20 mg, or about 30 mg;

a means for making the composition uniform with an acceptance value of less than 15 according to USP <905>; and one or more pharmaceutically acceptable excipients.

In some embodiments, provided herein is a pharmaceutically acceptable capsule encapsulating a uniform pharmaceutical composition comprising:

a crystalline anhydrous form of a compound represented by Formula (I):

Formula (I)

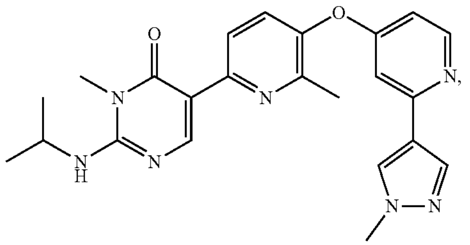

wherein the crystalline anhydrous form of the compound of Formula (I) is present in the capsule in an amount of about 2 mg, about 10 mg, about 14 mg, about 20 mg, or about 30 mg; and one or more pharmaceutically acceptable excipients.

In some embodiments, provided herein is a pharmaceutically acceptable oral dosage form having a uniform pharmaceutical composition comprising a compound represented by Formula (I):

Formula (I)

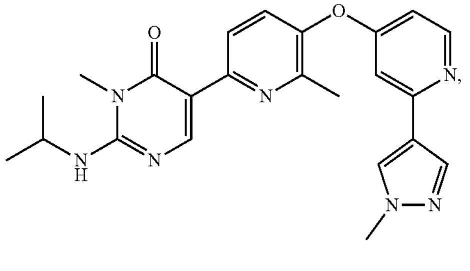

or a pharmaceutically acceptable salt and/or hydrate thereof; and a means for making a composition stable for 24 months.

In some embodiments, provided herein is a pharmaceutically acceptable oral dosage form having a uniform pharmaceutical composition comprising a compound represented by Formula (I):

Formula (I)

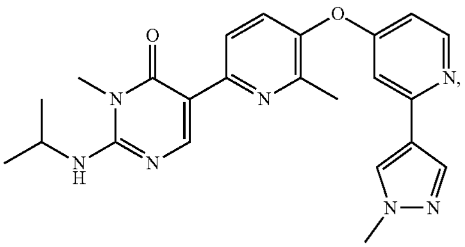

or a pharmaceutically acceptable salt and/or hydrate thereof, where the compound is present in the formulation in an amount to provide about 2 mg, about 10 mg, about 14 mg, about 20 mg or about 30 mg of the compound; and a means for making a composition stable for 24 months.

In some embodiments, provided herein pharmaceutically acceptable oral dosage form having a uniform pharmaceutical composition comprising a compound represented by Formula (I):

Formula (I)

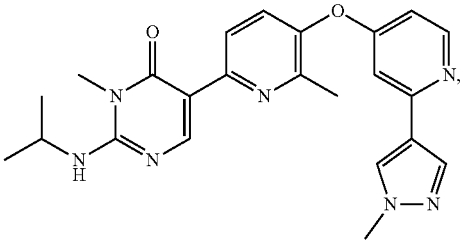

or a pharmaceutically acceptable salt and/or hydrate thereof, where the compound is present in the formulation in an amount to provide about 2 mg, about 10 mg, about 14 mg, about 20 mg or about 30 mg of the compound; and a means for making a composition stable for 12 months.

In some embodiments, provided herein is a pharmaceutically acceptable oral dosage form having a uniform pharmaceutical composition comprising a compound represented by Formula (I):

Formula (I)

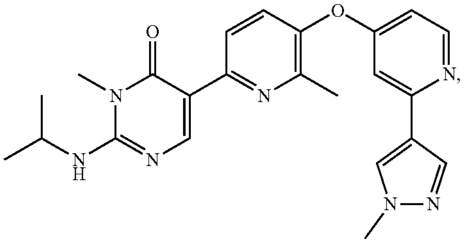

or a pharmaceutically acceptable salt and/or hydrate thereof, where the compound is present in the formulation in an amount to provide about 2 mg, about 10 mg, about 14 mg, about 20 mg or about 30 mg of the compound; and a means for making a composition stable for 10 months.

In some embodiments, provided herein is a pharmaceutically acceptable oral dosage form having a uniform pharmaceutical composition comprising a compound represented by Formula (I):

Formula (I)

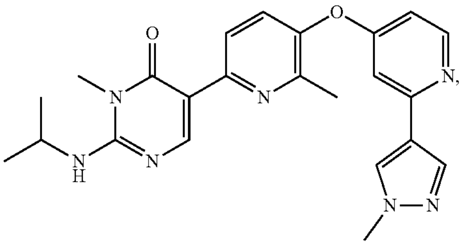

or a pharmaceutically acceptable salt and/or hydrate thereof, where the compound is present in the formulation in an amount to provide about 2 mg, about 10 mg, about 14 mg, about 20 mg or about 30 mg of the compound; and a means for making a composition stable for 9 months.

In some embodiments, provided herein is a pharmaceutically acceptable oral dosage form having a uniform pharmaceutical composition comprising a compound represented by Formula (I):

Formula (I)

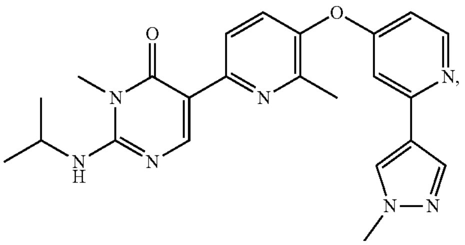

or a pharmaceutically acceptable salt and/or hydrate thereof, where the compound is present in the formulation in an amount to provide about 2 mg, about 10 mg, about 14 mg, about 20 mg or about 30 mg of the compound; and a means for making a composition stable for 6 months.

In some embodiments, provided herein is a pharmaceutically acceptable oral dosage form having a uniform pharmaceutical composition comprising a compound represented by Formula (I):

Formula (I)

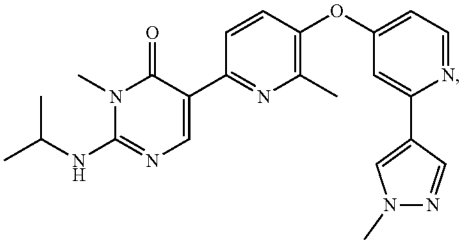

or a pharmaceutically acceptable salt and/or hydrate thereof, where the compound is present in the formulation in an amount to provide about 2 mg, about 10 mg, about 14 mg, about 20 mg or about 30 mg of the compound; and a means for making a composition stable for 5 months.

In some embodiments, provided herein is a pharmaceutically acceptable oral dosage form having a uniform pharmaceutical composition comprising a compound represented by Formula (I):

Formula (I)

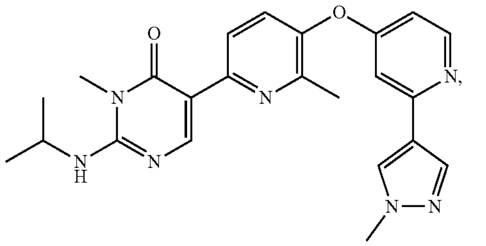

or a pharmaceutically acceptable salt and/or hydrate thereof, where the compound is present in the formulation in an amount to provide about 2 mg, about 10 mg, about 14 mg, about 20 mg or about 30 mg of the compound; and a means for making a composition stable for 3 months.

In some embodiments, provided herein is a pharmaceutically acceptable oral dosage form having a uniform pharmaceutical composition comprising a compound represented by Formula (I):

Formula (I)

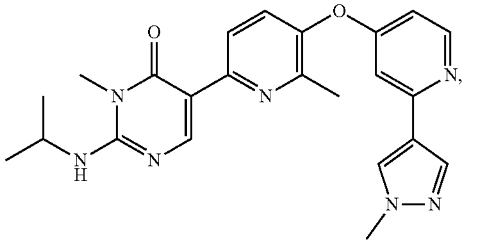

or a pharmaceutically acceptable salt and/or hydrate thereof, where the compound is present in the formulation in an amount to provide about 2 mg, about 10 mg, about 14 mg, about 20 mg or about 30 mg of the compound; and a means for making a composition stable for 1 month.

In some embodiments, the formulation (e.g., a pharmaceutically acceptable formulation described herein) releases about 85% of the compound of Formula (I) in under 30 min when the formulation (e.g., a pharmaceutically acceptable formulation described herein) is tested in 900 mL sodium citrate buffer at pH 2.9 using a USP Apparatus 2 (Paddle Method) at 37° C., with a paddle speed of 75 rpm. In some embodiments, the formulation (e.g., a pharmaceutically acceptable formulation described herein) releases about 90% of the compound of Formula (I) in under 30 min when the formulation (e.g., a pharmaceutically acceptable formulation described herein) is tested in 900 mL sodium citrate buffer at pH 2.9 using a USP Apparatus 2 (Paddle Method) at 37° C., with a paddle speed of 75 rpm. In some embodiments, the formulation (e.g., a pharmaceutically acceptable formulation described herein) releases about 95% of the compound of Formula (I) in under 30 min when the formulation (e.g., a pharmaceutically acceptable formulation described herein) is tested in 900 mL sodium citrate buffer at pH 2.9 using a USP Apparatus 2 (Paddle Method) at 37° C., with a paddle speed of 75 rpm. In some embodiments, the formulation (e.g., a pharmaceutically acceptable formulation described herein) releases about 100% of the compound of Formula (I) in under 30 min when the formulation (e.g., a pharmaceutically acceptable formulation described herein) is tested in 900 mL sodium citrate buffer at pH 2.9 using a USP Apparatus 2 (Paddle Method) at 37° C., with a paddle speed of 75 rpm.

In some embodiments, the formulation (e.g., a pharmaceutically acceptable formulation described herein) is stable for 1 month at 25° C./60% relative humidity (RH). In some embodiments, the formulation (e.g., a pharmaceutically acceptable formulation described herein) is stable for 1 month at 30° C./60% relative humidity (RH). In some embodiments, the formulation (e.g., a pharmaceutically acceptable formulation described herein) is stable for 1 month at 35° C./60% relative humidity (RH). In some embodiments, the formulation (e.g., a pharmaceutically acceptable formulation described herein) is stable for 1 month at 40° C./60% relative humidity (RH). In some embodiments, the formulation (e.g., a pharmaceutically acceptable formulation described herein) is stable for 1 month at 25° C./65% relative humidity (RH). In some embodiments, the formulation (e.g., a pharmaceutically acceptable formulation described herein) is stable for 1 month at 30° C./65% relative humidity (RH). In some embodiments, the formulation (e.g., a pharmaceutically acceptable formulation described herein) is stable for 1 month at 35° C./65% relative humidity (RH). In some embodiments, the formulation (e.g., a pharmaceutically acceptable formulation described herein) is stable for 1 month at 40° C./65% relative humidity (RH). In some embodiments, the formulation (e.g., a pharmaceutically acceptable formulation described herein) is stable for 1 month at 25° C./70% relative humidity (RH). In some embodiments, the formulation (e.g., a pharmaceutically acceptable formulation described herein) is stable for 1 month at 30° C./70% relative humidity (RH). In some embodiments, the formulation (e.g., a pharmaceutically acceptable formulation described herein) is stable for 1 month at 35° C./70% relative humidity (RH). In some embodiments, the formulation (e.g., a pharmaceutically acceptable formulation described herein) is stable for 1 month at 40° C./70% relative humidity (RH). In some embodiments, the formulation (e.g., a pharmaceutically acceptable formulation described herein) is stable for 1 month at 25° C./75% relative humidity (RH). In some embodiments, the formulation (e.g., a pharmaceutically acceptable formulation described herein) is stable for 1 month at 30° C./75% relative humidity (RH). In some embodiments, the formulation (e.g., a pharmaceutically acceptable formulation described herein) is stable for 1 month at 35° C./75% relative humidity (RH). In some embodiments, the formulation (e.g., a pharmaceutically acceptable formulation described herein) is stable for 1 month at 40° C./75% relative humidity (RH).

In some embodiments, the formulation (e.g., a pharmaceutically acceptable formulation described herein) is stable for 3 months at 25° C./60% relative humidity (RH). In some embodiments, the formulation (e.g., a pharmaceutically acceptable formulation described herein) is stable for 3 months at 30° C./60% relative humidity (RH). In some embodiments, the formulation (e.g., a pharmaceutically acceptable formulation described herein) is stable for 3 months at 35° C./60% relative humidity (RH). In some embodiments, the formulation (e.g., a pharmaceutically acceptable formulation described herein) is stable for 3 months at 40° C./60% relative humidity (RH). In some embodiments, the formulation (e.g., a pharmaceutically acceptable formulation described herein) is stable for 3 months at 25° C./65% relative humidity (RH). In some embodiments, the formulation (e.g., a pharmaceutically acceptable formulation described herein) is stable for 3 months at 30° C./65% relative humidity (RH). In some embodiments, the formulation (e.g., a pharmaceutically acceptable formulation described herein) is stable for 3 months at 35° C./65% relative humidity (RH). In some embodiments, the formulation (e.g., a pharmaceutically acceptable formulation described herein) is stable for 3 months at 40° C./65% relative humidity (RH). In some embodiments, the formulation (e.g., a pharmaceutically acceptable formulation described herein) is stable for 3 months at 25° C./70% relative humidity (RH). In some embodiments, the formulation (e.g., a pharmaceutically acceptable formulation described herein) is stable for 3 months at 30° C./70% relative humidity (RH). In some embodiments, the formulation (e.g., a pharmaceutically acceptable formulation described herein) is stable for 3 months at 35° C./70% relative humidity (RH). In some embodiments, the formulation (e.g., a pharmaceutically acceptable formulation described herein) is stable for 3 months at 40° C./70% relative humidity (RH). In some embodiments, the formulation (e.g., a pharmaceutically acceptable formulation described herein) is stable for 3 months at 25° C./75% relative humidity (RH). In some embodiments, the formulation (e.g., a pharmaceutically acceptable formulation described herein) is stable for 3 months at 30° C./75% relative humidity (RH). In some embodiments, the formulation (e.g., a pharmaceutically acceptable formulation described herein) is stable for 3 months at 35° C./75% relative humidity (RH). In some embodiments, the formulation (e.g., a pharmaceutically acceptable formulation described herein) is stable for 3 months at 40° C./75% relative humidity (RH).

In some embodiments, the formulation (e.g., a pharmaceutically acceptable formulation described herein) is stable for 6 months at 25° C./60% relative humidity (RH). In some embodiments, the formulation (e.g., a pharmaceutically acceptable formulation described herein) is stable for 6 months at 30° C./60% relative humidity (RH). In some embodiments, the formulation (e.g., a pharmaceutically acceptable formulation described herein) is stable for 6 months at 35° C./60% relative humidity (RH). In some embodiments, the formulation (e.g., a pharmaceutically acceptable formulation described herein) is stable for 6 months at 40° C./60% relative humidity (RH). In some embodiments, the formulation (e.g., a pharmaceutically acceptable formulation described herein) is stable for 6 months at 25° C./65% relative humidity (RH). In some embodiments, the formulation (e.g., a pharmaceutically acceptable formulation described herein) is stable for 6 months at 30° C./65% relative humidity (RH). In some embodiments, the formulation (e.g., a pharmaceutically acceptable formulation described herein) is stable for 6 months at 35° C./65% relative humidity (RH). In some embodiments, the formulation (e.g., a pharmaceutically acceptable formulation described herein) is stable for 6 months at 40° C./65% relative humidity (RH). In some embodiments, the formulation (e.g., a pharmaceutically acceptable formulation described herein) is stable for 6 months at 25° C./70% relative humidity (RH). In some embodiments, the formulation (e.g., a pharmaceutically acceptable formulation described herein) is stable for 6 months at 30° C./70% relative humidity (RH). In some embodiments, the formulation (e.g., a pharmaceutically acceptable formulation described herein) is stable for 6 months at 35° C./70% relative humidity (RH). In some embodiments, the formulation (e.g., a pharmaceutically acceptable formulation described herein) is stable for 6 months at 40° C./70% relative humidity (RH). In some embodiments, the formulation (e.g., a pharmaceutically acceptable formulation described herein) is stable for 6 months at 25° C./75% relative humidity (RH). In some embodiments, the formulation (e.g., a pharmaceutically acceptable formulation described herein) is stable for 6 months at 30° C./75% relative humidity (RH). In some embodiments, the formulation (e.g., a pharmaceutically acceptable formulation described herein) is stable for 6 months at 35° C./75% relative humidity (RH). In some embodiments, the formulation (e.g., a pharmaceutically acceptable formulation described herein) is stable for 6 months at 40° C./75% relative humidity (RH).

In some embodiments, the formulation (e.g., a pharmaceutically acceptable formulation described herein) is stable for 9 months at 25° C./60% relative humidity (RH). In some embodiments, the formulation (e.g., a pharmaceutically acceptable formulation described herein) is stable for 9 months at 30° C./60% relative humidity (RH). In some embodiments, the formulation (e.g., a pharmaceutically acceptable formulation described herein) is stable for 9 months at 35° C./60% relative humidity (RH). In some embodiments, the formulation (e.g., a pharmaceutically acceptable formulation described herein) is stable for 9 months at 40° C./60% relative humidity (RH). In some embodiments, the formulation (e.g., a pharmaceutically acceptable formulation described herein) is stable for 9 months at 25° C./65% relative humidity (RH). In some embodiments, the formulation (e.g., a pharmaceutically acceptable formulation described herein) is stable for 9 months at 30° C./65% relative humidity (RH). In some embodiments, the formulation (e.g., a pharmaceutically acceptable formulation described herein) is stable for 9 months at 35° C./65% relative humidity (RH). In some embodiments, the formulation (e.g., a pharmaceutically acceptable formulation described herein) is stable for 9 months at 40° C./65% relative humidity (RH). In some embodiments, the formulation (e.g., a pharmaceutically acceptable formulation described herein) is stable for 9 months at 25° C./70% relative humidity (RH). In some embodiments, the formulation (e.g., a pharmaceutically acceptable formulation described herein) is stable for 9 months at 30° C./70% relative humidity (RH). In some embodiments, the formulation (e.g., a pharmaceutically acceptable formulation described herein) is stable for 9 months at 35° C./70% relative humidity (RH). In some embodiments, the formulation (e.g., a pharmaceutically acceptable formulation described herein) is stable for 9 months at 40° C./70% relative humidity (RH). In some embodiments, the formulation (e.g., a pharmaceutically acceptable formulation described herein) is stable for 9 months at 25° C./75% relative humidity (RH). In some embodiments, the formulation (e.g., a pharmaceutically acceptable formulation described herein) is stable for 9 months at 30° C./75% relative humidity (RH). In some embodiments, the formulation (e.g., a pharmaceutically acceptable formulation described herein) is stable for 9 months at 35° C./75% relative humidity (RH). In some embodiments, the formulation (e.g., a pharmaceutically acceptable formulation described herein) is stable for 9 months at 40° C./75% relative humidity (RH).

In some embodiments, the formulation (e.g., a pharmaceutically acceptable formulation described herein) is stable for 12 months at 25° C./60% relative humidity (RH). In some embodiments, the formulation (e.g., a pharmaceutically acceptable formulation described herein) is stable for 12 months at 30° C./60% relative humidity (RH). In some embodiments, the formulation (e.g., a pharmaceutically acceptable formulation described herein) is stable for 12 months at 35° C./60% relative humidity (RH). In some embodiments, the formulation (e.g., a pharmaceutically acceptable formulation described herein) is stable for 12 months at 40° C./60% relative humidity (RH). In some embodiments, the formulation (e.g., a pharmaceutically acceptable formulation described herein) is stable for 12 months at 25° C./65% relative humidity (RH). In some embodiments, the formulation (e.g., a pharmaceutically acceptable formulation described herein) is stable for 12 months at 30° C./65% relative humidity (RH). In some embodiments, the formulation (e.g., a pharmaceutically acceptable formulation described herein) is stable for 12 months at 35° C./65% relative humidity (RH). In some embodiments, the formulation (e.g., a pharmaceutically acceptable formulation described herein) is stable for 12 months at 40° C./65% relative humidity (RH). In some embodiments, the formulation (e.g., a pharmaceutically acceptable formulation described herein) is stable for 12 months at 25° C./70% relative humidity (RH). In some embodiments, the formulation (e.g., a pharmaceutically acceptable formulation described herein) is stable for 12 months at 30° C./70% relative humidity (RH). In some embodiments, the formulation (e.g., a pharmaceutically acceptable formulation described herein) is stable for 12 months at 35° C./70% relative humidity (RH). In some embodiments, the formulation (e.g., a pharmaceutically acceptable formulation described herein) is stable for 12 months at 40° C./70% relative humidity (RH). In some embodiments, the formulation (e.g., a pharmaceutically acceptable formulation described herein) is stable for 12 months at 25° C./75% relative humidity (RH). In some embodiments, the formulation (e.g., a pharmaceutically acceptable formulation described herein) is stable for 12 months at 30° C./75% relative humidity (RH). In some embodiments, the formulation (e.g., a pharmaceutically acceptable formulation described herein) is stable for 12 months at 35° C./75% relative humidity (RH). In some embodiments, the formulation (e.g., a pharmaceutically acceptable formulation described herein) is stable for 12 months at 40° C./75% relative humidity (RH).

In some embodiments, the formulation (e.g., a pharmaceutically acceptable formulation described herein) is stable for 18 months at 25° C./60% relative humidity (RH). In some embodiments, the formulation (e.g., a pharmaceutically acceptable formulation described herein) is stable for 18 months at 30° C./60% relative humidity (RH). In some embodiments, the formulation (e.g., a pharmaceutically acceptable formulation described herein) is stable for 18 months at 35° C./60% relative humidity (RH). In some embodiments, the formulation (e.g., a pharmaceutically acceptable formulation described herein) is stable for 18 months at 40° C./60% relative humidity (RH). In some embodiments, the formulation (e.g., a pharmaceutically acceptable formulation described herein) is stable for 18 months at 25° C./65% relative humidity (RH). In some embodiments, the formulation (e.g., a pharmaceutically acceptable formulation described herein) is stable for 18 months at 30° C./65% relative humidity (RH). In some embodiments, the formulation (e.g., a pharmaceutically acceptable formulation described herein) is stable for 18 months at 35° C./65% relative humidity (RH). In some embodiments, the formulation (e.g., a pharmaceutically acceptable formulation described herein) is stable for 18 months at 40° C./65% relative humidity (RH). In some embodiments, the formulation (e.g., a pharmaceutically acceptable formulation described herein) is stable for 18 months at 25° C./70% relative humidity (RH). In some embodiments, the formulation (e.g., a pharmaceutically acceptable formulation described herein) is stable for 18 months at 30° C./70% relative humidity (RH). In some embodiments, the formulation (e.g., a pharmaceutically acceptable formulation described herein) is stable for 18 months at 35° C./70% relative humidity (RH). In some embodiments, the formulation (e.g., a pharmaceutically acceptable formulation described herein) is stable for 18 months at 40° C./70% relative humidity (RH). In some embodiments, the formulation (e.g., a pharmaceutically acceptable formulation described herein) is stable for 18 months at 25° C./75% relative humidity (RH). In some embodiments, the formulation (e.g., a pharmaceutically acceptable formulation described herein) is stable for 18 months at 30° C./75% relative humidity (RH). In some embodiments, the formulation (e.g., a pharmaceutically acceptable formulation described herein) is stable for 18 months at 35° C./75% relative humidity (RH). In some embodiments, the formulation (e.g., a pharmaceutically acceptable formulation described herein) is stable for 18 months at 40° C./75% relative humidity (RH).

In some embodiments, the formulation (e.g., a pharmaceutically acceptable formulation described herein) is stable for 24 months at 25° C./60% relative humidity (RH). In some embodiments, the formulation (e.g., a pharmaceutically acceptable formulation described herein) is stable for 24 months at 30° C./60% relative humidity (RH). In some embodiments, the formulation (e.g., a pharmaceutically acceptable formulation described herein) is stable for 24 months at 35° C./60% relative humidity (RH). In some embodiments, the formulation (e.g., a pharmaceutically acceptable formulation described herein) is stable for 24 months at 40° C./60% relative humidity (RH). In some embodiments, the formulation (e.g., a pharmaceutically acceptable formulation described herein) is stable for 24 months at 25° C./65% relative humidity (RH). In some embodiments, the formulation (e.g., a pharmaceutically acceptable formulation described herein) is stable for 24 months at 30° C./65% relative humidity (RH). In some embodiments, the formulation (e.g., a pharmaceutically acceptable formulation described herein) is stable for 24 months at 35° C./65% relative humidity (RH). In some embodiments, the formulation (e.g., a pharmaceutically acceptable formulation described herein) is stable for 24 months at 40° C./65% relative humidity (RH). In some embodiments, the formulation (e.g., a pharmaceutically acceptable formulation described herein) is stable for 24 months at 25° C./70% relative humidity (RH). In some embodiments, the formulation (e.g., a pharmaceutically acceptable formulation described herein) is stable for 24 months at 30° C./70% relative humidity (RH). In some embodiments, the formulation (e.g., a pharmaceutically acceptable formulation described herein) is stable for 24 months at 35° C./70% relative humidity (RH). In some embodiments, the formulation (e.g., a pharmaceutically acceptable formulation described herein) is stable for 24 months at 40° C./70% relative humidity (RH). In some embodiments, the formulation (e.g., a pharmaceutically acceptable formulation described herein) is stable for 24 months at 25° C./75% relative humidity (RH). In some embodiments, the formulation (e.g., a pharmaceutically acceptable formulation described herein) is stable for 24 months at 30° C./75% relative humidity (RH). In some embodiments, the formulation (e.g., a pharmaceutically acceptable formulation described herein) is stable for 24 months at 35° C./75% relative humidity (RH). In some embodiments, the formulation (e.g., a pharmaceutically acceptable formulation described herein) is stable for 24 months at 40° C./75% relative humidity (RH).

In some embodiments, the formulation (e.g., a pharmaceutically acceptable formulation described herein) is stable for 30 months at 25° C./60% relative humidity (RH). In some embodiments, the formulation (e.g., a pharmaceutically acceptable formulation described herein) is stable for 30 months at 30° C./60% relative humidity (RH). In some embodiments, the formulation (e.g., a pharmaceutically acceptable formulation described herein) is stable for 30 months at 35° C./60% relative humidity (RH). In some embodiments, the formulation (e.g., a pharmaceutically acceptable formulation described herein) is stable for 30 months at 40° C./60% relative humidity (RH). In some embodiments, the formulation (e.g., a pharmaceutically acceptable formulation described herein) is stable for 30 months at 25° C./65% relative humidity (RH). In some embodiments, the formulation (e.g., a pharmaceutically acceptable formulation described herein) is stable for 30 months at 30° C./65% relative humidity (RH). In some embodiments, the formulation (e.g., a pharmaceutically acceptable formulation described herein) is stable for 30 months at 35° C./65% relative humidity (RH). In some embodiments, the formulation (e.g., a pharmaceutically acceptable formulation described herein) is stable for 30 months at 40° C./65% relative humidity (RH). In some embodiments, the formulation (e.g., a pharmaceutically acceptable formulation described herein) is stable for 30 months at 25° C./70% relative humidity (RH). In some embodiments, the formulation (e.g., a pharmaceutically acceptable formulation described herein) is stable for 30 months at 30° C./70% relative humidity (RH). In some embodiments, the formulation (e.g., a pharmaceutically acceptable formulation described herein) is stable for 30 months at 35° C./70% relative humidity (RH). In some embodiments, the formulation (e.g., a pharmaceutically acceptable formulation described herein) is stable for 30 months at 40° C./70% relative humidity (RH). In some embodiments, the formulation (e.g., a pharmaceutically acceptable formulation described herein) is stable for 30 months at 25° C./75% relative humidity (RH). In some embodiments, the formulation (e.g., a pharmaceutically acceptable formulation described herein) is stable for 30 months at 30° C./75% relative humidity (RH). In some embodiments, the formulation (e.g., a pharmaceutically acceptable formulation described herein) is stable for 30 months at 35° C./75% relative humidity (RH). In some embodiments, the formulation (e.g., a pharmaceutically acceptable formulation described herein) is stable for 30 months at 40° C./75% relative humidity (RH).

In some embodiments, the formulation (e.g., a pharmaceutically acceptable formulation described herein) is stable for 36 months at 25° C./60% relative humidity (RH). In some embodiments, the formulation (e.g., a pharmaceutically acceptable formulation described herein) is stable for 36 months at 30° C./60% relative humidity (RH). In some embodiments, the formulation (e.g., a pharmaceutically acceptable formulation described herein) is stable for 36 months at 35° C./60% relative humidity (RH). In some embodiments, the formulation (e.g., a pharmaceutically acceptable formulation described herein) is stable for 36 months at 40° C./60% relative humidity (RH). In some embodiments, the formulation (e.g., a pharmaceutically acceptable formulation described herein) is stable for 36 months at 25° C./65% relative humidity (RH). In some embodiments, the formulation (e.g., a pharmaceutically acceptable formulation described herein) is stable for 36 months at 30° C./65% relative humidity (RH). In some embodiments, the formulation (e.g., a pharmaceutically acceptable formulation described herein) is stable for 36 months at 35° C./65% relative humidity (RH). In some embodiments, the formulation (e.g., a pharmaceutically acceptable formulation described herein) is stable for 36 months at 40° C./65% relative humidity (RH). In some embodiments, the formulation (e.g., a pharmaceutically acceptable formulation described herein) is stable for 36 months at 25° C./70% relative humidity (RH). In some embodiments, the formulation (e.g., a pharmaceutically acceptable formulation described herein) is stable for 36 months at 30° C./70% relative humidity (RH). In some embodiments, the formulation (e.g., a pharmaceutically acceptable formulation described herein) is stable for 36 months at 35° C./70% relative humidity (RH). In some embodiments, the formulation (e.g., a pharmaceutically acceptable formulation described herein) is stable for 36 months at 40° C./70% relative humidity (RH). In some embodiments, the formulation (e.g., a pharmaceutically acceptable formulation described herein) is stable for 36 months at 25° C./75% relative humidity (RH). In some embodiments, the formulation (e.g., a pharmaceutically acceptable formulation described herein) is stable for 36 months at 30° C./75% relative humidity (RH). In some embodiments, the formulation (e.g., a pharmaceutically acceptable formulation described herein) is stable for 36 months at 35° C./75% relative humidity (RH). In some embodiments, the formulation (e.g., a pharmaceutically acceptable formulation described herein) is stable for 36 months at 40° C./75% relative humidity (RH).

In some embodiments, the formulation (e.g., a pharmaceutically acceptable formulation described herein) is stable for 42 months at 25° C./60% relative humidity (RH). In some embodiments, the formulation (e.g., a pharmaceutically acceptable formulation described herein) is stable for 42 months at 30° C./60% relative humidity (RH). In some embodiments, the formulation (e.g., a pharmaceutically acceptable formulation described herein) is stable for 42 months at 35° C./60% relative humidity (RH). In some embodiments, the formulation (e.g., a pharmaceutically acceptable formulation described herein) is stable for 42 months at 40° C./60% relative humidity (RH). In some embodiments, the formulation (e.g., a pharmaceutically acceptable formulation described herein) is stable for 42 months at 25° C./65% relative humidity (RH). In some embodiments, the formulation (e.g., a pharmaceutically acceptable formulation described herein) is stable for 42 months at 30° C./65% relative humidity (RH). In some embodiments, the formulation (e.g., a pharmaceutically acceptable formulation described herein) is stable for 42 months at 35° C./65% relative humidity (RH). In some embodiments, the formulation (e.g., a pharmaceutically acceptable formulation described herein) is stable for 42 months at 40° C./65% relative humidity (RH). In some embodiments, the formulation (e.g., a pharmaceutically acceptable formulation described herein) is stable for 42 months at 25° C./70% relative humidity (RH). In some embodiments, the formulation (e.g., a pharmaceutically acceptable formulation described herein) is stable for 42 months at 30° C./70% relative humidity (RH). In some embodiments, the formulation (e.g., a pharmaceutically acceptable formulation described herein) is stable for 42 months at 35° C./70% relative humidity (RH). In some embodiments, the formulation (e.g., a pharmaceutically acceptable formulation described herein) is stable for 42 months at 40° C./70% relative humidity (RH). In some embodiments, the formulation (e.g., a pharmaceutically acceptable formulation described herein) is stable for 42 months at 25° C./75% relative humidity (RH). In some embodiments, the formulation (e.g., a pharmaceutically acceptable formulation described herein) is stable for 42 months at 30° C./75% relative humidity (RH). In some embodiments, the formulation (e.g., a pharmaceutically acceptable formulation described herein) is stable for 42 months at 35° C./75% relative humidity (RH). In some embodiments, the formulation (e.g., a pharmaceutically acceptable formulation described herein) is stable for 42 months at 40° C./75% relative humidity (RH).

In some embodiments, the formulation (e.g., a pharmaceutically acceptable formulation described herein) is stable for 48 months at 25° C./60% relative humidity (RH). In some embodiments, the formulation (e.g., a pharmaceutically acceptable formulation described herein) is stable for 48 months at 30° C./60% relative humidity (RH). In some embodiments, the formulation (e.g., a pharmaceutically acceptable formulation described herein) is stable for 48 months at 35° C./60% relative humidity (RH). In some embodiments, the formulation (e.g., a pharmaceutically acceptable formulation described herein) is stable for 48 months at 40° C./60% relative humidity (RH). In some embodiments, the formulation (e.g., a pharmaceutically acceptable formulation described herein) is stable for 48 months at 25° C./65% relative humidity (RH). In some embodiments, the formulation (e.g., a pharmaceutically acceptable formulation described herein) is stable for 48 months at 30° C./65% relative humidity (RH). In some embodiments, the formulation (e.g., a pharmaceutically acceptable formulation described herein) is stable for 48 months at 35° C./65% relative humidity (RH). In some embodiments, the formulation (e.g., a pharmaceutically acceptable formulation described herein) is stable for 48 months at 40° C./65% relative humidity (RH). In some embodiments, the formulation (e.g., a pharmaceutically acceptable formulation described herein) is stable for 48 months at 25° C./70% relative humidity (RH). In some embodiments, the formulation (e.g., a pharmaceutically acceptable formulation described herein) is stable for 48 months at 30° C./70% relative humidity (RH). In some embodiments, the formulation (e.g., a pharmaceutically acceptable formulation described herein) is stable for 48 months at 35° C./70% relative humidity (RH). In some embodiments, the formulation (e.g., a pharmaceutically acceptable formulation described herein) is stable for 48 months at 40° C./70% relative humidity (RH). In some embodiments, the formulation (e.g., a pharmaceutically acceptable formulation described herein) is stable for 48 months at 25° C./75% relative humidity (RH). In some embodiments, the formulation (e.g., a pharmaceutically acceptable formulation described herein) is stable for 48 months at 30° C./75% relative humidity (RH). In some embodiments, the formulation (e.g., a pharmaceutically acceptable formulation described herein) is stable for 48 months at 35° C./75% relative humidity (RH). In some embodiments, the formulation (e.g., a pharmaceutically acceptable formulation described herein) is stable for 48 months at 40° C./75% relative humidity (RH).

In some embodiments, the formulation (e.g., a pharmaceutically acceptable formulation described herein) is stable for 54 months at 25° C./60% relative humidity (RH). In some embodiments, the formulation (e.g., a pharmaceutically acceptable formulation described herein) is stable for 54 months at 30° C./60% relative humidity (RH). In some embodiments, the formulation (e.g., a pharmaceutically acceptable formulation described herein) is stable for 54 months at 35° C./60% relative humidity (RH). In some embodiments, the formulation (e.g., a pharmaceutically acceptable formulation described herein) is stable for 54 months at 40° C./60% relative humidity (RH). In some embodiments, the formulation (e.g., a pharmaceutically acceptable formulation described herein) is stable for 54 months at 25° C./65% relative humidity (RH). In some embodiments, the formulation (e.g., a pharmaceutically acceptable formulation described herein) is stable for 54 months at 30° C./65% relative humidity (RH). In some embodiments, the formulation (e.g., a pharmaceutically acceptable formulation described herein) is stable for 54 months at 35° C./65% relative humidity (RH). In some embodiments, the formulation (e.g., a pharmaceutically acceptable formulation described herein) is stable for 54 months at 40° C./65% relative humidity (RH). In some embodiments, the formulation (e.g., a pharmaceutically acceptable formulation described herein) is stable for 54 months at 25° C./70% relative humidity (RH). In some embodiments, the formulation (e.g., a pharmaceutically acceptable formulation described herein) is stable for 54 months at 30° C./70% relative humidity (RH). In some embodiments, the formulation (e.g., a pharmaceutically acceptable formulation described herein) is stable for 54 months at 35° C./70% relative humidity (RH). In some embodiments, the formulation (e.g., a pharmaceutically acceptable formulation described herein) is stable for 54 months at 40° C./70% relative humidity (RH). In some embodiments, the formulation (e.g., a pharmaceutically acceptable formulation described herein) is stable for 54 months at 25° C./75% relative humidity (RH). In some embodiments, the formulation (e.g., a pharmaceutically acceptable formulation described herein) is stable for 54 months at 30° C./75% relative humidity (RH). In some embodiments, the formulation (e.g., a pharmaceutically acceptable formulation described herein) is stable for 54 months at 35° C./75% relative humidity (RH). In some embodiments, the formulation (e.g., a pharmaceutically acceptable formulation described herein) is stable for 12 months at 40° C./75% relative humidity (RH).

In some embodiments, the formulation (e.g., a pharmaceutically acceptable formulation described herein) is stable for 60 months at 25° C./60% relative humidity (RH). In some embodiments, the formulation (e.g., a pharmaceutically acceptable formulation described herein) is stable for 60 months at 30° C./60% relative humidity (RH). In some embodiments, the formulation (e.g., a pharmaceutically acceptable formulation described herein) is stable for 60 months at 35° C./60% relative humidity (RH). In some embodiments, the formulation (e.g., a pharmaceutically acceptable formulation described herein) is stable for 60 months at 40° C./60% relative humidity (RH). In some embodiments, the formulation (e.g., a pharmaceutically acceptable formulation described herein) is stable for 60 months at 25° C./65% relative humidity (RH). In some embodiments, the formulation (e.g., a pharmaceutically acceptable formulation described herein) is stable for 60 months at 30° C./65% relative humidity (RH). In some embodiments, the formulation (e.g., a pharmaceutically acceptable formulation described herein) is stable for 60 months at 35° C./65% relative humidity (RH). In some embodiments, the formulation (e.g., a pharmaceutically acceptable formulation described herein) is stable for 60 months at 40° C./65% relative humidity (RH). In some embodiments, the formulation (e.g., a pharmaceutically acceptable formulation described herein) is stable for 60 months at 25° C./70% relative humidity (RH). In some embodiments, the formulation (e.g., a pharmaceutically acceptable formulation described herein) is stable for 60 months at 30° C./70% relative humidity (RH). In some embodiments, the formulation (e.g., a pharmaceutically acceptable formulation described herein) is stable for 60 months at 35° C./70% relative humidity (RH). In some embodiments, the formulation (e.g., a pharmaceutically acceptable formulation described herein) is stable for 60 months at 40° C./70% relative humidity (RH). In some embodiments, the formulation (e.g., a pharmaceutically acceptable formulation described herein) is stable for 60 months at 25° C./75% relative humidity (RH). In some embodiments, the formulation (e.g., a pharmaceutically acceptable formulation described herein) is stable for 60 months at 30° C./75% relative humidity (RH). In some embodiments, the formulation (e.g., a pharmaceutically acceptable formulation described herein) is stable for 60 months at 35° C./75% relative humidity (RH). In some embodiments, the formulation (e.g., a pharmaceutically acceptable formulation described herein) is stable for 60 months at 40° C./75% relative humidity (RH).

In some embodiments, the formulation (e.g., a pharmaceutically acceptable formulation described herein) is stable for 5 months at 15° C. In some embodiments, the formulation (e.g., a pharmaceutically acceptable formulation described herein) is stable for 10 months at 15° C. In some embodiments, the formulation (e.g., a pharmaceutically acceptable formulation described herein) is stable for 12 months at 15° C. In some embodiments, the formulation (e.g., a pharmaceutically acceptable formulation described herein) is stable for 18 months at 15° C. In some embodiments, the formulation (e.g., a pharmaceutically acceptable formulation described herein) is stable for 24 months at 15° C. In some embodiments, the formulation (e.g., a pharmaceutically acceptable formulation described herein) is stable for 30 months at 15° C. In some embodiments, the formulation (e.g., a pharmaceutically acceptable formulation described herein) is stable for 36 months at 15° C. In some embodiments, the formulation (e.g., a pharmaceutically acceptable formulation described herein) is stable for 42 months at 15° C. In some embodiments, the formulation (e.g., a pharmaceutically acceptable formulation described herein) is stable for 48 months at 15° C. In some embodiments, the formulation (e.g., a pharmaceutically acceptable formulation described herein) is stable for 54 months at 15° C. In some embodiments, the formulation (e.g., a pharmaceutically acceptable formulation described herein) is stable for 60 months at 15° C.

In some embodiments, the formulation (e.g., a pharmaceutically acceptable formulation described herein) is stable for 5 months at 20° C. In some embodiments, the formulation (e.g., a pharmaceutically acceptable formulation described herein) is stable for 10 months at 20° C. In some embodiments, the formulation (e.g., a pharmaceutically acceptable formulation described herein) is stable for 12 months at 20° C. In some embodiments, the formulation (e.g., a pharmaceutically acceptable formulation described herein) is stable for 18 months at 20° C. In some embodiments, the formulation (e.g., a pharmaceutically acceptable formulation described herein) is stable for 24 months at 20° C. In some embodiments, the formulation (e.g., a pharmaceutically acceptable formulation described herein) is stable for 30 months at 20° C. In some embodiments, the formulation (e.g., a pharmaceutically acceptable formulation described herein) is stable for 36 months at 20° C. In some embodiments, the formulation (e.g., a pharmaceutically acceptable formulation described herein) is stable for 42 months at 20° C. In some embodiments, the formulation (e.g., a pharmaceutically acceptable formulation described herein) is stable for 48 months at 20° C. In some embodiments, the formulation (e.g., a pharmaceutically acceptable formulation described herein) is stable for 54 months at 20° C. In some embodiments, the formulation (e.g., a pharmaceutically acceptable formulation described herein) is stable for 60 months at 20° C.

In some embodiments, the formulation (e.g., a pharmaceutically acceptable formulation described herein) is stable for 5 months at 25° C. In some embodiments, the formulation (e.g., a pharmaceutically acceptable formulation described herein) is stable for 10 months at 25° C. In some embodiments, the formulation (e.g., a pharmaceutically acceptable formulation described herein) is stable for 12 months at 25° C. In some embodiments, the formulation (e.g., a pharmaceutically acceptable formulation described herein) is stable for 18 months at 25° C. In some embodiments, the formulation (e.g., a pharmaceutically acceptable formulation described herein) is stable for 24 months at 25° C. In some embodiments, the formulation (e.g., a pharmaceutically acceptable formulation described herein) is stable for 30 months at 25° C. In some embodiments, the formulation (e.g., a pharmaceutically acceptable formulation described herein) is stable for 36 months at 25° C. In some embodiments, the formulation (e.g., a pharmaceutically acceptable formulation described herein) is stable for 42 months at 25° C. In some embodiments, the formulation (e.g., a pharmaceutically acceptable formulation described herein) is stable for 48 months at 25° C. In some embodiments, the formulation (e.g., a pharmaceutically acceptable formulation described herein) is stable for 54 months at 25° C. In some embodiments, the formulation (e.g., a pharmaceutically acceptable formulation described herein) is stable for 60 months at 25° C.

Methods of Use

Provided herein, in part, are methods for the treatment or prevention of a variety of diseases and disorders, which comprise administering to a patient in need of such treatment or prevention a therapeutically effective amount of one or more formulations (e.g., oral dosage formulations (e.g., capsules)) comprising a compound represented by Formula (I) as a free base, in its neutral form, in a solvate form, or in the form of a pharmaceutically acceptable salt; and one or more pharmaceutically acceptable excipients.

In some embodiments, provided herein is a formulation comprising the compound represented by Formula (I) which is for use in the treatment of a tenosynovial giant cell tumor (TGCT). In some embodiments, the tenosynovial giant cell tumor is a diffuse-type tenosynovial giant cell tumor. In some embodiments, the tenosynovial giant cell tumor is a localized tenosynovial giant cell tumor.

In some embodiments, provided herein is a formulation comprising the compound represented by Formula (I) which is for use in the treatment of graft versus host disease (GVHD). In some embodiments, the graft versus host disease (GVHD) is chronic graft versus host disease (cGVHD). In some embodiments, the graft versus host disease (GVHD) is acute graft versus host disease (aGVHD).

In some embodiments, provided herein is a formulation comprising the compound represented by Formula (I) which is for use in the treatment of a neurodegenerative disease. In some embodiments, the neurodegenerative disease is selected from the group consisting of Parkinson's disease (PD), Alzheimer's Disease (AD), frontotemporal dementia (FTD), amyotrophic lateral sclerosis (ALS), mild cognitive impairment, and Huntington's Disease (HD).

In some embodiments, provided herein is a formulation comprising the compound represented by Formula (I) which is for use in the treatment of a cancer selected from the group consisting of solid tumors, acute myeloid leukemia (AML), relapsed/refractory acute myeloid leukemia (AML), relapsed acute myeloid leukemia (AML), refractory acute myeloid leukemia (AML), myelodysplastic syndrome, acute lymphocytic leukemia (ALL), chronic lymphocytic leukemia (CLL), pancreatic ductal adenocarcinoma (PDAC), ovarian cancer, non-small cell lung cancer (NSCLC), prostate cancer, osteosarcoma, breast cancer, colon cancer, and glioblastoma. In some embodiments, the solid tumor is selected from the group consisting of ovarian cancer, pancreatic cancer, prostate cancer, lung cancer, breast cancer, kidney cancer, liver cancer, cervical cancer, bone metastatic cancer, papillary thyroid cancer, non-small cell lung cancer, colon cancer, and gastrointestinal stromal tumor.

In some embodiments, provided herein is a formulation comprising the compound represented by Formula (I) which is for use in the treatment of tumors known to have expression of colony-stimulating factor 1 receptor (CSF-1R) or its ligands, colony stimulating factor-1 (CSF-1), or interleukin (IL)-34 (IL-34).

In some embodiments, provided herein is a formulation comprising the compound represented by Formula (I) which is for use in the treatment of a disease or condition selected from the group consisting of metabolic diseases, rheumatoid arthritis, osteoarthritis, multiple sclerosis, autoimmune nephritis, lupus, Crohn's disease, asthma, chronic obstructive pulmonary diseases, osteoporosis, hypereosinophilic syndromes, mastocytosis, and histiocytosis.

In some embodiments, the formulation comprising the compound represented by Formula (I), can be useful in the treatment of diseases and conditions including, but not limited to, cancer, autoimmune diseases, and metabolic bone disorders, and other tumors related to the decreased proliferation, the depletion, or the repolarization of tumor-associated macrophages (TAMs) and treatment of associated disorders, for example but not limited to disorders disclosed herein such as tenosynovial giant cell tumor (TGCT), graft-versus-host disease (GVHD), or neurodegenerative diseases. In some embodiments, the treatment of the disease or conditions occurs through the inhibition of CSF-1R kinase.

In some embodiments, the formulation comprising the compound represented by Formula (I), can be useful in the inhibition of the proliferation of TAMs, the depletion of TAMs, the repolarization of protumoral M2 TAMs to antitumoral M1 type macrophages, and treatment of related disorders in patients, for example but not limited to disorders disclosed herein such as tenosynovial giant cell tumor (TGCT), graft-versus-host disease (GVHD), or neurodegenerative diseases. In some embodiments, the formulation comprising the compound represented by Formula (I), potently inhibit CSF-1R signaling. In some embodiments, the formulation comprising the compound represented by Formula (I), blocks macrophage-mediated tumor cell migration. In some embodiments, the formulation comprising the compound represented by Formula (I) blocks osteoclast differentiation. In some embodiments, formulation comprising the compound represented by Formula (I), blocks proliferation of a CSF-1R-dependent cell line. In some embodiments, the formulation comprising the compound represented by Formula (I), potently inhibit CSF-1R signaling in cellular assays, as well as blocks macrophage-mediated tumor cell migration, osteoclast differentiation, and proliferation of a CSF-1R-dependent cell line.

In some embodiments, the formulation comprising the compound represented by Formula (I), is selective in inhibiting CSF-1R over one or more of the FLT3, KIT, PDGFRα, PDGFRβ and VEGFR2 kinases. In some embodiments, the formulation comprising the compound represented by Formula (I), has greater than 100-fold selectivity in inhibiting CSF-1R over the FLT3, KIT, PDGFRα, PDGFRβ, and VEGFR2 kinases.

In some embodiments, the formulation comprising the compound represented by Formula (I), can be useful in the treatment of cancer. In some embodiments, such cancer may include glioblastoma (e.g., recurrent glioblastoma (GBM)), castrate resistant prostate cancer (CRPC), bone metastatic CRPC, cholangiocarcinoma (e.g., unresectable intrahepatic cholangiocarcinoma), ovarian cancer, pancreatic cancer, prostate cancer (e.g., advanced castration-resistant prostate cancer with bone metastasis and high circulating tumor cell counts), lung cancer, breast cancer, kidney cancer, liver cancer, cervical cancer, metastatic cancer (e.g., cancers that are metastatic to bone), papillary thyroid cancer, non-small cell lung cancer (NSCLC), colon cancer, colorectal cancer, gastrointestinal stromal tumor (GIST), solid tumors (e.g., refractory solid tumors, malignant solid tumors. metastatic breast or prostate cancer with bone disease, gastric, ovarian or non-small cell lung cancer that has malignant associated ascites or effusion(s)), advanced solid tumors (e.g., advanced incurable solid tumors in which the target kinases are linked to disease pathophysiology), melanoma, advanced melanoma, mesothelioma, multiple myeloma, follicular lymphoma, leukemia (e.g., refractory leukemia, acute myeloid leukemia (AML), relapsed/refractory acute myeloid leukemia (AML), relapsed acute myeloid leukemia (AML), refractory acute myeloid leukemia (AML), mast cell leukemia associated with CSF-1R), classic Hodgkin's lymphoma (cHL), relapsed or refractory cHL, peripheral T cell lymphoma, neurofibroma, sarcoma (e.g., soft tissue sarcoma, osteosarcoma, advanced sarcoma, high grade sarcoma, leiomyosarcoma, undifferentiated pleomorphic sarcoma, myxofibrosarcoma, dedifferentiated liposarcoma), refractory solid malignancies (e.g., colorectal, breast, pancreatic, prostate, NSCLC), endometrial, urothelial, salivary gland, trophoblastic tumor, gallbladder, renal cell carcinoma, chordoma, and gastric cancer, recurrent platinum-resistant epithelial ovarian, peritoneal, or fallopian tube cancer, squamous cell carcinoma of the head and neck, malignant peripheral nerve sheath tumors, hepatocellular carcinoma, and neoplasms (e.g., advanced malignant neoplasm, unresectable malignant neoplasm).

In some embodiments, the formulation comprising the compound represented by Formula (I), can be useful in the treatment of diseases and conditions including idiopathic pulmonary fibrosis (IPF), hyperproliferative diseases, metabolic diseases, myeloproliferative diseases, stroke, SARS-CoV2, hepatic inflammation, rheumatoid arthritis, osteoarthritis, multiple sclerosis, autoimmune nephritis, lupus (e.g., lupus nephritis, systemic lupus erythematosus (SLE), Crohn's disease, asthma, psoriasis, chronic obstructive pulmonary diseases, pulmonary arterial hypertension (PAH), osteoporosis, hypereosinophilic syndromes, neurofibromatosis type 1-associated plexiform neurofibromas and mastocytosis.

In some embodiments, provided herein is a method of treating a tenosynovial giant cell tumor, comprising administering to the patient a therapeutically effective amount of the compound represented by Formula (I), or a therapeutically effective amount of the formulation comprising the compound represented by Formula (I). In some embodiments, the tenosynovial giant cell tumor is a diffuse-type tenosynovial giant cell tumor. In some embodiments, the tenosynovial giant cell tumor is a localized tenosynovial giant cell tumor.

In some embodiments, such tenosynovial giant cell tumor may be localized, e.g., as a single, well-defined nodule. In some embodiments, such tenosynovial giant cell tumor may be diffuse-type tenosynovial giant cell tumor. In some embodiments, such tenosynovial giant cell tumor may be associated with benign tumors. In some embodiments, such tenosynovial giant cell tumor may be associated with multiple nodules which may be aggressive. In some embodiments, the method may include administering about 2 mg to about 150 mg of the compound of Formula (I) daily to a patient in need thereof. In some embodiments, the method may include administering about 10 mg to about 100 mg of the compound of Formula (I) daily to a patient in need thereof. In some embodiments, the method may include administering about 10 mg to about 60 mg of the compound of Formula (I) daily to a patient in need thereof. In some embodiments, the method may include administering about 10 mg to about 35 mg of the compound of Formula (I) daily to a patient in need thereof. In some embodiments, the method may include administering about 2 mg of the compound of Formula (I) daily to a patient in need thereof. In some embodiments, the method may include administering about 3 mg of the compound of Formula (I) daily to a patient in need thereof. In some embodiments, the method may include administering about 4 mg of the compound of Formula (I) daily to a patient in need thereof. In some embodiments, the method may include administering about 5 mg of the compound of Formula (I) daily to a patient in need thereof. In some embodiments, the method may include administering about 6 mg of the compound of Formula (I) daily to a patient in need thereof. In some embodiments, the method may include administering about 7 mg of the compound of Formula (I) daily to a patient in need thereof. In some embodiments, the method may include administering about 8 mg of the compound of Formula (I) daily to a patient in need thereof. In some embodiments, the method may include administering about 9 mg of the compound of Formula (I) daily to a patient in need thereof. In some embodiments, the method may include administering about 10 mg of the compound of Formula (I) daily to a patient in need thereof. In some embodiments, the method may include administering about 11 mg of the compound of Formula (I) daily to a patient in need thereof. In some embodiments, the method may include administering about 12 mg of the compound of Formula (I) daily to a patient in need thereof. In some embodiments, the method may include administering about 13 mg of the compound of Formula (I) daily to a patient in need thereof. In some embodiments, the method may include administering about 14 mg of the compound of Formula (I) daily to a patient in need thereof. In some embodiments, the method may include administering about 15 mg of the compound of Formula (I) daily to a patient in need thereof. In some embodiments, the method may include administering about 16 mg of the compound of Formula (I) daily to a patient in need thereof. In some embodiments, the method may include administering about 17 mg of the compound of Formula (I) daily to a patient in need thereof. In some embodiments, the method may include administering about 18 mg of the compound of Formula (I) daily to a patient in need thereof. In some embodiments, the method may include administering about 19 mg of the compound of Formula (I) daily to a patient in need thereof. In some embodiments, the method may include administering about 20 mg of the compound of Formula (I) daily to a patient in need thereof. In some embodiments, the method may include administering about 21 mg of the compound of Formula (I) daily to a patient in need thereof. In some embodiments, the method may include administering about 22 mg of the compound of Formula (I) daily to a patient in need thereof. In some embodiments, the method may include administering about 23 mg of the compound of Formula (I) daily to a patient in need thereof. In some embodiments, the method may include administering about 24 mg of the compound of Formula (I) daily to a patient in need thereof. In some embodiments, the method may include administering about 25 mg of the compound of Formula (I) daily to a patient in need thereof. In some embodiments, the method may include administering about 26 mg of the compound of Formula (I) daily to a patient in need thereof. In some embodiments, the method may include administering about 27 mg of the compound of Formula (I) daily to a patient in need thereof. In some embodiments, the method may include administering about 28 mg of the compound of Formula (I) daily to a patient in need thereof. In some embodiments, the method may include administering about 29 mg of the compound of Formula (I) daily to a patient in need thereof. In some embodiments, the method may include administering about 30 mg of the compound of Formula (I) daily to a patient in need thereof. In some embodiments, the method may include administering about 31 mg of the compound of Formula (I) daily to a patient in need thereof. In some embodiments, the method may include administering about 32 mg of the compound of Formula (I) daily to a patient in need thereof. In some embodiments, the method may include administering about 33 mg of the compound of Formula (I) daily to a patient in need thereof. In some embodiments, the method may include administering about 34 mg of the compound of Formula (I) daily to a patient in need thereof. In some embodiments, the method may include administering about 35 mg of the compound of Formula (I) daily to a patient in need thereof. In some embodiments, the method may include administering about 36 mg of the compound of Formula (I) daily to a patient in need thereof. In some embodiments, the method may include administering about 36 mg of the compound of Formula (I) daily to a patient in need thereof. In some embodiments, the method may include administering about 37 mg of the compound of Formula (I) daily to a patient in need thereof. In some embodiments, the method may include administering about 38 mg of the compound of Formula (I) daily to a patient in need thereof. In some embodiments, the method may include administering about 39 mg of the compound of Formula (I) daily to a patient in need thereof. In some embodiments, the method may include administering about 40 mg of the compound of Formula (I) daily to a patient in need thereof. In some embodiments, the method may include administering about 41 mg of the compound of Formula (I) daily to a patient in need thereof. In some embodiments, the method may include administering about 42 mg of the compound of Formula (I) daily to a patient in need thereof. In some embodiments, the method may include administering about 43 mg of the compound of Formula (I) daily to a patient in need thereof. In some embodiments, the method may include administering about 44 mg of the compound of Formula (I) daily to a patient in need thereof. In some embodiments, the method may include administering about 45 mg of the compound of Formula (I) daily to a patient in need thereof. In some embodiments, the method may include administering about 46 mg of the compound of Formula (I) daily to a patient in need thereof. In some embodiments, the method may include administering about 47 mg of the compound of Formula (I) daily to a patient in need thereof. In some embodiments, the method may include administering about 48 mg of the compound of Formula (I) daily to a patient in need thereof. In some embodiments, the method may include administering about 49 mg of the compound of Formula (I) daily to a patient in need thereof. In some embodiments, the method may include administering about 50 mg of the compound of Formula (I) daily to a patient in need thereof. In some embodiments, the method may include administering about 51 mg of the compound of Formula (I) daily to a patient in need thereof. In some embodiments, the method may include administering about 52 mg of the compound of Formula (I) daily to a patient in need thereof. In some embodiments, the method may include administering about 53 mg of the compound of Formula (I) daily to a patient in need thereof. In some embodiments, the method may include administering about 54 mg of the compound of Formula (I) daily to a patient in need thereof. In some embodiments, the method may include administering about 55 mg of the compound of Formula (I) daily to a patient in need thereof. In some embodiments, the method may include administering about 56 mg of the compound of Formula (I) daily to a patient in need thereof. In some embodiments, the method may include administering about 57 mg of the compound of Formula (I) daily to a patient in need thereof. In some embodiments, the method may include administering about 58 mg of the compound of Formula (I) daily to a patient in need thereof. In some embodiments, the method may include administering about 59 mg of the compound of Formula (I) daily to a patient in need thereof. In some embodiments, the method may include administering about 60 mg of the compound of Formula (I) daily to a patient in need thereof. In some embodiments, the method may include administering about 65 mg of the compound of Formula (I) daily to a patient in need thereof. In some embodiments, the method may include administering about 70 mg of the compound of Formula (I) daily to a patient in need thereof. In some embodiments, the method may include administering about 75 mg of the compound of Formula (I) daily to a patient in need thereof. In some embodiments, the method may include administering about 80 mg of the compound of Formula (I) daily to a patient in need thereof. In some embodiments, the method may include administering about 85 mg of the compound of Formula (I) daily to a patient in need thereof. In some embodiments, the method may include administering about 90 mg of the compound of Formula (I) daily to a patient in need thereof. In some embodiments, the method may include administering about 95 mg of the compound of Formula (I) daily to a patient in need thereof. In some embodiments, the method may include administering about 100 mg of the compound of Formula (I) daily to a patient in need thereof. In some embodiments, the method may include administering about 105 mg of the compound of Formula (I) daily to a patient in need thereof. In some embodiments, the method may include administering about 110 mg of the compound of Formula (I) daily to a patient in need thereof. In some embodiments, the method may include administering about 115 mg of the compound of Formula (I) daily to a patient in need thereof. In some embodiments, the method may include administering about 120 mg of the compound of Formula (I) daily to a patient in need thereof. In some embodiments, the method may include administering about 125 mg of the compound of Formula (I) daily to a patient in need thereof. In some embodiments, the method may include administering about 130 mg of the compound of Formula (I) daily to a patient in need thereof. In some embodiments, the method may include administering about 135 mg of the compound of Formula (I) daily to a patient in need thereof. In some embodiments, the method may include administering about 140 mg of the compound of Formula (I) daily to a patient in need thereof. In some embodiments, the method may include administering about 145 mg of the compound of Formula (I) daily to a patient in need thereof. In some embodiments, the method may include administering about 150 mg of the compound of Formula (I) daily to a patient in need thereof.

In some embodiments, the method may include administering about 2 mg to about 150 mg of the compound of Formula (I) once a week to a patient in need thereof. In some embodiments, the method may include administering about 10 mg to about 100 mg of the compound of Formula (I) once a week to a patient in need thereof. In some embodiments, the method may include administering about 10 mg to about 60 mg of the compound of Formula (I) once a week to a patient in need thereof. In some embodiments, the method may include administering about 10 mg to about 35 mg of the compound of Formula (I) once a week to a patient in need thereof. In some embodiments, the method may include administering about 2 mg of the compound of Formula (I) once a week to a patient in need thereof. In some embodiments, the method may include administering about 3 mg of the compound of Formula (I) once a week to a patient in need thereof. In some embodiments, the method may include administering about 4 mg of the compound of Formula (I) once a week to a patient in need thereof. In some embodiments, the method may include administering about 5 mg of the compound of Formula (I) once a week to a patient in need thereof. In some embodiments, the method may include administering about 6 mg of the compound of Formula (I) once a week to a patient in need thereof. In some embodiments, the method may include administering about 7 mg of the compound of Formula (I) once a week to a patient in need thereof. In some embodiments, the method may include administering about 8 mg of the compound of Formula (I) once a week to a patient in need thereof. In some embodiments, the method may include administering about 9 mg of the compound of Formula (I) once a week to a patient in need thereof. In some embodiments, the method may include administering about 10 mg of the compound of Formula (I) once a week to a patient in need thereof. In some embodiments, the method may include administering about 11 mg of the compound of Formula (I) once a week to a patient in need thereof. In some embodiments, the method may include administering about 12 mg of the compound of Formula (I) once a week to a patient in need thereof. In some embodiments, the method may include administering about 13 mg of the compound of Formula (I) once a week to a patient in need thereof. In some embodiments, the method may include administering about 14 mg of the compound of Formula (I) once a week to a patient in need thereof. In some embodiments, the method may include administering about 15 mg of the compound of Formula (I) once a week to a patient in need thereof. In some embodiments, the method may include administering about 16 mg of the compound of Formula (I) once a week to a patient in need thereof. In some embodiments, the method may include administering about 17 mg of the compound of Formula (I) once a week to a patient in need thereof. In some embodiments, the method may include administering about 18 mg of the compound of Formula (I) once a week to a patient in need thereof. In some embodiments, the method may include administering about 19 mg of the compound of Formula (I) once a week to a patient in need thereof. In some embodiments, the method may include administering about 20 mg of the compound of Formula (I) once a week to a patient in need thereof. In some embodiments, the method may include administering about 21 mg of the compound of Formula (I) once a week to a patient in need thereof. In some embodiments, the method may include administering about 22 mg of the compound of Formula (I) once a week to a patient in need thereof. In some embodiments, the method may include administering about 23 mg of the compound of Formula (I) once a week to a patient in need thereof. In some embodiments, the method may include administering about 24 mg of the compound of Formula (I) once a week to a patient in need thereof. In some embodiments, the method may include administering about 25 mg of the compound of Formula (I) once a week to a patient in need thereof. In some embodiments, the method may include administering about 26 mg of the compound of Formula (I) once a week to a patient in need thereof. In some embodiments, the method may include administering about 27 mg of the compound of Formula (I) once a week to a patient in need thereof. In some embodiments, the method may include administering about 28 mg of the compound of Formula (I) once a week to a patient in need thereof. In some embodiments, the method may include administering about 29 mg of the compound of Formula (I) once a week to a patient in need thereof. In some embodiments, the method may include administering about 30 mg of the compound of Formula (I) once a week to a patient in need thereof. In some embodiments, the method may include administering about 31 mg of the compound of Formula (I) once a week to a patient in need thereof. In some embodiments, the method may include administering about 32 mg of the compound of Formula (I) once a week to a patient in need thereof. In some embodiments, the method may include administering about 33 mg of the compound of Formula (I) once a week to a patient in need thereof. In some embodiments, the method may include administering about 34 mg of the compound of Formula (I) once a week to a patient in need thereof. In some embodiments, the method may include administering about 35 mg of the compound of Formula (I) once a week to a patient in need thereof. In some embodiments, the method may include administering about 36 mg of the compound of Formula (I) once a week to a patient in need thereof. In some embodiments, the method may include administering about 36 mg of the compound of Formula (I) once a week to a patient in need thereof. In some embodiments, the method may include administering about 37 mg of the compound of Formula (I) once a week to a patient in need thereof. In some embodiments, the method may include administering about 38 mg of the compound of Formula (I) once a week to a patient in need thereof. In some embodiments, the method may include administering about 39 mg of the compound of Formula (I) once a week to a patient in need thereof. In some embodiments, the method may include administering about 40 mg of the compound of Formula (I) once a week to a patient in need thereof. In some embodiments, the method may include administering about 41 mg of the compound of Formula (I) once a week to a patient in need thereof. In some embodiments, the method may include administering about 42 mg of the compound of Formula (I) once a week to a patient in need thereof. In some embodiments, the method may include administering about 43 mg of the compound of Formula (I) once a week to a patient in need thereof. In some embodiments, the method may include administering about 44 mg of the compound of Formula (I) once a week to a patient in need thereof. In some embodiments, the method may include administering about 45 mg of the compound of Formula (I) once a week to a patient in need thereof. In some embodiments, the method may include administering about 46 mg of the compound of Formula (I) once a week to a patient in need thereof. In some embodiments, the method may include administering about 47 mg of the compound of Formula (I) once a week to a patient in need thereof. In some embodiments, the method may include administering about 48 mg of the compound of Formula (I) once a week to a patient in need thereof. In some embodiments, the method may include administering about 49 mg of the compound of Formula (I) once a week to a patient in need thereof. In some embodiments, the method may include administering about 50 mg of the compound of Formula (I) once a week to a patient in need thereof. In some embodiments, the method may include administering about 51 mg of the compound of Formula (I) once a week to a patient in need thereof. In some embodiments, the method may include administering about 52 mg of the compound of Formula (I) once a week to a patient in need thereof. In some embodiments, the method may include administering about 53 mg of the compound of Formula (I) once a week to a patient in need thereof. In some embodiments, the method may include administering about 54 mg of the compound of Formula (I) once a week to a patient in need thereof. In some embodiments, the method may include administering about 55 mg of the compound of Formula (I) once a week to a patient in need thereof. In some embodiments, the method may include administering about 56 mg of the compound of Formula (I) once a week to a patient in need thereof. In some embodiments, the method may include administering about 57 mg of the compound of Formula (I) once a week to a patient in need thereof. In some embodiments, the method may include administering about 58 mg of the compound of Formula (I) once a week to a patient in need thereof. In some embodiments, the method may include administering about 59 mg of the compound of Formula (I) once a week to a patient in need thereof. In some embodiments, the method may include administering about 60 mg of the compound of Formula (I) once a week to a patient in need thereof. In some embodiments, the method may include administering about 65 mg of the compound of Formula (I) once a week to a patient in need thereof. In some embodiments, the method may include administering about 70 mg of the compound of Formula (I) once a week to a patient in need thereof. In some embodiments, the method may include administering about 75 mg of the compound of Formula (I) once a week to a patient in need thereof. In some embodiments, the method may include administering about 80 mg of the compound of Formula (I) once a week to a patient in need thereof. In some embodiments, the method may include administering about 85 mg of the compound of Formula (I) once a week to a patient in need thereof. In some embodiments, the method may include administering about 90 mg of the compound of Formula (I) once a week to a patient in need thereof. In some embodiments, the method may include administering about 95 mg of the compound of Formula (I) once a week to a patient in need thereof. In some embodiments, the method may include administering about 100 mg of the compound of Formula (I) once a week to a patient in need thereof. In some embodiments, the method may include administering about 105 mg of the compound of Formula (I) once a week to a patient in need thereof. In some embodiments, the method may include administering about 110 mg of the compound of Formula (I) once a week to a patient in need thereof. In some embodiments, the method may include administering about 115 mg of the compound of Formula (I) once a week to a patient in need thereof. In some embodiments, the method may include administering about 120 mg of the compound of Formula (I) once a week to a patient in need thereof. In some embodiments, the method may include administering about 125 mg of the compound of Formula (I) once a week to a patient in need thereof. In some embodiments, the method may include administering about 130 mg of the compound of Formula (I) once a week to a patient in need thereof. In some embodiments, the method may include administering about 135 mg of the compound of Formula (I) once a week to a patient in need thereof. In some embodiments, the method may include administering about 140 mg of the compound of Formula (I) once a week to a patient in need thereof. In some embodiments, the method may include administering about 145 mg of the compound of Formula (I) once a week to a patient in need thereof. In some embodiments, the method may include administering about 150 mg of the compound of Formula (I) once a week to a patient in need thereof.

In some embodiments, the method may include administering about 2 mg to about 150 mg of the compound of Formula (I) twice a week to a patient in need thereof. In some embodiments, the method may include administering about 10 mg to about 100 mg of the compound of Formula (I) twice a week to a patient in need thereof. In some embodiments, the method may include administering about 10 mg to about 60 mg of the compound of Formula (I) twice a week to a patient in need thereof. In some embodiments, the method may include administering about 10 mg to about 35 mg of the compound of Formula (I) twice a week to a patient in need thereof. In some embodiments, the method may include administering about 2 mg of the compound of Formula (I) twice a week to a patient in need thereof. In some embodiments, the method may include administering about 3 mg of the compound of Formula (I) twice a week to a patient in need thereof. In some embodiments, the method may include administering about 4 mg of the compound of Formula (I) twice a week to a patient in need thereof. In some embodiments, the method may include administering about 5 mg of the compound of Formula (I) twice a week to a patient in need thereof. In some embodiments, the method may include administering about 6 mg of the compound of Formula (I) twice a week to a patient in need thereof. In some embodiments, the method may include administering about 7 mg of the compound of Formula (I) twice a week to a patient in need thereof. In some embodiments, the method may include administering about 8 mg of the compound of Formula (I) twice a week to a patient in need thereof. In some embodiments, the method may include administering about 9 mg of the compound of Formula (I) twice a week to a patient in need thereof. In some embodiments, the method may include administering about 10 mg of the compound of Formula (I) twice a week to a patient in need thereof. In some embodiments, the method may include administering about 11 mg of the compound of Formula (I) twice a week to a patient in need thereof. In some embodiments, the method may include administering about 12 mg of the compound of Formula (I) twice a week to a patient in need thereof. In some embodiments, the method may include administering about 13 mg of the compound of Formula (I) twice a week to a patient in need thereof. In some embodiments, the method may include administering about 14 mg of the compound of Formula (I) twice a week to a patient in need thereof. In some embodiments, the method may include administering about 15 mg of the compound of Formula (I) twice a week to a patient in need thereof. In some embodiments, the method may include administering about 16 mg of the compound of Formula (I) twice a week to a patient in need thereof. In some embodiments, the method may include administering about 17 mg of the compound of Formula (I) twice a week to a patient in need thereof. In some embodiments, the method may include administering about 18 mg of the compound of Formula (I) twice a week to a patient in need thereof. In some embodiments, the method may include administering about 19 mg of the compound of Formula (I) twice a week to a patient in need thereof. In some embodiments, the method may include administering about 20 mg of the compound of Formula (I) twice a week to a patient in need thereof. In some embodiments, the method may include administering about 21 mg of the compound of Formula (I) twice a week to a patient in need thereof. In some embodiments, the method may include administering about 22 mg of the compound of Formula (I) twice a week to a patient in need thereof. In some embodiments, the method may include administering about 23 mg of the compound of Formula (I) twice a week to a patient in need thereof. In some embodiments, the method may include administering about 24 mg of the compound of Formula (I) twice a week to a patient in need thereof. In some embodiments, the method may include administering about 25 mg of the compound of Formula (I) twice a week to a patient in need thereof. In some embodiments, the method may include administering about 26 mg of the compound of Formula (I) twice a week to a patient in need thereof. In some embodiments, the method may include administering about 27 mg of the compound of Formula (I) twice a week to a patient in need thereof. In some embodiments, the method may include administering about 28 mg of the compound of Formula (I) twice a week to a patient in need thereof. In some embodiments, the method may include administering about 29 mg of the compound of Formula (I) twice a week to a patient in need thereof. In some embodiments, the method may include administering about 30 mg of the compound of Formula (I) twice a week to a patient in need thereof. In some embodiments, the method may include administering about 31 mg of the compound of Formula (I) twice a week to a patient in need thereof. In some embodiments, the method may include administering about 32 mg of the compound of Formula (I) twice a week to a patient in need thereof. In some embodiments, the method may include administering about 33 mg of the compound of Formula (I) twice a week to a patient in need thereof. In some embodiments, the method may include administering about 34 mg of the compound of Formula (I) twice a week to a patient in need thereof. In some embodiments, the method may include administering about 35 mg of the compound of Formula (I) twice a week to a patient in need thereof. In some embodiments, the method may include administering about 36 mg of the compound of Formula (I) twice a week to a patient in need thereof. In some embodiments, the method may include administering about 36 mg of the compound of Formula (I) twice a week to a patient in need thereof. In some embodiments, the method may include administering about 37 mg of the compound of Formula (I) twice a week to a patient in need thereof. In some embodiments, the method may include administering about 38 mg of the compound of Formula (I) twice a week to a patient in need thereof. In some embodiments, the method may include administering about 39 mg of the compound of Formula (I) twice a week to a patient in need thereof. In some embodiments, the method may include administering about 40 mg of the compound of Formula (I) twice a week to a patient in need thereof. In some embodiments, the method may include administering about 41 mg of the compound of Formula (I) twice a week to a patient in need thereof. In some embodiments, the method may include administering about 42 mg of the compound of Formula (I) twice a week to a patient in need thereof. In some embodiments, the method may include administering about 43 mg of the compound of Formula (I) twice a week to a patient in need thereof. In some embodiments, the method may include administering about 44 mg of the compound of Formula (I) twice a week to a patient in need thereof. In some embodiments, the method may include administering about 45 mg of the compound of Formula (I) twice a week to a patient in need thereof. In some embodiments, the method may include administering about 46 mg of the compound of Formula (I) twice a week to a patient in need thereof. In some embodiments, the method may include administering about 47 mg of the compound of Formula (I) twice a week to a patient in need thereof. In some embodiments, the method may include administering about 48 mg of the compound of Formula (I) twice a week to a patient in need thereof. In some embodiments, the method may include administering about 49 mg of the compound of Formula (I) twice a week to a patient in need thereof. In some embodiments, the method may include administering about 50 mg of the compound of Formula (I) twice a week to a patient in need thereof. In some embodiments, the method may include administering about 51 mg of the compound of Formula (I) twice a week to a patient in need thereof. In some embodiments, the method may include administering about 52 mg of the compound of Formula (I) twice a week to a patient in need thereof. In some embodiments, the method may include administering about 53 mg of the compound of Formula (I) twice a week to a patient in need thereof. In some embodiments, the method may include administering about 54 mg of the compound of Formula (I) twice a week to a patient in need thereof. In some embodiments, the method may include administering about 55 mg of the compound of Formula (I) twice a week to a patient in need thereof. In some embodiments, the method may include administering about 56 mg of the compound of Formula (I) twice a week to a patient in need thereof. In some embodiments, the method may include administering about 57 mg of the compound of Formula (I) twice a week to a patient in need thereof. In some embodiments, the method may include administering about 58 mg of the compound of Formula (I) twice a week to a patient in need thereof. In some embodiments, the method may include administering about 59 mg of the compound of Formula (I) twice a week to a patient in need thereof. In some embodiments, the method may include administering about 60 mg of the compound of Formula (I) twice a week to a patient in need thereof. In some embodiments, the method may include administering about 65 mg of the compound of Formula (I) twice a week to a patient in need thereof. In some embodiments, the method may include administering about 70 mg of the compound of Formula (I) twice a week to a patient in need thereof. In some embodiments, the method may include administering about 75 mg of the compound of Formula (I) twice a week to a patient in need thereof. In some embodiments, the method may include administering about 80 mg of the compound of Formula (I) twice a week to a patient in need thereof. In some embodiments, the method may include administering about 85 mg of the compound of Formula (I) twice a week to a patient in need thereof. In some embodiments, the method may include administering about 90 mg of the compound of Formula (I) twice a week to a patient in need thereof. In some embodiments, the method may include administering about 95 mg of the compound of Formula (I) twice a week to a patient in need thereof. In some embodiments, the method may include administering about 100 mg of the compound of Formula (I) twice a week to a patient in need thereof. In some embodiments, the method may include administering about 105 mg of the compound of Formula (I) twice a week to a patient in need thereof. In some embodiments, the method may include administering about 110 mg of the compound of Formula (I) twice a week to a patient in need thereof. In some embodiments, the method may include administering about 115 mg of the compound of Formula (I) twice a week to a patient in need thereof. In some embodiments, the method may include administering about 120 mg of the compound of Formula (I) twice a week to a patient in need thereof. In some embodiments, the method may include administering about 125 mg of the compound of Formula (I) twice a week to a patient in need thereof. In some embodiments, the method may include administering about 130 mg of the compound of Formula (I) twice a week to a patient in need thereof. In some embodiments, the method may include administering about 135 mg of the compound of Formula (I) twice a week to a patient in need thereof. In some embodiments, the method may include administering about 140 mg of the compound of Formula (I) twice a week to a patient in need thereof. In some embodiments, the method may include administering about 145 mg of the compound of Formula (I) twice a week to a patient in need thereof. In some embodiments, the method may include administering about 150 mg of the compound of Formula (I) twice a week to a patient in need thereof.

In some embodiments, the method may include administering about 2 mg to about 150 mg of the compound of Formula (I) three times a week to a patient in need thereof. In some embodiments, the method may include administering about 10 mg to about 100 mg of the compound of Formula (I) three times a week to a patient in need thereof. In some embodiments, the method may include administering about 10 mg to about 60 mg of the compound of Formula (I) three times a week to a patient in need thereof. In some embodiments, the method may include administering about 10 mg to about 35 mg of the compound of Formula (I) three times a week to a patient in need thereof. In some embodiments, the method may include administering about 2 mg of the compound of Formula (I) three times a week to a patient in need thereof. In some embodiments, the method may include administering about 3 mg of the compound of Formula (I) three times a week to a patient in need thereof. In some embodiments, the method may include administering about 4 mg of the compound of Formula (I) three times a week to a patient in need thereof. In some embodiments, the method may include administering about 5 mg of the compound of Formula (I) three times a week to a patient in need thereof. In some embodiments, the method may include administering about 6 mg of the compound of Formula (I) three times a week to a patient in need thereof. In some embodiments, the method may include administering about 7 mg of the compound of Formula (I) three times a week to a patient in need thereof. In some embodiments, the method may include administering about 8 mg of the compound of Formula (I) three times a week to a patient in need thereof. In some embodiments, the method may include administering about 9 mg of the compound of Formula (I) three times a week to a patient in need thereof. In some embodiments, the method may include administering about 10 mg of the compound of Formula (I) three times a week to a patient in need thereof. In some embodiments, the method may include administering about 11 mg of the compound of Formula (I) three times a week to a patient in need thereof. In some embodiments, the method may include administering about 12 mg of the compound of Formula (I) three times a week to a patient in need thereof. In some embodiments, the method may include administering about 13 mg of the compound of Formula (I) three times a week to a patient in need thereof. In some embodiments, the method may include administering about 14 mg of the compound of Formula (I) three times a week to a patient in need thereof. In some embodiments, the method may include administering about 15 mg of the compound of Formula (I) three times a week to a patient in need thereof. In some embodiments, the method may include administering about 16 mg of the compound of Formula (I) three times a week to a patient in need thereof. In some embodiments, the method may include administering about 17 mg of the compound of Formula (I) three times a week to a patient in need thereof. In some embodiments, the method may include administering about 18 mg of the compound of Formula (I) three times a week to a patient in need thereof. In some embodiments, the method may include administering about 19 mg of the compound of Formula (I) three times a week to a patient in need thereof. In some embodiments, the method may include administering about 20 mg of the compound of Formula (I) three times a week to a patient in need thereof. In some embodiments, the method may include administering about 21 mg of the compound of Formula (I) three times a week to a patient in need thereof. In some embodiments, the method may include administering about 22 mg of the compound of Formula (I) three times a week to a patient in need thereof. In some embodiments, the method may include administering about 23 mg of the compound of Formula (I) three times a week to a patient in need thereof. In some embodiments, the method may include administering about 24 mg of the compound of Formula (I) three times a week to a patient in need thereof. In some embodiments, the method may include administering about 25 mg of the compound of Formula (I) three times a week to a patient in need thereof. In some embodiments, the method may include administering about 26 mg of the compound of Formula (I) three times a week to a patient in need thereof. In some embodiments, the method may include administering about 27 mg of the compound of Formula (I) three times a week to a patient in need thereof. In some embodiments, the method may include administering about 28 mg of the compound of Formula (I) three times a week to a patient in need thereof. In some embodiments, the method may include administering about 29 mg of the compound of Formula (I) three times a week to a patient in need thereof. In some embodiments, the method may include administering about 30 mg of the compound of Formula (I) three times a week to a patient in need thereof. In some embodiments, the method may include administering about 31 mg of the compound of Formula (I) three times a week to a patient in need thereof. In some embodiments, the method may include administering about 32 mg of the compound of Formula (I) three times a week to a patient in need thereof. In some embodiments, the method may include administering about 33 mg of the compound of Formula (I) three times a week to a patient in need thereof. In some embodiments, the method may include administering about 34 mg of the compound of Formula (I) three times a week to a patient in need thereof. In some embodiments, the method may include administering about 35 mg of the compound of Formula (I) three times a week to a patient in need thereof. In some embodiments, the method may include administering about 36 mg of the compound of Formula (I) three times a week to a patient in need thereof. In some embodiments, the method may include administering about 36 mg of the compound of Formula (I) three times a week to a patient in need thereof. In some embodiments, the method may include administering about 37 mg of the compound of Formula (I) three times a week to a patient in need thereof. In some embodiments, the method may include administering about 38 mg of the compound of Formula (I) three times a week to a patient in need thereof. In some embodiments, the method may include administering about 39 mg of the compound of Formula (I) three times a week to a patient in need thereof. In some embodiments, the method may include administering about 40 mg of the compound of Formula (I) three times a week to a patient in need thereof. In some embodiments, the method may include administering about 41 mg of the compound of Formula (I) three times a week to a patient in need thereof. In some embodiments, the method may include administering about 42 mg of the compound of Formula (I) three times a week to a patient in need thereof. In some embodiments, the method may include administering about 43 mg of the compound of Formula (I) three times a week to a patient in need thereof. In some embodiments, the method may include administering about 44 mg of the compound of Formula (I) three times a week to a patient in need thereof. In some embodiments, the method may include administering about 45 mg of the compound of Formula (I) three times a week to a patient in need thereof. In some embodiments, the method may include administering about 46 mg of the compound of Formula (I) three times a week to a patient in need thereof. In some embodiments, the method may include administering about 47 mg of the compound of Formula (I) three times a week to a patient in need thereof. In some embodiments, the method may include administering about 48 mg of the compound of Formula (I) three times a week to a patient in need thereof. In some embodiments, the method may include administering about 49 mg of the compound of Formula (I) three times a week to a patient in need thereof. In some embodiments, the method may include administering about 50 mg of the compound of Formula (I) three times a week to a patient in need thereof. In some embodiments, the method may include administering about 51 mg of the compound of Formula (I) three times a week to a patient in need thereof. In some embodiments, the method may include administering about 52 mg of the compound of Formula (I) three times a week to a patient in need thereof. In some embodiments, the method may include administering about 53 mg of the compound of Formula (I) three times a week to a patient in need thereof. In some embodiments, the method may include administering about 54 mg of the compound of Formula (I) three times a week to a patient in need thereof. In some embodiments, the method may include administering about 55 mg of the compound of Formula (I) three times a week to a patient in need thereof. In some embodiments, the method may include administering about 56 mg of the compound of Formula (I) three times a week to a patient in need thereof. In some embodiments, the method may include administering about 57 mg of the compound of Formula (I) three times a week to a patient in need thereof. In some embodiments, the method may include administering about 58 mg of the compound of Formula (I) three times a week to a patient in need thereof. In some embodiments, the method may include administering about 59 mg of the compound of Formula (I) three times a week to a patient in need thereof. In some embodiments, the method may include administering about 60 mg of the compound of Formula (I) three times a week to a patient in need thereof. In some embodiments, the method may include administering about 65 mg of the compound of Formula (I) three times a week to a patient in need thereof. In some embodiments, the method may include administering about 70 mg of the compound of Formula (I) three times a week to a patient in need thereof. In some embodiments, the method may include administering about 75 mg of the compound of Formula (I) three times a week to a patient in need thereof. In some embodiments, the method may include administering about 80 mg of the compound of Formula (I) three times a week to a patient in need thereof. In some embodiments, the method may include administering about 85 mg of the compound of Formula (I) three times a week to a patient in need thereof. In some embodiments, the method may include administering about 90 mg of the compound of Formula (I) three times a week to a patient in need thereof. In some embodiments, the method may include administering about 95 mg of the compound of Formula (I) three times a week to a patient in need thereof. In some embodiments, the method may include administering about 100 mg of the compound of Formula (I) three times a week to a patient in need thereof. In some embodiments, the method may include administering about 105 mg of the compound of Formula (I) three times a week to a patient in need thereof. In some embodiments, the method may include administering about 110 mg of the compound of Formula (I) three times a week to a patient in need thereof. In some embodiments, the method may include administering about 115 mg of the compound of Formula (I) three times a week to a patient in need thereof. In some embodiments, the method may include administering about 120 mg of the compound of Formula (I) three times a week to a patient in need thereof. In some embodiments, the method may include administering about 125 mg of the compound of Formula (I) three times a week to a patient in need thereof. In some embodiments, the method may include administering about 130 mg of the compound of Formula (I) three times a week to a patient in need thereof. In some embodiments, the method may include administering about 135 mg of the compound of Formula (I) three times a week to a patient in need thereof. In some embodiments, the method may include administering about 140 mg of the compound of Formula (I) three times a week to a patient in need thereof. In some embodiments, the method may include administering about 145 mg of the compound of Formula (I) three times a week to a patient in need thereof. In some embodiments, the method may include administering about 150 mg of the compound of Formula (I) three times a week to a patient in need thereof.

In some embodiments, such a disclosed method may include, administering a loading dose of the compound of Formula (I) daily to a patient in need thereof, once a week to a patient in need thereof, twice a week to a patient in need thereof, or three times a week to a patient in need thereof, for a first time period; and administering a maintenance dose of the compound of Formula (I) to a patient in need thereof daily to a patient in need thereof, once a week to a patient in need thereof, twice a week to a patient in need thereof, or three times a week to a patient in need thereof for a second time period.

In some embodiments, the loading dose is about 2 mg to about 100 mg of the compound of Formula (I) once a day. In some embodiments, the loading dose is about 5 mg to about 90 mg of the compound of Formula (I) once a day. In some embodiments, the loading dose is about 10 mg to about 80 mg of the compound of Formula (I) once a day. In some embodiments, the loading dose is about 10 mg to about 70 mg of the compound of Formula (I) once a day. In some embodiments, the loading dose is about 10 mg to about 60 mg of the compound of Formula (I) once a day. In some embodiments, the loading dose is about 10 mg to about 50 mg of the compound of Formula (I) once a day. In some embodiments, the loading dose is about 10 mg to about 40 mg of the compound of Formula (I) once a day. In some embodiments, the loading dose is about 10 mg to about 30 mg of the compound of Formula (I) once a day. In some embodiments, the loading dose is about 10 mg to about 20 mg of the compound of Formula (I) once a day. In some embodiments, the loading dose is about 2 mg of the compound of Formula (I) once a day. In some embodiments, the loading dose is about 3 mg of the compound of Formula (I) once a day. In some embodiments, the loading dose is about 4 mg of the compound of Formula (I) once a day. In some embodiments, the loading dose is about 5 mg of the compound of Formula (I) once a day. In some embodiments, the loading dose is about 10 mg of the compound of Formula (I) once a day. In some embodiments, the loading dose is about 11 mg of the compound of Formula (I) once a day. In some embodiments, the loading dose is about 12 mg of the compound of Formula (I) once a day. In some embodiments, the loading dose is about 13 mg of the compound of Formula (I) once a day. In some embodiments, the loading dose is about 14 mg of the compound of Formula (I) once a day. In some embodiments, the loading dose is about 15 mg of the compound of Formula (I) once a day. In some embodiments, the loading dose is about 16 mg of the compound of Formula (I) once a day. In some embodiments, the loading dose is about 17 mg of the compound of Formula (I) once a day. In some embodiments, the loading dose is about 18 mg of the compound of Formula (I) once a day. In some embodiments, the loading dose is about 19 mg of the compound of Formula (I) once a day. In some embodiments, the loading dose is about 20 mg of the compound of Formula (I) once a day. In some embodiments, the loading dose is about 22 mg of the compound of Formula (I) once a day. In some embodiments, the loading dose is about 24 mg of the compound of Formula (I) once a day. In some embodiments, the loading dose is about 26 mg of the compound of Formula (I) once a day. In some embodiments, the loading dose is about 28 mg of the compound of Formula (I) once a day. In some embodiments, the loading dose is about 30 mg of the compound of Formula (I) once a day. In some embodiments, the loading dose is about 32 mg of the compound of Formula (I) once a day. In some embodiments, the loading dose is about 34 mg of the compound of Formula (I) once a day. In some embodiments, the loading dose is about 36 mg of the compound of Formula (I) once a day. In some embodiments, the loading dose is about 38 mg of the compound of Formula (I) once a day. In some embodiments, the loading dose is about 40 mg of the compound of Formula (I) once a day. In some embodiments, the loading dose is about 42 mg of the compound of Formula (I) once a day. In some embodiments, the loading dose is about 44 mg of the compound of Formula (I) once a day. In some embodiments, the loading dose is about 46 mg of the compound of Formula (I) once a day. In some embodiments, the loading dose is about 48 mg of the compound of Formula (I) once a day. In some embodiments, the loading dose is about 50 mg of the compound of Formula (I) once a day.

In some embodiments, the loading dose is about 2 mg to about 100 mg of the compound of Formula (I) once a day for one day. In some embodiments, the loading dose is about 5 mg to about 90 mg of the compound of Formula (I) once a day for one day. In some embodiments, the loading dose is about 10 mg to about 80 mg of the compound of Formula (I) once a day for one day. In some embodiments, the loading dose is about 10 mg to about 70 mg of the compound of Formula (I) once a day for one day. In some embodiments, the loading dose is about 10 mg to about 60 mg of the compound of Formula (I) once a day for one day. In some embodiments, the loading dose is about 10 mg to about 50 mg of the compound of Formula (I) once a day for one day. In some embodiments, the loading dose is about 10 mg to about 40 mg of the compound of Formula (I) once a day for one day. In some embodiments, the loading dose is about 10 mg to about 30 mg of the compound of Formula (I) once a day for one day. In some embodiments, the loading dose is about 10 mg to about 20 mg of the compound of Formula (I) once a day for one day. In some embodiments, the loading dose is about 2 mg of the compound of Formula (I) once a day for one day. In some embodiments, the loading dose is about 3 mg of the compound of Formula (I) once a day for one day. In some embodiments, the loading dose is about 4 mg of the compound of Formula (I) once a day for one day. In some embodiments, the loading dose is about 5 mg of the compound of Formula (I) once a day for one day. In some embodiments, the loading dose is about 10 mg of the compound of Formula (I) once a day for one day. In some embodiments, the loading dose is about 11 mg of the compound of Formula (I) once a day for one day. In some embodiments, the loading dose is about 12 mg of the compound of Formula (I) once a day for one day. In some embodiments, the loading dose is about 13 mg of the compound of Formula (I) once a day for one day. In some embodiments, the loading dose is about 14 mg of the compound of Formula (I) once a day for one day. In some embodiments, the loading dose is about 15 mg of the compound of Formula (I) once a day for one day. In some embodiments, the loading dose is about 16 mg of the compound of Formula (I) once a day for one day. In some embodiments, the loading dose is about 17 mg of the compound of Formula (I) once a day for one day. In some embodiments, the loading dose is about 18 mg of the compound of Formula (I) once a day for one day. In some embodiments, the loading dose is about 19 mg of the compound of Formula (I) once a day for one day. In some embodiments, the loading dose is about 20 mg of the compound of Formula (I) once a day for one day. In some embodiments, the loading dose is about 22 mg of the compound of Formula (I) once a day for one day. In some embodiments, the loading dose is about 24 mg of the compound of Formula (I) once a day for one day. In some embodiments, the loading dose is about 26 mg of the compound of Formula (I) once a day for one day. In some embodiments, the loading dose is about 28 mg of the compound of Formula (I) once a day for one day. In some embodiments, the loading dose is about 30 mg of the compound of Formula (I) once a day for one day. In some embodiments, the loading dose is about 32 mg of the compound of Formula (I) once a day for one day. In some embodiments, the loading dose is about 34 mg of the compound of Formula (I) once a day for one day. In some embodiments, the loading dose is about 36 mg of the compound of Formula (I) once a day for one day. In some embodiments, the loading dose is about 38 mg of the compound of Formula (I) once a day for one day. In some embodiments, the loading dose is about 40 mg of the compound of Formula (I) once a day for one day. In some embodiments, the loading dose is about 42 mg of the compound of Formula (I) once a day for one day. In some embodiments, the loading dose is about 44 mg of the compound of Formula (I) once a day for one day. In some embodiments, the loading dose is about 46 mg of the compound of Formula (I) once a day for one day. In some embodiments, the loading dose is about 48 mg of the compound of Formula (I) once a day for one day. In some embodiments, the loading dose is about 50 mg of the compound of Formula (I) once a day for one day.

In some embodiments, the loading dose is about 2 mg to about 100 mg of the compound of Formula (I) once a day for two days. In some embodiments, the loading dose is about 5 mg to about 90 mg of the compound of Formula (I) once a day for two days. In some embodiments, the loading dose is about 10 mg to about 80 mg of the compound of Formula (I) once a day for two days. In some embodiments, the loading dose is about 10 mg to about 70 mg of the compound of Formula (I) once a day for two days. In some embodiments, the loading dose is about 10 mg to about 60 mg of the compound of Formula (I) once a day for two days. In some embodiments, the loading dose is about 10 mg to about 50 mg of the compound of Formula (I) once a day for two days. In some embodiments, the loading dose is about 10 mg to about 40 mg of the compound of Formula (I) once a day for two days. In some embodiments, the loading dose is about 10 mg to about 30 mg of the compound of Formula (I) once a day for two days. In some embodiments, the loading dose is about 10 mg to about 20 mg of the compound of Formula (I) once a day for two days. In some embodiments, the loading dose is about 2 mg of the compound of Formula (I) once a day for two days. In some embodiments, the loading dose is about 3 mg of the compound of Formula (I) once a day for two days. In some embodiments, the loading dose is about 4 mg of the compound of Formula (I) once a day for two days. In some embodiments, the loading dose is about 5 mg of the compound of Formula (I) once a day for two days. In some embodiments, the loading dose is about 10 mg of the compound of Formula (I) once a day for two days. In some embodiments, the loading dose is about 11 mg of the compound of Formula (I) once a day for two days. In some embodiments, the loading dose is about 12 mg of the compound of Formula (I) once a day for two days. In some embodiments, the loading dose is about 13 mg of the compound of Formula (I) once a day for two days. In some embodiments, the loading dose is about 14 mg of the compound of Formula (I) once a day for two days. In some embodiments, the loading dose is about 15 mg of the compound of Formula (I) once a day for two days. In some embodiments, the loading dose is about 16 mg of the compound of Formula (I) once a day for two days. In some embodiments, the loading dose is about 17 mg of the compound of Formula (I) once a day for two days. In some embodiments, the loading dose is about 18 mg of the compound of Formula (I) once a day for two days. In some embodiments, the loading dose is about 19 mg of the compound of Formula (I) once a day for two days. In some embodiments, the loading dose is about 20 mg of the compound of Formula (I) once a day for two days. In some embodiments, the loading dose is about 22 mg of the compound of Formula (I) once a day for two days. In some embodiments, the loading dose is about 24 mg of the compound of Formula (I) once a day for two days. In some embodiments, the loading dose is about 26 mg of the compound of Formula (I) once a day for two days. In some embodiments, the loading dose is about 28 mg of the compound of Formula (I) once a day for two days. In some embodiments, the loading dose is about 30 mg of the compound of Formula (I) once a day for two days. In some embodiments, the loading dose is about 32 mg of the compound of Formula (I) once a day for two days. In some embodiments, the loading dose is about 34 mg of the compound of Formula (I) once a day for two days. In some embodiments, the loading dose is about 36 mg of the compound of Formula (I) once a day for two days. In some embodiments, the loading dose is about 38 mg of the compound of Formula (I) once a day for two days. In some embodiments, the loading dose is about 40 mg of the compound of Formula (I) once a day for two days. In some embodiments, the loading dose is about 42 mg of the compound of Formula (I) once a day for two days. In some embodiments, the loading dose is about 44 mg of the compound of Formula (I) once a day for two days. In some embodiments, the loading dose is about 46 mg of the compound of Formula (I) once a day for two days. In some embodiments, the loading dose is about 48 mg of the compound of Formula (I) once a day for two days. In some embodiments, the loading dose is about 50 mg of the compound of Formula (I) once a day for two days.

In some embodiments, the loading dose is about 2 mg to about 100 mg of the compound of Formula (I) once a day for three days. In some embodiments, the loading dose is about 5 mg to about 90 mg of the compound of Formula (I) once a day for three days. In some embodiments, the loading dose is about 10 mg to about 80 mg of the compound of Formula (I) once a day for three days. In some embodiments, the loading dose is about 10 mg to about 70 mg of the compound of Formula (I) once a day for three days. In some embodiments, the loading dose is about 10 mg to about 60 mg of the compound of Formula (I) once a day for three days. In some embodiments, the loading dose is about 10 mg to about 50 mg of the compound of Formula (I) once a day for three days. In some embodiments, the loading dose is about 10 mg to about 40 mg of the compound of Formula (I) once a day for three days. In some embodiments, the loading dose is about 10 mg to about 30 mg of the compound of Formula (I) once a day for three days. In some embodiments, the loading dose is about 10 mg to about 20 mg of the compound of Formula (I) once a day for three days. In some embodiments, the loading dose is about 2 mg of the compound of Formula (I) once a day for three days. In some embodiments, the loading dose is about 3 mg of the compound of Formula (I) once a day for three days. In some embodiments, the loading dose is about 4 mg of the compound of Formula (I) once a day for three days. In some embodiments, the loading dose is about 5 mg of the compound of Formula (I) once a day for three days. In some embodiments, the loading dose is about 10 mg of the compound of Formula (I) once a day for three days. In some embodiments, the loading dose is about 11 mg of the compound of Formula (I) once a day for three days. In some embodiments, the loading dose is about 12 mg of the compound of Formula (I) once a day for three days. In some embodiments, the loading dose is about 13 mg of the compound of Formula (I) once a day for three days. In some embodiments, the loading dose is about 14 mg of the compound of Formula (I) once a day for three days. In some embodiments, the loading dose is about 15 mg of the compound of Formula (I) once a day for three days. In some embodiments, the loading dose is about 16 mg of the compound of Formula (I) once a day for three days. In some embodiments, the loading dose is about 17 mg of the compound of Formula (I) once a day for three days. In some embodiments, the loading dose is about 18 mg of the compound of Formula (I) once a day for three days. In some embodiments, the loading dose is about 19 mg of the compound of Formula (I) once a day for three days. In some embodiments, the loading dose is about 20 mg of the compound of Formula (I) once a day for three days. In some embodiments, the loading dose is about 22 mg of the compound of Formula (I) once a day for three days. In some embodiments, the loading dose is about 24 mg of the compound of Formula (I) once a day for three days. In some embodiments, the loading dose is about 26 mg of the compound of Formula (I) once a day for three days. In some embodiments, the loading dose is about 28 mg of the compound of Formula (I) once a day for three days. In some embodiments, the loading dose is about 30 mg of the compound of Formula (I) once a day for three days. In some embodiments, the loading dose is about 32 mg of the compound of Formula (I) once a day for three days. In some embodiments, the loading dose is about 34 mg of the compound of Formula (I) once a day for three days. In some embodiments, the loading dose is about 36 mg of the compound of Formula (I) once a day for three days. In some embodiments, the loading dose is about 38 mg of the compound of Formula (I) once a day for three days. In some embodiments, the loading dose is about 40 mg of the compound of Formula (I) once a day for three days. In some embodiments, the loading dose is about 42 mg of the compound of Formula (I) once a day for three days. In some embodiments, the loading dose is about 44 mg of the compound of Formula (I) once a day for three days. In some embodiments, the loading dose is about 46 mg of the compound of Formula (I) once a day for three days. In some embodiments, the loading dose is about 48 mg of the compound of Formula (I) once a day for three days. In some embodiments, the loading dose is about 50 mg of the compound of Formula (I) once a day for three days.

In some embodiments, the loading dose is about 2 mg to about 100 mg of the compound of Formula (I) once a day for four days. In some embodiments, the loading dose is about 5 mg to about 90 mg of the compound of Formula (I) once a day for four days. In some embodiments, the loading dose is about 10 mg to about 80 mg of the compound of Formula (I) once a day for four days. In some embodiments, the loading dose is about 10 mg to about 70 mg of the compound of Formula (I) once a day for four days. In some embodiments, the loading dose is about 10 mg to about 60 mg of the compound of Formula (I) once a day for four days. In some embodiments, the loading dose is about 10 mg to about 50 mg of the compound of Formula (I) once a day for four days.

In some embodiments, the loading dose is about 10 mg to about 40 mg of the compound of Formula (I) once a day for four days. In some embodiments, the loading dose is about 10 mg to about 30 mg of the compound of Formula (I) once a day for four days. In some embodiments, the loading dose is about 10 mg to about 20 mg of the compound of Formula (I) once a day for four days. In some embodiments, the loading dose is about 2 mg of the compound of Formula (I) once a day for four days. In some embodiments, the loading dose is about 3 mg of the compound of Formula (I) once a day for four days. In some embodiments, the loading dose is about 4 mg of the compound of Formula (I) once a day for four days. In some embodiments, the loading dose is about 5 mg of the compound of Formula (I) once a day for four days. In some embodiments, the loading dose is about 10 mg of the compound of Formula (I) once a day for four days. In some embodiments, the loading dose is about 11 mg of the compound of Formula (I) once a day for four days. In some embodiments, the loading dose is about 12 mg of the compound of Formula (I) once a day for four days. In some embodiments, the loading dose is about 13 mg of the compound of Formula (I) once a day for four days. In some embodiments, the loading dose is about 14 mg of the compound of Formula (I) once a day for four days. In some embodiments, the loading dose is about 15 mg of the compound of Formula (I) once a day for four days. In some embodiments, the loading dose is about 16 mg of the compound of Formula (I) once a day for four days. In some embodiments, the loading dose is about 17 mg of the compound of Formula (I) once a day for four days. In some embodiments, the loading dose is about 18 mg of the compound of Formula (I) once a day for four days. In some embodiments, the loading dose is about 19 mg of the compound of Formula (I) once a day for four days. In some embodiments, the loading dose is about 20 mg of the compound of Formula (I) once a day for four days. In some embodiments, the loading dose is about 22 mg of the compound of Formula (I) once a day for four days. In some embodiments, the loading dose is about 24 mg of the compound of Formula (I) once a day for four days. In some embodiments, the loading dose is about 26 mg of the compound of Formula (I) once a day for four days. In some embodiments, the loading dose is about 28 mg of the compound of Formula (I) once a day for four days. In some embodiments, the loading dose is about 30 mg of the compound of Formula (I) once a day for four days. In some embodiments, the loading dose is about 32 mg of the compound of Formula (I) once a day for four days. In some embodiments, the loading dose is about 34 mg of the compound of Formula (I) once a day for four days. In some embodiments, the loading dose is about 36 mg of the compound of Formula (I) once a day for four days. In some embodiments, the loading dose is about 38 mg of the compound of Formula (I) once a day for four days. In some embodiments, the loading dose is about 40 mg of the compound of Formula (I) once a day for four days. In some embodiments, the loading dose is about 42 mg of the compound of Formula (I) once a day for four days. In some embodiments, the loading dose is about 44 mg of the compound of Formula (I) once a day for four days. In some embodiments, the loading dose is about 46 mg of the compound of Formula (I) once a day for four days. In some embodiments, the loading dose is about 48 mg of the compound of Formula (I) once a day for four days. In some embodiments, the loading dose is about 50 mg of the compound of Formula (I) once a day for four days.

In some embodiments, the loading dose is about 2 mg to about 100 mg of the compound of Formula (I) once a day for five days. In some embodiments, the loading dose is about 5 mg to about 90 mg of the compound of Formula (I) once a day for five days. In some embodiments, the loading dose is about 10 mg to about 80 mg of the compound of Formula (I) once a day for five days. In some embodiments, the loading dose is about 10 mg to about 70 mg of the compound of Formula (I) once a day for five days. In some embodiments, the loading dose is about 10 mg to about 60 mg of the compound of Formula (I) once a day for five days. In some embodiments, the loading dose is about 10 mg to about 50 mg of the compound of Formula (I) once a day for five days. In some embodiments, the loading dose is about 10 mg to about 40 mg of the compound of Formula (I) once a day for five days. In some embodiments, the loading dose is about 10 mg to about 30 mg of the compound of Formula (I) once a day for five days. In some embodiments, the loading dose is about 10 mg to about 20 mg of the compound of Formula (I) once a day for five days. In some embodiments, the loading dose is about 2 mg of the compound of Formula (I) once a day for five days. In some embodiments, the loading dose is about 3 mg of the compound of Formula (I) once a day for five days. In some embodiments, the loading dose is about 4 mg of the compound of Formula (I) once a day for five days. In some embodiments, the loading dose is about 5 mg of the compound of Formula (I) once a day for five days. In some embodiments, the loading dose is about 10 mg of the compound of Formula (I) once a day for five days. In some embodiments, the loading dose is about 11 mg of the compound of Formula (I) once a day for five days. In some embodiments, the loading dose is about 12 mg of the compound of Formula (I) once a day for five days. In some embodiments, the loading dose is about 13 mg of the compound of Formula (I) once a day for five days. In some embodiments, the loading dose is about 14 mg of the compound of Formula (I) once a day for five days. In some embodiments, the loading dose is about 15 mg of the compound of Formula (I) once a day for five days. In some embodiments, the loading dose is about 16 mg of the compound of Formula (I) once a day for five days. In some embodiments, the loading dose is about 17 mg of the compound of Formula (I) once a day for five days. In some embodiments, the loading dose is about 18 mg of the compound of Formula (I) once a day for five days. In some embodiments, the loading dose is about 19 mg of the compound of Formula (I) once a day for five days. In some embodiments, the loading dose is about 20 mg of the compound of Formula (I) once a day for five days. In some embodiments, the loading dose is about 22 mg of the compound of Formula (I) once a day for five days. In some embodiments, the loading dose is about 24 mg of the compound of Formula (I) once a day for five days. In some embodiments, the loading dose is about 26 mg of the compound of Formula (I) once a day for five days. In some embodiments, the loading dose is about 28 mg of the compound of Formula (I) once a day for five days. In some embodiments, the loading dose is about 30 mg of the compound of Formula (I) once a day for five days. In some embodiments, the loading dose is about 32 mg of the compound of Formula (I) once a day for five days. In some embodiments, the loading dose is about 34 mg of the compound of Formula (I) once a day for five days. In some embodiments, the loading dose is about 36 mg of the compound of Formula (I) once a day for five days. In some embodiments, the loading dose is about 38 mg of the compound of Formula (I) once a day for five days. In some embodiments, the loading dose is about 40 mg of the compound of Formula (I) once a day for five days. In some embodiments, the loading dose is about 42 mg of the compound of Formula (I) once a day for five days. In some embodiments, the loading dose is about 44 mg of the compound of Formula (I) once a day for five days. In some embodiments, the loading dose is about 46 mg of the compound of Formula (I) once a day for five days. In some embodiments, the loading dose is about 48 mg of the compound of Formula (I) once a day for five days. In some embodiments, the loading dose is about 50 mg of the compound of Formula (I) once a day for five days.

In some embodiments, the loading dose is about 2 mg to about 100 mg of the compound of Formula (I) once a day for six days. In some embodiments, the loading dose is about 5 mg to about 90 mg of the compound of Formula (I) once a day for six days. In some embodiments, the loading dose is about 10 mg to about 80 mg of the compound of Formula (I) once a day for six days. In some embodiments, the loading dose is about 10 mg to about 70 mg of the compound of Formula (I) once a day for six days. In some embodiments, the loading dose is about 10 mg to about 60 mg of the compound of Formula (I) once a day for six days. In some embodiments, the loading dose is about 10 mg to about 50 mg of the compound of Formula (I) once a day for six days. In some embodiments, the loading dose is about 10 mg to about 40 mg of the compound of Formula (I) once a day for six days. In some embodiments, the loading dose is about 10 mg to about 30 mg of the compound of Formula (I) once a day for six days. In some embodiments, the loading dose is about 10 mg to about 20 mg of the compound of Formula (I) once a day for six days. In some embodiments, the loading dose is about 2 mg of the compound of Formula (I) once a day for six days. In some embodiments, the loading dose is about 3 mg of the compound of Formula (I) once a day for six days. In some embodiments, the loading dose is about 4 mg of the compound of Formula (I) once a day for six days. In some embodiments, the loading dose is about 5 mg of the compound of Formula (I) once a day for six days. In some embodiments, the loading dose is about 10 mg of the compound of Formula (I) once a day for six days. In some embodiments, the loading dose is about 11 mg of the compound of Formula (I) once a day for six days. In some embodiments, the loading dose is about 12 mg of the compound of Formula (I) once a day for six days. In some embodiments, the loading dose is about 13 mg of the compound of Formula (I) once a day for six days. In some embodiments, the loading dose is about 14 mg of the compound of Formula (I) once a day for six days. In some embodiments, the loading dose is about 15 mg of the compound of Formula (I) once a day for six days. In some embodiments, the loading dose is about 16 mg of the compound of Formula (I) once a day for six days. In some embodiments, the loading dose is about 17 mg of the compound of Formula (I) once a day for six days. In some embodiments, the loading dose is about 18 mg of the compound of Formula (I) once a day for six days. In some embodiments, the loading dose is about 19 mg of the compound of Formula (I) once a day for six days. In some embodiments, the loading dose is about 20 mg of the compound of Formula (I) once a day for six days. In some embodiments, the loading dose is about 22 mg of the compound of Formula (I) once a day for six days. In some embodiments, the loading dose is about 24 mg of the compound of Formula (I) once a day for six days. In some embodiments, the loading dose is about 26 mg of the compound of Formula (I) once a day for six days. In some embodiments, the loading dose is about 28 mg of the compound of Formula (I) once a day for six days. In some embodiments, the loading dose is about 30 mg of the compound of Formula (I) once a day for six days. In some embodiments, the loading dose is about 32 mg of the compound of Formula (I) once a day for six days. In some embodiments, the loading dose is about 34 mg of the compound of Formula (I) once a day for six days. In some embodiments, the loading dose is about 36 mg of the compound of Formula (I) once a day for six days. In some embodiments, the loading dose is about 38 mg of the compound of Formula (I) once a day for six days. In some embodiments, the loading dose is about 40 mg of the compound of Formula (I) once a day for six days. In some embodiments, the loading dose is about 42 mg of the compound of Formula (I) once a day for six days. In some embodiments, the loading dose is about 44 mg of the compound of Formula (I) once a day for six days. In some embodiments, the loading dose is about 46 mg of the compound of Formula (I) once a day for six days. In some embodiments, the loading dose is about 48 mg of the compound of Formula (I) once a day for six days. In some embodiments, the loading dose is about 50 mg of the compound of Formula (I) once a day for six days.

In some embodiments, the loading dose is about 2 mg to about 100 mg of the compound of Formula (I) once a day for seven days. In some embodiments, the loading dose is about 5 mg to about 90 mg of the compound of Formula (I) once a day for seven days. In some embodiments, the loading dose is about 10 mg to about 80 mg of the compound of Formula (I) once a day for seven days. In some embodiments, the loading dose is about 10 mg to about 70 mg of the compound of Formula (I) once a day for seven days. In some embodiments, the loading dose is about 10 mg to about 60 mg of the compound of Formula (I) once a day for seven days. In some embodiments, the loading dose is about 10 mg to about 50 mg of the compound of Formula (I) once a day for seven days. In some embodiments, the loading dose is about 10 mg to about 40 mg of the compound of Formula (I) once a day for seven days. In some embodiments, the loading dose is about 10 mg to about 30 mg of the compound of Formula (I) once a day for seven days. In some embodiments, the loading dose is about 10 mg to about 20 mg of the compound of Formula (I) once a day for seven days. In some embodiments, the loading dose is about 2 mg of the compound of Formula (I) once a day for seven days. In some embodiments, the loading dose is about 3 mg of the compound of Formula (I) once a day for seven days. In some embodiments, the loading dose is about 4 mg of the compound of Formula (I) once a day for seven days. In some embodiments, the loading dose is about 5 mg of the compound of Formula (I) once a day for seven days. In some embodiments, the loading dose is about 10 mg of the compound of Formula (I) once a day for seven days. In some embodiments, the loading dose is about 11 mg of the compound of Formula (I) once a day for seven days. In some embodiments, the loading dose is about 12 mg of the compound of Formula (I) once a day for seven days. In some embodiments, the loading dose is about 13 mg of the compound of Formula (I) once a day for seven days. In some embodiments, the loading dose is about 14 mg of the compound of Formula (I) once a day for seven days. In some embodiments, the loading dose is about 15 mg of the compound of Formula (I) once a day for seven days. In some embodiments, the loading dose is about 16 mg of the compound of Formula (I) once a day for seven days. In some embodiments, the loading dose is about 17 mg of the compound of Formula (I) once a day for seven days. In some embodiments, the loading dose is about 18 mg of the compound of Formula (I) once a day for seven days. In some embodiments, the loading dose is about 19 mg of the compound of Formula (I) once a day for seven days. In some embodiments, the loading dose is about 20 mg of the compound of Formula (I) once a day for seven days. In some embodiments, the loading dose is about 22 mg of the compound of Formula (I) once a day for seven days. In some embodiments, the loading dose is about 24 mg of the compound of Formula (I) once a day for seven days. In some embodiments, the loading dose is about 26 mg of the compound of Formula (I) once a day for seven days. In some embodiments, the loading dose is about 28 mg of the compound of Formula (I) once a day for seven days. In some embodiments, the loading dose is about 30 mg of the compound of Formula (I) once a day for seven days. In some embodiments, the loading dose is about 32 mg of the compound of Formula (I) once a day for seven days. In some embodiments, the loading dose is about 34 mg of the compound of Formula (I) once a day for seven days. In some embodiments, the loading dose is about 36 mg of the compound of Formula (I) once a day for seven days. In some embodiments, the loading dose is about 38 mg of the compound of Formula (I) once a day for seven days. In some embodiments, the loading dose is about 40 mg of the compound of Formula (I) once a day for seven days. In some embodiments, the loading dose is about 42 mg of the compound of Formula (I) once a day for seven days. In some embodiments, the loading dose is about 44 mg of the compound of Formula (I) once a day for seven days. In some embodiments, the loading dose is about 46 mg of the compound of Formula (I) once a day for seven days. In some embodiments, the loading dose is about 48 mg of the compound of Formula (I) once a day for seven days. In some embodiments, the loading dose is about 50 mg of the compound of Formula (I) once a day for seven days.

In some embodiments, the loading dose is about 2 mg to about 100 mg of the compound of Formula (I) once a day for eight days. In some embodiments, the loading dose is about 5 mg to about 90 mg of the compound of Formula (I) once a day for eight days. In some embodiments, the loading dose is about 10 mg to about 80 mg of the compound of Formula (I) once a day for eight days. In some embodiments, the loading dose is about 10 mg to about 70 mg of the compound of Formula (I) once a day for eight days. In some embodiments, the loading dose is about 10 mg to about 60 mg of the compound of Formula (I) once a day for eight days. In some embodiments, the loading dose is about 10 mg to about 50 mg of the compound of Formula (I) once a day for eight days. In some embodiments, the loading dose is about 10 mg to about 40 mg of the compound of Formula (I) once a day for eight days. In some embodiments, the loading dose is about 10 mg to about 30 mg of the compound of Formula (I) once a day for eight days. In some embodiments, the loading dose is about 10 mg to about 20 mg of the compound of Formula (I) once a day for eight days. In some embodiments, the loading dose is about 2 mg of the compound of Formula (I) once a day for eight days. In some embodiments, the loading dose is about 3 mg of the compound of Formula (I) once a day for eight days. In some embodiments, the loading dose is about 4 mg of the compound of Formula (I) once a day for eight days. In some embodiments, the loading dose is about 5 mg of the compound of Formula (I) once a day for eight days. In some embodiments, the loading dose is about 10 mg of the compound of Formula (I) once a day for eight days. In some embodiments, the loading dose is about 11 mg of the compound of Formula (I) once a day for eight days. In some embodiments, the loading dose is about 12 mg of the compound of Formula (I) once a day for eight days. In some embodiments, the loading dose is about 13 mg of the compound of Formula (I) once a day for eight days. In some embodiments, the loading dose is about 14 mg of the compound of Formula (I) once a day for eight days. In some embodiments, the loading dose is about 15 mg of the compound of Formula (I) once a day for eight days. In some embodiments, the loading dose is about 16 mg of the compound of Formula (I) once a day for eight days. In some embodiments, the loading dose is about 17 mg of the compound of Formula (I) once a day for eight days. In some embodiments, the loading dose is about 18 mg of the compound of Formula (I) once a day for eight days. In some embodiments, the loading dose is about 19 mg of the compound of Formula (I) once a day for eight days. In some embodiments, the loading dose is about 20 mg of the compound of Formula (I) once a day for eight days. In some embodiments, the loading dose is about 22 mg of the compound of Formula (I) once a day for eight days. In some embodiments, the loading dose is about 24 mg of the compound of Formula (I) once a day for eight days. In some embodiments, the loading dose is about 26 mg of the compound of Formula (I) once a day for eight days. In some embodiments, the loading dose is about 28 mg of the compound of Formula (I) once a day for eight days. In some embodiments, the loading dose is about 30 mg of the compound of Formula (I) once a day for eight days. In some embodiments, the loading dose is about 32 mg of the compound of Formula (I) once a day for eight days. In some embodiments, the loading dose is about 34 mg of the compound of Formula (I) once a day for eight days. In some embodiments, the loading dose is about 36 mg of the compound of Formula (I) once a day for eight days. In some embodiments, the loading dose is about 38 mg of the compound of Formula (I) once a day for eight days. In some embodiments, the loading dose is about 40 mg of the compound of Formula (I) once a day for eight days. In some embodiments, the loading dose is about 42 mg of the compound of Formula (I) once a day for eight days. In some embodiments, the loading dose is about 44 mg of the compound of Formula (I) once a day for eight days. In some embodiments, the loading dose is about 46 mg of the compound of Formula (I) once a day for eight days. In some embodiments, the loading dose is about 48 mg of the compound of Formula (I) once a day for eight days. In some embodiments, the loading dose is about 50 mg of the compound of Formula (I) once a day for eight days.

In some embodiments, the loading dose is about 2 mg to about 100 mg of the compound of Formula (I) once a day for nine days. In some embodiments, the loading dose is about 5 mg to about 90 mg of the compound of Formula (I) once a day for nine days. In some embodiments, the loading dose is about 10 mg to about 80 mg of the compound of Formula (I) once a day for nine days. In some embodiments, the loading dose is about 10 mg to about 70 mg of the compound of Formula (I) once a day for nine days. In some embodiments, the loading dose is about 10 mg to about 60 mg of the compound of Formula (I) once a day for nine days. In some embodiments, the loading dose is about 10 mg to about 50 mg of the compound of Formula (I) once a day for nine days. In some embodiments, the loading dose is about 10 mg to about 40 mg of the compound of Formula (I) once a day for nine days. In some embodiments, the loading dose is about 10 mg to about 30 mg of the compound of Formula (I) once a day for nine days. In some embodiments, the loading dose is about 10 mg to about 20 mg of the compound of Formula (I) once a day for nine days. In some embodiments, the loading dose is about 2 mg of the compound of Formula (I) once a day for nine days. In some embodiments, the loading dose is about 3 mg of the compound of Formula (I) once a day for nine days. In some embodiments, the loading dose is about 4 mg of the compound of Formula (I) once a day for nine days. In some embodiments, the loading dose is about 5 mg of the compound of Formula (I) once a day for nine days. In some embodiments, the loading dose is about 10 mg of the compound of Formula (I) once a day for nine days. In some embodiments, the loading dose is about 11 mg of the compound of Formula (I) once a day for nine days. In some embodiments, the loading dose is about 12 mg of the compound of Formula (I) once a day for nine days. In some embodiments, the loading dose is about 13 mg of the compound of Formula (I) once a day for nine days. In some embodiments, the loading dose is about 14 mg of the compound of Formula (I) once a day for nine days. In some embodiments, the loading dose is about 15 mg of the compound of Formula (I) once a day for nine days. In some embodiments, the loading dose is about 16 mg of the compound of Formula (I) once a day for nine days. In some embodiments, the loading dose is about 17 mg of the compound of Formula (I) once a day for nine days. In some embodiments, the loading dose is about 18 mg of the compound of Formula (I) once a day for nine days. In some embodiments, the loading dose is about 19 mg of the compound of Formula (I) once a day for nine days. In some embodiments, the loading dose is about 20 mg of the compound of Formula (I) once a day for nine days. In some embodiments, the loading dose is about 22 mg of the compound of Formula (I) once a day for nine days. In some embodiments, the loading dose is about 24 mg of the compound of Formula (I) once a day for nine days. In some embodiments, the loading dose is about 26 mg of the compound of Formula (I) once a day for nine days. In some embodiments, the loading dose is about 28 mg of the compound of Formula (I) once a day for nine days. In some embodiments, the loading dose is about 30 mg of the compound of Formula (I) once a day for nine days. In some embodiments, the loading dose is about 32 mg of the compound of Formula (I) once a day for nine days. In some embodiments, the loading dose is about 34 mg of the compound of Formula (I) once a day for nine days. In some embodiments, the loading dose is about 36 mg of the compound of Formula (I) once a day for nine days. In some embodiments, the loading dose is about 38 mg of the compound of Formula (I) once a day for nine days. In some embodiments, the loading dose is about 40 mg of the compound of Formula (I) once a day for nine days. In some embodiments, the loading dose is about 42 mg of the compound of Formula (I) once a day for nine days. In some embodiments, the loading dose is about 44 mg of the compound of Formula (I) once a day for nine days. In some embodiments, the loading dose is about 46 mg of the compound of Formula (I) once a day for nine days. In some embodiments, the loading dose is about 48 mg of the compound of Formula (I) once a day for nine days. In some embodiments, the loading dose is about 50 mg of the compound of Formula (I) once a day for nine days.

In some embodiments, the loading dose is about 2 mg to about 100 mg of the compound of Formula (I) once a day for ten days. In some embodiments, the loading dose is about 5 mg to about 90 mg of the compound of Formula (I) once a day for ten days. In some embodiments, the loading dose is about 10 mg to about 80 mg of the compound of Formula (I) once a day for ten days. In some embodiments, the loading dose is about 10 mg to about 70 mg of the compound of Formula (I) once a day for ten days. In some embodiments, the loading dose is about 10 mg to about 60 mg of the compound of Formula (I) once a day for ten days. In some embodiments, the loading dose is about 10 mg to about 50 mg of the compound of Formula (I) once a day for ten days. In some embodiments, the loading dose is about 10 mg to about 40 mg of the compound of Formula (I) once a day for ten days. In some embodiments, the loading dose is about 10 mg to about 30 mg of the compound of Formula (I) once a day for ten days. In some embodiments, the loading dose is about 10 mg to about 20 mg of the compound of Formula (I) once a day for ten days. In some embodiments, the loading dose is about 2 mg of the compound of Formula (I) once a day for ten days. In some embodiments, the loading dose is about 3 mg of the compound of Formula (I) once a day for ten days. In some embodiments, the loading dose is about 4 mg of the compound of Formula (I) once a day for ten days. In some embodiments, the loading dose is about 5 mg of the compound of Formula (I) once a day for ten days. In some embodiments, the loading dose is about 10 mg of the compound of Formula (I) once a day for ten days. In some embodiments, the loading dose is about 11 mg of the compound of Formula (I) once a day for ten days. In some embodiments, the loading dose is about 12 mg of the compound of Formula (I) once a day for ten days. In some embodiments, the loading dose is about 13 mg of the compound of Formula (I) once a day for ten days. In some embodiments, the loading dose is about 14 mg of the compound of Formula (I) once a day for ten days. In some embodiments, the loading dose is about 15 mg of the compound of Formula (I) once a day for ten days. In some embodiments, the loading dose is about 16 mg of the compound of Formula (I) once a day for ten days. In some embodiments, the loading dose is about 17 mg of the compound of Formula (I) once a day for ten days. In some embodiments, the loading dose is about 18 mg of the compound of Formula (I) once a day for ten days. In some embodiments, the loading dose is about 19 mg of the compound of Formula (I) once a day for ten days. In some embodiments, the loading dose is about 20 mg of the compound of Formula (I) once a day for ten days. In some embodiments, the loading dose is about 22 mg of the compound of Formula (I) once a day for ten days. In some embodiments, the loading dose is about 24 mg of the compound of Formula (I) once a day for ten days. In some embodiments, the loading dose is about 26 mg of the compound of Formula (I) once a day for ten days. In some embodiments, the loading dose is about 28 mg of the compound of Formula (I) once a day for ten days. In some embodiments, the loading dose is about 30 mg of the compound of Formula (I) once a day for ten days. In some embodiments, the loading dose is about 32 mg of the compound of Formula (I) once a day for ten days. In some embodiments, the loading dose is about 34 mg of the compound of Formula (I) once a day for ten days. In some embodiments, the loading dose is about 36 mg of the compound of Formula (I) once a day for ten days. In some embodiments, the loading dose is about 38 mg of the compound of Formula (I) once a day for ten days. In some embodiments, the loading dose is about 40 mg of the compound of Formula (I) once a day for ten days. In some embodiments, the loading dose is about 42 mg of the compound of Formula (I) once a day for ten days. In some embodiments, the loading dose is about 44 mg of the compound of Formula (I) once a day for ten days. In some embodiments, the loading dose is about 46 mg of the compound of Formula (I) once a day for ten days. In some embodiments, the loading dose is about 48 mg of the compound of Formula (I) once a day for ten days. In some embodiments, the loading dose is about 50 mg of the compound of Formula (I) once a day for ten days.

In some embodiments, the loading dose is about 2 mg to about 100 mg of the compound of Formula (I) once a week. In some embodiments, the loading dose is about 5 mg to about 90 mg of the compound of Formula (I) once a week. In some embodiments, the loading dose is about 10 mg to about 80 mg of the compound of Formula (I) once a week. In some embodiments, the loading dose is about 10 mg to about 70 mg of the compound of Formula (I) once a week. In some embodiments, the loading dose is about 10 mg to about 60 mg of the compound of Formula (I) once a week. In some embodiments, the loading dose is about 10 mg to about 50 mg of the compound of Formula (I) once a week. In some embodiments, the loading dose is about 10 mg to about 40 mg of the compound of Formula (I) once a week. In some embodiments, the loading dose is about 10 mg to about 30 mg of the compound of Formula (I) once a week. In some embodiments, the loading dose is about 10 mg to about 20 mg of the compound of Formula (I) once a week. In some embodiments, the loading dose is about 2 mg of the compound of Formula (I) once a week. In some embodiments, the loading dose is about 3 mg of the compound of Formula (I) once a week. In some embodiments, the loading dose is about 4 mg of the compound of Formula (I) once a week. In some embodiments, the loading dose is about 5 mg of the compound of Formula (I) once a week. In some embodiments, the loading dose is about 10 mg of the compound of Formula (I) once a week. In some embodiments, the loading dose is about 11 mg of the compound of Formula (I) once a week. In some embodiments, the loading dose is about 12 mg of the compound of Formula (I) once a week. In some embodiments, the loading dose is about 13 mg of the compound of Formula (I) once a week. In some embodiments, the loading dose is about 14 mg of the compound of Formula (I) once a week. In some embodiments, the loading dose is about 15 mg of the compound of Formula (I) once a week. In some embodiments, the loading dose is about 16 mg of the compound of Formula (I) once a week. In some embodiments, the loading dose is about 17 mg of the compound of Formula (I) once a week. In some embodiments, the loading dose is about 18 mg of the compound of Formula (I) once a week. In some embodiments, the loading dose is about 19 mg of the compound of Formula (I) once a week. In some embodiments, the loading dose is about 20 mg of the compound of Formula (I) once a week. In some embodiments, the loading dose is about 22 mg of the compound of Formula (I) once a week. In some embodiments, the loading dose is about 24 mg of the compound of Formula (I) once a week. In some embodiments, the loading dose is about 26 mg of the compound of Formula (I) once a week. In some embodiments, the loading dose is about 28 mg of the compound of Formula (I) once a week. In some embodiments, the loading dose is about 30 mg of the compound of Formula (I) once a week. In some embodiments, the loading dose is about 32 mg of the compound of Formula (I) once a week. In some embodiments, the loading dose is about 34 mg of the compound of Formula (I) once a week. In some embodiments, the loading dose is about 36 mg of the compound of Formula (I) once a week. In some embodiments, the loading dose is about 38 mg of the compound of Formula (I) once a week. In some embodiments, the loading dose is about 40 mg of the compound of Formula (I) once a week. In some embodiments, the loading dose is about 42 mg of the compound of Formula (I) once a week. In some embodiments, the loading dose is about 44 mg of the compound of Formula (I) once a week. In some embodiments, the loading dose is about 46 mg of the compound of Formula (I) once a week. In some embodiments, the loading dose is about 48 mg of the compound of Formula (I) once a week. In some embodiments, the loading dose is about 50 mg of the compound of Formula (I) once a week.

In some embodiments, the loading dose is about 2 mg to about 100 mg of the compound of Formula (I) twice a week. In some embodiments, the loading dose is about 5 mg to about 90 mg of the compound of Formula (I) twice a week. In some embodiments, the loading dose is about 10 mg to about 80 mg of the compound of Formula (I) twice a week. In some embodiments, the loading dose is about 10 mg to about 70 mg of the compound of Formula (I) twice a week. In some embodiments, the loading dose is about 10 mg to about 60 mg of the compound of Formula (I) twice a week. In some embodiments, the loading dose is about 10 mg to about 50 mg of the compound of Formula (I) twice a week. In some embodiments, the loading dose is about 10 mg to about 40 mg of the compound of Formula (I) twice a week. In some embodiments, the loading dose is about 10 mg to about 30 mg of the compound of Formula (I) twice a week. In some embodiments, the loading dose is about 10 mg to about 20 mg of the compound of Formula (I) twice a week. In some embodiments, the loading dose is about 2 mg of the compound of Formula (I) twice a week. In some embodiments, the loading dose is about 3 mg of the compound of Formula (I) twice a week. In some embodiments, the loading dose is about 4 mg of the compound of Formula (I) twice a week. In some embodiments, the loading dose is about 5 mg of the compound of Formula (I) twice a week. In some embodiments, the loading dose is about 10 mg of the compound of Formula (I) twice a week. In some embodiments, the loading dose is about 11 mg of the compound of Formula (I) twice a week. In some embodiments, the loading dose is about 12 mg of the compound of Formula (I) twice a week. In some embodiments, the loading dose is about 13 mg of the compound of Formula (I) twice a week. In some embodiments, the loading dose is about 14 mg of the compound of Formula (I) twice a week. In some embodiments, the loading dose is about 15 mg of the compound of Formula (I) twice a week. In some embodiments, the loading dose is about 16 mg of the compound of Formula (I) twice a week. In some embodiments, the loading dose is about 17 mg of the compound of Formula (I) twice a week. In some embodiments, the loading dose is about 18 mg of the compound of Formula (I) twice a week. In some embodiments, the loading dose is about 19 mg of the compound of Formula (I) twice a week. In some embodiments, the loading dose is about 20 mg of the compound of Formula (I) twice a week. In some embodiments, the loading dose is about 22 mg of the compound of Formula (I) twice a week. In some embodiments, the loading dose is about 24 mg of the compound of Formula (I) twice a week. In some embodiments, the loading dose is about 26 mg of the compound of Formula (I) twice a week. In some embodiments, the loading dose is about 28 mg of the compound of Formula (I) twice a week. In some embodiments, the loading dose is about 30 mg of the compound of Formula (I) twice a week. In some embodiments, the loading dose is about 32 mg of the compound of Formula (I) twice a week. In some embodiments, the loading dose is about 34 mg of the compound of Formula (I) twice a week. In some embodiments, the loading dose is about 36 mg of the compound of Formula (I) twice a week. In some embodiments, the loading dose is about 38 mg of the compound of Formula (I) twice a week. In some embodiments, the loading dose is about 40 mg of the compound of Formula (I) twice a week. In some embodiments, the loading dose is about 42 mg of the compound of Formula (I) twice a week. In some embodiments, the loading dose is about 44 mg of the compound of Formula (I) twice a week. In some embodiments, the loading dose is about 46 mg of the compound of Formula (I) twice a week. In some embodiments, the loading dose is about 48 mg of the compound of Formula (I) twice a week. In some embodiments, the loading dose is about 50 mg of the compound of Formula (I) twice a week.

In some embodiments, the loading dose is about 2 mg to about 100 mg of the compound of Formula (I) three times a week. In some embodiments, the loading dose is about 5 mg to about 90 mg of the compound of Formula (I) three times a week. In some embodiments, the loading dose is about 10 mg to about 80 mg of the compound of Formula (I) three times a week. In some embodiments, the loading dose is about 10 mg to about 70 mg of the compound of Formula (I) three times a week. In some embodiments, the loading dose is about 10 mg to about 60 mg of the compound of Formula (I) three times a week. In some embodiments, the loading dose is about 10 mg to about 50 mg of the compound of Formula (I) three times a week. In some embodiments, the loading dose is about 10 mg to about 40 mg of the compound of Formula (I) three times a week. In some embodiments, the loading dose is about 10 mg to about 30 mg of the compound of Formula (I) three times a week. In some embodiments, the loading dose is about 10 mg to about 20 mg of the compound of Formula (I) three times a week. In some embodiments, the loading dose is about 2 mg of the compound of Formula (I) three times a week. In some embodiments, the loading dose is about 3 mg of the compound of Formula (I) three times a week. In some embodiments, the loading dose is about 4 mg of the compound of Formula (I) three times a week. In some embodiments, the loading dose is about 5 mg of the compound of Formula (I) three times a week. In some embodiments, the loading dose is about 10 mg of the compound of Formula (I) three times a week. In some embodiments, the loading dose is about 11 mg of the compound of Formula (I) three times a week. In some embodiments, the loading dose is about 12 mg of the compound of Formula (I) three times a week. In some embodiments, the loading dose is about 13 mg of the compound of Formula (I) three times a week. In some embodiments, the loading dose is about 14 mg of the compound of Formula (I) three times a week. In some embodiments, the loading dose is about 15 mg of the compound of Formula (I) three times a week. In some embodiments, the loading dose is about 16 mg of the compound of Formula (I) three times a week. In some embodiments, the loading dose is about 17 mg of the compound of Formula (I) three times a week. In some embodiments, the loading dose is about 18 mg of the compound of Formula (I) three times a week. In some embodiments, the loading dose is about 19 mg of the compound of Formula (I) three times a week. In some embodiments, the loading dose is about 20 mg of the compound of Formula (I) three times a week. In some embodiments, the loading dose is about 22 mg of the compound of Formula (I) three times a week. In some embodiments, the loading dose is about 24 mg of the compound of Formula (I) three times a week. In some embodiments, the loading dose is about 26 mg of the compound of Formula (I) three times a week. In some embodiments, the loading dose is about 28 mg of the compound of Formula (I) three times a week. In some embodiments, the loading dose is about 30 mg of the compound of Formula (I) three times a week. In some embodiments, the loading dose is about 32 mg of the compound of Formula (I) three times a week. In some embodiments, the loading dose is about 34 mg of the compound of Formula (I) three times a week. In some embodiments, the loading dose is about 36 mg of the compound of Formula (I) three times a week. In some embodiments, the loading dose is about 38 mg of the compound of Formula (I) three times a week. In some embodiments, the loading dose is about 40 mg of the compound of Formula (I) three times a week. In some embodiments, the loading dose is about 42 mg of the compound of Formula (I) three times a week. In some embodiments, the loading dose is about 44 mg of the compound of Formula (I) three times a week. In some embodiments, the loading dose is about 46 mg of the compound of Formula (I) three times a week. In some embodiments, the loading dose is about 48 mg of the compound of Formula (I) three times a week. In some embodiments, the loading dose is about 50 mg of the compound of Formula (I) three times a week.

In some embodiments, administering a maintenance dose may include administering about 2 mg to about 150 mg of the compound of Formula (I) daily to a patient in need thereof. In some embodiments, the maintenance dose is about 2 mg to about 100 mg of the compound of Formula (I) daily. In some embodiments, the maintenance dose is about 5 mg to about 90 mg of the compound of Formula (I) daily. In some embodiments, the maintenance dose is about 10 mg to about 80 mg of the compound of Formula (I) daily. In some embodiments, the maintenance dose is about 10 mg to about 70 mg of the compound of Formula (I) daily. In some embodiments, the maintenance dose is about 10 mg to about 60 mg of the compound of Formula (I) daily. In some embodiments, the maintenance dose is about 10 mg to about 50 mg of the compound of Formula (I) daily. In some embodiments, the maintenance dose is about 10 mg to about 40 mg of the compound of Formula (I) daily. In some embodiments, the maintenance dose is about 10 mg to about 30 mg of the compound of Formula (I) daily. In some embodiments, the maintenance dose is about 10 mg to about 20 mg of the compound of Formula (I) daily. In some embodiments, the maintenance dose is about 2 mg of the compound of Formula (I) daily. In some embodiments, the maintenance dose is about 3 mg of the compound of Formula (I) daily. In some embodiments, the maintenance dose is about 4 mg of the compound of Formula (I) daily. In some embodiments, the maintenance dose is about 5 mg of the compound of Formula (I) daily. In some embodiments, the maintenance dose is about 6 mg of the compound of Formula (I) daily. In some embodiments, the maintenance dose is about 7 mg of the compound of Formula (I) daily. In some embodiments, the maintenance dose is about 8 mg of the compound of Formula (I) daily. In some embodiments, the maintenance dose is about 9 mg of the compound of Formula (I) daily. In some embodiments, the maintenance dose is about 10 mg of the compound of Formula (I) daily. In some embodiments, the maintenance dose is about 11 mg of the compound of Formula (I) daily. In some embodiments, the maintenance dose is about 12 mg of the compound of Formula (I) daily. In some embodiments, the maintenance dose is about 13 mg of the compound of Formula (I) daily. In some embodiments, the maintenance dose is about 14 mg of the compound of Formula (I) daily.

In some embodiments, the maintenance dose is about 15 mg of the compound of Formula (I) daily. In some embodiments, the maintenance dose is about 16 mg of the compound of Formula (I) daily. In some embodiments, the maintenance dose is about 17 mg of the compound of Formula (I) daily. In some embodiments, the maintenance dose is about 18 mg of the compound of Formula (I) daily. In some embodiments, the maintenance dose is about 19 mg of the compound of Formula (I) daily. In some embodiments, the maintenance dose is about 20 mg of the compound of Formula (I) daily. In some embodiments, the maintenance dose is about 22 mg of the compound of Formula (I) daily. In some embodiments, the maintenance dose is about 24 mg of the compound of Formula (I) daily. In some embodiments, the maintenance dose is about 26 mg of the compound of Formula (I) daily. In some embodiments, the maintenance dose is about 28 mg of the compound of Formula (I) daily. In some embodiments, the maintenance dose is about 30 mg of the compound of Formula (I) daily. In some embodiments, the maintenance dose is about 32 mg of the compound of Formula (I) daily. In some embodiments, the maintenance dose is about 34 mg of the compound of Formula (I) daily. In some embodiments, the maintenance dose is about 36 mg of the compound of Formula (I) daily. In some embodiments, the maintenance dose is about 38 mg of the compound of Formula (I) daily. In some embodiments, the maintenance dose is about 40 mg of the compound of Formula (I) daily. In some embodiments, the maintenance dose is about 42 mg of the compound of Formula (I) daily. In some embodiments, the maintenance dose is about 44 mg of the compound of Formula (I) daily. In some embodiments, the maintenance dose is about 46 mg of the compound of Formula (I) daily. In some embodiments, the maintenance dose is about 48 mg of the compound of Formula (I) daily. In some embodiments, the maintenance dose is about 50 mg of the compound of Formula (I) daily.

In some embodiments, administering a maintenance dose may include administering about 2 mg to about 150 mg of the compound of Formula (I) once a week to a patient in need thereof. In some embodiments, the maintenance dose is about 2 mg to about 100 mg of the compound of Formula (I) once a week. In some embodiments, the maintenance dose is about 5 mg to about 90 mg of the compound of Formula (I) once a week. In some embodiments, the maintenance dose is about 10 mg to about 80 mg of the compound of Formula (I) once a week. In some embodiments, the maintenance dose is about 10 mg to about 70 mg of the compound of Formula (I) once a week. In some embodiments, the maintenance dose is about 10 mg to about 60 mg of the compound of Formula (I) once a week. In some embodiments, the maintenance dose is about 10 mg to about 50 mg of the compound of Formula (I) once a week. In some embodiments, the maintenance dose is about 10 mg to about 40 mg of the compound of Formula (I) once a week. In some embodiments, the maintenance dose is about 10 mg to about 30 mg of the compound of Formula (I) once a week. In some embodiments, the maintenance dose is about 10 mg to about 20 mg of the compound of Formula (I) once a week. In some embodiments, the maintenance dose is about 2 mg of the compound of Formula (I) once a week. In some embodiments, the maintenance dose is about 3 mg of the compound of Formula (I) once a week. In some embodiments, the maintenance dose is about 4 mg of the compound of Formula (I) once a week. In some embodiments, the maintenance dose is about 5 mg of the compound of Formula (I) once a week. In some embodiments, the maintenance dose is about 6 mg of the compound of Formula (I) once a week. In some embodiments, the maintenance dose is about 7 mg of the compound of Formula (I) once a week. In some embodiments, the maintenance dose is about 8 mg of the compound of Formula (I) once a week. In some embodiments, the maintenance dose is about 9 mg of the compound of Formula (I) once a week. In some embodiments, the maintenance dose is about 10 mg of the compound of Formula (I) once a week. In some embodiments, the maintenance dose is about 11 mg of the compound of Formula (I) once a week. In some embodiments, the maintenance dose is about 12 mg of the compound of Formula (I) once a week. In some embodiments, the maintenance dose is about 13 mg of the compound of Formula (I) once a week. In some embodiments, the maintenance dose is about 14 mg of the compound of Formula (I) once a week. In some embodiments, the maintenance dose is about 15 mg of the compound of Formula (I) once a week. In some embodiments, the maintenance dose is about 16 mg of the compound of Formula (I) once a week. In some embodiments, the maintenance dose is about 17 mg of the compound of Formula (I) once a week. In some embodiments, the maintenance dose is about 18 mg of the compound of Formula (I) once a week. In some embodiments, the maintenance dose is about 19 mg of the compound of Formula (I) once a week. In some embodiments, the maintenance dose is about 20 mg of the compound of Formula (I) once a week. In some embodiments, the maintenance dose is about 22 mg of the compound of Formula (I) once a week. In some embodiments, the maintenance dose is about 24 mg of the compound of Formula (I) once a week. In some embodiments, the maintenance dose is about 26 mg of the compound of Formula (I) once a week. In some embodiments, the maintenance dose is about 28 mg of the compound of Formula (I) once a week. In some embodiments, the maintenance dose is about 30 mg of the compound of Formula (I) once a week. In some embodiments, the maintenance dose is about 32 mg of the compound of Formula (I) once a week. In some embodiments, the maintenance dose is about 34 mg of the compound of Formula (I) once a week. In some embodiments, the maintenance dose is about 36 mg of the compound of Formula (I) once a week. In some embodiments, the maintenance dose is about 38 mg of the compound of Formula (I) once a week. In some embodiments, the maintenance dose is about 40 mg of the compound of Formula (I) once a week. In some embodiments, the maintenance dose is about 42 mg of the compound of Formula (I) once a week. In some embodiments, the maintenance dose is about 44 mg of the compound of Formula (I) once a week. In some embodiments, the maintenance dose is about 46 mg of the compound of Formula (I) once a week. In some embodiments, the maintenance dose is about 48 mg of the compound of Formula (I) once a week. In some embodiments, the maintenance dose is about 50 mg of the compound of Formula (I) once a week.

In some embodiments, administering a maintenance dose may include administering about 2 mg to about 150 mg of the compound of Formula (I) twice a week to a patient in need thereof. In some embodiments, the maintenance dose is about 2 mg to about 100 mg of the compound of Formula (I) twice a week. In some embodiments, the maintenance dose is about 5 mg to about 90 mg of the compound of Formula (I) twice a week. In some embodiments, the maintenance dose is about 10 mg to about 80 mg of the compound of Formula (I) twice a week. In some embodiments, the maintenance dose is about 10 mg to about 70 mg of the compound of Formula (I) twice a week. In some embodiments, the maintenance dose is about 10 mg to about 60 mg of the compound of Formula (I) twice a week. In some embodiments, the maintenance dose is about 10 mg to about 50 mg of the compound of Formula (I) twice a week. In some embodiments, the maintenance dose is about 10 mg to about 40 mg of the compound of Formula (I) twice a week. In some embodiments, the maintenance dose is about 10 mg to about 30 mg of the compound of Formula (I) twice a week. In some embodiments, the maintenance dose is about 10 mg to about 20 mg of the compound of Formula (I) twice a week. In some embodiments, the maintenance dose is about 2 mg of the compound of Formula (I) twice a week. In some embodiments, the maintenance dose is about 3 mg of the compound of Formula (I) twice a week. In some embodiments, the maintenance dose is about 4 mg of the compound of Formula (I) twice a week. In some embodiments, the maintenance dose is about 5 mg of the compound of Formula (I) twice a week. In some embodiments, the maintenance dose is about 6 mg of the compound of Formula (I) twice a week. In some embodiments, the maintenance dose is about 7 mg of the compound of Formula (I) twice a week. In some embodiments, the maintenance dose is about 8 mg of the compound of Formula (I) twice a week. In some embodiments, the maintenance dose is about 9 mg of the compound of Formula (I) twice a week. In some embodiments, the maintenance dose is about 10 mg of the compound of Formula (I) twice a week. In some embodiments, the maintenance dose is about 11 mg of the compound of Formula (I) twice a week. In some embodiments, the maintenance dose is about 12 mg of the compound of Formula (I) twice a week. In some embodiments, the maintenance dose is about 13 mg of the compound of Formula (I) twice a week. In some embodiments, the maintenance dose is about 14 mg of the compound of Formula (I) twice a week. In some embodiments, the maintenance dose is about 15 mg of the compound of Formula (I) twice a week. In some embodiments, the maintenance dose is about 16 mg of the compound of Formula (I) twice a week. In some embodiments, the maintenance dose is about 17 mg of the compound of Formula (I) twice a week. In some embodiments, the maintenance dose is about 18 mg of the compound of Formula (I) twice a week. In some embodiments, the maintenance dose is about 19 mg of the compound of Formula (I) twice a week. In some embodiments, the maintenance dose is about 20 mg of the compound of Formula (I) twice a week. In some embodiments, the maintenance dose is about 22 mg of the compound of Formula (I) twice a week. In some embodiments, the maintenance dose is about 24 mg of the compound of Formula (I) twice a week. In some embodiments, the maintenance dose is about 26 mg of the compound of Formula (I) twice a week. In some embodiments, the maintenance dose is about 28 mg of the compound of Formula (I) twice a week. In some embodiments, the maintenance dose is about 30 mg of the compound of Formula (I) twice a week. In some embodiments, the maintenance dose is about 32 mg of the compound of Formula (I) twice a week. In some embodiments, the maintenance dose is about 34 mg of the compound of Formula (I) twice a week. In some embodiments, the maintenance dose is about 36 mg of the compound of Formula (I) twice a week. In some embodiments, the maintenance dose is about 38 mg of the compound of Formula (I) twice a week. In some embodiments, the maintenance dose is about 40 mg of the compound of Formula (I) twice a week. In some embodiments, the maintenance dose is about 42 mg of the compound of Formula (I) twice a week. In some embodiments, the maintenance dose is about 44 mg of the compound of Formula (I) twice a week. In some embodiments, the maintenance dose is about 46 mg of the compound of Formula (I) twice a week. In some embodiments, the maintenance dose is about 48 mg of the compound of Formula (I) twice a week. In some embodiments, the maintenance dose is about 50 mg of the compound of Formula (I) twice a week.

In some embodiments, administering a maintenance dose may include administering about 2 mg to about 150 mg of the compound of Formula (I) three times a week to a patient in need thereof. In some embodiments, the maintenance dose is about 2 mg to about 100 mg of the compound of Formula (I) three times a week. In some embodiments, the maintenance dose is about 5 mg to about 90 mg of the compound of Formula (I) three times a week. In some embodiments, the maintenance dose is about 10 mg to about 80 mg of the compound of Formula (I) three times a week. In some embodiments, the maintenance dose is about 10 mg to about 70 mg of the compound of Formula (I) three times a week. In some embodiments, the maintenance dose is about 10 mg to about 60 mg of the compound of Formula (I) three times a week. In some embodiments, the maintenance dose is about 10 mg to about 50 mg of the compound of Formula (I) three times a week. In some embodiments, the maintenance dose is about 10 mg to about 40 mg of the compound of Formula (I) three times a week. In some embodiments, the maintenance dose is about 10 mg to about 30 mg of the compound of Formula (I) three times a week. In some embodiments, the maintenance dose is about 10 mg to about 20 mg of the compound of Formula (I) three times a week. In some embodiments, the maintenance dose is about 2 mg of the compound of Formula (I) three times a week. In some embodiments, the maintenance dose is about 3 mg of the compound of Formula (I) three times a week. In some embodiments, the maintenance dose is about 4 mg of the compound of Formula (I) three times a week. In some embodiments, the maintenance dose is about 5 mg of the compound of Formula (I) three times a week. In some embodiments, the maintenance dose is about 6 mg of the compound of Formula (I) three times a week. In some embodiments, the maintenance dose is about 7 mg of the compound of Formula (I) three times a week. In some embodiments, the maintenance dose is about 8 mg of the compound of Formula (I) three times a week. In some embodiments, the maintenance dose is about 9 mg of the compound of Formula (I) three times a week. In some embodiments, the maintenance dose is about 10 mg of the compound of Formula (I) three times a week. In some embodiments, the maintenance dose is about 11 mg of the compound of Formula (I) three times a week. In some embodiments, the maintenance dose is about 12 mg of the compound of Formula (I) three times a week. In some embodiments, the maintenance dose is about 13 mg of the compound of Formula (I) three times a week. In some embodiments, the maintenance dose is about 14 mg of the compound of Formula (I) three times a week. In some embodiments, the maintenance dose is about 15 mg of the compound of Formula (I) three times a week. In some embodiments, the maintenance dose is about 16 mg of the compound of Formula (I) three times a week. In some embodiments, the maintenance dose is about 17 mg of the compound of Formula (I) three times a week. In some embodiments, the maintenance dose is about 18 mg of the compound of Formula (I) three times a week. In some embodiments, the maintenance dose is about 19 mg of the compound of Formula (I) three times a week. In some embodiments, the maintenance dose is about 20 mg of the compound of Formula (I) three times a week. In some embodiments, the maintenance dose is about 22 mg of the compound of Formula (I) three times a week. In some embodiments, the maintenance dose is about 24 mg of the compound of Formula (I) three times a week. In some embodiments, the maintenance dose is about 26 mg of the compound of Formula (I) three times a week. In some embodiments, the maintenance dose is about 28 mg of the compound of Formula (I) three times a week. In some embodiments, the maintenance dose is about 30 mg of the compound of Formula (I) three times a week. In some embodiments, the maintenance dose is about 32 mg of the compound of Formula (I) three times a week. In some embodiments, the maintenance dose is about 34 mg of the compound of Formula (I) three times a week. In some embodiments, the maintenance dose is about 36 mg of the compound of Formula (I) three times a week. In some embodiments, the maintenance dose is about 38 mg of the compound of Formula (I) three times a week. In some embodiments, the maintenance dose is about 40 mg of the compound of Formula (I) three times a week. In some embodiments, the maintenance dose is about 42 mg of the compound of Formula (I) three times a week. In some embodiments, the maintenance dose is about 44 mg of the compound of Formula (I) three times a week. In some embodiments, the maintenance dose is about 46 mg of the compound of Formula (I) three times a week. In some embodiments, the maintenance dose is about 48 mg of the compound of Formula (I) three times a week. In some embodiments, the maintenance dose is about 50 mg of the compound of Formula (I) three times a week.

In some embodiments, such a disclosed method may include, administering a loading dose of 30 mg daily for 5 days, followed by a maintenance dose of 30 mg twice a week, of the compound of Formula (I) to a patient in need thereof.

In some embodiments, such a disclosed method may include, administering a loading dose of 30 mg daily for 3 days, followed by a maintenance dose of 10 mg daily, of the compound of Formula (I) to a patient in need thereof.

In some embodiments, such a disclosed method may include, administering a loading dose of 20 mg daily for 3 days, followed by a maintenance dose of 6 mg daily, of the compound of Formula (I) to a patient in need thereof.

In some embodiments, such a disclosed method may include, administering a dose of 30 mg twice a week, of the compound of Formula (I) to a patient in need thereof.

In some embodiments, administration of the compound of Formula (I), may be effected by any appropriate route including, but not limited to, oral routes, intravenous routes, intramuscular routes, subcutaneous, intratumoral injection, intraarticular injection, and direct absorption through mucous membrane tissues. In some embodiments, administration of the compound of Formula (I), may be effected by oral routes. In some embodiments, administration of the compound of Formula (I), may be effected by intraarticular injection. In some embodiments, administration of the compound of Formula (I), may be effected by intratumoral injection.

In some embodiments, the most suitable administration in any given case will depend on the nature and severity of the condition being treated. The dosages can be conveniently presented in unit dosage form and prepared by any of the methods well-known in the pharmaceutical arts.

In some embodiments, provided herein is a method of treating graft versus host disease (GVHD), comprising administering to the patient a therapeutically effective amount of the formulation comprising the compound represented by Formula (I). In some embodiments, the graft versus host disease (GVHD) is chronic graft versus host disease (cGVHD). In some embodiments, the graft versus host disease (GVHD) is acute graft versus host disease (aGVHD).

In some embodiments, provided herein is a method of treating a neurodegenerative disease, comprising administering to the patient a therapeutically effective amount of the formulation comprising the compound represented by Formula (I). In some embodiments, the neurodegenerative disease is selected from the group consisting of Parkinson's disease (PD), Alzheimer's Disease (AD), frontotemporal dementia (FTD), amyotrophic lateral sclerosis (ALS), mild cognitive impairment, and Huntington's Disease (HD).

In some embodiments, provided herein is a method of treating a cancer selected from the group consisting of solid tumors, acute myeloid leukemia (AML), relapsed/refractory acute myeloid leukemia (AML), relapsed acute myeloid leukemia (AML), refractory acute myeloid leukemia (AML), myelodysplastic syndrome, acute lymphocytic leukemia (ALL), chronic lymphocytic leukemia (CLL), pancreatic ductal adenocarcinoma (PDAC), ovarian cancer, non-small cell lung cancer (NSCLC), prostate cancer, osteosarcoma, breast cancer, colon cancer, and glioblastoma, comprising administering to the patient a therapeutically effective amount of the formulation comprising the compound represented by Formula (I). In some embodiments, the solid tumor is selected from the group consisting of ovarian cancer, pancreatic cancer, prostate cancer, lung cancer, breast cancer, kidney cancer, liver cancer, cervical cancer, bone metastatic cancer, papillary thyroid cancer, non-small cell lung cancer, colon cancer, and gastrointestinal stromal tumor.

In some embodiments, provided herein is a method of treating tumors known to have expression of colony-stimulating factor 1 receptor (CSF-1R) or its ligands, colony stimulating factor-1 (CSF-1), or interleukin (IL)-34 (IL-34), comprising administering to the patient a therapeutically effective amount of the formulation comprising the compound represented by Formula (I).

In some embodiments, provided herein is a method of treating a disease or condition selected from the group consisting of metabolic diseases, rheumatoid arthritis, osteoarthritis, multiple sclerosis, autoimmune nephritis, lupus, Crohn's disease, asthma, chronic obstructive pulmonary diseases, osteoporosis, hypereosinophilic syndromes, mastocytosis, and histiocytosis, comprising administering to the patient a therapeutically effective amount of the formulation comprising the compound represented by Formula (I).

The disclosure contemplates administration of the formulation comprising the compound represented by Formula (I), to a patient in need thereof prior (neo-adjuvant) or after (adjuvant) surgery (e.g., surgical treatment of TGCT). In some embodiments, the formulation comprising the compound represented by Formula (I), is administered as an adjuvant. In some embodiments, the formulation comprising the compound represented by Formula (I), is administered as a neo-adjuvant. In some embodiments, the formulation comprising the compound represented by Formula (I), is administered as a neo-adjuvant and an adjuvant. In some embodiments, the formulation comprising the compound represented by Formula (I), is administered to a patient in need thereof as a neo-adjuvant for a period of 1 month to 6 months, followed by administration of the formulation comprising the compound represented by Formula (I), as an adjuvant for a period from 1 day to 100 years. In some embodiments, administration of the formulation comprising the compound represented by Formula (I), is administered to a patient in need thereof as a neo-adjuvant for a period of 1 month to 6 months, followed by administration of the formulation comprising the compound represented by Formula (I), as an adjuvant for a period from 1 day to 5 years. In some embodiments, administration of the formulation comprising the compound represented by Formula (I), is administered to a patient in need thereof as a neo-adjuvant for a period of 3 months to 6 months, followed by administration of the formulation comprising the compound represented by Formula (I), as an adjuvant for a period from 1 day to 5 years. In some embodiments, no administration of the formulation comprising the compound represented by Formula (I), occurs prior to surgery. In some embodiments, the formulation comprising the compound represented by Formula (I), is administered as an adjuvant for a period from 1 day to 100 years. In some embodiments, the formulation comprising the compound represented by Formula (I), is administered as an adjuvant for a period from 1 day to 5 years.

In some embodiments, provided herein is a method of treating a disease or condition of any other aspects of the disclosure, further comprising administering to the patient a therapeutically effective amount of one or more additional therapeutic agents. In some embodiments, the disease or condition is graft versus host disease (GVHD). In some embodiments, the disease or condition is chronic graft versus host disease (cGVHD). In some embodiments, the disease or condition is acute graft versus host disease (aGVHD). In some embodiments, the one or more additional therapeutic agents is selected from the group consisting of methoxsalen, abatacept, everolimus, alemtuzumab, antithymocyte globulin, autologous serum eye drops, azathioprine, belumosudil, bortezomib, mycophenolate mofetil, cyclophosphamide, cyclosporine, extracorporeal photopheresis, etanercept, imatinib mesylate, ibrutinib, interleukin-2, infliximab, ruxolitinib, methotrexate, muromab-CD3, pentostatin, denileukin diftitox, prednisone, prednisolone, tacrolimus, psoralen with ultraviolet A light, sirolimus, rituximab, methylprednisolone, budesonide, thalidomide, halofuginone, and hydroxychloroquine. In some embodiments, the one or more additional therapeutic agents is belumosudil.

In some embodiments, provided herein is a method of treating a disease or condition of any other aspects of the disclosure, further comprising administering to the patient a therapeutically effective amount of one or more additional therapeutic agents. In some embodiments, the disease or condition is a cancer selected from the group consisting of solid tumors, acute myeloid leukemia (AML), relapsed/refractory acute myeloid leukemia (AML), relapsed acute myeloid leukemia (AML), refractory acute myeloid leukemia (AML), myelodysplastic syndrome, acute lymphocytic leukemia (ALL), chronic lymphocytic leukemia (CLL), pancreatic ductal adenocarcinoma (PDAC), ovarian cancer, non-small cell lung cancer (NSCLC), prostate cancer, osteosarcoma, breast cancer, colon cancer, and glioblastoma. In some embodiments, the one or more additional therapeutic agents is an immunomodulatory therapeutic. In some embodiments, the one or more additional therapeutic agents is a chemotherapeutic agent. In some embodiments, the one or more additional therapeutic agents is an immunomodulatory therapeutic and a chemotherapeutic agent.

The compound represented by Formula (I), can be administered in combination with one or more additional therapeutic agents to treat a disorder described herein, such as cancer. For example, provided in the present disclosure is a formulation comprising the compound represented by Formula (I), one or more additional therapeutic agents, and a pharmaceutically acceptable excipient. In some embodiments, the compound represented by Formula (I), and one additional therapeutic agent is administered. In some embodiments, the compound represented by Formula (I), and two additional therapeutic agents are administered. In some embodiments, the compound represented by Formula (I), and three additional therapeutic agents are administered. Combination therapy can be achieved by administering two or more therapeutic agents, each of which is formulated and administered separately. For example, the compound represented by Formula (I), and an additional therapeutic agent can be formulated and administered separately. Combination therapy can also be achieved by administering two or more therapeutic agents in a single formulation, for example a formulation comprising the compound represented by Formula (I), as one therapeutic agent and one or more additional therapeutic agents. For example, the compound represented by Formula (I), and an additional therapeutic agent can be administered in a single formulation. Other combinations are also encompassed by combination therapy. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or weeks of each other. In some cases, even longer intervals are possible. While in many cases it is desirable that the two or more agents used in a combination therapy be present in within the patient's body at the same time, this need not be so.

"Combination therapy" (or "co-therapy") includes the administration of the compound represented by Formula (I), and at least a second agent, e.g., an anti-PD1 or anti-PD-L1 therapeutic, an anti-PD1 or anti-PD-L1 antibody, an immune-check point inhibitor, or a chemotherapeutic agent, as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination can be carried out over a defined time period (usually minutes, hours, days or weeks depending upon the combination selected) or until disease progression. Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single tablet or capsule having a fixed ratio of each therapeutic agent or in multiple, single unit doses for each of the therapeutic agents. Sequential or substantially simultaneous administration of each therapeutic agent can be effected by any appropriate route including, but not limited to, oral routes, intravenous routes, intramuscular routes, subcutaneous, intratumoral injection, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally, or all therapeutic agents may be administered by intravenous injection. The sequence in which the therapeutic agents are administered is not narrowly critical.

Combination therapy also can embrace the administration of the therapeutic agents as described above in further combination with other biologically active ingredients and non-drug therapies, including, but not limited to, radiation therapy. Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The components of the combination may be administered to a patient simultaneously, sequentially or in combination. It will be appreciated that when using a formulation or method the components may be in the same pharmaceutically acceptable excipient and therefore administered simultaneously. They may be in separate pharmaceutical excipients such as conventional oral dosage forms which are taken simultaneously. The term "combination" further refers to the case where the compounds are provided in separate dosage forms and are administered sequentially.

Although not wishing to be bound by theory, it is thought that the administration of the compound represented by Formula (I), in accordance with the methods described herein, in combination with one or more anti-PD1 or anti-PD-L1 therapeutics may provide additive effects in significantly inhibiting primary tumor growth and modulating the immune system into an antitumoral state, which can be beneficial in the treatment of disorders associated with the proliferation, survival, or biological action of macrophages, including the treatment of TGCT. Examples of anti-PD1 or anti-PD-L1 therapeutics that may be administered in combination with CSF-1R inhibitors described herein include, but are not limited to, nivolumab, pidilizumab, cemiplimab, tislelizumab, AMP-224, AMP-514, and pembrolizumab.

The compound represented by Formula (I), can be used in combination with other immunomodulatory agents including but not limited to anti-PD-L1 therapeutics including atezolizumab, durvalumab, BMS-936559, and avelumab, anti-TIM3 therapeutics including TSR-022 and MBG453, anti-LAG3 therapeutics including relatlimab, LAG525, and TSR-033, CD40 agonist therapeutics including SGN-40, CP-870,893 and RO7009789, anti-CD47 therapeutics including Hu5F9-G4, anti-CD20 therapeutics, anti-CD38 therapeutics, or other immunomodulatory therapeutics including thalidomide, lenalidomide, pomalidomide, mezigdomide, prednisone, and dexamethasone.

Sarcomas comprise a diverse group of malignancies including more than fifty subtypes of bone and soft tissue origin. In some embodiments, a method of treating a cancer comprises administering to a patient with locally advanced and metastatic high-grade sarcoma the compound represented by Formula (I), in combination with avelumab. In some embodiments, a method of treating a cancer comprises administering to a patient with locally advanced sarcoma the compound represented by Formula (I), in combination with avelumab. In some embodiments, a method of treating a cancer comprises administering to a patient with metastatic high-grade sarcoma the compound represented by Formula (I), in combination with avelumab. In some embodiments, a method of treating a cancer comprises administering to a patient with advanced metastatic sarcoma the compound represented by Formula (I), in combination with avelumab. In some embodiments, a method of treating a cancer comprises administering to a patient with undifferentiated pleomorphic sarcoma (UPS) the compound represented by Formula (I), in combination with avelumab. In some embodiments, a method of treating a cancer comprises administering to a patient with myxofibrosarcoma (MFS) the compound represented by Formula (I), in combination with avelumab. In some embodiments, a method of treating a cancer comprises administering to a patient with leiomyosarcoma (LMS) the compound represented by Formula (I), in combination with avelumab. In some embodiments, a method of treating a cancer comprises administering to a patient with dedifferentiated liposarcoma (DDLPS) the compound represented by Formula (I), in combination with avelumab.

The compound represented by Formula (I), can also be used in combination with one or more chemotherapeutic agents including but not limited to anti-tubulin agents (e.g., paclitaxel, paclitaxel protein-bound particles for injectable suspension, eribulin, abraxane, docetaxel, ixabepilone, vincristine or vinorelbine), LHRH antagonists including but not limited to leuprolide, goserelin, triptorelin, or histrelin, anti-androgen agents including but not limited to abiraterone, flutamide, bicalutamide, nilutamide, cyproterone acetate, enzalutamide, and apalutamide, anti-estrogen agents including but not limited to tamoxifen, fulvestrant, anastrozole, letrozole, and exemestane, DNA-alkylating agents (including cisplatin, carboplatin, oxaliplatin, cyclophosphamide, ifosfamide, and temozolomide), DNA intercalating agents (including doxorubicin, pegylated liposomal doxorubicin, daunorubicin, idarubicin, and epirubicin), 5-fluorouracil, capecitabine, cytarabine, decitabine, 5-aza cytidine, gemcitabine methotrexate, bortezomib, and carfilzomib.

The compound represented by Formula (I), can also be used in combination with targeted therapeutics including kinase inhibitors erlotinib, gefitinib, lapatanib, everolimus, temsirolimus, abemaciclib, LEE011, palbociclib, ribociclib, crizotinib, cabozantinib, sunitinib, pazopanib, sorafenib, regorafenib, axitinib, dasatinib, imatinib, nilotinib, vemurafenib, dabrafenib, trametinib, cobimetinib, binimetinib, idelalisib, quizartinib, avapritinib, BLU-667, BLU-263, Loxo 292, larotrectinib, and quizartinib, anti-estrogen agents including but not limited to tamoxifen, fulvestrant, anastrozole, letrozole, and exemestane, anti-androgen agents including but not limited to abiraterone acetate, enzalutamide, nilutamide, bicalutamide, flutamide, cyproterone acetate, steroid agents including but not limited to prednisone and dexamethasone, PARP inhibitors including but not limited to neraparib, olaparib, and rucaparib, topoisomerase I inhibitors including but not limited to irinotecan, camptothecin, and topotecan, topoisomerase II inhibitors including but not limited to etoposide, etoposide phosphate, and mitoxantrone, Histone Deacetylase (HDAC) inhibitors including but not limited to vorinostat, romidepsin, panobinostat, valproic acid, and belinostat, DNA methylation inhibitors including but not limited to DZNeP and 5-aza-2'-deoxycytidine, proteasome inhibitors including but not limited to bortezomib and carfilzomib, thalidomide, lenalidomide, pomalidomide, biological agents including but not limited to trastuzumab, ado-trastuzumab, pertuzumab, cetuximab, panitumumab, ipilimumab, tremelimumab, vaccines including but not limited to sipuleucel-T, and radiotherapy.

The represented by Formula (I), can also be used in combination with anti-angiogenic agents including AMG386, bevacizumab and aflibercept, and antibody-drug-conjugates (ADCs) including but not limited to gemtuzumab ozogamicin, brentuximab vedotin, trastuzumab emtansine, inotuzumab ozogamicin, polatuzumab vedotin, enfortumab vedotin, trastuzumab deruxtecan, sacituzumab govitecan, belantamab mafodotin, moxetumomab pasudotox, loncastuximab tesirine, wherein the payload contained in the ADCs includes but is not limited to a derivative of camptothecin, a pyrrolobenzodiazepine dimer (PBD), an indolinobenzodiazepine dimer (IGN), DM1, DM4, MMAE, or MMAF.

In some embodiments, the additional therapeutic agent is selected from a luteinizing hormone-releasing hormone (LHRH) analog, including goserelin and leuprolide.

In some embodiments, the additional therapeutic agent is selected from the group consisting of everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, pemetrexed, erlotinib, dasatanib, nilotinib, decatanib, panitumumab, amrubicin, oregovomab, Lep-etu, nolatrexed, AZD2171, batabulin, of atumtunab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, $IPdR_1$ KRX-0402, lucanthone, LY 317615, neuradiab, vitespan, RTA 744, SDX 102, talampanel, atrasentan, XR 311, romidepsin, ADS-100380, sunitinib, 5-fluorouracil, vorinostat, etoposide, gemcitabine, doxorubicin, irinotecan, liposomal doxorubicin, 5'-deoxy-5-fluorouridine, vincristine, temozolomide, ZK-304709, seliciclib, PD0325901, AZD-6244, capecitabine, L-Glutamic acid, N-[4-[2-(2-amino-4,7-dihydro-4-oxo-1H-pyrrolo[2,3-d]pyrimidin-5-yl)-ethyl] benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258), 3-[5-(methylsulfonylpiperadinemethyl)-indolylj-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutanide, nilutamide, megestrol acetate, CP-724714, TAK-165, HKI-272, erlotinib, lapatanib, canertinib, ABX-EGF antibody, erbitux, EKB-569, PKI-166, GW-572016, Ionafarnib, BMS-214662, tipifarnib, amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, *Bacillus* Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, gleevac, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, irinotecan, topotecan, doxorubicin, docetaxel, vinorelbine, bevacizumab (monoclonal antibody) and erbitux, cremophor-free paclitaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa, ipilumumab, vemurafenib, and mixtures thereof.

In some embodiments of any other aspects of the disclosure, the therapeutically effective amount of the formulation comprising the compound represented by Formula (I), is administered orally.

In some embodiments, provided herein is a method of treating a tenosynovial giant cell tumor, comprising orally administering to the patient a therapeutically effective amount of the formulation comprising the compound represented by Formula (I). In some embodiments, the tenosynovial giant cell tumor is a diffuse-type tenosynovial giant cell tumor. In some embodiments, the tenosynovial giant cell tumor is a localized tenosynovial giant cell tumor.

In some embodiments, provided herein is a method of treating graft versus host disease (GVHD), comprising orally administering to the patient a therapeutically effective amount of the formulation comprising the compound represented by Formula (I). In some embodiments, the graft versus host disease (GVHD) is chronic graft versus host disease (cGVHD). In some embodiments, the graft versus host disease (GVHD) is acute graft versus host disease (aGVHD).

In some embodiments, provided herein is a method of treating a neurodegenerative disease, comprising orally administering to the patient a therapeutically effective amount of the formulation comprising the compound represented by Formula (I). In some embodiments, the neurodegenerative disease is selected from the group consisting of Parkinson's disease (PD), Alzheimer's Disease (AD), frontotemporal dementia (FTD), amyotrophic lateral sclerosis (ALS), mild cognitive impairment, and Huntington's Disease (HD).

In some embodiments, provided herein is a method of treating a cancer selected from the group consisting of solid tumors, acute myeloid leukemia (AML), relapsed/refractory acute myeloid leukemia (AML), relapsed acute myeloid leukemia (AML), refractory acute myeloid leukemia (AML), myelodysplastic syndrome, acute lymphocytic leukemia (ALL), chronic lymphocytic leukemia (CLL), pancreatic ductal adenocarcinoma (PDAC), ovarian cancer, non-small cell lung cancer (NSCLC), prostate cancer, osteosarcoma, breast cancer, colon cancer, and glioblastoma, comprising orally administering to the patient a therapeutically effective amount of the formulation comprising the compound represented by Formula (I). In some embodiments, the solid tumor is selected from the group consisting of ovarian cancer, pancreatic cancer, prostate cancer, lung cancer, breast cancer, kidney cancer, liver cancer, cervical cancer, bone metastatic cancer, papillary thyroid cancer, non-small cell lung cancer, colon cancer, and gastrointestinal stromal tumor.

In some embodiments, provided herein is a method of treating tumors known to have expression of colony-stimulating factor 1 receptor (CSF-1R) or its ligands, colony stimulating factor-1 (CSF-1), or interleukin (IL)-34 (IL-34), comprising orally administering to the patient a therapeutically effective amount of the formulation comprising the compound represented by Formula (I).

In some embodiments, provided herein is a method of treating a disease or condition selected from the group consisting of metabolic diseases, rheumatoid arthritis, osteoarthritis, multiple sclerosis, autoimmune nephritis, lupus, Crohn's disease, asthma, chronic obstructive pulmonary diseases, osteoporosis, hypereosinophilic syndromes, mastocytosis, and histiocytosis, comprising orally administering to the patient a therapeutically effective amount of the formulation comprising the compound represented by Formula (I).

In some embodiments, provided herein is a method of treating a disease or condition of any other aspects of the disclosure, further comprising administering to the patient a therapeutically effective amount of one or more additional therapeutic agents. In some embodiments, the disease or condition is graft versus host disease (GVHD). In some embodiments, the disease or condition is chronic graft versus host disease (cGVHD). In some embodiments, the disease or condition is acute graft versus host disease (aGVHD). In some embodiments, the one or more additional therapeutic agents is selected from the group consisting of methoxsalen, abatacept, everolimus, alemtuzumab, antithymocyte globulin, autologous serum eye drops, azathioprine, belumosudil, bortezomib, mycophenolate mofetil, cyclophosphamide, cyclosporine, extracorporeal photopheresis, etanercept, imatinib mesylate, ibrutinib, interleukin-2, infliximab, ruxolitinib, methotrexate, muromab-CD3, pentostatin, denileukin diftitox, prednisone, prednisolone, tacrolimus, psoralen with ultraviolet A light, sirolimus, rituximab, methylprednisolone, budesonide, thalidomide, halofuginone, and hydroxychloroquine. In some embodiments, the one or more additional therapeutic agents is belumosudil.

In some embodiments, provided herein is a method of treating a disease or condition of any other aspects of the disclosure, further comprising administering to the patient a therapeutically effective amount of one or more additional therapeutic agents. In some embodiments, the disease or condition is a cancer selected from the group consisting of solid tumors, acute myeloid leukemia (AML), relapsed/refractory acute myeloid leukemia (AML), relapsed acute myeloid leukemia (AML), refractory acute myeloid leukemia (AML), myelodysplastic syndrome, acute lymphocytic leukemia (ALL), chronic lymphocytic leukemia (CLL), pancreatic ductal adenocarcinoma (PDAC), ovarian cancer, non-small cell lung cancer (NSCLC), prostate cancer, osteosarcoma, breast cancer, colon cancer, and glioblastoma. In some embodiments, the one or more additional therapeutic agents is an immunomodulatory therapeutic. In some embodiments, the one or more additional therapeutic agents is a chemotherapeutic agent. In some embodiments, the one or more additional therapeutic agents is an immunomodulatory therapeutic and a chemotherapeutic agent.

In some embodiments, provided herein is a use of the formulation comprising the compound represented by Formula (I), in the manufacture of a medicament for the treatment of a tenosynovial giant cell tumor. In some embodiments, the tenosynovial giant cell tumor is a diffuse-type tenosynovial giant cell tumor. In some embodiments, the tenosynovial giant cell tumor is a localized tenosynovial giant cell tumor.

In some embodiments, provided herein is a use of the formulation comprising the compound represented by Formula (I), in the manufacture of a medicament for the treatment of graft versus host disease (GVHD). In some embodiments, the graft versus host disease (GVHD) is chronic graft versus host disease (cGVHD). In some embodiments, the graft versus host disease (GVHD) is acute graft versus host disease (aGVHD).

In some embodiments, provided herein is a use of the formulation comprising the compound represented by Formula (I), in the manufacture of a medicament for the treatment of a neurodegenerative disease. In some embodiments, the neurodegenerative disease is selected from the group consisting of Parkinson's disease (PD), Alzheimer's Disease (AD), frontotemporal dementia (FTD), amyotrophic lateral sclerosis (ALS), mild cognitive impairment, and Huntington's Disease (HD).

In some embodiments, provided herein is a use of the formulation comprising the compound represented by Formula (I), in the manufacture of a medicament for the treatment of a cancer selected from the group consisting of solid tumors, acute myeloid leukemia (AML), relapsed/refractory acute myeloid leukemia (AML), relapsed acute myeloid leukemia (AML), refractory acute myeloid leukemia (AML), myelodysplastic syndrome, acute lymphocytic leukemia (ALL), chronic lymphocytic leukemia (CLL), pancreatic ductal adenocarcinoma (PDAC), ovarian cancer, non-small cell lung cancer (NSCLC), prostate cancer, osteosarcoma, breast cancer, colon cancer, and glioblastoma. In some embodiments, the solid tumor is selected from the group consisting of ovarian cancer, pancreatic cancer, prostate cancer, lung cancer, breast cancer, kidney cancer, liver cancer, cervical cancer, bone metastatic cancer, papillary thyroid cancer, non-small cell lung cancer, colon cancer, and gastrointestinal stromal tumor.

In some embodiments, provided herein is a use of the formulation comprising the compound represented by Formula (I), in the manufacture of a medicament for the treatment of tumors known to have expression of colony-stimulating factor 1 receptor (CSF-1R) or its ligands, colony stimulating factor-1 (CSF-1), or interleukin (IL)-34 (IL-34.

In some embodiments, provided herein is a use of the formulation comprising the compound represented by Formula (I), in the manufacture of a medicament for the treatment of a disease or condition selected from the group consisting of metabolic diseases, rheumatoid arthritis, osteoarthritis, multiple sclerosis, autoimmune nephritis, lupus, Crohn's disease, asthma, chronic obstructive pulmonary diseases, osteoporosis, hypereosinophilic syndromes, mastocytosis, and histiocytosis.

In some aspects of the disclosure, in the use of the compound represented by Formula (I) of the compound represented by Formula (I), in the manufacture of a medicament for the treatment of a disease or condition, the amount of the compound represented by Formula (I) is about 1 mg to about 150 mg. In some embodiments, the amount of the compound represented by Formula (I) is about 2 mg to about 35 mg. In some embodiments, the amount of the compound represented by Formula (I) is about 1.0 mg, about 1.1 mg, about 1.2 mg, about 1.3 mg, about 1.4 mg, about 1.5 mg, about 1.6 mg, about 1.7 mg, about 1.8 mg, about 1.9 mg, about 2.0 mg, about 2.1 mg, about 2.2 mg, about 2.3 mg, about 2.4 mg, about 2.5 mg, about 2.6 mg, about 2.7 mg, about 2.8 mg, about 2.9 mg, or about 3.0 mg. In some embodiments, the amount of the compound represented by Formula (I) is about 2.0 mg. In some embodiments, the amount of the compound represented by Formula (I) is about 9.0 mg, about 9.1 mg, about 9.2 mg, about 9.3 mg, about 9.4 mg, about 9.5 mg, about 9.6 mg, about 9.7 mg, about 9.8 mg, about 9.9 mg, about 10.0 mg, about 10.1 mg, about 10.2 mg, about 10.3 mg, about 10.4 mg, about 10.5 mg, about 10.6 mg, about 10.7 mg, about 10.8 mg, about 10.9 mg, or about 11.0 mg. In some embodiments, the amount of the compound represented by Formula (I) is about 10.0 mg. In some embodiments, the amount of the compound represented by Formula (I) is about 13.0 mg, about 13.1 mg, about 13.2 mg, about 13.3 mg, about 13.4 mg, about 13.5 mg, about 13.6 mg, about 13.7 mg, about 13.8 mg, about 13.9 mg, 14.0 mg, about 14.1 mg, about 14.2 mg, about 14.3 mg, about 14.4 mg, about 14.5 mg, about 14.6 mg, about 14.7 mg, about 14.8 mg, about 14.9 mg, or about 15.0 mg. In some embodiments, the amount of the compound represented by Formula (I) is about 14.0 mg. In some embodiments, the amount of the compound represented by Formula (I) is about 19.1 mg, about 19.2 mg, about 19.3 mg, about 19.4 mg, about 19.5 mg, about 19.6 mg, about 19.7 mg, about 19.8 mg, about 19.9 mg, or about 20.0 mg, about 20.1 mg, about 20.2 mg, about 20.3 mg, about 20.4 mg, about 20.5 mg, about 20.6 mg, about 20.7 mg, about 20.8 mg, about 20.9 mg, or about 21.0 mg. In some embodiments, the amount of the compound represented by Formula (I) is about 20.0 mg. In some embodiments, the amount of the compound represented by Formula (I) is about 29.0 mg, about 29.1 mg, about 29.2 mg, about 29.3 mg, about 29.4 mg, about 29.5 mg, about 29.6 mg, about 29.7 mg, about 29.8 mg, about 29.9 mg, about 30.0 mg, about 30.0 mg, about 30.1 mg, about 30.2 mg, about 30.3 mg, about 30.4 mg, about 30.5 mg, about 30.6 mg, about 30.7 mg, about 30.8 mg, about 30.9 mg, about 31.0 mg. In some embodiments, the amount of the amount of the compound represented by Formula (I) is about 30.0 mg.

In some aspects of the disclosure, in the use of the crystalline dihydrate form of the compound represented by Formula (I), in the manufacture of a medicament for the treatment of a disease or condition, the amount of the crystalline dihydrate form is about 1 mg to about 150 mg. In some embodiments, the amount of the crystalline dihydrate form is about 2 mg to about 35 mg. In some embodiments, the amount of the crystalline dihydrate form is about 2.0 mg, about 2.1 mg, about 2.2 mg, about 2.3 mg, about 2.4 mg, about 2.5 mg, about 2.6 mg, about 2.7 mg, about 2.8 mg, about 2.9 mg, or about 3.0 mg. In some embodiments, the amount of the crystalline dihydrate form is about 2.2 mg. In some embodiments, the amount of the crystalline dihydrate form is about 10.0 mg, about 10.1 mg, about 10.2 mg, about 10.3 mg, about 10.4 mg, about 10.5 mg, about 10.6 mg, about 10.7 mg, about 10.8 mg, about 10.9 mg, or about 11.0 mg. In some embodiments, the amount of the crystalline dihydrate form is about 10.8 mg. In some embodiments, the amount of the crystalline dihydrate form is about 15.0 mg, about 15.1 mg, about 15.2 mg, about 15.3 mg, about 15.4 mg, about 15.5 mg, about 15.6 mg, about 15.7 mg, about 15.8 mg, about 15.9 mg, or about 16.0 mg. In some embodiments, the amount of the crystalline dihydrate form is about 15.2 mg. In some embodiments, the amount of the crystalline dihydrate form is about 21.1 mg, about 21.2 mg, about 21.3 mg, about 21.4 mg, about 21.5 mg, about 21.6 mg, about 21.7 mg, about 21.8 mg, about 21.9 mg, or about 22.0 mg. In some embodiments, the amount of the crystalline dihydrate form is about 21.7 mg. In some embodiments, the amount of the solid-state crystalline dihydrate form is about 32.0 mg, about 32.1 mg, about 32.2 mg, about 32.3 mg, about 32.4 mg, about 32.5 mg, about 32.6 mg, about 32.7 mg, about 32.8 mg, about 32.9 mg, or about 33.0 mg. In some embodiments, the amount of the crystalline dihydrate form is about 32.5 mg.

In some aspects of the disclosure, in the use of the anhydrous form of the compound represented by Formula (I) of the anhydrous form of the compound represented by Formula (I), in the manufacture of a medicament for the treatment of a disease or condition, the amount of the anhydrous form of the compound represented by Formula (I) is about 1 mg to about 150 mg. In some embodiments, the amount of the anhydrous form of the compound represented by Formula (I) is about 2 mg to about 35 mg. In some embodiments, the amount of the anhydrous form of the compound represented by Formula (I) is about 1.0 mg, about 1.1 mg, about 1.2 mg, about 1.3 mg, about 1.4 mg, about 1.5 mg, about 1.6 mg, about 1.7 mg, about 1.8 mg, about 1.9 mg, about 2.0 mg, about 2.1 mg, about 2.2 mg, about 2.3 mg, about 2.4 mg, about 2.5 mg, about 2.6 mg, about 2.7 mg, about 2.8 mg, about 2.9 mg, or about 3.0 mg. In some embodiments, the amount of the anhydrous form of the compound represented by Formula (I) is about 2.0 mg. In some embodiments, the amount of the anhydrous form of the compound represented by Formula (I) is about 9.0 mg, about 9.1 mg, about 9.2 mg, about 9.3 mg, about 9.4 mg, about 9.5 mg, about 9.6 mg, about 9.7 mg, about 9.8 mg, about 9.9 mg, about 10.0 mg, about 10.1 mg, about 10.2 mg, about 10.3 mg, about 10.4 mg, about 10.5 mg, about 10.6 mg, about 10.7 mg, about 10.8 mg, about 10.9 mg, or about 11.0 mg. In some embodiments, the amount of the anhydrous form of the compound represented by Formula (I) is about 10.0 mg. In some embodiments, the amount of the anhydrous form of the compound represented by Formula (I) is about 13.0 mg, about 13.1 mg, about 13.2 mg, about 13.3 mg, about 13.4 mg, about 13.5 mg, about 13.6 mg, about 13.7 mg, about 13.8 mg, about 13.9 mg, 14.0 mg, about 14.1 mg, about 14.2 mg, about 14.3 mg, about 14.4 mg, about 14.5 mg, about 14.6 mg, about 14.7 mg, about 14.8 mg, about 14.9 mg, or about 15.0 mg. In some embodiments, the amount of the anhydrous form of the compound represented by Formula (I) is about 14.0 mg. In some embodiments, the amount of the anhydrous form of the compound represented by Formula (I) is about 19.1 mg, about 19.2 mg, about 19.3 mg, about 19.4 mg, about 19.5 mg, about 19.6 mg, about 19.7 mg, about 19.8 mg, about 19.9 mg, or about 20.0 mg, about 20.1 mg, about 20.2 mg, about 20.3 mg, about 20.4 mg, about 20.5 mg, about 20.6 mg, about 20.7 mg, about 20.8 mg, about 20.9 mg, or about 21.0 mg. In some embodiments, the amount of the anhydrous form of the compound represented by Formula (I) is about 20.0 mg. In some embodiments, the amount of the anhydrous form of the compound represented by Formula (I) is about 29.0 mg, about 29.1 mg, about 29.2 mg, about 29.3 mg, about 29.4 mg, about 29.5 mg, about 29.6 mg, about 29.7 mg, about 29.8 mg, about 29.9 mg, about 30.0 mg, about 30.0 mg, about 30.1 mg, about 30.2 mg, about 30.3 mg, about 30.4 mg, about 30.5 mg, about 30.6 mg, about 30.7 mg, about 30.8 mg, about 30.9 mg, about 31.0 mg. In some embodiments, the amount of the amount of the anhydrous form of the compound represented by Formula (I) is about 30.0 mg.

Kits

Also provided herein are kits comprising one or more containers comprising one or more formulations, dosage forms, or capsules disclosed herein and optionally a notice in the form prescribed by a governmental agency regulating the manufacture, use or sale of pharmaceuticals or biological products, wherein the notice reflects approval by the agency of manufacture, use or sale for human administration for treating a condition, disease, or disorder described herein and/or instruction for use of the kit in treating a condition, disease, or disorder described herein in a subject in need thereof. In some embodiments, the kit comprises a specific amount of the individual doses in a package containing one or more formulations, dosage forms, or capsules disclosed herein. The specified amount of individual doses may contain about 1 to about 100 individual dosages, alternatively about 1 to about 60 individual dosages, alternatively about 10 to about 30 individual dosages, including, about 1, about 2, about 5, about 10, about 15, about 20, about 25, about 30, about 35, about 40, about 45, about 50, about 55, about 60, about 70, about 80, about 100, and include any additional increments thereof, for example, 1, 2, 5, 10 and multiplied factors thereof, (e.g., ×1, ×2, ×2.5, ×5, ×10, ×100, etc.). In some embodiments, the kit comprises the one or more formulations, dosage forms, or capsules disclosed herein in a blister pack. In some embodiments, the kit comprises the one or more formulations, dosage forms, or capsules disclosed herein contained within a bottle or container. For example, the bottle or container may contain about 10, about 25, about 50, about 75, about 100, about 125, about 150, about 175, or about 200 oral dosage forms such as capsules or tablets. In some embodiments, the kit further comprises a desiccant such as, but not limited to, silica (e.g., silica gel) and activated carbon (e.g., activated carbon pouch).

EXAMPLES

The present disclosure is not to be limited in scope by the specific embodiments disclosed in the examples which are intended as illustrations of a few aspects of the disclosure and any embodiments that are functionally equivalent are within the scope of this disclosure. Indeed, various modifications in addition to those shown and described herein will become apparent to those skilled in the art and are intended to fall within the scope of the appended claims.

Example 1. Exemplary Crystallization Procedure for the Dihydrate of the Compound of Formula (I)

An exemplary crystallization procedure for the crystalline dihydrate form of the compound of Formula (I) (vimseltinib) is as follows. Dimethylacetamide was added to a clean reactor. Then, the dry solid compound cake was added into the reactor, followed by deionized water. The reactor contents were heated to a temperature of about 80° C. for at least 3 hours. Then, the reactor contents were cooled to a temperature of about 65° C. for at least 1 hour. Next, the reactor contents were stirred for at least 20 minutes at a temperature of about 65° C. Then, the reactor was charged with micronized seeds of the compound of Formula (I), and the reactor contents were stirred for at least 15 minutes (but less than 1 hour) at a temperature of about 65° C. Deionized water was added to the reactor while a temperature of about 65° C. was maintained for at least 4 hours. Then, the reactor contents were cooled to a temperature of about 25° C. for at least 6.5 hours (a cooling ramp of about 0.1° C./min is recommended). Next, the reactor contents were stirred for at least 5 hours at a temperature of about 25° C. Afterwards, the reactor contents were filtered, and the filter cake washed twice with deionized water. Then, the filter cake was dried under vacuum with nitrogen flow at a jacket temperature of about 40° C.

For example, the crystalline dihydrate form of the compound of Formula (I) was prepared according to Example 1A:

Example 1A: The compound represented by Formula (I) was dispensed into a vessel with impeller and thermocouple. DMAC (dimethylacetamide) and water were charged to the vessel to give 5 volumes of DMAC:$H_2O$ (4.25 volumes DMAC and 0.75 volumes $H_2O$) ratio. The system was stirred to give complete suspension of material and heated to about 80° C. to access clear solution. The system was then cooled to about 65° C. and held for about 15 minutes. Milled seed material of the crystalline dihydrate form of the Compound of Formula (I) (prepared by, for example, by Example 1B) (about 5 wt. % of the weight of the compound of Formula (I)) was charged to the vessel. The system was held for 15-60 minutes. Water (2 volumes) was charged to the vessel at 65° C. over about 4 hours (0.5 volumes/hour). The system was allowed to cool to about 25° C. at about 0.1° C./min over about 6.5 hours before the mixture was stirred at room temperature for about 5 hours. The solid precipitate was isolated via vacuum filtration, washed with water (about 10 volumes) and dried under vacuum and nitrogen flow at a temperature no higher than 40° C. until moisture content by Karl Fischer analysis (KF) was no more than about 8% and no less than about 6%.

Example 1B describes another exemplary method of preparing the crystalline dihydrate form of the compound of Formula (I):

Example 1B: To a solution of the compound of Formula (I) in DCM (dichloromethane)-methanol (about 2 liters) at a temperature not higher than 45° C. was added acetone (about 5 liters). The resulting mixture was concentrated under reduced pressure to a volume of about 2 liters at a temperature not higher than 45° C. Acetone (about 5 liters) was added and the resulting mixture was concentrated under reduced pressure to a volume of about 2 liters at a temperature not higher than 45° C. To the resulting mixture, was added acetone (about 10 liters, 11.6 volumes) and water (about 0.5 liters, 0.61 volumes). The mixture was heated at about 50° C. for at least 8 h and then cooled to ambient temperature. The solid was filtered, washed with a mixture of acetone (about 3 liters) and water (about 0.2 liters), and dried under reduced pressure at no higher than 40° C. until moisture content determined by Karl Fischer analysis (KF) was no more than about 8% and no less than about 6%.

Example 2: Preparation of the Crystalline Anhydrous Form of the Compound of Formula (I)

The crystalline dihydrate form was combined with DMSO (5 volumes) and heated to about 70° C. to obtain a clear solution. The solution was cooled to about 65° C. and isopropanol (1.5 volumes) was charged to the vessel, followed by seeds of the crystalline anhydrous form (5 wt. % of the initial crystalline dihydrate form). The resulting suspension was stirred at about 65° C. for about 1 hour and then isopropanol (3.5 volumes) was added via a syringe pump over about 2 hours. The suspension was cooled to about 5° C. at about 0.1° C./min and stirred overnight. Alternatively, the clear solution (DMSO, 5 volumes, 70° C.) was cooled to about 60° C. and seeds of the crystalline anhydrous form (5 wt. % of the initial crystalline dihydrate form) were added. The resulting suspension was stirred at about 60° C. for about 1 h and then isopropanol (5.0 volumes) was added over about 2 hours. The suspension was cooled to about 5° C. at about 0.1° C./min and stirred overnight. In each case, the resulting solid was isolated by filtration, washed with isopropanol and dried under reduced pressure to afford the crystalline anhydrous form.

Example 3: Controlled Particle Size Seeding

Surprisingly, it was found that during the DMAC-water crystallization using controlled particle sized milled crystalline dihydrate form of the compound represented by Formula (I) as seeds enabled controlling the particle size distribution (PSD) of the resulting crystalline dihydrate form of the compound represented by Formula (I). In some embodiments, the PSD of the crystalline dihydrate form of the Compound of Formula (I) is controlled by the PSD of the seeds used in the crystallization. In some embodiments, the PSD of the crystalline dihydrate form of the Compound of Formula (I) is controlled by the PSD of the seeds used in the crystallization, without the need of a particle size adjustment step.

The solid of the compound of Formula (I) was dissolved in DMAC-water and the crystallization procedure was developed at a seeding temperature of about 65° C. using about 3% seeds (by weight of the solid of the compound of Formula (I). The crystalline dihydrate form of the compound represented by Formula (I) was crystallized at laboratory and production scale using milled seeds with the particle size of about 3 μm ($d_{10}$) μm, about 6 μm ($d_{50}$), and about 12 μm ($d_{90}$) (Table 1), to afford the crystalline dihydrate form of the compound of Formula (I) with a consistent particle size of about 6-8 μm ($d_{10}$), about 16-22 μm ($d_{50}$), and about 33-40 μm ($d_{90}$) (Table 2). Further crystallization development using seeds of a smaller size (about 1 μm ($d_{10}$), about 3 μm ($d_{50}$), and about 5 μm ($d_{90}$)), resulted in the crystallization outputs with PSD of about 4 μm ($d_{10}$), about 8 μm ($d_{50}$), and about 16 μm ($d_{90}$) (Table 3). Whether using seeds with larger or smaller PSD, the respective outputs were that the $d_{90}$ of the crystalline dihydrate form of the Compound of Formula (I) was about 3 times the $d_{90}$ of the seeds, the $d_{50}$ of the crystalline dihydrate form of the Compound of Formula (I) was about 3 times the $d_{50}$ of the seeds, and the $d_{10}$ of the crystalline dihydrate form of the Compound of Formula (I) was about 2 times to about 3 times the $d_{10}$ of the seeds.

TABLE 1

PSD of milled seeds of crystalline dihydrate form of the compound represented by Formula (I) used as seeds in DMAC-water crystallization

| Lot No | Particle Size (microns) $d_{10}$ | $d_{50}$ | $d_{90}$ |
|---|---|---|---|
| 1 | 2 | 5 | 13 |
| 2 | 2 | 6 | 11 |
| 3 | 3 | 6 | 12 |

TABLE 2

PSD of batches of the crystalline dihydrate form of the compound represented by Formula (I) batches crystallized using seeds

| Batch No | Seed Lot | Particle Size (microns) $d_{10}$ | $d_{50}$ | $d_{90}$ |
|---|---|---|---|---|
| 1 | 1 | 6.2 | 16.0 | 34.3 |
| 2 | 1 | 5.8 | 16.1 | 38.1 |
| 3 | 1 | 5.9 | 17.2 | 39.1 |
| 4 | 2 | 6.5 | 18.4 | 37.4 |
| 5 | 3 | 6.8 | 19.2 | 40.4 |
| 6 | 3 | 7.9 | 20.0 | 39.0 |
| 7 | 2 | 6.2 | 17.9 | 36.7 |
| 8 | 3 | 6.1 | 16.8 | 32.9 |
| 9 | 3 | 6.9 | 18.6 | 35.8 |
| 10 | 3 | 5.0 | 17.0 | 37.0 |

TABLE 3

PSD of batches of the crystalline dihydrate form of the compound represented by Formula (I) produced using seeds

| Batch No | Process details | Particle Size (microns) $d_{10}$ | $d_{50}$ | $d_{90}$ |
|---|---|---|---|---|
| Seed batch | obtained by jet milling | 1.4 | 2.7 | 5.0 |
| Crystalline dihydrate form of the compound represented by Formula (I) (crystallization 1) | Crystallization at 60° C. with 7% seeds | 3.6 | 8.4 | 16.2 |
| Crystalline dihydrate form of the compound represented by Formula (I) (crystallization 2) | Crystallization at 64° C. with 5% seeds | 3.9 | 8.5 | 16.0 |

A larger particle size batch was prepared by crystallization from DMAC-water using a non-milled batch of crystalline dihydrate form of the compound represented by Formula (I) with a particle size distribution of about 5 μm ($d_{10}$), about 15 μm ($d_{50}$), and about 36 μm ($d_{90}$), as seeds. The resulting material displayed a particle size distribution of about 13.6 μm ($d_{10}$), about 42.2 μm ($d_{50}$), and about 95.1 μm ($d_{90}$), revealing a similar trend as observed earlier wherein the $d_{10}$, $d_{50}$, and $d_{90}$ of the output were about 3-fold that of the respective $d_{10}$, $d_{50}$, and $d_{90}$ of the seeds.

Analytical Methods:

X-Ray Powder Diffraction Method

The XRPD data was collected on a Bruker AXS D8 Advance using Cu Ka radiation (40 kV, 40 mA) in reflection geometry and a θ-2θ goniometer fitted with a Ge monochromator. The incident beam passes through a 2.0 mm divergence slit followed by a 0.2 mm antiscatter slit and knife edge. The diffracted beam passes through an 8.0 mm receiving slit with 2.5° Soller slits followed by the Lynxeye Detector. The software used for data collection was Diffrac Plus XRD Commander and data analysis was HighScore Plus.

Samples were run under ambient conditions as flat plate specimens using powder as received. The sample was prepared on a polished, zero-background (510) silicon wafer by gently pressing onto the flat surface or packed into a cut cavity. The sample was rotated in its own plane.

The Details of the Standard Data Collection Method:

Angular range: 2 to 42° 2θ

Step size: 0.05° 2θ

Collection time: 0.5 s/step (total collection time: 6.40 min)

TABLE 4

| XRPD parameters for 4 min method | |
|---|---|
| Parameters | Reflection Mode |
| X-Ray wavelength | Cu, kα, Kα1 (Å): 1.540598, Kα2 (Å): 1.544426<br>Kα2/Kα1 intensity ratio: 0.50 |
| X-Ray tube setting | 45 kV, 40 mA |
| Divergence slit | Automatic |
| Scan mode | Continuous |
| Scan range (°2TH) | 3°-40° |
| Step size (°2TH) | 0.0131 |
| Scan speed (°/s) | 0.16 |
| Experiment time | ~4 min |

DSC Method:

DSC data was collected on a TA Instruments Q2000 equipped with a 50-position auto-sampler. Typically, 0.5-3 mg of each sample, in a pin-holed aluminum pan unless otherwise specified, was heated at either 10° C./min or 2° C./min from 25° C. to 300° C. A purge of dry nitrogen at 50 mL/min was maintained over the sample.

The instrument control software was Advantage for Q Series and Thermal Advantage, and the data were analyzed using Universal Analysis or TRIOS.

TGA Method:

TGA data were collected on a TA Instruments Q500 TGA, equipped with a 16-position auto-sampler. Typically, 5-10 mg of each sample was loaded onto a pre-tared aluminum DSC pan and heated at 10° C./min maintained over the sample.

The instrument control software was Advantage for Q Series and Thermal Advantage, and the data were analyzed using Universal Analysis or TRIOS.

TABLE 5

| TGA and DSC parameters | | |
|---|---|---|
| Parameters | TGA | DSC |
| Method | Ramp | Ramp |
| Sample pan | Aluminum, open | Aluminum, crimped |
| Heating rate | 10° C./min | 10° C./min |
| Procedure | RT-300° C. | 25° C.-desired temperature |
| Purge gas | $N_2$ | $N_2$ |

$^{13}C$ solid-state Nuclear Magnetic Resonance ("ssNMR" or $^{13}C$ solid-state NMR) method Solid-state NMR spectra Solid-state NMR (ssNMR) experiments were acquired on a Bruker Avance Neo console using a wide bore Bruker 4 mm BB/1H WVT MAS prone and TopSpin 4.0 software at a static magnetic field strength of 14.1 T ($V^{\circ}$ ($^1H$)=600 MHz). For $^{13}C$, the probe was tuned to 150.94 MHz and spectra referenced to the aniline $CH_3$ signal at 20.5 ppm. Powdered samples were packed into zirconia MAS rotors with Kel-F caps, with before and after weightings providing the sample mass. The rotors were spun using room-temperature purified compressed air.

All spectra were recorded using cross polarization (CP), in which magnetism is transferred from $^1H$ to $^{13}C$ nuclei via dipolar coupling (i.e., through space rather than through bond-interaction). This method enhances the observed signal, and significantly reduces the time taken to record a spectrum; however, a CP spectrum is not fully quantitative, as the peak intensity is partially dependent on the magnitude of the $^1H$-($^{13}C$/$^{15}N$) interaction. A contact time of 1.6 ms was used for the $^{13}C$ experiments. High power (100 W) SPINAL-64 decoupling was applied to the $^1H$ channel during acquisition.

Polymorphic Forms

Solid-state forms of the compound represented by Formula (I) were characterized by X-ray powder diffraction ("XRPD") patterns, differential scanning calorimetry ("DSC") curves, thermogravimetric analysis ("TGA") curves, and solid-state NMR ("ssNMR") spectra.

Crystalline Dihydrate Form

Figure 2:
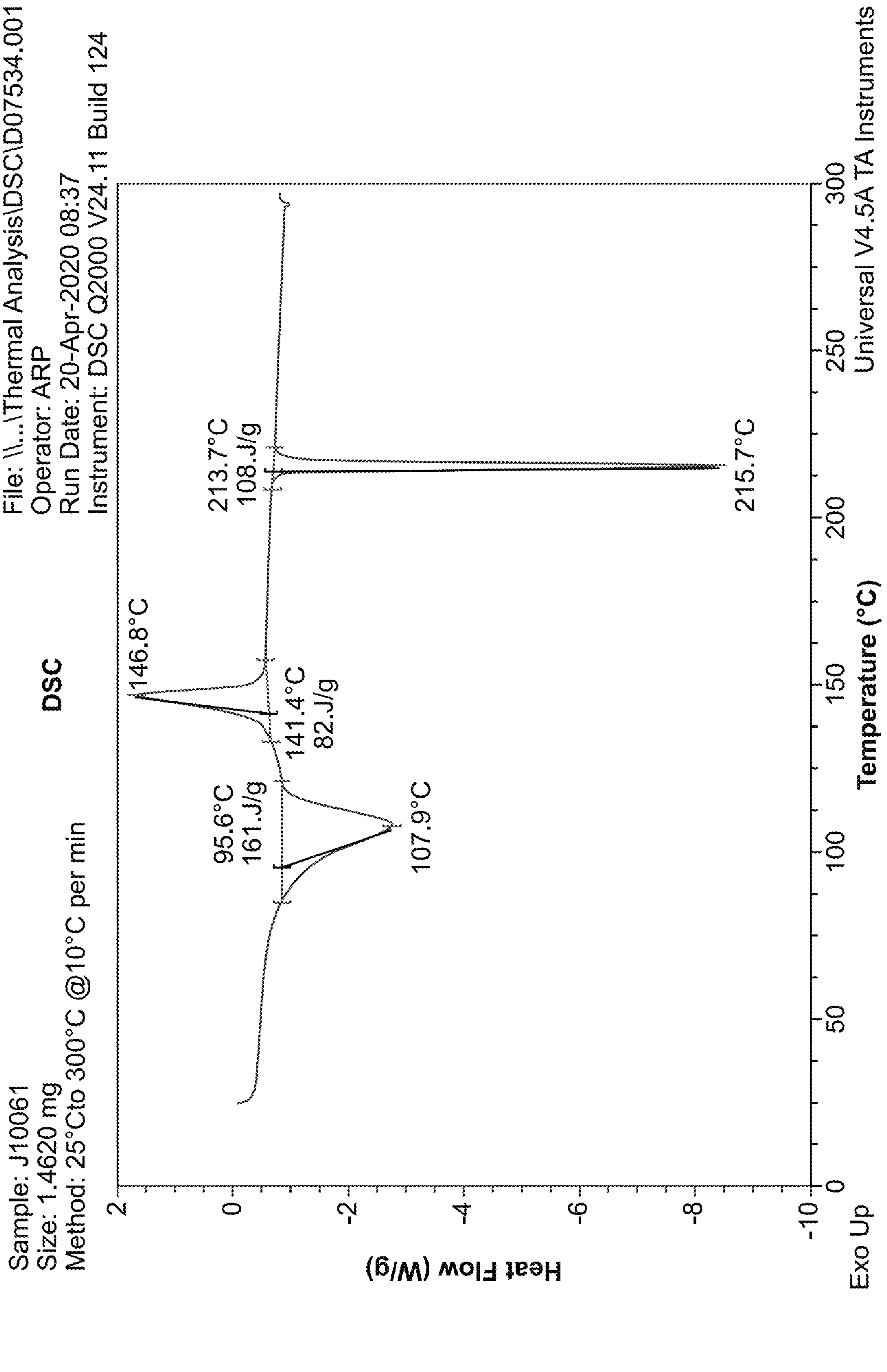
FIG. 2 shows a differential scanning calorimetry ("DSC") thermogram of the crystalline dihydrate form of the compound represented by Formula (I).
Figure 3:
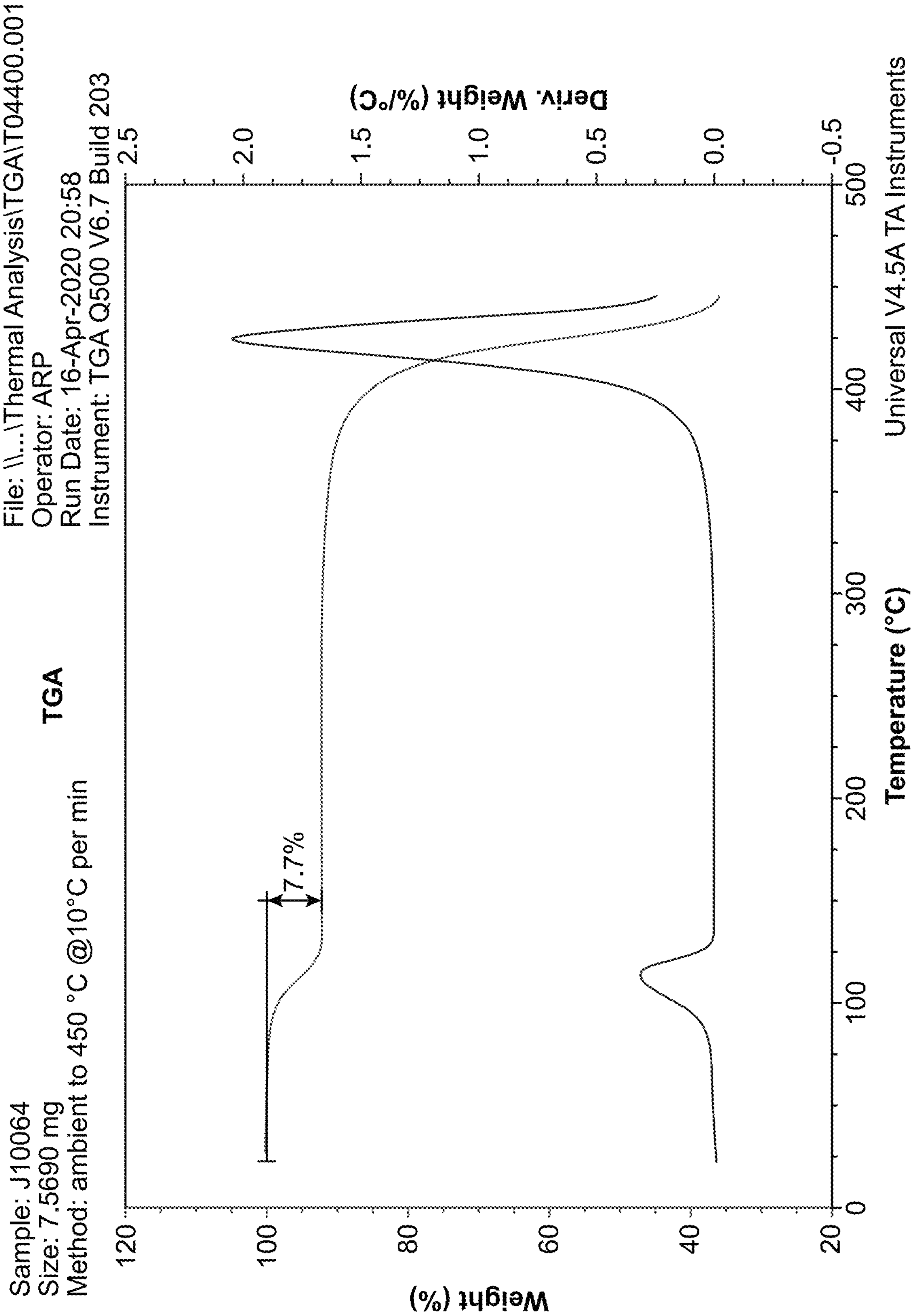
FIG. 3 shows a thermogravimetric analysis ("TGA") thermogram of crystalline dihydrate form of the compound represented by Formula (I) derived from Example 2.
Figure 4:
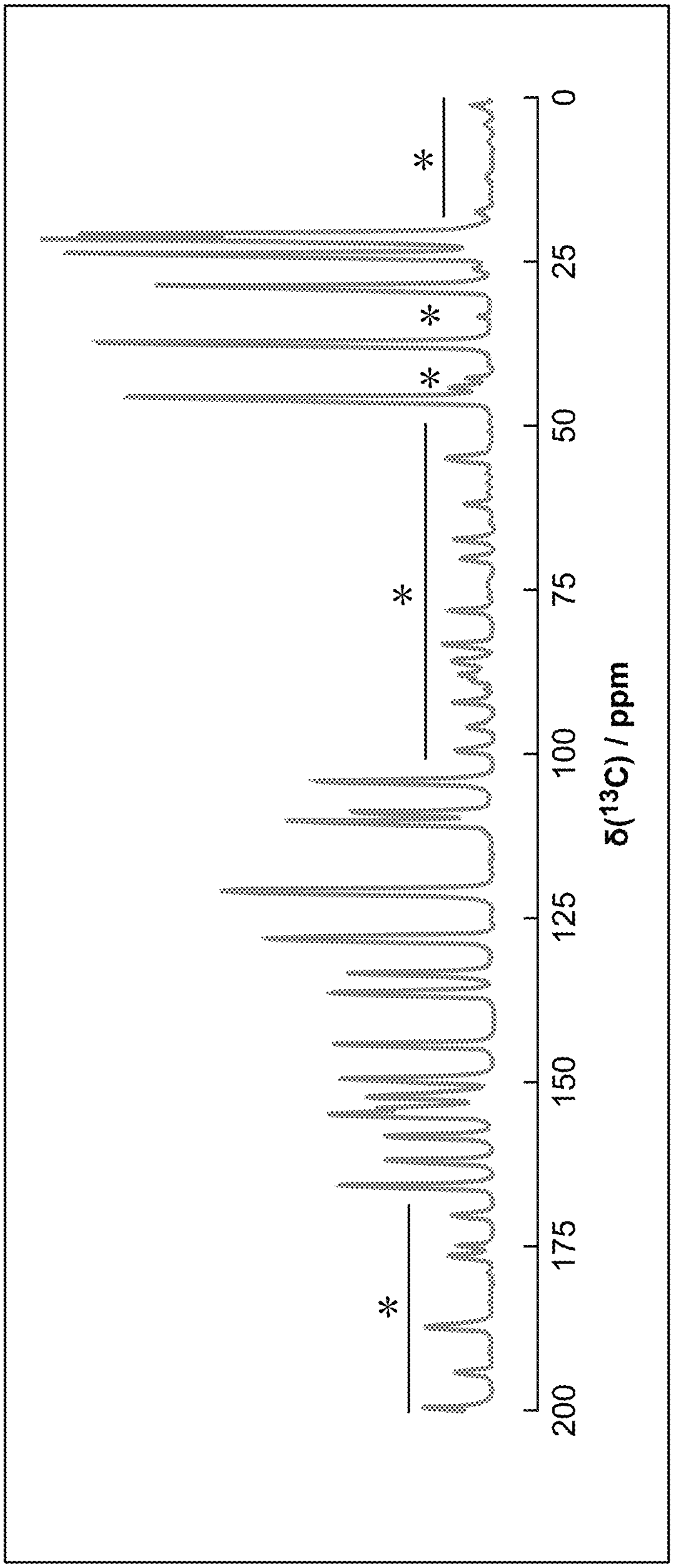
FIG. 4 shows a $^{13}$C solid-state NMR ("ssNMR") spectrum of the crystalline dihydrate form of the compound represented by Formula (I).

The crystalline dihydrate form of the compound represented by Formula (I) is represented by the XRPD pattern of FIG. 1, the DSC thermogram of FIG. 2, the TGA thermogram of FIG. 3, and the ssNMR analysis as shown in FIG. 4. The TGA thermogram (FIG. 3) of the crystalline dihydrate form of the compound represented by Formula (I) exhibits weight loss of ca. 7.5-8% between room temperature and ca. 150-220° C., corresponding to the loss of ca. 2 moles of water. The DSC thermogram (FIG. 2) for the crystalline dihydrate form of the compound represented by Formula (I) in an open pan exhibits the following transitions: 1. a broad endothermic event with onset varying between ca. 75-95° C., corresponding to volatilization of water (dehydration); 2. an exothermic event with onset varying between ca. 123-150° C., corresponding to recrystallization (of the anhydrous form of the compound represented by Formula (I)); and 3. a sharp endotherm with onset at ca. 214° C., corresponding to the melt of the anhydrous form of the compound represented by Formula (I). The DSC thermogram comprises a sharp endothermic peak at about 215° C. The ssNMR analysis is as shown in FIG. 4, asterisks indicating spinning side bands. These analyses indicate a crystalline dihydrate form.

The crystalline dihydrate form of the compound represented by Formula (I) has an X-ray powder diffraction pattern comprising peaks in terms of 2-theta, as shown in Table 6, below.

TABLE 6

XRPD pattern comprising peaks in terms of 2-theta below for crystalline solid-state dihydrate form of the compound represented by Formula (I)

| No. | Pos. [°2θ] | FWHM Left [°2θ] | d-spacing [Å] | Rel. Int. [%] |
|---|---|---|---|---|
| 1 | 5.917 | 0.1476 | 14.93661 | 17.3 |
| 2 | 8.284 | 0.1476 | 10.67348 | 8.7 |
| 3 | 10.872 | 0.1476 | 8.13828 | 23.3 |
| 4 | 11.861 | 0.1476 | 7.4617 | 29.4 |
| 5 | 12.214 | 0.1476 | 7.24674 | 30.5 |
| 6 | 13.101 | 0.1476 | 6.75799 | 72.5 |
| 7 | 13.666 | 0.1476 | 6.47981 | 14.5 |

TABLE 6-continued

XRPD pattern comprising peaks in terms of 2-theta below for crystalline solid-state dihydrate form of the compound represented by Formula (I)

| No. | Pos. [°2θ] | FWHM Left [°2θ] | d-spacing [Å] | Rel. Int. [%] |
|---|---|---|---|---|
| 8 | 15.461 | 0.0984 | 5.73114 | 8.8 |
| 9 | 15.813 | 0.1476 | 5.60445 | 17.8 |
| 10 | 16.815 | 0.1476 | 5.27265 | 8.2 |
| 11 | 17.833 | 0.1476 | 4.97383 | 25.7 |
| 12 | 18.323 | 0.246 | 4.84209 | 10.6 |
| 13 | 18.996 | 0.1476 | 4.67207 | 22.6 |
| 14 | 20.806 | 0.1476 | 4.2695 | 100 |
| 15 | 21.787 | 0.1476 | 4.0794 | 44 |
| 16 | 22.143 | 0.0984 | 4.01461 | 7.4 |
| 17 | 22.623 | 0.1476 | 3.93042 | 56.2 |
| 18 | 24.151 | 0.0984 | 3.6851 | 7.4 |
| 19 | 24.599 | 0.2952 | 3.61901 | 19.9 |
| 20 | 25.275 | 0.1968 | 3.5237 | 50.9 |
| 21 | 25.809 | 0.1968 | 3.4521 | 24.7 |
| 22 | 26.212 | 0.09 | 3.39709 | 11.7 |
| 23 | 26.412 | 0.1476 | 3.3746 | 31.2 |
| 24 | 27.106 | 0.1968 | 3.28973 | 71.9 |
| 25 | 28.303 | 0.1968 | 3.15327 | 13.9 |
| 26 | 28.666 | 0.1476 | 3.11423 | 9.9 |
| 27 | 29.67 | 0.1476 | 3.01104 | 14.8 |
| 28 | 30.026 | 0.1476 | 2.9762 | 15.9 |
| 29 | 30.827 | 0.1476 | 2.90061 | 6.3 |
| 30 | 31.209 | 0.1476 | 2.86601 | 5.6 |

Crystalline Anhydrous Form

Figure 5:
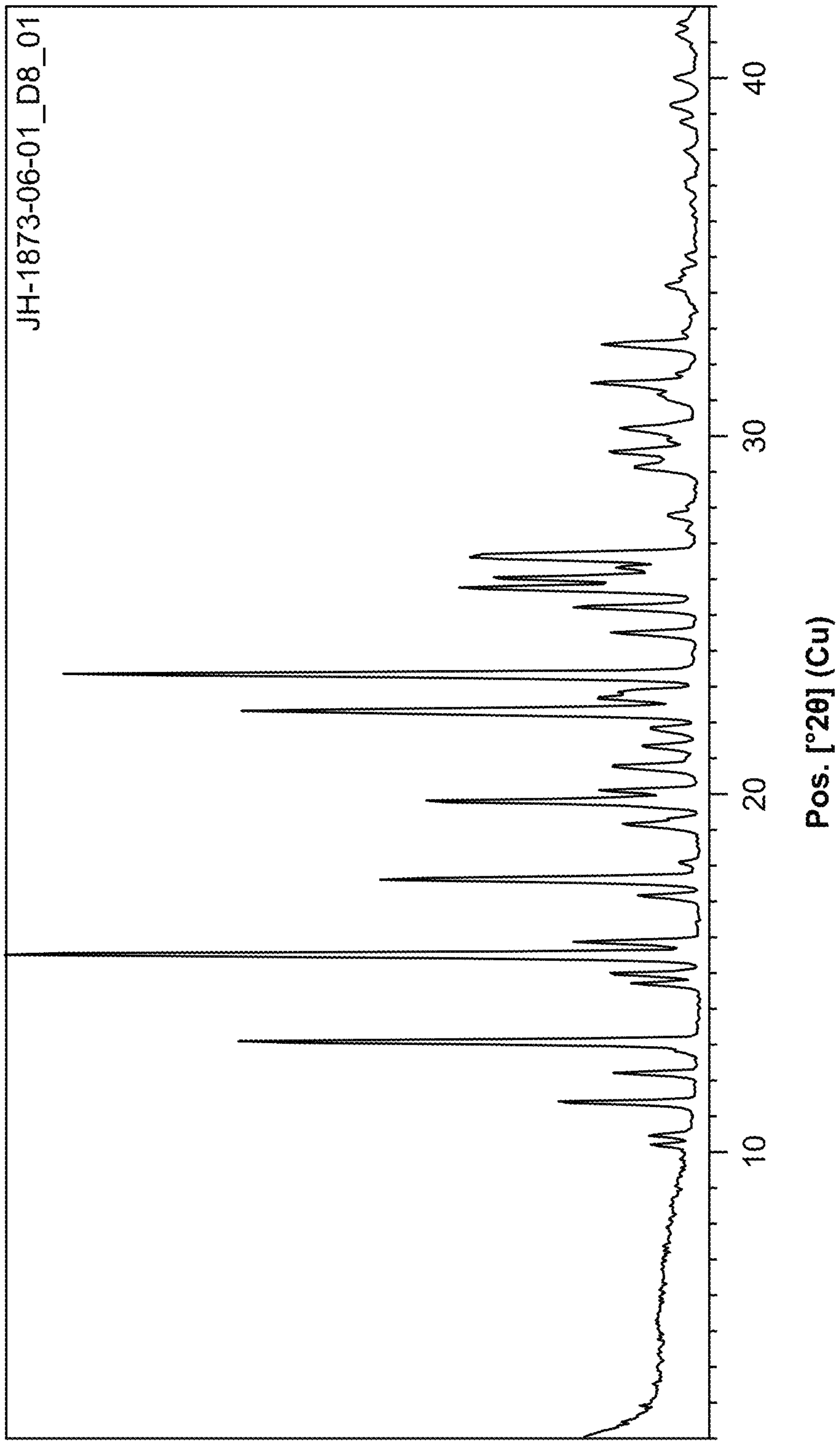
FIG. 5 shows an XRPD pattern of the crystalline anhydrous form of the compound represented by Formula (I).
Figure 6:
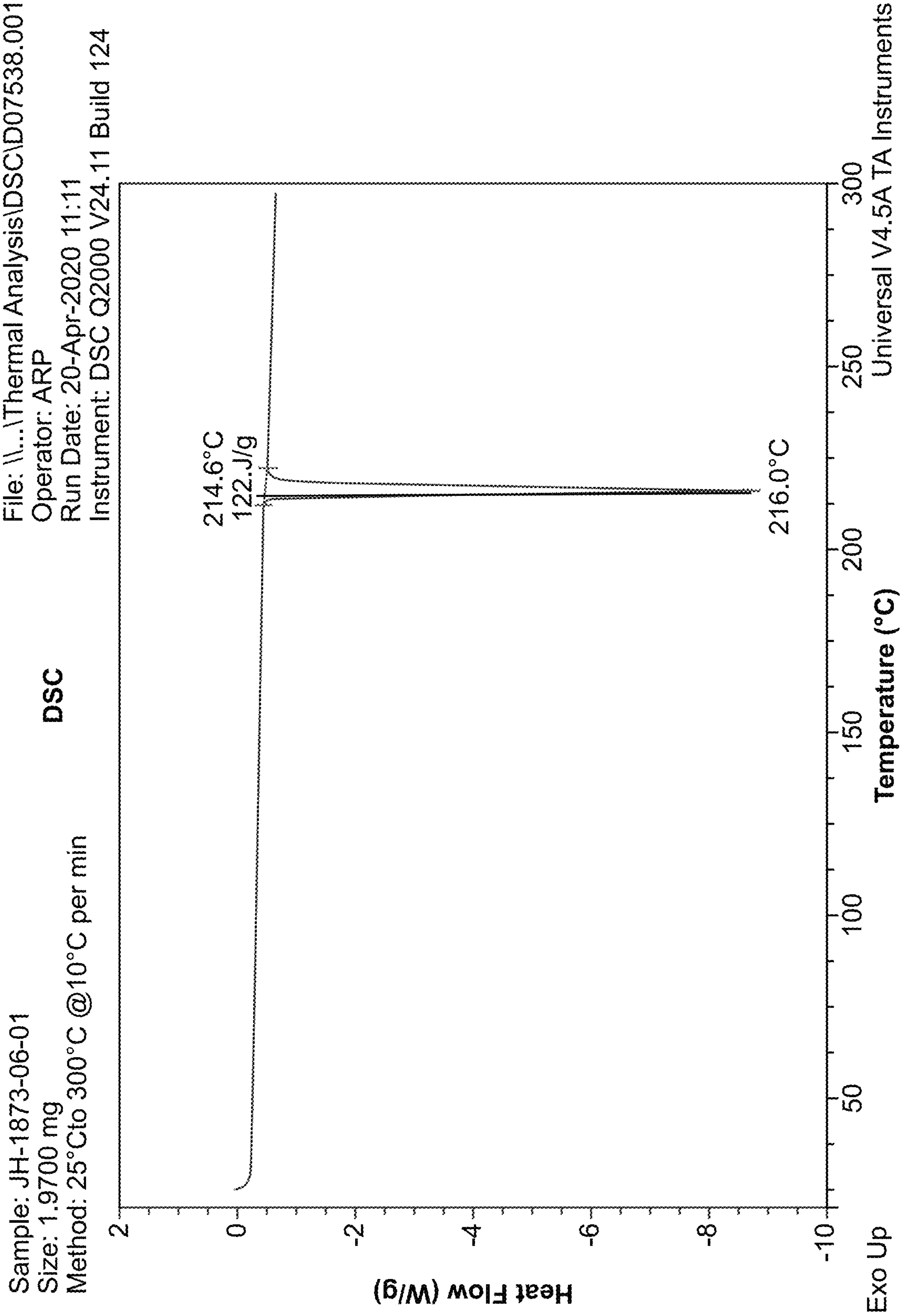
FIG. 6 shows a DSC thermogram of the crystalline anhydrous form of the compound represented by Formula (I).
Figure 7:
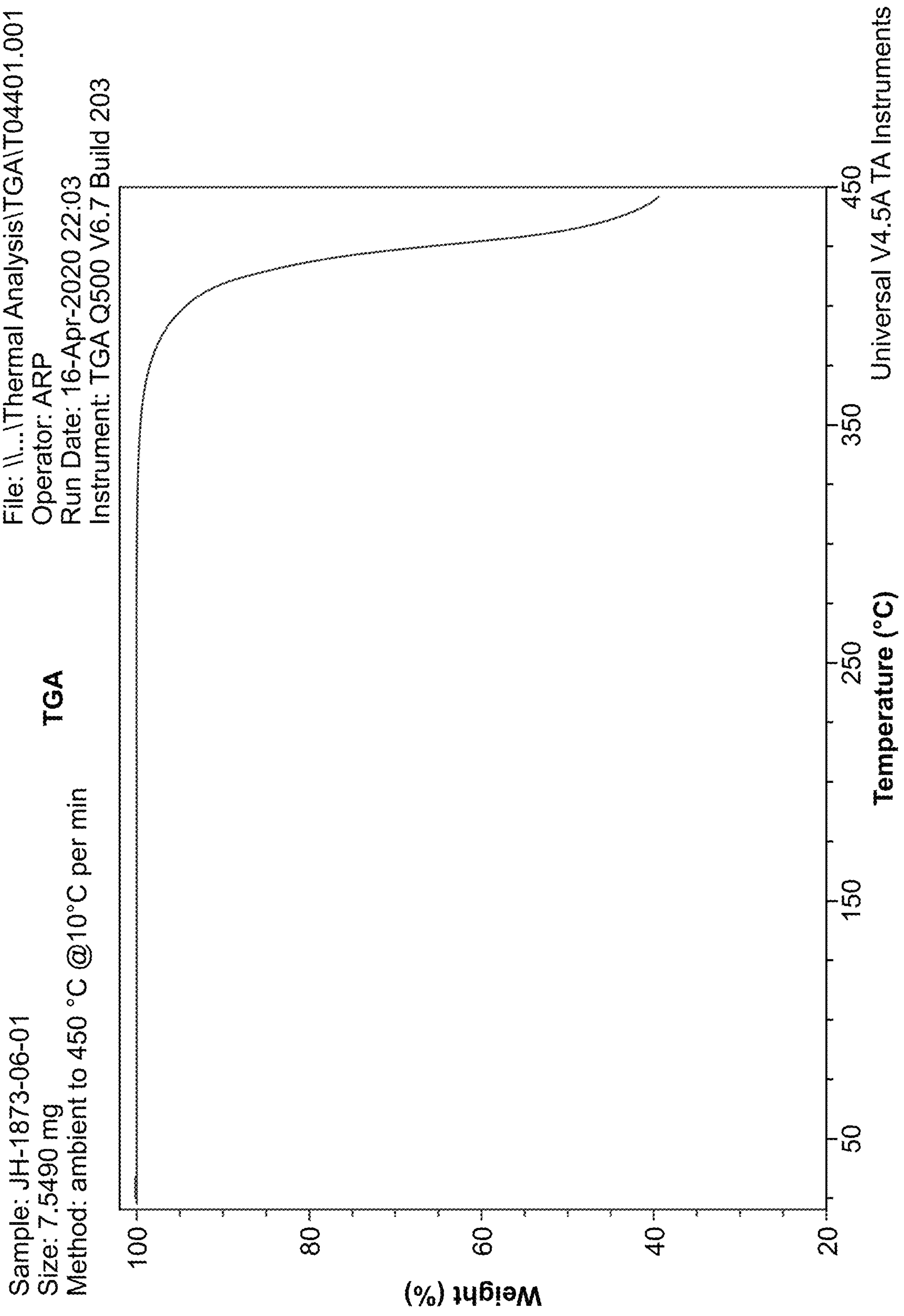
FIG. 7 shows a TGA thermogram of the crystalline anhydrous form of the compound represented by Formula (I).
Figure 8:
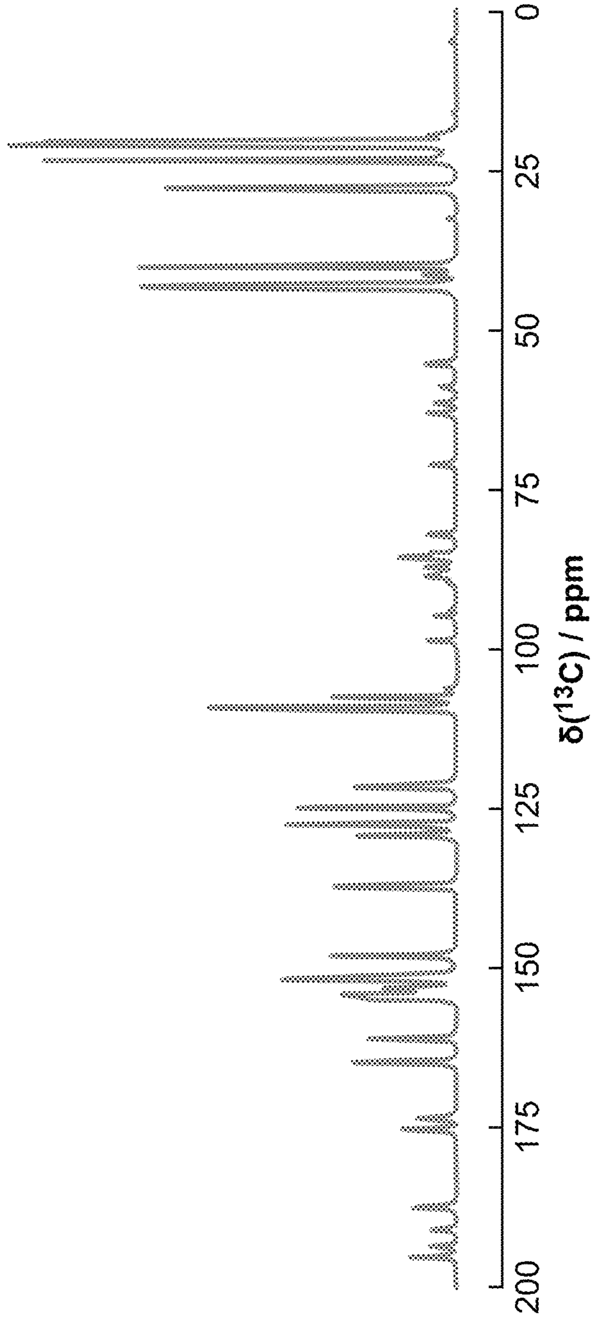
FIG. 8 shows a $^{13}$C ssNMR spectrum of the crystalline anhydrous form of the compound represented by Formula (I).

The crystalline anhydrous form of the compound represented by Formula (I) is represented by the XRPD pattern of FIG. 5, the DSC thermogram of FIG. 6, the TGA thermogram of FIG. 7, and the ssNMR analysis as shown in FIG. 8. The TGA and DSC analyses (FIGS. 6 and 7, respectively) for the crystalline anhydrous form of the compound represented by Formula (I) showed no weight loss with a sharp endotherm at 215° C. (onset) rising to about 330° C. before decomposition. The ssNMR analysis is as shown in FIG. 8). The crystalline anhydrous form of the compound represented by Formula (I) has a DSC thermogram comprising an endothermic peak between about 215° C. and substantially as shown in FIG. 6, corresponding to the melt of the crystalline anhydrous form of the compound represented by Formula (I). The TGA thermogram (FIG. 6) does not show weight loss until ca. 330° C., the onset of decomposition. These analyses indicate a crystalline anhydrous form.

The anhydrous form of the compound represented by Formula (I) has an XRPD pattern comprising peaks in terms of 2-theta, as shown in Table 7, below.

TABLE 7

XRPD pattern comprising peaks in terms of 2-theta below for crystalline solid-state form of compound Formula (I)

| No. | Pos. [°2θ] | FWHM Left [°2θ] | d-spacing [Å] | Rel. Int. [%] |
|---|---|---|---|---|
| 1 | 10.462 | 0.1476 | 8.45576 | 5.7 |
| 2 | 11.364 | 0.1476 | 7.7867 | 18.8 |
| 3 | 12.181 | 0.1476 | 7.26609 | 11.4 |
| 4 | 13.063 | 0.1476 | 6.77756 | 62.7 |
| 5 | 14.664 | 0.0984 | 6.041 | 8.2 |
| 6 | 14.964 | 0.1476 | 5.92048 | 12.9 |
| 7 | 15.5 | 0.1968 | 5.71708 | 100 |
| 8 | 15.849 | 0.0984 | 5.59199 | 18.2 |
| 9 | 17.12 | 0.1476 | 5.17954 | 8.4 |
| 10 | 17.603 | 0.1968 | 5.03849 | 46.3 |

TABLE 7-continued

XRPD pattern comprising peaks in terms of 2-theta below for crystalline solid-state form of compound Formula (I)

| No. | Pos. [°2θ] | FWHM Left [°2θ] | d-spacing [Å] | Rel. Int. [%] |
|---|---|---|---|---|
| 11 | 19.107 | 0.1968 | 4.64508 | 10.1 |
| 12 | 19.772 | 0.1476 | 4.49027 | 39.6 |
| 13 | 20.099 | 0.0984 | 4.4179 | 14.4 |
| 14 | 20.75 | 0.1968 | 4.28083 | 12.4 |
| 15 | 21.316 | 0.1476 | 4.16836 | 8.2 |
| 16 | 21.802 | 0.1476 | 4.07659 | 6.9 |
| 17 | 22.294 | 0.1968 | 3.98776 | 66 |
| 18 | 22.665 | 0.1476 | 3.92338 | 15 |
| 19 | 22.837 | 0.0984 | 3.89407 | 11.9 |
| 20 | 23.328 | 0.1476 | 3.81326 | 91.2 |
| 21 | 24.477 | 0.1476 | 3.63688 | 12.6 |
| 22 | 25.198 | 0.1968 | 3.53434 | 18 |
| 23 | 25.714 | 0.1476 | 3.46455 | 32.2 |
| 24 | 26.008 | 0.09 | 3.42331 | 29.4 |
| 25 | 26.294 | 0.09 | 3.38672 | 11.2 |
| 26 | 26.653 | 0.1968 | 3.34463 | 32.3 |
| 27 | 29.103 | 0.1968 | 3.06843 | 9.4 |
| 28 | 29.547 | 0.1476 | 3.02331 | 13 |

Example 4: Stability Testing of Crystalline Dihydrate and Anhydrous Forms of the Compound Represented by Formula (I)

The stability of crystalline dihydrate and anhydrous forms of the compound represented by Formula (I) at varying relative humidity (RH) and temperature was investigated.

For example, the stability of crystalline dihydrate and anhydrous forms of the compound represented by Formula (I), as prepared according to Example 1 and Example 2, respectively, was studied under other conditions by placing aliquots of each form in static storage at conditions of 40° C./75% RH, 25° C./97% RH, 40° C./0% RH and 25° C./0% RH and analyzing the aliquots once weekly for four weeks using XRPD, DSC, and KF.

The crystalline dihydrate form (having average crystal sizes of about 1 mm) partially converted to the crystalline anhydrous form after 4 weeks of storage at 40° C./0% RH. In addition, the crystalline dihydrate form partially converted to the crystalline anhydrous form after 4 weeks of storage at 25° C./0% RH. The corresponding KF analysis indicated a water content of 5.8% for the crystalline dihydrate form stored at 25° C./0% RH for 4 weeks, which was higher than that of the crystalline dihydrate form stored at 40° C./0% RH for 4 weeks (0.2% as determined by KF), indicating a lower degree of conversion to the crystalline anhydrous form at the lower temperature. The crystalline dihydrate form remained stable and unchanged as evidenced by XRPD under the other storage conditions for the full 4 week timeframe (40° C./75% RH and 25° C./97% RH). The crystalline anhydrous form remained stable under all storage conditions after 4 weeks.

Figure 9:
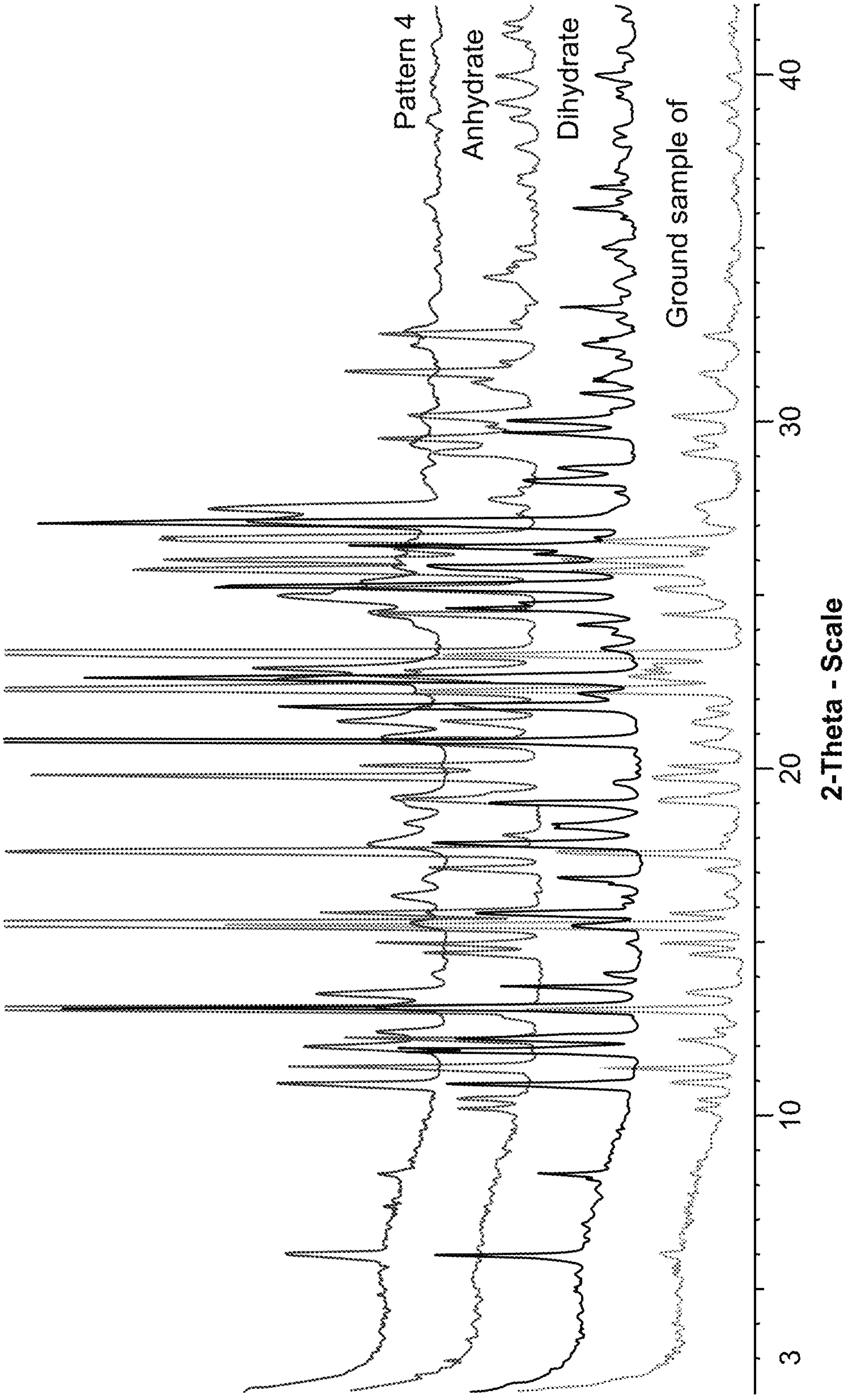
FIG. 9 shows an XRPD pattern of the ground crystalline dihydrate form subjected to static storage at 40° C./0% RH for one week.

When crystalline dihydrate form (having crystal sizes in the range of about 10-50 μm estimated by polarized light microscopy) was stored at 40° C./0% RH, Pattern 4 (a hemi-hydrate form of the compound represented by Formula (I)) was observed at weeks 1-2. By weeks 3-4 at 40° C./0% RH, Pattern 4 and peaks at 9.9° and 10.6°, corresponding to Pattern 5 peaks, were observed. When the crystalline dihydrate form (having average crystal sizes of about 1 mm) was ground in a mortar and pestle (thus having crystal sizes about 10 μm to about 100 μm) and stored at 40° C./0% RH for 1 week, Pattern 4 and the crystalline anhydrous form were observed (FIG. 9). When Pattern 4 was subsequently stored at higher humidities (e.g., 40° C./75% RH) for one week, it was converted to the crystalline dihydrate form.

Tables 8-9 summarize the stability of crystalline dihydrate and anhydrous forms of the compound represented by Formula (I).

TABLE 8

Stability of the crystalline dihydrate and anhydrous forms of the compound represented by Formula (I)

Dihydrate form of the compound represented by Formula (I) (having average crystal sizes of about 1 mm)

| | Week 1 | | | Week 2 | | |
|---|---|---|---|---|---|---|
| Storage Condition | XRPD | DSC | KF (%) | XRPD | DSC | KF (%) |
| 40° C./75% RH | Dihydrate form | Broad endotherm onset 99.2° C. (96 J/g) Exotherm onset 136.4° C. (5 J/g) Multi-endotherm onset 159.2° C. (87 J/g) Sharp endotherm split into two, onset 214.7° C. (25 J/g and 28 J/g) | 7.7 | Dihydrate form | Broad endotherm onset 94.8° C. (67 J/g) Broad multi-endotherm onset 151.6° C. (104 J/g) Sharp endotherm onset 215.0° C. (33 J/g) | 7.6 |
| 25° C./97% RH | Dihydrate form | Broad endotherm onset 93.3° C. (69 J/g) Multi-endotherm onset 151.9° C. (96 J/g) Sharp endotherm onset 214.4° C. (39 J/g | 7.7 | Dihydrate form | Broad endotherm onset 99.1° C. (97 J/g) Multi-endotherm onset 151.8° C. (75 J/g) Sharp endotherm onset 214.8° C. (46 J/g | 7.7 |
| 40° C./0% RH | Dihydrate and Anhydrous forms | Multi-endotherm onset 144.9° C. (2 J/g) Double endotherm onset 156.7° C. (4 J/g) Sharp endotherm onset 214.4° C. (122 J/g) | 0.8 | Dihydrate and Anhydrous forms | Sharp endotherm onset 214.3° C. (123 J/g) | 0.3 |
| 25° C./0% RH | Dihydrate form | Broad endotherm onset 95.6° C. (99 J/g) Multi-endotherm onset 157.4° C. (104. J/g) Sharp endotherm onset 214.7° C. (70 J/g | 7.7 | Dihydrate form | Broad multi-endotherm onset 155.3° C. (215 J/g) Sharp endotherm split into two, onset 214.7° C. (57 J/g and 34 J/g) | 7.6 |

| | Week 3 | | | Week 4 | | |
|---|---|---|---|---|---|---|
| Storage Condition | XRPD | DSC | KF (%) | XRPD | DSC | KF (%) |
| 40° C./75% RH | Dihydrate form | Broad endotherm onset 96.8° C. (99 J/g) Multi-endotherm onset 154.2 (80 J/g) Sharp endotherm onset 214.0° C. (65 J/g) | 7.7 | Dihydrate form | Broad endotherm onset 90.9° C. (113 J/g) Multi-endotherm onset 156.9° C. (70 J/g) Endotherm onset 158.4° C. (0 J/g) Sharp endotherm onset 214.5° C. (18 J/g) | 7.7 |
| 25° C./97% RH | Dihydrate form | Broad endotherm onset 91.3 °C. (72 J/g) Multi-endotherm onset 153.2° C. (93 J/g) Sharp endotherm onset 214.0° C. (69 J/g) | 7.4 | Dihydrate form | Broad endotherm onset 93.4° C. (68 J/g) Multi-endotherm onset 152.9° C. (124 J/g) Small endotherms onset (160.3° C. (1 J/g), 161.5° C. (0 J/g), 162.0° C. (0 J/g), 164.2° C. (0 J/g) Small endotherm onset 173.8° C. (0 J/g) Sharp endotherm onset 214.4° C. (82 J/g) | 7.7 |
| 40° C./0% RH | Anhydrous form* | Sharp endotherm onset 214.4° C. (121 J/g) | 0.1 | Dihydrate and Anhydrous forms | Sharp endotherm onset 213.8° C. (116 J/g) | 0.2 |
| 25° C./0% RH | Dihydrate form | Broad endotherm onset 96.0° C. (28 J/g) Multi-endotherm onset 148.3° (50 J/g) Two small endotherms onset 162.2° C. (0 J/g) and 166.6° C. (0 J/g) Sharp endotherm onset 215.0° (18 J/g) | 7.2 | Dihydrate and Anhydrous forms | Broad endotherm onset 95.4° C. (25 J/g) Multi-endotherm onset 155.1° C. (66 J/g) Two small endotherms onset 162.7° C. (0 J/g) and 171.8° C. (0 J/g) Sharp endotherm onset 214.3° C. (98 J/g) | 5.8 |

TABLE 8-continued

Stability of the crystalline dihydrate and anhydrous forms of the compound represented by Formula (I)

Anhydrous form of the compound represented by Formula (I)

| Storage Condition | Week 1 XRPD | Week 1 DSC | Week 1 KF (%) | Week 2 XRPD | Week 2 DSC | Week 2 KF (%) |
|---|---|---|---|---|---|---|
| 40° C./75% RH | Anhydrous form | Sharp endotherm onset 214.5° C. (119 J/g) | 0.3 | Anhydrous form | Sharp endotherm onset 214.5° C. (180 J/g) | 0.2 |
| 25° C./97% RH | Anhydrous form | Sharp endotherm onset 214.3° C. (121 J/g) | 0.3 | Anhydrous form | Sharp endotherm onset 213.0° C. (1 J/g) immediately followed by sharp endotherm onset 214.9° C. (120 J/g | 0.3 |
| 40° C./0% RH | Anhydrous form | Sharp endotherm split into two, onset 214.7° C. (98 J/g and 22 J/g) | 0.1 | Anhydrous form | Multi-endotherm onset 214.9° C. (124 J/g) | 0.0 |
| 25° C./0% RH | Anhydrous form | Sharp endotherm onset 214.4° C. (119 J/g) | 0.1 | Anhydrous form | Multi-endotherm onset 214.2° C. (124 J/g) | 0.1 |

| Storage Condition | Week 3 XRPD | Week 3 DSC | Week 3 KF (%) | Week 4 XRPD | Week 4 DSC | Week 4 KF (%) |
|---|---|---|---|---|---|---|
| 40° C./75% RH | Anhydrous form | Sharp endotherm onset 214.1° C. (124 J/g) | 0.1 | Anhydrous form | Sharp endotherm onset 214.1° C. (125 J/g) | 0.3 |
| 25° C./97% RH | Anhydrous form | Sharp endotherm onset 214.3° C. (126 J/g) | 0.2 | Anhydrous form | Sharp endotherm onset 214.6° C. (123 J/g) | 0.4 |
| 40° C./0% RH | Anhydrous form | Sharp endotherm onset 214.7° C. (121 J/g) | 0.0 | Anhydrous form | Sharp endotherm onset 214.9° C. (118 J/g) | 0.2 |
| 25° C./0% RH | Anhydrous form | Sharp endotherm onset 214.5° C. (123 J/g) | 0.0 | Anhydrous form | Sharp endotherm onset 214.4° C. (119 J/g) | 0.2 |

*due to sample homogeneity

TABLE 9

Stability of the crystalline dihydrate form of the compound represented by Formula (I)
Dihydrate form of the compound represented by Formula (I) (having crystal sizes in the range of about 10-50 μm)

| Storage Condition | Week 1 XRPD | Week 1 DSC | Week 1 KF (%) | Week 2 XRPD | Week 2 DSC | Week 2 KF (%) |
|---|---|---|---|---|---|---|
| 40° C./75% RH | Dihydrate form | Endotherm onset 95.6° C. (158 J/g) Exotherm onset 131.0° C. (42 J/g) Sharp endotherm split into two onset 213.7° C. (9 J/g and 63 J/g) | 7.5 | Dihydrate form | Endotherm onset 95.0° C. (169 J/g) Exotherm onset 136.2° C. (76 J/g) Sharp endotherm onset 213.8° C. (108 J/g) | 7.9 |
| 25° C./97% RH | Dihydrate form | Endotherm onset 93.6° C. (252 J/g) Exotherm onset 129.5° C. (78 J/g) Sharp endotherm split into two onset 213.7° C. (70 J/g and 42 J/g) | 7.6 | Dihydrate form | Endotherm onset 95.5° C. (171 J/g) Exotherm onset 132.0° C. (74 J/g) Sharp endotherm onset 213.7° C. (110 J/g) | 7.5 |
| 40° C./0% RH | Pattern 4 | Endotherm onset 99.1° C. (35 J/g) Exotherm onset 128.8° C. (84 J/g) Sharp endotherm split into two onset 213.7° C. (83 J/g and 32 J/g) | 7.5 | Pattern 4 | Endotherm onset 102.1° C. (33.4 J/g) Exotherm onset 130.6° C. (84 J/g) Sharp endotherm onset 213.7° C. (116 J/g) | 7.4 |
| 25° C./0% RH | Dihydrate form | Endotherm onset 96.6° C. (266 J/g) Exotherm onset 132.2° C. (68 J/g) Sharp endotherm split into two onset 213.7° C. (86 J/g and 20 J/g) | 7.5 | Dihydrate form | Endotherm onset 95.3° C. (170 J/g) Exotherm onset 131.9° C. (73 J/g) Sharp endotherm onset 213.6° C. (105 J/g) | 7.7 |

TABLE 9-continued

Stability of the crystalline dihydrate form of the compound represented by Formula (I)
Dihydrate form of the compound represented by Formula (I) (having crystal sizes in the range of about 10-50 μm)

| | Week 3 | | | Week 4 | | |
|---|---|---|---|---|---|---|
| Storage Condition | XRPD | DSC | KF (%) | XRPD | DSC | KF (%) |
| 40° C./75% RH | Dihydrate form | Broad endotherm onset 95.2° C. (231 J/g) Exotherm onset 138.3° C. (79 J/g) Sharp endotherm onset 213.7° C. (109 J/g) | 8.0 | Dihydrate form | Broad endotherm onset 95.6° C. (172 J/g) Exotherm onset 132.2° C. (72 J/g) Endotherm onset 213.6° C. (114 J/g) | 7.9 |
| 25° C./97% RH | Dihydrate form | Broad endotherm onset 94.9° C. (235 J/g) Exotherm onset 145.5° C. (91 J/g) Sharp endotherm onset 213.8° C. (112 J/g) | 7.9 | Dihydrate form | Broad endotherm onset 103.1° C. (163 J/g) Exotherm onset 133.0° C. (76 J/g) Endotherm onset 213.7° C. (112 J/g) | 7.9 |
| 40° C./0% RH | Pattern 4 with additional peaks at 2θ = 9.9° and 10.6° | Broad endotherm onset 99.4° C. (34 J/g) Exotherm onset 129.5° C. (87 J/g) Sharp endotherm onset 213.8° C. (125 J/g) | 7.0 | Pattern 4 with additional peaks at 2θ = 9.9° and 10.6° | Broad endotherm onset 97.8° C. (131 J/g) Exotherm onset 129.6° C. (88 J/g) Small endotherm onset 196.2° C. (0 J/g) Sharp endotherm onset 213.5° C. (121 J/g) | 3.4 |
| 25° C./0% RH | Dihydrate form | Broad endotherm onset 95.6° C. (155 J/g) Exotherm onset 130.4° C. (65 J/g) | 8.1 | Dihydrate form | Broad endotherm onset 95.0° C. (193 J/g) Exotherm onset 134.4° C. (89 J/g) Small endotherm onset 147.8° C. (0 J/g) Sharp endotherm onset 213.6° C. (114 J/g) | 7.9 |

Example 5: Solvent Screening for the Compound Represented by Formula (I)

The effect of solvent systems and crystallization conditions on the compound represented by Formula (I) was studied using an amorphous sample of the compound represented by Formula (I). Table 10 summarizes the crystalline form produced under certain solvent conditions and techniques.

For the temperature cycling, the amorphous compound represented by Formula (I) in each solvent was heated to 40° C. for about 20 minutes. Where dissolution occurred, additional amorphous material was added to obtain a slurry. The resultant slurries were subjected to successive 4-hour heat-cool cycles between 40° C. and room temperature for 72 hours. The solid materials were isolated from the slurries by filtration then analyzed by XRPD. The filtrate was used for evaporation, crash cooling, and anti-solvent addition experiments. For the evaporation experiment, the solution of the compound of Formula (I) was left uncapped in a vial to evaporate the solvent at ambient conditions. For the crash cooling experiments at 2° C. and −20° C., the solutions of the compound of Formula (I) were left to cool to 2° C. and −20° C. in the fridge and freezer, respectively. For the anti-solvent experiment, an anti-solvent was added to the saturated solution of the compound of Formula (I). The anti-solvent for samples 1-5, 7-9, 14-18, 20-21, and 23-24 was MTBE; the anti-solvent for samples 10-13 and 22 was DIPE; and the anti-solvent for sample 19 was acetone.

TABLE 10

Summary of the solvent screening for the compound represented by Formula (I)

| | | Technique | | | | |
|---|---|---|---|---|---|---|
| Sample | Solvent | Temperature cycling | Evaporation | Crash Cooling (2° C.) | Crash Cooling (−20° C.) | Anti-solvent Addition |
| 1 | Acetone | Anhydrous | Anhydrous | NS | NS | NS |
| 2 | Acetone/water 75:25 | Dihydrate | Dihydrate | NS | NS | Amorphous |
| 3 | Acetonitrile | Anhydrous | Anhydrous | Anhydrous | NS | NS |
| 4 | Anisole | Anhydrous | Dihydrate | NS | Dihydrate | NS |
| 5 | 1-Butanol | Anhydrous | Anhydrous | NS | NS | NS |
| 6 | Chloroform | Anhydrous | Dihydrate | NS | NS | NS |
| 7 | Cyclohexane | Anhydrous | Anhydrous | NS | NS | NS |
| 8 | Dichloromethane | Anhydrous | Anhydrous | Anhydrous | Anhydrous | Anhydrous |
| 9 | Diisopropyl ether | Anhydrous | Anhydrous | NS | NS | NS |
| 10 | 1,4-Dioxane | Anhydrous | Anhydrous | NS | NS | Anhydrous |

TABLE 10-continued

Summary of the solvent screening for the compound represented by Formula (I)

| | | Technique | | | | |
|---|---|---|---|---|---|---|
| Sample | Solvent | Temperature cycling | Evaporation | Crash Cooling (2° C.) | Crash Cooling (−20° C.) | Anti-solvent Addition |
| 11 | Ethanol | Anhydrous | Anhydrous | NS | NS | NS |
| 12 | Ethanol/water 97:3 | Dihydrate | Dihydrate | Dihydrate | Dihydrate | Dihydrate |
| 13 | Ethanol/water 75:25 | Dihydrate | Dihydrate | Dihydrate | Dihydrate | Dihydrate |
| 14 | Ethyl acetate | Anhydrous | Anhydrous | NS | NS | NS |
| 15 | Heptane | Anhydrous | Anhydrous | NS | NS | NS |
| 16 | Methanol | Anhydrous | Anhydrous | Anhydrous | Anhydrous | NS |
| 17 | Methanol/water 90:10 | Dihydrate | Dihydrate | NS | Dihydrate | NS |
| 18 | Methanol/water 60:40 | Dihydrate | Dihydrate | NS | NS | NS |
| 19 | 2-Methoxyethanol | Anhydrous | Anhydrous | NS | NS | NS |
| 20 | Methyl acetate | Anhydrous | Anhydrous | Anhydrous | Anhydrous | Anhydrous |
| 21 | Methylethyl ketone | Anhydrous | Anhydrous | NS | Anhydrous | Anhydrous |
| 22 | Methylisobutyl ketone | Dihydrate | Anhydrous | NS | NS | NS |
| 23 | Tetrahydrofuran | Anhydrous | Anhydrous | NS | NS | Anhydrous |
| 24 | Acetonitrile/water 75:25 | Dihydrate | Dihydrate | Dihydrate | Dihydrate | NS |

NS in Table 10 refers to no solid formed for XRPD analysis.

In a hydration experiment, a slurry of the crystalline anhydrous form of the compound represented by Formula (I) and deionized water was subjected to successive 4-hour heat-cool cycles between 40° C. and room temperature for 72 hours. The isolated solid was identified as the crystalline dihydrate form of the compound represented by Formula (I) by XRPD.

In a competitive slurry experiment, a 1:1 mixture of the crystalline anhydrous form and the crystalline dihydrate form was slurried for 48 hours at room temperature or 60° C. Table 11 summarizes the experiment conditions and the isolated crystalline forms, as determined by XRPD.

TABLE 11

Summary of the competitive slurry experiments

| Solvent | Approximate water activity | Temperature | Observed form |
|---|---|---|---|
| Acetone/water (99:1) | 0.1 | Ambient | Dihydrate |
| Acetone/water (70:30) | 0.9 | Ambient | Dihydrate |
| 1,4-Dioxane/water (90:10) | 0.1 | Ambient | Dihydrate |
| 1,4-Dioxane/water (35:65) | 0.9 | Ambient | Dihydrate |
| Acetone/water (99:1) | 0.1 | 60° C. | Anhydrous |
| Acetone/water (70:30) | 0.9 | 60° C. | Dihydrate |
| 1,4-Dioxane/water (90:10) | 0.1 | 60° C. | Dihydrate |
| 1,4-Dioxane/water (35:65) | 0.9 | 60° C. | Dihydrate |

The hydration of the crystalline anhydrous form was studied using aqueous solvent systems with low water activity of 0.1. Slurries of the crystalline anhydrous form in the respective solvent were agitated for 6 days at room temperature. Aliquots of isolated materials were analyzed after 24, 48, and 144 hours of agitation. Table 12 summarizes the experiment conditions and isolated crystalline forms, as determined by XRPD.

TABLE 12

Summary of hydration experiment in low water activity solvents

| | | Observed Forms | | |
|---|---|---|---|---|
| Solvent | Temperature | 24 h | 48 h | 144 h |
| Acetone/water (99:1) | Ambient | Anhydrous | Mixture of Anhydrous and Dihydrate | Anhydrous |
| MEK/water (99:1) | Ambient | Anhydrous | Mixture of Anhydrous and Dihydrate | Dihydrate |

At least the solid forms of Examples 4 and 5 demonstrate the means for providing a stable solid-state and/or crystalline and/or anhydrous and/or dihydrate form of Formula I.

Example 6. Exemplary Processes of Preparing Formulations of the Compound of Formula (I) (Process I)

Exemplary drug product capsule formulations are supplied as powder filled, hard gelatin capsules in active strengths of 2 mg and 10 mg for oral administration. Dosing in the clinical study is conducted at 30 mg biweekly, which is achieved with 3×10 mg capsule dosage units. Options for down dosing (if required) to either 20 mg or 14 mg biweekly is achieved by using multiples of the 10 mg strength and 2 mg strength capsules (2×10 mg capsules for the 20 mg dose and 1×10 mg+2×2 mg capsules for the 14 mg dose). The hard gelatin capsules are Size 4 blue/blue (2 mg) and Size 4 white/white (10 mg).

Process I: Both active strengths of vimseltinib drug product were prepared using the same excipients. The 10 mg strength drug product was prepared from a blend comprising dry-mixed excipients with crystalline dihydrate vimseltinib drug substance at 10.84% w/w. Each 10 mg capsule contains 10.84 mg of crystalline dihydrate vimseltinib drug substance (as the dihydrate) equivalent to 10 mg of vimseltinib on an anhydrous basis. The 2 mg strength drug product was prepared from a similar blend with crystalline dihydrate vimseltinib drug substance at 1.55% w/w. Each 2 mg capsule contains 2.167 mg of crystalline dihydrate vimseltinib drug substance (as the dihydrate) equivalent to 2 mg of vimseltinib on an anhydrous basis. The quantitative composition of vimseltinib drug product is presented in Table 13 (2 mg capsule) and Table 14 (10 mg capsule).

TABLE 13

Composition of Vimseltinib Process I Capsules, 2 mg

| Component | Function | Grade | Composition: Blend, % | Composition: mg/capsule 2 mg |
|---|---|---|---|---|
| Vimseltinib drug substance (dihydrate) | Active | In house | 1.55[b] | 2.167[c] |
| Lactose monohydrate (Foremost 316 FastFlo) | Filler | NF, EP | 95.95[b] | 134.3 |
| Crospovidone (Polyplasdone XL-10) | Disintegrant | NF, EP | 2.00 | 2.800 |
| Magnesium stearate (Non-Bovine Hyqual) | Lubricant | NF, EP | 0.50 | 0.700 |
| Empty Hard Gelatin Capsule, Size 4, Opaque, Blue[d] | Encapsulator | In house[e] | N/A | Size 4 each |
| Total | | | 100% | 140.0 |

[b]actual proportion of Vimseltinib and lactose monohydrate are adjusted based on purity correction factor for Vimseltinib (anhydrous basis) at the time of preparing common blend. A correction factor of 0.9229 has been applied for the theoretical hydrate content only.
[c]2 mg on anhydrous basis.
[d]blue capsule shells contain FD&C Blue #1(E133), FD&C Red #40 (E129), Titanium Dioxide (E171) USP/NF or Ph. Eur., and Gelatin USP/NF or Ph. Eur.
[e]gelatin capsules are released based on in house release criteria in combination with manufacturer's Certificate of Analysis,
N/A Not applicable;
NF = National Formulary;
EP = European Pharmacopoeia.

TABLE 14

Composition of Vimseltinib Process I Capsules, 10 mg

| Component | Function | Grade | Composition: Blend, % | Composition: mg/capsule 10 mg |
|---|---|---|---|---|
| Vimseltinib drug substance (dihydrate) | Active | In house | 10.84[b] | 10.84[c] |
| Lactose monohydrate (Foremost 316 FastFlo) | Filler | NF, EP | 86.66[b] | 86.66 |
| Crospovidone (Polyplasdone XL-10) | Disintegrant | NF, EP | 2.00 | 2.000 |
| Magnesium stearate (Non-Bovine Hyqual) | Lubricant | NF, EP | 0.50% | 0.500 |
| Empty Hard Gelatin White/White Capsule[d] | Encapsulator | In house[e] | N/A | Size 4 each |
| Total | | | 100% | 100.0 |

[b]actual proportion of Vimseltinib and lactose monohydrate are adjusted based on purity correction factor forVimseltinib (anhydrous basis) at the time of preparing common blend. A correction factor of 0.9229 has been applied for the theoretical hydrate content only.
[c]10 mg on anhydrous basis.
[d]white capsule shells contain Titanium Dioxide (E171) USP/NF or Ph. Eur. and Gelatin USP/NF or Ph. Eur. and Gelatin USP/NF or Ph. Eur.
[e]gelatin capsules are released based on in house release criteria in combination with manufacturer's Certificate of Analysis,
N/A Not applicable;
NF = National Formulary;
EP = European Pharmacopoeia.

Exemplary drug product manufacturing processes (Process I) for the 2 mg and 10 mg capsules was as follows:

For 2 mg capsules: Lactose monohydrate and the compound of Formula (I) were weighed and screened, then blended. The blend was screened. Separately, lactose monohydrate and Crospovidone were weighed and screened, then blended. Separately, lactose monohydrate was weighed and screened, then the blend was de-lumped. The three components were blended. Separately, magnesium stearate was weighed and screened, then blended with the three component-blend. The blend was then filled in empty hard gelatin capsules. The capsules were weigh-sorted then packaged.

For 10 mg capsules: Lactose monohydrate, Crospovidone, and the compound of Formula (I) were weighed and screened, then blended. The blend was de-lumped, then blended again. Separately, magnesium stearate was weighed and screened, then blended with the three component-blend. The blend was then filled in empty hard gelatin capsules. The capsules were weigh-sorted then packaged.

Example 7. Exemplary Processes of Preparing Formulations of the Compound of Formula (I) (Process II)

Process II drug products were formulated as powder-filled hard gelatin capsules in active strengths of 14 mg, 20 mg, and 30 mg for oral administration. The hard gelatin capsules are Size 4 orange/white (14 mg) and Size 2 yellow/white (20 mg) and Size 1 blue/white (30 mg). All 3 active strengths of drug product were prepared using a blend comprising dry-mixed excipients with dihydrate vimseltinib drug substance at 10.84% w/w (as the dihydrate) with blend fill amounts equivalent to 14 mg, 20 mg, or 30 mg of vimseltinib on an anhydrous basis. The quantitative composition of the Process II vimseltinib drug products is presented in Table 15.

TABLE 15

Composition of Process II Vimseltinib Capsules

| Component | Function | Grade | Composition: Blend, % | mg/capsule 14 mg | mg/capsule 20 mg | mg/capsule 30 mg |
|---|---|---|---|---|---|---|
| Vimseltinib drug substance (dihydrate) | Active | In house | 10.84[b] | 15.18[c] | 21.68 | 32.52[c] |

TABLE 15-continued

| Composition of Process II Vimseltinib Capsules | | | | | | |
|---|---|---|---|---|---|---|
| | | | Composition | | | |
| | | | Blend, | mg/capsule | | |
| Component | Function | Grade | % | 14 mg | 20 mg | 30 mg |
| Lactose monohydrate (Foremost 316 FastFlo) | Filler | NF, EP | 86.66[b] | 121.32 | 173.32 | 259.98 |
| Crospovidone (Polyplasdone XL-10) | Disintegrant | NF, EP | 2.00 | 2.800 | 4.00 | 6.000 |
| Magnesium stearate (Non-Bovine Hyqual) | Lubricant | NF, EP | 0.50% | 0.700 | 1.00 | 1.500 |
| Empty Hard Gelatin White/White Capsule[d] | Encapsulator | In house[c] | N/A | Size 4 each Orange/white | Size 2 each Yellow/white | Size 1 each Blue/white |
| | | Total | 100% | 140.0 | 200 | 300.0 |

[b]actual proportion of Vimseltinib and lactose monohydrate are adjusted based on purity correction factor for Vimseltinib (anhydrous basis) at the time of preparing common blend. A correction factor of 0.9229 has been applied for the theoretical hydrate content only.
[c]Gelatin capsules are released based on in house release criteria in combination with manufacturer's Certificate of Analysis, N/A Not applicable; NF = National Formulary; EP = European Pharmacopoeia.
[d]white capsule shells contain Titanium Dioxide (E171) USP/NF or Ph. Eur. and Gelatin USP/NF or Ph. Eur.

Process II: Drug product manufacturing process for the 14 mg, 20 mg, and 30 mg strength capsules is as follows. Lactose monohydrate, Crospovidone, and the compound of Formula (I) were weighed and screened, then blended. The blend was de-lumped, then blended again. Separately, magnesium stearate was weighed and screened, then blended with the three component-blend. The blend was then filled in empty hard gelatin capsules. The capsules were weigh-sorted then packaged.

Example 8. X-Ray Powder Diffraction (XRPD) Analysis

X-ray powder diffraction (XRPD) analysis was conducted on an X-ray diffraction system PANalytical X'pert PRO diffractometer with an X'Celerator detector. Powder samples of crystalline dihydrate vimseltinib drug substance were packed "as is" into PW1811/16 sample holder covered with a Kapton film (x-ray polyimide film) and seated on a PW1811/00 aluminum bottom plate. XRPD patterns were obtained using the scanning parameters provided in Table 16.

TABLE 16

| XRPD Instrumental Parameters for Dihydrate Vimseltinib Drug Substance. | |
|---|---|
| Settings | A-X'pert PRO diffractometer with a X'Celerator detector |
| Configuration | Reflection Transmission Spinner |
| Generator | Cu 45 kV/40 mA |
| Focus | Line Focus |
| Geometry | Bragg-Brentano |
| Radiation | Cu Kα |
| Sample Stage mode | Spinning |
| Spinner revolution time | 1 rps |
| Beam Knife | Beam Knife for linear detectors at lower position |
| Scan axis | Gonio |
| Scan Mode | Continuous |
| Scan Range | 4-40° 2theta |

TABLE 16-continued

| XRPD Instrumental Parameters for Dihydrate Vimseltinib Drug Substance. | |
|---|---|
| Settings | A-X'pert PRO diffractometer with a X'Celerator detector |
| Step size | 0.017° |
| Time per step | 100 s |

Figure 10:
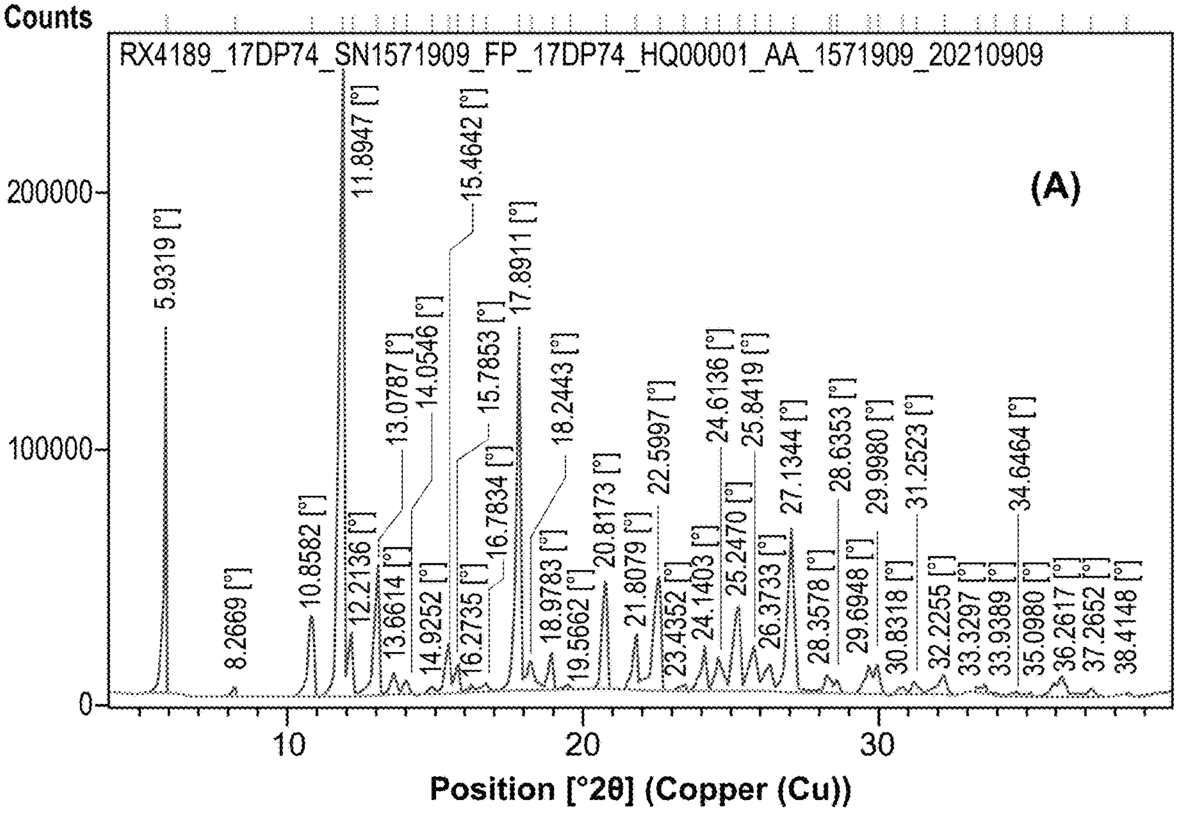
FIG. 10 depicts a comparison of XRPD patterns of vimseltinib produced by (A) Process II and (B) Process I.
Figure 10:
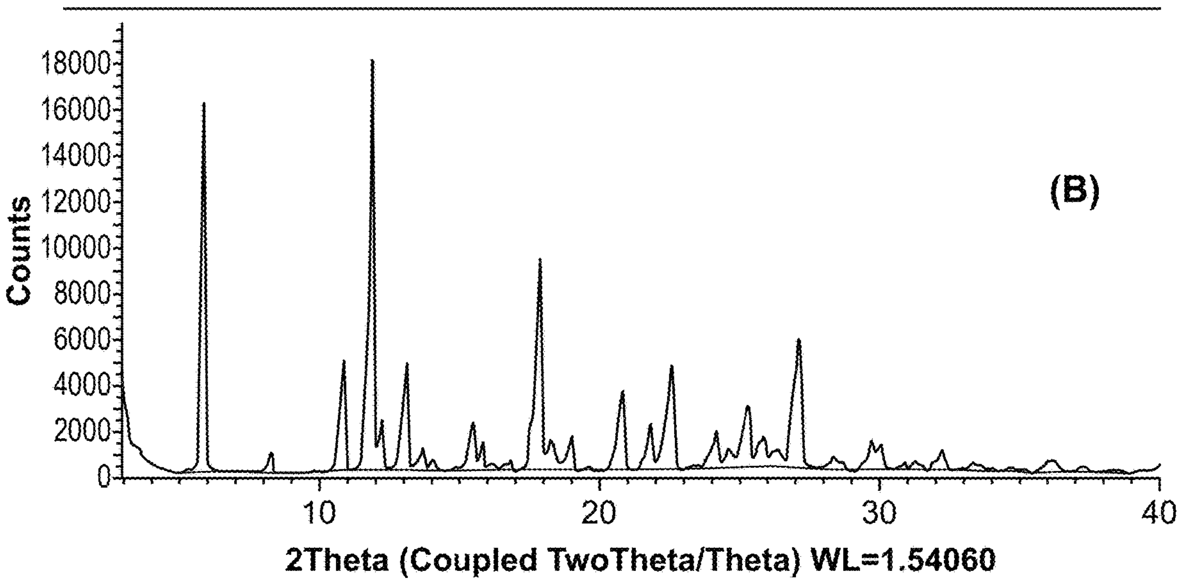
Figure 11A:
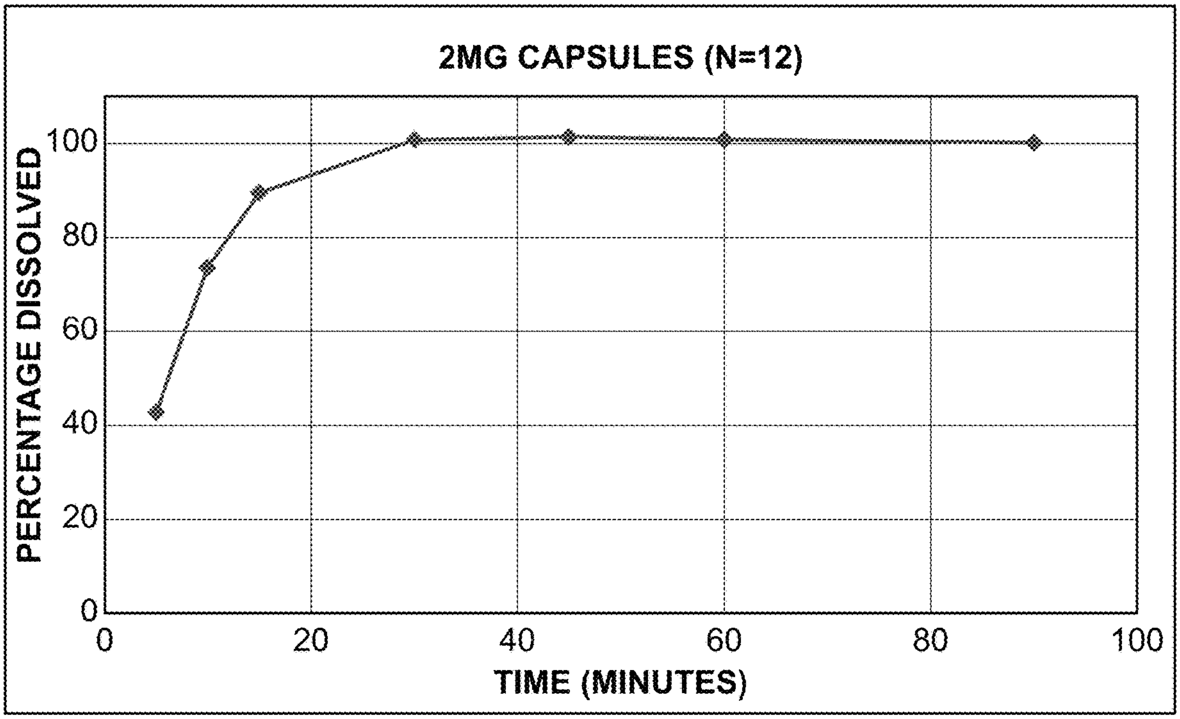
FIG. 11A, FIG. 11B, FIG. 11C, FIG. 11D, and FIG. 11E depict exemplary dissolution profiles for 2 mg (FIG. 11A), 10 mg (FIG. 11B), 14 mg (FIG. 11C), 20 mg (FIG. 11D), and 30 mg (FIG. 11E) capsules (N=12), respectively.
Figure 11B:
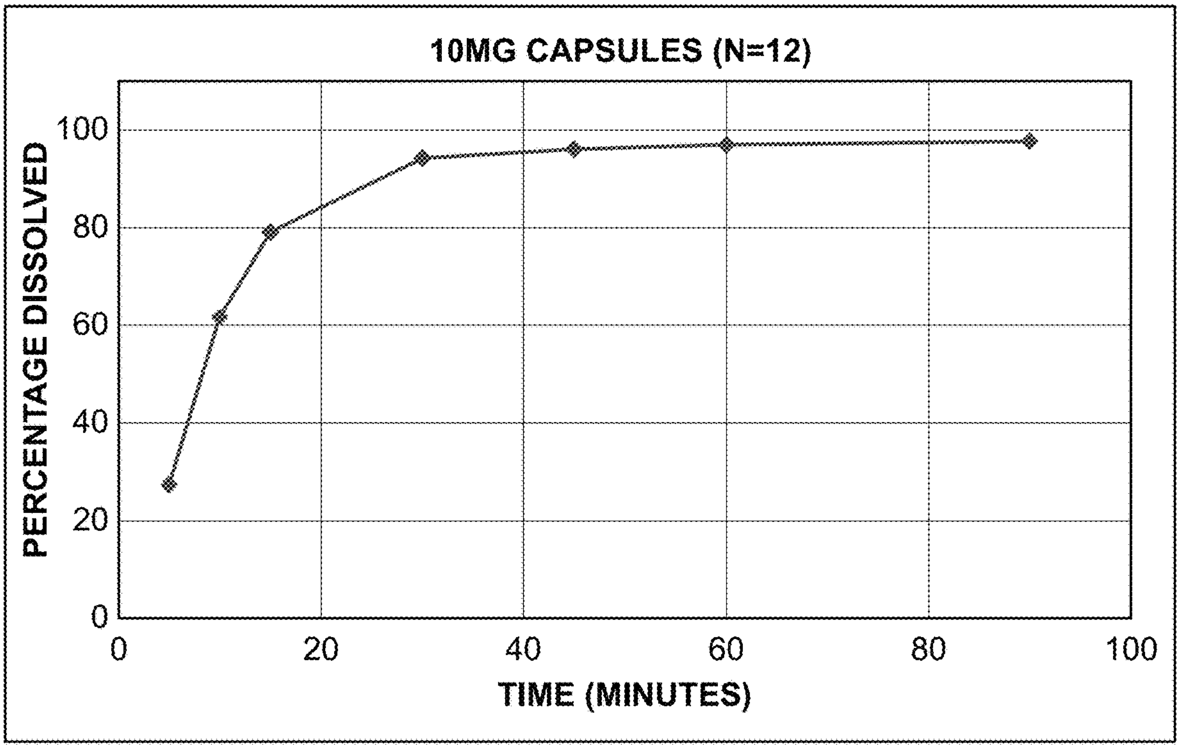
Figure 11C:
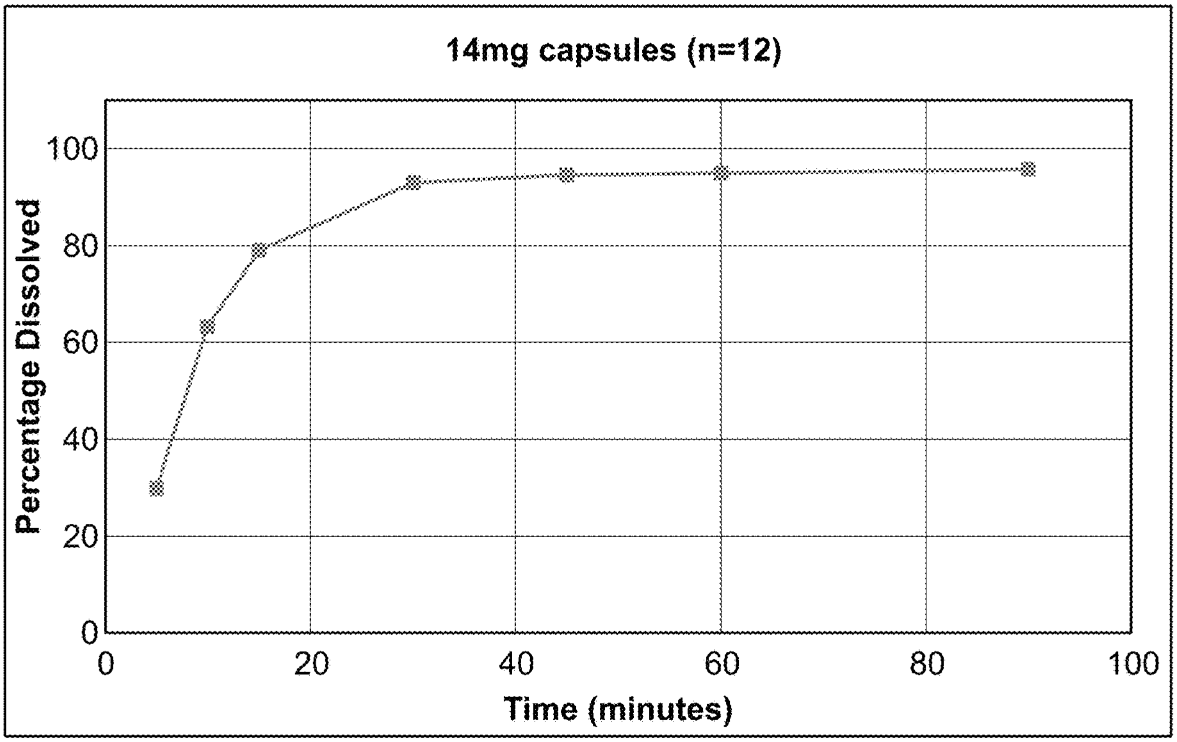
Figure 11D:
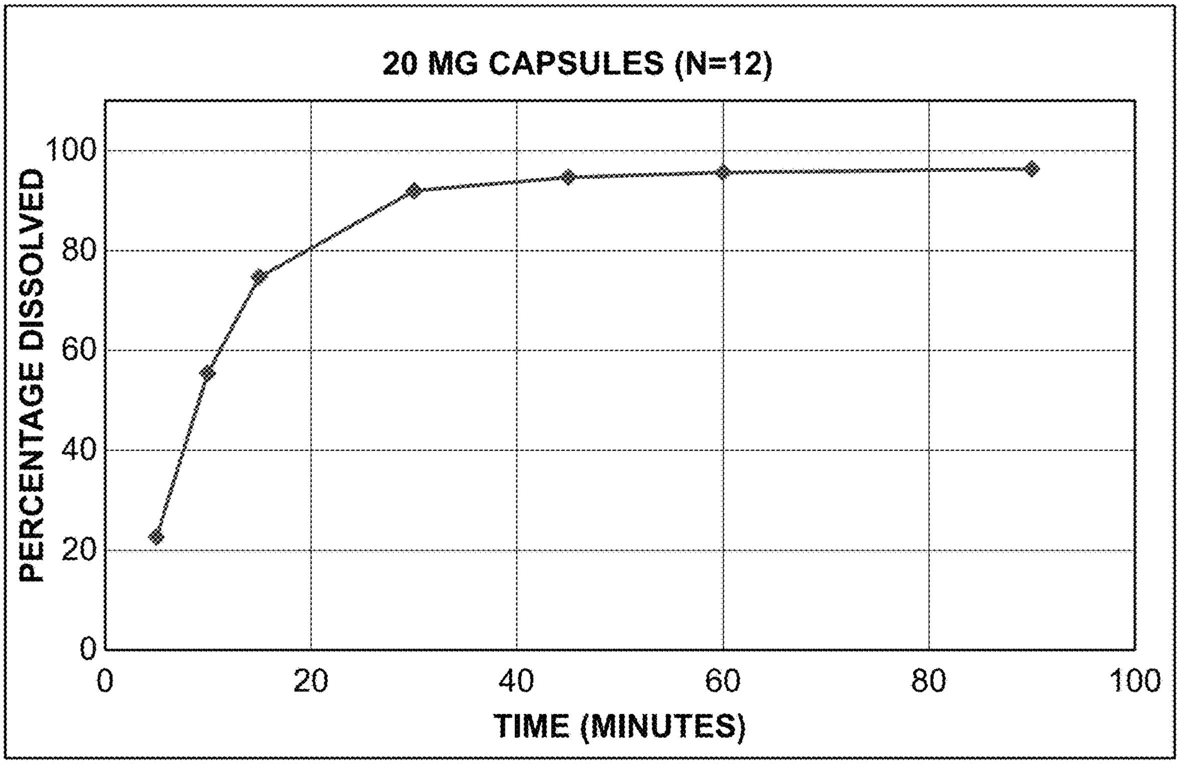
Figure 11E:
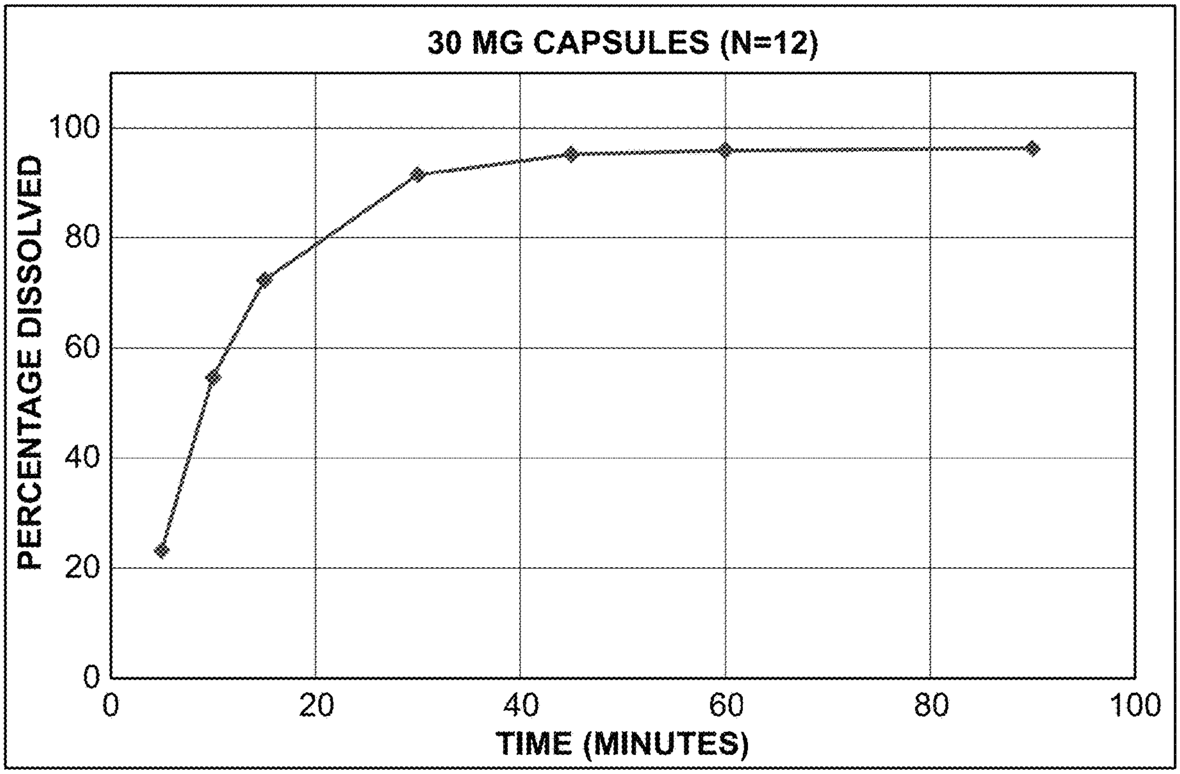

Both the Process I and Process II Vimseltinib manufacturing processes have shown to consistently produce the same solid form, the dihydrate Form 1. FIG. 10 provides a comparison of the XRPD patterns for the drug substances made using two different processes (Process I and II). Both patterns show diffraction peaks at the same 2θ angles and relative intensities (with minor differences due to preferred orientation effects) with comparable peak widths indicating highly crystalline materials of the same solid form.

Example 9. Particle Size Measurements

Particle size analysis of dihydrate vimseltinib drug substance samples was determined by laser diffraction using a Malvern Mastersizer 3000 instrument in a wet dispersion mode.

Sample Preparation

Prior to analysis, dihydrate drug substance samples were rotated and inverted in the sample container at least 10 times to ensure homogeneity. Between 20 and 25 mg of sample was weighed into a Malvern Glass tube. 20 mL of the Dispersant Solution (0.1% Span 85 in Isoparaffin G) was added and vortexed until a homogeneous suspension was obtained (~30 s). The sample was then placed in a Vibra-Cell ultrasonic processor. The amplitude was set to the target of 30% (4 Watts) using an external probe (Vibra-Cell) during 90 sec.

Measurement/Data Acquisition

After background measurement, the sample dispersion was slowly added to the dispersion unit of the instrument to achieve an obscuration level target of 5%. The sample was stirred at 3250 rpm for at least 1 minute to ensure dispersion and stabilization of the sample. After stabilization, the measurement was started and performed using a Malvern Mastersizer 3000 according to the method conditions provided in Table 17.

TABLE 17

Malvern Mastersizer 3000 Operating Conditions

| Settings | Sample(s) |
|---|---|
| Sample handling unit | Hydro MV (Mastersizer 3000) |
| Stirrer speed (rpm) | 3250 |
| External Ultrasonic (watts) | 3-4 (~30%) |
| Ultrasonic options | Vibra-Cell |
| Ultrasonic time (seconds) | 90 s |
| Particle type | Non-spherical |
| Sample material name | (1.78; 0.001) |
| Particle refractive Index | 1.78 |
| Particle absorption index | 0.001 |
| Different blue-light properties | Unchecked (red and blue light have the same properties) |
| Dispersant name | Isoparaffin G |
| Refractive Index of the dispersing agent | 1.42 |
| Background measurement duration | 10 s |
| Sample measurement duration | 10 s |
| Don't perform blue light measurement | Unchecked |
| Number of measurements | 3 |
| Delay between measurements | 5 s |
| Pre-measurement delay | 0 s |
| Pre-alignment delay | 0 s |
| Obscuration limits | 3-7% |
| Analysis model | General Purpose |
| Keep a single result mode | Unchecked |
| Number of inner detectors to kill | 0 |
| Remove blue light from analysis | Unchecked |
| Sensitivity | Normal (default) |
| Use fine powder mode | Checked |
| Limit the result size range | Unchecked |
| Result Type | Volume distribution |
| Extend the result | All options unchecked |
| Average | Create average result |

Table 18 provides a comparison of the particle size distribution data obtained on crystalline dihydrate vimseltinib drug substance samples prepared from the procedure of Example 1 using laser diffraction particle size analysis. Table 18 also provides a representative particle size distribution for spray dried lactose monohydrate.

TABLE 18

Particle Size Comparison of Dihydrate Vimseltinib Drug Substance

| | API Particle Size Distribution | | |
|---|---|---|---|
| Lot No. | D(10) (μm) | D(50) (μm) | D(90) (μm) |
| 1 | 9 | 29 | 59 |
| 2 | 6 | 18 | 37 |
| 3 | 6 | 17 | 33 |
| 4 | 7 | 19 | 36 |
| Spray Dried Lactose | 67 | 129 | 243 |

Capsules made in accordance with Example 7 (Process II) using vimseltinib lots of Table 18 were prepared. Content uniformity studies were conducted for various capsules prepared by Process II. Results are provided in Tables 19-25. Below, "AV" refers to acceptance value in accordance with USP Uniformity of Dosage Unit <905>.

Capsules were formulated using the drug substance batch numbers from Table 18 (i.e., 1, 2, 3, 4), which were prepared in accordance with the processes described in Examples 6-7 (e.g., 10 mg, 14 mg, 20 mg, and 30 mg dose formulations). Tables 19-21 below describe content uniformity (CU) studies for Lot 1 (i.e., 14 mg, 20 mg, and 30 mg dose formulations) capsules prepared in accordance with Example 7.

TABLE 19

Content Uniformity Results at 25,200 Capsules per Hour for DS Lot 1, 14 mg Capsules
DS Lot 1
Capsule Sample 14 mg, CU @ 25,200 capsules/hr

| Run No. | % Assay |
|---|---|
| 1 | 99.3 |
| 2 | 101 |
| 3 | 103.4 |
| 4 | 101.1 |
| 5 | 96.7 |
| 6 | 101.8 |
| 7 | 99 |
| 8 | 101.4 |
| 9 | 103.5 |
| 10 | 100.4 |
| Average | 100.8 |
| Min | 96.7 |
| Max | 103.5 |
| % RSD | 2.0 |
| AV | 4.9 |

TABLE 20

Content Uniformity Results at 25,200 Capsules per Hour for DS Lot 1, 20 mg Capsules
DS Lot 1
Capsule Sample 20 mg, CU @ 25,200 capsules/hr

| Run No. | % Assay |
|---|---|
| 1 | 99.8 |
| 2 | 103.0 |
| 3 | 100.7 |
| 4 | 100.8 |
| 5 | 99.7 |
| 6 | 100.7 |
| 7 | 100.0 |
| 8 | 103.1 |
| 9 | 98.6 |
| 10 | 99.5 |
| Average | 100.6 |
| Min | 1.4 |
| Max | 98.6 |
| % RSD | 103.1 |
| AV | 3.5 |

TABLE 21

Content Uniformity Results at 25,200 Capsules per Hour for DS Lot 1, 30 mg Capsules
DS Lot 1
Capsule Sample 30 mg, CU @ 25,200 capsules/hr

| Run No. | % Assay |
|---|---|
| 1 | 97.6 |
| 2 | 100.0 |
| 3 | 99.1 |
| 4 | 98.9 |
| 5 | 98.7 |
| 6 | 99.9 |
| 7 | 101.2 |
| 8 | 103.8 |
| 9 | 100.4 |
| 10 | 100.0 |
| Average | 100.0 |

TABLE 21-continued

| Content Uniformity Results at 25,200 Capsules per Hour for DS Lot 1, 30 mg Capsules<br>DS Lot 1<br>Capsule Sample 30 mg, CU @ 25,200 capsules/hr | |
|---|---|
| Run No. | % Assay |
| Min | 1.7 |
| Max | 97.6 |
| % RSD | 103.8 |
| AV | 4.0 |

Tables 22-24 below describe content uniformity (CU) studies for DS Lot 2 (i.e., 14 mg, 20 mg, and 30 mg dose formulations) capsules prepared in accordance with Example 7.

TABLE 22

| Content Uniformity Results at 25,200 Capsules per Hour for DS Lot 2, 14 mg Capsules<br>DS Lot 2<br>Capsule Sample 14 mg, CU @ 25,200 capsules/hr | |
|---|---|
| Run No. | % Assay |
| 1-1 | 99.6 |
| 2-1 | 99.3 |
| 3-1 | 99.5 |
| 4-1 | 103.8 |
| 5-1 | 98.2 |
| 6-1 | 101.4 |
| 7-1 | 102.2 |
| 8-1 | 102.4 |
| 9-1 | 97.1 |
| 10-1 | 100.7 |
| Average | 100.4 |
| SD | 2.1 |
| AV | 4.9 |

TABLE 23

| Content Uniformity Results at 25,200 Capsules per Hour for DS Lot 2, 20 mg Capsules<br>DS Lot 2<br>Capsule Sample 20 mg, CU @ 25,200 capsules/hr | | | |
|---|---|---|---|
| Run No. | Weight (mg) | % Assay | Location Mean |
| CU-Start-1 | 260.49 | 98.4 | 101.3 |
| CU-Start-2 | 265.50 | 104.0 | |
| CU-Start-3 | 256.00 | 99.3 | |
| CU-Start-4 | 262.81 | 102.3 | |
| CU-Start-5 | 257.58 | 100.9 | |
| CU-Start-6 | 262.86 | 101.3 | |
| CU-Start-7 | 261.55 | 103.1 | |
| CU-Start-8 | 256.33 | 99.0 | |
| CU-Start-9 | 262.38 | 103.0 | |
| CU-Start-10 | 264.41 | 102.1 | |
| CU-Middle-1 | 260.30 | 101.2 | 101.7 |
| CU-Middle-2 | 268.75 | 104.0 | |
| CU-Middle-3 | 265.00 | 103.6 | |
| CU-Middle-4 | 263.31 | 101.9 | |
| CU-Middle-5 | 262.21 | 100.4 | |
| CU-Middle-6 | 256.37 | 99.2 | |
| CU-Middle-7 | 262.26 | 101.8 | |
| CU-Middle-8 | 263.23 | 102.2 | |
| CU-Middle-9 | 260.14 | 100.7 | 101.4 |
| CU-Middle-10 | 264.03 | 102.2 | |
| CU-End-1 | 256.00 | 97.7 | |
| CU-End-2 | 264.43 | 102.4 | |
| CU-End-3 | 260.19 | 101.2 | |
| CU-End-4 | 261.52 | 101.4 | |
| CU-End-5 | 262.22 | 102.8 | |
| CU-End-6 | 262.70 | 101.3 | |

TABLE 23-continued

| Content Uniformity Results at 25,200 Capsules per Hour for DS Lot 2, 20 mg Capsules<br>DS Lot 2<br>Capsule Sample 20 mg, CU @ 25,200 capsules/hr | | | |
|---|---|---|---|
| Run No. | Weight (mg) | % Assay | Location Mean |
| CU-End-7 | 260.22 | 101.4 | |
| CU-End-8 | 259.52 | 101.7 | |
| CU-End-9 | 258.41 | 102.1 | |
| CU-End-10 | 260.64 | 101.6 | |
| Mean Results | 261.38 | 101.47 | |
| SD | 3.0 | 1.6 | |
| RSD | 1.2 | 1.5 | |
| Min | 256.00 | 97.70 | |
| Max | 268.75 | 104.00 | |

TABLE 24

| Content Uniformity Results at 25,200 Capsules per Hour for DS Lot 2, 30 mg Capsules<br>DS Lot 2<br>Capsule Sample 30 mg, CU @ 25,200 capsules/hr | |
|---|---|
| Run No. | % Assay |
| 1-1 | 98.8 |
| 2-1 | 103.6 |
| 3-1 | 97.0 |
| 4-1 | 104.3 |
| 5-1 | 99.5 |
| 6-1 | 95.5 |
| 7-1 | 105.3 |
| 8-1 | 98.8 |
| 9-1 | 101.4 |
| 10-1 | 100.1 |
| Average | 100.4 |
| SD | 3.2 |
| AV | 7.7 |

Table 25 below describe content uniformity (CU) studies for DS Lot 4 (i.e., 10 mg) capsules prepared in accordance with Example 6.

TABLE 25

| Content Uniformity Results at 25,200 Capsules per Hour for (medium speed) for DS Lot 4, 10 mg Capsules<br>DS Lot 4<br>Capsule Sample 10 mg, CU @ 23AS2108 (medium speed) | | |
|---|---|---|
| Run No. | Weight of Capsule (mg) | % Assay |
| 1 | 135.04 | 96.2 |
| 2 | 137.34 | 98.6 |
| 3 | 141.26 | 101.9 |
| 4 | 141.85 | 101.1 |
| 5 | 140.90 | 102.5 |
| 6 | 139.86 | 98.5 |
| 7 | 142.19 | 104.1 |
| 8 | 137.09 | 100.1 |
| 9 | 142.77 | 103.9 |
| 10 | 138.49 | 100.5 |
| | Weight of Tablet (mg) | % Assay |
| Average | 139.7 | 100.7 |
| % RSD | 1.8 | 2.5 |
| Min | 135.0 | 96.2 |
| Max | 142.8 | 104.1 |
| Acceptance Value (AV) | | 6.0 |

The above data in Tables 19-25 show that capsule formulations of vimseltinib achieve high content uniformity, as, for example, characterized by acceptance values consistently under 15. Such results are unexpected in view of, for example, the large difference in particle sizes of vimseltinib dihydrate drug substance and lactose monohydrate. Surprisingly, lactose monohydrate as a filler contributes to the production of blends (e.g., formulations, oral dosages, capsules) with acceptable uniformity at various vimseltinib dihydrate drug loads, as shown by the acceptance values in Tables 19-22 and 24-25 consistently lower than 15, as determined according to the USP Uniformity of Dosage Unit <905>. The acceptable content uniformity was achieved with regular blending process (for example convection blenders like V-shaped blender or bin blenders) without necessarily the need for high shear mixer or granulation steps, i.e., wet or dry granulation steps which typically require additional excipients and are typically more difficult to scale up or transfer from one commercial facility to another, which simplifies the manufacturing process and renders it suitable for scale up and technology transfer. In addition, lactose monohydrate as a filler is superior to other fillers such as starch by providing improved content uniformity. Table 26 below shows the compositions of lactose-based and starch-based formulations. For the lactose-based formulation, the drug substance, filler, and disintegrant were blended, sieved through 30 mesh hand screen and was added lubricant which was passed through a 30-mesh hand screen. Then the blend was mixed for 3 minutes. For the starch-based formulation, the drug substance and filler were blended, sieved through a 30-mesh screen and was added a lubricant which was passed through a 30 mesh hand screen. Then the blend was mixed for 3 minutes. The formulations were encapsulated in hard gelatin, size 4, white/white, opaque, plain capsules.

TABLE 26

Formulations of lactose-based and starch-based formulations

| Ingredient | % Composition (w/w) | Weight per Batch (g) |
|---|---|---|
| Lactose-based | | |
| Vimseltinib drug substance (dihydrate) | 10.0 | 9.50 |
| Lactose monohydrate (Foremost 316 FastFlo) | 87.5 | 83.13 |
| Crospovidone (Polyplasdone XL-10) | 2.0 | 1.90 |
| Magnesium stearate | 0.5 | 0.48 |
| Starch-based | | |
| Vimseltinib drug substance (dihydrate) | 8.3 | 9.50 |
| Starch 1500 | 91.2 | 103.93 |
| Magnesium stearate | 0.5 | 0.57 |

The content uniformity for the lactose-based formulation and starch-base formulation was 94.2% (AV 16.8) and 88.6% (AV 42.1), respectively. This AV for the starch-based formulation was not acceptable for further development. In contrast, the lower AV value for the lactose-based formulation enabled the development of the lactose-containing commercial formulations routinely achieving AVs<15 (see e.g., Tables 19-25). At least the formulations of Examples 6 and 7 demonstrate the means for achieving such a uniformity profile, i.e., an AV of about less than 15.

Example 10. Dissolution Studies

TABLE 27

Specification of the Drug Product

| Test Attribute | Analytical Method | Acceptance Criteria |
|---|---|---|
| Description | Visual | 10 mg: White opaque body and medium blue opaque cap, Size 4, hard gelatin capsules with black "DCV10" 14 mg: White opaque body and orange opaque cap, Size 4, hard gelatin capsules with black "DCV14" 20 mg: White opaque body and yellow opaque cap, Size 2, hard gelatin capsules with black "DCV20" 30 mg: White opaque body and light blue opaque cap, Size 1, hard gelatin capsules with black "DCV30" |
| Identification | RP-UPLC/ Retention Time | Retention time of the major peak corresponds to that of the reference standard (within ±2.0%) |
| | RP-UPLC/ UV Spectrum | Corresponds to the Reference Standard |
| Assay (% Label Claim) | RP-UPLC | 90.0-110.0% |
| Degradation Products (% area) Each unspecified degradation product[a] | RP-UPLC | NMT 0.2% each |
| Total degradation products | | NMT 2.0% |
| Uniformity of Dosage Units (Content Uniformity) | RP-UPLC USP <905> Ph. Eur. 2.9.40 | Conforms to Ph. Eur. 2.9.40; USP <905> |

TABLE 27-continued

| Specification of the Drug Product | | |
|---|---|---|
| Test Attribute | Analytical Method | Acceptance Criteria |
| Dissolution (% vimseltinib released) | RP-UPLC USP <711> Ph. Eur. 2.9.3 Apparatus 2 (paddles) | Q = 75% in 30 minutes |
| Water Content (% w/w) | Karl Fischer USP <921> Ph. Eur. 2.5.32 | NMT 8.0% |

AV: acceptance value;
CFU: colony forming units;
NMT: not more than;
Ph. Eur .: European Pharmacopoeia;
RP-UPLC: reverse phase ultra-high performance liquid chromatography;
USP: United States Pharmacopeia;
UV: ultraviolet
[a]Report each ≥0.1% area

TABLE 28

| Analytical Procedures Used to Test Drug Product | |
|---|---|
| Test | Analytical Method (Method #) |
| Description | Visual |
| Identification by Retention Time | RP-UPLC |
| Identification by UV Spectrum | (METR-0919-AS) |
| Assay (% label claim) | |
| Individual unspecified degradation products | |
| Total degradation products | |
| Uniformity of dosage units (Content Uniformity) | RP-UPLC (METR-0919-AS) USP <905>; Ph. Eur. 2.9.40 |
| Water Content | Karl Fischer (METR-0919-AS) USP <921>; Ph. Eur. 2.5.32 |
| Dissolution | RP-UPLC (METR-0919-AS) USP <711>; Ph. Eur. 2.9.3 Apparatus 2 (paddles) |

Abbreviations:
RP-UPLC: reversed phase ultra-high performance liquid chromatography;
UV: ultra-violet;
USP: United States pharmacopoeia;
Ph. Eur .: European pharmacopoeia.

TABLE 29

| Equipment, Reagents | |
|---|---|
| Equipment | |
| UPLC system | UPLC with UV detection (Waters Acquity UPLC) |
| Column | Acquity UPLC CSH C18, 2.1 × 100 mm, 1.7 um or equivalent |
| Reagents | |
| Water, HPLC grade or equivalent | |
| Acetonitrile (ACN) , HPLC grade or equivalent | |
| 1N HCL, HPLC grade or equivalent | |
| Methanol, HPLC grade or equivalent | |
| Ammonium Formate, HPLC grade or equivalent | |
| Formic acid, LC-MS grade or equivalent | |

HPLC: high-performance liquid chromatography;
LC-MS: liquid chromatography-mass spectrometry;
UV: ultraviolet;
UPLC: ultra-high performance liquid chromatography.

TABLE 30

| UPLC Instrument Parameters for Identification, Assay, Degradation Products, and Uniformity of Dosage Units | | | |
|---|---|---|---|
| Parameter | Value | | |
| Column temperature | 34° C. ± 2° C. | | |
| Autosampler temperature | 20° C. ± 2° C. | | |
| Flow rate | 0.47 mL/min | | |
| Injection volume | 2.5 μL | | |
| Detection | UV at 260 nm Spectra collection 190-400 nm | | |
| Acquisition run time | 20 minutes | | |
| Mobile phase | Mobile Phase A: 10 mM Ammonium Formate, pH 3.5 Mobile Phase B: Acetonitrile | | |
| Diluent Blank/Needle Wash | 75% Methanol/25% 0.01N HCl | | |
| Gradient | Minutes | % Mobile Phase A | % Mobile Phase B |
| | 0.0 | 96 | 4 |
| | 2.5 | 82 | 18 |
| | 15.5 | 21 | 79 |
| | 16.5 | 10 | 90 |
| | 17.5 | 10 | 90 |
| | 18.0 | 96 | 4 |
| | 20.0 | 96 | 4 |

HCl: hydrochloric acid;
UV: ultraviolet

Dissolution of the drug product prepared according to Examples 6-7 was studied. Discrimination was demonstrated for the key parameters impacting dissolution of the powder-filled, hard gelatin capsule drug product, namely, the particle size and specific surface area of the vimseltinib dihydrate drug substance. A USP apparatus 2 (paddles) was used with 900 mL of media and a stir rate of 75 rpm. The composition of the dissolution media was a 200 mM sodium citrate buffer at pH 2.90. Details of the dissolution test are summarized below.

TABLE 31

| Dissolution Study Conditions | |
|---|---|
| Apparatus | USP Apparatus 2 (paddles) |
| Dissolution Medium | 200 mM sodium citrate buffer, pH 2.90 |
| Volume | 900 mL |
| Paddle Speed | 75 rpm |
| Temperature | 37° C. +− 0.5° C. |
| Sample Volume | 3 mL |
| Sampling Time Points | 5, 10, 15, 30, 45, 60 minutes |
| Quantitation | HPLC/UV |

Samples

3×10 mg clinical-process capsules (N=12)
1×30 mg commercial-process capsules (N=12)
1×10 mg+2×2 clinical-process capsules (N=12)
1×14 mg commercial-process capsules (N=12)

Sample Preparation

Each capsule was inserted into an appropriately sized sinker. The appropriate number of capsules was added to each of 6 vessels. Prior to the first sampling time point, the filters were pre-conditioned by withdrawing and expelling 3 mL of media back into the vessel at least twice. At each sampling time point, 3 mL of sample were removed from the vessel using a stainless-steel cannula and filtered through a 1-micron filter. Samples aliquots were collected in HPLC vials for analysis.

Stock Standard Preparation (Nominal Concentration: 0.5 mg/mL Vimseltinib)

4.0 mL of stock standard solution was transferred into a 50 mL volumetric flask. The solution was diluted to volume with dissolution medium. Approximately 50 mg (corrected based on purity factor) of vimseltinib reference standard was weighed and transferred into a 100 mL volumetric flask. Approximately 45 mL of methanol sonicate was added. The solution was diluted to volume with methanol and mixed.

Working Standard Preparation (Nominal Concentration: 0.04 mg/mL Vimseltinib)

4.0 mL of stock standard solution was transferred into a 50 mL volumetric flask. The solution was diluted to volume with dissolution medium and mixed.

Instrumental Conditions

Column was Zorbax Eclipse XDB-C18 Rapid Resolution HD, 3.0×100 mm, 1.8 m. Column temperature was 40° C. Sample temperature was ambient. Flow rate was 0.425 mL/min. The mobile phase was 62.5:37.5%, v/v, 50 mM Ammonium Formate+, 0.1% Formic Acid: Acetonitrile. Detection was with UV at 260 nm.

Results

FIG. 11A-11E illustrate the dissolution profiles for 2 mg, 10 mg, 14 mg, 20 mg, and 30 mg capsules prepared according to Examples 6-7. The use of the formulations of the disclosure allowed for faster drug release from the finished dosage forms, as demonstrated by the dissolution profiles shown in FIG. 11A-11E. For each dose, >90% of the compound of Formula (I) was released in under 30 minutes. At least the formulations of Examples 6 and 7 demonstrate the means for achieving such dissolution profiles.

Example 11. Packaging

The dissolution performance was increased with utilization of less moisture permeable blister materials. The increased thickness and smaller water permeability of the packaging material should prevent moisture intake of the water into the capsules during long storage in blisters and should delay the occurrence of cross-linking.

Example 12. Stability Studies

A stability study was initiated for batches of drug product. Batches were manufactured according to the same composition and manufacturing process described above. Stability samples were packaged as described above and placed on storage at 25° C./60% RH and 40/75% RH. Tests for description, assay, related substances, dissolution, and water content are performed at regular intervals following the analytical procedures presented.

The results demonstrate the physical and chemical stability of the drug product after storage for at least 12 months at 25° C./60% RH and 40° C./75% RH. No significant changes were observed in appearance, assay, related substances, dissolution or water content and all results comply with specification.

At least the formulations of Examples 6 and 7 demonstrate the means for achieving such stability profiles.

TABLE 32

Stability Data for Vimseltinib Capsules (10 mg)

| | | Test | | | | | |
|---|---|---|---|---|---|---|---|
| | | | | Degradation Products (% area) | | | |
| Storage Condition | Time (Months) | Description | Assay (% Label Claim) | Individual Unspecified Report by RRT | Total Degradation Products | Water Content (% w/w) | Dissolution (% released in 30 min) |
| BATCH 1 | | | | | | | |
| Initial | 0 | Conforms | 98.9 | NR | 0.0 | 5.5 | Min: 85<br>Max: 91<br>Mean: 87 |
| 25 ± 2° C./ 60 ± 5% RH | 3 | Conforms | 100.1 | NR | 0.0 | 5.6 | Min: 87<br>Max: 92<br>Mean: 90 |
| | 6 | Conforms | 98.4 | NR | 0.0 | 5.6 | Min: 86<br>Max: 89<br>Mean: 88 |
| BATCH 2 | | | | | | | |
| Initial | 0 | Conforms | 101.0 | NR | 0.0 | 5.5 | Min 86<br>Max: 92<br>Mean: 88 |
| 25 ± 2° C./ 60 ± 5% RH | 3 | Conforms | 101.6 | NR | 0.0 | 5.3 | Min: 96<br>Max: 99<br>Mean: 97 |
| | 6 | Conforms | 100.1 | NR | 0.0 | 5.6 | Min: 94<br>Max: 98<br>Mean: 97 |

NMT: not more than;
NR: not reportable (<LOQ = 0.05% area);
NT: not tested;
RRT: relative retention time.

TABLE 33

Stability Data for Vimseltinib Capsules (10 mg)

| Storage Condition | Time (Months) | Description | Test: Assay (% Label Claim) | Degradation Products (% area): Individual Unspecified Report by RRT | Degradation Products (% area): Total Degradation Products | Water Content (% w/w) | Dissolution (% released in 30 min) |
|---|---|---|---|---|---|---|---|
| BATCH 3 | | | | | | | |
| Initial | 0 | Conforms | 101.1 | NR | 0.0 | 5.5 | Min: 85<br>Max: 91<br>Mean: 89 |
| 40 ± 2° C./ 75 ± 5% RH | 1 | Conforms | 99.9 | NR | 0.0 | 5.8 | Min: 85<br>Max: 92<br>Mean: 89 |
| | 3 | Conforms | 101.7 | NR | 0.0 | 5.3 | Min: 76<br>Max: 90<br>Mean: 83 |
| | 6 | Conforms | 100.5 | NR | 0.0 | 5.7 | Min: 61<br>Max: 91<br>Mean: 78 |
| BATCH 1 | | | | | | | |
| Initial | 0 | Conforms | 98.9 | NR | 0.0 | 5.5 | Min: 85<br>Max: 91<br>Mean: 87 |
| 40 ± 2° C./ 75 ± 5% RH | 1 | Conforms | 98.1 | NR | 0.0 | 5.6 | Min: 92<br>Max: 97<br>Mean: 95 |
| | 3 | Conforms | 99.8 | NR | 0.0 | 5.4 | Min: 76<br>Max: 90<br>Mean: 84 |
| | 6 | Conforms | 98.8 | NR | 0.0 | 5.7 | Min: 66<br>Max: 107<br>Mean: 85 |
| BATCH 2 | | | | | | | |
| Initial | 0 | Conforms | 101.0 | NR | 0.0 | 5.5 | Min: 86<br>Max: 92<br>Mean: 88 |
| 40 ± 2° C./ 75 ± 5% RH | 1 | Conforms | 100.2 | NR | 0.0 | 5.6 | Min: 95<br>Max: 101<br>Mean: 98 |
| | 3 | Conforms | 100.9 | NR | 0.0 | 5.3 | Min: 78<br>Max: 89<br>Mean: 83 |
| | 6 | Conforms | 100.7 | NR | 0.0 | 5.7 | Min: 31<br>Max: 97<br>Mean: 74 |

NMT: not more than;
NR: not reportable (<LOQ = 0.05% area);
NT: not tested;
RRT: relative retention time.

TABLE 34

Stability Data for Vimseltinib Capsules (14 mg)

| Storage Condition | Time (Months) | Description | Test: Assay (% Label Claim) | Degradation Products (% area): Individual Unspecified Report by RRT | Degradation Products (% area): Total Degradation Products | Water Content (% w/w) | Dissolution (% released in 30 min) |
|---|---|---|---|---|---|---|---|
| BATCH 4 | | | | | | | |
| Initial | 0 | Conforms | 96.8 | NR | 0.0 | 5.4 | Min: 80<br>Max: 104<br>Mean: 93 |

TABLE 34-continued

Stability Data for Vimseltinib Capsules (14 mg)

| Storage Condition | Time (Months) | Test: Description | Test: Assay (% Label Claim) | Degradation Products (% area): Individual Unspecified Report by RRT | Degradation Products (% area): Total Degradation Products | Water Content (% w/w) | Dissolution (% released in 30 min) |
|---|---|---|---|---|---|---|---|
| 25 ± 2° C./ 60 ± 5% RH | 3 | Conforms | 98.3 | NR | 0.0 | 5.3 | Min: 82<br>Max: 90<br>Mean: 87 |
| | 6 | Conforms | 98.3 | NR | 0.0 | 5.4 | Min: 94<br>Max: 99<br>Mean: 97 |
| | 9 | Conforms | 102.5 | NR | 0.0 | 5.3 | Min: 85<br>Max: 92<br>Mean: 87 |
| | 12 | Conforms | 103.0 | NR | 0.0 | 5.3 | Min: 82<br>Max: 91<br>Mean: 86 |
| BATCH 5 | | | | | | | |
| Initial | 0 | Conforms | 96.5 | NR | 0 | 5.8 | Min: 94<br>Max: 99<br>Mean: 96 |
| 25 ± 2° C./ 60 ± 5% RH | 3 | Conforms | 98.5 | NR | 0 | 5.4 | Min: 89<br>Max: 94<br>Mean: 92 |
| | 6 | Conforms | 98.7 | NR | 0 | 5.5 | Min: 90<br>Max: 98<br>Mean: 95 |
| | 9 | Conforms | 101.9 | NR | 0 | 5.2 | Min: 86<br>Max: 92<br>Mean: 90 |
| | 12 | Conforms | 102.3 | NR | 0 | 5.5 | Min: 92<br>Max: 97<br>Mean: 95 |
| BATCH 6 | | | | | | | |
| Initial | 0 | Conforms | 96.5 | NR | 0.0 | 5.5 | Min: 87<br>Max: 95<br>Mean: 91 |
| 25 ± 2° C./ 60 ± 5% RH | 3 | Conforms | 97.4 | NR | 0.0 | 5.4 | Min: 86<br>Max: 94<br>Mean: 88 |
| | 6 | Conforms | 97.1 | NR | 0.0 | 5.5 | Min: 84<br>Max: 94<br>Mean: 89 |
| | 9 | Conforms | 101.4 | NR | 0.0 | 5.4 | Min: 86<br>Max: 94<br>Mean: 90 |
| | 12 | Conforms | 101.7 | NR | 0.0 | 5.4 | Min: 92<br>Max: 96<br>Mean: 95 |

NMT: not more than;

NR: not reportable (<LOQ = 0.05% area);

NT: not tested;

RRT: relative retention time.

TABLE 35

Stability Data for Vimseltinib Capsules (14 mg)

| Storage Condition | Time (Months) | Description | Test: Assay (% Label Claim) | Test: Degradation Products (% area): Individual Unspecified Report by RRT | Test: Degradation Products (% area): Total Degradation Products | Test: Water Content (% w/w) | Test: Dissolution (% released in 30 min) |
|---|---|---|---|---|---|---|---|
| BATCH 4 | | | | | | | |
| Initial | 0 | Conforms | 96.8 | NR | 0.0 | 5.4 | Min: 80<br>Max: 104<br>Mean: 93 |
| 40 ± 2° C./ 75 ± 5% RH | 1 | Conforms | 101.1 | NR | 0.0 | 5.3 | Min: 86<br>Max: 96<br>Mean: 91 |
| | 3 | Conforms | 99.2 | NR | 0.0 | 5.4 | Min: 76<br>Max: 91<br>Mean: 87 |
| | 6 | Conforms | 99.9 | NR | 0.0 | 5.3 | Min: 53<br>Max: 92<br>Mean: 79 |
| BATCH 5 | | | | | | | |
| Initial | 0 | Conforms | 96.5 | NR | 0.0 | 5.8 | Min: 94<br>Max: 99<br>Mean: 96 |
| 40 ± 2° C./ 75 ± 5% RH | 1 | Conforms | 99.7 | NR | 0.0 | 5.5 | Min: 78<br>Max: 96<br>Mean: 87 |
| | 3 | Conforms | 99.1 | NR | 0.0 | 5.5 | Min: 57<br>Max: 93<br>Mean: 81 |
| | 6 | Conforms | 98.9 | NR | 0.0 | 5.6 | Min: 31<br>Max: 99<br>Mean: 82 |
| BATCH 6 | | | | | | | |
| Initial | 0 | Conforms | 96.5 | NR | 0.0 | 5.5 | Min: 87<br>Max: 95<br>Mean: 91 |
| 40 ± 2° C./ 75 ± 5% RH | 1 | Conforms | 100.0 | NR | 0.0 | 5.4 | Min: 82<br>Max: 92<br>Mean: 89 |
| | 3 | Conforms | 97.9 | NR | 0.0 | 5.4 | Min: 86<br>Max: 92<br>Mean: 90 |
| | 6 | Conforms | 98.2 | NR | 0.0 | 5.6 | Min: 59<br>Max: 92<br>Mean: 79 |

NMT: not more than;
NR: not reportable (<LOQ = 0.05% area);
NT: not tested;
RRT: relative retention time.

TABLE 36

Stability Data for Vimseltinib Capsules (14 mg)

| Storage Condition | Time (Months) | Description | Test: Assay (% Label Claim) | Test: Degradation Products (% area): Individual Unspecified Report by RRT | Test: Degradation Products (% area): Total Degradation Products | Test: Water Content (% w/w) | Test: Dissolution (% released in 30 min) |
|---|---|---|---|---|---|---|---|
| BATCH 5 | | | | | | | |
| Initial | 0 | Conforms | 96.5 | NR | 0.0 | 5.8 | Min: 94<br>Max: 99<br>Mean: 96 |

TABLE 36-continued

| Stability Data for Vimseltinib Capsules (14 mg) | | | | | | | |
|---|---|---|---|---|---|---|---|
| | | Test | | | | | |
| | | | | Degradation Products (% area) | | | |
| Storage Condition | Time (Months) | Description | Assay (% Label Claim) | Individual Unspecified Report by RRT | Total Degradation Products | Water Content (% w/w) | Dissolution (% released in 30 min) |
| 20 +/− 5° C. | 5 | Conforms | 97.5 | NR | 0.0 | 5.5 | Min: 93<br>Max: 99<br>Mean: 97 |
| | 10 | Conforms | 103.5 | NR | 0.0 | 5.1 | Min: 90<br>Max: 98<br>Mean: 95 |

NMT: not more than;
NR: not reportable (<LOQ = 0.05% area);
NT: not tested;
RRT: relative retention time

TABLE 37

| Stability Data for Vimseltinib Capsules (20 mg) | | | | | | | |
|---|---|---|---|---|---|---|---|
| | | Test | | | | | |
| | | | | Degradation Products (% area) | | | |
| Storage Condition | Time (Months) | Description | Assay (% Label Claim) | Individual Unspecified Report by RRT | Total Degradation Products | Water Content (% w/w) | Dissolution (% released in 30 min) |
| Batch 7 (25 ± 2° C./60 ± 5% RH) | | | | | | | |
| Initial | 0 | Conforms | 94.3 | NR | 0.0 | 5.5 | Min: 90<br>Max: 97<br>Mean: 94 |
| 25 ± 2° C./ 60 ± 5% RH | 3 | Conforms | 96.9 | NR | 0.0 | 5.4 | Min: 75<br>Max: 94<br>Mean: 87 |
| | 6 | Conforms | 96.6 | NR | 0.0 | 5.3 | Min: 91<br>Max: 95<br>Mean: 93 |
| | 9 | Conforms | 101.3 | NR | 0.0 | 5.0 | Min: 84<br>Max: 89<br>Mean: 86 |
| | 12 | Conforms | 101.7 | NR | 0.0 | 5.4 | Min: 93<br>Max: 97<br>Mean: 95 |
| Batch 7 (40 ± 2° C./75 ± 5% RH) | | | | | | | |
| Initial | 0 | Conforms | 94.3 | NR | 0.0 | 5.5 | Min: 90<br>Max: 97<br>Mean: 94 |
| 40 ± 2° C./ 75 ± 5% RH | 1 | Conforms | 98.9 | NR | 0.0 | 5.4 | Min: 86<br>Max: 92<br>Mean: 91 |
| | 3 | Conforms | 97.5 | NR | 0.0 | 5.5 | Min: 28<br>Max: 90<br>Mean: 77 |
| | 6 | Conforms | 100.1 | NR | 0.0 | 5.5 | Min: 82<br>Max: 92<br>Mean: 89 |
| Batch 7 (20 +/− 5° C.) | | | | | | | |
| Initial | 0 | Conforms | 94.3 | NR | 0.0 | 5.5 | Min: 90<br>Max: 97<br>Mean: 94 |
| 20 +/− 5° C. | 5 | Conforms | 96.4 | NR | 0.0 | 5.4 | Min: 94<br>Max: 98<br>Mean: 95 |

TABLE 37-continued

Stability Data for Vimseltinib Capsules (20 mg)

| | | Test | | | | | |
|---|---|---|---|---|---|---|---|
| | | | | Degradation Products (% area) | | | |
| Storage Condition | Time (Months) | Description | Assay (% Label Claim) | Individual Unspecified Report by RRT | Total Degradation Products | Water Content (% w/w) | Dissolution (% released in 30 min) |
| | 10 | Conforms | 101.9 | NR | 0.0 | 5.3 | Min: 85<br>Max: 94<br>Mean: 89 |

NMT: not more than;
NR: not reportable (<LOQ = 0.05% area);
NT: not tested;
RRT: relative retention time.

TABLE 38

Stability Data for Vimseltinib Capsules (30 mg)

| | | Test | | | | | |
|---|---|---|---|---|---|---|---|
| | | | | Degradation Products (% area) | | | |
| Storage Condition | Time (Months) | Description | Assay (% Label Claim) | Individual Unspecified Report by RRT | Total Degradation Products | Water Content (% w/w) | Dissolution (% released in 30 min) |
| BATCH 8 | | | | | | | |
| Initial | 0 | Conforms | 95.3 | NR | 0.0 | 5.6 | Min: 76<br>Max: 93<br>Mean: 86 |
| 25 ± 2° C./ 60 ± 5% RH | 3 | Conforms | 96.7 | NR | 0.0 | 5.4 | Min: 85<br>Max: 94<br>Mean: 90 |
| | 6 | Conforms | 96.8 | NR | 0.0 | 5.4 | Min: 86<br>Max: 93<br>Mean: 90 |
| | 9 | Conforms | 101.8 | NR | 0.0 | 4.8 | Min: 79<br>Max: 90<br>Mean: 83 |
| | 12 | Conforms | 102.2 | NR | 0.0 | 5.4 | Min: 94<br>Max: 101<br>Mean: 97 |
| BATCH 9 | | | | | | | |
| Initial | 0 | Conforms | 95.9 | NR | 0.0 | 5.6 | Min: 86<br>Max: 90<br>Mean: 88 |
| 25 ± 2° C./ 60 ± 5% RH | 3 | Conforms | 97.5 | NR | 0.0 | 5.3 | Min: 86<br>Max: 88<br>Mean: 87 |
| | 6 | Conforms | 97.4 | NR | 0.0 | 5.5 | Min: 83<br>Max: 88<br>Mean: 86 |
| | 9 | Conforms | 101.8 | NR | 0.0 | 5.2 | Min: 81<br>Max: 86<br>Mean: 84 |
| | 12 | Conforms | 102.8 | NR | 0.0 | 5.5 | Min: 94<br>Max: 99<br>Mean: 97 |
| BATCH 10 | | | | | | | |
| Initial | 0 | Conforms | 96.6 | NR | 0.0 | 5.6 | Min: 84<br>Max: 89<br>Mean: 86 |
| 25 ± 2° C./ 60 ± 5% RH | 3 | Conforms | 97.6 | NR | 0.0 | 5.4 | Min: 86<br>Max: 93<br>Mean: 89 |

TABLE 38-continued

Stability Data for Vimselinib Capsules (30 mg)

| Storage Condition | Time (Months) | Description | Assay (% Label Claim) | Degradation Products (% area): Individual Unspecified Report by RRT | Degradation Products (% area): Total Degradation Products | Water Content (% w/w) | Dissolution (% released in 30 min) |
|---|---|---|---|---|---|---|---|
| | 6 | Conforms | 98.6 | NR | 0.0 | 5.4 | Min: 87<br>Max: 92<br>Mean: 90 |
| | 9 | Conforms | 101.5 | NR | 0.0 | 4.8 | Min: 82<br>Max: 89<br>Mean: 87 |
| | 12 | Conforms | 101.6 | NR | 0.0 | 5.4 | Min: 89<br>Max: 92<br>Mean: 91 |

NMT: not more than;
NR: not reportable (<LOQ = 0.05% area);
NT: not tested;
RRT: relative retention time.

TABLE 39

Stability Data for Vimselinib Capsules (30 mg)

| Storage Condition | Time (Months) | Description | Assay (% Label Claim) | Degradation Products (% area): Individual Unspecified Report by RRT | Degradation Products (% area): Total Degradation Products | Water Content (% w/w) | Dissolution (% released in 30 min) |
|---|---|---|---|---|---|---|---|
| BATCH 8 | | | | | | | |
| Initial | 0 | Conforms | 95.3 | NR | 0.0 | 5.6 | Min: 76<br>Max: 93<br>Mean: 86 |
| 40 ± 2° C./ 75 ± 5% RH | 1 | Conforms | 100.9 | NR | 0.0 | 5.4 | Min: 80<br>Max: 87<br>Mean: 83 |
| | 3 | Conforms | 97.2 | NR | 0.0 | 5.4 | Min: 88<br>Max: 93<br>Mean: 91 |
| | 6 | Conforms | 98.3 | NR | 0.0 | 5.5 | Min: 59<br>Max: 90<br>Mean: 80 |
| BATCH 9 | | | | | | | |
| Initial | 0 | Conforms | 95.9 | NR | 0.0 | 5.6 | Min: 86<br>Max: 90<br>Mean: 88 |
| 40 ± 2° C./ 75 ± 5% RH | 1 | Conforms | 99.4 | NR | 0.0 | 5.4 | Min: 79<br>Max: 86<br>Mean: 84 |
| | 3 | Conforms | 96.4 | NR | 0.0 | 5.5 | Min: 36<br>Max: 94<br>Mean: 79 |
| | 6 | Conforms | 99.7 | NR | 0.0 | 5.4 | Min: 11<br>Max: 66<br>Mean: 45 |
| BATCH 10 | | | | | | | |
| Initial | 0 | Conforms | 96.6 | NR | 0.0 | 5.6 | Min: 84<br>Max: 89<br>Mean: 86 |
| 40 ± 2° C./ 75 ± 5% RH | 1 | Conforms | 100.1 | NR | 0.0 | 5.5 | Min: 78<br>Max: 83<br>Mean: 81 |

TABLE 39-continued

| Stability Data for Vimselinib Capsules (30 mg) | | | | | | | |
|---|---|---|---|---|---|---|---|
| | | Test | | | | | |
| | | | | Degradation Products (% area) | | | |
| Storage Condition | Time (Months) | Description | Assay (% Label Claim) | Individual Unspecified Report by RRT | Total Degradation Products | Water Content (% w/w) | Dissolution (% released in 30 min) |
| | 3 | Conforms | 97.6 | NR | 0.0 | 5.5 | Min: 36<br>Max: 90<br>Mean: 76 |
| | 6 | Conforms | 98.6 | NR | 0.0 | 5.6 | Min: 45<br>Max: 86<br>Mean: 68 |

NMT: not more than;
NR: not reportable (<LOQ = 0.05% area);
NT: not tested;
RRT: relative retention time.

TABLE 40

| Stability Data for Vimseltinib Capsules (30 mg) | | | | | | | |
|---|---|---|---|---|---|---|---|
| | | Test | | | | | |
| | | | | Degradation Products (% area) | | | |
| Storage Condition | Time (Months) | Description | Assay (% Label Claim) | Individual Unspecified Report by RRT | Total Degradation Products | Water Content (% w/w) | Dissolution (% released in 30 min) |
| BATCH 9 | | | | | | | |
| Initial | 0 | Conforms | 95.9 | NR | 0.0 | 5.6 | Min: 86<br>Max: 90<br>Mean: 88 |
| 20 +/− 5° C. | 5 | Conforms | 95.9 | NR | 0.0 | 5.4 | Min: 95<br>Max: 98<br>Mean: 97 |
| | 10 | Conforms | 102.0 | NR | 0.0 | 5.4 | Min: 90<br>Max: 99<br>Mean: 95 |

NMT: not more than;
NR: not reportable (<LOQ = 0.05% area);
NT: not tested;
RRT: relative retention time

EQUIVALENTS

Those skilled in the art will recognize or be able to ascertain using no more than routine experimentation, numerous equivalents to the specific embodiments described specifically in this disclosure. Such equivalents are intended to be encompassed in the scope of the following claims.

The invention claimed is:

1. A pharmaceutically acceptable uniform oral dosage form comprising:

a crystalline dihydrate form of a compound of Formula (I):

Formula (I)

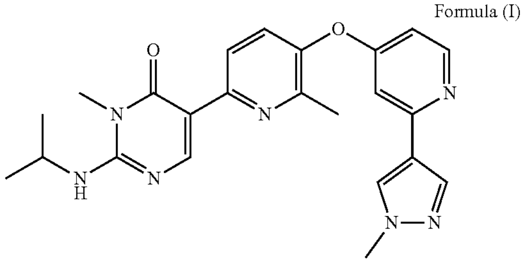 [SMILES: Cc1nc(-c2cnc(NC(C)C)n(C)c2=O)ccc1Oc1ccnc(-c2cnn(C)c2)c1]

wherein the crystalline dihydrate form is present in the oral dosage form in an amount selected from the group consisting of about 15.2 mg, about 21.7 mg, and about 32.5 mg;

about 70% by weight to about 90% by weight lactose monohydrate based on the total weight of the oral dosage form;

about 1% by weight to about 10% by weight cross-linked polyvinylpyrrolidone based on the total weight of the uniform oral dosage form; and about 0.1% by weight to about 3% by weight of one or more lubricants based on the total weight of the oral dosage form;

wherein the uniform oral dosage form has an acceptance value of less than about 15 as determined by United States Pharmacopeia (USP) Uniformity of Dosage Unit <905>, wherein the crystalline dihydrate form of the compound of Formula (I) has an X-ray powder diffraction (XRPD) pattern comprising peaks, in terms of 2-theta, at about 10.9°, 16.8°, and 27.1° as measured by CuKa radiation.

2. The pharmaceutically acceptable uniform oral dosage form of claim 1, where in wherein the uniform oral dosage form has not more than about 10 mol % of a crystalline form of the compound of Formula (I) not having a diffraction pattern comprising peaks in terms of 2-theta, at about 10.9°, 16.8°, and 27.1° as measured by CuKa radiation.

3. The pharmaceutically acceptable uniform oral dosage form of claim 1, where in wherein the uniform oral dosage form has not more than about 5 mol % of a crystalline form of the compound of Formula (I) not having a diffraction pattern comprising peaks in terms of 2-theta, at about 10.9°, 16.8°, and 27.1° as measured by CuKa radiation.

4. The pharmaceutically acceptable uniform oral dosage form of claim 1, where in wherein the uniform oral dosage form has not more than about 3 mol % of a crystalline form of the compound of Formula (I) not having a diffraction pattern comprising peaks in terms of 2-theta, at about 10.9°, 16.8°, and 27.1° as measured by CuKa radiation.

5. The pharmaceutically acceptable uniform oral dosage form of claim 1, where in wherein the uniform oral dosage form has not more than about 1 mol % of a crystalline form of the compound of Formula (I) not having a diffraction pattern comprising peaks in terms of 2-theta, at about 10.9°, 16.8°, and 27.1° as measured by CuKa radiation.

6. The pharmaceutically acceptable uniform oral dosage form of claim 1, wherein the crystalline dihydrate form of the compound of Formula (I) has having an XRPD pattern substantially as shown in FIG. 1.

7. The pharmaceutically acceptable uniform oral dosage form of claim 1, wherein the crystalline dihydrate form of the compound of Formula (I) has having a differential scanning calorimetry (DSC) thermogram comprising an endothermic event with onset between about 75° C. to about 95° C., an exothermic event with onset between about 123° C. to about 150° C., and an endothermic peak at about 215° C.

8. The pharmaceutically acceptable uniform oral dosage form of claim 1, wherein the crystalline dihydrate form of the compound of Formula (I) has having a differential scanning calorimetry (DSC) thermogram substantially as shown in FIG. 2.

9. The pharmaceutically acceptable uniform oral dosage form of claim 1, wherein the crystalline dihydrate form of the compound of Formula (I) has having a thermogravimetric analysis (TGA) thermogram substantially as shown in FIG.

10. The pharmaceutically acceptable uniform oral dosage form of claim 1, wherein the crystalline dihydrate form of the compound of Formula (I) has an X-ray powder diffraction XRPD pattern comprising peaks, in terms of 2-theta, at about 5.9°, 10.9°, 11.9°, 13.7°, 16.8°, and 27.1° as measured by CuKa radiation.

11. A pharmaceutically acceptable capsule encapsulating a uniform pharmaceutical composition comprising:

a solid-state dihydrate form of a compound represented by Formula (I):

Formula (I)

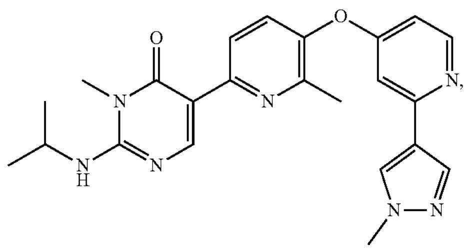

wherein the solid-state dihydrate form of the compound of Formula (I) is present in the capsule in an amount to provide about 2 mg, about 10 mg, about 14 mg, about 20 mg or about 30 mg of the free base of the compound;

a means for making the composition uniform with an acceptance value of less than 15 according to USP <905>; and one or more pharmaceutically acceptable excipients, wherein the solid-state dihydrate form of the compound represented by Formula (I) has an X-ray powder diffraction (XRPD) pattern comprising peaks, in terms of 2-theta, at about 10.9°, 16.8°, and 27.1° as measured by CuKa radiation.

12. The pharmaceutically acceptable capsule of claim 11, wherein the one or more pharmaceutically acceptable excipients comprises: about 1% by weight to about 20% by weight of one or more disintegrants based on the weight of the uniform pharmaceutical composition; and about 0.1% by weight to about 10% by weight of one or more lubricants based on the weight of the pharmaceutically acceptable unit formulation uniform pharmaceutical composition.

13. The pharmaceutically acceptable capsule of claim 11, wherein the one or more pharmaceutically acceptable excipients comprises: about 1% by weight to about 10% by weight of one or more disintegrants based on the weight of the uniform pharmaceutical composition; and about 0.1% by weight to about 3% by weight of one or more lubricants based on the weight of the pharmaceutically acceptable unit formulation uniform pharmaceutical composition.

14. The pharmaceutically acceptable capsule of claim 11, where in the one or more pharmaceutically acceptable excipients includes about 1% by weight to about 10% by weight cross-linked polyvinylpyrrolidone based on the weight of the uniform pharmaceutical composition.

15. The pharmaceutically acceptable capsule of claim 11, wherein the solid-state dihydrate form of the compound of Formula (I) has an X-ray powder diffraction XRPD pattern comprising peaks, in terms of 2-theta, at about 5.9°, 10.9°, 11.9°, 13.7°, 16.8°, and 27.1° as measured by CuKa radiation.

16. The pharmaceutically acceptable capsule of claim 11, wherein the solid-state dihydrate form of the compound of Formula (I) has having an XRPD pattern substantially as shown in FIG. 1.

17. An oral dosage form comprising a compound of Formula (I):

Formula (I)

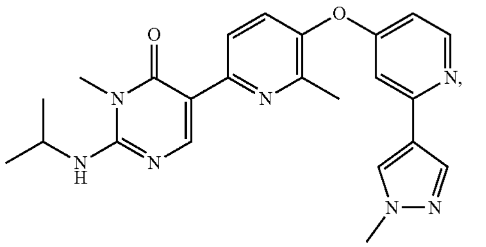

wherein the compound is present in the oral dosage form as a free base, or a pharmaceutically acceptable salt of the compound and wherein the free base or pharmaceutically acceptable salt is in a crystalline dihydrate hydrate form; wherein the compound crystalline dihydrate form is present in the oral dosage form in an amount to provide about 2 mg, about 10 mg, about 14 mg, about 20 mg or about 30 mg of the free base of the compound;

about 80% by weight to about 90% by weight of a filler based on the total weight of the oral dosage form, wherein the filler is selected from the group consisting of anhydrous lactose, lactose monohydrate, and lactose dihydrate;

about 1% by weight to about 10% by weight cross-linked polyvinylpyrrolidone based on the total weight of the uniform oral dosage form; and about 0.1% by weight to about 3% by weight by weight of one or more lubricants based on the total weight of the oral dosage form, wherein the one or more lubricants are selected from the group consisting of sodium lauryl sulfate, magnesium stearate, aluminum stearate, calcium stearate, sodium stearyl fumarate, stearic acid and magnesium lauryl stearate, wherein the crystalline dihydrate form of the compound of Formula (I) has an X-ray powder diffraction pattern (XRPD) pattern comprising peaks, in terms of 2-theta, at about 10.9°, 16.8°, and 27.1° as measured by CuKa radiation.

18. The oral dosage form of claim 17, wherein greater than 90% of the compound of Formula (I) is released in 30 minutes, as determined by USP <711>, Apparatus 2 (paddles).

19. The oral dosage form of claim 17, wherein the one or more lubricants is magnesium stearate.

20. The oral dosage form of claim 17, wherein the filler is lactose monohydrate.

21. The oral dosage form of claim 17, wherein the crystalline dihydrate form of the compound of Formula (I) has an XRPD pattern comprising peaks, in terms of 2-theta, at about 5.9°, 10.9°, 11.9°, 13.7°, 16.8°, and 27.1° as measured by CuKa radiation.

22. The oral dosage form of claim 17, wherein the crystalline dihydrate form of the compound of Formula (I) has an XRPD pattern substantially as shown in FIG. 1.

* * * * *